(12) United States Patent
Bamdad et al.

(10) Patent No.: US 11,897,967 B2
(45) Date of Patent: *Feb. 13, 2024

(54) HUMANIZED ANTI-MUC1* ANTIBODIES

(71) Applicant: Minerva Biotechnologies Corporation, Waltham, MA (US)

(72) Inventors: Cynthia Bamdad, Waltham, MA (US); Benoit Smagghe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,515

(22) Filed: Aug. 4, 2022

(65) Prior Publication Data
US 2023/0279142 A1    Sep. 7, 2023

Related U.S. Application Data

(63) Continuation of application No. 15/549,942, filed as application No. PCT/US2016/017422 on Feb. 10, 2016, now Pat. No. 11,746,159.

(60) Provisional application No. 62/114,526, filed on Feb. 10, 2015.

(51) Int. Cl.
*C07K 16/30* (2006.01)
*A61K 39/00* (2006.01)

(52) U.S. Cl.
CPC .... *C07K 16/3092* (2013.01); *A61K 39/00117* (2018.08); *A61K 2039/5156* (2013.01); *A61K 2039/5158* (2013.01); *C07K 2317/24* (2013.01); *C07K 2317/34* (2013.01); *C07K 2317/52* (2013.01); *C07K 2317/622* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,108,933 A | 4/1992 | Liberti et al. |
| 5,133,974 A | 7/1992 | Paradissis et al. |
| 5,342,947 A | 8/1994 | Lackey et al. |
| 5,407,686 A | 4/1995 | Patel et al. |
| 5,736,152 A | 4/1998 | Dunn |
| 5,767,135 A | 6/1998 | Fernandez-Pol |
| 6,127,393 A | 10/2000 | Fernandez-Pol |
| 6,548,643 B1 | 4/2003 | McKENZIE et al. |
| 7,538,088 B2 | 5/2009 | Anderson et al. |
| 7,825,092 B2 | 11/2010 | Vesely |
| 9,932,407 B2 | 4/2018 | Bamdad |
| 10,412,819 B2 | 9/2019 | Wang |
| 10,421,819 B2 | 9/2019 | Bamdad et al. |
| 2002/0018750 A1 | 2/2002 | Hansen et al. |
| 2002/0042089 A1 | 4/2002 | Bodmer et al. |
| 2002/0052311 A1 | 5/2002 | Solomon et al. |
| 2002/0064528 A1 | 5/2002 | Zhu et al. |
| 2002/0136725 A1 | 9/2002 | Blackburn et al. |
| 2002/0156112 A1 | 10/2002 | Bamdad et al. |
| 2003/0036199 A1 | 2/2003 | Bamdad et al. |
| 2003/0119018 A1 | 6/2003 | Omura et al. |
| 2003/0119834 A1 | 6/2003 | Bamdad |
| 2003/0130293 A1 | 7/2003 | Bamdad |
| 2003/0170237 A1 | 9/2003 | Ni et al. |
| 2003/0235868 A1 | 12/2003 | Hoogenboom et al. |
| 2004/0057952 A1 | 3/2004 | Payne et al. |
| 2004/0120955 A1 | 6/2004 | Anderson et al. |
| 2004/0131612 A1 | 7/2004 | Watkins et al. |
| 2005/0019324 A1 | 1/2005 | Wreschner et al. |
| 2005/0287145 A1 | 12/2005 | Stewart et al. |
| 2006/0122377 A1 | 6/2006 | Dennis |
| 2006/0147451 A1 | 7/2006 | Kirchhofer et al. |
| 2006/0173171 A1 | 8/2006 | Bamdad |
| 2006/0222637 A1 | 10/2006 | Bamdad |
| 2007/0212350 A1 | 9/2007 | Govindan et al. |
| 2009/0299039 A1 | 12/2009 | Kataoka et al. |
| 2010/0150918 A1 | 6/2010 | Kufer et al. |
| 2010/0316688 A1 | 12/2010 | Bamdad |
| 2011/0165167 A1 | 7/2011 | Pullen |
| 2011/0318757 A1 | 12/2011 | Behrens et al. |
| 2012/0040375 A1 | 2/2012 | Nishimura et al. |
| 2013/0177555 A1 | 7/2013 | Wilkinson et al. |

(Continued)

FOREIGN PATENT DOCUMENTS

| | | |
|---|---|---|
| CA | 2947646 A1 | 11/2015 |
| CN | 102264754 A | 11/2011 |

(Continued)

OTHER PUBLICATIONS

Aboud-Pirak et al. Inhibition of human tumor growth in nude mice by a conjugate of doxorubicin with monoclonal antibodies to epidermal growth factor receptor. PNAS USA 86(10):3778-81 (1989).

Bachmann et al., Recall proliferation potential of memory CD8+ T cells and antiviral protection. J Immunol. 175(7):4677-4685 (2005).

Baeckstrom et al., Purification and characterization of a membrane-bound and a secreted mucin-type glycoprotein carrying the carcinoma-associated sialyl-Lea epitope on distinct core proteins. J Biol Chem. 266(32):21537-21547 (1991).

Baeuerle et al. Bispecific T-cell engaging antibodies for cancer therapy. Cancer Res 69:4941-4944 (2009).

Baker et al., Humanization of an anti-mucin antibody for breast and ovarian cancer therapy. Adv Exp Med Biol. 353:61-82 (1994).

(Continued)

*Primary Examiner* — Peter J Reddig
(74) *Attorney, Agent, or Firm* — WILSON SONSINI GOODRICH & ROSATI

(57) ABSTRACT

The present application discloses humanized antibodies and antibody like proteins and fragments thereof.

30 Claims, 62 Drawing Sheets
(57 of 62 Drawing Sheet(s) Filed in Color)
Specification includes a Sequence Listing.

(56) References Cited

U.S. PATENT DOCUMENTS

| | | | |
|---|---|---|---|
| 2013/0266551 A1* | 10/2013 | Campana | A61K 39/0011 435/328 |
| 2016/0340442 A1 | 11/2016 | Kufe et al. | |
| 2017/0051037 A1 | 2/2017 | Galetto | |
| 2017/0204191 A1 | 7/2017 | Bamdad et al. | |
| 2018/0044424 A1 | 2/2018 | June et al. | |
| 2018/0112007 A1 | 4/2018 | Bamdad et al. | |
| 2019/0290692 A1 | 9/2019 | Bamdad et al. | |
| 2020/0239594 A1 | 7/2020 | Bamdad et al. | |
| 2020/0390870 A1* | 12/2020 | Bamdad | C07K 14/5418 |
| 2022/0184120 A1 | 6/2022 | Bamdad et al. | |
| 2023/0183373 A1 | 6/2023 | Bamdad et al. | |

FOREIGN PATENT DOCUMENTS

| | | |
|---|---|---|
| CN | 102574926 A | 7/2012 |
| CN | 103483453 A | 1/2014 |
| CN | 103880956 A | 6/2014 |
| EP | 0369816 | 5/1990 |
| EP | 2329822 A1 | 6/2011 |
| WO | WO-9109134 A1 | 6/1991 |
| WO | WO-9207000 A1 | 4/1992 |
| WO | WO-9524929 A2 | 9/1995 |
| WO | WO-9603502 A2 | 2/1996 |
| WO | WO-9735024 A1 | 9/1997 |
| WO | WO-9835554 A2 | 8/1998 |
| WO | WO-0029029 A1 | 5/2000 |
| WO | WO-0034783 A1 | 6/2000 |
| WO | WO-0043783 A2 | 7/2000 |
| WO | WO-0043791 A2 | 7/2000 |
| WO | WO-0134145 A1 | 5/2001 |
| WO | WO-0222685 A2 | 3/2002 |
| WO | WO-02056022 A2 | 7/2002 |
| WO | WO-02078598 A2 | 10/2002 |
| WO | WO-03020279 A2 | 3/2003 |
| WO | WO-03020280 A2 | 3/2003 |
| WO | WO-03054154 A2 | 7/2003 |
| WO | WO-03089451 A2 | 10/2003 |
| WO | WO-2004005470 A2 | 1/2004 |
| WO | WO-2005019269 A2 | 3/2005 |
| WO | WO-2008070171 A2 | 6/2008 |
| WO | WO-2008073817 A2 | 6/2008 |
| WO | WO-2008101231 A2 | 8/2008 |
| WO | WO-2010042562 A2 | 4/2010 |
| WO | WO-2010042891 A2 | 4/2010 |
| WO | WO-2013059373 A2 | 4/2013 |
| WO | WO-2013157102 A1 | 10/2013 |
| WO | WO-2014018679 A2 | 1/2014 |
| WO | WO-2014028668 A2 | 2/2014 |
| WO | WO-2014055657 A1 | 4/2014 |
| WO | WO-2014079000 A1 | 5/2014 |
| WO | WO-2014130741 A2 | 8/2014 |
| WO | WO-2015009740 A2 | 1/2015 |
| WO | WO-2015157322 A2 | 10/2015 |
| WO | WO-2016008973 A1 | 1/2016 |
| WO | WO-2016130726 A1 | 8/2016 |

OTHER PUBLICATIONS

Bakhtiari et al. Anti-MUC1 nanobody can redirect T-body cytotoxic effector function. Hybridoma (Larchmt). 28(2):85-92 (2009).
Baldus et al., Correlation of the immunohistochemical reactivity of mucin peptide cores MUC1 and MUC2 with the histopathological subtype and prognosis of gastric carcinomas. Int J Cancer 79(2):133-138 (1998).
Blockzjil et al., Epitope characterization of MUC1 antibodies. Tumour Biol. 19 Suppl 1:46-56 (1998).
Bortoletto et al. Optimizing anti-CD3 affinity for effective T cell targeting against tumor cells. Eur J Immunol 32:3102-3107 (2002).
Brand et al. Prospect for Anti-HER2 Receptor Therapy in Breast Cancer. Anticancer Research 26(1B):463-470 (2006).
Bruenke et al. Effective lysis of lymphoma cells with a stabilized bispecific single-chain Fv antibody against CD19 and FcgammaRIII (CD16). Br J Haematol. 130(2):218-28 (2005).
Brugger et al., Expression of MUC-1 epitopes on normal bone marrow: implications for the detection of micrometastatic tumor cells. J Clin Oncol. 17(5):1535-1544 (1999).
Burgess et al. Possible dissociation of the heparin-binding and mitogenic activities of heparin-binding (acidic fibroblast) growth factor-1 from its receptor-binding activities by site-directed mutagenesis of a single lysine residue. J Cell Biol. 111:2129-2138 (1990).
Byrd et al., Deglycosylation of mucin from LS174T colon cancer cells by hydrogen fluoride treatment. Biochem J. 261(2):617-625 (1989).
Cao et al. Construction and characterization of an enhanced GFP-tagged anti-BAFF scFv antibody. Appl Microbiol Biotechnol. 79(3):423-31 (2008).
Chames et al. Bispecific Antibodies for Cancer Therapy. Curr Opin Drug Discov Devel. 12(2):276-83 (2009).
Chen et al., Labeling of proteins with [35S]methionine and/or [35S]cysteine in the absence of cells. Anal Biochem. 269(1):179-188 (1999).
Czajkowsky, et al. Fc-fusion proteins: new developments and future perspectives. EMBO Mol Med. Oct. 2012; 4(10): 1015-1028. Published online Jul. 26, 2012.
Dai et al. Chimeric Antigen Receptors Modified T-Cells for Cancer Therapy. J Natl Cancer Inst. 108(7):djv439 (2016).
Devine et al., Expression of MUC1 and MUC2 mucins by human tumor cell lines. Tumour Biol. 13(5-6):268-277 (1992).
Efferson et al., Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15. Anticancer Res. 25(2A):715-724 (2005).
Ellison et al. Linkage and sequence homology of two human immunoglobulin γ heavy chain constant region genes. Proc. Nat. Acad. Sci. 79:1984-1988 (1982).
Fessler et al. MUC1* is a determinant of trastuzumab (Herceptin) resistance in breast cancer cells. Breast Cancer Res Treat 118:113-134 (2009).
Finlay et al. Affinity maturation of a humanized rat antibody for anti-RAGE therapy: comprehensive mutagenesis reveals a high level of mutational plasticity both inside and outside the complementarity-determining regions. J Mol Biol. 388(3):541-58 (2009).
Fraley et al. New generation liposomes: the engineering of an efficient vehicle for intracellular delivery of nucleic acids. Trends Biochem. Sci. 6:77 (1981).
Gendler, et al. Molecular cloning and expression of human tumor-associated polymorphic epithelial mucin. J Biol Chem. 265:15286-15293 (1990).
Girling et al., A core protein epitope of the polymorphic epithelial mucin detected by the monoclonal antibody SM-3 is selectively exposed in a range of primary carcinomas. Int J Cancer 43(6):1072-1076 (1989).
Gottlieb et al., The covalent structure of a human gamma G-immunoglobulin. VI. Amino acid sequence of the light chain. Biochemistry 9(16):3155-3161 (1970).
Gregoriadis. Liposomes for drugs and vaccines. Trends in Biotechnology 3:235-241 (1985).
Hartman et al., MUC1 isoform specific monoclonal antibody 6E6/2 detects preferential expression of the novel MUC1/Y protein in breast and ovarian cancer. Int J Cancer 82(2):256-267 (1999).
Hartsough M., Nm23/nucleoside diphosphate kinase in human cancers. J Bioenerg Biomembr. 32(3):301-308 (2000).
Hieken et al., Beta3 integrin expression in melanoma predicts subsequent metastasis. J Surg Res. 63(1):169-173 (1996).
Hikita et al. MUC1* Mediates the Growth of Human Pluripotent Stem Cells. PLoS One 3(10):1-13 (2008).
Holliger et al. "Diabodies": small bivalent and bispecific antibody fragments. PNAS USA 90(14):6444-6448 (1993).
Hombach et al. 0X40 costimulation by a chimericantigen receptor abrogates CD28 and IL-2 induced IL-10 secretion by redirectedCD4(+) T cells. Oncoimmunology 1(4):458-466 (2012).

(56) References Cited

OTHER PUBLICATIONS

Horton. The aV133 integrin 'vitronectin receptor. Int Biochem Cell Biol 29:721 (1997).
Hurwitz et al. The Covalent Binding of Daunomycin and Adriamycin to Antibodies, with Retention of Both Drug and Antibody Activities. Cancer Res 35:1175-1181 (1975).
Ikezoe et al., A novel treatment strategy targeting Aurora kinases in acute myelogenous leukemia. Mol Cancer Ther. 6(6):1851-1857 (2007).
ImmunoGlobe GmbH, The art of selecting an epitope. pp. 1-3 https://www.immunoglobe.com/epitope-selection.html (2011).
Iri-Sofla et al. Nanobody-based chimeric receptor gene integration in Jurkat cells mediated by φC31 integrase. Exp Cell Res 317(18):2630-2641 (2011).
Jakobovits et al. From XenoMouse technoloby to panitumumab, the first fully human antibody product from transgenic mice. Nat Biotechnol. 25(10):1134-43 (2007).
Johansson et al. Efficient expression of recombinant human monoclonal antibodies in *Drosophila* S2 cells. J Immunol Methods 318(1-2):37-46 (2007).
Juarez-Gonzalez et al Directed Evolution, Phage Display and Combination of Evolved Mutants: A Strategy to Recover the Neutralization Properties of the scFv Version of BCF2 a Neutralizing Monoclonal Antibody Specific to Scorpion Toxin Cn2). J Mol Biol. 346(5):1287-97 (2005).
Katayose et al., MUC1-specific targeting immunotherapy with bispecific antibodies: inhibition of xenografted human bile duct carcinoma growth. Cancer Res. 56(18):4205-4212 (1996).
Kettleborough et al. Optimization of primers for cloning libraries of mouse immunoglobulin genes using the polymerase chain reaction. Eur. J. Immunol. 23:206-211 (1993).
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Kufe, et al. Differential reactivity of a novel monoclonal antibody (DF3) with human malignant versus benign breast tumors. Hybridoma 3:223-232 (1984).
Lan et al., Cloning and sequencing of a human pancreatic tumor mucin cDNA. J Biol Chem. 265(25):15294-15299 (1990).
Lazar et al. Transforming growth factor alpha: mutation of aspartic acid 47 and leucine 48 results in different biological activities. Mol Cell Biol. 8:1247-1252 (1988).
Ligtenberg et al., Cell-associated episialin is a complex containing two proteins derived from a common precursor. J Biol Chem. 267(9):6171-6177 (1992).
Lonberg et al., Human antibodies from transgenic animals. Nature Biotechnology 23(9):1117-1125 (2005).
Loskog et al. Addition of the CD28 signaling domain to chimeric T-cell receptors enhances chimeric T-cell resistance to T regulatory cells. Leukemia 20(10):1819-1828 (2006).
Lu et al. Simultaneous Blockade of Both the Epidermal Growth Factor Receptor and the Insulin-like Growth Factor Receptor Signaling Pathways in Cancer Cells with a Fully Human Recombinant Bispecific Antibody. J Biol Chem. 279(4):2856-65 (2004).
Lyman G., A comparison of international guidelines for the prevention of chemotherapy-induced neutropenia. Curr Opin Hematol. 18(1):1-10 (2011).
Ma et al., Specific cytotoxicity of MUC1 chimeric antigen receptor-engineered Jurkat T cells against hepatocellular carcinoma. Academic Journal of Second Military Medical University 35(11):1177-1182 (2014).
Mahanta et al. A Minimal Fragment of MUCI Mediates Growth of Cancer Cells. PLoS One 3(4):e2054 (2008).
Maher et al., CAR mechanics: driving T cells into the MUC of cancer. Cancer Res. 69(11):4559-4562 (2009).
Majors et al. MC1-1 overexpression leads to higher viabilities and increased production of humanized monoclonal antibody in Chinese hamster ovary cells. Biotechnol Prog. Jul. 2009-Aug.;25(4):1161-8.

Mao et al., Loss of nm23 expression predicts distal metastases and poorer survival for breast cancer. Int J Oncol. 18(3):587-591 (2001).
Mazor et al., Humanization and epitope mapping of the H23 anti-MUC1 monoclonal antibody reveals a dual epitope specificity. Mol Immunol. 42(1):55-69 (2005).
Mccall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
Mccarron et al. Antibody Conjugates and Therapeutic Strategies. Mol Interv 5:368-380 (2005).
Meerzaman et al., Involvement of the MAP kinase ERK2 in MUC1 mucin signaling. Am J Physiol Lung Cell Mol Physiol. 281(1):L86-L91 (2001).
Milone et al. Chimeric receptors containing CD137 signal transduction domains mediate enhanced survival of T cells and increased antileukemic efficacy in vivo. Mol Ther 17(8):1453-1464 (2009).
Morrison. Cloning, expression, and modification of antibody V regions. Curr Protoc Immunol Chapter 2:Unit 2.12 (2002).
Muller et al., Localization of O-glycosylation sites on glycopeptide fragments from lactation- associated MUC1. All putative sites within the tandem repeat are glycosylation targets in vivo. J Biol Chem. 272(40):24780-24793 (1997).
Muzard J et al. Design and humanization of a murine scFv that blocks human platelet glycoprotein VI in vitro. FEBS J. 276(15):4207-22 (2009).
Nahary et al. Design of a human synthetic combinatorial library of single-chain antibodies. Methods Mol Biol 525:61-80 (2009).
Paterson et al., Variation in IgG1 heavy chain allotype does not contribute to differences in biological activity of two human anti-Rhesus (D) monoclonal antibodies. Immunotechnology 4(1):37-47 (1998).
PCT/US2016/017422 International Search Report and Written Opinion dated Jul. 26, 2016.
Pegram et al., Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. J Clin Oncol. 16(8):2659-2671 (1998).
Pemberton et al., Antibodies to the cytoplasmic domain of the MUC1 mucin show conservation throughout mammals. J.Biochem Biophys Res Commun. 185(1):167-175 (1992).
Pemberton et al., The epithelial mucin MUC1 contains at least two discrete signals specifying membrane localization in cells. J Biol Chem. 271(4):2332-2340 (1996).
Pilkington et al., Recombinant human Fab antibody fragments to HIV-1 Rev and Tat regulatory proteins: direct selection from a combinatorial phage display library. Mol Immunol. 33(4-5):439-450 (1996).
Pule et al. A chimeric T cell antigen receptor that augments cytokine release and supports clonal expansion of primary human T cells. Mol Ther 12(5):933-941 (2005).
Razai et al. Molecular evolution of antibody affinity for sensitive detection of botulinum neurotoxin type A. J Mol Biol. 351(1):158-69 (2005).
Robinson et al. Targeting ErbB2 and ErbB3 with a bispecific single-chain Fv enhances targeting specificity and induces a therapeutic effect in vitro. Br J Cancer 99(9):1415-25 (2008).
Ross et al., The HER-2/neu oncogene in breast cancer: prognostic factor, predictive factor, and target for therapy. Stem Cells 16(6):413-428 (1998).
Salek et al., Quantitative phosphoproteome analysis unveils LAT as a modulator of CD3ζ, and ZAP-70 tyrosine phosphorylation. PLoS One 8(10):e77423 [1-9] (2013).
Sawhney, et al. Bioerodible hydrogels based on photopolymerized poly(ethylene glycol)-co-poly(.alpha.-hydroxy acid) diacrylate macromers. Macromolecules 26(4):581-587 (1993).
Schneider et al., nm23 expression in advanced and borderline ovarian carcinoma. Anticancer Res. 16(3A):1197-1202 (1996).
Skolnick, et al. From genes to protein structure and function: novel applications of computational approaches in the genomic era. Trends Biotechnol. Jan. 2000;18(1):34-9.

(56) References Cited

OTHER PUBLICATIONS

Song et al. In Vivo Persistence, Tumor Localization, and Antitumor Activity of CAR-Engineered T Cells Is Enhanced by Costimulatory Signaling through CD137 (4-1BB). Cancer Res 71(13):4617-4627 (2011).

Spicer et al. Molecular cloning and analysis of the mouse homologue of the tumor-associated mucin, MUC1, reveals conservation of potential O-glycosylation sites, transmembrane, and cytoplasmic domains and a loss of minisatellite-like polymorphism. J. Biol. Chem 266(23):15099-15109 (1991).

Strausberg, et al. Generation and initial analysis of more than 15,000 full-length human and mouse cDNA sequences. Proc Natl Acad Sci U S A. Dec. 24, 2002;99(26):16899-903. Epub Dec. 11, 2002.

Strome et al. A mechanistic perspective of monoclonal antibodies in cancer therapy beyond target-related effects. The Oncologist 12:1084-95 (2007).

Treon et al., Muc-1 core protein is expressed on multiple myeloma cells and is induced by dexamethasone. Blood 93(4):1287-1298 (1999).

U.S. Appl. No. 15/549,942 Office Action dated Apr. 10, 2019.
U.S. Appl. No. 15/549,942 Office Action dated Aug. 26, 2020.
U.S. Appl. No. 15/549,942 Office Action dated Dec. 18, 2019.
U.S. Appl. No. 15/549,942 Office Action dated Jan. 10, 2022.
U.S. Appl. No. 15/549,942 Office Action dated Jun. 27, 2022.
U.S. Appl. No. 15/549,942 Office Action dated Mar. 19, 2021.
U.S. Appl. No. 15/549,942 Restriction Requirement dated Dec. 12, 2018.
U.S. Appl. No. 16/539,247 Office Action dated Jun. 1, 2022.
U.S. Appl. No. 16/539,247 Terminal Disclaimer filed Aug. 30, 2022.

Vailhe et al. In vitro angiogenesis is modulated by the mechanical properties of fibrin gels and is related to alpha(v)beta3 integrin localization. In Vitro Cell Dev Biol Anim. 33:763-73 (1997).

Varner et al., Integrins and cancer. Curr Opin Cell Biol. 8:724 (1996).

Wang et al. Universal PCR amplification of mouse immunoglobulin gene variable regions: The design of degenerate primers and an assessment of the effect of DNA polymerase 3' to 5' exonuclease activity. J. Immunol. Methods 233:167-177 (2000).

Wheeler C., Preventive vaccines for cervical cancer. Salud Publica Mex. 39(4):283-287 (1997).

Wilkie et al., Retargeting of human T cells to tumor-associated MUC1: the evolution of a chimeric antigen receptor. J Immunol. 180(7):4901-4909 (2008).

Wilkinson et al., Monovalent IgG4 molecules: immunoglobulin Fc mutations that result in a monomeric structure. MAbs 5(3):406-417 (2013).

Xiong et al. Development of tumor targeting anti-MUC-1 multimer: effects of di-scFv unpaired cysteine location on PEGylation and tumor binding. Protein Eng Des Sel 19(8):359-367 (2006).

Yang et al., Identification of glycosylated 38-kDa connective tissue growth factor (IGFBP-related protein 2) and proteolytic fragments in human biological fluids, and up-regulation of IGFBP-rP2 expression by TGF-beta in Hs578T human breast cancer cells. J Clin Endocrinol Metab. 83(7):2593-2596 (1998).

Yonezawa et al., Differential mucin gene expression in human pancreatic and colon cancer cells. Biochem J. 276(Pt 3):599-605 (1991).

Macian. NFAT Proteins: Key Regulators of T-Cell Development and Function. Nat. Rev. Immunol. 5(6):472-84 (2005).

Panka et al. Variable region framework differences result in decreased or increased affinity of variant anti-digoxin antibodies. PNAS USA 85:3080-3084 (1988).

Rudikoff et al.: Single amino acid substitution altering antigen-binding specificity. Proc Natl Acad Sci U S A. 79(6):1979-83 (1982).

U.S. Appl. No. 15/549,942 Office Action dated Jan. 11, 2023.
U.S. Appl. No. 17/817,525 Office Action dated Aug. 22, 2023.

Desimone et al. Recent advances in primary cutaneous T-cell lymphoma. Curr Opin Oncol. 27(2):128-133 (2015).

Jain et al. Mucin 1 is a potential therapeutic target in cutaneous T-cell lymphoma. Blood 126(3):354-62 (2015).

Kufe. Functional targeting of the MUC1 oncogene in human cancers. Cancer Biol ther 8(13):1197-1203 (2009).

U.S. Appl. No. 17/817,525 Office Action dated Sep. 29, 2023.

* cited by examiner

HUMANIZED ANTI-MUC1* ANTIBODIES

CROSS-REFERENCE TO RELATED APPLICATIONS

This application is a continuation of U.S. patent application Ser. No. 15/549,942, filed Aug. 9, 2017, which is a national stage entry of International Application No. PCT/US2016/017422, filed Feb. 10, 2016, which claims the benefit of U.S. Provisional Application No. 62/114,526, filed Feb. 10, 2015, which applications are incorporated herein by reference in their entirety.

SEQUENCE LISTING

The instant application contains a Sequence Listing which has been submitted electronically in XML format and is hereby incorporated by reference in its entirety. Said XML copy, created on Aug. 3, 2022, is named 56699-731_301SL.xml and is 993,070 bytes in size.

BACKGROUND OF THE INVENTION

1. Field of the Invention

The present application relates to humanized anti-MUC1* antibodies and methods of making and using them.

2. General Background and State of the Art

We previously discovered that a cleaved form of the MUC1 (SEQ ID NO:1) transmembrane protein is a growth factor receptor that drives the growth of over 75% of all human cancers. The cleaved form of MUC1, which we called MUC1* (pronounced muk 1 star), is a powerful growth factor receptor. Cleavage and release of the bulk of the extracellular domain of MUC1 unmasks a binding site for activating ligands dimeric NME1, NME6 or NME7. It is an ideal target for cancer drugs as it is aberrantly expressed on over 75% of all cancers and is likely overexpressed on an even higher percentage of metastatic cancers (Fessler S P, Wotkowicz M T, Mahanta S K and Bamdad C. (2009). MUC1* is a determinant of trastuzumab (Herceptin) resistance in breast cancer cells. Breast Cancer Res Treat. 118 (1):113-124). After MUC1 cleavage most of its extracellular domain is shed from the cell surface. The remaining portion has a truncated extracellular domain that at least comprises the primary growth factor receptor sequence, PSMGFR (SEQ ID NO:2).

Antibodies are increasingly used to treat human diseases. Antibodies generated in non-human species have historically been used as therapeutics in humans, such as horse antibodies. More recently, antibodies are engineered or selected so that they contain mostly human sequences in order to avoid a generalized rejection of the foreign antibody. The process of engineering recognition fragments of a non-human antibody into a human antibody is generally called 'humanizing'. The amount of non-human sequences that are used to replace the human antibody sequences determines whether they are called chimeric, humanized or fully human.

Alternative technologies exist that enable generation of humanized or fully human antibodies. These strategies involve screening libraries of human antibodies or antibody fragments and identifying those that bind to the target antigen, rather than immunizing an animal with the antigen. Another approach is to engineer the variable region(s) of an antibody into an antibody-like molecule. The present invention is intended to also encompass these approaches for use with recognition fragments of antibodies that the inventors have determined bind to the extracellular domain of MUC1*.

In addition to treating patients with an antibody, cancer immunotherapies have recently been shown to be effective in the treatment of cancers. T-cell based cancer immunotherapy is an attractive approach to overcome the cancer cells evasion from the immune system. A first immunotherapy, called CAR T (chimeric antigen receptor T cell) therapy relies on the expression of a CAR on the surface of the patient T cells for adoptive T-cell therapy (Dai H, Wang Y, Lu X, Han W. (2016) Chimeric Antigen Receptors Modified T-Cells for Cancer Therapy. J Natl Cancer Inst. 108(7): djv439). Such receptor is composed of an anti cancer scFv linked to a T cell transmembrane and signaling domains. Upon binding of the receptor to a cancer associated antigen, a signal is transmitted resulting in T-cell activation, propagation and the targeted killing of the cancer cells. In practice, a patient's T cells are isolated and transduced with a CAR, expanded and then injected back into the patient. When the patient's CAR T cells bind to the antigen on a cancer cell, the CAR T cells expand and attack the cancer cells. A drawback of this method is the risk of activating the patient's immune system to destroy cells bearing the target antigen, when most cancer antigens are expressed on some healthy tissues, but overexpressed on cancerous tissues. To minimize the risk of off-tumor/on-target effects, the cancer antigen should be minimally expressed on healthy tissues.

A second cancer immunotherapy involves BiTEs (Bi-specific T cell Engagers). The BiTE approach attempts to eliminate the CAR T associated risk of off-tumor/on-target effects. Unlike CAR T, BiTEs are bispecific antibodies that should not pose any greater risk than regular antibody-based therapies. However, unlike typical anti-cancer antibodies that bind to and block a cancer antigen, BiTEs are designed to bind to an antigen on the tumor cell and simultaneously bind to an antigen on an immune cell, such as a T cell. In this way, a BiTE recruits the T cell to the tumor. BiTEs are engineered proteins that simultaneously bind to a cancer associated antigen and a T-cell surface protein such as CD3-epsilon. BiTEs are antibodies made by genetically linking the scFv's of an antibody that binds to a T cell antigen, like anti-CD3-epsilon to a scFv of a therapeutic monoclonal antibody that binds to a cancer antigen (Patrick A. Baeuerle, and Carsten Reinhardt (2009) Bispecific T-cell engaging antibodies for cancer therapy. Cancer Res. 69(12): 4941-4944).

SUMMARY OF THE INVENTION

In one aspect, the present invention is directed to a human or humanized anti-MUC1* antibody or antibody fragment or antibody-like protein that binds to a region on extracellular domain of MUC1 isoform or cleavage product that is devoid of the tandem repeat domains. The human or humanized anti-MUC1* antibody or antibody fragment or antibody-like protein may specifically bind to
  (i) PSMGFR region of MUC1;
  (ii) PSMGFR peptide;
  (iii) a peptide having amino acid sequence of SNIKFRPGSVVVQLTLAFREGTINVHD-VETQFNQYKTEAASRY (SEQ ID NO:620);
  (iv) a peptide having amino acid sequence of SVVVQLT-LAFREGTINVHDVETQFNQYKTEAASRY (SEQ ID NO:621);

(v) a peptide having amino acid sequence of VQLT-LAFREGTINVHDVETQFNQY (SEQ ID NO:622); or
(vi) a peptide having amino acid sequence of SNIKFRPGSVVVQLTLAFREGTIN (SEQ ID NO:623).

The human or humanized antibody may be IgG1, IgG2, IgG3, IgG4 or IgM. The human or humanized antibody fragment or antibody-like protein may be scFv or scFv-Fc.

The human or humanized antibody, antibody fragment or antibody-like protein as in above may comprise a heavy chain variable region and light chain variable region which is derived from mouse monoclonal MN-E6 antibody, and has at least 80%, 90% or 95% or 98% sequence identity to the mouse monoclonal MN-E6 antibody. The heavy chain variable region may have at least 90% or 95% or 98% sequence identity to SEQ ID NO:13 and the light chain variable region may have at least 90% or 95% or 98% sequence identity to SEQ ID NO:66.

The human or humanized antibody, antibody fragment or antibody-like protein according to above may include complementarity determining regions (CDRs) in the heavy chain variable region and light chain variable region having at least 90% or 95% or 98% sequence identity to CDR1, CDR2 or CDR3 regions having sequence as follows:
CDR1 heavy chain SEQ ID NO:17
CDR1 light chain SEQ ID NO:70,
CDR2 heavy chain SEQ ID NO:21
CDR2 light chain SEQ ID NO:74,
CDR3 heavy chain SEQ ID NO:25
CDR3 light chain SEQ ID NO:78.

The human or humanized antibody, antibody fragment or antibody-like protein described above may include a heavy chain variable region and light chain variable region which is derived from mouse monoclonal MN-C2 antibody, and has at least 80%, 90% or 95% or 98% sequence identity to the mouse monoclonal MN-C2 antibody. The heavy chain variable region may have at least 90% or 95% or 98% sequence identity to SEQ ID NO:119 and the light chain variable region has at least 90% or 95% or 98% sequence identity to SEQ ID NO:169. The complementarity determining regions (CDRs) in the heavy chain variable region and light chain variable region may have at least 90% or 95% or 98% sequence identity to CDR1, CDR2 or CDR3 regions having sequence as follows:
CDR1 heavy chain SEQ ID NO:123
CDR1 light chain SEQ ID NO:173,
CDR2 heavy chain SEQ ID NO:127
CDR2 light chain SEQ ID NO:177,
CDR3 heavy chain SEQ ID NO:131
CDR3 light chain SEQ ID NO:181.

The human or humanized antibody, antibody fragment or antibody-like protein as in above may include a heavy chain variable region and light chain variable region which is derived from mouse monoclonal MN-C3 antibody, and may have at least 80%, 90% or 95% or 98% sequence identity to the mouse monoclonal MN-C3 antibody. The heavy chain variable region may have at least 90% or 95% or 98% sequence identity to SEQ ID NO:414 and the light chain variable region may have at least 90% or 95% or 98% sequence identity to SEQ ID NO:459. The complementarity determining regions (CDRs) in the heavy chain variable region and light chain variable region may have at least 90% or 95% or 98% sequence identity to CDR1, CDR2 or CDR3 regions having sequence as follows:
CDR1 heavy chain SEQ ID NO:418
CDR1 light chain SEQ ID NO:463,
CDR2 heavy chain SEQ ID NO:422
CDR2 light chain SEQ ID NO:467,
CDR3 heavy chain SEQ ID NO:426,
CDR3 light chain SEQ ID NO:471.

The human or humanized antibody, antibody fragment or antibody-like protein described above may include a heavy chain variable region and light chain variable region which is derived from mouse monoclonal MN-C8 antibody, and has at least 80%, 90% or 95% or 98% sequence identity to the mouse monoclonal MN-C8 antibody. The heavy chain variable region may have at least 90% or 95% or 98% sequence identity to SEQ ID NO:506 and the light chain variable region may have at least 90% or 95% or 98% sequence identity to SEQ ID NO:544. The complementarity determining regions (CDRs) in the heavy chain variable region and light chain variable region may have at least 90% or 95% or 98% sequence identity to CDR1, CDR2 or CDR3 regions having sequence as follows:
CDR1 heavy chain SEQ ID NO:508
CDR1 light chain SEQ ID NO:546,
CDR2 heavy chain SEQ ID NO:510
CDR2 light chain SEQ ID NO:548,
CDR3 heavy chain SEQ ID NO:512,
CDR3 light chain SEQ ID NO:550.

In another aspect, the present invention is directed to an anti-MUC1* extracellular domain antibody comprised of sequences of a humanized MN-E6 represented by humanized IgG2 heavy chain, or humanized IgG1 heavy chain, paired with humanized Kappa light chain, or humanized Lambda light chain. The humanized IgG2 heavy chain may be SEQ ID NOS:53, humanized IgG1 heavy chain may be SEQ ID NO:57, humanized Kappa light chain may be SEQ ID NO:108, and humanized Lambda light chain may be SEQ ID NO:112, or a sequence having 90%, 95% or 98% sequence identity thereof.

In another aspect, the invention is directed to an anti-MUC1* extracellular domain antibody comprised of sequences of a humanized MN-C2 represented by humanized IgG1 heavy chain, humanized IgG2 heavy chain, paired with humanized Lambda light chain, and humanized Kappa light chain. The humanized IgG1 heavy chain MN-C2 may be SEQ ID NOS:159 or IgG2 heavy chain may be SEQ ID NOS:164 paired with Lambda light chain (SEQ ID NO:219) or Kappa light chain (SEQ ID NO:213), or a sequence having 90%, 95% or 98% sequence identity thereof.

In another aspect, the invention is directed to an anti-MUC1* extracellular domain antibody comprised of sequences of a humanized MN-C3 represented by humanized IgG1 heavy chain or humanized IgG2 heavy chain paired with humanized Lambda light chain or humanized Kappa light chain. The humanized MN-C3 IgG1 heavy chain may be SEQ ID NOS:454, IgG2 heavy chain may be SEQ ID NOS:456, Lambda light chain may be SEQ ID NO:501, and Kappa light chain may be SEQ ID NO:503, or a sequence having 90%, 95% or 98% sequence identity thereof.

In another aspect, the invention is directed to an anti-MUC1* extracellular domain antibody comprised of sequences of a humanized MN-C8 represented by humanized IgG1 heavy chain or humanized IgG2 heavy chain paired with humanized Lambda light chain or humanized Kappa light chain. The humanized MN-C8 IgG1 heavy chain may be SEQ ID NOS:540, IgG2 heavy chain may be SEQ ID NOS:542, Lambda light chain may be SEQ ID NO:580 and Kappa light chain may be SEQ ID NO:582, or a sequence having 90%, 95% or 98% sequence identity thereof.

In another aspect, the invention is directed to a human or humanized anti-MUC1* antibody or antibody fragment or antibody-like protein according to above, which inhibits the binding of NME protein to MUC1*. The NME may be NME1, NME6, NME7AB, NME7 or NME8.

In yet another aspect, the invention is directed to a single chain variable fragment (scFv) comprising a heavy and light chain variable regions connected via a linker, further comprising CDRs of antibodies that bind to MUC1* extracellular domain. The CDRs may be derived from MN-E6, MN-C2, MN-C3 or MN-C8 antibodies or humanized antibodies thereof. The scFv may be one that possesses the SEQ ID NOS:233, 235 and 237 (E6); SEQ ID NOS:239, 241, and 243 (C2); SEQ ID NOS:245, 247, and 249 (C3); or SEQ ID NOS:251, 253, and 255 (C8).

In still another aspect, the invention is directed to a chimeric antigen receptor (CAR) comprising a scFv or a humanized variable region that binds to the extracellular domain of a MUC1 that is devoid of tandem repeats, a linker molecule, a transmembrane domain and a cytoplasmic domain. The single chain antibody fragment may bind to
 (i) PSMGFR region of MUC1,
 (ii) PSMGFR peptide,
 (iii) a peptide having amino acid sequence SNIKFRPGSVVVQLTLAFREGTINVHD-VETQFNQYKTEAASRY (SEQ ID NO:620);
 (iv) a peptide having amino acid sequence of SVVVQLTLAFREGTINVHDVETQFNQYKTEAASRY (SEQ ID NO:621);
 (v) a peptide having amino acid sequence of VQLTLAFREGTINVHDVETQFNQY (SEQ ID NO:622); or
 (vi) a peptide having amino acid sequence of SNIKFRPGSVVVQLTLAFREGTIN (SEQ ID NO:623).

In the CAR as describe above, portions of any of the variable regions set forth and described above, or combination thereof may be used in the extracellular domain, a transmembrane region and a cytoplasmic tail that comprises sequence motifs that signal immune system activation. The extracellular domain may be comprised of humanized single chain antibody fragments of an MN-E6 scFv, MN-C2 scFv, MN-C3 scFv or MN-C8 scFv.

In the CAR as described above, the extracellular domain include humanized single chain antibody fragments of an MN-E6 scFv set forth as SEQ ID NOS: 233, 235, or 237), MN-C2 scFv (SEQ ID NOS:239, 241, or 243), MN-C3 scFv (SEQ ID NOS: 245, 247, or 249) or MN-C8 scFv (SEQ ID NOS:251, 253, or 255).

In any of the CAR described above, the cytoplasmic tail may be comprised of one or more of signaling sequence motifs CD3-zeta, CD27, CD28, 4-1BB, OX40, CD30, CD40, PD-1, ICAm-1, LFA-1, ICOS, CD2, CD5, or CD7.

In any of the CAR described above, the sequence may be CARMN-E6 CD3z (SEQ ID NOS:295), CARMN-E6 CD28/CD3z (SEQ ID NOS:298); CARMN-E6 4-1BB/CD3z (SEQ ID NOS:301); CARMN-E6 OX40/CD3z (SEQ ID NOS:617); CARMN-E6 CD28/4-1BB/CD3z (SEQ ID NOS:304); CARMN-E6 CD28/OX40/CD3z (SEQ ID NOS: 619); CAR MN-C2 CD3z (SEQ ID NOS:607); CAR MN-C2 CD28/CD3z (SEQ ID NOS:609); CAR MN-C2 4-1BB/CD3z (SEQ ID NOS:611); CAR MN-C2 OX40/CD3z (SEQ ID NOS:613); CAR MN-C2 CD28/4-1BB/CD3z (SEQ ID NOS:307); or CAR MN-C2 CD28/OX40/CD3z (SEQ ID NOS:615).

In another aspect, the CAR may have an extracellular domain unit that recognizes a peptide. The peptide may be PSMGFR (SEQ ID NO:2). The peptide may be a peptide derived from NME7. The peptide may be
 NME7A peptide 1 (A domain): MLSRKEALDFHVDHQS (SEQ ID NO:7);
 NME7A peptide 2 (A domain): SGVARTDASES (SEQ ID NO:8);
 NME7B peptide 1 (B domain): DAGFEISAMQMFNMDRVNVE (SEQ ID NO:9);
 NME7B peptide 2 (B domain): EVYKGVVTEYHDMVTE (SEQ ID NO:10); or
 NME7B peptide 3 (B domain): AIFGKTKIQ-NAVHCTDLPEDGLLEVQYFF (SEQ ID NO:11).

In another aspect, the invention is directed a composition that includes at least two CARs with different extracellular domain units transfected into the same cell.

The at least two CARs may have one CAR that does not have a targeting recognition unit and the other CAR does have a targeting recognition unit. Or, one of the extracellular domain recognition units may bind to MUC1* extracellular domain. Or, one of the extracellular domain recognition units may bind PD-1. Or, one of the extracellular domain recognition units is an antibody fragment and the other is a peptide. Or, one is an anti-MUC1* scFv chosen from the group consisting of scFv of MN-E6 antibody, scFv of MN-C2 antibody, scFv of MN-C3 antibody or scFv of MN-C8 antibody and the other is a peptide derived from NME7 or chosen from the group consisting of
 NME7A peptide 1 (A domain): MLSRKEALDFHVDHQS (SEQ ID NO:7);
 NME7A peptide 2 (A domain): SGVARTDASES (SEQ ID NO:8);
 NME7B peptide 1 (B domain): DAGFEISAMQMFNMDRVNVE (SEQ ID NO:9);
 NME7B peptide 2 (B domain): EVYKGVVTEYHDMVTE (SEQ ID NO:10); and
 NME7B peptide 3 (B domain): AIFGKTKIQ-NAVHCTDLPEDGLLEVQYFF (SEQ ID NO:11).

In another aspect, the invention is directed to a cell comprising a CAR with an extracellular domain that binds to MUC1* transfected or transduced cell. The cell that includes the CAR may be an immune system cell, preferably a T cell or dendritic cell or mast cell.

In another aspect, the invention is directed to an engineered antibody-like protein.

In another aspect, the invention is directed to a method of screening a library of antibodies or antibody fragments that are human, for those that bind to
 (i) PSMGFR peptide;
 (ii) a peptide having amino acid sequence SNIKFRPGSVVVQLTLAFREGTINVHD-VETQFNQYKTEAASRY (SEQ ID NO:620);
 (iii) a peptide having amino acid sequence of SVVVQLTLAFREGTINVHDVETQFNQYKTEAASRY (SEQ ID NO:621);
 (iv) a peptide having amino acid sequence of VQLTLAFREGTINVHDVETQFNQY (SEQ ID NO:622);
 (v) a peptide having amino acid sequence of SNIKFRPGSVVVQLTLAFREGTIN (SEQ ID NO:623);
 (vi) NME7 protein; or
 (vii) a peptide fragment of NME7 protein.

In another aspect, the invention is directed to a method for treating a disease in a subject comprising administering an antibody according to any claim above, to a person suffering from the disease, wherein the subject expresses MUC1 aberrantly. The disease may be cancer, such as breast cancer, lung cancer, colon cancer, gastric cancer.

In another aspect, the invention is directed to a method for treating a disease in a subject comprising administering an NME peptide, to a person suffering from the disease, wherein the subject expresses MUC1 aberrantly.

In another aspect, the invention is directed to a method of proliferating or expanding stem cell population comprising contacting the cells with the antibody according to any method or composition described above.

In another aspect, the invention is directed to a method of facilitating stem cell attachment to a surface comprising coating the surface with a humanized MN-C3 or MN-C8 antibody, antibody fragment or single chain antibody thereof and contacting stem cell to the surface.

In another aspect, the invention is directed to a method of delivering stem cell in vitro or in vivo comprising the steps of coating a surface with a humanized MN-C3 or MN-C8 antibody, antibody fragment or single chain antibody thereof, contacting the stem cell to the surface and delivering the stem cell to a specific location.

In another aspect, the invention is directed to a method of isolating stem cell comprising the steps of coating a surface with a humanized MN-C3 or MN-C8 antibody, antibody fragment or single chain antibody thereof, and contacting a mixed population of cells to the surface and isolating stem cell.

In another aspect, the invention is directed to a scFv comprising variable domain fragments derived from an antibody that binds to a extracellular domain of MUC1 isoform or cleavage product that is devoid of the tandem repeat domains. The variable domain fragments may be derived from mouse monoclonal antibody MN-E6 (SEQ ID NO:13 and 66) or from the humanized MN-E6 (SEQ ID NO: 39 and 94), or from MN-E6 scFv (SEQ ID NO: 233, 235 and 237). Or, the variable domain fragments may be derived from mouse monoclonal antibody MN-C2 (SEQ ID NO: 119 and 169) or from the humanized MN-C2 (SEQ ID NO: 145 and 195), or from MN-C2 scFv (SEQ ID NO: 239, 241 and 243). Or, the variable domain fragments may be derived from mouse monoclonal antibody MN-C3 (SEQ ID NO: 414 and 459) or from the humanized MN-C3 (SEQ ID NO: 440 and 487), or from MN-C3 scFv (SEQ ID NO: 245, 247 and 249). Or, the variable domain fragments may be derived from mouse monoclonal antibody MN-C8 (SEQ ID NO: 505 and 544) or from the humanized MN-C8 (SEQ ID NO: 526 and 566), or from MN-C8 scFv (SEQ ID NO: 251, 253, 255).

In another aspect, the invention is directed to a method for the treatment of a person diagnosed with, suspected of having or at risk of developing a MUC1 Or MUC1* positive cancer involving administering to the person an effective amount of the scFv described above.

In another aspect, the invention is directed to a scFv-Fc construct comprising the scFv as described above. The scFv-Fc may be dimerized. Or, the Fc component may be mutated so that scFv-Fc is monomeric. The mutation may include mutating or deleting hinge region on Fc, making F405Q, Y407R, T366W/L368W, and T364R/L368R mutation or combinations thereof on the Fc represented by SEQ ID NO: 281, 279, 285 and 287.

In another aspect, the invention is directed to a polypeptide comprising at least two different scFv sequences, wherein one of the scFv sequences is a sequence that binds to extracellular domain of MUC1 isoform or cleavage product that is devoid of the tandem repeat domains. The polypeptide may bind to
(i) PSMGFR region of MUC1;
(ii) PSMGFR peptide;
(iii) peptide having amino acid sequence of SNIKFRPGSVVVQLTLAFREGTINVHD-VETQFNQYKTEAASRY (SEQ ID NO:620);
(iv) a peptide having amino acid sequence of VQLT-LAFREGTINVHDVETQFNQYKTEAASRY (SEQ ID NO:621);
(v) a peptide having amino acid sequence of VQLT-LAFREGTINVHDVETQFNQY (SEQ ID NO:622); or
(vi) a peptide having amino acid sequence of SNIKFRPGSVVVQLTLAFREGTIN (SEQ ID NO:623).

The polypeptide may bind to a receptor on an immune cell, such as T cell, and in particular, CD3 on T-cell.

In another aspect, the invention is directed to a method of detecting presence of a cell that expresses MUC1* aberrantly, comprising contacting a sample of cells with the scFv-Fc described above and detecting for the presence of the binding of scFv-Fc to the cell. The cell may be cancer cell.

In another aspect, the invention is directed to a method for testing a subject's cancer for suitability of treatment with a composition comprising portions of the variable regions of MN-E6, MN-C2, MN-C3 or MN-C8, comprising the steps of contacting a bodily specimen from the patient with the corresponding MN-E6 scFv-Fc, MN-C3 scFv-Fc, MN-C3 scFv-Fc or MN-C8 scFv-Fc.

In another aspect, the invention is directed to a method of treating a subject suffering from a disease comprising, exposing T cells from the subject to MUC1* peptides wherein through various rounds of maturation, T cells develop MUC1* specific receptors, creating adapted T cells, and expanding and administering the adapted T cells to the donor patient who is diagnosed with, suspected of having, or is at risk of developing a MUC1* positive cancer.

These and other objects of the invention will be more fully understood from the following description of the invention, the referenced drawings attached hereto and the claims appended hereto.

BRIEF DESCRIPTION OF THE DRAWINGS

The patent or application file contains at least one drawing executed in color. Copies of this patent or parent application publication with color drawings will be provided by the Office upon request and payment of the necessary fee.

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
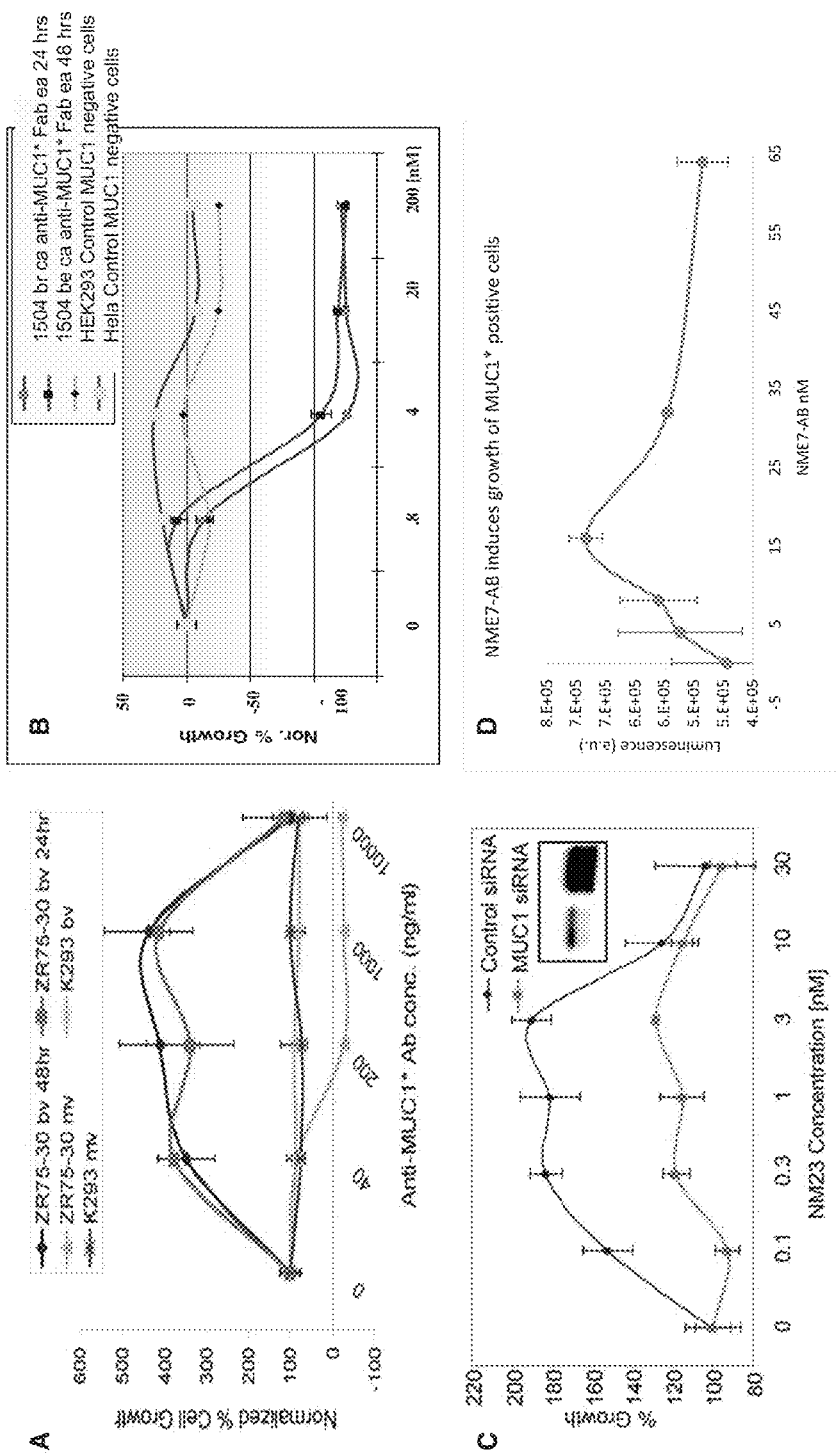
FIG. 1 shows cell growth assay graphs of MUC1* positive cells treated with either bivalent 'by' anti-MUC1* antibody, monovalent 'my' or Fab, NM23-H1 dimers or NME7-AB. Bivalent anti-MUC1* antibodies stimulate growth of cancer cells whereas the monovalent Fab inhibits growth (A, B). Classic bell-shaped curve indicates ligand induced dimerization stimulates growth. Dimeric NM23-H1, aka NME1, stimulates growth of MUC1* positive cancer cells but siRNA to suppress MUC1 expression eliminate its effect (C). NME7-AB also stimulates the growth of MUC1* positive cells (D).

In the present application, "a" and "an" are used to refer to both single and a plurality of objects.

As used herein, "h" or "hu" placed before an antibody construct is short-hand for humanized.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human Fabs that are then screened for binding to peptide epitopes from target proteins. The selected Fab regions can then be engineered into a scaffold or framework so that they resemble antibodies.

As used herein, the antibodies MN-C2, MN-E6, MN-C3 and MN-C8, may also be referred to as C2, E6, C3 and C8, respectively.

As used herein, "PSMGFR" is abbreviation for Primary Sequence of the MUC1 Growth Factor Receptor which is identified by SEQ ID NO:2, and thus is not to be confused with a six amino acid sequence. "PSMGFR peptide" or "PSMGFR region" refers to a peptide or region that incorporates the Primary Sequence of the MUC1 Growth Factor Receptor (SEQ ID NO:2).

As used herein, the "MUC1*" extra cellular domain is defined primarily by the PSMGFR sequence (GTINVHDVETQFNQYKTEAAS-RYNLTISDVSVSDVPFPFSAQSGA (SEQ ID NO:2)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

Other clipped amino acid sequences may include SNIKFRPGSVVVQLTLAFREGTINVHDVETQFNQYK-TEAASRY (SEQ ID NO:620); or SVVVQLTLAFREGT-INVHDVETQFNQYKTEAASRY (SEQ ID NO:621).

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:2). In this regard, the "N-number" as in "N-10 PSMGFR", "N-15 PSMGFR", or "N-20 PSMGFR" refers to the number of amino acid residues that have been deleted at the N-terminal end of PSMGFR. Likewise "C-number" as in "C-10 PSMGFR", "C-15 PSMGFR", or "C-20 PSMGFR" refers to the number of amino acid residues that have been deleted at the C-terminal end of PSMGFR.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein "sequence identity" means homology in sequence of a particular polypeptide or nucleic acid to a reference sequence of nucleic acid or amino acid such that the function of the homologous peptide is the same as the reference peptide or nucleic acid. Such homology can be so close with the reference peptide such that at times the two sequences may be 90%, 95% or 98% identical yet possess the same function in binding or other biological activities.

MUC1* Antibodies (Anti-PSMGFR) for Treatment or Prevention of Cancers

We discovered that a cleaved form of the MUC1 (SEQ ID NO:1) transmembrane protein is a growth factor receptor that drives the growth of over 75% of all human cancers. The cleaved form of MUC1, which we called MUC1* (pronounced muk 1 star), is a powerful growth factor receptor. Enzymatic cleavage releases the bulk of the MUC1 extracellular domain. It is the remaining portion comprising a truncated extracellular domain, transmembrane and cytoplasmic tail that is called MUC1*. Cleavage and release of the bulk of the extracellular domain of MUC1 unmasks a binding site for activating ligands dimeric NME1, NME6, NME8, NME7-AB or NME7. Cell growth assays show that it is ligand-induced dimerization of the MUC1* extracellular domain that promotes growth (FIG. 1A-D). MUC1* positive cells treated with either bivalent 'by' anti-MUC1* antibody, monovalent 'my' or Fab, NM23-H1 dimers or NME7-AB. Bivalent anti-MUC1* antibodies stimulate growth of cancer cells whereas the monovalent Fab inhibits growth. Classic bell-shaped curve indicates ligand induced dimerization stimulates growth. Dimeric NM23-H1, aka NME1, stimulates growth of MUC1* positive cancer cells but siRNA to suppress MUC1 expression eliminate its effect (C). NME7-AB also stimulates the growth of MUC1* positive cells (D).

Figure 2:
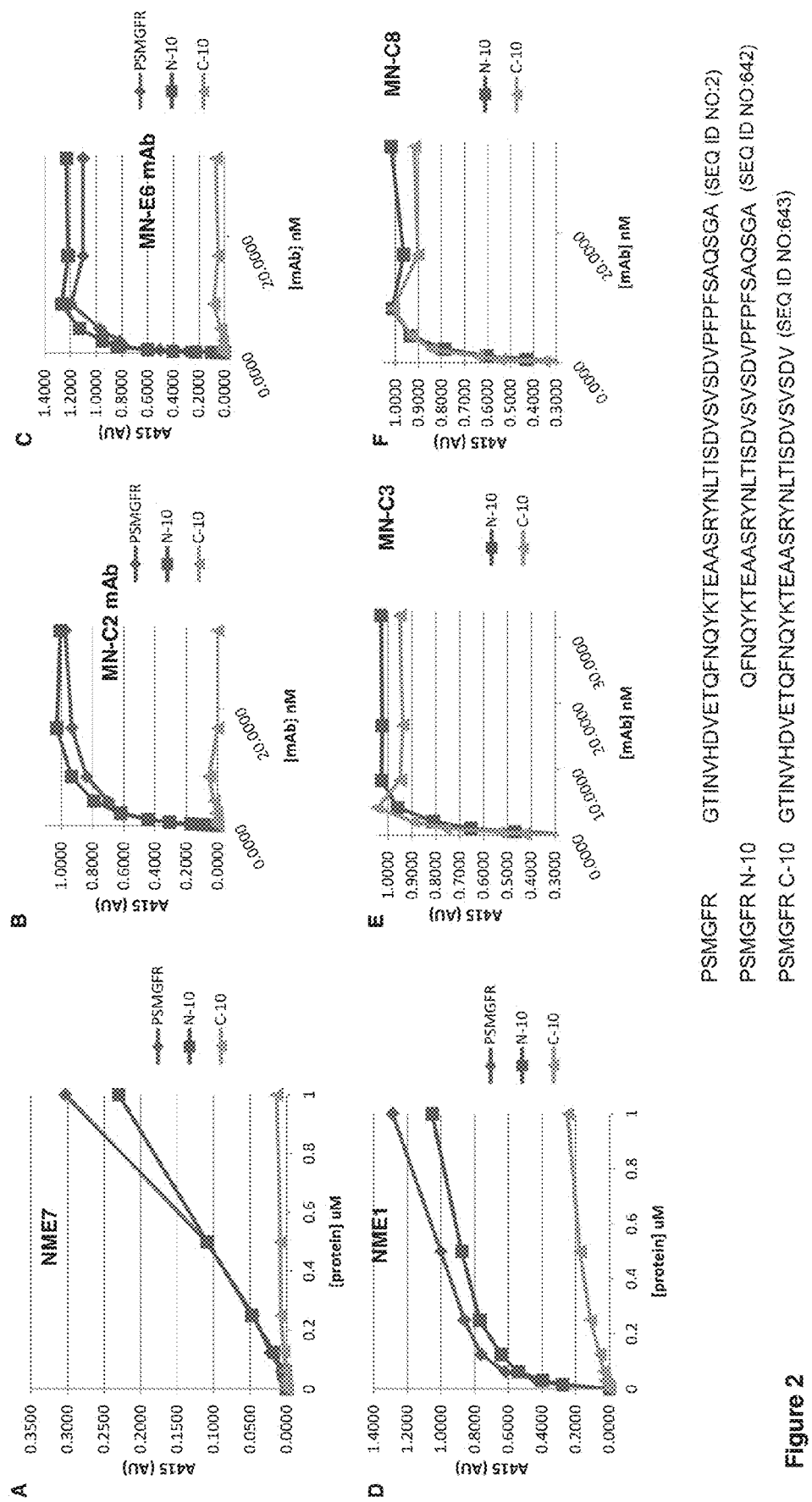
FIG. 2 shows results of ELISA assays. MUC1* peptides PSMGFR, PSMGFR minus 10 amino acids from the N-terminus aka N-10, or PSMGFR minus 10 amino acids from the C-terminus, aka C-10 are immobilized on the plate and the following are assayed for binding: NME7-AB (A), MN-C2 monoclonal antibody (B), MN-E6 monoclonal antibody (C), or dimeric NME1 (D). These assays show that NME1, NME7-AB and monoclonal antibodies MN-C2 and MN-E6 all require the first membrane proximal 10 amino acids of the MUC1* extracellular domain to bind. MUC1* peptides PSMGFR minus 10 amino acids from the N-terminus aka N-10, or PSMGFR minus 10 amino acids from the C-terminus, aka C-10, are immobilized on the plate and the following are assayed for binding: MN-C3 (E) and MN-C8 (F).

MUC1* is an ideal target for cancer drugs as it is aberrantly expressed on over 75% of all cancers and is likely overexpressed on an even higher percentage of metastatic cancers (Fessler S P, Wotkowicz M T, Mahanta S K and Bamdad C. (2009). MUC1* is a determinant of trastuzumab (Herceptin) resistance in breast cancer cells. Breast Cancer Res Treat. 118(1):113-124). After MUC1 cleavage most of its extracellular domain is shed from the cell surface. The remaining portion has a truncated extracellular domain that at least comprises the primary growth factor receptor sequence, PSMGFR (SEQ ID NO:2). Antibodies that bind to the PSMGFR sequence and especially those that competitively inhibit the binding of activating ligands such as NME proteins, including NME1, NME6, NME8 and NME7, are ideal therapeutics and can be used to treat or prevent MUC1 positive or MUC1* positive cancers, as stand-alone antibodies, antibody fragments or variable region fragments thereof incorporated into bispecific antibodies, or chimeric antigen receptors also called CARs. Therapeutics anti-MUC1* antibodies can be monoclonal, polyclonal, antibody mimics, engineered antibody-like molecules, full antibodies or antibody fragments. Examples of antibody fragments include but are not limited to Fabs, scFv, and scFv-Fc. Human or humanized antibodies are preferred for use in the treatment or prevention of cancers. In any of these antibody-like molecules, mutations can be introduced to prevent or minimize dimer formation. Anti-MUC1* antibodies that are monovalent or bispecific are preferred because MUC1* function is activated by ligand induced dimerization. Typical binding assays show that NME1 and NME7 bind to the PSMGFR peptide portion of MUC1* (FIG. 2A, D). Further, they show that these activating growth factors bind to the membrane proximal portion of MUC1*, as they do not bind to the PSMGFR peptide if the 10 C-terminal amino acids are missing. Similarly, anti-MUC1* antibodies MN-C2 and MN-E6 bind to the PSMGFR peptide if an only if the 10 C-terminal amino acids are present (FIG. 2 B, C). Antibodies MN-C3 and MN-C8 bind to epitopes that are different from MN-C2 and MN-E6, as they do not depend on the presence of the 10 C-terminal amino acids of the PSMGFR peptide (FIG. 2 E, F). Antibodies MN-C2, MN-E6, MN-C3 or MN-C8, or fragments derived from them, as stand-alone antibodies or incorporated into bispecific antibodies, BiTEs or chimeric antigen receptors also called CARs expressed by immune cells are all potent anti-cancer therapeutics.

Therapeutic anti-MUC1* antibodies for use as a stand alone antibody therapeutic or for integration into a BiTE or a CAR can be selected based on specific criteria. The parent antibody can be generated using typical methods for generating monoclonal antibodies in animals. Alternatively, they can be selected by screening antibody and antibody fragment libraries for their ability to bind to a MUC1* peptide, which can be the PSMGFR peptide (SEQ ID NO:2), SNIKFRPGSVVVQLTLAFREGTINVHDVETQFNQYKTEAASRY (SEQ ID NO:620); or SVVVQLTLAFREGTINVHDVETQFNQYKTEAASRY (SEQ ID NO:621).

Figure 3:
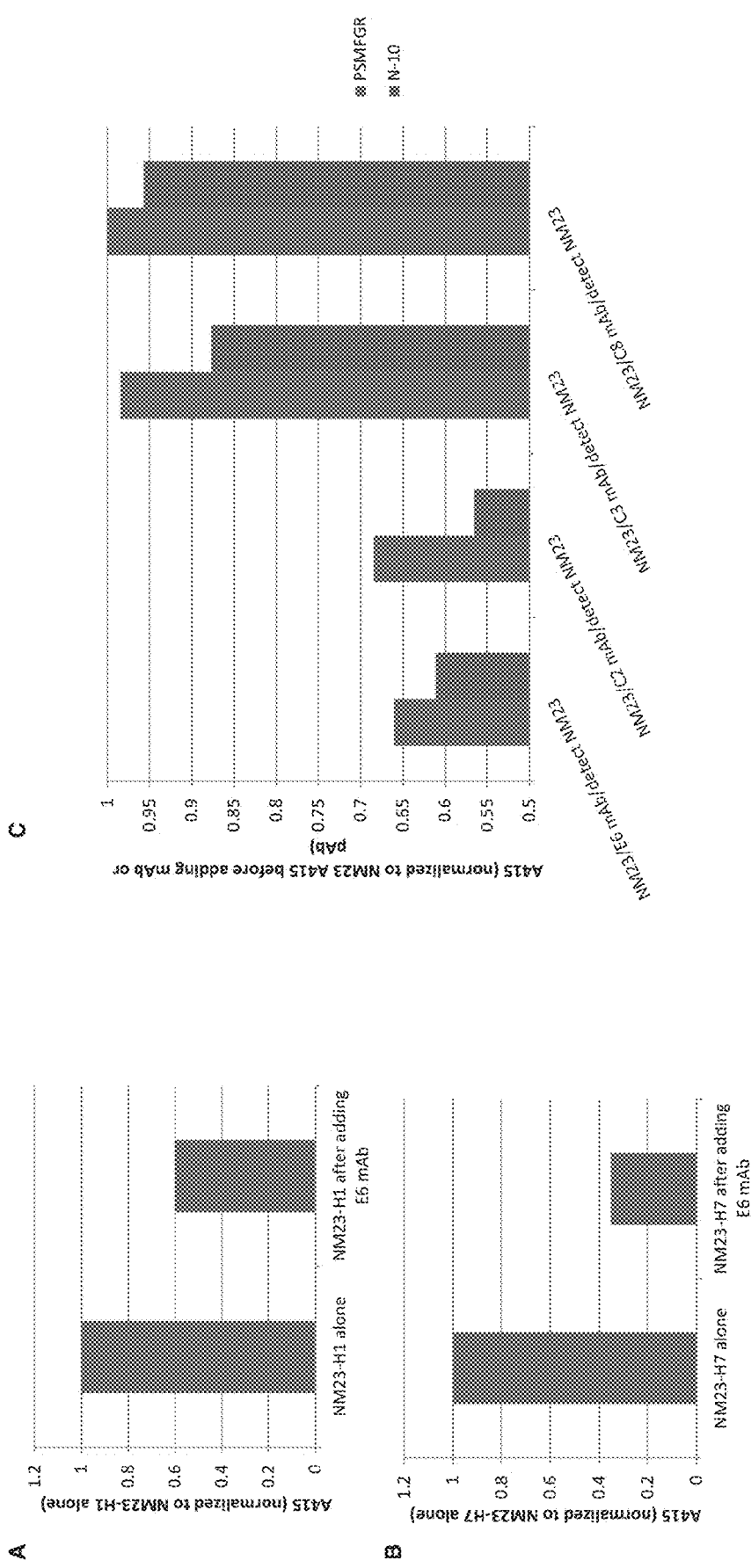
FIG. 3 shows results of competitive ELISA assays. The PSMGFR MUC1* peptide is immobilized on the plate and dimeric NM23-H1, aka NME1, is added either alone or after the MN-E6 antibody has been added (A). The same experiment was performed wherein NM23-H7, NME7-AB, is added alone or after MN-E6 has been added (B). Results show that MN-E6 competitively inhibits the binding of MUC1* activating ligands NME1 and NME7. In a similar experiment (C), PSMGFR or PSMGFR minus 10 amino acids from the N-terminus, aka N-10, is immobilized on the plate. Dimeric NM23-H1 is then added. Anti-MUC1* antibodies MN-E6, MN-C2, MN-C3 or MN-C8 are then tested for their ability to compete off the NM23-H1. Results show that although all three antibodies bind to the PSMGFR peptides, MN-E6 and MN-C2 competitively inhibit binding of the MUC1* activating ligands.

Resultant antibodies or antibody fragments generated or selected in this way can then be further selected by passing additional screens. For example, antibodies or antibody fragments become more preferred based on their ability to bind to MUC1* positive cancer cells or tissues but not to MUC1 negative cancer cells or tissues. Further, anti-MUC1* antibodies or antibody fragments may be de-selected as anti-cancer therapeutics if they bind to stem or progenitor cells. Anti-MUC1* antibodies or antibody fragments become more preferred if they have the ability to competitively inhibit the binding of activating ligands to MUC1*. FIG. 3A-C shows that MN-E6 and MN-C2 competitively inhibit the binding of activating ligands NME1 and NME7 to MUC1*. A process for selecting anti-MUC1* antibodies for use in treating a patient diagnosed with a MUC1 positive cancer, at risk of developing a MUC1 positive cancer or suspected of having a MUC1 positive cancer comprises one or more of the following steps of selecting antibodies or antibody fragments that 1) bind to the PSMGFR peptide; 2) bind to the N-10 PSMGFR peptide; 3) bind to cancer cells; 4) do not bind to stem or progenitor cells; and 5) competitively inhibited the binding of dimeric NME1 or NME7-AB to the PSMGFR peptide. For example, FIG. 3A-C show that monoclonals MN-E6 and MN-C2 satisfy all five criteria, while monoclonals MN-C3 and MN-C8 do not competitively inhibit the binding of activating ligands NME1 and NME7 (Figure M3 C). However, antibodies or antibody fragments derived from MN-C3 and MN-C8 are equally potent as anti-cancer agents when integrated into a BiTE or a CAR as in these methods, the killing effect of the immune cells is more important than the ability to inhibit the binding of activating ligands. In addition, toxic agents conjugated to MN-E6, MN-C2, MN-C3 or MN-C8 are potent anti-cancer therapeutics. Recall that the MUC1* growth factor receptor is activated by ligand-induced dimerization of its extracellular domain. Therefore the ideal antibody therapeutic should not dimerize the MUC1* extracellular domain. Preferably, suitable antibodies in this regard include monovalent antibodies such as those generated in lamas and camels, Fabs, scFv's, single domain antibodies (sdAb), scFv-Fc as long as the Fc portion is constructed such that it does not homo-dimerize.

Figure 4:
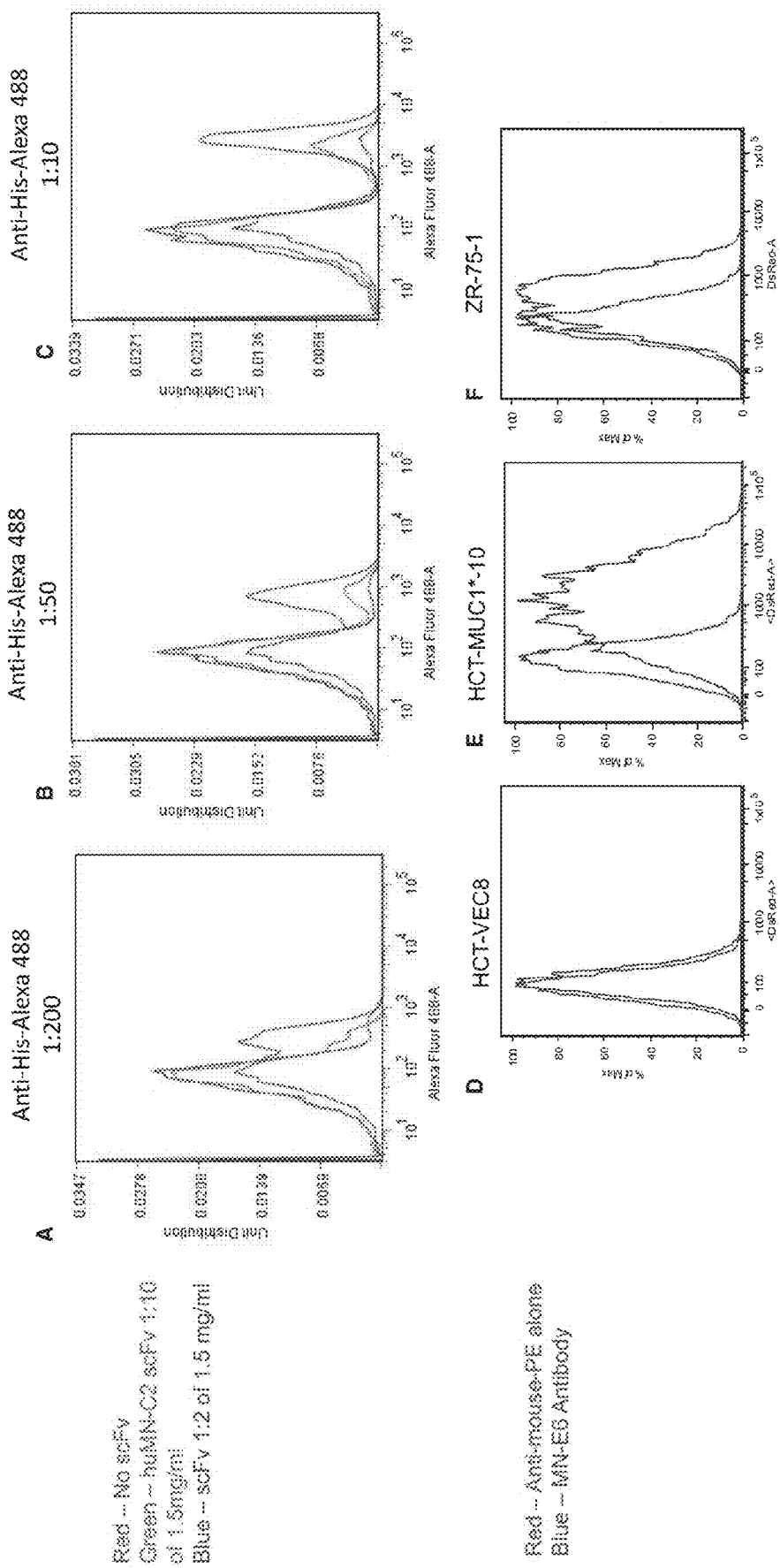
FIG. 4 shows FACS scans of anti-MUC1* antibodies binding specifically to MUC1* positive cancer cells and MUC1* transfected cells but not MUC1* or MUC1 negative cells. ZR-75-1, aka 1500, MUC1* positive breast cancer cells were stained with 1:2 or 1:10 dilutions of the 1.5 ug/ml humanized MN-C2. After two washes, cells were stained with secondary antibody, Anti-Penta-His antibody at conjugated to Alexa 488 (Qiagen) dilutions of 1:200 (A), 1:50 (B), or 1:10 (C) to detect the 6× His tag on the huMN-C2 scFv. Flow cytometric analysis revealed a concentration-dependent shift of a subset of cells, indicating specific binding, which is unseen in the absence of the MN-C2 scFv (A-C). In another case, MN-E6 was used to stain MUC1 negative HCT-116 colon cancer cells transfected with the empty vector, single cell clone #8 (D), HCT-116 colon cancer cells transfected with MUC1* single cell clone #10 (E), or ZR-75-1 (F), aka 1500, MUC1* positive breast cancer cells. As the FACS scans show, both MN-C2 and MN-E6 only stain MUC1* positive cells and not MUC1 or MUC1* negative cells.
Figure 5:
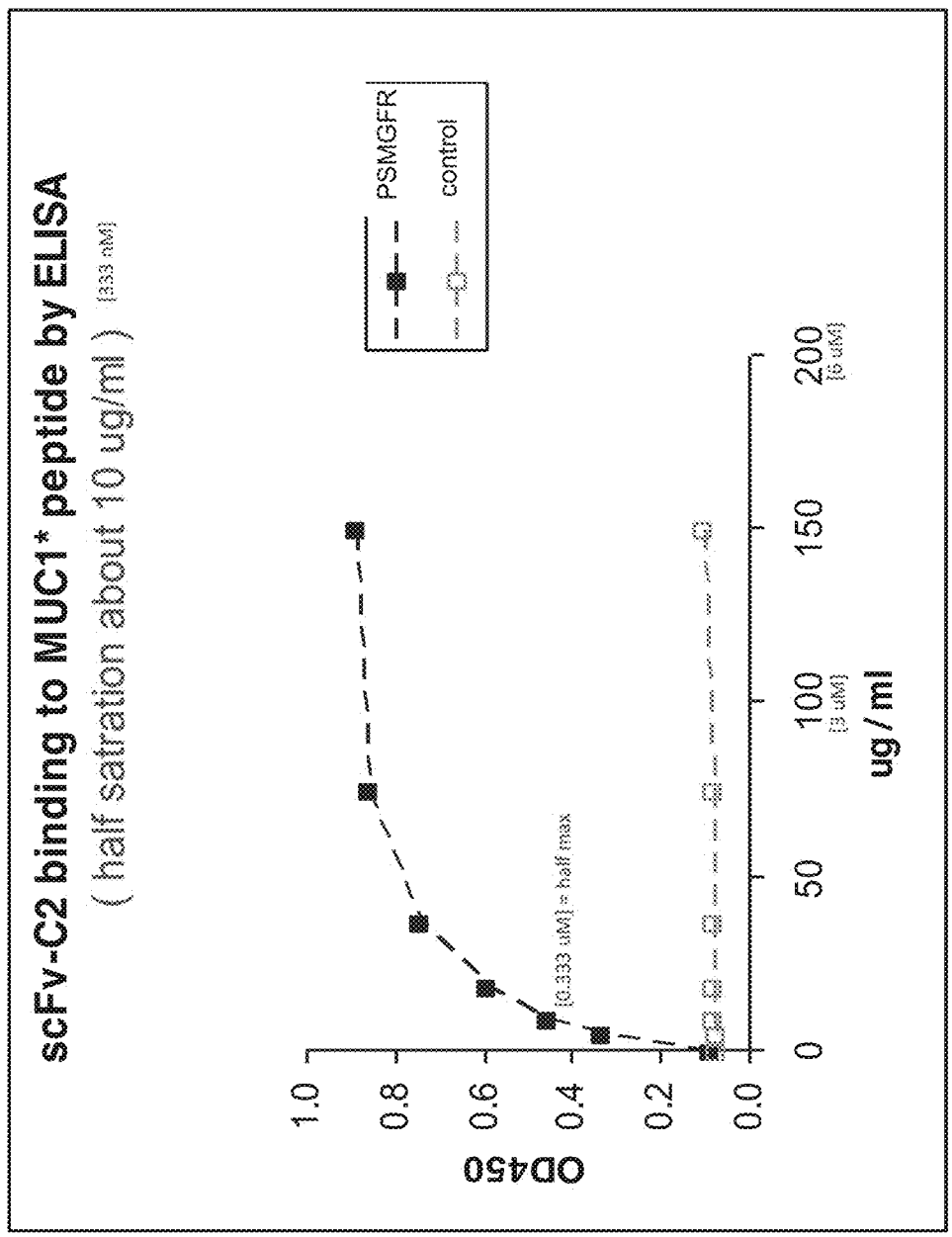
FIG. 5 shows a graph of an ELISA in which surface is coated with either the MUC1* PSMGFR peptide or a control peptide. Humanized MN-C2 scFv is then incubated with the surface, washed and detected according to standard methods. The ELISA shows that the huMN-C2 scFv binds to the MUC1* peptide with an EC-50 of about 333 nM.
Figure 6:
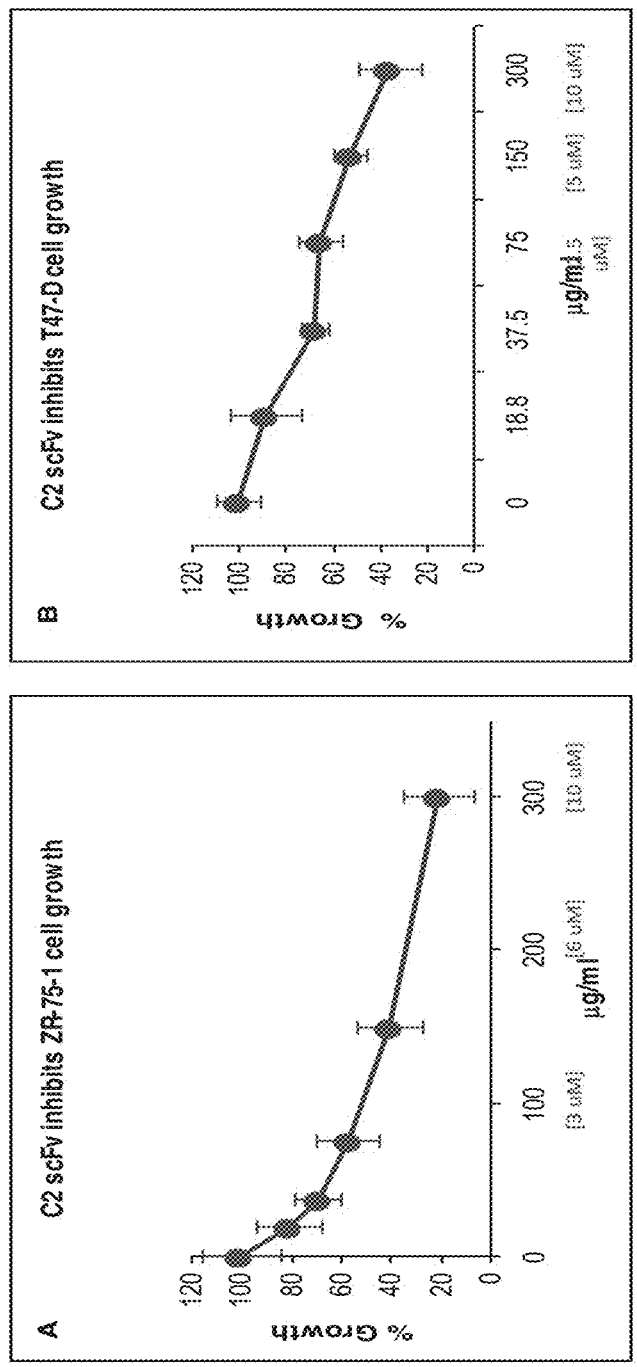
FIG. 6 shows graphs of cancer cell growth inhibition by MUC1* antibody variable region fragment humanized MN-C2 scFv. hMN-C2 scFv potently inhibited the growth of ZR-75-1, aka 1500, MUC1* positive breast cancer cells (A) and T47D MUC1* positive breast cancer cells (B) with approximately the same EC-50 as the in vitro ELISAs.

FACS scans show that anti-MUC1* antibodies MN-C2, MN-E6, MN-C3 and MN-C8 specifically bind to MUC1* positive cancer cells and MUC1* transfected cells but not MUC1* or MUC1 negative cells. In one example, a humanized MN-C2 scFv is shown to bind to ZR-75-1, aka 1500, MUC1* positive breast cancer cells (FIG. 4A-C). MN-E6 was shown to bind to MUC1 negative HCT-116 colon cancer cells if an only if they were transfected with MUC1*. MN-E6 also bound to MUC1* positive cancer cells such as ZR-75-1, aka 1500, MUC1* positive breast cancer cells (FIG. 4 D-F). Binding assays such as ELISAs, immunofluorescence, and the like all confirm that MN-C2 and MN-E6 bind to the PSMGFR peptide and to live MUC1 positive cancer cells. Humanized anti-MUC1* antibodies are selected based on their ability to also bind to the PSMGFR peptide or to MUC1 positive cancer cells. FIG. 5 shows that humanized MN-C2 scFv binds with high affinity to the MUC1* peptide PSMGFR with an EC-50 of about 333 nM. Humanized MN-C2 scFv, like Fabs, potently inhibits the growth of MUC1* positive cancer cells as is shown in one example in FIG. 6A, B.

Figure 7:
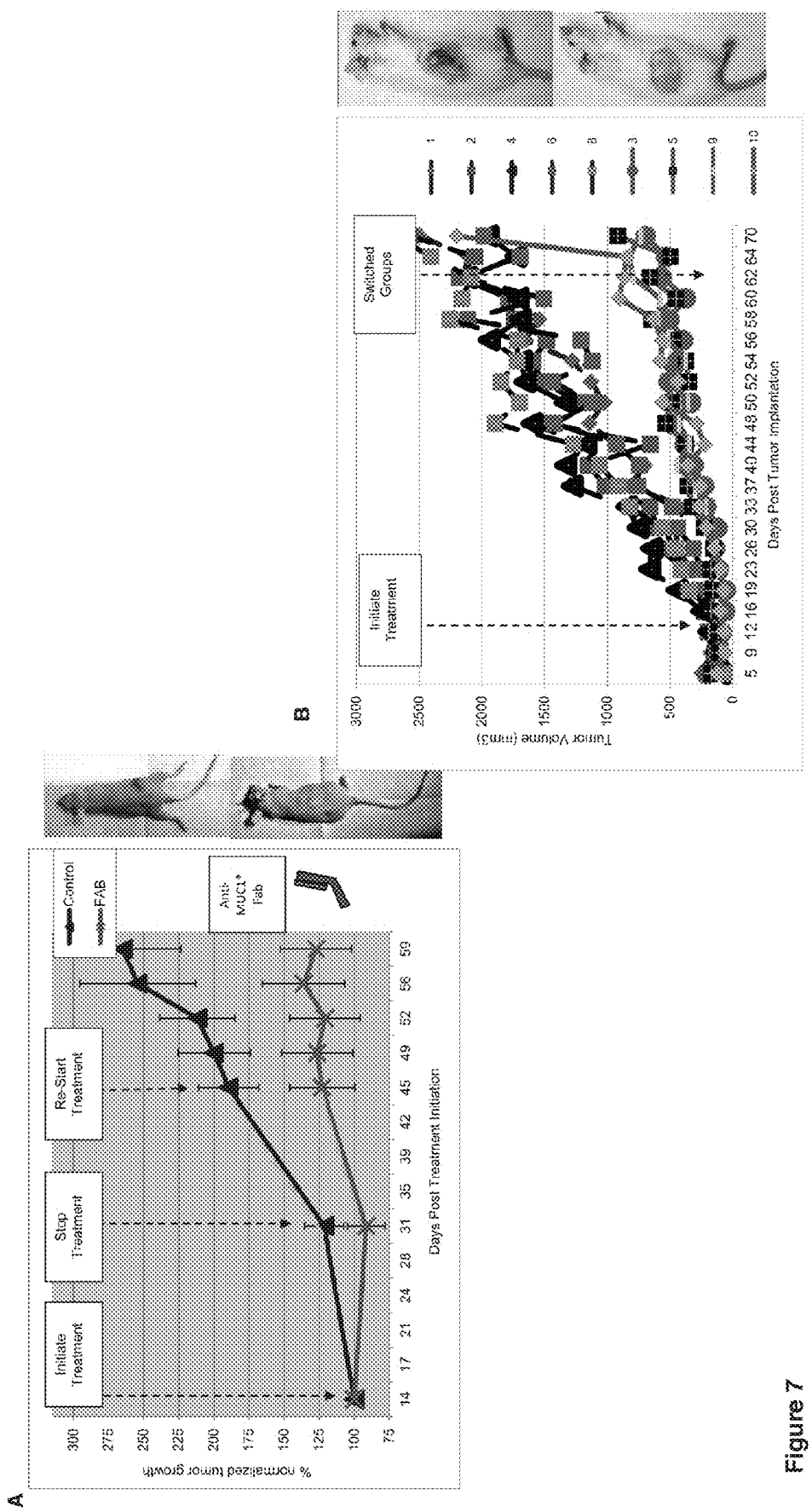
FIG. 7 shows graphs of tumor growth in immune compromised mice that have been implanted with human tumors then treated with anti-MUC1* antibody MN-E6 Fab or mock treatment. Female nu/nu mice implanted with 90-day estrogen pellets were implanted with 6 million T47D human breast cancer cells that had been mixed 50/50 with Matrigel. Mice bearing tumors that were at least 150 mm$^3$ and had three successive increases in tumor volume were selected for treatment. Animals were injected sub cutaneously twice per week with 80 mg/kg MN-E6 Fab and an equal number of mice fitting the same selection criteria were injected with vehicle alone (A). Male NOD/SCID mice were implanted with 6 million DU-145 human prostate cancer cells that had been mixed 50/50 with Matrigel. Mice bearing tumors that were at least 150 mm$^3$ and had three successive increases in tumor volume were selected for treatment. Animals were injected sub-cutaneously every 48 hours with 160 mg/kg MN-E6 Fab and an equal number of mice fitting the same selection criteria were injected with vehicle alone (B). Tumors were measured independently by two researchers twice per week and recorded. Statistics were blindly calculated by independent statistician, giving a P value of 0.0001 for each. Anti-MUC1* Fab inhibited breast cancer growth and prostate cancer growth. Treatment had no effect on weight, bone marrow cell type or number.

The Fabs of MN-E6 and MN-C2 or the comparable single chain variable regions derived from them potently inhibit the growth of MUC1* positive cancers in vitro and in vivo. In several examples, the Fabs of Anti-MUC1* antibodies inhibited the growth of human MUC1* positive cancers in vivo. In one case, immune-compromised mice were implanted with human breast tumors then treated with MN-E6 Fab after tumor engraftment. FIG. 7A shows that MN-E6 Fab potently inhibited the growth of MUC1* positive breast cancers. Female nu/nu mice implanted with 90-day estrogen pellets were implanted with 6 million T47D human breast cancer cells that had been mixed 50/50 with Matrigel. Mice bearing tumors that were at least 150 mm^3 and had three successive increases in tumor volume were selected for treatment. Animals were injected sub cutaneously twice per week with 80 mg/kg MN-E6 Fab and an equal number of mice fitting the same selection criteria were injected with vehicle alone (A). In another aspect, MN_E6 was shown to halt the growth of prostate cancer. FIG. 7B shows that MN-E6 Fab potently inhibited the growth of MUC1* positive prostate cancers. Male NOD/SCID mice were implanted with 6 million DU-145 human prostate cancer cells that had been mixed 50/50 with Matrigel. Mice bearing tumors that were at least 150 mm^3 and had three successive increases in tumor volume were selected for treatment. Animals were injected sub-cutaneously every 48 hours with 160 mg/kg MN-E6 Fab and an equal number of mice fitting the same selection criteria were injected with vehicle alone (B). Tumors were measured independently by two researchers twice per week and recorded. Statistics were blindly calculated by independent statistician, giving a P value of 0.0001 for each. Anti-MUC1* Fab inhibited breast cancer growth and prostate cancer growth. Treatment had no effect on weight, bone marrow cell type or number. The MN-E6 Fab effectively inhibited the growth of the tumors, while the control group's tumors continued to grow until sacrifice. No adverse effects of treatment were observed or detected.

Figure 13:
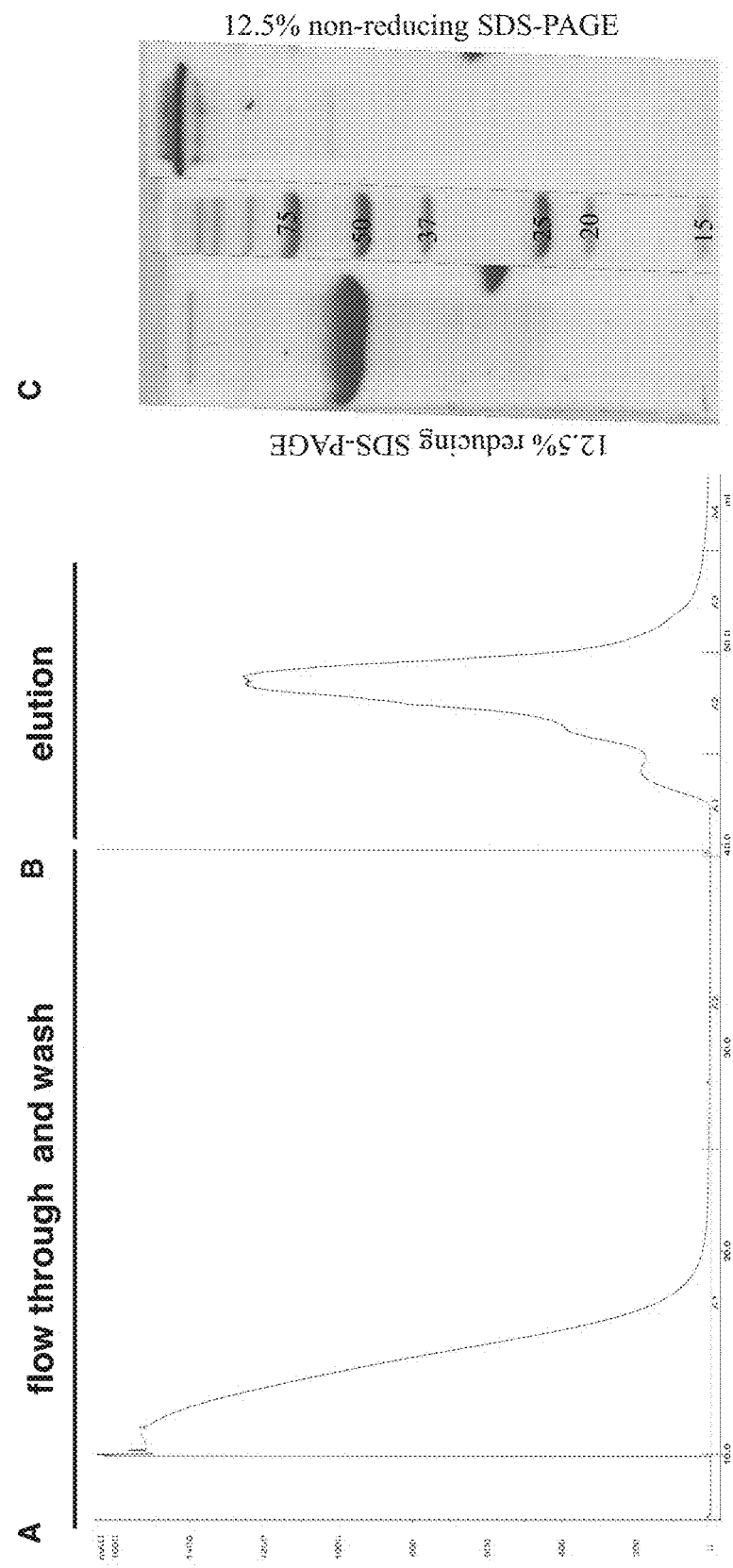
FIG. 13 shows FPLC traces of the purification of MN-E6 scFv-Fc fusion protein that was grown in low IgG FBS over a Protein A affinity column. A) is the trace of the flow through. B) is the trace of the elution. C) shows the purified protein on a reducing or non-reducing gel.
Figure 14:
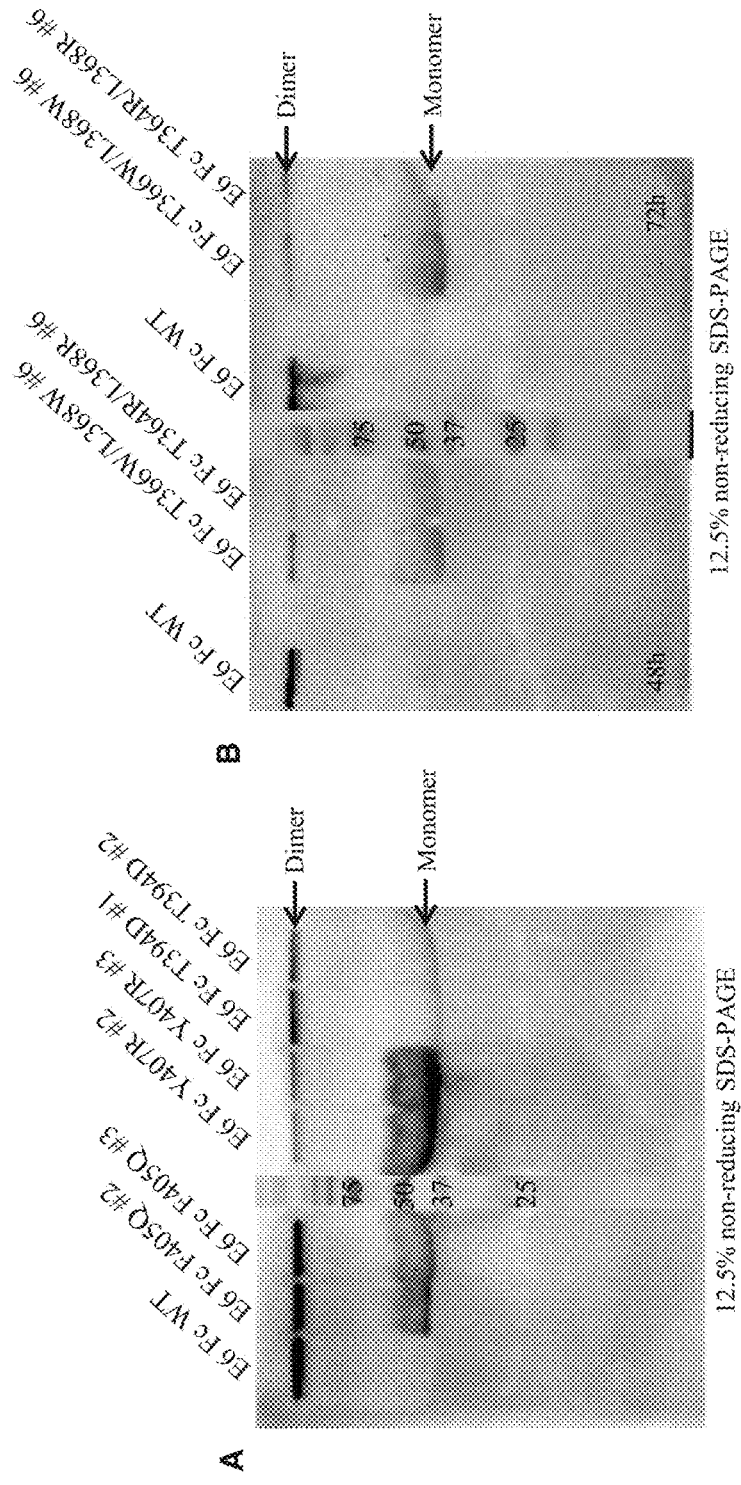
FIG. 14 shows photographs of SDS-PAGE characterization of purified MN-E6 scFv-Fc fusion proteins on a non-reducing gels, wherein the Fc portion that was fused to the MN-E6 was either wild type (wt) or mutated as follows: A) F405Q, Y407R, T394D; B) T366W/L368W, T364R/L368R, T366W/L368W or T364R/L368R. Fc mutants F405Q, Y407R, T366W/L368W, T364R/L368R, T366W/L368W and T364R/L368R all favored monomer over dimer formation. The reference construct amino acid sequence for the indicated mutations is SEQ ID NO:273.
Figure 15:
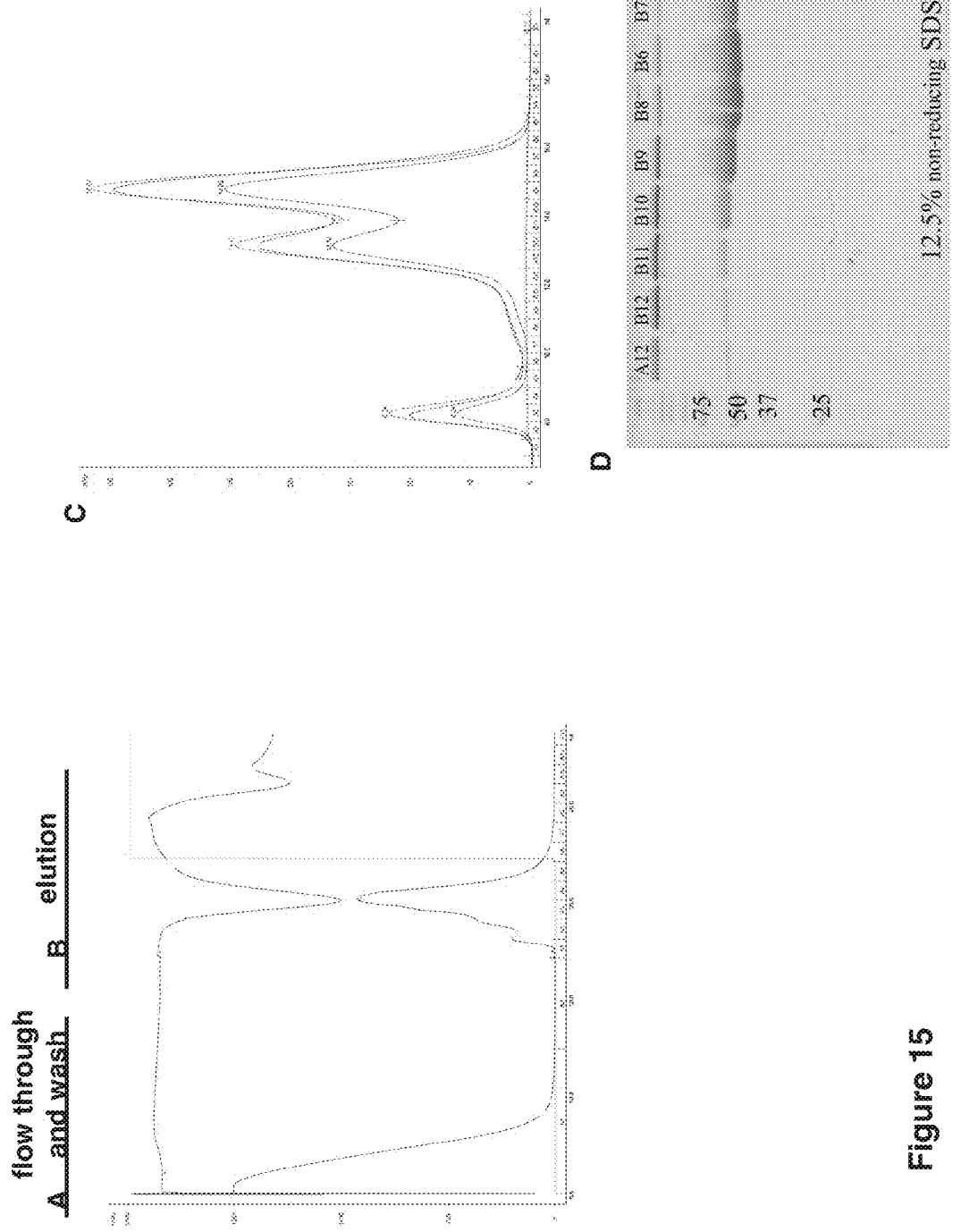
FIG. 15 shows FPLC traces of the purification of MN-E6 scFv-Fc Y407Q fusion protein that was grown in low IgG FBS over a Protein A affinity column. A) is the trace of the flow through. B) is the trace of the elution. The protein was further purified by size exclusion over an S200 column (C). (D) is a photograph of an SDS-PAGE gel showing which fractions had a predominance of monomer. The reference construct amino acid sequence for the indicated mutations is SEQ ID NO:273.
Figure 16:
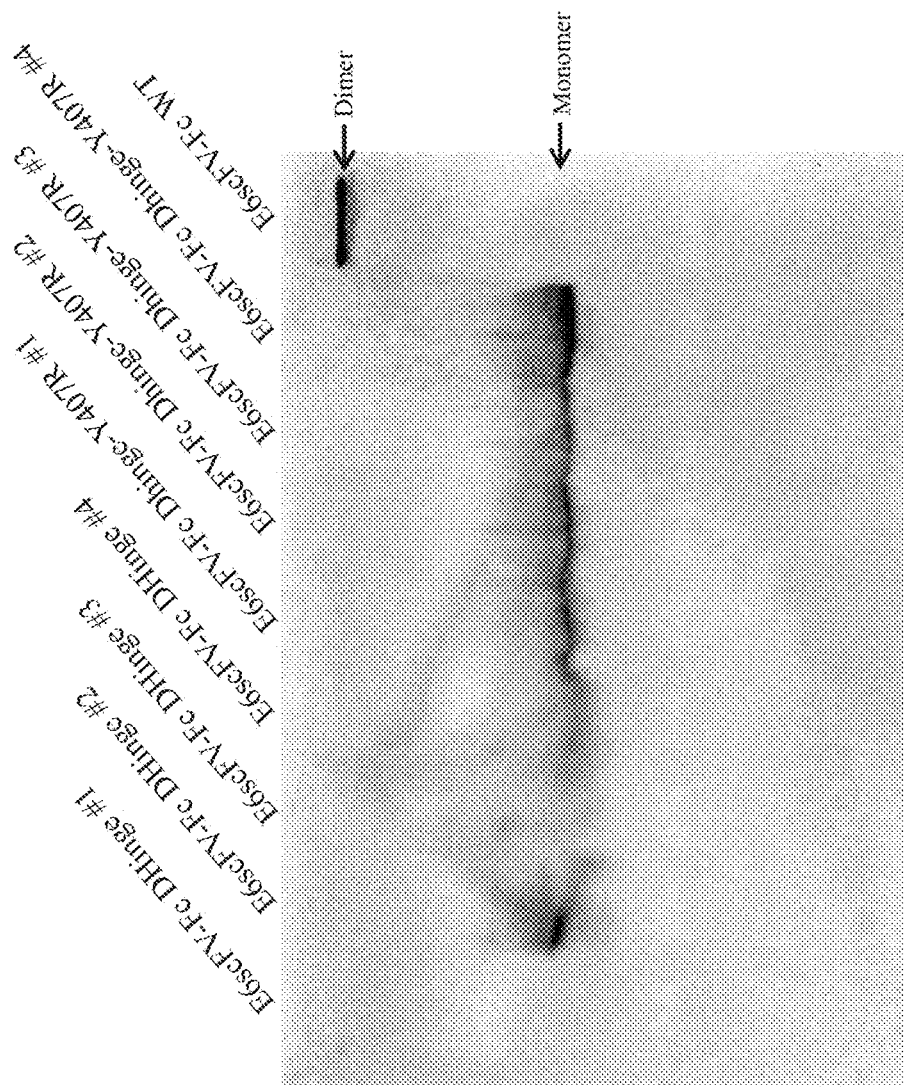
FIG. 16 shows a photograph of SDS-PAGE characterization of purified MN-E6 scFv-Fc-mutant fusion proteins on a non-reducing gel, wherein the Fc portion that was fused to the MN-E6 scFv was either wild type (wt) or mutated by elimination of the hinge region, 'DHinge', of the Fc or elimination of the hinge region of the Fc and also bearing the Y407R mutation. All the Fc mutants favored monomer over dimer formation. The reference construct amino acid sequence for the indicated mutations is SEQ ID NO:273.
Figure 17:
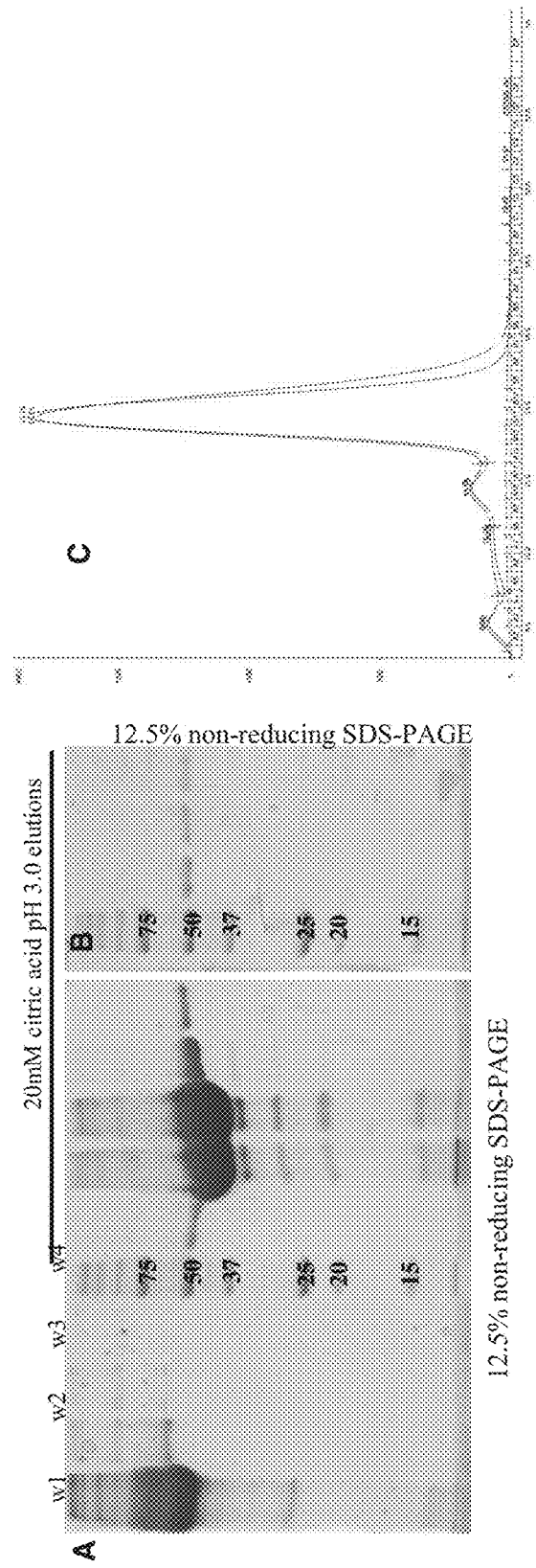
FIG. 17. A and B show photograph of non-reducing SDS-PAGE characterization of large scale expression and purification of MN-E6 scFv-Fc hingeless mutant, showing that it is a monomer. FPLC characterization and purification of MN-E6 scFv-Fc hingeless mutant is shown (C).
Figure 18:
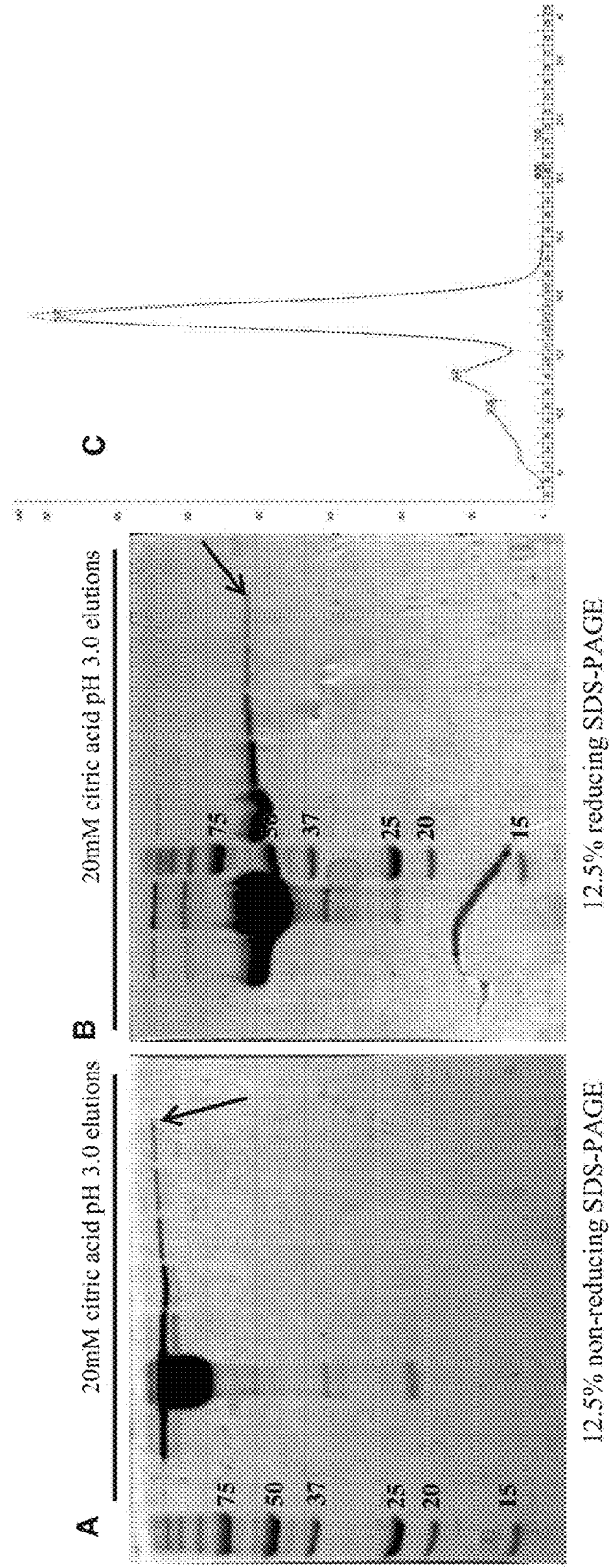
FIG. 18 shows photographs of the SDS-PAGE characterization of the purified MN-C3 scFv-Fc fusion protein on a non-reducing gel (A) or a reducing gel (B). The protein was purified by size exclusion. The FPLC trace is shown (C).
Figure 19:
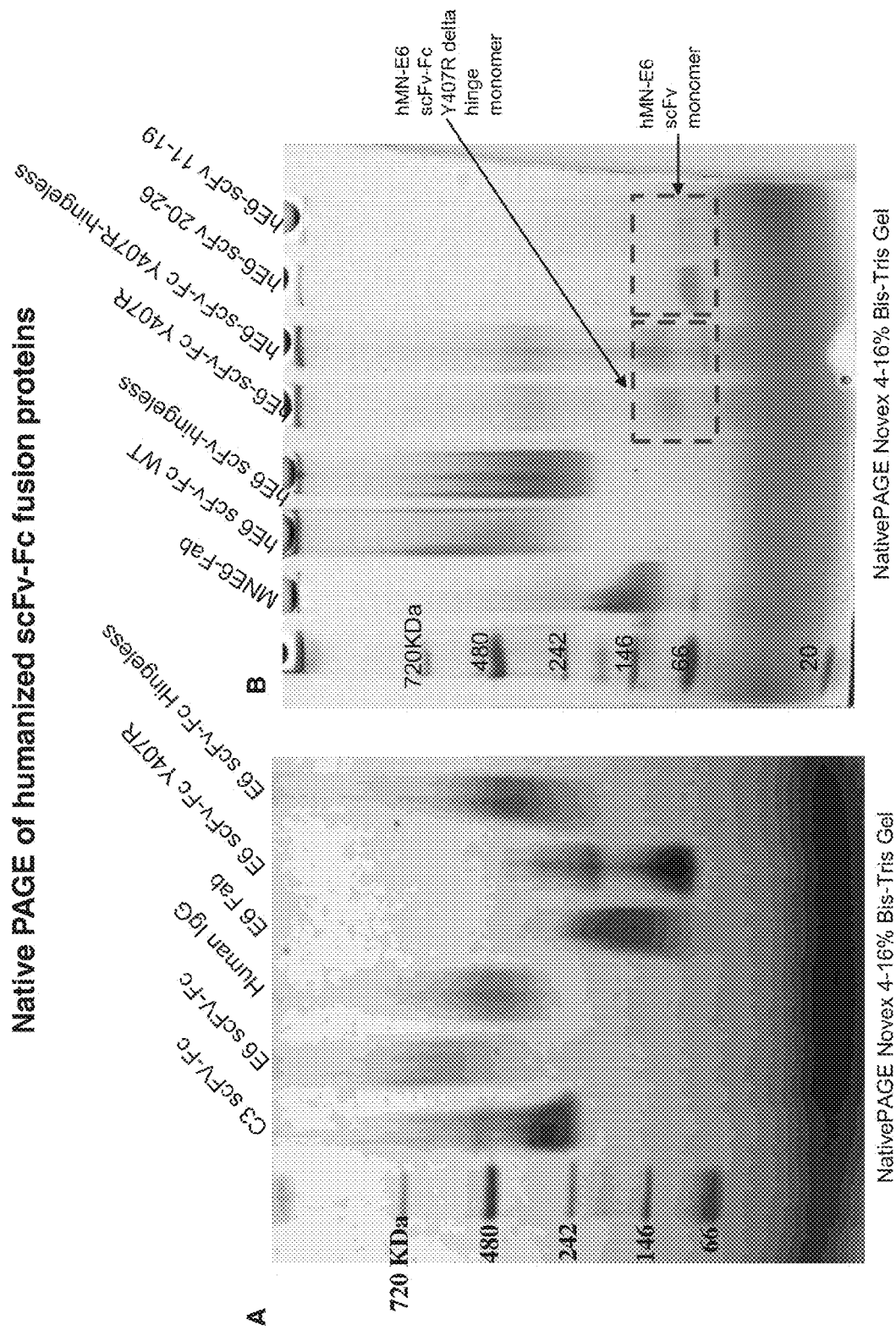
FIG. 19 shows photographs of Native gels of MN-C3 or MN-E6 Fabs, scFv, scFv-Fc, wherein the Fc portion is wild type or mutants that prefer or are exclusively monomers. Native gels show that the Y407R Fc mutation (A) and the double mutant Y407R and a deleted hinge (B) favor monomer over dimer the best. Note that proteins are loaded onto a gel at much higher concentrations than typical use concentrations. The dimer formation of other Fc mutants may only reflect the fact that loading concentration is very high.

A recombinant MN-E6 was constructed that like the Fab is monomeric. In this case, MN-E6 was humanized. There are a number of methods known to those skilled in the art for humanizing antibodies. In addition to humanizing, libraries of human antibodies can be screened to identify other fully human antibodies that bind to the PSMGFR. A single chain of the humanized MN-E6 variable region, called an scFv, was genetically engineered such that it was connected to the Fc portion of the antibody (SEQ ID NO:256 and 257). Fc regions impart certain benefits to antibody fragments for use as therapeutics. The Fc portion of an antibody recruits complement, which in general means it can recruit other aspects of the immune system and thus amplify the anti-tumor response beyond just inhibiting the target. The addition of the Fc portion also increases the half-life of the antibody fragment (Czajkowsky D M, Hu J, Shao Z and Pleass R J. (2012) Fc-fusion proteins: new developments and future perspectives. EMBO Mol Med. 4(10):1015-1028). However, the Fc portion of an antibody homo-dimerizes, which in the case of anti-MUC1* antibody based therapeutics is not optimal since ligand-induced dimerization of the MUC1* receptor stimulates growth. As can be seen in FIG. 13 B, humanized MN-E6 scFv-Fc is a dimer, in part due to disulfide bonding. Therefore, mutations in the Fc region that resist dimer formation are preferred for anti-MUC1* anti-cancer therapeutics. Deletion of the hinge region (hingeless also called delta hinge or Dhinge in some figures and examples SEQ ID NO: 288 and 289) and other mutations in the Fc region that make the Fc-mutant resistant to dimerization were made. The following mutations were made in the CH3 domain to create a monomeric scFv-Fc fusion protein: Y407R (SEQ ID NO: 278 and 279), F405Q (SEQ ID NO: 280 and 281), T394D (SEQ ID NO: 282 and 283), T366W/L368W (SEQ ID NO: 284 and 285), T364R/L368R (SE ID NO: 286 and 287). FIG. 14 shows photographs of SDS-PAGE characterization of purified MN-E6 scFv-Fc fusion proteins on a non-reducing gels, wherein the Fc portion that was fused to the MN-E6 was either wild type (wt) or mutated as follows: A) F405Q, Y407R, T394D; B) T366W/L368W, T364R/L368R, T366W/L368W or T364R/L368R. Fc mutants F405Q, Y407R, T366W/L368W, T364R/L368R, T366W/L368W and T364R/L368R all favored monomer over dimer formation. FIG. 15 shows FPLC traces of the purification of MN-E6 scFv-Fc Y407Q fusion protein that was grown in low IgG FBS over a Protein A affinity column. A) is the trace of the flow through. B) is the trace of the elution. The protein was further purified by size exclusion over an 5200 column (C). (D) is a photograph of an SDS-PAGE gel showing which fractions had a predominance of monomer. FIG. 16 shows a photograph of SDS-PAGE characterization of purified MN-E6 scFv-Fc-mutant fusion proteins on a non-reducing gel, wherein the Fc portion that was fused to the MN-E6 scFv was either wild type (wt) or mutated by elimination of the hinge region, 'DHinge', of the Fc or elimination of the hinge region of the Fc and also bearing the Y407R mutation. All the Fc mutants favored monomer over dimer formation. The reference construct amino acid sequence for the indicated mutation is SEQ ID NO:273. Other relevant sequences are SEQ ID NOS:289 and 279. FIG. 17A-C. A and B show photograph of non-reducing SDS-PAGE characterization of large scale expression and purification of MN-E6 scFv-Fc hingeless mutant, showing that it is a monomer. FPLC characterization and purification of MN-E6 scFv-Fc hingeless mutant is shown (C). FIG. 18A-C shows photographs of the SDS-PAGE characterization of the purified MN-C3 scFv-Fc fusion protein on a non-reducing gel (A) or a reducing gel (B). The protein was purified by size exclusion. The FPLC trace is shown (C). FIG. 19A-B shows photographs of Native gels of MN-C3 or MN-E6 Fabs, scFv, scFv-Fc, wherein the Fc portion is wild type or mutants that prefer or are exclusively monomers. Native gels show that the Y407R Fc mutation (A) and the double mutant Y407R and a deleted hinge (B) favor monomer over dimer the best. Note that proteins are loaded onto a gel at much higher concentrations than typical use concentrations. The dimer formation of other Fc mutants may only reflect the fact that loading concentration is very high.

Figure 10:
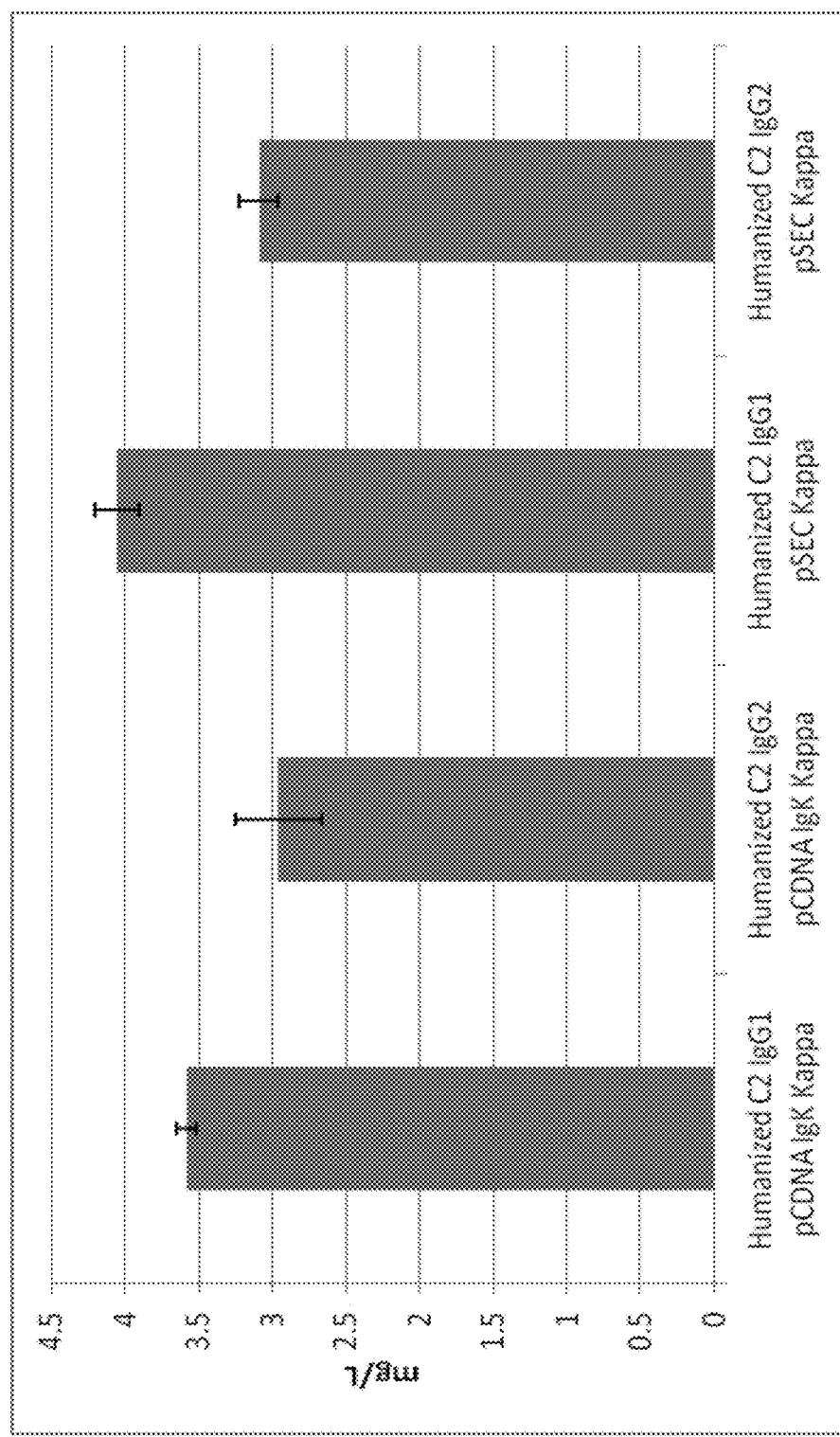
FIG. 10 is a graph of an ELISA assay showing differing levels of expression of humanized MN-C2 anti-MUC1* antibody depending on whether the light chain was kappa or lambda and whether the variable portion was fused to a human IgG1 or IgG2.

Some mutations or deletions were so effective that, even when loaded onto a gel at high concentrations, they resist dimer formation (FIG. 14A, B). The Y407R mutation results in a nearly pure population of dimeric scFv-Fc (FIG. 10). Similarly deletions of the hinge region of the Fc result in fusion proteins that are monomers rather than dimers. Combinations of mutations can result in even more effective resistance of dimer formation (FIGS. 16 and 17). These and other mutations and combinations thereof were introduced into CH2-CH3 (SEQ ID NO:274 and 275) and CH3 (SEQ ID NO:276 and 277) fusion proteins such as scFv or in the hingeless Fc-fusion proteins such as scFv and were shown to eliminate or minimize dimerization.

Figure 20:
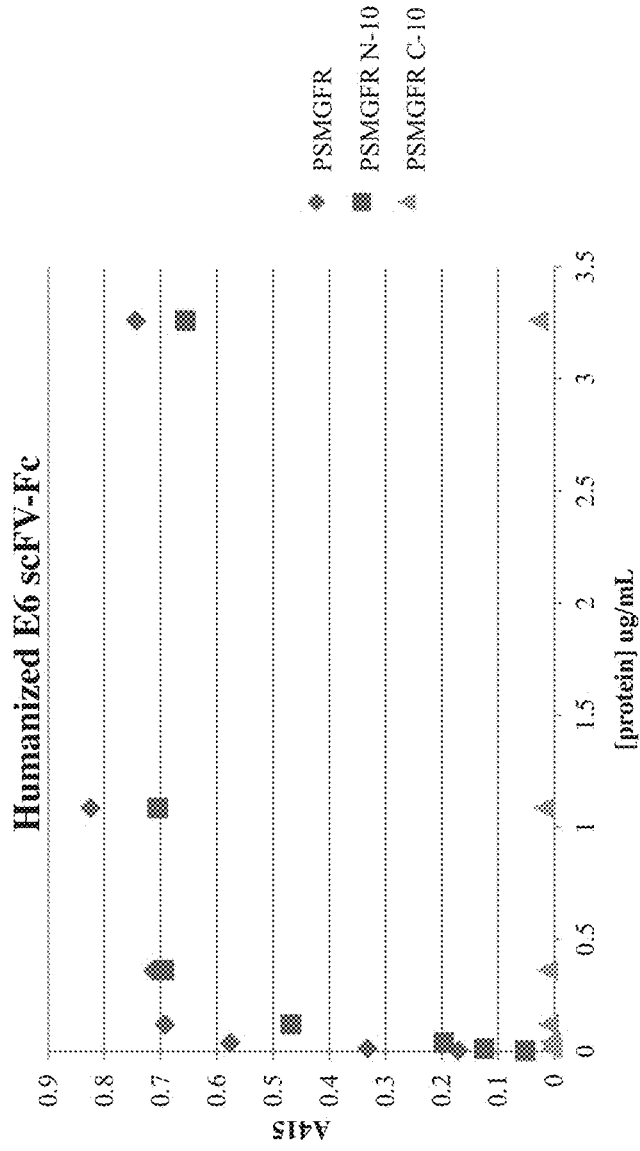
FIG. 20 shows a graph of an ELISA wherein the surface was immobilized with either PSMGFR peptide, PSMGFR minus 10 amino acids from the N-terminus or minus 10 amino acids from the C-terminus. The hu MN-E6 scFv-Fc bound to the PSMGFR peptide and to the PSMGFR N-10 peptide but not to the PSMGFR C-10 peptide. The parent MN-E6 antibody and the humanized MN-E6 require the C-terminal 10 amino acids of PSMGFR for binding.
Figure 21:
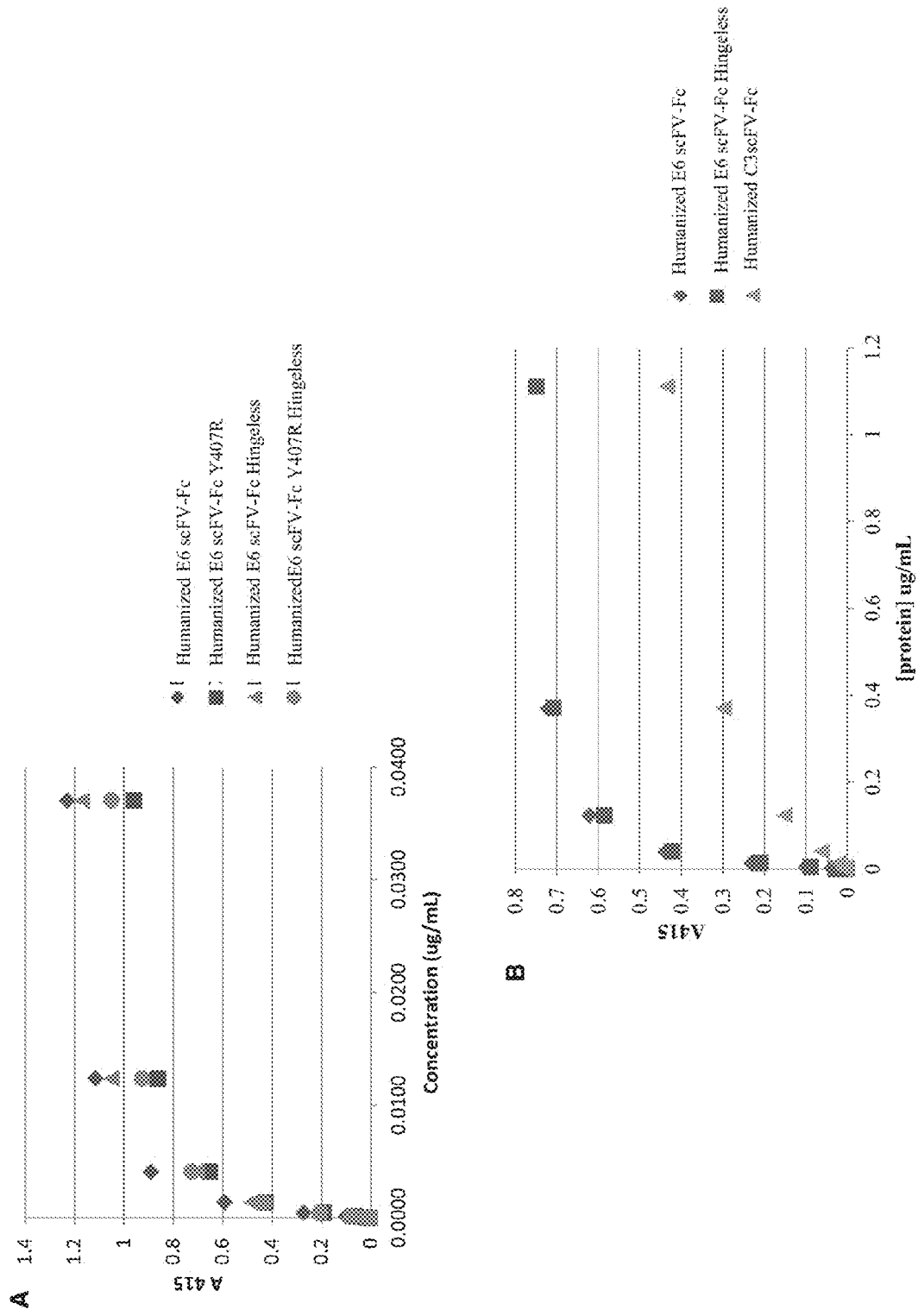
FIG. 21 shows an ELISA graph of several anti-MUC1* scFv-Fc fusion proteins wherein the Fc region has been eliminated or mutated. Shown are hu MN-E6 scFv-Fc-wt, hu MN-E6 scFv-Fc-Y407R, hu MN-E6 scFv-Fc-hingeless, and hu MN-E6 scFv-Fc-Y407R-hingeless. All mutants bind to the PSMGFR peptide of the MUC1* extracellular domain (A). An ELISA graph of several anti-MUC1* scFv-Fc fusion proteins wherein the Fc region is either wild type or mutated. Shown are hu MN-E6 scFv-Fc-wt, hu MN-E6 scFv-Fc-hingeless, and hu MN-C3 scFv-Fc is shown (B). All bind to the PSMGFR peptide of the MUC1* extracellular domain.
Figure 22:
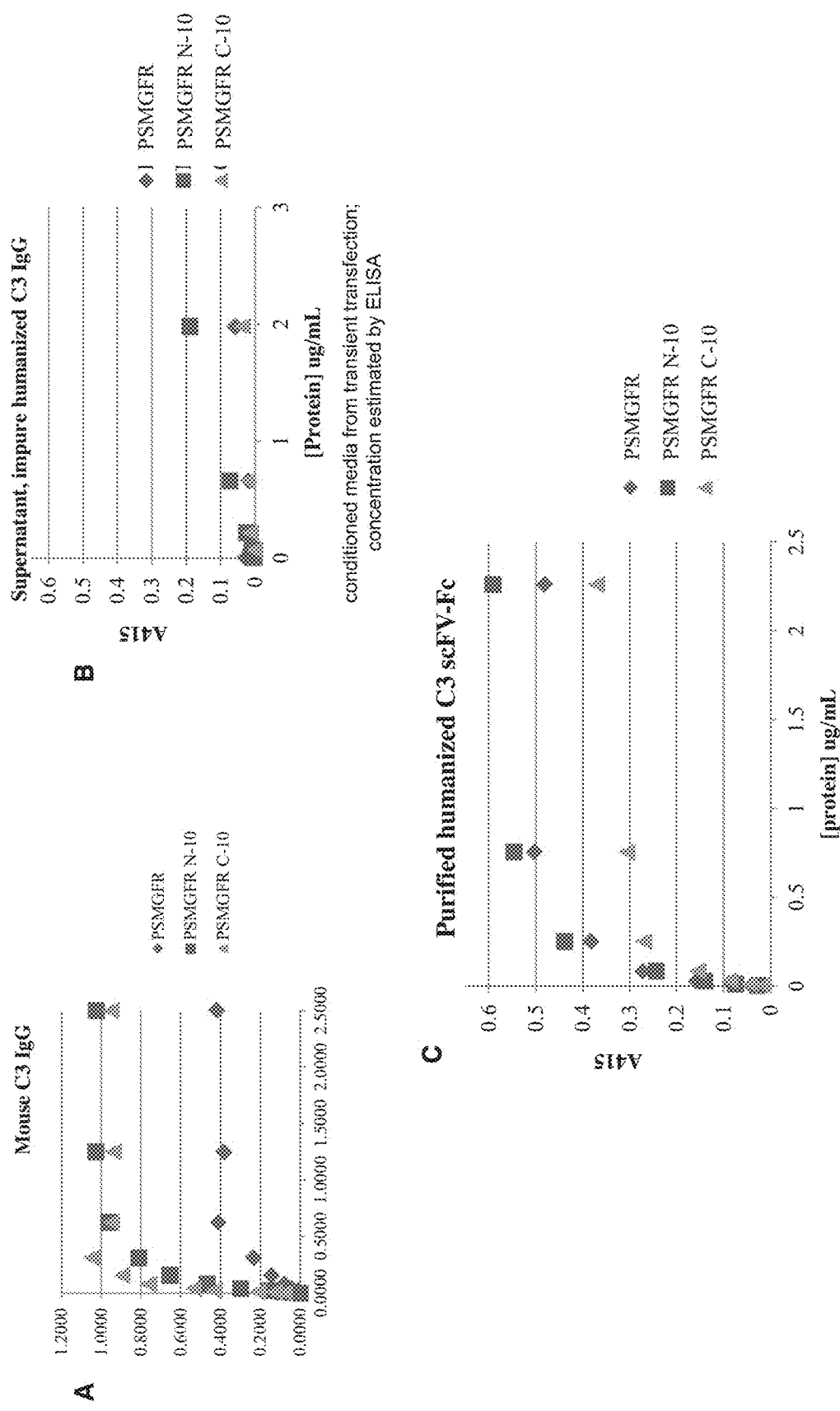
FIG. 22 shows graphs of ELISAs wherein the assay plate surface was immobilized with either PSMGFR peptide, PSMGFR minus 10 amino acids from the N-terminus or minus 10 amino acids from the C-terminus. The MN-C3 antibody variants were then assayed for binding to the various MUC1* peptides. A) Purified mouse monoclonal MN-C3 antibody; B) Impure humanized MN-C3 antibody; and C) the humanized MN-C3 scFv-Fc. ELISAs show binding to the PSMGFR peptide as well as to certain deletion peptides.
Figure 23:
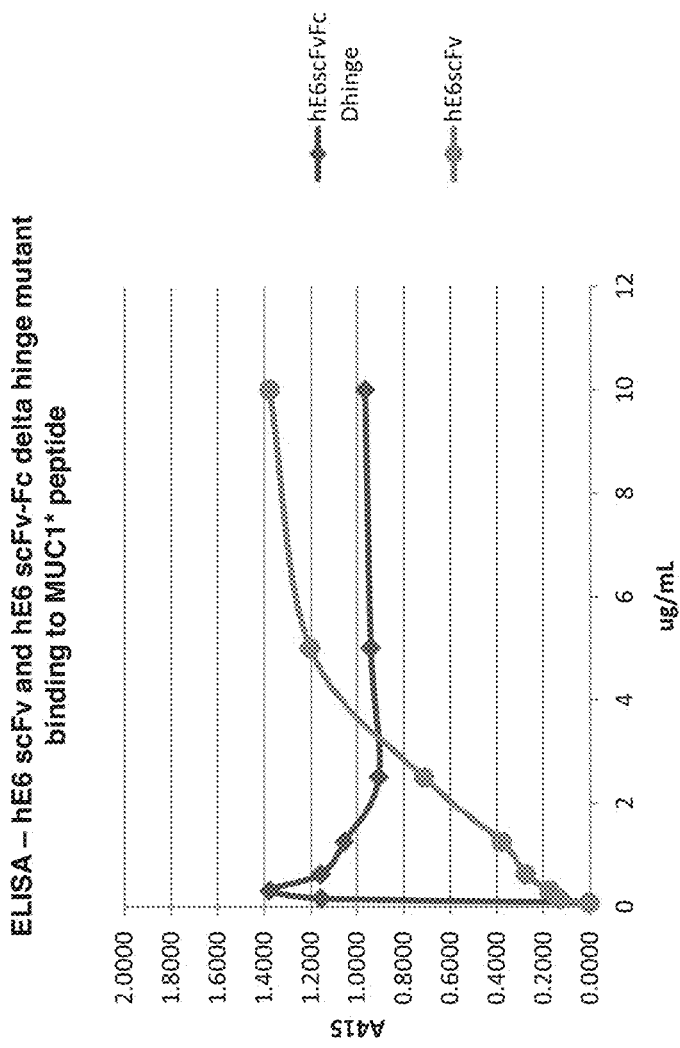
FIG. 23 shows a graph of an ELISA assay that quantifies the binding of humanized MN-E6 scFv-Fc-delta hinge, aka Dhinge or hingeless, and humanized MN-E6 scFv to the MUC1* peptide PSMGFR.

Like the parent mouse monoclonal antibodies, human or humanized antibodies as well as single chain constructs, scFv's, scFv-Fc fusions or scFv-Fc-mutants specifically bind to the synthetic MUC1* peptides (FIGS. 20-22). Figure E23 shows a graph of an ELISA assay that quantifies the binding of humanized MN-E6 scFv-Fc-delta hinge, aka Dhinge or hingeless, and humanized MN-E6 scFv to the MUC1* peptide PSMGFR.

Figure 24:
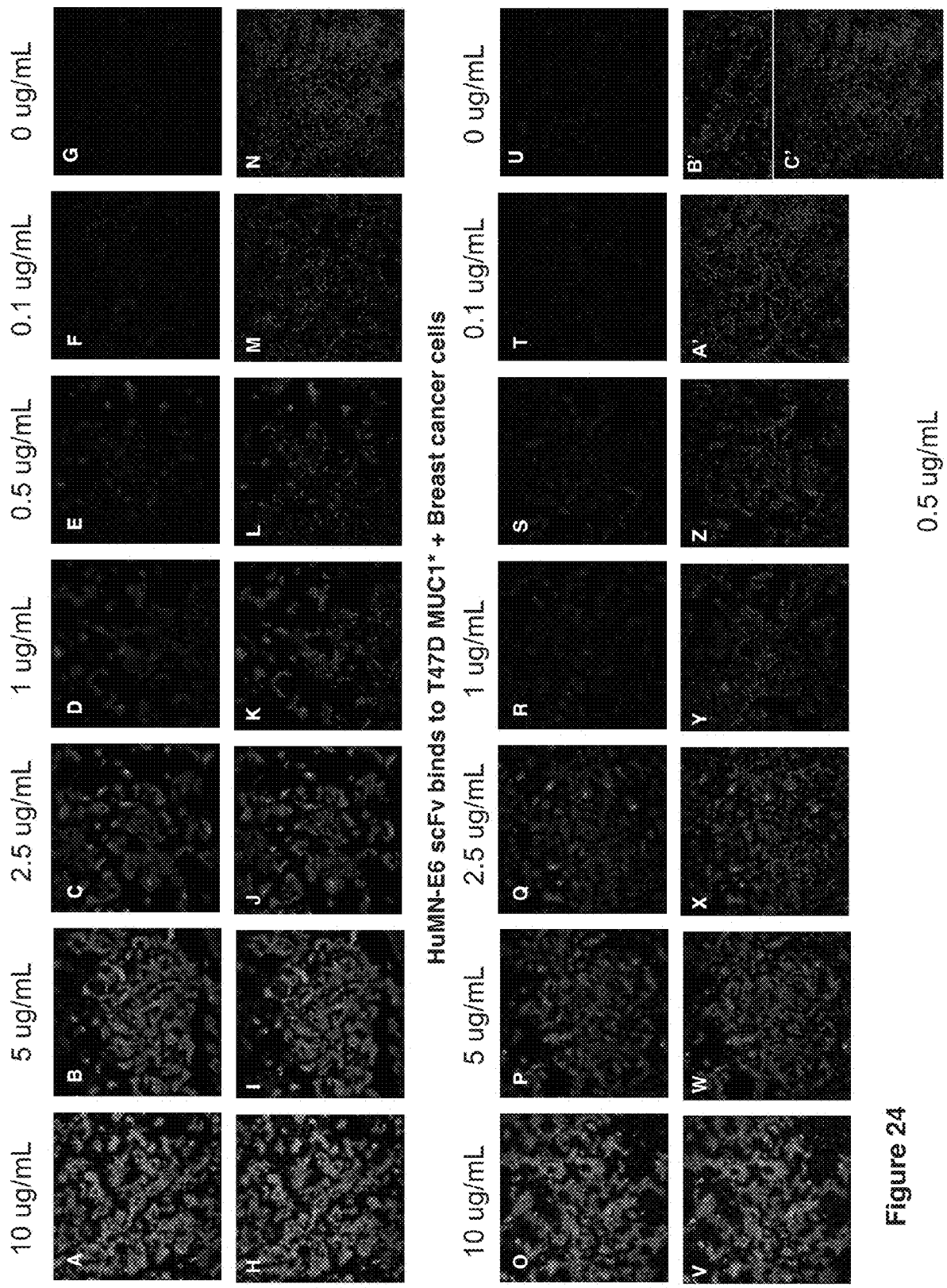
FIG. 24 shows photographs of immunofluorescence experiments in which humanized MN-C2 scFv or MN-E6 scFv specifically binds to MUC1* positive breast cancer cells in an identical concentration dependent manner. A-G: hu MN-C2 scFv binding to T47D breast cancer cells at concentrations indicated. H-N shows the fluorescently labeled scFv and DAPI. O-U: hu MN-E6 scFv binding to T47D breast cancer cells at concentrations indicated. V-B' shows the fluorescently labeled scFv and DAPI. C' is the secondary antibody control.
Figure 25:
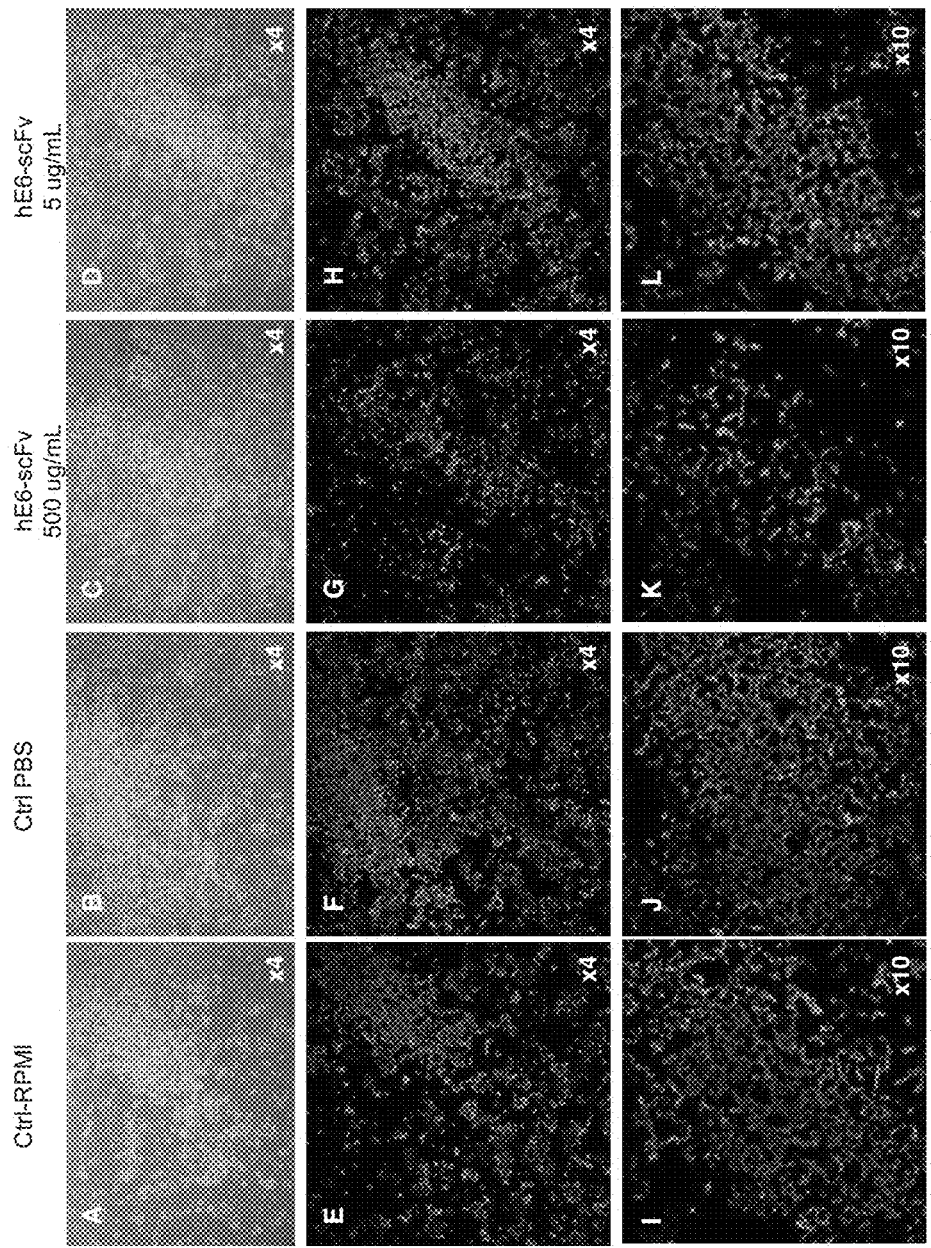
FIG. 25 shows photographs of 1500 MUC1* positive breast cancer cells that have been cultured in normal medium or in the presence of humanized MN-E6 scFv. A-D are bright field images taken at 4× magnification. E-H are calcein fluorescent images taken at 4× magnification. I-L are calcein fluorescent images taken at 10× magnification. A, E, I show control cells cultured in normal RPMI medium. B, F, J show control cells cultured in normal RPMI medium plus a volume of PBS equal to the volume of MN-E6 scFv in PBS that is added to experimental wells. C, G, K show cells cultured in normal RPMI medium plus 500 ug/mL MN-E6 scFv. D, H, L show cells cultured in normal RPMI medium plus 5 ug/mL MN-E6 scFv. The photographs show killing and/or growth inhibition of MUC1* positive cells by MN-E6 scFv at 5 ug/mL and an even greater effect at 500 ug/mL. Images were taken at 96 hours post addition of test molecule.
Figure 26:
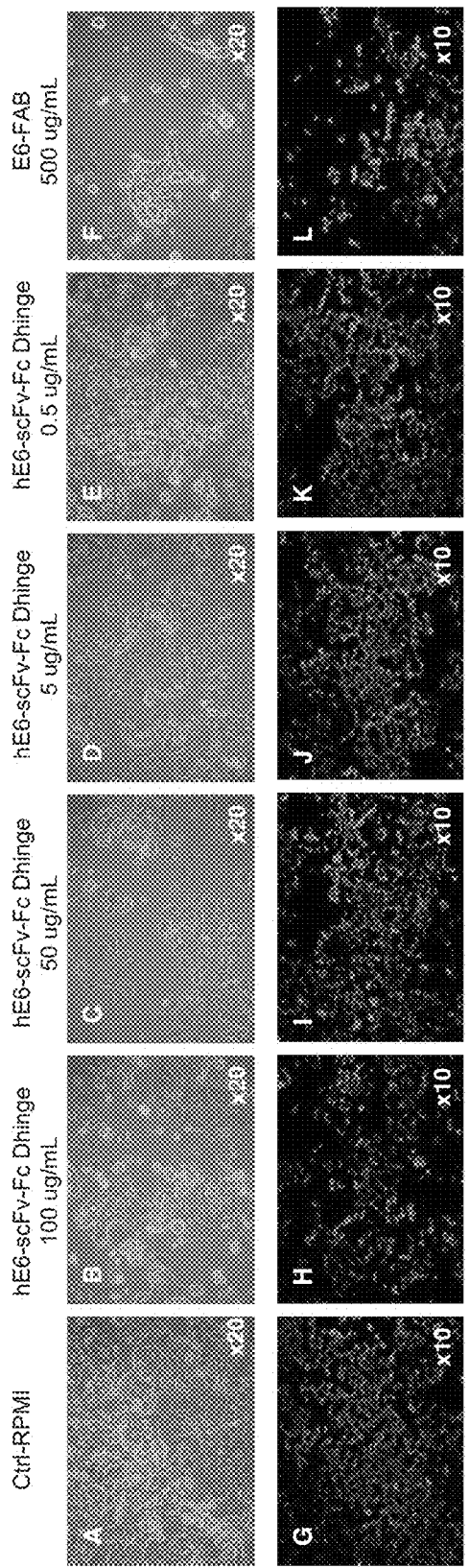
FIG. 26 shows photographs of 1500 MUC1* positive breast cancer cells that have been cultured in normal medium or in the presence of humanized MN-E6 scFv-Fc Dhinge, which is a hingeless or delta hinge mutant. A-F are bright field images taken at 20× magnification. G-L are calcein fluorescent images taken at 4× magnification. A, G show control cells cultured in normal RPMI medium. B, H show cells cultured in normal RPMI medium plus 100 ug/mL hMN-E6 scFv-Fc Dhinge. C, I show cells cultured in normal RPMI medium plus 50 ug/mL hMN-E6 scFv-Fc Dhinge. D, J show cells cultured in normal RPMI medium plus 5 ug/mL hMN-E6 scFv-Fc Dhinge. E, K show cells cultured in normal RPMI medium plus 0.5 ug/mL hMN-E6 scFv-Fc Dhinge. F, L show cells cultured in normal RPMI medium plus 500 ug/mL of MN-E6 Fab. The photographs show killing and/or growth inhibition of MUC1* positive cells by hMN-E6 scFv-Fc Dhinge 5 ug/mL, an even greater effect at 50 ug/mL and yet an even greater effect at 100 ug/mL. Comparing cell morphology to the control cells, cancer cells grown in MN-E6 Fab or in an effective amount of hMN-E6 scFv-Fc Dhinge, show rounding up of the cells which morphology change occurs before cell death. Images were taken at 96 hours post addition of test molecule.

The human or humanized anti-MUC1* antibody fragments described here specifically bind to MUC1 and MUC1* positive cancer cells. FIG. 24 shows photographs of immunofluorescence experiments in which humanized MN-C2 scFv or MN-E6 scFv specifically binds to MUC1* positive breast cancer cells in an identical concentration dependent manner. A-G: hu MN-C2 scFv binding to T47D breast cancer cells at concentrations indicated. H-N shows the fluorescently labeled scFv and DAPI. O-U: hu MN-E6 scFv binding to T47D breast cancer cells at concentrations indicated. V-B' shows the fluorescently labeled scFv and DAPI. C' is the secondary antibody control.

Figure 27:
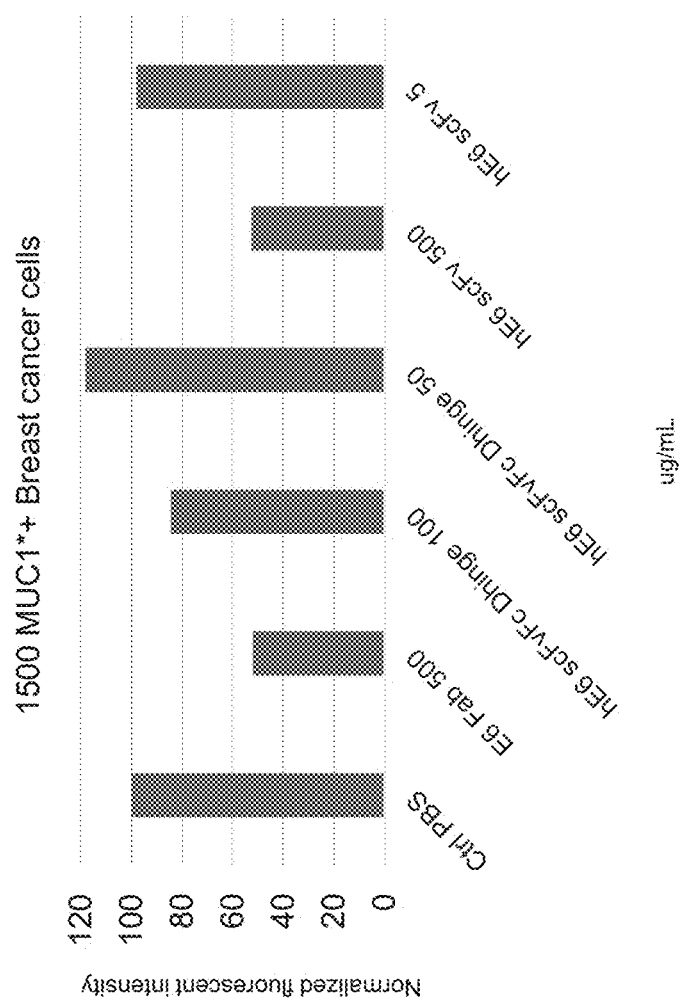
FIG. 27 shows a graph of the image analysis of the fluorescent images of FIGS. 25 and 26. Image J was used to quantify the number of cells remaining after 96 hours treatment in humanized MN-E6scFv or MN-E6 scFv-Fc-delta hinge, aka Dhinge. The analysis software uses pixel counting and pixel fluorescence intensity to quantify the number of cells in each photograph. Analysis was performed over the entire image 512×512 pixels, 8-bit image. For comparison, the inhibition of mouse monoclonal MN-E6 Fab is also analyzed.

In addition to binding to MUC1* positive cancer cells, the anti-MUC1* antibody variable region fragments, scFv's, scFv-Fc's and scFv-Fc-mutants inhibited growth of MUC1-positive cancer cells. FIG. 25A-L shows photographs of MUC1* positive breast cancer cells that have been cultured in normal medium or in the presence of humanized MN-E6 scFv. The photographs show killing and/or growth inhibition of MUC1* positive cells by MN-E6 scFv at 5 ug/mL and an even greater effect at 500 ug/mL. FIG. 26A-L shows photographs of MUC1* positive breast cancer cells that have been cultured in normal medium or in the presence of humanized MN-E6 scFv-Fc Dhinge, which is a hingeless or delta hinge mutant. The photographs show killing and/or growth inhibition of MUC1* positive cells by hMN-E6 scFv-Fc Dhinge 5 ug/mL, an even greater effect at 50 ug/mL and yet an even greater effect at 100 ug/mL. FIG. 27 shows a graph of the image analysis of the fluorescent images of FIGS. 25 and 26. Image J was used to quantify the number of cells remaining after 96 hours treatment in humanized MN-E6scFv or MN-E6 scFv-Fc-delta hinge, aka Dhinge. The analysis software uses pixel counting and pixel fluorescence intensity to quantify the number of cells in each photograph. Analysis was performed over the entire image 512×512 pixels, 8-bit image. For comparison, the inhibition of mouse monoclonal MN-E6 Fab is also analyzed.

These data show that a human or humanized MN-E6 antibody or antibody fragment, Fab, MN-E6 scFv or hu MN-E6 scFv-Fc$_{mut}$ are effective anti-cancer agents that can be administered to a person diagnosed with a MUC1 or MUC1* positive cancer, suspected of having a MUC1 or MUC1* positive cancer or is at risk of developing a MUC1 or MUC1* positive cancer.

In these specific examples, the dimer resistant Fc that was fused onto an antibody fragment or scFv is hu MN-E7 scFv. However, any of these Fc region mutations or combinations thereof that eliminate or minimize dimerization can be fused onto variable region fragments or single chain constructs of MN-E6, MN-C2, MN-C3 or MN-C8 or other antibodies identified that selectively bind to MUC1* as it exists on cancer cells or tissues. In addition, the Fabs of these antibodies can be used as an anti-cancer therapeutic. In one aspect of the invention, a person diagnosed with, suspected of having or is at risk of developing a MUC1* or MUC1 positive cancer is treated with an effective amount of human or humanized MN-E6 scFv, MN-C2 scFv, MN-C3 scFv, or MN-C8 scFv. In another aspect of the invention, a person diagnosed with, suspected of having or is at risk of developing a MUC1* or MUC1 positive cancer is treated with an effective amount of human or humanized MN-E6 scFv-Fc$_{Y407R}$, MN-C2 scFv-Fc$_{Y407R}$, MN-C3 scFv-Fc$_{Y407R}$, or MN-C8 scFv-Fc$_{Y407R}$. In another aspect of the invention, a person diagnosed with, suspected of having or is at risk of developing a MUC1* or MUC1 positive cancer is treated with an effective amount of human or humanized MN-E6 scFv-Fc mutant$_{Dhinge}$, MN-C2 scFv-Fc mutant$_{Dhinge}$, MN-C3 scFv-Fc mutant$_{Dhinge}$, or MN-C8 scFv-Fc mutant$_{Dhinge}$. In yet another aspect of the invention, a person diagnosed with, suspected of having or is at risk of developing a MUC1* or MUC1 positive cancer is treated with an effective amount of human or humanized MN-E6 scFv-Fc mutant$_{Y407R-Dhinge}$, MN-C2 SCFV-FC mutant$_{Y407R-Dhinge}$, MN-C3 SCFV-Fc mutant$_{Y407R-Dhinge}$, or MN-C8 scFv-Fc mutant$_{Y407R-Dhinge}$. One aspect of the invention is a method for treating a patient diagnosed with, suspected of having, or at risk of developing a MUC1 positive or MUC1* positive cancer, wherein the patient is administered an effective amount of a monomeric MN-E6 scFv, MN-C2 scFv, MN-C3 scFv, MN-C8 scFv, or MN-E6 scFv-Fc, MN-C2 scFv-Fc, MN-C3 scFv-Fc, MN-C8 scFv-Fc, wherein the Fc portion of the antibody-like protein has been mutated such that it resists dimer formation.

Humanizing

Humanized antibodies or antibody fragments or fully human antibodies that bind to the extracellular domain of –MUC1* are preferred for therapeutic use. The techniques described herein for humanizing antibodies are but a few of a variety of methods known to those skilled in the art. The invention is not meant to be limited by the technique used to humanize the antibody.

Humanization is the process of replacing the non-human regions of a therapeutic antibody (usually mouse monoclonal antibody) by human one without changing its binding specificity and affinity. The main goal of humanization is to reduce immunogenicity of the therapeutic monoclonal antibody when administered to human. Three distinct types of humanization are possible. First, a chimeric antibody is made by replacing the non-human constant region of the antibody by the human constant region. Such antibody will contain the mouse Fab region and will contain about 80-90% of human sequence. Second, a humanized antibody is made by grafting of the mouse CDR regions (responsible of the binding specificity) onto the variable region of a human antibody, replacing the human CDR (CDR-grafting method). Such antibody will contain about 90-95% of human sequence. Third and last, a full human antibody (100% human sequence) can be created by phage display, where a library of human antibodies is screened to select antigen specific human antibody or by immunizing transgenic mice expressing human antibody.

A general technique for humanizing an antibody is practiced approximately as follows. Monoclonal antibodies are generated in a host animal, typically in mice. Monoclonal antibodies are then screened for affinity and specificity of binding to the target. Once a monoclonal antibody that has the desired effect and desired characteristics is identified, it is sequenced. The sequence of the animal-generated antibody is then aligned with the sequences of many human antibodies in order to find human antibodies with sequences that are the most homologous to the animal antibody. Biochemistry techniques are employed to paste together the human antibody sequences and the animal antibody sequences. Typically, the non-human CDRs are grafted into the human antibodies that have the highest homology to the non-human antibody. This process can generate many candidate humanized antibodies that need to be tested to identify which antibody or antibodies has the desired affinity and specificity.

Once a human antibody or a humanized antibody has been generated it can be further modified for use as an Fab fragment, as a full antibody, or as an antibody-like entity such as a single chain molecule containing the variable regions, such as scFv or an scFv-Fc. In some cases it is desirable to have Fc region of the antibody or antibody-like molecule mutated such that it does not dimerize.

In addition to methods that introduce human sequences into antibodies generated in non-human species, fully human antibodies can be obtained by screening human antibody libraries with a peptide fragment of an antigen. A fully human antibody that functions like MN-E6 or MN-C2 is generated by screening a human antibody library with a peptide having the sequence of the PSMGFR N-10 peptide. A fully human antibody that functions like MN-C3 or MN-C8 is generated by screening a human antibody library with a peptide having the sequence of the PSMGFR C-10 peptide.

Humanized anti-MUC1* antibodies were generated based on the sequences of the mouse monoclonal antibodies MN-E6, MN-C2, MN-C3 and MN-C8. In one aspect of the invention, a patient diagnosed with a MUC1* positive cancer is treated with an effective amount of humanized MN-E6, MN-C2, MN-C3 or MN-C8. In a preferred embodiment, a patient diagnosed with a MUC1* positive cancer is treated with an effective amount of humanized MN-E6 or MN-C2. In another aspect of the invention, a patient diagnosed with a MUC1* positive cancer is treated with an effective amount of humanized monovalent MN-E6, MN-C2, MN-C3 or MN-C8, wherein monovalent means the corresponding Fab fragment, the corresponding scFv or the corresponding scFv-Fc fusion. In a preferred embodiment, a patient diagnosed with a MUC1* positive cancer is treated with an effective amount of a humanized scFv or monomeric humanized scFv-Fc of MN-E6 or MN-C2. Since the MUC1* growth factor receptor is activated by ligand induced dimerization of its extracellular domain, and because the Fc portion of an antibody homo-dimerizes, it is preferable that a construct that includes an Fc portion uses a mutated Fc region that prevents or minimizes dimerization.

Antibodies that bind to PSMGFR (SEQ ID NO:2) peptide of the extracellular domain of the MUC1* receptor are potent anti-cancer therapeutics that are effective for the treatment or prevention of MUC1* positive cancers. They have been shown to inhibit the binding of activating ligands dimeric NME1 (SEQ ID NOS: 3 and 4) and NME7 (SEQ ID NOS: 5 and 6) to the extracellular domain of MUC1*. Anti-MUC1* antibodies that bind to the PSMGFR sequence inhibit the growth of MUC1*-positive cancer cells, specifically if they inhibit ligand-induced receptor dimerization. Fabs of anti-MUC1* antibodies have been demonstrated to block tumor growth in animals. Thus, antibodies or antibody fragments that bind to the extracellular domain of MUC1* would be beneficial for the treatment of cancers wherein the cancerous tissues express MUC1*.

Antibodies that bind to PSMGFR region of MUC1* or bind to a synthetic PSMGFR peptide are preferred. We have identified several monoclonal antibodies that bind to the extracellular domain of MUC1*. Among this group are mouse monoclonal antibodies MN-E6, MN-C2, MN-C3 and MN-C8, the variable regions of which were sequenced and are given as for MN-E6 SEQ ID NOS: 12-13 and 65-66, for MN-C2 SEQ ID NOS: 118-119 and 168-169, for MN-C3 SEQ ID NOS: 413-414 and 458-459 and for MN-C8 SEQ ID NOS: 505-506 and 543-554. The CDRs of these antibodies make up the recognition units of the antibodies and are the most important parts of the mouse antibody that should be retained when grafting into a human antibody. The sequences of the CDRs for each mouse monoclonal are as follows, heavy chain sequence followed by light chain: MN-E6 CDR1 (SEQ ID NO:16-17 and 69-70) CDR2 (SEQ ID NO:20-21 and 73-74) CDR3 (SEQ ID NO: 24-25 and 77-78), MN-C2 CDR1 (SEQ ID NO:122-123 and 172-173) CDR2 (SEQ ID NO:126-127 and 176-177) CDR3 (SEQ ID NO:130-131 and 180-181), MN-C3 CDR1 (SEQ ID NO:417-418 and 462-463) CDR2 (SEQ ID NO:421-422 and 466-467) CDR3 (SEQ ID NO:425-426 and 470-471), MN-C8 CDR1 (SEQ ID NO:507-508 and 545-546) CDR2 (SEQ ID NO:509-510 and 547-548) CDR3 (SEQ ID NO:511-512 and 549-550). In some cases, portions of the framework regions that by modeling are thought to be important for the 3-dimensional structure of the CDRs, are also imported from the mouse sequence.

Monoclonal antibodies MN-E6 and MN-C2 have greater affinity for MUC1* as it appears on cancer cells. Monoclonal antibodies MN-C3 and MN-C8 have greater affinity for MUC1* as it appears on stem cells. By sequence alignment the following human antibodies were chosen as being sufficiently homologous to the mouse antibody that substitution of the mouse CDRs would result in an antibody that retained ability to recognize the target. Mouse MN-E6 heavy chain variable region was homologous to human IGHV3-21*03 heavy chain variable region (SEQ ID NO: 26-27) and the light chain variable region was homologous to human IGKV3-11*02 light chain variable region (SEQ ID NO: 79-80). Mouse MN-C2 heavy chain variable region was homologous to human IGHV3-21*04 heavy chain variable region (SEQ ID NO: 132-133) and the light chain variable region was homologous to human IGKV7-3*01 light chain variable region (SEQ ID NO: 182-183). Mouse MN-C3 heavy chain variable region was homologous to human IGHV1-18*04 heavy chain variable region (SEQ ID NO: 427-428) and the light chain variable region was homologous to human IGKV2-29*03 light chain variable region (SEQ ID NO:472-473). Mouse MN-C8 heavy chain variable region was homologous to human IGHV3-21*04 heavy chain variable region (SEQ ID NO: 513-514) and the light chain variable region was homologous to human Z00023 light chain variable region (SEQ ID NO:551-552).

All four antibodies have been humanized, which process has resulted in several humanized forms of each antibody. CDRs derived from the variable regions of the mouse antibodies were biochemically grafted into a homologous human antibody variable region sequence. Humanized variable regions of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 543-544) were generated by grafting the mouse CDRs into the variable region of a homologous human antibody. The humanized heavy chain variable constructs were then fused into constant regions of either human IgG1 heavy chain constant region (SEQ ID NOS:58-59) or human IgG2 heavy chain constant region (SEQ ID NO:54-55), which are then paired with either humanized light chain variable constructs fused to a human kappa chain (SEQ ID NO: 109-110) or human lambda chain (SEQ ID NO: 113-114) constant region. Other IgG isotypes could be used as constant region including IgG3 or IgG4.

Examples of humanized MN-E6 variable region into an IgG2 heavy chain (SEQ ID NOS:52-53) and into an IgG1 heavy chain (SEQ ID NOS:56-57), humanized MN-C2 variable into an IgG1 heavy chain (SEQ ID NOS: 158-159) or into an IgG2 heavy chain (SEQ ID NOS: 163-164) paired with either Lambda light chain (SEQ ID NO: 111-112 and 216-219) or Kappa chain (SEQ ID NO:107-108 and 210-213) and, humanized MN-C3 (SEQ ID NOS: 455-456, 453-454 and 500-501, 502-503) and MN-C8 (SEQ ID NOS: 541-542, 539-540 and 579-580, 581-582) antibodies were generated. Which IgG constant region is fused to the humanized variable region depends on the desired effect since each isotype has its own characteristic activity. The isotype of the human constant region is selected on the basis of things such as whether antibody dependent cell cytotoxicity (ADCC) or complement dependent cytotoxicity (CDC) is desired but can also depend on the yield of antibody that is generated in cell-based protein expression systems. In a preferred embodiment, humanized anti-MUC1* antibodies or antibody fragments are administered to a person diagnosed with or at risk of developing a MUC1-positive cancer.

One method for testing and selecting the humanized anti-MUC1* antibodies that would be most useful for the treatment of persons with cancer or at risk of developing cancers is to test them for their ability to inhibit the binding of activating ligands to the MUC1* extracellular domain. Dimeric NME1 can bind to and dimerize the MUC1* extracellular domain and in so doing stimulates cancer cell growth. Antibodies and antibody fragments that compete with NME1 for binding to the MUC1* extracellular domain are therefore anti-cancer agents. NME7 is another activating ligand of MUC1*. In some cases, it is preferable to identify antibodies that block the binding of NME7, or an NME7 truncation or cleavage product, to the MUC1* extracellular domain. Antibodies and antibody fragments that compete with NME7 and NME7 variants for binding to the MUC1* extracellular domain are effective as anti-cancer therapeutics. These antibodies include but are not limited to MN-E6, MN-C2, MN-C3, MN-C8 as well as single chain versions, such as scFv, of these antibodies and humanized version thereof. Other NME proteins also bind to MUC1 or MUC1* including NME6 and NME8. Antibodies that compete with these proteins for binding to MUC1* may also be useful as therapeutics. In a preferred embodiment, humanized anti-MUC1* antibodies or antibody fragments are administered to a person diagnosed with or at risk of developing a MUC1-positive cancer. In a more preferred embodiment, single chain antibody fragments, or monomeric scFv-Fc fusions, derived from humanized sequences of MN-E6 and MN-C2 are administered to a person diagnosed with or at risk of developing a MUC1-positive cancer.

Single chain variable fragments, scFv, or other forms that result in a monovalent antibody or antibody-like protein are also useful. In some cases it is desired to prevent dimerization of the MUC1* extracellular domain. Single chain variable fragments, Fabs and other monovalent antibody-like proteins have been shown to be effective in binding to the extracellular domain of MUC1* and blocking MUC1* dimerization. These single chain variable fragments, Fabs and other monovalent antibody-like molecules effectively blocked cancer growth in vitro and in animals xenografted with human MUC1-positive cancer cells. Thus, humanized single chain variable fragments or monovalent anti-MUC1* antibodies or antibody-like molecules would be very effective as an anti-cancer therapeutic. Such humanized single chain antibodies, Fabs and other monovalent antibody-like molecules that bind to the MUC1* extracellular domain or to a PSMGFR peptide are therefore useful as anti-cancer therapeutics. Anti-MUC1* single chain variable fragments are generated by grafting non-human CDRs of antibodies, which bind to extracellular domain of MUC1* or bind to PSMGFR peptide, into a framework of a homologous variable region human antibody. The resultant humanized heavy and light chain variable regions are then connected to each other via a suitable linker, wherein the linker should be flexible and of length that it allows heavy chain binding to light chain but discourages heavy chain of one molecule binding to the light chain of another. For example a linker of about 10-15 residues. Preferably, the linker includes [(Glycine)$_4$ (Serine)$_1$]$_3$ (SEQ ID NOS: 401-402), but is not limited to this sequence as other sequences are possible.

In one aspect, the humanized variable regions of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566) are biochemically grafted into a construct that connects heavy and light chains via a linker. Examples of humanized single chain anti-MUC1* antibodies comprising humanized sequences from the variable regions of MN-E6, MN-C2, MN-C3 and MN-C8 were generated. Several humanized MN-E6 single chain proteins were generated (SEQ ID NOS: 232-237). Several humanized MN-C2 single chain proteins were generated (SEQ ID NOS: 238-243). Several humanized MN-C3 single chain proteins were generated (SEQ ID NOS: 244-249). Several humanized MN-C8 single chain proteins were generated (SEQ ID NOS: 250-255). In a preferred embodiment, humanized anti-MUC1* antibody fragments, including variable fragments, scFv antibody fragments MN-E6 scFv, MN-C2 scFv, MN-C3 scFv, or MN-C8 scFv are administered to a person diagnosed with or at risk of developing a MUC1-positive cancer. In a more preferred embodiment, single chain antibody fragments, such as variable fragments derived from humanized sequences of MN-E6 and MN-C2, are administered to a person diagnosed with or at risk of developing a MUC1-positive cancer.

In another aspect, the humanized variable regions of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566) are biochemically grafted into a single chain variable fragment, scFv, that also contains an Fc portion of an antibody. Examples of humanized single chain variable fragment of MN-E6, MN-C2, MN-C3 and MN-C8 fused to a Fc region of an antibody were generated (SEQ ID NOS: 256-257, 260-261, 264-265 and 268-269). Inclusion of an Fc region serves several purposes. It increases the molecular weight of the antibody fragment, which slows degradation and increases half-life. An Fc region also recruits immune system complement to the tumor site. Additionally, the addition of an antibody Fc region makes the scFv a convenient diagnostic tool, as the secondary antibodies detect and label the Fc portion. However, the Fc portion homo-dimerizes. Thus an scFv-Fc would be bivalent and could dimerize and activate the MUC1* growth factor receptor. In order to get the benefits of having an Fc attached to an anti-MUC1* scFv, without the drawback of inducing MUC1* dimerization, the Fc region was mutated to minimize or eliminate Fc homo-dimerization. The following mutations were made in the CH3 domain to create a monomeric scFv-Fc fusion protein: Y407R (SEQ ID NOS: 278 and 279), F405Q (SEQ ID NOS: 280 and 281), T394D (SEQ ID NOS: 282 and 283), T366W/L368W (SEQ ID NOD: 284 and 285), T364R/L368R (SEQ ID NOS: 286 and 285). Any combinations of those mutations can be tested and could be introduced into Fc (SEQ ID NOS: 272-273), CH2-CH3 (SEQ ID NOS: 274-275) or CH3 (SEQ ID NOS: 276-277) fusion proteins or in the hingeless Fc-fusion proteins (SEQ ID NOS: 288-289).

One aspect of the invention is a method for treating a patient diagnosed with, suspected of having, or at risk of developing a MUC1 positive or MUC1* positive cancer, wherein the patient is administered an effective amount of a monomeric MN-E6 scFv, MN-C2 scFv, MN-C3 scFv, MN-C8 scFv, or MN-E6 scFv-Fc, MN-C2 scFv-Fc, MN-C3 scFv-Fc, MN-C8 scFv-Fc, wherein the antibody variable fragment portions are human or have been humanized and wherein the Fc portion of the antibody-like protein has been mutated such that it resists dimer formation.

CAR T and Cancer Immuno Therapy Techniques

In another aspect of the invention, some or all of the single chain portions of anti-MUC1* antibody fragments are biochemically fused onto immune system molecules, using several different chimeric antigen receptor, 'CAR' strategies. The idea is to fuse the recognition portion of an antibody, typically as a single chain variable fragment, to an immune system molecule that has a transmembrane domain and a cytoplasmic tail that is able to transmit signals that activate the immune system. The recognition unit can be an antibody fragment, a single chain variable fragment, scFv, or a peptide. In one aspect, the recognition portion of the extracellular domain of the CAR is comprised of sequences from the humanized variable region of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566). In another aspect, it is comprised of sequences from a single chain variable fragment. Examples of single chain constructs are given. Several humanized MN-E6 single chain proteins, scFv, were generated (SEQ ID NOS: 232-237). Several humanized MN-C2 single chain proteins, scFv, were generated (SEQ ID NOS: 238-243). Several humanized MN-C3 single chain proteins, scFv, were generated (SEQ ID NOS: 244-249). Several humanized MN-C8 single chain proteins, scFv, were generated (SEQ ID NOS: 250-255). The transmembrane region of the CAR can be derived from CD8, CD4, antibody domains or other transmembrane region, including the transmembrane region of the proximal cytoplasmic co-stimulatory domain. The cytoplasmic tail of the CAR can be comprised of one or more motifs that signal immune system activation. This group of cytoplasmic signaling motifs, sometimes referred to as, co-stimulatory cytoplasmic domains, includes but is not limited to CD3-zeta, CD27, CD28, 4-1BB, OX40, CD30, CD40, PD-1, ICAm-1, LFA-1, ICOS, CD2, CD5, CD7 and Fc receptor gamma domain. A minimal CAR may have the CD3-zeta or an Fc receptor gamma domain then one or two of the above domains in tandem on the cytoplasmic tail. In one aspect, the cytoplasmic tail comprises CD3-zeta, CD28, 4-1BB and/or OX40. Several examples of humanized MN-E6 CARs were generated: CAR MN-E6 CD3z (SEQ ID NOS: 294-295); CAR MN-E6 CD28/CD3z (SEQ ID NOS: 297-298); CAR MN-E6 4-1BB/CD3z (SEQ ID NOS: 300-301); CAR MN-E6 OX40/CD3z (SEQ ID NOS: 616-617); CAR MN-E6 CD28/OX40/CD3z (SEQ ID NOS: 618-619); CAR MN-E6 CD28/4-1BB/CD3z (SEQ ID NOS: 303-304). Several examples of humanized MN-C2 CARs were generated: CAR MN-C2 CD3z (SEQ ID NOS: 606-607); CAR MN-C2 CD28/CD3z (SEQ ID NOS: 608-609); CAR MN-C2 4-1BB/CD3z (SEQ ID NOS: 610-611); CAR MN-C2 OX40/CD3z (SEQ ID NOS: 612-613); CAR MN-C2 CD28/ 4-1BB/CD3z (SEQ ID NOS: 306-307); CAR MN-C2 CD28/OX40/CD3z (SEQ ID NOS: 614-615). Humanized MN-C3 CAR was generated: CAR MN-C3 4-1BB/CD3z (SEQ ID NOS: 600-601).

Several examples of humanized MN-E6 CARs with different hinge regions (SEQ ID NOS:345-360) were generated: CAR MN-E6-Fc/8/41BB/CD3z (SEQ ID NOS:310-311); CAR MN-E6 FcH/8/41BB/CD3z (SEQ ID NOS:315-316); CAR MN-E6 Fc/4/41BB/CD3z (SEQ ID NOS:318-319); CAR MN-E6 FcH/4/41BB/CD3z (SEQ ID NOS:321-322); CAR MN-E6 IgD/8/41BB/CD3z (SEQ ID NOS:323-324); CAR MN-E6 IgD/4/41BB/CD3z (SEQ ID NOS:327-328); CAR MN-E6 X4/8/41BB/CD3z (SEQ ID NOS:330-331); CAR MN-E6 X4/4/41BB/CD3z (SEQ ID NOS:333-334); CAR MN-E6 8+4/4/41BB/CD3z (SEQ ID NOS:336-337). In addition, several humanized MN-C3 single chain variable fragment and humanized MN-C8 single chain variable fragments were also generated.

The extracellular domain recognition unit of a MUC1* targeting CAR can comprise the variable regions of humanized MN-E6, MN-C2, MN-C3 or MN-C8 or other antibody that binds to the PSMGFR portion of MUC1* or a PSMGFR peptide. In one aspect, the extracellular domain recognition unit of a CAR is comprised essentially of a humanized unit of MN-E6, MN-C2, MN-C3 or MN-C8 single chain variable fragment scFv. The transmembrane region of the CAR can be derived from CD8 (SEQ ID NOS:363-364), or can be the transmembrane domain of CD3-zeta, CD28, 41bb, OX40 or other transmembrane region (SEQ ID NOS:361-372) and the cytoplasmic domain of a CAR with antibody fragment targeting MUC1* extracellular domain can be comprised of one or more selected from the group comprising an immune system co-stimulatory cytoplasmic domain. The group of immune system co-stimulatory domains includes but is not limited to CD3-zeta, CD27, CD28, 4-1BB, OX40, CD30, CD40, PD-1, ICAm-1, LFA-1, ICOS, CD2, CD5, CD7 and Fc receptor gamma domain (SEQ ID NOS:373-382). Alternatively, the recognition unit portion of a CAR can comprise a peptide wherein the peptide binds to the target. NME7 binds to and activates MUC1*. In one aspect of the invention, the recognition unit of a CAR is a peptide derived from NME7 (SEQ ID NOS: 5-6) or a peptide derived from NME7, including but not limited to NME7 peptide A1 (SEQ ID NO: 7), NME7 peptide A2 (SEQ ID NO: 8), NME7 peptide B1 (SEQ ID NO: 9), NME7 peptide B2 (SEQ ID NO: 10) and NME7 peptide B3 (SEQ ID NO: 11).

Some strategies for generating CARs include a portion of the molecule that dimerizes with itself. In some cases, dimerization of the target is not desirable. Therefore CARs can be constructed such that they heterodimerize. In one case the recognition unit of the first CAR binds to a first target while the recognition unit of the second CAR binds to a second target. Both recognition units can be antibody fragments, both can be peptides or one can be an antibody fragment and the other a peptide. A first target of the CAR can be the extracellular domain of MUC1*. The recognition unit of the CAR would be comprised of an antibody fragment that binds to MUC1* extracellular domain or to a PSMGFR peptide. Alternatively, the recognition unit of the CAR would be comprised of a peptide that binds to MUC1* extracellular domain, such peptides include peptides derived from an NME protein such as NME1 or NME7, more particularly NME7 derived peptides listed as SEQ ID NOS: 7-11. A second target of a heterodimeric CAR may be a peptide or antibody fragment that binds to NME7. Alternatively, a second target of a heterodimeric CAR may be a peptide or antibody fragment that binds to PD1 or other target on a MUC1*-presenting cell. A second target may be a peptide or antibody fragment that binds to NME1. Because it is desirable to prevent dimerization of MUC1 induced by a CAR, heterodimeric CARs can be constructed so that only the extracellular domain of one molecule has an extracellular recognition unit that binds to a target (SEQ ID NOS: 584-587). The other molecule can have a truncated extracellular domain that is devoid of a target recognition unit or antibody fragment (SEQ ID NOS:588-599). The CARs described can be transfected or transduced into a cell of the immune system. In a preferred embodiment, a MUC1* targeting CAR is transfected or transduced into a T cell. In one aspect the T cell is a CD3+/CD28+ T cell. In another case it is a dendritic cell. In another case it is a B cell. In another case it is a mast cell. The recipient cell can be from a patient or from a donor. If from a donor, it can be engineered to remove molecules that would trigger rejection. Cells transfected or transduced with a CAR of the invention can be expanded ex vivo or in vitro then administered to a patient. Administrative routes are chosen from a group containing but not limited to bone marrow transplant, intravenous injection, in situ injection or transplant. In a preferred embodiment, the MUC1* targeting CAR is administered to a person diagnosed with or at risk of developing a MUC1-positive cancer.

There are many possible anti-MUC1* CAR constructs that can be transduced into T cells or other immune cells for the treatment or prevention of MUC1* positive cancers. CARs are made up of modules and the identity of some of the modules is relatively unimportant, while the identity of other modules is critically important.

Figure 28:
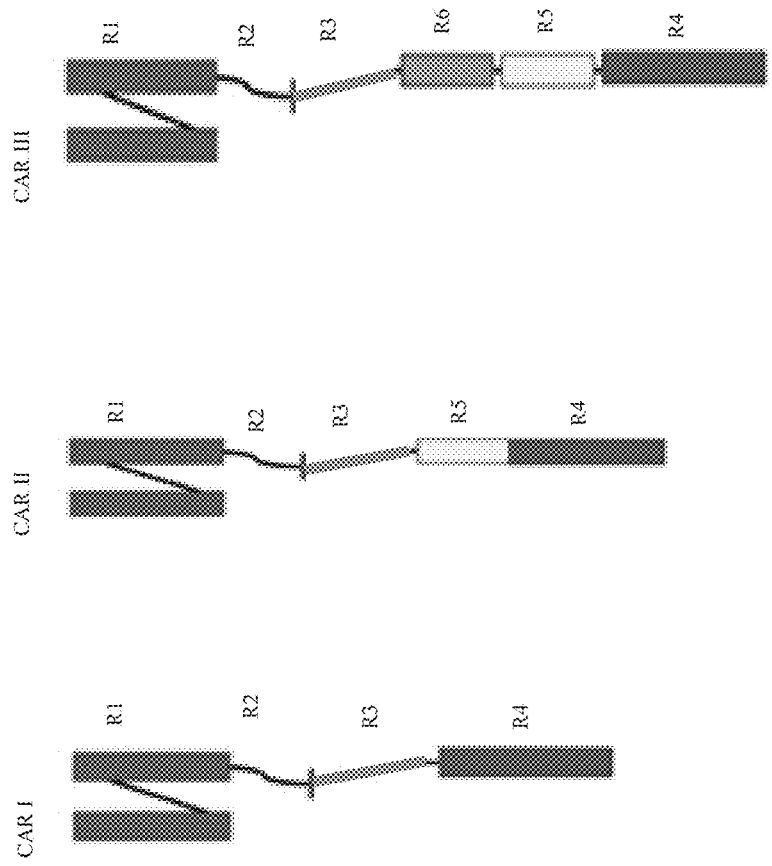
FIG. 28 shows schematics of CAR sequence components.

Our experiments demonstrate that the antibody recognition fragment at the outermost portion of the CAR is critically important because it targets the immune cell bearing the CAR to the tumor site. The intracellular signaling motifs are also very important but can be interchanged. FIG. 28 shows a schematic of the components of CAR and the various sequences that may be included in a CAR. Referring to FIG. 28, R1 is: nothing; or
a ligand or a fragment of a ligand of a cancer associated antigen; or
a ligand or a fragment of a ligand of MUC1 or MUC1*; or
an antibody or antibody fragment wherein the antibody or antibody fragment binds to MUC1 or MUC1*; or an antibody or antibody fragment wherein the antibody or antibody fragment binds to PSMGFR*, wherein the antibody may be human or humanized; or an antibody or antibody fragment of MN-E6, MN-C2, MN-C3 or MN-C8 or humanized MN-E6, MN-C2, MN-C3 or MN-C8; or a single chain variable fragment of an antibody, scFv, that binds to a cleaved MUC1 or MUC1*; or a scFv of MN-E6, MN-C2, MN-C3 or MN-C8, which may be humanized; or a peptide that binds to MUC1* or PSMGFR peptide; or is an antibody fragment, a scFv, or a peptide that binds the PSMGFR portion of MUC1*; or is comprised of sequence from the humanized variable region of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566). In one aspect R1 is a scFv that binds the PSMGFR portion of MUC1* comprised of sequence from humanized MN-E6 scFv (SEQ ID NOS: 232-237), humanized MN-C2 scFv (SEQ ID NOS: 238-243), humanized MN-C3 scFv (SEQ ID NOS: 244-249) or humanized MN-C8 scFv (SEQ ID NOS: 250-255). In another aspect R1 is a scFv that binds the PSMGFR portion of MUC1* comprised of sequence from humanized MN-E6 scFv (SEQ ID NOS: 232-237) or humanized MN-C2 scFv (SEQ ID NOS: 238-243). In one example R1 is a scFv that binds the PSMGFR portion of MUC1* comprised of sequence from humanized MN-E6 scFv (SEQ ID NOS: 232-237)

R2 is a polypeptide flexible linker that connects the recognition portion to the transmembrane domain of the CAR. In one aspect, R2 can be a polypeptide linker of different length from 5 to 250 amino acids. In another aspect, R2 is a polypeptide linker of human origin. In one aspect R2 can be made of or a modification of the Fc region of a human immunoglobulin (IgG, IgA, IgE, IgM or IgD). I another aspect, R2 can be the hinge region or a modification of the hinge region of a human immunoglobulin (IgG, IgA, IgE, IgM or IgD). In one aspect, R2 can be the hinge region or a modification of the hinge region of a T-cell receptor (CD8a, CD28 or CD4). In one example, R2 is the hinge region of CD8a, the hinge region of human IgD or the Fc domain of human IgG1.

R3 is a transmembrane domain. In one aspect, R3 can be a transmembrane domain or a modification of a transmembrane domain of any transmembrane human proteins. In another aspect, R3 can be a transmembrane domain or a modification of a transmembrane domain from human cell receptor. In one aspect, R3 can be a transmembrane domain or a modification of a transmembrane domain of a T-cell receptor (CD8a, CD4, CD28, CD3z, OX40 or 41-BB). In another aspect, R3 is a transmembrane domain from the first cytoplasmic co-stimulatory domain of the CAR. In one aspect, R3 can be a transmembrane domain or a modification of a transmembrane domain of a T-cell receptor extended with 1,2,3,4 or 5 amino acids of the cytoplasmic domain associated to the transmembrane domain. In another aspect, R3 can be a transmembrane domain or a modification of a transmembrane domain of a T-cell receptor extended with 1,2,3,4 or five amino acids of the cytoplasmic domain associated to the transmembrane domain followed by a cystein for disulfide bond formation. In one example, R3 is the transmembrane domain of CD8a or CD4.

R4 is a signaling domain from a T-cell receptor. In one aspect, R4 can be the cytoplasmic signaling domain of CD3-zeta, CD27, CD28, 4-1BB, OX40, CD30, CD40, PD-1, ICAm-1, LFA-1, ICOS, CD2, CD5, CD7 and Fc receptor gamma domain. In one example, R4 is the cytoplasmic domain of CD3-zeta. Several examples of humanized CAR with single signaling domain (CAR I) were regenerated: CAR MN-E6 CD3z (SEQ ID NOS: 294-295); CAR MN-C2 CD3z (SEQ ID NOS: 606-607)

R5 is a co-stimulatory domain from a T-cell receptor. In one aspect, R5 can be the cytoplasmic signaling domain of CD27, CD28, 4-1BB, OX40, CD30, CD40, PD-1, ICAm-1, LFA-1, ICOS, CD2, CD5, CD7 and Fc receptor gamma domain. R5 will be different from R4 and R6. In one example, R5 is the cytoplasmic domain of CD28, 4-1BB or OX40. Several examples of humanized CAR with two signaling domain (CAR II) were regenerated: CAR MN-E6 CD28/CD3z (SEQ ID NOS: 297-298); CAR MN-E6 4-1BB/CD3z (SEQ ID NOS: 300-301); CAR MN-E6 OX40/CD3z (SEQ ID NOS: 616-617); CAR MN-C2 CD28/CD3z (SEQ ID NOS: 608-609); CAR MN-C2 4-1BB/CD3z (SEQ ID NOS: 610-611); CAR MN-C2 OX40/CD3z (SEQ ID NOS: 612-613); MN-C3 4-1BB/CD3z (SEQ ID NOS: 600-601); CAR MN-E6-Fc/8/41BB/CD3z (SEQ ID NOS: 310-311); CAR MN-E6 FcH/8/41BB/CD3z (SEQ ID NOS:315-316); CAR MN-E6 Fc/4/41BB/CD3z (SEQ ID NOS:318-319); CAR MN-E6 FcH/4/41BB/CD3z (SEQ ID NOS:321-322); CAR MN-E6 IgD/8/41BB/CD3z (SEQ ID NOS:323-324); CAR MN-E6 IgD/4/41BB/CD3z (SEQ ID NOS:327-328); CAR MN-E6 X4/8/41BB/CD3z (SEQ ID NOS:330-331); CAR MN-E6 X4/4/41BB/CD3z (SEQ ID NOS:333-334); CAR MN-E6 8+4/4/41BB/CD3z (SEQ ID NOS:336-337).

R6 is a co-stimulatory domain from a T-cell receptor. In one aspect, R6 can be the cytoplasmic signaling domain of CD27, CD28, 4-1BB, OX40, CD30, CD40, PD-1, ICAm-1, LFA-1, ICOS, CD2, CD5, CD7 and Fc receptor gamma domain. R6 will be different from R4 and R5. In one example, R5 is the cytoplasmic domain of CD28. Several examples of humanized CAR with two signaling domain (CAR III) were regenerated: CAR MN-E6 CD28/OX40/CD3z (SEQ ID NOS: 618-619); CAR MN-E6 CD28/4-1BB/CD3z (SEQ ID NOS: 303-304); CAR MN-C2 CD28/4-1BB/CD3z (SEQ ID NOS: 306-307); CAR MN-C2 CD28/OX40/CD3z (SEQ ID NOS: 614-615)

We and others (Pule M A, Straathof K C, Dotti G, Heslop H E, Rooney C M and Brenner M K. (2005) A chimeric T cell antigen receptor that augments cytokine release and supports clonal expansion of primary human T cells. Mol Ther. 12(5):933-941; Hombach A A, Heiders J, Foppe M, Chmielewski M and Abken H. (2012) OX40 costimulation by a chimeric antigen receptor abrogates CD28 and IL-2 induced IL-10 secretion by redirected CD4(+) T cells. Oncoimmunology. 1(4):458-466; Kowolik C M, Topp M S, Gonzalez S, Pfeiffer T, Olivares S, Gonzalez N, Smith D D, Forman S J, Jensen M C and Cooper L J. (2006) CD28 costimulation provided through a CD19-specific chimeric antigen receptor enhances in vivo persistence and antitumor efficacy of adoptively transferred T cells. Cancer Res. 66(22):10995-11004; Loskog A, Giandomenico V, Rossig C, Pule M, Dotti G and Brenner M K. (2006) Addition of the CD28 signaling domain to chimeric T-cell receptors enhances chimeric T-cell resistance to T regulatory cells. Leukemia. 20(10):1819-1828; Milone M C, Fish J D, Carpenito C, Carroll R G, Binder G K, Teachey D, Samanta M, Lakhal M, Gloss B, Danet-Desnoyers G, Campana D, Riley J L, Grupp S A and June C H. (2009) Chimeric receptors containing CD137 signal transduction domains mediate enhanced survival of T cells and increased antileukemic efficacy in vivo. Mol Ther. 17(8):1453-1464; Song D G, Ye Q, Carpenito C, Poussin M, Wang L P, Ji C, Figini M, June C H, Coukos G, Powell D J Jr. (2011) In vivo persistence, tumor localization, and antitumor activity of CAR-engineered T cells is enhanced by costimulatory signaling through CD137 (4-1BB). Cancer Res. 71(13):4617-4627) have shown that intracellular signaling modules, such as CD3-zeta (SEQ ID NOS: 373-376), CD28 (SEQ ID NOS: 377-378) and 41BB (SEQ ID NOS: 379-380), alone or in combinations stimulate immune cell expansion, cytokine secretion and immune cell mediated killing of the targeted tumor cells. Less important is the identity of the short extracellular piece that presents the antibody fragment, the transmembrane domain, and the short cytoplasmic tail that comes before the intracellular signaling motifs.

The identity of the recognition antibody fragment that targets the CAR to a tumor is critically important. For the treatment of MUC1 positive or MUC1* positive cancers, that antibody recognition fragment must bind to the extracellular domain of portion of MUC1 that remains after cleavage and shedding of the bulk of the extracellular domain, which contains the tandem repeat domains. In one aspect of the invention, the portion that remains comprises the PSMGFR sequence. In another aspect of the invention, the portion of MUC1 that remains after cleavage and shedding contains the PSMGFR sequence plus nine (9) more amino acids extended at the N-terminus. In another aspect of the invention, the portion of MUC1 that remains after cleavage and shedding contains the PSMGFR sequence plus twenty one (21) more amino acids extended at the N-terminus. In one aspect the antibody recognition fragment binds to a PSMGFR peptide. In another aspect of the invention, the antibody recognition fragment binds to a peptide comprising the sequence SNIKFRPGSVVVQLTLAFREGTINVHD-VETQFNQYKTEAASRY (SEQ ID NO:620); or SVVVQLTLAFREGTINVHDVETQFNQYKTEAASRY (SEQ ID NO:621) As a demonstration, a single chain antibody fragment that included the variable domain of the monoclonal anti-MUC1* antibodies called MN-E6 or MN-C2 were engineered into a panel of CARs. The MUC1* targeting CARs were then transduced, separately or in combinations, into immune cells. When challenged with surfaces presenting a MUC1* peptide, an antigen presenting cell transfected with MUC1*, or MUC1* positive cancer cells, the immune cells that were transduced with MUC1* targeting CARs elicited immune responses, including cytokine release, killing of the targeted cells and expansion of the immune cells. In one case, human jurkat cells were transduced with MUC1*-targeting CARs and upon exposure to a surface presenting the PSMGFR peptide, K562 antigen presenting cells that had been transfected with MUC1* or MUC1* positive cancer cells, the jurkhat cells secreted IL-2. In another case, purified human T cells were transduced with MUC1*-targeting CARs and upon exposure to a surface presenting the PSMGFR peptide, K562 antigen presenting cells that had been transfected with MUC1* or MUC1* positive cancer cells, the T cells secreted IL-2, interferon gamma, and killed the targeted antigen presenting cells and cancer cells, while the T cells expanded. As demonstrated, CARs that comprise an antibody fragment, wherein the antibody fragment is able to bind to the PSMGFR peptide, a transmembrane domain and a cytoplasmic tail bearing co-stimulatory domains, elicit an immune system anti-tumor cell response when said CARs are transduced into immune cells, which include T cells. Therefore, other antibodies, antibody fragments or antibody mimics that are able to bind to the PSMGFR peptide will perform similarly and can be used to treat or prevent cancers. Those skilled in the art will recognize that there are a number of technologies available for transfecting or transducing cells with CARs and the invention is not limited by the method used for making the immune cell express a MUC1*-targeting CAR. For example, retroviruses, adeno viruses, lenti viruses and the like can be used. Similarly, the identity of molecules that make up the non-targeting, portions of the CAR such as the extracellular domain, transmembrane domain and membrane proximal portion of the cytoplasmic domain, are not essential to the function of a MUC1*-targeting CAR. For example, the extracellular domain, transmembrane domain and membrane proximal portion of the cytoplasmic domain can be comprised of portions of CD8, CD4, CD28, or generic antibody domains such as Fc, CH2CH3, or CH3. Further, the non-targeting portions of a CAR can be a composite of portions of one or more of these molecules or other family members.

One aspect of the invention is a method for treating a patient diagnosed with, suspected of having, or at risk of developing a MUC1 positive or MUC1* positive cancer, wherein the patient is administered an effective amount of immune cells that have been transduced with a MUC1* targeting CAR. In another aspect of the invention, the immune cells are T cells isolated from a patient, which are then transduced with CARs wherein the targeting head of the CAR binds to MUC1*, and after expansion of transduced T cells, the CAR T cells are administered in an effective amount to the patient. In yet another aspect of the invention, the immune cells are T cells isolated from a patient, which are then transduced with CARs wherein the targeting head of the CAR comprises portions of huMN-E6, huMN-C2, huMN-C3 or huMN-C8, and after optional expansion of transduced T cells, the CAR T cells are administered in an effective amount to the patient.

Specifics of CARs Made and Tested

Figure 29:
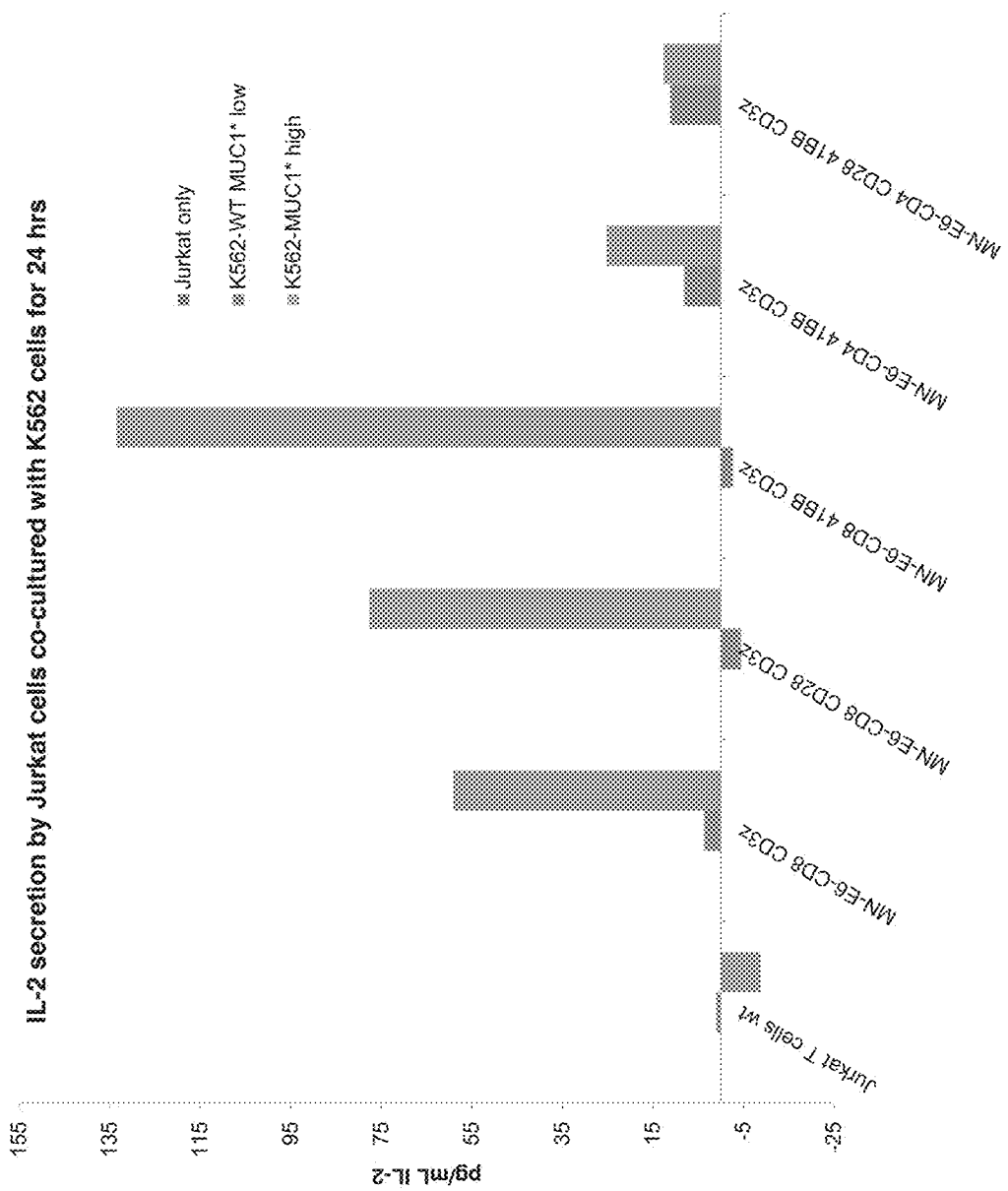
FIG. 29 is a graph of an experiment measuring IL-2 cytokine secretion by Jurkat T cells that were transduced with a panel of CARs, including MN-E6-CD8-3z, MN-E6-CD8-CD28-3z, MN-E6-CD8-41BB-3z, MN-E6-CD4-CD28-3z and MN-E6-CD4-CD28-41BB-3z, when the CAR T cells were exposed to K562-wt cells or K562 cells that had been transfected with MUC1*.
Figure 30:
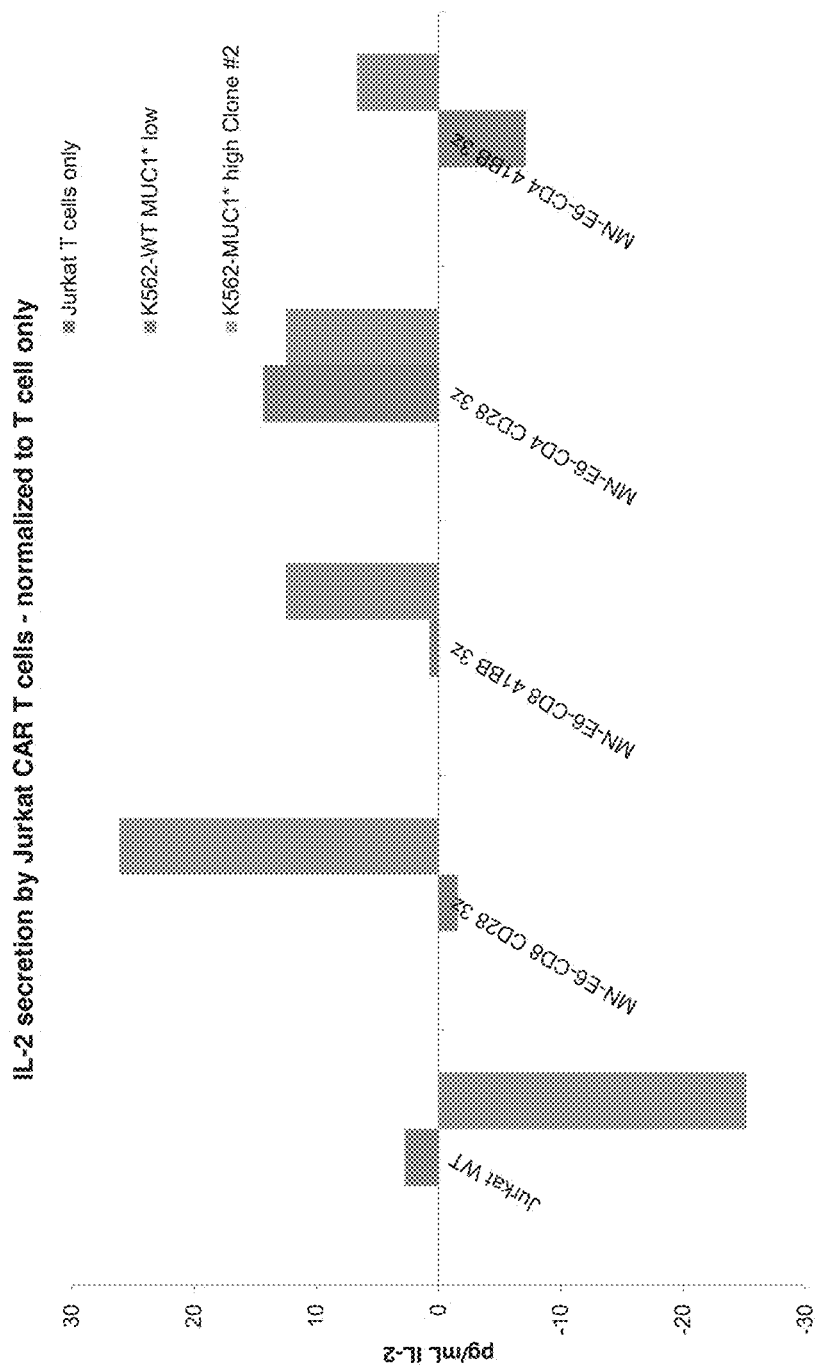
FIG. 30 is a graph of an experiment measuring IL-2 cytokine secretion by Jurkat T cells that were transduced with a panel of CARs, including MN-E6-CD8-CD28-3z, MN-E6-CD8-41BB-3z, MN-E6-CD4-CD28-3z and MN-E6-CD4-41BB-3z, when the CAR T cells were exposed to K562-wt cells or K562 cells that had been transfected with MUC1*.
Figure 31:
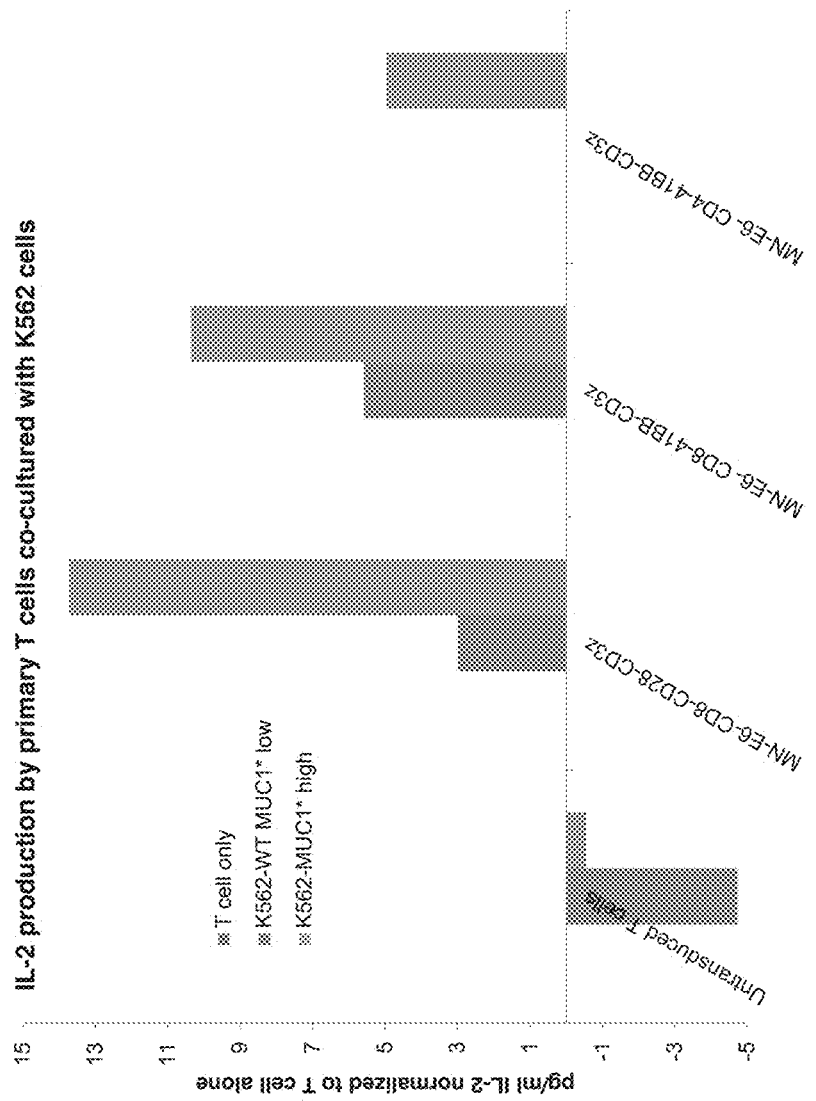
FIG. 31 is a graph of an experiment measuring IL-2 cytokine secretion by primary human T cells, isolated from a blood sample, that were transduced with a panel of CARs, including MN-E6-CD8-CD28-3z, MN-E6-CD8-41BB-3z and MN-E6-CD4-41BB-3z, when the CAR T cells were exposed to K562-wt cells or K562 cells that had been transfected with MUC1*.
Figure 32:
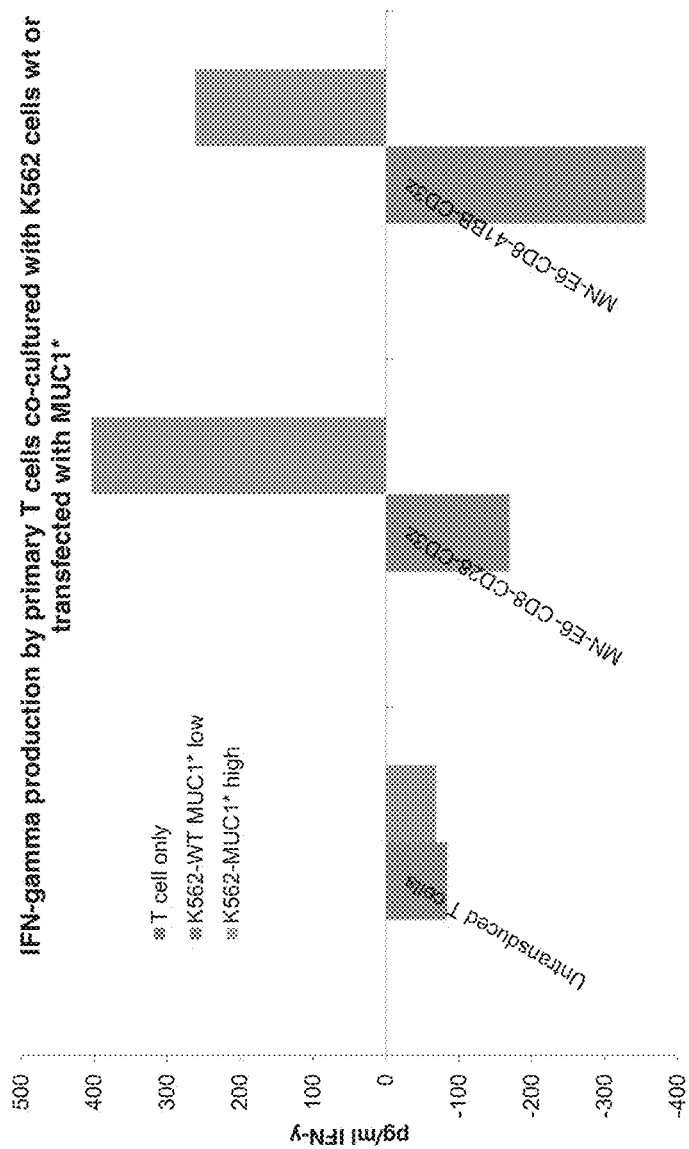
FIG. 32 is a graph of an experiment measuring interferon-gamma (IFN-g) cytokine secretion by primary human T cells, isolated from a blood sample, that were transduced with a panel of CARs, including MN-E6-CD8-CD28-3z and MN-E6-CD4-41BB-3z, when the CAR T cells were exposed to K562-wt cells or K562 cells that had been transfected with MUC1*.
Figure 33:
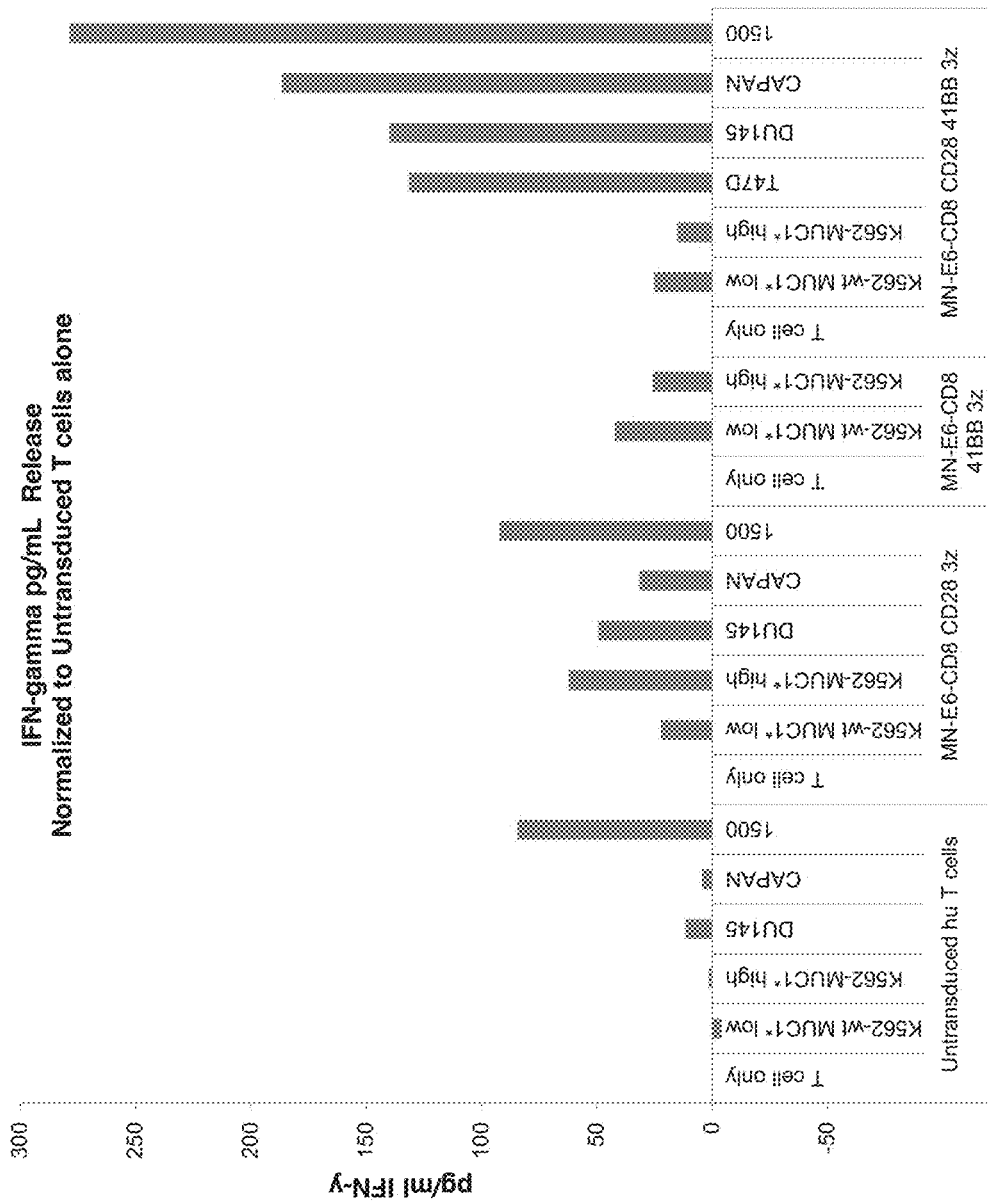
FIG. 33 is a graph of an experiment measuring interferon-gamma (IFN-g) cytokine secretion by primary human T cells, isolated from a blood sample, that were transduced with a panel of CARs, including MN-E6-CD8-CD28-3z, MN-E6-CD8-41BB-3z and MN-E6-CD8-CD28-41BB-3z, when the CAR T cells were exposed to K562-wt cells, K562 cells that had been transfected with MUC1*, or MUC1* positive cancer cells of prostate cancer, breast cancer or pancreatic cancer.

Many MUC1* targeting CARs were generated wherein the targeting antibody fragment at the distal end of the CAR was either MN-E6, MN-C2, MN-C3 or MN-C8. The DNA of each CAR was sequenced to verify that cloning was correctly done. Each construct was then shuffled into an expression plasmid, transfected into cells and then verified that the construct had successfully inserted by Western blot. Surface expression was verified by FACS. The MUC1* targeting CARs were then virally transduced into immune cells. In one aspect they were transduced into Jurkat cells. In another aspect they were transduced into primary human T cells that were purified from blood. A series of functional assays were performed and verified that the CARs were functional. Functional assays showed that both Jurkat cells and primary T cells transduced with MUC1* targeting CAR secreted the cytokine IL-2 when challenged with cells presenting MUC1*. FIG. 29 is a graph of an experiment measuring IL-2 cytokine secretion by Jurkat cells that were transduced with a panel of CARs, including MN-E6 CD8/CD3z, MN-E6 CD8/CD28/CD3z, MN-E6 CD8/41BB/CD3z, MN-E6 CD4/CD28/CD3z and MN-E6 CD4/CD28/41BB/CD3z. IL-2 was secreted only when the CAR Jurkat cells were exposed to K562-wt cells or K562 cells that had been transfected with MUC1*. It should be noted that the parent K562-wt cells express very low levels of MUC1*. Another group of CARs transfected into Jurkat cells was similarly tested for cytokine secretion. FIG. 30 shows IL-2 secretion by Jurkat T cells that were transduced with MN-E6 CD8/CD28/CD3z, MN-E6 CD8/41BB/CD3z, MN-E6 CD4/CD28/CD3z or MN-E6 CD4/41BB/CD3z, when the CAR T cells were exposed to K562-wt cells or K562 cells that had been transfected with MUC1*. Similarly, FIG. 31 shows IL-2 cytokine secretion by primary human T cells that were transduced with MN-E6 CD8/CD28/CD3z, MN-E6 CD8/41BB/CD3z or MN-E6 CD4/41BB/CD3z. Cytokine secretion only occurred when the MUC1* targeting CAR T cells were exposed to K562-wt cells or K562 cells that had been transfected with MUC1*. Another cytokine that is secreted by activated T cells when they see a target cell is interferon-gamma (IFN-g). FIG. 32 shows that interferon-gamma was secreted by primary human T cells that were transduced with a panel of CARs, including MN-E6 CD8/CD28/CD3z and MN-E6 CD4/41BB/CD3z, when the CAR T cells were exposed to K562-wt cells or K562 cells that had been transfected with MUC1*. Interferon-gamma was similarly secreted by primary human T cells that were transduced with a panel of CARs, including MN-E6 CD8/CD28/CD3z, MN-E6 CD8/41BB/CD3z and MN-E6 CD8/CD28/41BB/CD3z, when the MUC1* targeting CAR T cells were exposed to K562-wt cells, K562 cells that had been transfected with MUC1*, or MUC1* positive cancer cells of prostate cancer (DU145), breast cancer (1500) or pancreatic cancer (Capan) (FIG. 33).

Figure 34:
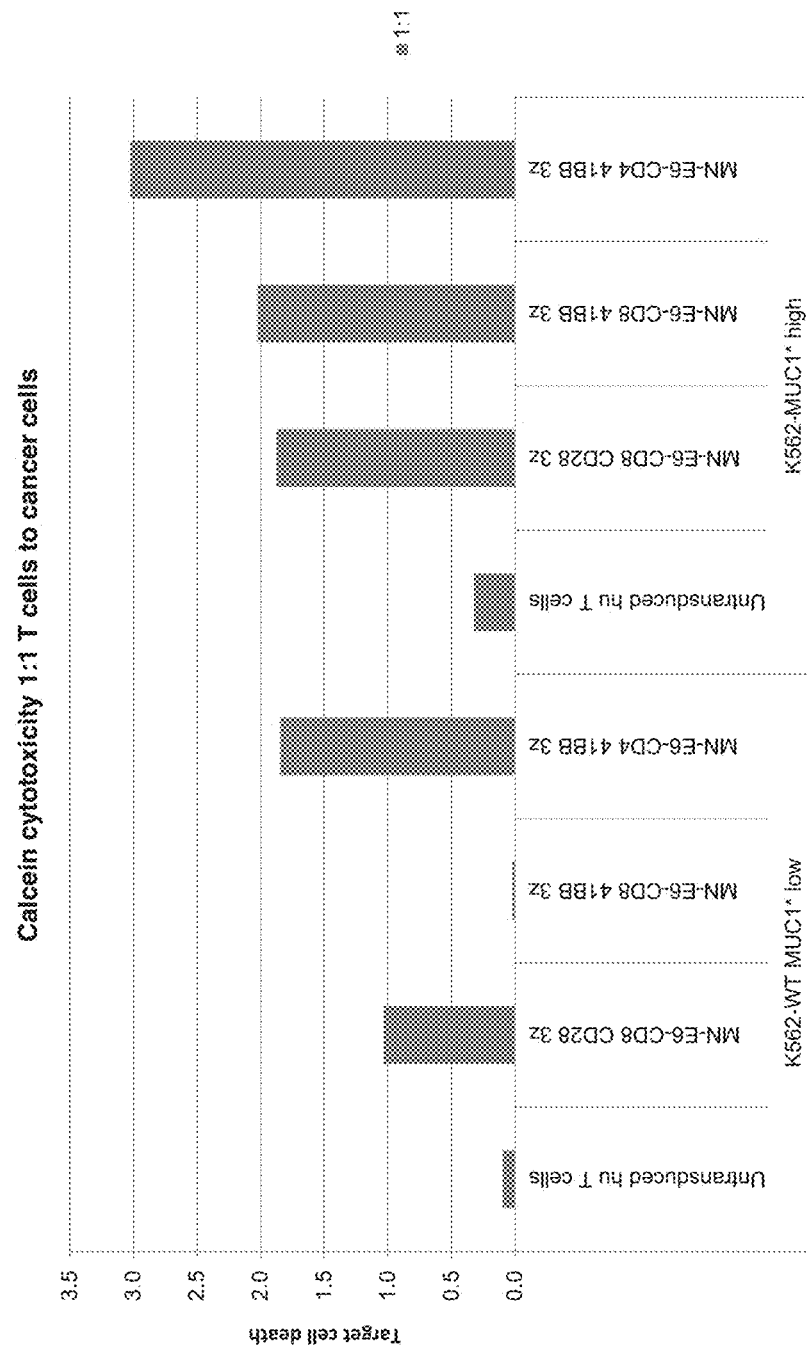
FIG. 34 is a graph of an experiment measuring target cell death when primary human T cells, isolated from a blood sample, that were transduced with a panel of CARs, including MN-E6-CD8-CD28-3z, MN-E6-CD8-41BB-3z and MN-E6-CD4-41BB-3z, when the CAR T cells were exposed to K562-wt cells or K562 cells that had been transfected with MUC1*. The ratio of T cells to target cells was 1:1 and the cells were co-cultured for 24 hours.
Figure 35:
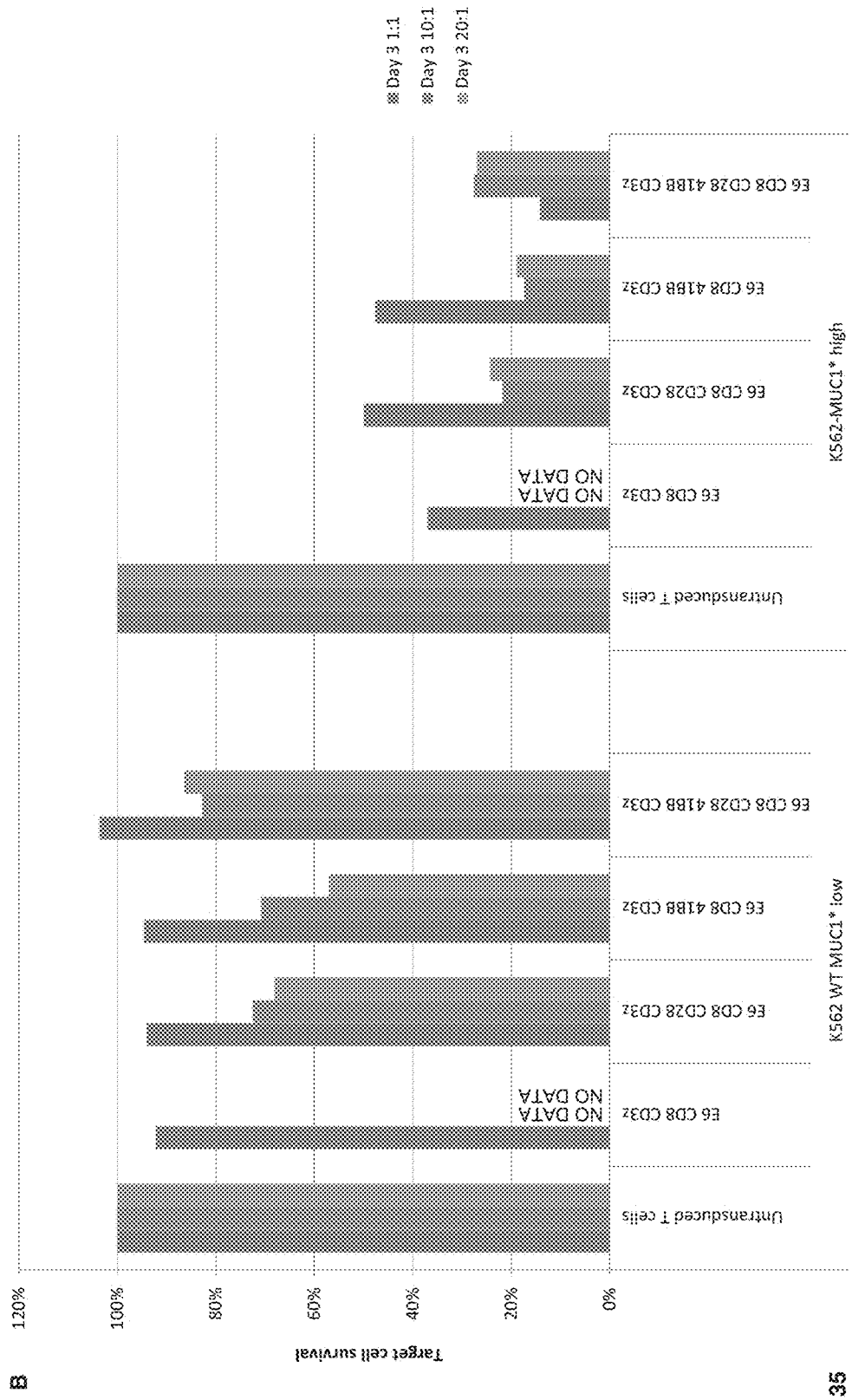
FIG. 35 is a graph of FACS measuring a time course of target cell survival from Day 1 to Day 3. Primary human T cells, isolated from a blood sample, were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to K562-wt cells that naturally express low levels of MUC1*, or K562 cells that had been transfected with MUC1* high. The ratio of MUC1* targeting CAR T cells to target cells was either 1:1, 10:1, or 20:1. Surviving cells were detected and measured at Day 1 or Day 3 (B).

Another measure of function of CAR T cells is whether or not they induce killing of the targeted cells. T cells transfected with a variety of CARs comprising antibody fragments that bind to the PSMGFR sequence of MUC1* killed MUC1* expressing cells in co-culture assays. In one assay, target MUC1* expressing cells are incubated with calcein. When they are mixed with CAR T cells wherein the CAR comprises an antibody fragment such as MN-E6, MN-C2, MN-C3 or MN-C8 the CAR T cells kill the MUC1* presenting cells which causes the target cells to lyse and releases calcein into the supernatant. FIG. 34 is a graph of an experiment measuring target cell death when primary human T cells, isolated from a blood sample, that were transduced with a panel of CARs, including MN-E6 CD8/CD28/CD3z, MN-E6 CD8/41BB/CD3z and MN-E6 CD4/41BB/CD3z, when the CAR T cells were exposed to K562-wt cells or K562 cells that had been transfected with MUC1*. The ratio of T cells to target cells was 1:1 and the cells were co-cultured for 24 hours. FIG. 35 B is a graph of FACS measuring a time course of target cell survival from Day 1 to Day 3. Primary human T cells, isolated from a blood sample, were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to K562-wt cells that naturally express low levels of MUC1*, or K562 cells that had been transfected with MUC1* high. The ratio of MUC1* targeting CART cells to target cells was either 1:1, 10:1, or 20:1. Surviving cells were detected and measured at Day 1 or Day 3 (B).

Figure 36:
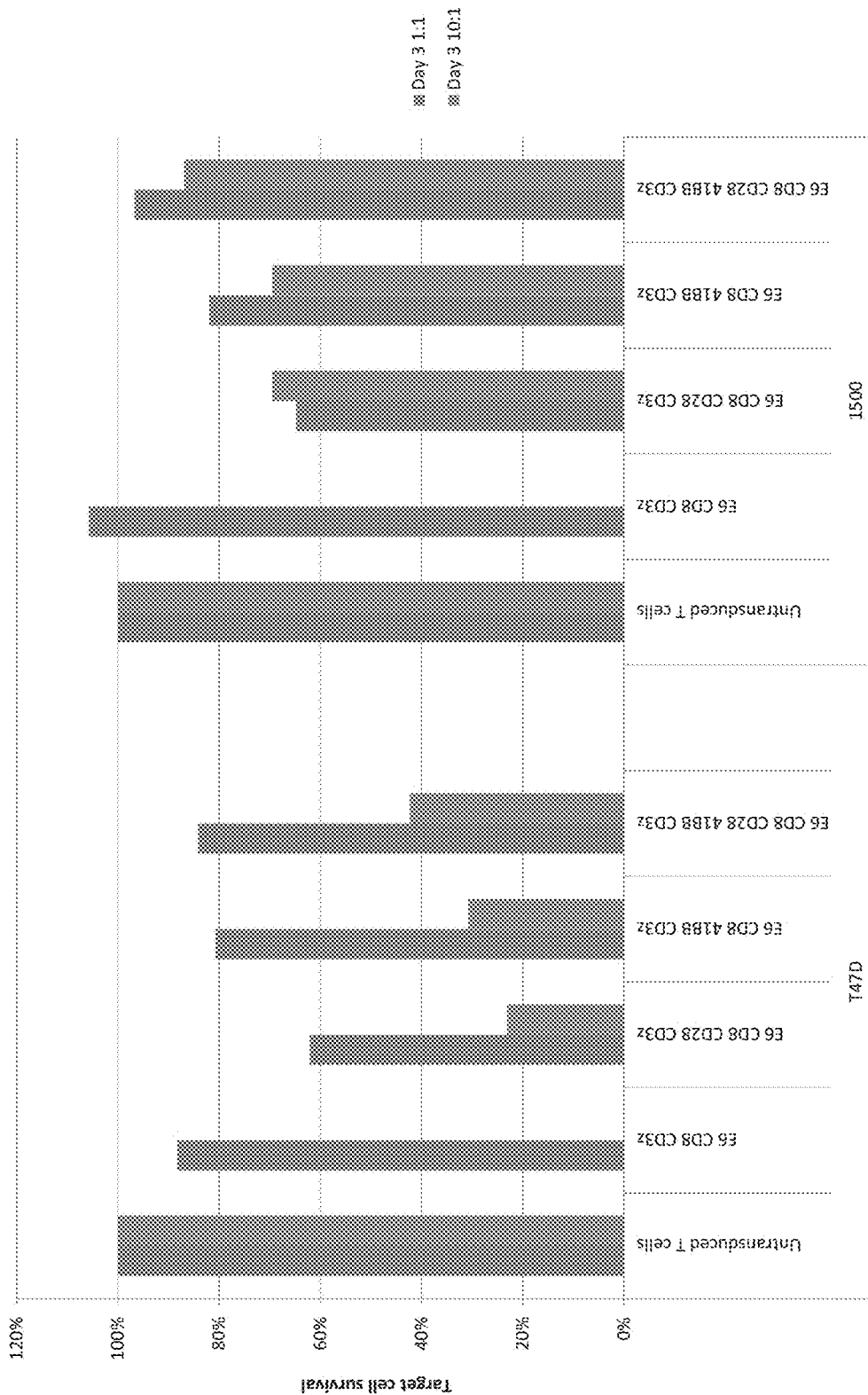
FIG. 36 is a graph of FACS measurements of target cell survival at Day 3 of co-culture experiment. Primary human T cells were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to MUC1* positive T47D breast cancer cells or MUC1* positive 1500 aka ZR-75-1 breast cancer cells. The ratio of MUC1* targeting CAR T cells to target cells was either 1:1 or 10:1. As can be seen from the graph, T cells transduced with a MUC1* targeting CAR have a much greater killing effect on MUC1* cancer cells than the untransduced control T cells. In addition, the killing effect is much greater when the ratio of T cells: target cells is increased.
Figure 37:
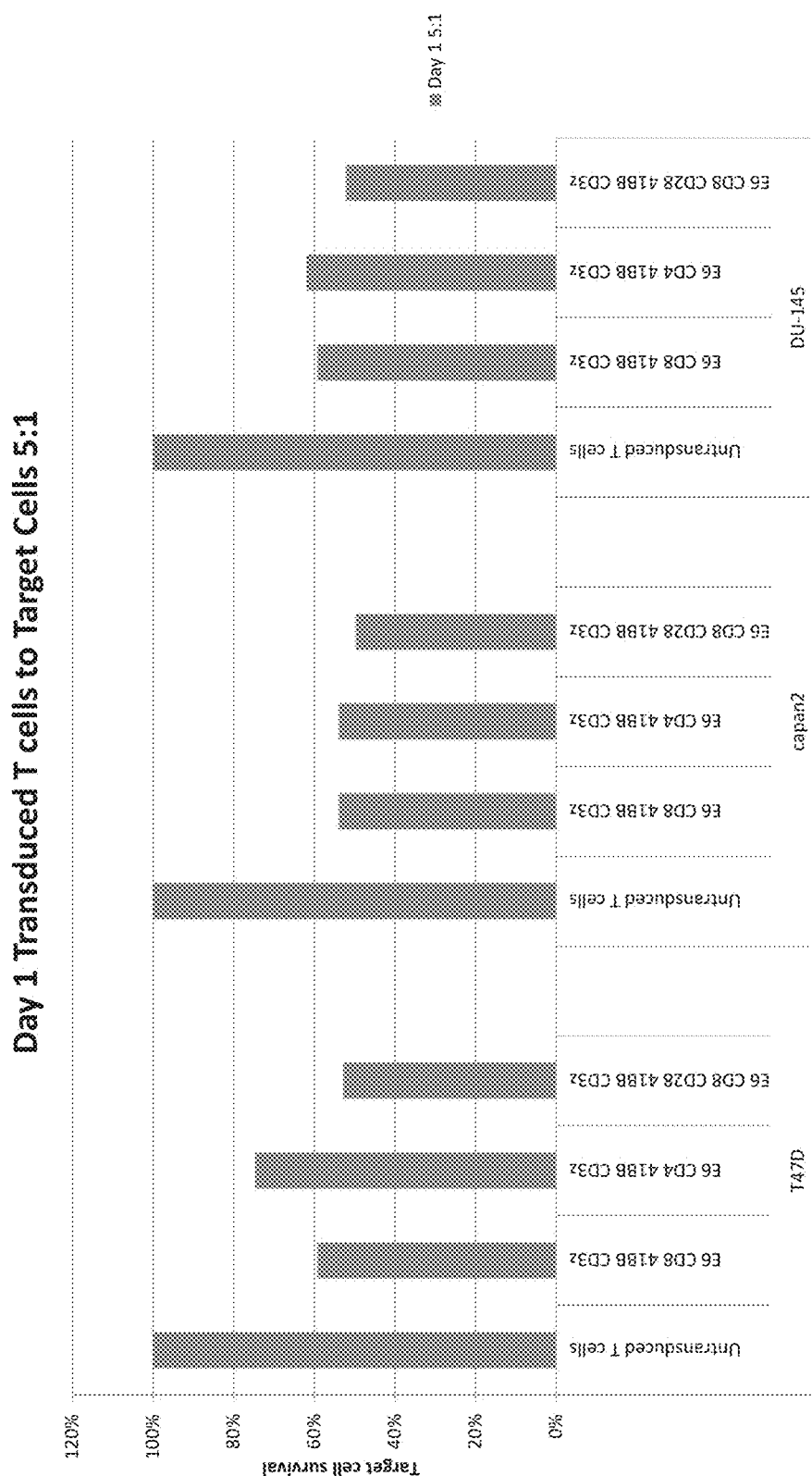
FIG. 37 is a graph of FACS measurements of target cell survival at Day 1 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CART cells were then exposed to the following MUC1* positive cancer cells: T47D breast cancer; capan2 pancreatic cancer; or DU-145 prostate cancer. The ratio of MUC1* targeting CAR T cells to target cells was 5:1. As can be seen from the graph, T cells transduced with a MUC1* targeting CAR have a much greater killing effect on MUC1* cancer cells than the untransduced control T cells. Note that the measurements were taken after 24 hours with only a 5:1 T cell to target cell ratio. Also note that MUC1* targeting CARs that have a CD4 extracellular domain-transmembrane-cytoplasmic tail work equally well as CD8 constructs.
Figure 38:
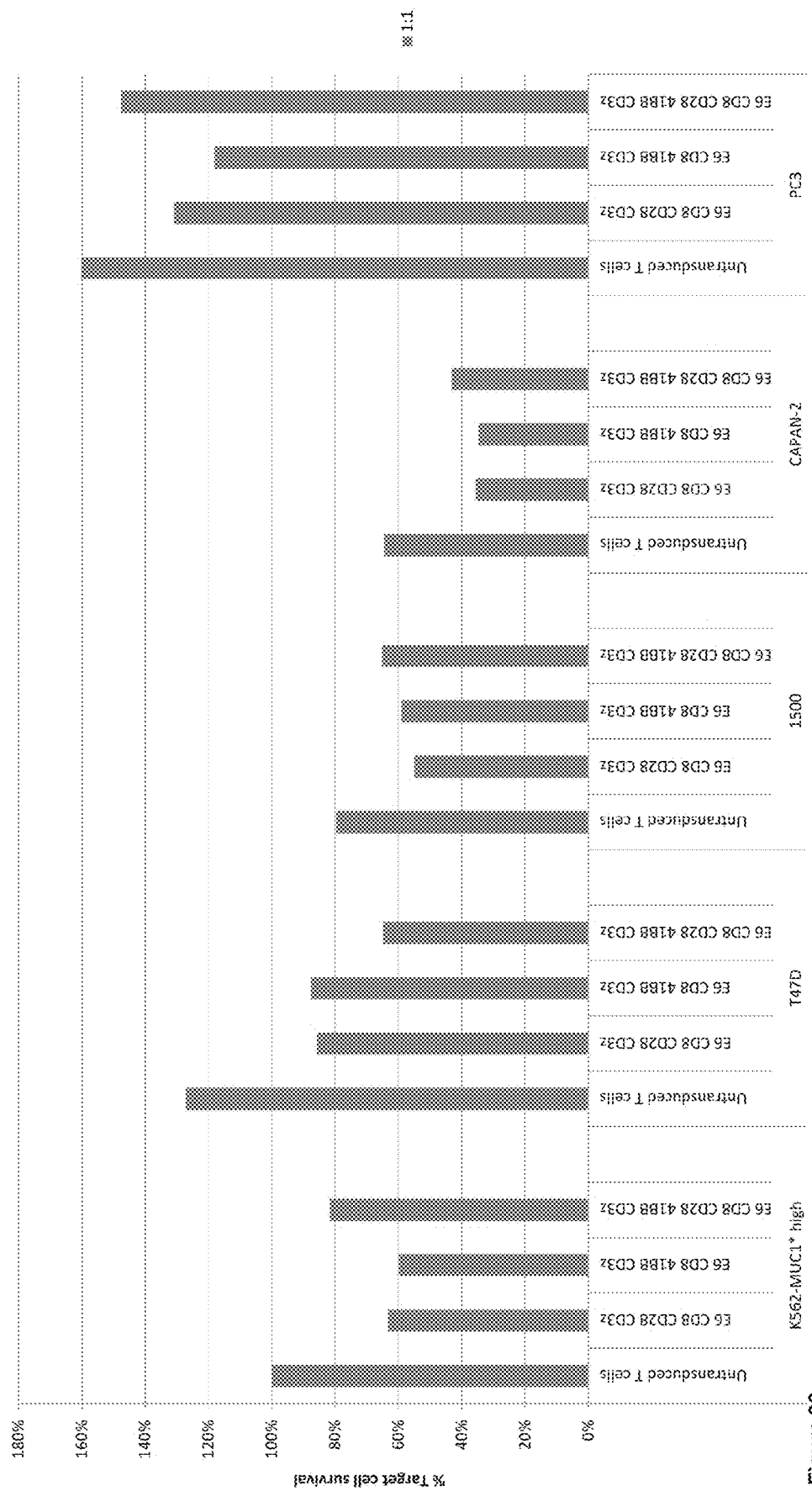
FIG. 38 is a graph of FACS measurements of target cell survival at Day 3 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CAR T cells were then exposed to the following MUC1* positive cancer cells: K562 leukemia cells transfected with MUC1*; T47D breast cancer; 1500 aka ZR-75-1 breast cancer cells; or CAPAN-2 pancreatic cancer cells. In addition to the untransduced T cell controls, the assay was performed on PC3 MUC1* negative prostate cancer cells. The ratio of MUC1* targeting CAR T cells to target cells was 1:1. As can be seen from the graph, T cells transduced with a MUC1* targeting CAR have a much greater killing effect on MUC1* cancer cells than the untransduced control T cells. In addition, the killing effect is specific for MUC1* positive cells. Note that MUC1* targeting CARs that have a CD4 extracellular domain-transmembrane-cytoplasmic tail work equally well as CD8 constructs.
Figure 39:
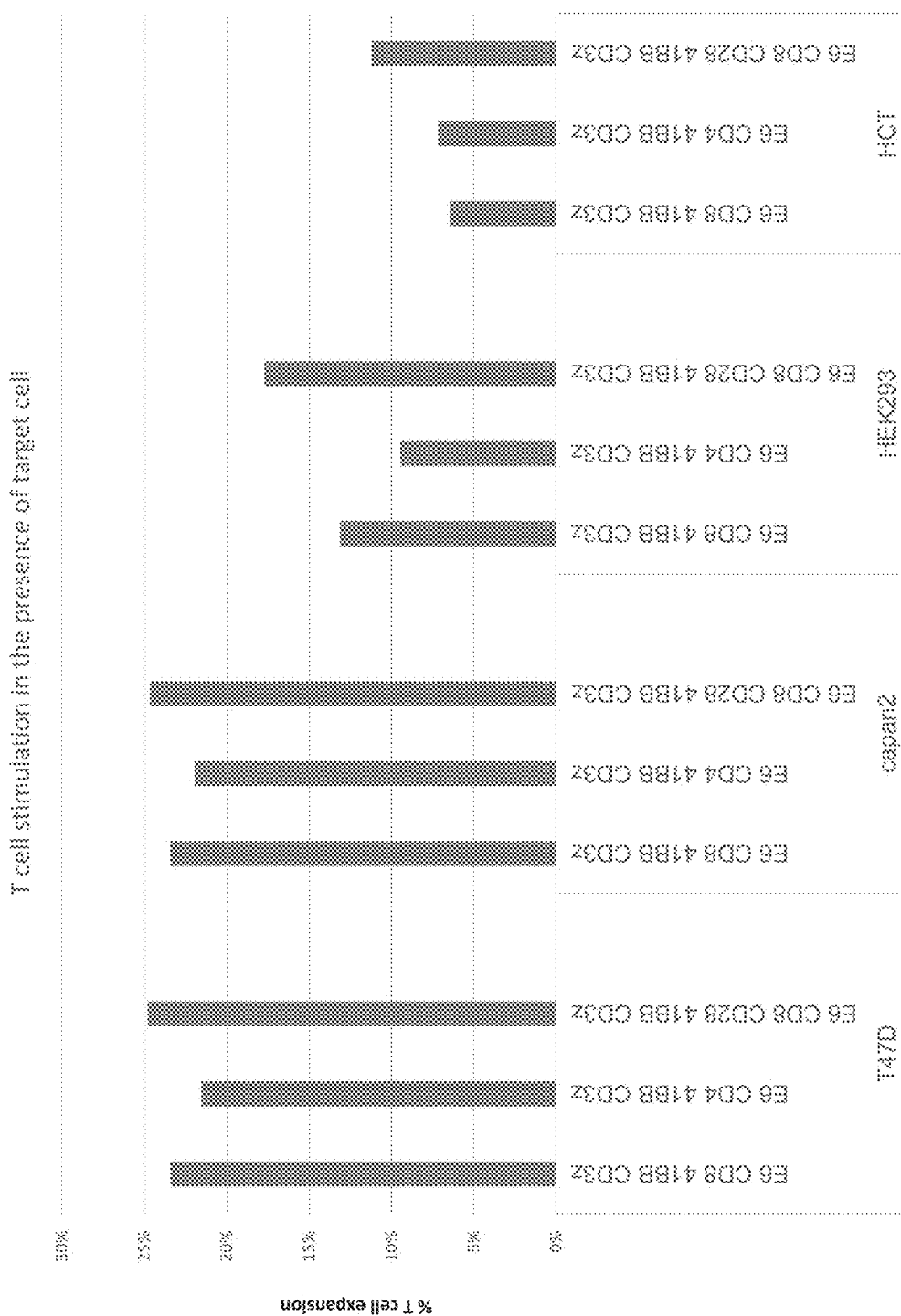
FIG. 39 is a graph of FACS measurements of CAR T cell expansion over 24 hours in co-culture with target cells at a ratio of 5:1 CAR T cells to target cells. The primary human T cells were transduced with a panel of CARs, including humanized MN-E6-CD8-41BB-3z, MN-E6-CD4-41BB-3z, and MN-E6-CD8-CD28-41BB-3z. The CAR T cells were co-cultured with MUC1* positive T47D breast cancer cells, MUC1* positive Capan pancreatic cancer cells, and MUC1-negative cells HCT-116 colon cancer cells and HEK-293 human embryonic kidney cells. As can be seen from the graph, the CAR T population is increased in the presence of MUC1* positive cells.
Figure 40:
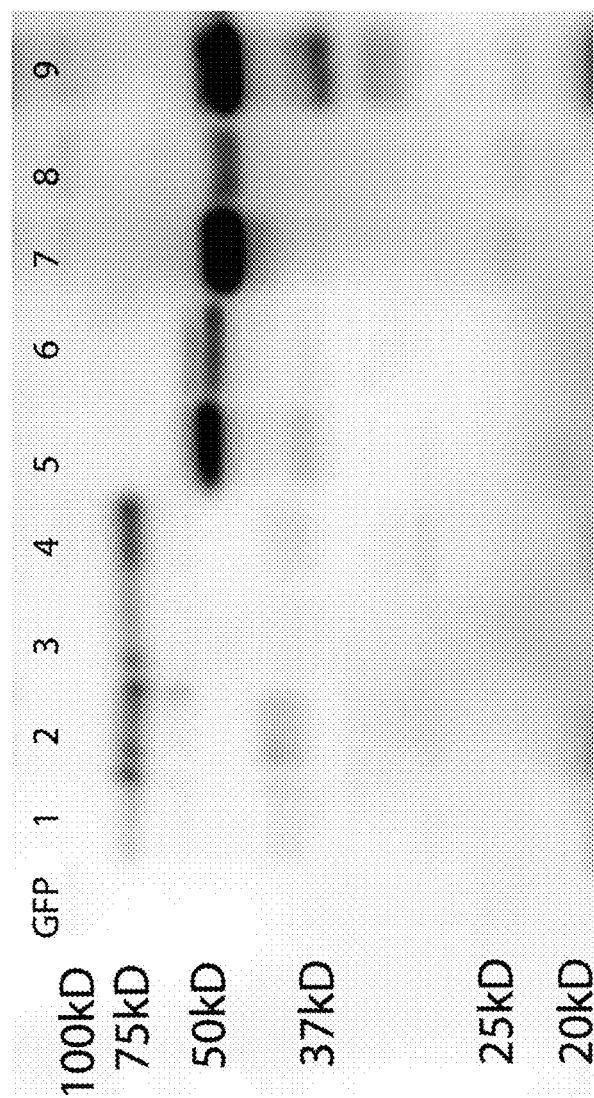
FIG. 40 shows a photograph of a Western blot of MUC1* targeting CARs. From 1 to 9 are:
1. E6scFv-Fc-8-41BB-CD3z (Human Fc as hinge region with CD8 TM);
2: E6scFv-FcH-8-41BB-CD3z (Human Fc hingeless as hinge region with CD8 TM)
3: E6scFv-Fc-4-41BB-CD3z (Human Fc as hinge region with CD4 TM)
4: E6scFv-FcH-4-41BB-CD3z (Human Fc as hingeless hinge region with CD4 TM)
5: E6scFv-IgD-8-41BB-CD3z (hinge region from human IgD with CD8 TM)
6: E6scFv-IgD-4-41BB-CD3z (hinge region from human IgD with CD4 TM)
7: E6scFv-X4-8-41BB-CD3z (Long flexible linker as hinge region with CD8 TM)
8: E6scFv-X4-4-41BB-CD3z (Long flexible linker as hinge region with CD4 TM)
9: E6scFv-8-4-41BB-CD3z (Hinge region from CD8 and CD4 a with CD4 TM).

FIG. 36 is a graph of FACS measurements of target cell survival at Day 3 of co-culture experiment. Primary human T cells were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to MUC1* positive T47D breast cancer cells or MUC1* positive 1500 aka ZR-75-1 breast cancer cells. The ratio of MUC1* targeting CAR T cells to target cells was either 1:1 or 10:1. As can be seen from the graph, T cells transduced with a MUC1* targeting CAR have a much greater killing effect on MUC1* cancer cells than the untransduced control T cells. In addition, the killing effect is much greater when the ratio of T cells: target cells is increased. FIG. 37 is a graph of FACS measurements of target cell survival at Day 1 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CAR T cells were then exposed to the following MUC1* positive cancer cells: T47D breast cancer; capan2 pancreatic cancer; or DU-145 prostate cancer. The ratio of MUC1* targeting CAR T cells to target cells was 5:1. As can be seen from the graph, T cells transduced with a MUC1* targeting CAR have a much greater killing effect on MUC1* cancer cells than the untransduced control T cells. Note that the measurements were taken after 24 hours with only a 5:1 T cell to target cell ratio. Also note that MUC1* targeting CARs that have a CD4 extracellular domain-transmembrane-cytoplasmic tail work equally well as CD8 constructs. FIG. 38 is a graph of FACS measurements of target cell survival at Day 3 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CART cells were then exposed to the following MUC1* positive cancer cells: K562 leukemia cells transfected with MUC1*; T47D breast cancer; 1500 aka ZR-75-1 breast cancer cells; or CAPAN-2 pancreatic cancer cells. In addition to the untransduced T cell controls, the assay was performed on PC3 MUC1* negative prostate cancer cells. The ratio of MUC1* targeting CAR T cells to target cells was 1:1. As can be seen from the graph, T cells transduced with a MUC1* targeting CAR have a much greater killing effect on MUC1* cancer cells than the untransduced control T cells. In addition, the killing effect is specific for MUC1* positive cells. Note that MUC1* targeting CARs that have a CD4 extracellular domain-transmembrane-cytoplasmic tail work equally well as CD8 constructs. FIG. 39 is a graph of FACS measurements of CAR T cell expansion over 24 hours in co-culture with target cells at a ratio of 5:1 CAR T cells to target cells. The primary human T cells were transduced with a panel of CARs, including humanized MN-E6-CD8-41BB-3z, MN-E6-CD4-41BB-3z, and MN-E6-CD8-CD28-41BB-3z. The CAR T cells were co-cultured with MUC1* positive T47D breast cancer cells, MUC1* positive Capan pancreatic cancer cells, and MUC1-negative cells HCT-116 colon cancer cells and HEK-293 human embryonic kidney cells. As can be seen from the graph, the CAR T population is increased in the presence of MUC1* positive cells. FIG. 40 shows a photograph of a Western blot of MUC1* targeting CARs. From 1 to 9 are: 1. MN-E6scFv-Fc-8-41BB-CD3z (Human Fc as hinge region with CD8 TM); 2: MN-E6scFv-FcH-8-41BB-CD3z (Human Fc hingeless as hinge region with CD8 TM); 3: MN-E6scFv-Fc-4-41BB-CD3z (Human Fc as hinge region with CD4 TM); 4: MN-E6scFv-FcH-4-41BB-CD3z (Human Fc as hingeless hinge region with CD4 TM); 5: MN-E6scFv-IgD-8-41BB-CD3z (hinge region from human IgD with CD8 TM); 6: MN-E6scFv-IgD-4-41BB-CD3z (hinge region from human IgD with CD4 TM); 7: MN-E6scFv-X4-8-41BB-CD3z (Long flexible linker as hinge region with CD8 TM); 8: MN-E6scFv-X4-4-41BB-CD3z (Long flexible linker as hinge region with CD4 TM); 9: MN-E6scFv-8-4-41BB-CD3z (Hinge region from CD8 and CD4 a with CD4 TM).

Figure 41:
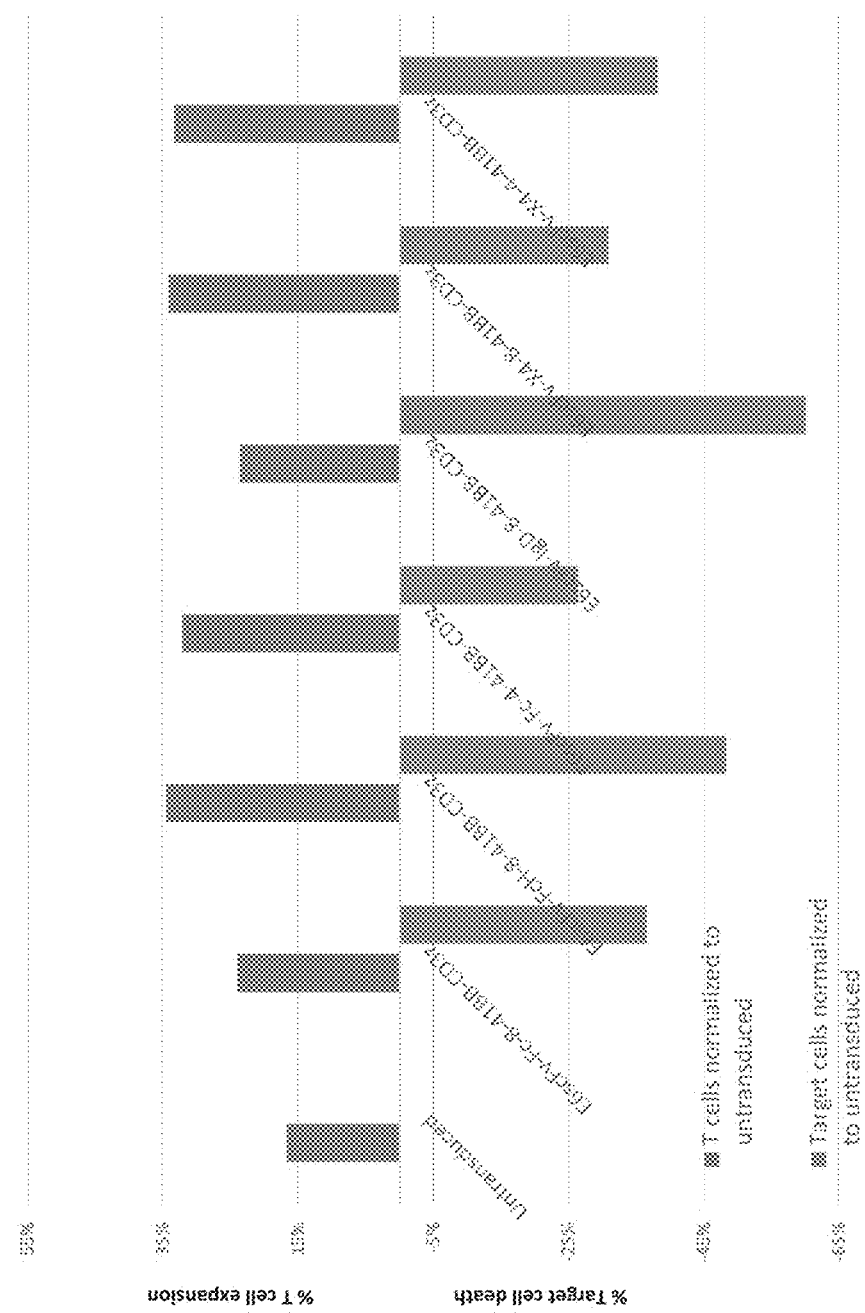
FIG. 41 shows graphs of FACS scans of T47D breast cancer cells co-cultured with human T cells that were transduced with MN-E6scFv-Fc-8-41BB-CD3z, MN-E6scFv-FcH-8-41BB-CD3z, MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

FIG. 41 shows graphs of FACS scans of T47D breast cancer cells co-cultured with human T cells that were transduced with MN-E6scFv-Fc-8-41BB-CD3z, MN-E6scFv-FcH-8-41BB-CD3z (hingeless), MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

Figure 42:
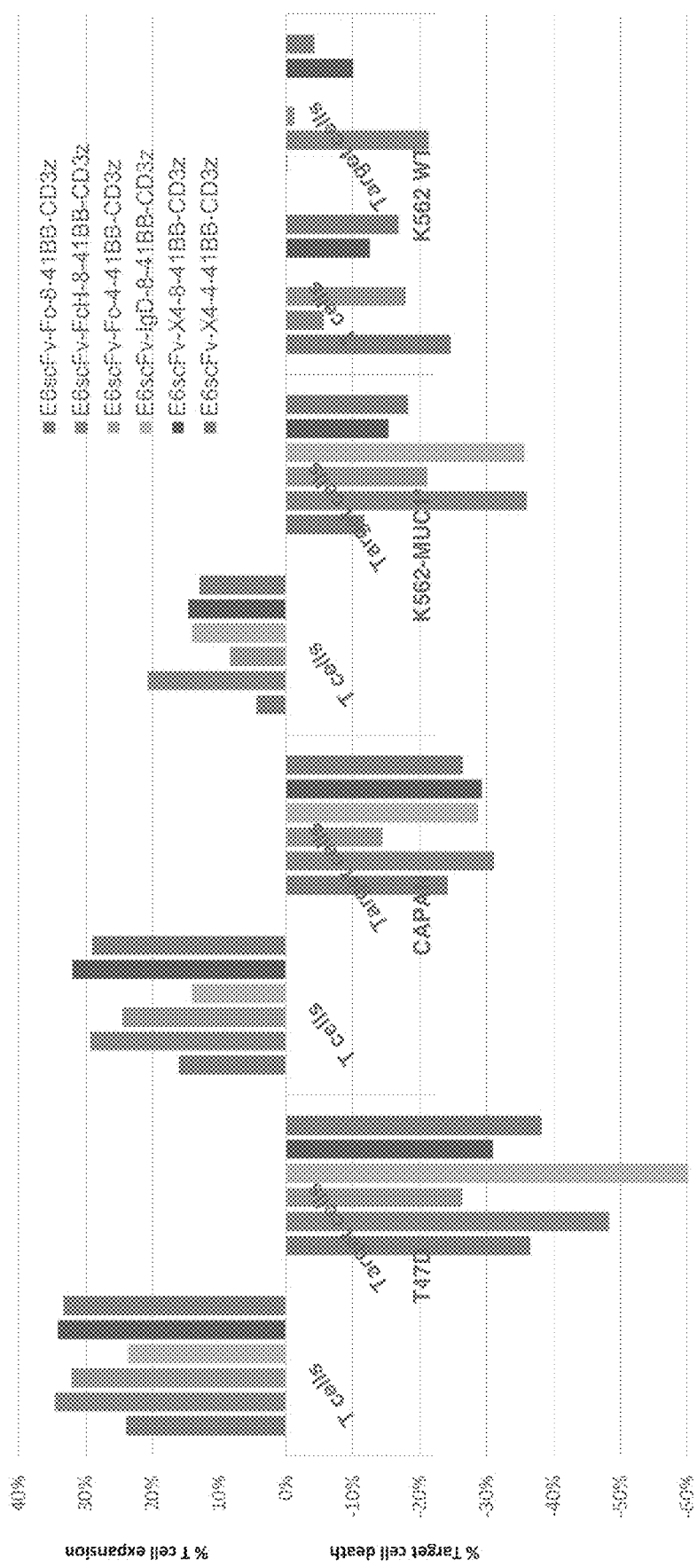
FIG. 42 shows graphs of FACS scans of T47D breast cancer cells, Capan-2 pancreatic cancer cells, K562-MUC1* transfected cells, and K562-wt cells that were co-cultured with human T cells that were transduced with MN-E6scFv-Fc-8-41BB-CD3z, MN-E6scFv-FcH-8-41BB-CD3z, MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

FIG. 42 shows graphs of FACS scans of T47D breast cancer cells, Capan-2 pancreatic cancer cells, K562-MUC1* transfected cells, and K562-wt cells that were co-cultured with human T cells that were transduced with MN-E6scFv-Fc-8-41BB-CD3z, MN-E6scFv-FcH-8-41BB-CD3z, MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

As these experiments demonstrate, the critical portion of a CAR is the antibody fragment that directs the immune cell to the tumor cell. As we will show in the following section, MN-E6 and MN-C2 are specific for the form of MUC1* that is expressed on tumor cells. The next most important part of a CAR is the cytoplasmic tail bearing immune system co-stimulatory domains. The identity of these domains modulates the degree of immune response but in no way effect the specificity. As shown, the identity of the transmembrane portion of a CAR is the least important. It appears that as long as the transmembrane portion has some flexibility and is long enough to allow the antibody fragment to reach its cognate receptor on the tumor cell, it will suffice. This is demonstrated in FIGS. 40-42. CARs comprising the MN-E6 targeting antibody fragment, and intracellular co-stimulatory domains 41BB and CD3-zeta but having a variety of different extracellular, transmembrane and short cytoplasmic tail all worked in that they specifically killed the targeted cells while stimulating the expansion of the host T cells. These CARs with variable mid-sections are: MN-E6scFv-Fc-8-41BB-CD3z (Human Fc as hinge region with CD8 TM); 2: MN-E6scFv-FcH-8-41BB-CD3z (Human Fc hingeless as hinge region with CD8 TM); 3: MN-E6scFv-Fc-4-41BB-CD3z (Human Fc as hinge region with CD4 TM); 4: MN-E6scFv-FcH-4-41BB-CD3z (Human Fc as hingeless hinge region with CD4 TM); 5: MN-E6scFv-IgD-8-41BB-CD3z (hinge region from human IgD with CD8 TM); 6: MN-E6scFv-IgD-4-41BB-CD3z (hinge region from human IgD with CD4 TM); 7: MN-E6scFv-X4-8-41BB-CD3z (Long flexible linker as hinge region with CD8 TM); 8: MN-E6scFv-X4-4-41BB-CD3z (Long flexible linker as hinge region with CD4 TM); 9: MN-E6scFv-8-4-41BB-CD3z (Hinge region from CD8 and CD4 a with CD4 TM).

One aspect of the invention is a method for treating a patient diagnosed with, suspected of having, or at risk of developing a MUC1 positive or MUC1* positive cancer, wherein the patient is administered an effective amount of immune cells that have been transduced with a MUC1* targeting CAR, wherein the CAR is chosen from among the group consisting of MN-E6-CD8-3z; MN-E6-CD4-3z; MN-E6-CD8-CD28-3z; MN-E6-CD4-CD28-3z; MN-E6-CD8-41BB-3z; MN-E6-CD4-41BB-3z; MN-E6-CD8-CD28-41BB-3z; MN-E6-CD4-CD28-41BB-3z; MN-E6scFv-Fc-8-41BB-CD3z; MN-E6scFv-FcH-8-41BB-CD3z; MN-E6scFv-Fc-4-41BB-CD3z; MN-E6scFv-FcH-4-41BB-CD3z; MN-E6scFv-IgD-8-41BB-CD3z; MN-E6scFv-IgD-4-41BB-CD3z; MN-E6scFv-X4-8-41BB-CD3z; MN-E6scFv-X4-4-41BB-CD3z; MN-E6scFv-8-4-41BB-CD3z, or any of the aforementioned CARs wherein the MN-E6 is replaced by MN-C2, MN-C3 or MN-C8. Another aspect of the invention is a method for treating a patient diagnosed with, suspected of having, or at risk of developing a cancer, wherein the patient is administered an effective amount of immune cells that have been transduced with one of the aforementioned CARs wherein the MN-E6 is replaced by a peptide comprising antibody variable domain fragments that are specific for a cancer antigen. In any of the above methods, the immune cell may be a T cell and may further be isolated from the patient to be treated.

Specificity of Anti-MUC1* Targeting Antibodies

Figure 43:
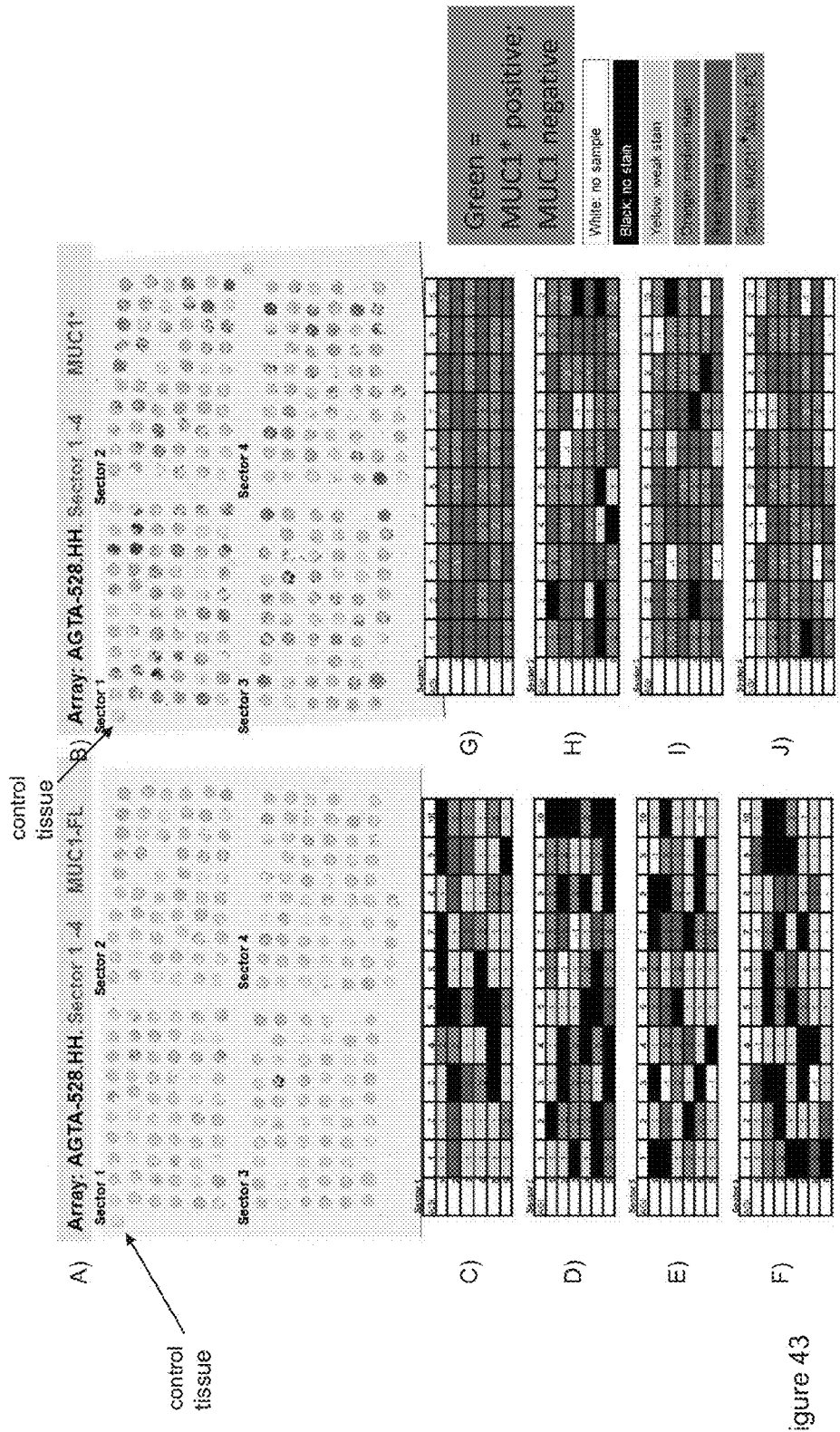
FIG. 43 are photographs of breast cancer tissue arrays. A) was stained with VU4H5 which recognizes MUC1-FL (full length); B) was stained with mouse monoclonal antibody MN-C2 which recognizes cancerous MUC1*. Following automated staining (Clarient Diagnostics), the tissue staining was scored using Allred scoring method which combines an intensity score and a distribution score. C,D,E,F are color coded graphs showing the score calculated for MUC1 full-length staining for each patient's tissue. G,H,I,J are color coded graphs showing the score calculated for MUC1* staining for each patient's tissue.
Figure 44:
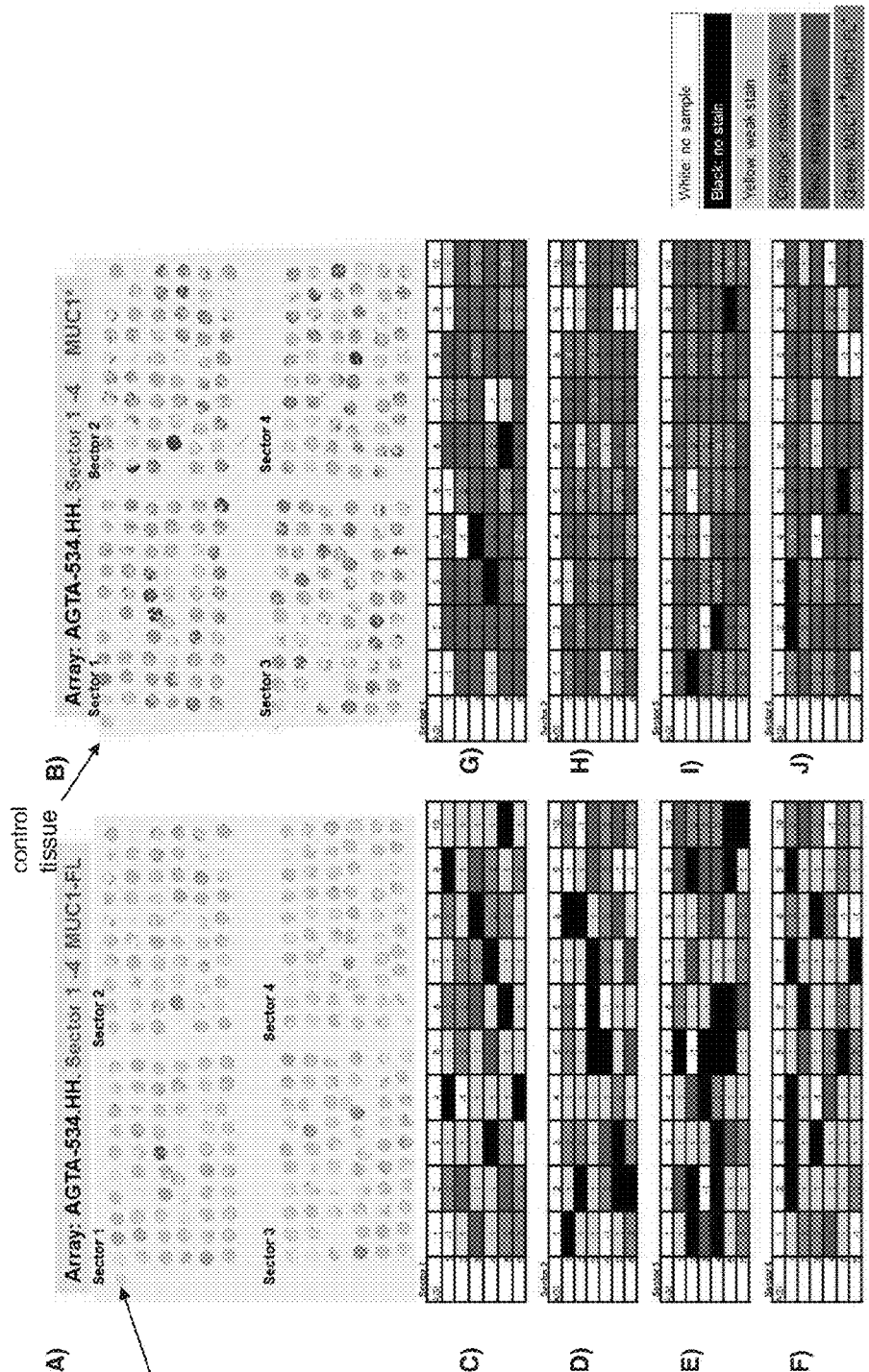
FIG. 44 are photographs of breast cancer tissue arrays. A) was stained with VU4H5 which recognizes MUC1-FL (full length); B) was stained with mouse monoclonal antibody MN-C2 which recognizes cancerous MUC1*. Following automated staining (Clarient Diagnostics), the tissue staining was scored using Allred scoring method which combines an intensity score and a distribution score. C,D,E,F are color coded graphs showing the score calculated for MUC1 full-length staining for each patient's tissue. G,H,I,J are color coded graphs showing the score calculated for MUC1* staining for each patient's tissue.
Figure 45:
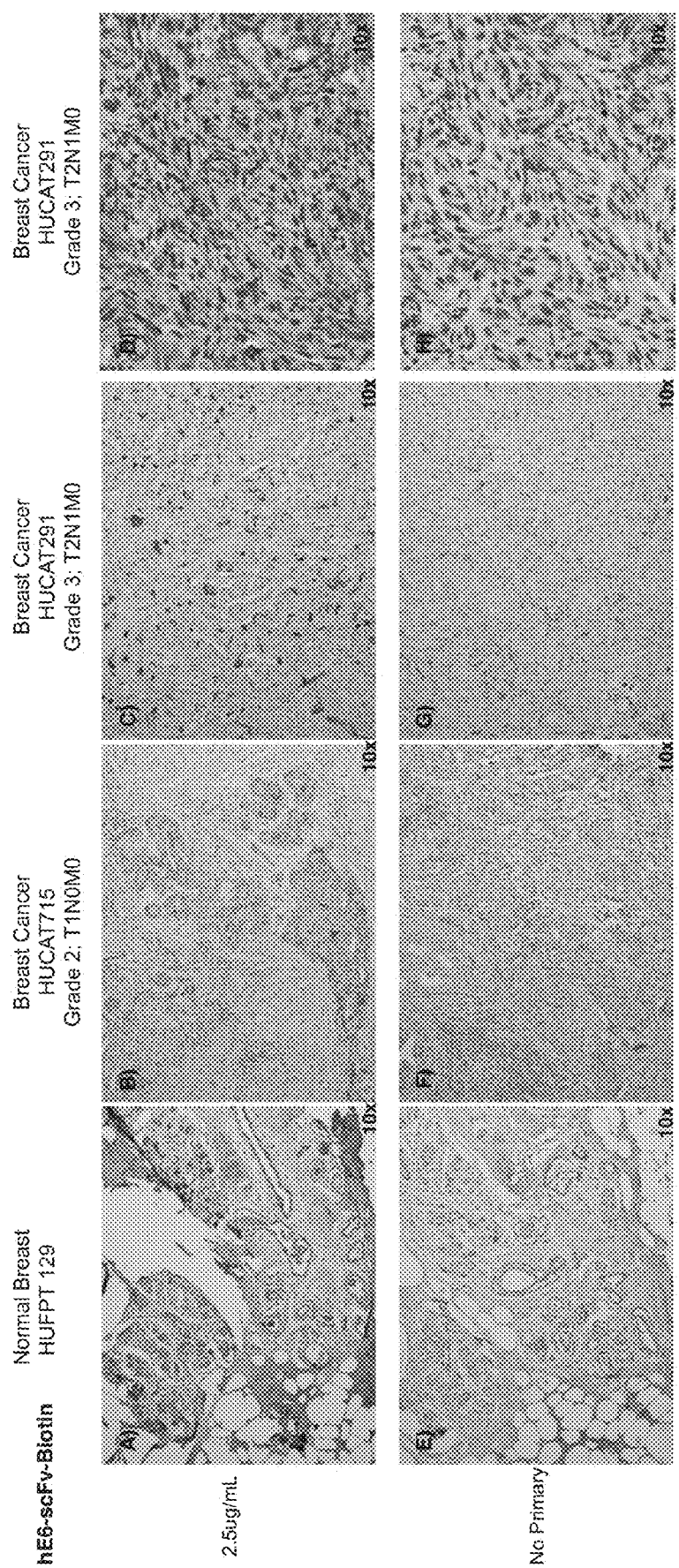
FIG. 45 shows photographs of normal breast and breast cancer tissues stained with humanized MN-E6-scFv-Fc biotinylated anti-MUC1* antibody at 2.5 ug/mL, then stained with a secondary streptavidin HRP antibody. A) is a normal breast tissue. B-D are breast cancer tissues from patients as denoted in the figure. E-H are photographs of the corresponding serial sections that were stained with the secondary antibody alone.
Figure 46:
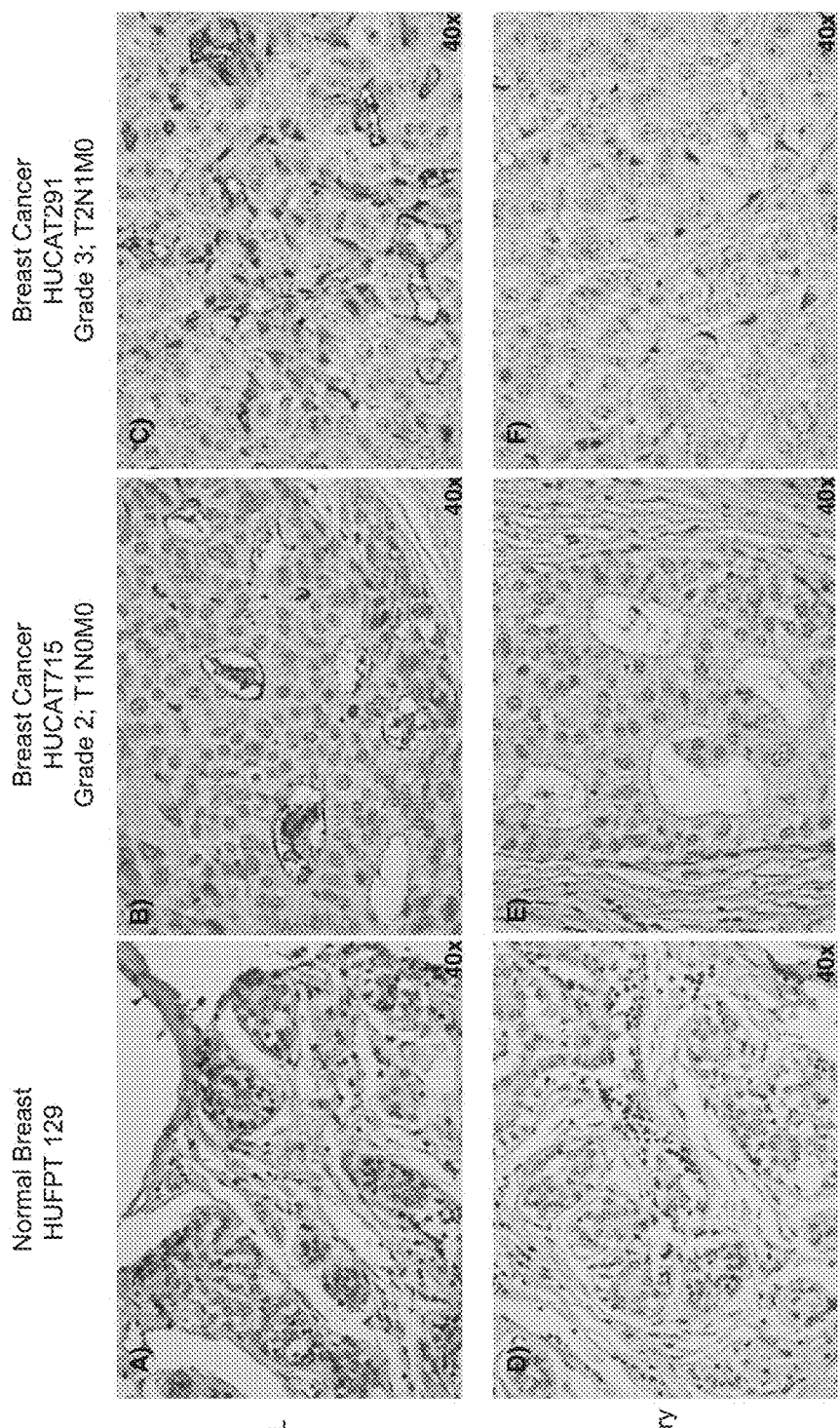
FIG. 46 shows photographs of normal breast and breast cancer tissues stained with humanized MN-E6-scFv-Fc biotinylated anti-MUC1* antibody at 2.5 ug/mL, then stained with a secondary streptavidin HRP antibody. A) is a normal breast tissue. B-C are breast cancer tissues from patients as denoted in the figure. D-F are photographs of the corresponding serial sections that were stained with the secondary antibody alone.
Figure 47:
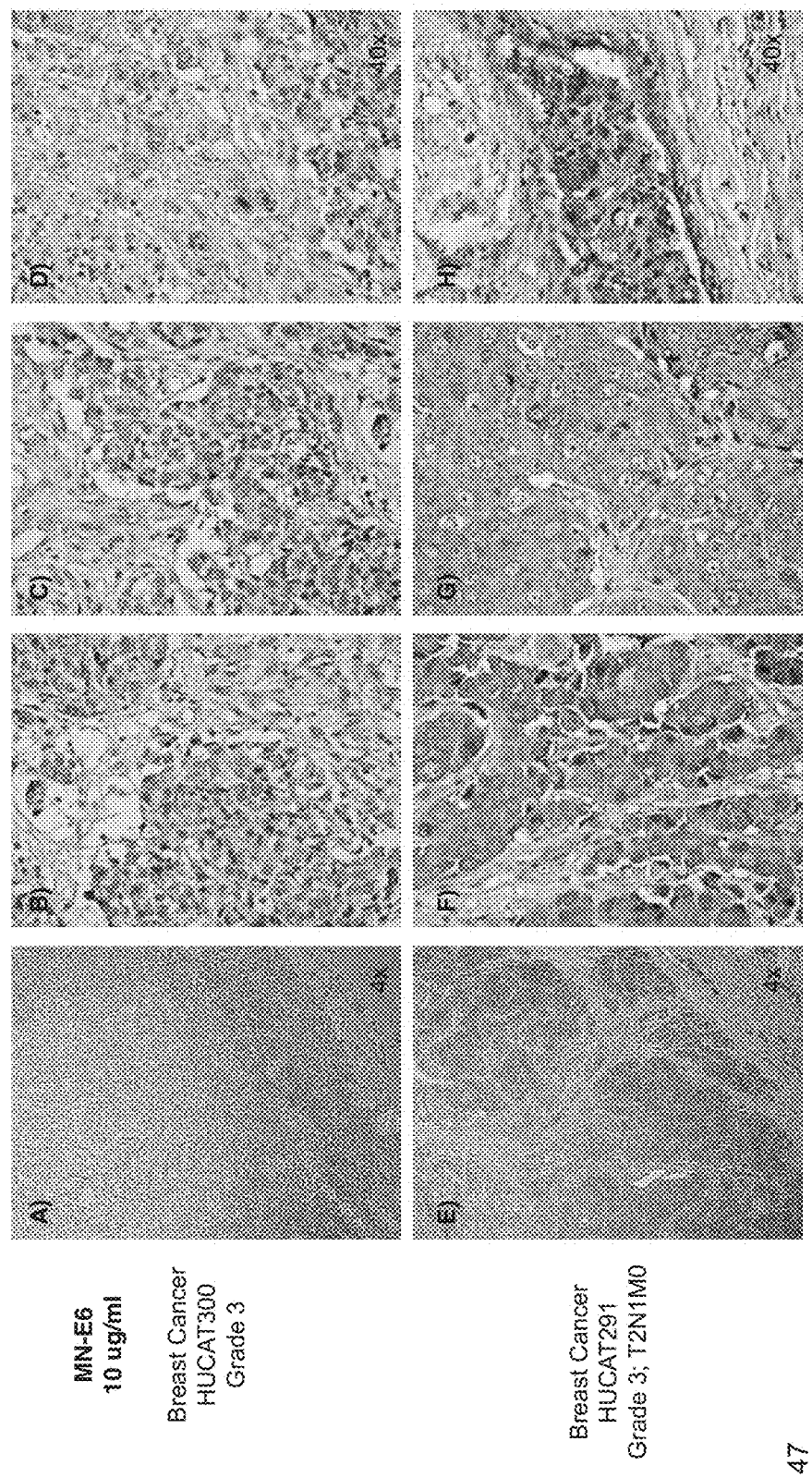
FIG. 47 shows photographs of breast cancer tissues stained with MN-E6 anti-MUC1* antibody at 10 ug/mL, then stained with a rabbit anti mouse secondary HRP antibody. A-D are breast cancer tissues from patient #300. E-H are breast cancer tissues from metastatic patient #291.
Figure 48:
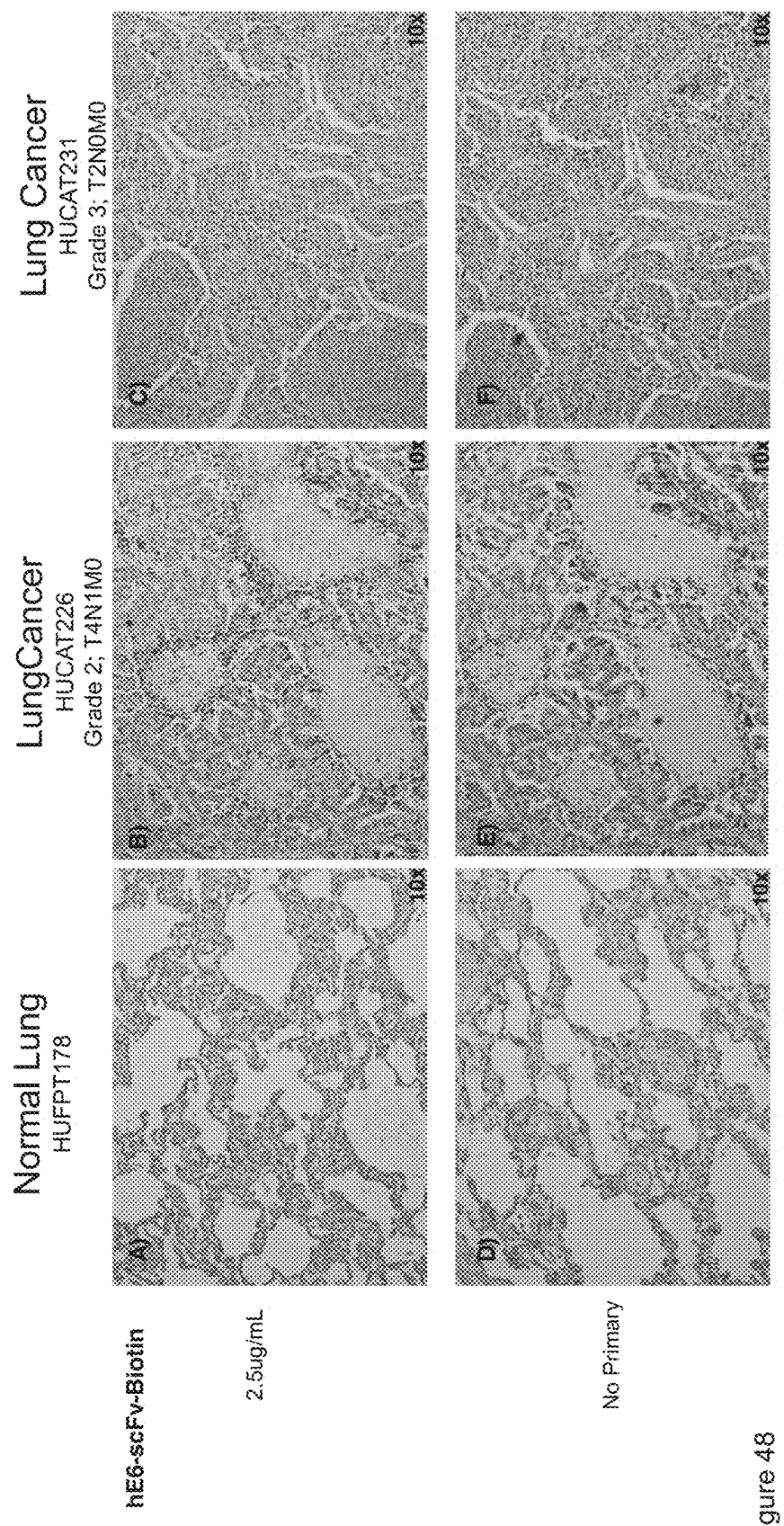
FIG. 48 shows photographs of normal lung and lung cancer tissues stained with humanized MN-E6-scFv-Fc biotinylated anti-MUC1* antibody at 2.5 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.
Figure 49:
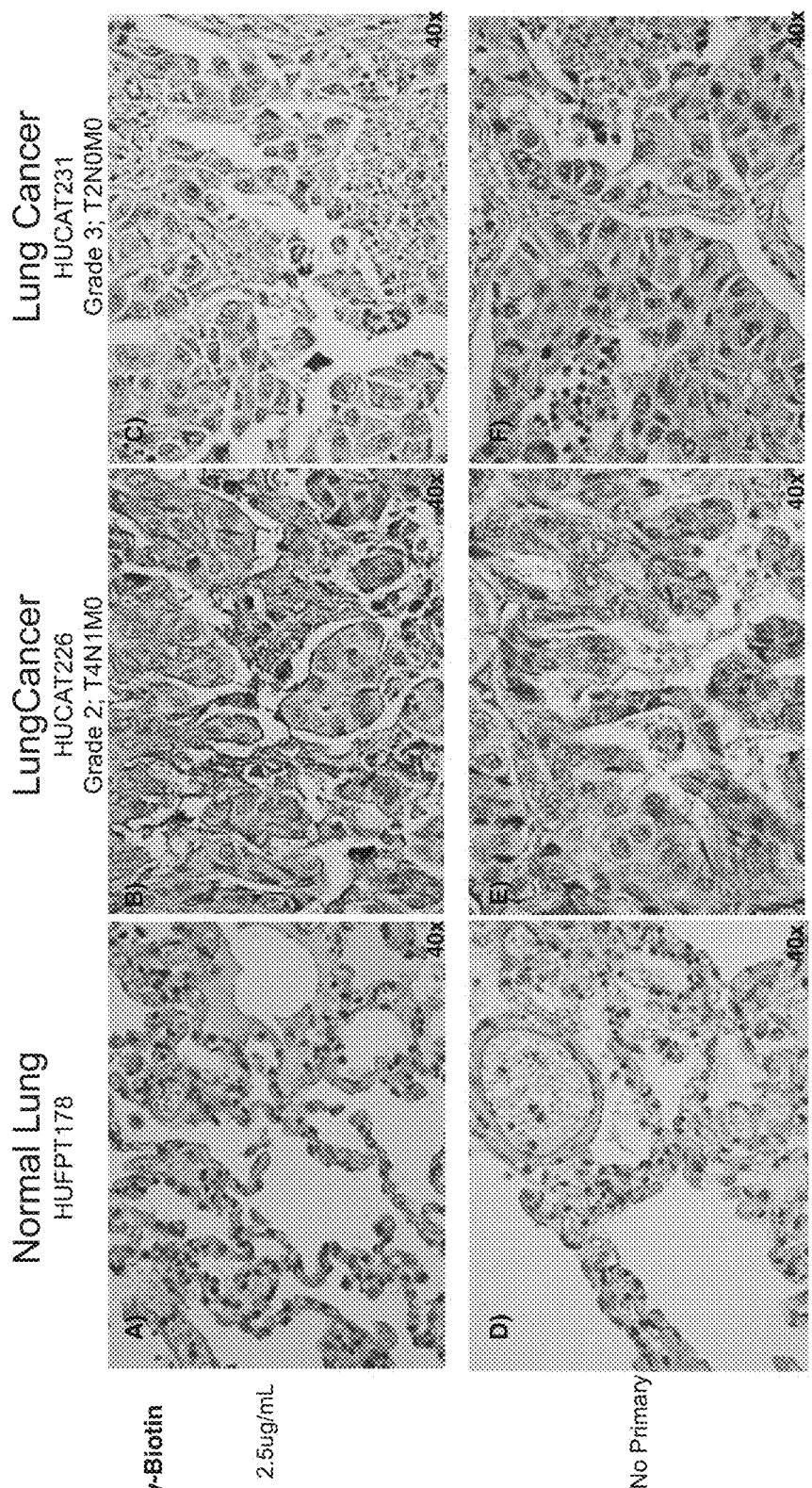
FIG. 49 shows photographs of normal lung and lung cancer tissues stained with humanized MN-E6-scFv-Fc biotinylated anti-MUC1* antibody at 2.5 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.
Figure 50:
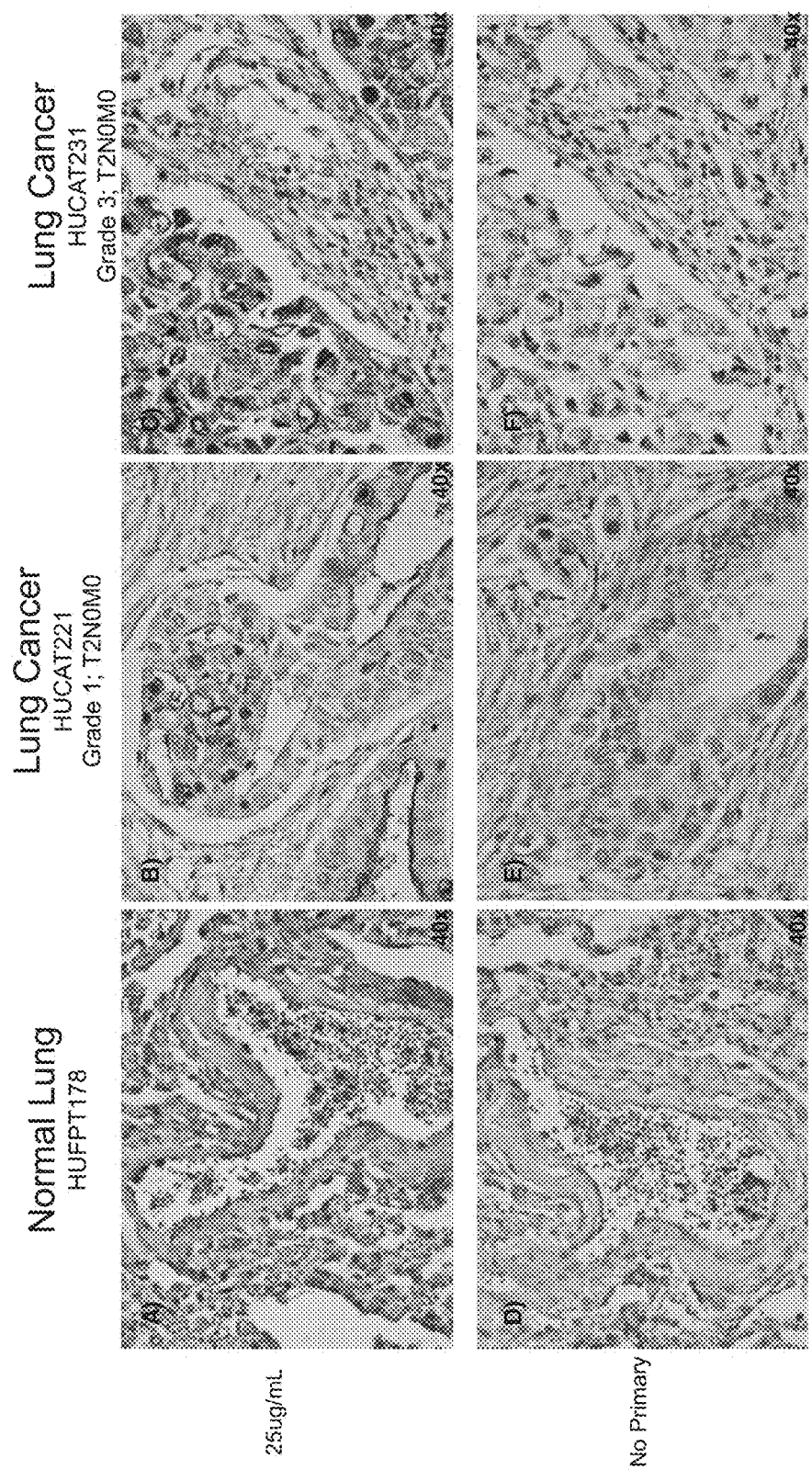
FIG. 50 shows photographs of normal lung and lung cancer tissues stained with humanized MN-E6-scFv-Fc biotinylated anti-MUC1* antibody at 25 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.
Figure 51:
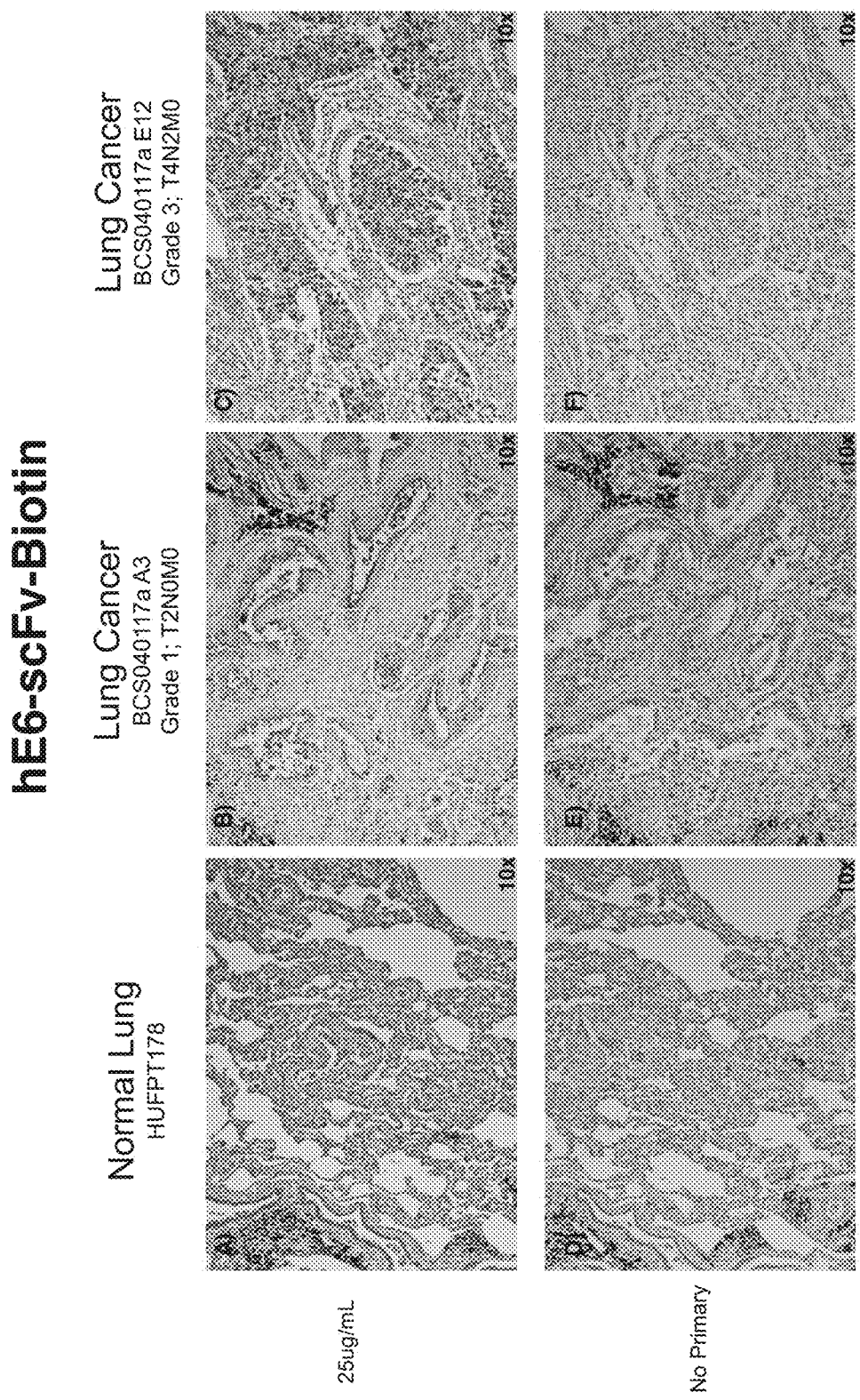
FIG. 51 shows photographs of normal lung and lung cancer tissues stained with humanized MN-E6-scFv-Fc biotinylated anti-MUC1* antibody at 25 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.
Figure 52:
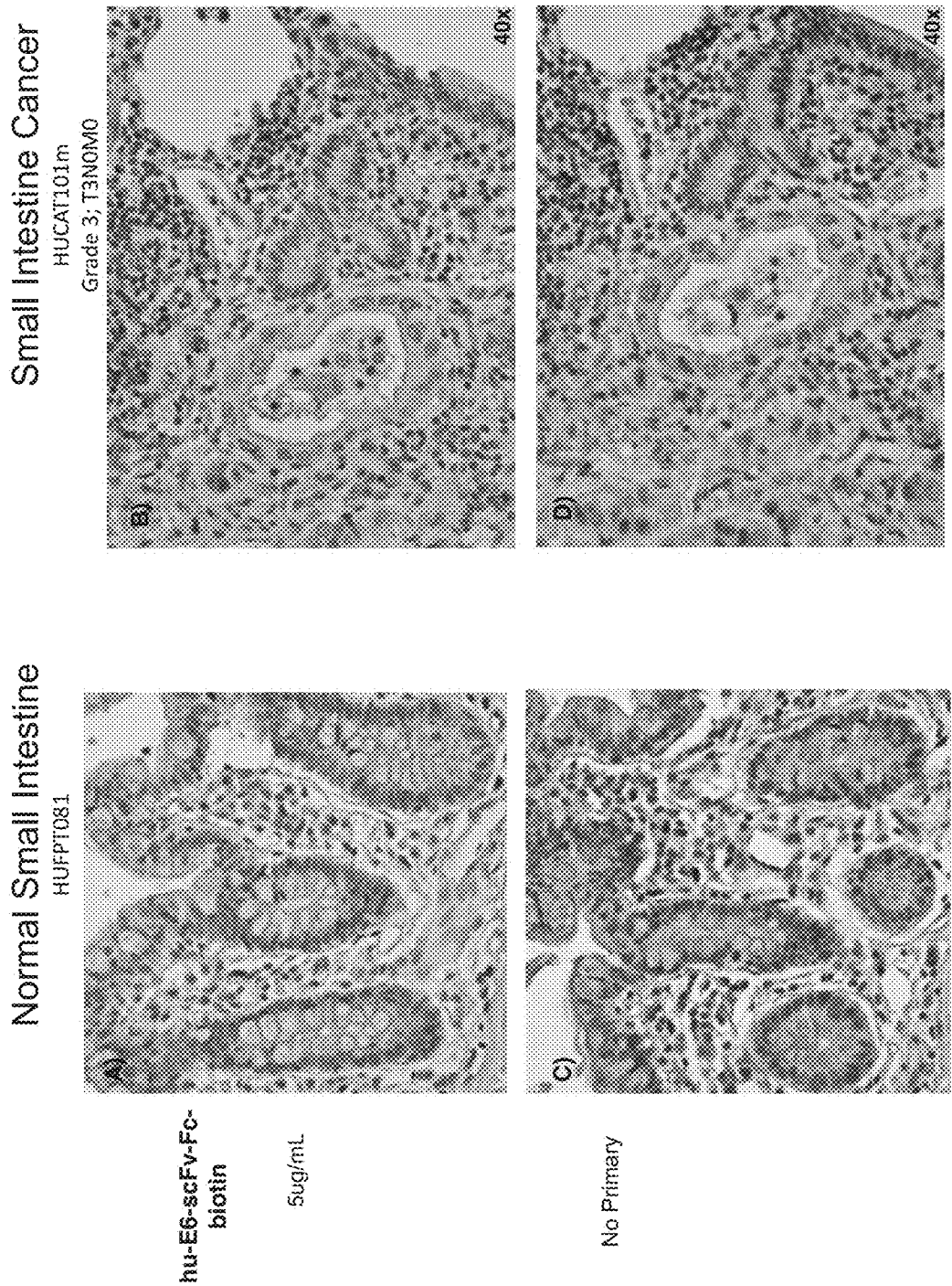
FIG. 52 shows photographs of normal small intestine and cancerous small intestine tissues stained with humanized MN-E6-scFv-Fc biotinylated anti-MUC1* antibody at 5 ug/mL, then stained with a secondary streptavidin HRP antibody. A) is a normal small intestine tissue. B) is small intestine cancer from patient as denoted in the figure. C,D are photographs of the corresponding serial sections that were stained with the secondary antibody alone.
Figure 53:
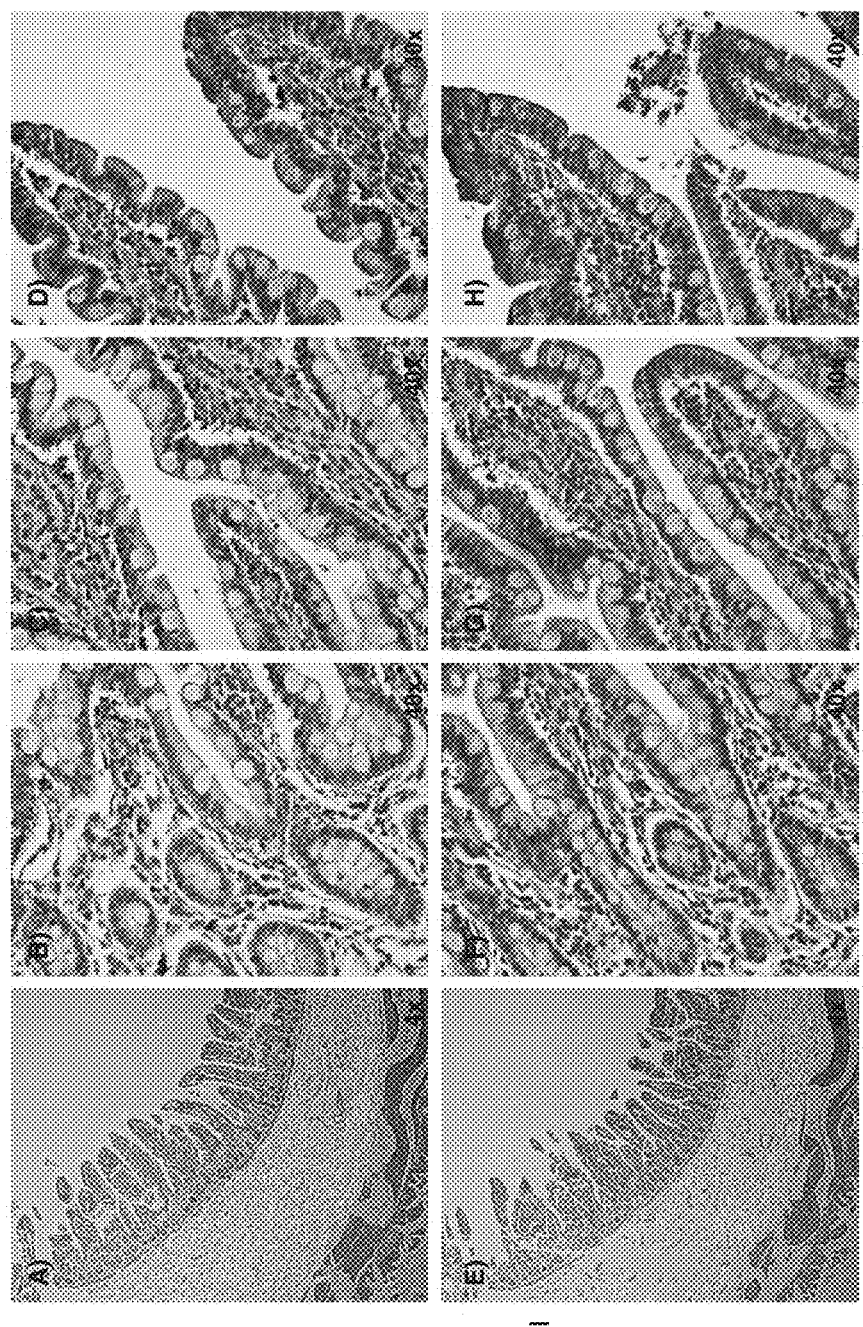
FIG. 53 shows photographs of normal small intestine tissues stained with humanized MN-E6-scFv-Fc anti-MUC1* antibody at 50 ug/mL, then stained with a secondary goat-anti-human HRP antibody. A-D are normal small intestine tissue. E-H are photographs of the corresponding serial sections that were stained with the secondary antibody alone.
Figure 54:
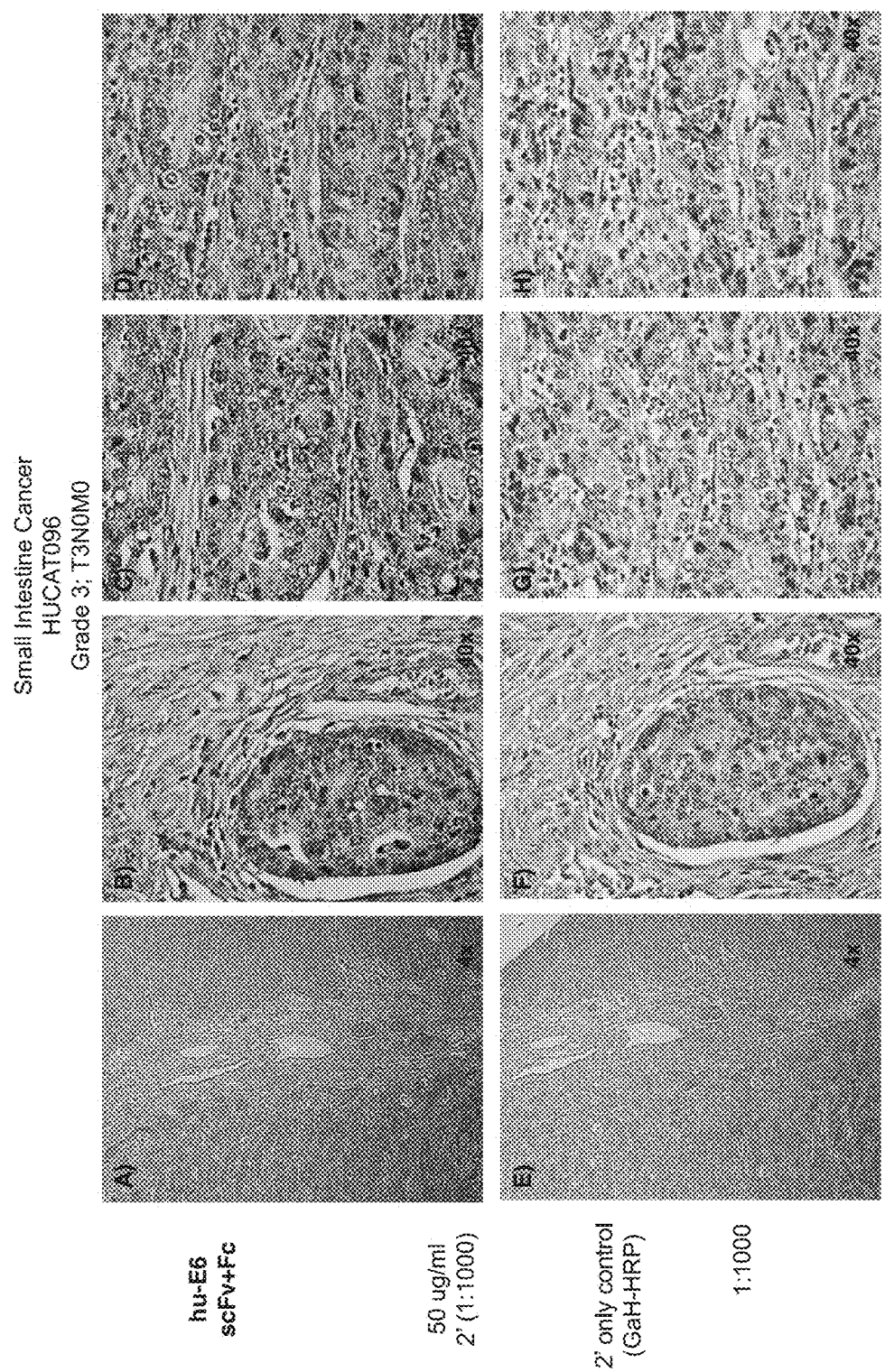
FIG. 54 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone.
Figure 55:
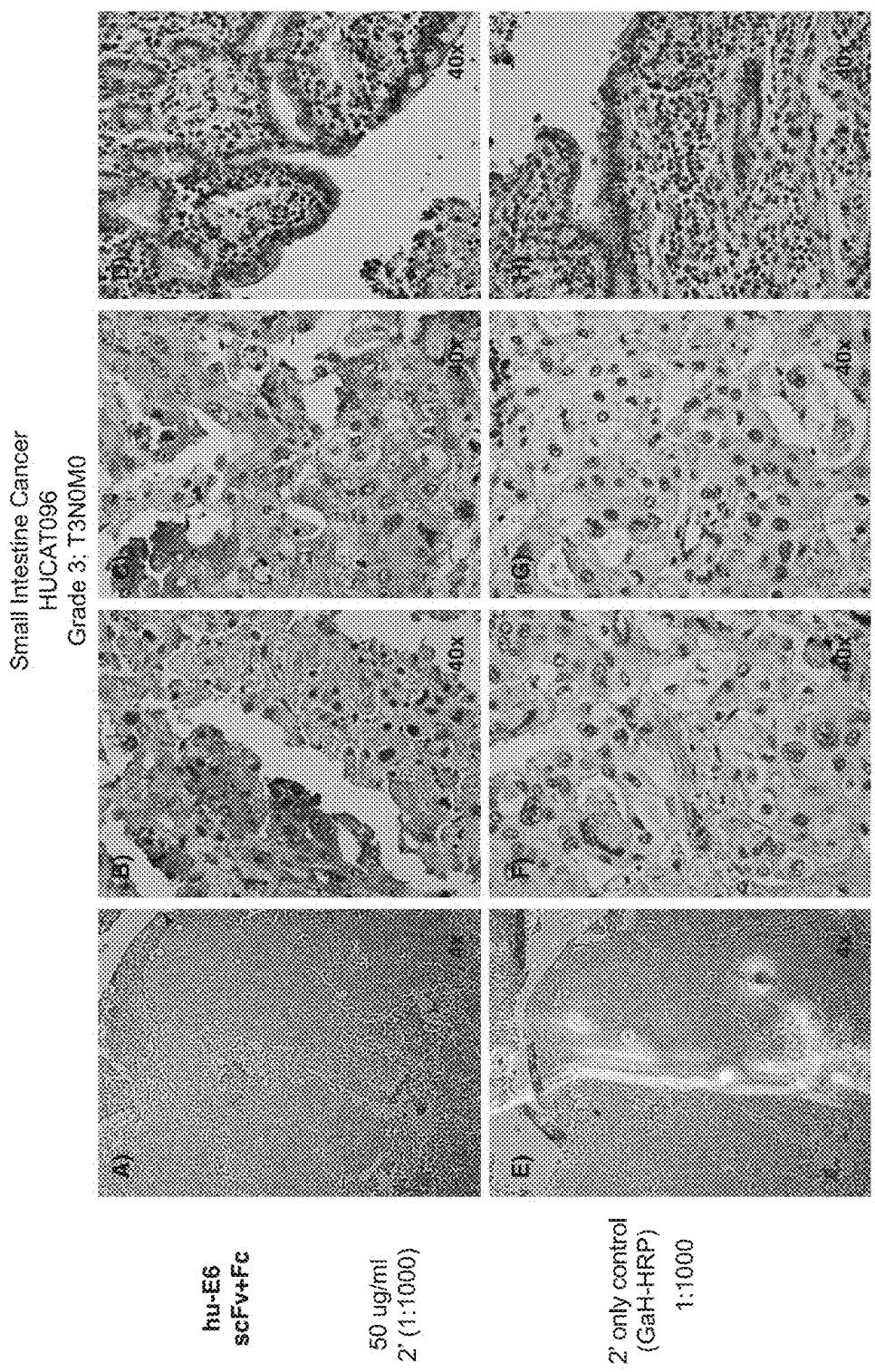
FIG. 55 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone.
Figure 56:
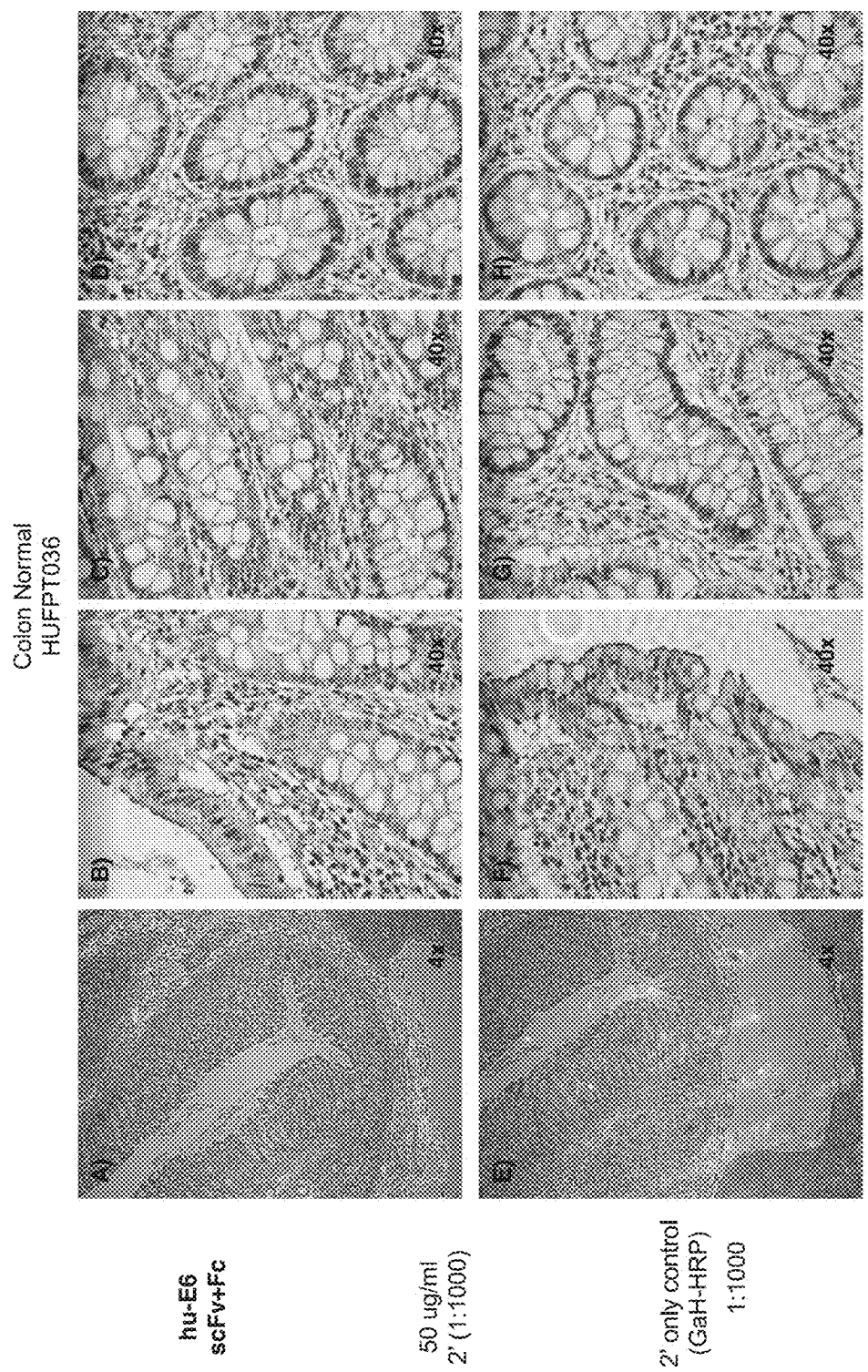
FIG. 56 shows photographs of normal colon tissues stained with humanized MN-E6-scFv-Fc anti-MUC1* antibody at 50 ug/mL, then stained with a secondary goat-anti-human HRP antibody. A-D are normal colon. E-H are photographs of the corresponding serial sections that were stained with the secondary antibody alone.
Figure 57:
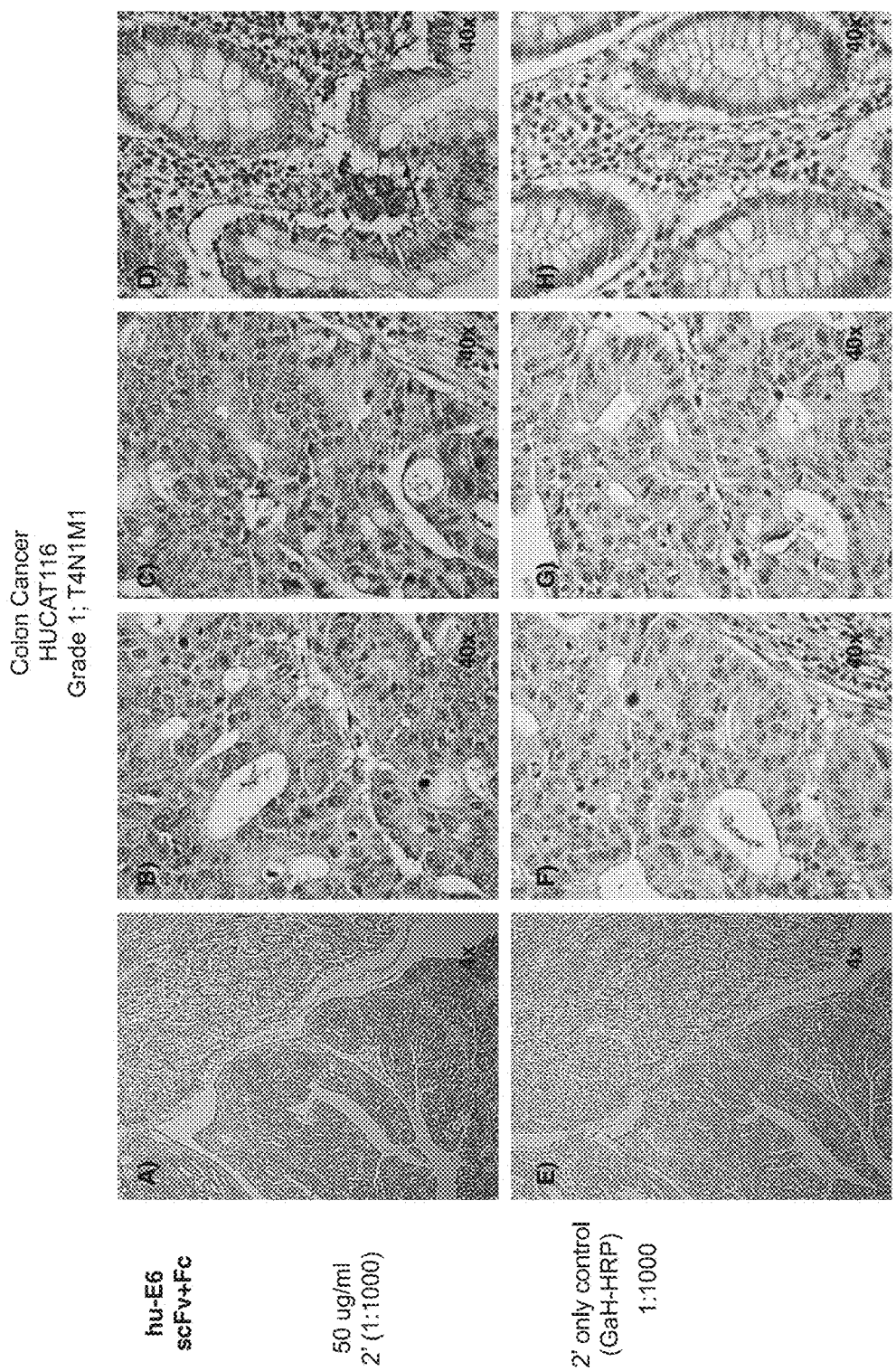
FIG. 57 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone.
Figure 58:
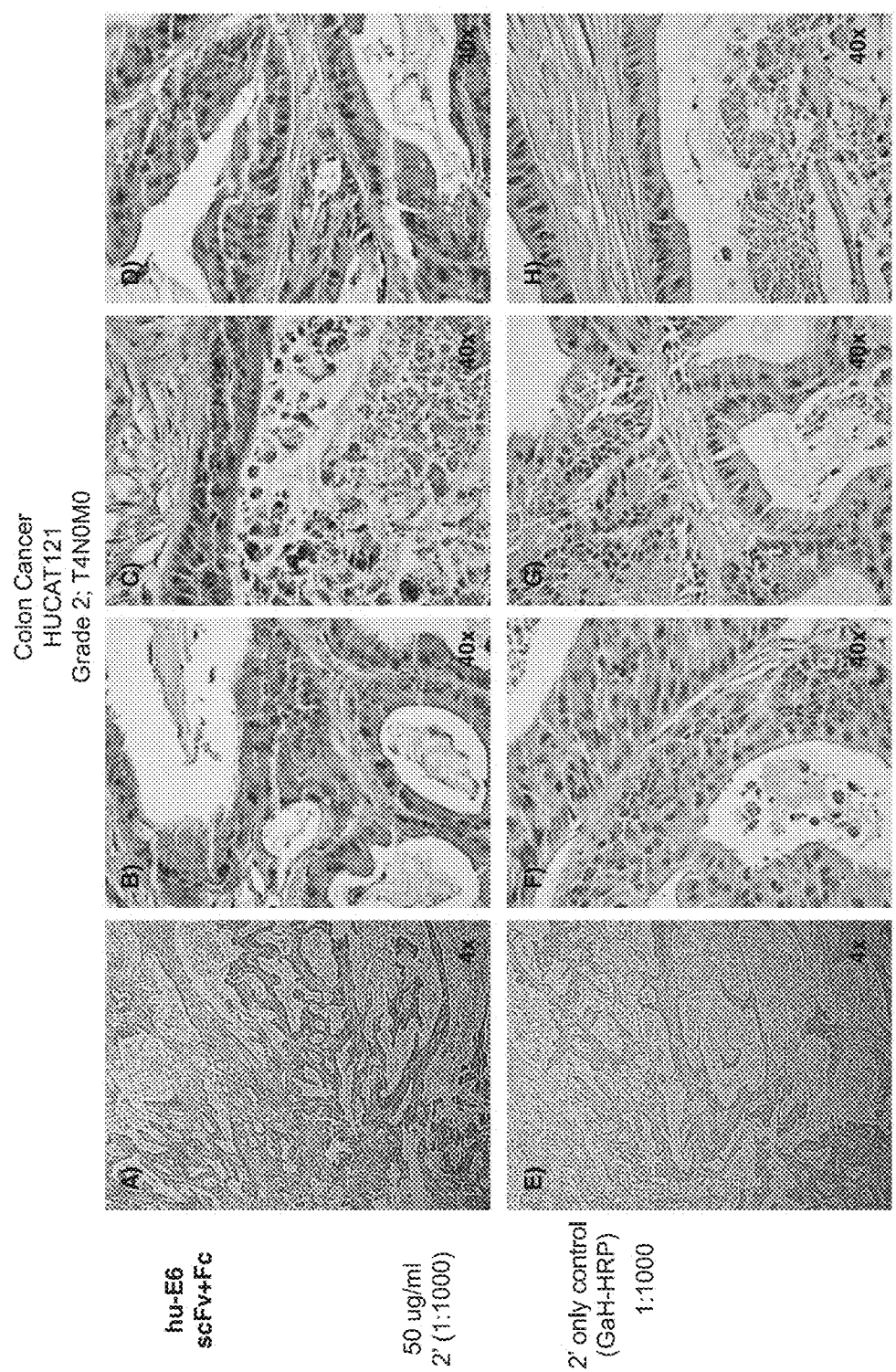
FIG. 58 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a Grade 2 patient as denoted in figure. E-H are photographs of the corresponding serial sections that were stained with the secondary antibody alone.
Figure 59:
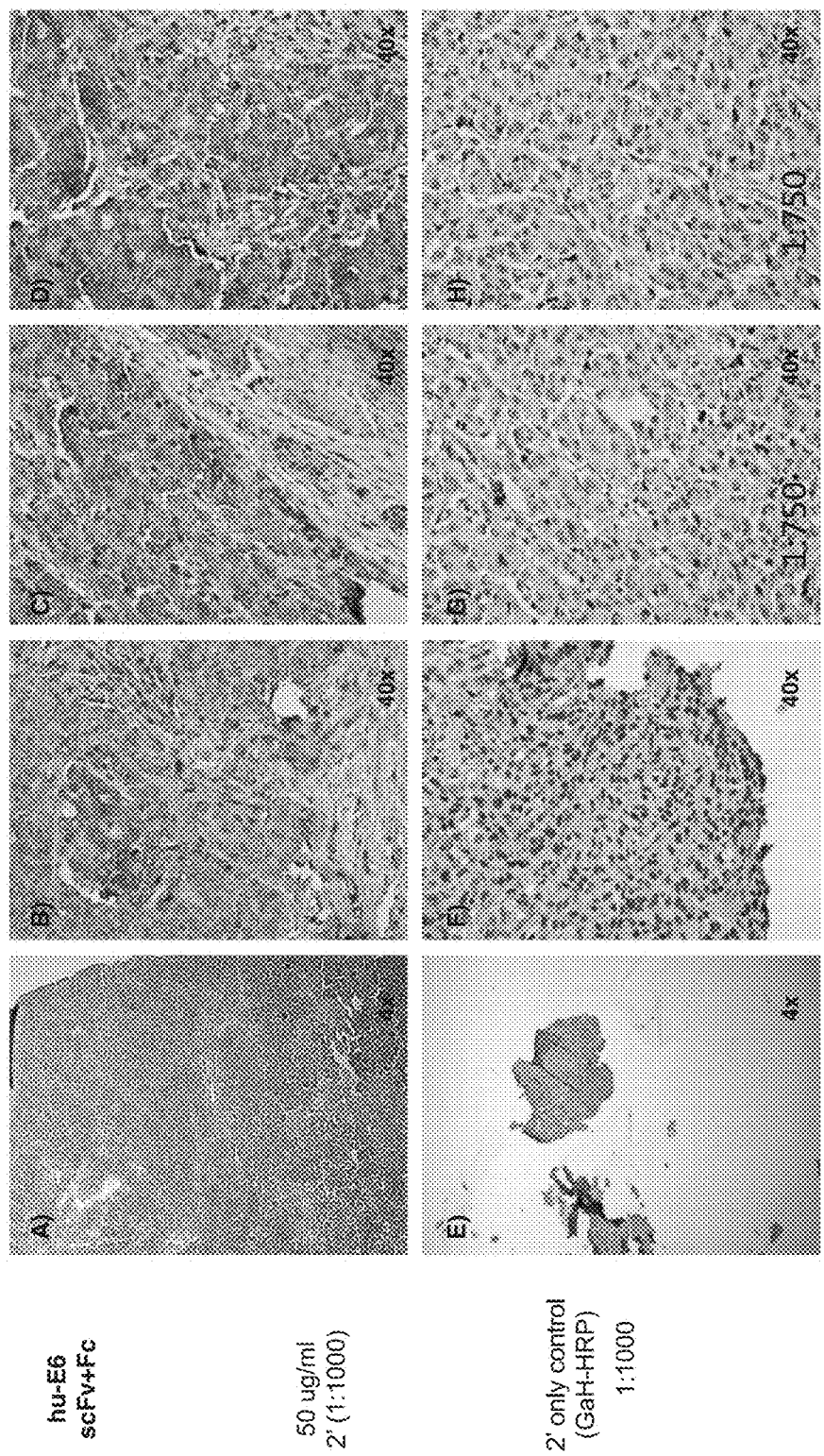
FIG. 59 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone.
Figure 60:
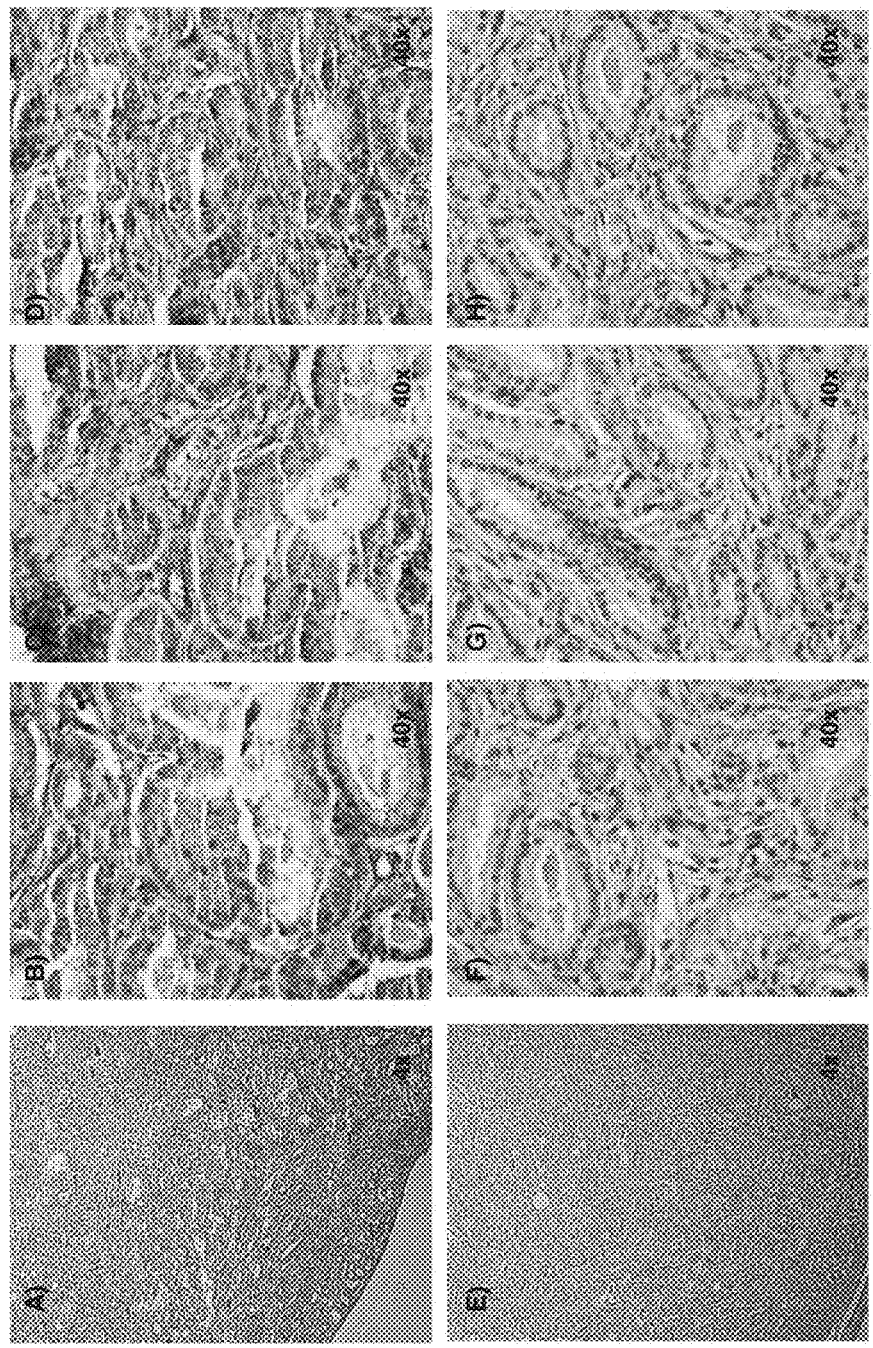
FIG. 60 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.
Figure 61:
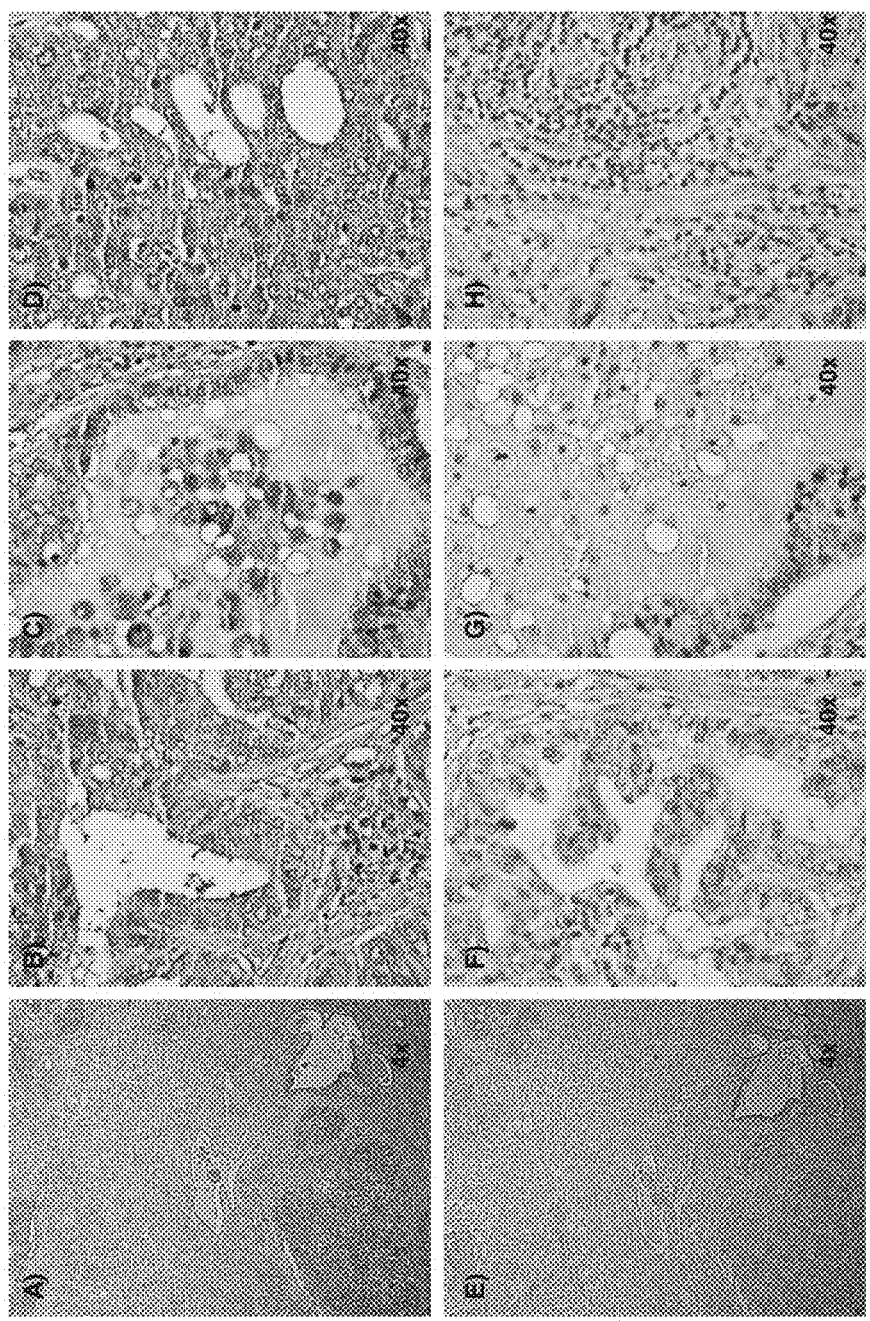
FIG. 61 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.
Figure 62:
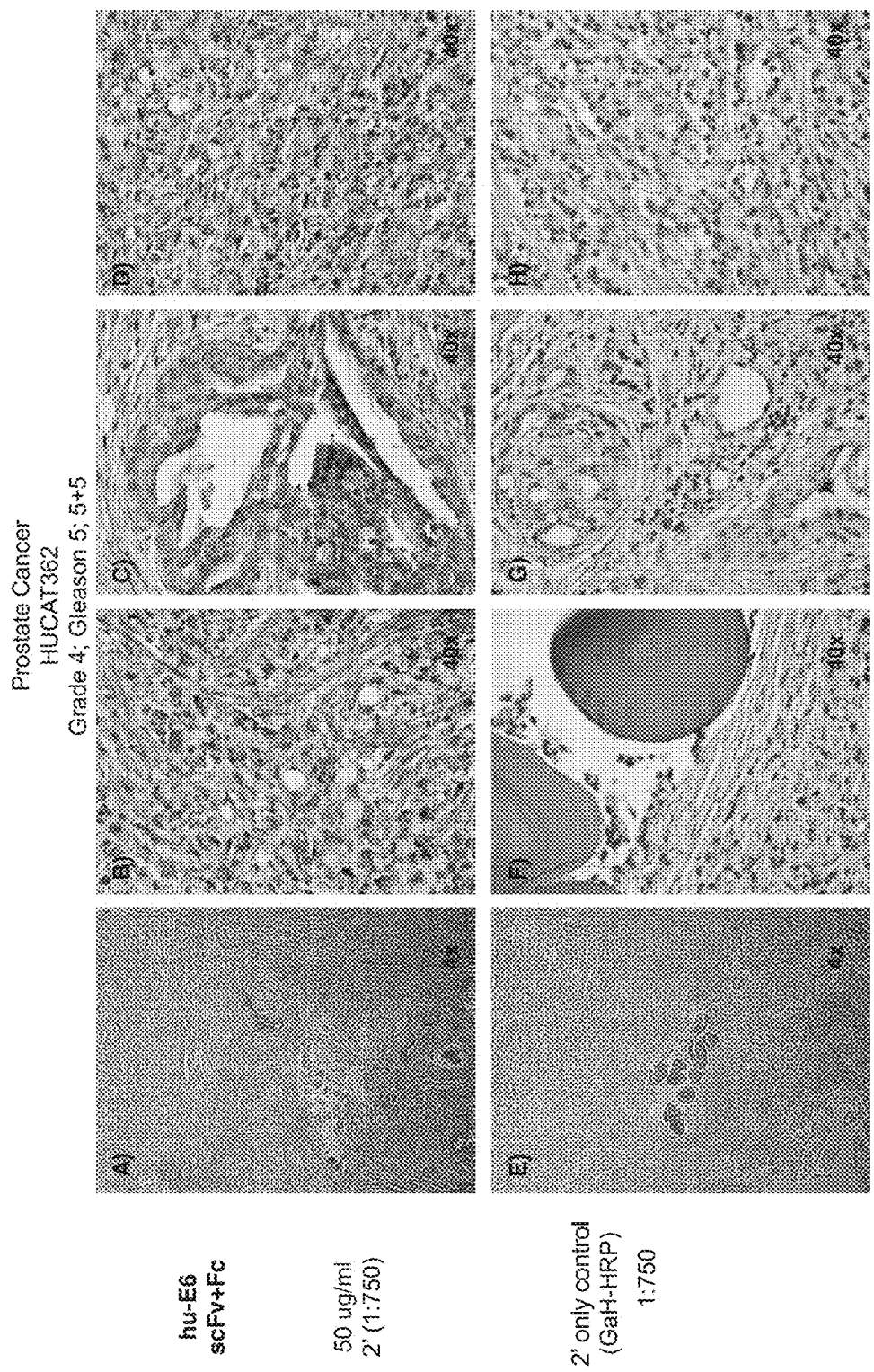
FIG. 62 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.

The most accurate way of demonstrating antibody specificity is testing the antibody on normal human tissue specimens compared to cancerous tissue specimens. MN-C2 and MN-E6 were shown to specifically bind to MUC1 or MUC1* positive cancer cells. Several breast tumor arrays were assayed using several anti-MUC1 or MUC1* antibodies. Essentially the studies involving serial sections of breast cancer tissue specimens from over 1,200 different breast cancer patients showed that very little full-length MUC1 remains on breast cancer tissues. The vast majority of the MUC1 expressed is MUC1* and is stained by MN-C2. The analysis was performed by Clarient Diagnostics and tissue staining was scored using the Allred method. For example, FIG. 43 shows serial sections of breast cancer tissue arrays that were stained with either VU4H5, a commercially available anti-MUC1 antibody that binds to the tandem repeats, or MN-C2 that binds to MUC1*. FIGS. 43 and 44 are photographs of breast cancer tissue arrays stained with either VU4H5 which recognizes MUC1-FL (full length) or MN-C2 which recognizes cancerous MUC1*. Tissue staining was scored using Allred scoring method which combines an intensity score and a distribution score. Below the photographs of the tissue arrays are color-coded graphs displaying the results. As can be seen, the arrays stained with VU4H5 are very light and many tissues do not stain at all despite the published reports that MUC1 is aberrantly expressed on over 96% of all breast cancers as evidenced by nucleic acid based diagnostics. In contrast, the arrays stained with MN-C2 are very dark (red versus yellow or white in graph). Additionally, many tissues did not stain at all with anti-full-length MUC1 but stained very dark with MN-C2, (see green boxes in graph). Similarly, we stained normal or cancerous breast tissues with humanized MN-E6 scFv-Fc. The antibody fragment was biotinylated so it could be visualized by a secondary streptavidin based secondary. As can be seen in FIG. 45, hMN-E6 scFv-Fc does not stain normal breast tissue but stains cancerous breast tissue. Further, the intensity and homogeneity of staining increases with tumor grade and/or metastatic grade of the patient (FIGS. 45 and 46). Similarly, hMN-E6 scFv-Fc did not stain normal lung tissue but did stain lung cancer tissue (FIGS. 47-51) and the intensity and distribution of staining increased as tumor grade or metastatic grade increased. FIG. 52 shows photographs of normal small intestine and cancerous small intestine tissues stained with humanized MN-E6-scFv-Fc biotinylated anti-MUC1* antibody at 5 ug/mL, then stained with a secondary streptavidin HRP antibody. A) is a normal small intestine tissue. B) is small intestine cancer from patient as denoted in the figure. C,D are photographs of the corresponding serial sections that were stained with the secondary antibody alone. FIG. 53 shows photographs of normal small intestine tissues stained with humanized MN-E6-scFv-Fc anti-MUC1* antibody at 50 ug/mL, then stained with a secondary goat-anti-human HRP antibody. A-D are normal small intestine tissue. E-H are photographs of the corresponding serial sections that were stained with the secondary antibody alone. FIG. 54 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone. FIG. 55 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone. FIG. 56 shows photographs of normal colon tissues stained with humanized MN-E6-scFv-Fc anti-MUC1* antibody at 50 ug/mL, then stained with a secondary goat-anti-human HRP antibody. A-D are normal colon. E-H are photographs of the corresponding serial sections that were stained with the secondary antibody alone. FIG. 57 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone. FIG. 58 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a Grade 2 patient as denoted in figure. E-H are photographs of the corresponding serial sections that were stained with the secondary antibody alone. FIG. 59 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone. FIG. 60 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone. FIG. 61 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone. FIG. 62 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.

One aspect of the invention is a method for treating a patient diagnosed with, suspected of having, or at risk of developing a MUC1 positive or MUC1* positive cancer, wherein a specimen is obtained from the patient's cancer and is tested for reactivity with an antibody that binds to PSMGFR SEQ ID NO:2, SNIKFRPGSVVVQLTLAFREGTINVHDVETQFNQYKTEAASRY (SEQ ID NO:620) or SVVVQLTLAFREGTINVHDVETQFNQYKTEAASRY (SEQ ID NO:621). The patient is then treated with an scFv, scFv-Fc or CAR T that comprises antibody variable fragments from the antibody that reacted with their cancer specimen. Another aspect of the invention is a method for treating a patient diagnosed with, suspected of having, or at risk of developing a MUC1 positive or MUC1* positive cancer, wherein a specimen is obtained from the patient's cancer and is tested for reactivity with MN-E6-scFv, MN-C2-scFv, MN-C3-scFv or MN-C8-scFv; the patient is then treated with the scFv, scFv-Fc-mut or CAR T that comprises portions of the antibody that reacted with their cancer specimen.

BiTEs

Divalent (or bivalent) single-chain variable fragments (di-scFvs, bi-scFvs) can be engineered by linking two scFvs. This can be done by producing a single peptide chain with two $V_H$ and two $V_L$ regions, yielding tandem scFvs. Another possibility is the creation of scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Consequently, diabody drugs could be dosed much lower than other therapeutic antibodies and are capable of highly specific targeting of tumors in vivo. Still shorter linkers (one or two amino acids) lead to the formation of trimers, so-called or tribodies. Tetrabodies have also been produced. They exhibit an even higher affinity to their targets than diabodies.

All of these formats can be composed from variable fragments with specificity for two different antigens, in which case they are types of bispecific antibodies. The furthest developed of these are bispecific tandem di-scFvs, known as hi-specific T-cell engagers (BiTE antibody constructs). BiTEs are fusion proteins consisting of two scFvs of different antibodies, on a single peptide chain of about 55 kilodaltons. One of the scFvs may bind to T cells such as via the CD3 receptor, and the other to a tumor cell via a tumor specific molecule, such aberrantly expressed MUC1*.

Another aspect of the invention is a method for treating a patient diagnosed with, suspected of having, or at risk of developing a MUC1 positive or MUC1* positive cancer, wherein the patient is administered an effective amount of a BiTE wherein one antibody variable fragment of the BiTE binds to a T cell surface antigen and the other antibody variable fragment of the BiTE binds to PSMGFR SEQ ID NO:2, SNIKFRPGSVVVQLTLAFREGTINVHD-VETQFNQYKTEAASRY (SEQ ID NO:620) or SVVVQLTLAFREGTINVHDVETQFNQYKTEAASRY (SEQ ID NO:621). In one case, the antibody variable fragment of the BiTE that binds to MUC1* comprises portions of huMN-E6, huMN-C2, huMN-C3, or huMN-C8.

In another aspect of the invention, MUC1* peptides including PSMGFR SEQ ID NO:2, most or all of SNIKFRPGSVVVQLTLAFREGTINVHDVETQFNQYK-TEAASRY (SEQ ID NO:620) or SVVVQLTLAFREGT-INVHDVETQFNQYKTEAASRY (SEQ ID NO:621) are used in adoptive T cell approaches. In this case, a patient's T cells are exposed to the MUC1* peptides and through various rounds of maturation, the T cells develop MUC1* specific receptors. The adapted T cells are then expanded and administered to the donor patient who is diagnosed with, suspected of having, or is at risk of developing a MUC1* positive cancer.

Other MUC1 Cleavage Sites

However, MUC1 is cleaved to the growth factor receptor form, MUC1*, on some healthy cells in addition to cancer cells. For example, MUC1 is cleaved to MUC1* on healthy stem and progenitor cells. A large percentage of bone marrow cells are MUC1* positive. Portions of the intestine are MUC1* positive.

The inventors have discovered that MUC1 can be cleaved at different positions that are relatively close to each other but the location of cleavage changes the fold of the remaining portion of the extracellular domain. As a result, monoclonal antibodies can be identified that bind to MUC1* cleaved at a first position but do not bind to MUC1* that has been cleaved at a second position. This discovery is disclosed in WO2014/028668, filed Aug. 14, 2013, the contents of which are incorporated by reference herein its entirety. We identified a set of anti-MUC1* monoclonal antibodies that bind to a MUC1* as it appears on cancer cells but do not bind to MUC1* as it appears on stem and progenitor cells. Conversely, we identified a second set of monoclonal antibodies that bind to stem and progenitor cells but do not bind to cancer cells. One method used to identify stem specific antibodies is as follows: supernatants from monoclonal hybridomas were separately adsorbed onto 2 multi-well plates. Stem cells, which are non-adherent cells, were put into one plate and cancer cells which are adherent were put into an identical plate. After an incubation period, the plates were rinsed and inverted. If the non-adherent stem cells stuck to the plate, then the monoclonal in that particular well recognizes stem cells and will not recognize cancer cells. Antibodies that did not capture stem cells or antibodies that captured cancer cells were identified as cancer specific stem cells. FACS analysis has confirmed this method works. Antibodies MN-E6 and MN-C2 are examples of cancer-specific antibodies. Antibodies MN-C3 and MN-C8 are examples of stem-specific antibodies. Although both sets of antibodies are able to bind to a peptide having the PSMGFR sequence, FACS analysis shows that the anti-MUC1* polyclonal antibody and MN-C3 bind to MUC1* positive bone marrow cells but MN-E6 does not. The MUC1* polyclonal antibody was generated by immunizing a rabbit with the PSMGFR peptide. Similarly, MN-C3 binds to stem cells of the intestinal crypts but MN-E6 does not. Conversely, MN-E6 antibody binds to cancerous tissue while the stem-specific MN-C3 does not. Competition ELISA experiments indicate that the C-terminal 10 amino acids of the PSMGFR peptide are required for MN-E6 and MN-C2 binding, but not for MN-C3 and MN-C8. Therefore, another method for identifying antibodies that are cancer specific is to immunize with a peptide having the sequence of the PSMGFR peptide minus the 10 N-terminal amino acids or use that peptide to screen for antibodies or antibody fragments that will be cancer specific. Antibodies that bind to a peptide with a sequence of PSMGFR peptide minus the N-terminal 10 amino acids but do not bind to a peptide with a sequence of PSMGFR peptide minus the C-terminal 10 amino acids are cancer specific antibodies for use in the treatment or prevention of cancers.

The extracellular domain of MUC1 is also cleaved on stem cells and some progenitor cells, where activation of cleaved MUC1 by ligands NME1 in dimer form or NME7 promotes growth and pluripotency and inhibits differentiation. The transmembrane portion of MUC1 that remains after cleavage is called MUC1* and the extracellular domain is comprised essentially of the Primary Sequence of MUC1 Growth Factor Receptor (PSMGFR) sequence. However, the exact site of cleavage can vary depending on cell type, tissue type, or which cleavage enzyme a particular person expresses or overexpresses. In addition to the cleavage site that we previously identified which leaves the transmembrane portion of MUC1* comprising most or all of the PSMGFR SEQ ID NO:2, other cleavage sites result in an extended MUC1* comprised of most or all of SNIKFRPGSVVVQLTLAFREGTINVHDVETQFNQYK-TEAASRY (SEQ ID NO:620); or SVVVQLTLAFREGT-INVHDVETQFNQYKTEAASRY (SEQ ID NO:621). The site of MUC1 cleavage affects how the remaining extracellular domain folds. We have identified monoclonal antibodies that bind to cleaved MUC1* on cancer cells but do not bind to cleaved MUC1* as it exists on healthy stem and progenitor cells.

Whereas an anti-MUC1* antibody or antibody-like molecule may be most effective if it competitively inhibits the binding of NME1, NME6, NME8 or NME7 or NME7-AB to MUC1*, for example an antibody that binds to the PSMGFR sequence especially if said antibody is unable to bind to a PSMGFR peptide if the 10 C-terminal amino acids are missing, antibodies or antibody-like molecules that carry a payload need not competitively inhibit the binding of MUC1* ligands to be effective as anti-cancer agents. For example antibodies or antibody-like molecules that are conjugated to a toxin could be effective at killing target cancer cells without necessarily inhibiting binding of the activating ligands. For example, antibodies or antibody-like molecules such as CARs or BiTEs which recruit the patient's immune system to the tumor can be effective as anti-cancer agents even if the antibody fragment targets a portion of MUC1* such that antibody fragment binding does not competitively inhibit the binding of NME1, NME6, NME8, NME7-AB or NME7. In a preferred embodiment the antibody fragment incorporated into a CAR, an adaptive T cell receptor or a BiTE does competitively inhibit the binding of NME1, NME6, NME8, NME7-AB or NME7 to MUC1*.

Antibodies that are able to bind to the extracellular domain of the remaining transmembrane portion block the interaction between the MUC1* extracellular domain and activating ligands and in this way can be used as therapeutic agents, for example for the treatment of cancers. Anti-MUC1* antibodies are also useful for the growth, delivery, identification or isolation of stem cells both in vitro and in vivo.

General Strategy for Using Antibodies, Antibody Fragments and CARs that Target the Extracellular Domain of MUC1*

Monoclonal antibodies MN-C3 and MN-C8 have a greater binding affinity for stem cells than cancer cells. Humanized antibodies and antibody fragments containing sequences derived from the variable regions of MN-C3 and MN-C8 can be used as an adhesion surface coating for human stem cells.

Alternatively, humanized antibodies and antibody fragments containing sequences derived from the variable regions of MN-C3 and MN-C8 can be used to deliver stem cells to a specific location such as for in situ human therapeutics. In one case, a substrate coated with humanized MN-C3 or MN-C8 derived antibodies or antibody fragments is loaded with stem cells then inserted into a patient. In another case, a substrate coated with humanized MN-C3 or MN-C8 derived antibodies or antibody fragments is inserted into a patient in order to recruit the patient's own stem cells to a specific area for therapy. Human therapies in which antibodies that bind to human stem cells will be of therapeutic use include spinal cord repair. Substrates coated with humanized MN-C3 or MN-C8 derived antibodies or antibody fragments are also used to identify or isolate human antibodies. Humanized MN-C3 or MN-C8 derived antibodies can also be used to stimulate the growth of stem cells.

Sequence Listing Free Text: xml text file named "56699-731_301SL" having byte size of 993,070, created Aug. 3, 2022 is incorporated by reference herein.

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
MUC1 Receptor
(Mucin 1 precursor, Genbank Accession number: P15941)
                                                          (SEQ ID NO: 1)
MTPGTQSPFFLLLLLTVLTVVTGSGHASSTPGGEKETSATQRSSVPSSTEKNAVSMTSSVLSSHSPGS

GSSTTQGQDVTLAPATEPASGSAATWGQDVTSVPVTRPALGSTTPPAHDVTSAPDNKPAPGSTAPPAH

GVTSAPDTRPAPGSTAPPAHGVTSAPDTRPAPGSTAPPAHGVTSAPDTRPAPGSTAPPAHGVTSAPDT

RPAPGSTAPPAHGVTSAPDTRPAPGSTAPPAHGVTSAPDTRPAPGSTAPPAHGVTSAPDTRPAPGSTA

PPAHGVTSAPDTRPAPGSTAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGSTAPPAHGVTSAPDTRPAP

GSTAPPAHGVTSAPDTRPAPGSTAPPAHGVTSAPDTRPAPGSTAPPAHGVTSAPDTRPAPGSTAPPAH

GVTSAPDTRPAPGSTAPPAHGVTSAPDTRPAPGSTAPPAHGVTSAPDTRPAPGSTAPPAHGVTSAPDT

RPAPGSTAPPAHGVTSAPDTRPAPGSTAPPAHGVTSAPDTRPAPGSTAPPAHGVTSAPDTRPAPGSTA

PPAHGVTSAPDTRPAPGSTAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGSTAPPAHGVTSAPDTRPAP

GSTAPPAHGVTSAPDTRPAPGSTAPPAHGVTSAPDTRPAPGSTAPPAHGVTSAPDTRPAPGSTAPPAH

GVTSAPDTRPAPGSTAPPAHGVTSAPDTRPAPGSTAPPAHGVTSAPDTRPAPGSTAPPAHGVTSAPDT

RPAPGSTAPPAHGVTSAPDTRPAPGSTAPPAHGVTSAPDTRPAPGSTAPPAHGVTSAPDNRPALGSTA

PPVHNVTSASGSASGSASTLVHNGTSARATTTPASKSTPFSIPSHHSDTPTTLASHSTKTDASSTHHS

SVPPLTSSNHSTSPQLSTGVSFFFLSFHISNLQFNSSLEDPSTDYYQELQRDISEMFLQIYKQGGFLG

LSNIKFRPGSVVVQLTLAFREGTINVHDVETQFNQYKTEAASRYNLTISDVSVSDVPFPFSAQSGAGV

PGWGIALLVLVCVLVALAIVYLIALAVCQCRRKNYGQLDIFPARDTYHPMSEYPTYHTHGRYVPPSST

DRSPYEKVSAGNGGSSLSYTNPAVAAASANL

PSMGFR (SEQ ID NO: 2)
GTINVHDVETQFNQYKTEAASRYNLTISDVSVSDVPFPFSAQSGA
```

Human NME1
(DNA)
(SEQ ID NO: 3)
atggccaactgtgagcgtaccttcattgcgatcaaaccagatggggtccagcggggtcttgtgggaga gattatcaagcgttttgagcagaaaggattccgccttgttggtctgaaattcatgcaagcttccgaag atcttctcaaggaacactacgttgacctgaaggaccgtccattctttgccggcctggtgaaatacatg cactcagggccggtagttgccatggtctgggaggggctgaatgtggtgaagacgggccgagtcatgct cggggagaccaaccctgcagactccaagcctgggaccatccgtggagacttctgcatacaagttggca ggaacattatacatggcagtgattctgtggagagtgcagagaaggagatcggcttgtggtttcaccct gaggaactggtagattacacgagctgtgctcagaactggatctatgaatga (amino acids)
(SEQ ID NO: 4)
MANCERTFIAIKPDGVQRGLVGEIIKRFEQKGFRLVGLKFMQASEDLLKEHYVDLKDRPFFAGLVKYM

HSGPVVAMVWEGLNVVKTGRVMLGETNPADSKPGTIRGDFCIQVGRNIIHGSDSVESAEKEIGLWFHP

EELVDYTSCAQNWIYE-

Human NME7
(DNA)
(SEQ ID NO: 5)
atgaatcatagtgaaagattcgttttcattgcagagtggtatgatccaaatgcttcacttcttcgacg ttatgagcttttattttacccaggggatggatctgttgaaatgcatgatgtaaagaatcatcgcacct ttttaaagcggaccaaatatgataacctgcacttggaagatttatttataggcaacaaagtgaatgtc ttttctcgacaactggtattaattgactatggggatcaatatacagctcgccagctgggcagtaggaa agaaaaaacgctagccctaattaaaccagatgcaatatcaaaggctggagaaataattgaaataataa acaaagctggatttactataaccaaactcaaaatgatgatgctttcaaggaaagaagcattggatttt catgtagatcaccagtcaagacccttttttcaatgagctgatccagtttattacaactggtcctattat tgccatggagattttaagagatgatgctatatgtgaatggaaaagactgctgggacctgcaaactctg gagtggcacgcacagatgcttctgaaagcattagagccctctttggaacagatggcataagaaatgca gcgcatggccctgattcttttgcttctgcggccagagaaatggagttgttttttccttcaagtggagg ttgtgggccggcaaacactgctaaatttactaattgtacctgttgcattgttaaaccccatgctgtca gtgaaggactgttgggaaagatcctgatggctatccgagatgcaggttttgaaatctcagctatgcag atgttcaatatggatcgggttaatgttgaggaattctatgaagtttataaggagtagtgaccgaata tcatgacatggtgacagaaatgtattctggccccttgtgtagcaatggagattcaacagaataatgcta caaagacatttcgagaattttgtggacctgctgatcctgaaattgcccggcatttacgccctggaact ctcagagcaatctttggtaaaactaagatccagaatgctgttcactgtactgatctgccagaggatgg cctattagaggttcaatacttcttcaagatcttggataattag (amino acids)
(SEQ ID NO: 6)
MNHSERFVFIAEWYDPNASLLRRYELLFYPGDGSVEMHDVKNHRTFLKRTKYDNLHLEDLFIGNKVNV

FSRQLVLIDYGDQYTARQLGSRKEKTLALIKPDAISKAGEIIEIINKAGFTITKLKMMMLSRKEALDF

HVDHQSRPFFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIRDAGFEISAMQ

MFNMDRVNVEEFYEVYKGVVTEYHDMVTEMYSGPCVAMEIQQNNATKTFREFCGPADPEIARHLRPGT

LRAIFGKTKIQNAVHCTDLPEDGLLEVQYFFKILDN-

-continued

NME7 peptides
NME 7A peptide 1 (A domain):
(SEQ ID NO: 7)
MLSRKEALDFHVDHQS

NME 7A peptide 2 (A domain):
(SEQ ID NO: 8)
SGVARTDASES

NME 7B peptide 1 (B domain):
(SEQ ID NO: 9)
DAGFEISAMQMFNMDRVNVE

NME 7B peptide 2 (B domain):
(SEQ ID NO: 10)
EVYKGVVTEYHDMVTE

NME7B peptide 3 (B domain):
(SEQ ID NO: 11)
AIFGKTKIQNAVHCTDLPEDGLLEVQYFF

Mouse E6 Heavy chain variable region sequence:
(DNA)
(SEQ ID NO: 12)
gaggtgaaggtggtggagtctggggggagacttagtgaagcctggagggtccctgaaactctcctgtgt agtctctggattcactttcagtagatatggcatgtcttgggttcgccagactccaggcaagaggctgg agtgggtcgcaaccattagtggtggcggtacttacatctactatccagacagtgtgaagggggcgattc accatctccagagacaatgccaagaacacccctgtacctgcaaatgagcagtctgaagtctgaggacac agccatgtatcactgtacaagggataactacggtaggaactacgactacggtatggactactggggtc aaggaacctcagtcaccgtctcctca (amino acids)
(SEQ ID NO: 13)
EVKVVESGGDLVKPGGSLKLSCVVSGFTFSRYGMSWVRQTPGKRLEWVATISGGGTYIYYPDSVKGRF

TISRDNAKNTLYLQMSSLKSEDTAMYHCTRDNYGRNYDYGMDYWGQGTSVTVSS

Mouse E6 heavy chain variable framework region 1 (FWR1) sequence:
(DNA)
(SEQ ID NO: 14)
gaggtgaaggtggtggagtctggggggagacttagtgaagcctggagggtccctgaaactctcctgtgt agtctct (amino acids)
(SEQ ID NO: 15)
EVKVVESGGDLVKPGGSLKLSCVVSGFTFS Mouse E6 heavy chain variable complementarity determining regions 1
(CDR1) sequence:
(DNA)
(SEQ ID NO: 16)
ggattcactttcagtagatatggcatgtct (amino acids)
(SEQ ID NO: 17)
RYGMS Mouse E6 heavy chain variable framework region 2 (FWR2) sequence:
(DNA)
(SEQ ID NO: 18)
tgggttcgccagactccaggcaagaggctggagtgggtcgca (amino acids)
(SEQ ID NO: 19)
WVRQTPGKRLEWVA Mouse E6 heavy chain variable complementarity determining regions 2
(CDR2) sequence:
(DNA)
(SEQ ID NO: 20)
accattagtggtggcggtacttacatctactatccagacagtgtgaagggg (amino acids)
(SEQ ID NO: 21)
TISGGGTYIYYPDSVKG Mouse E6 heavy chain variable framework region 3 (FWR3) acid sequence:
(DNA)
(SEQ ID NO: 22)
cgattcaccatctccagagacaatgccaagaacaccctgtacctgcaaatgagcagtctgaagtctga ggacacagccatgtatcactgtacaagg (amino acids)
(SEQ ID NO: 23)
RFTISRDNAKNTLYLQMSSLKSEDTAMYHCTR Mouse E6 heavy chain variable complementarity determining regions 3 (CDR3) sequence:
(DNA)
(SEQ ID NO: 24)
gataactacggtaggaactacgactacggtatggactac (amino acids)
(SEQ ID NO: 25)
DNYGRNYDYGMDY IGHV3-21*03 heavy chain variable region sequence:
(DNA)
(SEQ ID NO: 26)
gaggtgcagctggtggagtctgggggaggcctggtcaagcctggggggtccctgagactctcctgtgc agcctctggattcaccttcagtagctatagcatgaactgggtccgccaggctccaggaaggggctgg agtgggtctcatccattagtagtagtagtagttacatatactacgcagactcagtgaagggccgattc accatctccagagacaacgccaagaactcactgtatctgcaaatgaacagcctgagagccgaggacac ggctgtgtattactgtgcgaga (amino acids)
(SEQ ID NO: 27)
EVQLVESGGGLVKPGGSLRLSCAASGFTFSSYSMNWVRQAPGKRLEWVSSISSSSSYIYYPDSVKGRF

TISRDNAKNSLYLQMNSLRAEDTAVYYCAR

IGHV3-21*01 heavy chain variable framework region 1 (FWR1) sequence:
(DNA)
(SEQ ID NO: 28)
gaggtgcagctggtggagtctgggggaggcctggtcaagcctggggggtccctgagactctcctgtg agcctctggattcaccttcagt (amino acids)
(SEQ ID NO: 29)
EVQLVESGGGLVKPGGSLRLSCAASGFTFS IGHV3-21*01 heavy chain variable complementarity determining regions 1 (CDR1) sequence:
(DNA)
(SEQ ID NO: 30)
agctatagcatgaac (amino acids)
(SEQ ID NO: 31)
SYSMN IGHV3-21*01 heavy chain variable framework region 2 (FWR2) sequence:
(DNA)
(SEQ ID NO: 32)
tgggtccgccaggctccagggaaggggctggagtgggtctca (amino acids)
(SEQ ID NO: 33)
WVRQAPGKGLEWVS IGHV3-21*01 heavy chain variable complementarity determining regions 2 (CDR2) sequence:
(DNA)
(SEQ ID NO: 34)
tccattagtagtagtagtagttacatatactacgcagactcagtgaagggc

```
(amino acids)
                                                       (SEQ ID NO: 35)
SISSSSSYIYYADSVKG IGHV3-21*01 heavy chain variable framework region 3 (FWR3) sequence:
(DNA)
                                                       (SEQ ID NO: 36)
cgattcaccatctccagagacaacgccaagaactcactgtatctgcaaatgaacagcctgagagccga ggacacggctgtgtattactgtgcgaga (amino acids)
                                                       (SEQ ID NO: 37)
RFTISRDNAKNSLYLQMNSLRAEDTAVYYCAR Humanized E6 heavy chain variable region sequence:
(DNA)
                                                       (SEQ ID NO: 38)
gaggtgcagctggtggagtctgggggaggcctggtcaagcctggggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacaccctgtatctgcaaatgaacagcctgagagccgaggacac ggctgtgtattactgtaccagagataactatggccgcaactatgattatggcatggattattggggcc agggcaccctggtgaccgtgagcagc (amino acids)
                                                       (SEQ ID NO: 39)
EVQLVESGGGLVKPGGSLRLSCAASGFTFSRYGMSWVRQAPGKRLEWVSTISGGGTYIYYPDSVKGRF

TISRDNAKNTLYLQMNSLRAEDTAVYYCTRDNYGRNYDYGMDYWGQGTLVTVSS

Humanized E6 heavy chain variable framework region 1 (FWR1) acid
sequence:
(DNA)
                                                       (SEQ ID NO: 40)
gaggtgcagctggtggagtctgggggaggcctggtcaagcctggggggtccctgagactctcgg agcctctggattcaccttcagt (amino acids)
                                                       (SEQ ID NO: 41)
EVQLVESGGGLVKPGGSLRLSCAASGFTFS Humanized E6 heavy chain variable complementarity determining regions 1 (CDR1) sequence:
(DNA)
                                                       (SEQ ID NO: 42)
aggtatggcatgagc (amino acids)
                                                       (SEQ ID NO: 43)
RYGMS Humanized E6 heavy chain variable framework region 2 (FWR2) acid
sequence:
(DNA)
                                                       (SEQ ID NO: 44)
tgggtccgccaggctccagggaagaggctggagtgggtctca (amino acids)
                                                       (SEQ ID NO: 45)
WVRQAPGKRLEWVS Humanized E6 heavy chain variable complementarity determining
regions 2 (CDR2) sequence:
(DNA)
                                                       (SEQ ID NO: 46)
accattagtggcggaggcacctacatatactacccagactcagtgaagggc (amino acids)
                                                       (SEQ ID NO: 47)
TISGGGTYIYYPDSVKG
```

-continued

Humanized E6 heavy chain variable framework region 3 (FWR3) acid
sequence:
(DNA)
(SEQ ID NO: 48)
cgattcaccatctccagagacaacgccaagaacaccctgtatctgcaaatgaacagcctgagagccga ggacacggctgtgtattactgtaccaga (amino acids)
(SEQ ID NO: 49)
RFTISRDNAKNTLYLQMNSLRAEDTAVYYCTR Humanized E6 heavy chain variable complementarity determining
regions 3 (CDR3) sequence:
(DNA)
(SEQ ID NO: 50)
gataactatggccgcaactatgattatggcatggattat (amino acids)
(SEQ ID NO: 51)
DNYGRNYDYGMDY Humanized E6 IgG2 heavy chain synthesized by Genescript:
(DNA)
(SEQ ID NO: 52)
gaattctaagcttgggccaccatggaactggggctccgctgggttttccttgttgctattttagaagg tgtccagtgtgaggtgcagctggtggagtctgggggaggcctggtcaagcctggggggtccctgagac tctcctgtgcagcctctggattcaccttcagtaggtatggcatgagctgggtccgccaggctccaggg aagaggctggagtgggtctcaaccattagtggcggaggcacctacatatactacccagactcagtgaa gggccgattcaccatctccagagacaacgccaagaacaccctgtatctgcaaatgaacagcctgagag ccgaggacacggctgtgtattactgtaccagagataactatggccgcaactatgattatggcatggat tattggggccagggcaccctggtgaccgtgagcagcgcctccaccaagggcccatcggtcttccccct ggcgccctgctccaggagcacctccgagagcacagcagccctgggctgcctggtcaaggactacttcc ccgaaccggtgacggtgtcgtggaactcaggcgctctgaccagcggcgtgcacaccttcccagctgtc ctacagtcctcaggactctactccctcagcagcgtggtgaccgtgccctccagcaacttcggcaccca gacctacacctgcaacgtagatcacaagcccagcaacaccaaggtggacaagacagttgagcgcaaat gttgtgtcgagtgcccaccgtgcccagcaccacctgtggcaggaccgtcagtcttcctcttccccca aaacccaaggacaccctcatgatctcccggacccctgaggtcacgtgcgtggtggtggacgtgagcca cgaagaccccgaggtccagttcaactggtacgtggacggcgtggaggtgcataatgccaagacaaagc cacgggaggagcagttcaacagcacgttccgtgtggtcagcgtcctcaccgttgtgcaccaggactgg ctgaacggcaaggagtacaagtgcaaggtctccaacaaaggcctcccagcccccatcgagaaaaccat ctccaaaaccaaagggcagccccgagaaccacaggtgtacaccctgcccccatcccgggaggagatga ccaagaaccaggtcagcctgacctgcctggtcaaaggcttctaccccagcgacatcgccgtggagtgg gagagcaatgggcagccggagaacaactacaagaccacacctcccatgctggactccgacggctcctt cttcctctacagcaagctcaccgtggacaagagcaggtggcagcaggggaacgtcttctcatgctccg tgatgcatgaggctctgcacaaccactacacgcagaagagcctctccctgtctccgggtaaatagtaa gtttaaactctaga (amino acids)
(SEQ ID NO: 53)
EF*AWATMELGLRWVFLVAILEGVQCEVQLVESGGGLVKPGGSLRLSCAASGFTFSRYGMSWVRQAPG

KRLEWVSTISGGGTYIYYPDSVKGRFTISRDNAKNTLYLQMNSLRAEDTAVYYCTRDNYGRNYDYGMD

YWGQGTLVTVSSASTKGPSVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEALHNHYTQKSLSLSPGK**

V*TLX

Human IgG2 heavy chain constant region sequence:
(DNA)
(SEQ ID NO: 54)
gcctccaccaagggcccatcggtcttccccctggcgccctgctccaggagcacctccgagagcacagc cgccctgggctgcctggtcaaggactactccccgaaccggtgacggtgtcgtggaactcaggcgctc tgaccagcggcgtgcacaccttcccagctgtcctacagtcctcaggactctactccctcagcagcgtg gtgaccgtgccctccagcaacttcggcacccagacctacacctgcaacgtagatcacaagcccagcaa caccaaggtggacaagacagttgagcgcaaatgttgtgtcgagtgcccaccgtgcccagcaccacctg tggcaggaccgtcagtcttcctcttccccccaaaacccaaggacaccctcatgatctcccggacccct gaggtcacgtgcgtggtggtggacgtgagccacgaagaccccgaggtccagttcaactggtacgtgga cggcgtggaggtgcataatgccaagacaaagccacgggaggagcagttcaacagcacgttccgtgtgg tcagcgtcctcaccgttgtgcaccaggactggctgaacggcaaggagtacaagtgcaaggtctccaac aaaggcctcccagcccccatcgagaaaaccatctccaaaaccaaagggcagccccgagaaccacaggt gtacaccctgcccccatcccgggaggagatgaccaagaaccaggtcagcctgacctgcctggtcaaag gcttctaccccagcgacatcgccgtggagtgggagagcaatgggcagccggagaacaactacaagacc acacctcccatgctggactccgacggctccttcttcctctacagcaagctcaccgtggacaagagcag gtggcagcaggggaacgtcttctcatgctccgtgatgcatgaggctctgcacaaccactacacgcaga agagcctctccctgtctccgggtaaatag (amino acids)
(SEQ ID NO: 55)
ASTKGPSVFPLAPCSRSTSESTAALGCLVKDYFPEPVTVSWNSGALTSGVHTFPAVLQSSGLYSLSSV

VTVPSSNFGTQTYTCNVDHKPSNTKVDKTVERKCCVECPPCPAPPVAGPSVFLFPPKPKDTLMISRTP

EVTCVVVDVSHEDPEVQFNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLSLSPGK

Humanized E6 IgG1 heavy chain sequence:
(DNA)
(SEQ ID NO: 56)
gaggtgcagctggtggagtctgggggaggcctggtcaagcctggggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacccactgtatctgcaaatgaacagcctgagagccgaggacac ggctgtgtattactgtcccagagataactatggccgcaactatgattatggcatggattattgggcc agggcacccggtgaccgtgagcagcgctagcaccaagggcccatcggtcttccccctggcaccctcc tccaagagcacctctgggggcacagcggccctgggctgcctggtcaaggactactccccgaaccggt gacggtgtcgtggaactcaggcgccctgaccagcggcgtgcacaccttcccggctgtcctacagtcct caggactctactccctcagcagcgtggtgacagtgccctccagcagcttgggcacccagacctacatc tgcaacgtgaatcacaagcccagcaacaccaaggtggacaagaaagttgagcccaaatcttgtgacaa aactcacacatgcccaccgtgcccagcacctgaactcctggggggaccgtcagtcttcctcttccccc caaaacccaaggacaccctcatgatctcccggacccctgaggtcacatgcgtggtggtggacgtgagc cacgaagaccctgaggtcaagttcaactggtacgtggacggcgtggaggtgcataatgccaagacaaa -continued

```
gccgcgggaggagcagtacaacagcacgtaccgtgtggtcagcgtcctcaccgtcctgcaccaggact ggctgaatggcaaggagtacaagtgcaaggtctccaacaaagcccctcccagcccccatcgagaaaacc atctccaaagccaaagggcagccccgagaaccacaggtgtacaccctgcccccatcccgggaggagat gaccaagaaccaggtcagcctgacctgcctggtcaaaggcttctatcccagcgacatcgccgtggagt gggagagcaatgggcagccggagaacaactacaagaccacgcctcccgtgctggactccgacggctcc ttcttcctctacagcaagctcaccgtggacaagagcaggtggcagcaggggaacgtcttctcatgctc cgtgatgcatgaggctctgcacaaccactacacgcagaagagcctctccctgtctccgggtaaatgat aa
```

(amino acids)
(SEQ ID NO: 57)

EVQLVESGGGLVKPGGSLRLSCAASGFTGSRYGMSWVRQAPGKRLEWVSTISGGGTYIYYPDSVKGRF

TISRDNAKNPLYLQMNSLRAEDTAVYYCPRDNYGRNYDYGMDYWGQGTLVTVSSASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK**

Human IgG1 heavy chain constant region sequence:
(DNA)
(SEQ ID NO: 58)

```
gctagcaccaagggcccatcggtcttccccctggcaccctcctccaagagcacctctgggggcacagc ggccctgggctgcctggtcaaggactacttccccgaaccggtgacggtgtcgtggaactcaggcgccc tgaccagcggcgtgcacaccttcccggctgtcctacagtcctcaggactctactccctcagcagcgtg gtgacagtgccctccagcagcttgggcacccagacctacatctgcaacgtgaatcacaagcccagcaa caccaaggtggacaagaaagttgagcccaaatcttgtgacaaaactcacacatgcccaccgtgcccag cacctgaactcctggggggaccgtcagtcttcctcttccccccaaaacccaaggacaccctcatgatc tcccggacccctgaggtcacatgcgtggtggtggacgtgagccacgaagaccctgaggtcaagttcaa ctggtacgtggacggcgtggaggtgcataatgccaagacaaagccgcgggaggagcagtacaacagca cgtaccgtgtggtcagcgtcctcaccgtcctgcaccaggactggctgaatggcaaggagtacaagtgc aaggtctccaacaaagcccctcccagccccatcgagaaaaccatctccaaagccaaagggcagcccg agaaccacaggtgtacaccctgcccccatcccgggaggagatgaccaagaaccaggtcagcctgacct gcctggtcaaaggcttctatcccagcgacatcgccgtggagtgggagagcaatgggcagccggagaac aactacaagaccacgcctcccgtgctggactccgacggctccttcttcctctacagcaagctcaccgt ggacaagagcaggtggcagcaggggaacgtcttctcatgctccgtgatgcatgaggctctgcacaacc actacacgcagaagagcctctccctgtctccgggtaaatgataa
```

(amino acids)
(SEQ ID NO: 59)

ASTKGPSVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPGK**

```
Human IgG1 heavy chain constant region gBLOCK#1 sequence:
(DNA)
                                                    (SEQ ID NO: 60)
atggcatggattattggggccagggcaccctggtgaccgtgagcagcgctagcaccaagggcccatcg gtcttccccctggcaccctcctccaagagcacctctgggggcacagcggccctgggctgcctggtcaa ggactacttccccgaaccggtgacggtgtcgtggaactcaggcgccctgaccagcggcgtgcacacct tcccggctgtcctacagtcctcaggactctactccctcagcagcgtggtgacagtgccctccagcagc ttgggcacccagacctacatctgcaacgtgaatcacaagcccagcaacaccaaggtggacaagaaagt tgagcccaaatcttgtgacaaaactcacacatgcccaccgtgcccagcacctgaactcctggggggac cgtcagtcttcctcttccccccaaaacccaaggacaccctcatgatctcccggacccctgaggtcaca tgcgtggtggtggacgtgagccacgaagaccctgaggtcaagttcaactggtacgtggacggcgtgga ggtgcataatgccaag Human IgG1 heavy chain constant region gBLOCK#2 sequence:
(DNA)
                                                    (SEQ ID NO: 61)
tacgtggacggcgtggaggtgcataatgccaagacaaagccgcgggaggagcagtacaacagcacgta ccgtgtggtcagcgtcctcaccgtcctgcaccaggactggctgaatggcaaggagtacaagtgcaagg tctccaacaaagcccttcccagccccatcgagaaaaccatctccaaagccaaagggcagccccgagaa ccacaggtgtacaccctgccccatcccgggaggagatgaccaagaaccaggtcagcctgacctgcct ggtcaaaggcttctatcccagcgacatcgccgtggagtgggagagcaatgggcagccggagaacaact acaagaccacgcctcccgtgctggactccgacggctccttcttcctctacagcaagctcaccgtggac aagagcaggtggcagcaggggaacgtcttctcatgctccgtgatgcatgaggctctgcacaaccacta cacgcagaagagcctctccctgtctccgggtaaatgataagtttaaacccgctgatcagcctcgactg tgccttctagttg E6 heavy chain variable region overlapping sequence:
(DNA)
                                                    (SEQ ID NO: 62)
atggcatggattattggggccagggcaccct IgG1 heavy chain constant region overlapping region sequence:
(DNA)
                                                    (SEQ ID NO: 63)
tacgtggacggcgtggaggtgcataatgccaag pCDNA3.1 V5 and pSECTag2 overlapping sequence:
(DNA)
                                                    (SEQ ID NO: 64)
ccgctgatcagcctcgactgtgccttctagttg Mouse E6 Light Chain variable region sequence:
(DNA)
                                                    (SEQ ID NO: 65)
caaattgttctcacccagtctccagcaatcatgtctgcatctccaggggaggaggtcaccct aacctgcagtgccacctcaagtgtaagttacatacactggttccagcagaggccaggcactt ctcccaaactctggatttatagcacatccaacctggcttctggagtcccgttcgcttcagt ggcagtggatatgggacctcttactctctcacaatcagccgaatggaggctgaagatgctgc cacttattactgccagcaaaggagtagttccccattcacgttcggctcggggacaaagttgg aaataaaa (amino acids)
                                                    (SEQ ID NO: 66)
QIVLTQSPAIMSASPGEEVTLTCSATSSVSYIHWFQQRPGTSPKLWIYSTSNLASGVPVRFSGSGYGT

SYSLTISRMEAEDAATYYCQQRSSSPFTFGSGTKLEIK
```

Mouse E6 light chain variable framework region 1 (FWR1) sequence:
(DNA)
(SEQ ID NO: 67)
caaattgttctcacccagtctccagcaatcatgtctgcatctccaggggaggaggtcaccctaacctg c (amino acids)
(SEQ ID NO: 68)
QIVLTQSPAIMSASPGEEVTLTC Mouse E6 light chain variable complementarity determining regions 1 (CDR1) sequence:
(DNA)
(SEQ ID NO: 69)
AGTGCCACCTCAAGTGTAAGTTACATACAC (amino acids)
(SEQ ID NO: 70)
SATSSVSYIH Mouse E6 light chain variable framework region 2 (FWR2) sequence:
(DNA)
(SEQ ID NO: 71)
tggttccagcagaggccaggcacttctcccaaactctggatttat (amino acids)
(SEQ ID NO: 72)
WFQQRPGTSPKLWIY Mouse E6 light chain variable complementarity determining regions 2 (CDR2) sequence:
(DNA)
(SEQ ID NO: 73)
agcacatccaacctggcttct (amino acids)
(SEQ ID NO: 74)
STSNLAS Mouse E6 light chain variable framework region 3 (FWR3) sequence:
(DNA)
(SEQ ID NO: 75)
ggagtccctgttcgcttcagtggcagtggatatgggacctcttactctctcacaatcagccgaatgga ggctgaagatgctgccacttattactgc (amino acids)
(SEQ ID NO: 76)
GVPVRFSGSGYGTSYSLTISRMEAEDAATYYC Mouse E6 light chain variable complementarity determining regions 3 (CDR3) sequence:
(DNA)
(SEQ ID NO: 77)
cagcaaaggagtagttccccattcacg (amino acids)
(SEQ ID NO: 78)
QQRSSSPFT IGKV3-11*02 light chain variable region sequence:
(DNA)
(SEQ ID NO: 79)
gaaattgtgttgacacagtctccagccaccctgtctttgtctccaggggaaagagccaccctctcctg cagggccagtcagagtgttagcagctacttagcctggtaccaacagaaacctggccaggctcccaggc tcctcatctatgatgcatccaacagggccactggcatcccagccaggttcagtggcagtgggtctggg agagacttcactctcaccatcagcagcctagagcctgaagattttgcagtttattactgtcagcagcg tagcaactggcctcc (amino acids)
(SEQ ID NO: 80)
EIVLTQSPATLSLSPGERATLSCRASQSVSSYLAWYQQKPGQAPRLLIYDASNRATGIPA

RFSGSGSGRDFTLTISSLEPEDFAVYYCQQRSNWPP

-continued

IGKV3-11*02 light chain variable framework region 1 (FWR1) acid
sequence:
(DNA)
(SEQ ID NO: 81)
gaaattgtgttgacacagtctccagccaccctgtctttgtctccaggggaaagagccaccctctcctg c (amino acids)
(SEQ ID NO: 82)
EIVLTQSPATLSLSPGERATLSC IGKV3-11*02 light chain variable complementarity determining regions
1 (CDR1) sequence:
(DNA)
(SEQ ID NO: 83)
agggccagtcagagtgttagcagctacttagcc (amino acids)
(SEQ ID NO: 84)
RASQSVSSYLA IGKV3-11*02 light chain variable framework region 2 (FWR2) sequence:
(DNA)
(SEQ ID NO: 85)
tggtaccaacagaaacctggccaggctcccaggctcctcatctat (amino acids)
(SEQ ID NO 86)
WYQQKPGQAPRLLIY IGKV3-11*02 light chain variable complementarity determining regions
2 (CDR2) sequence:
(DNA)
(SEQ ID NO: 87)
gatgcatccaacagggccact (amino acids)
(SEQ ID NO: 88)
DASNRAT IGKV3-11*02 light chain variable framework region 3 (FWR3) sequence:
(DNA)
(SEQ ID NO: 89)
ggcatcccagccaggttcagtggcagtgggtctgggagagacttcactctcaccatcagcagcctaga gcctgaagattttgcagtttattactgt (amino acids)
(SEQ ID NO: 90)
GIPARFSGSGSGTDFTLTISSLEPEDFAVYYC IGKV3-11*02 light chain variable complementarity determining
regions3 (CDR3) sequence:
(DNA)
(SEQ ID NO: 91)
cagcagcgtagcaactggcctcc (amino acids)
(SEQ ID NO: 92)
QQRSNWPP Humanized E6 light chain variable region sequence:
(DNA)
(SEQ ID NO: 93)
gaaattgtgttgacacagtctccagccaccctgtctttgtctccaggggaaagagccaccctcacctg cagcgccaccagcagtgttagctacatccactggtaccaacagagggcctggccagagcccaggctcc tcatctatagcacctccaacctggccagcggcatcccagccaggttcagtggcagtgggtctgggagc gactacactctcaccatcagcagcctagagcctgaagattttgcagtttattactgtcagcagcgtag cagctccccctttcacctttggcagcggcaccaaagtggaaattaaa (amino acids)
(SEQ ID NO: 94)
EIVLTQSPATLSLSPGERATLTCSATSSVSYIHWYQQRPGQSPRLLIYSTSNLASGIPARFSGSGSGS

DYTLTISSLEPEDFAVYYCQQRSSSPFTFGSGTKVEIK

-continued

Humanized E6 light chain variable framework region 1 (FWR1) acid sequence:
(DNA)
(SEQ ID NO: 95)
gaaattgtgttgacacagtctccagccaccctgtctttgtctccaggggaaagagccaccctcacctg c (amino acids)
(SEQ ID NO: 96)
EIVLTQSPATLSLSPGERATLTC Humanized E6 light chain variable complementarity determining regions 1 (CDR1) sequence:
(DNA)
(SEQ ID NO: 97)
agcgccaccagcagtgttagctacatccac (amino acids)
(SEQ ID NO: 98)
SATSSVSYIH Humanized E6 heavy light variable framework region 2 (FWR2) acid sequence:
(DNA)
(SEQ ID NO: 99)
tggtaccaacagaggcctggccagagccccaggctcctcatctat (amino acids)
(SEQ ID NO: 100)
WYQQRPGQSPRLLIY Humanized E6 light chain variable complementarity determining regions 2 (CDR2) sequence:
(DNA)
(SEQ ID NO: 101)
agcacctccaacctggccagc (amino acids)
(SEQ ID NO: 102)
STSNLAS Humanized E6 light chain variable framework region 3 (FWR3) acid sequence:
(DNA)
(SEQ ID NO: 103)
ggcatcccagccaggttcagtggcagtgggtctgggagcgactacactctcaccatcagcagcctaga gcctgaagattttgcagtttattactgt (amino acids)
(SEQ ID NO: 104)
GIPARFSGSGSGSDYTLTISSLEPEDFAVYYC Humanized E6 light chain variable complementarity determining regions 3 (CDR3) sequence:
(DNA)
(SEQ ID NO: 105)
cagcagcgtagcagctccccttttcacc (amino acids)
(SEQ ID NO: 106)
QQRSSSPFT Humanized E6 Kappa light chain synthesized by Genescript:
(DNA)
(SEQ ID NO: 107)
gaattctaagcttgggccaccatggaagcccagcgcagcttctcttcctcctgctactctggctccc agataccactggagaaattgtgttgacacagtctccagccaccctgtctttgtctccaggggaaagag ccaccctcacctgcagcgccaccagcagtgttagctacatccactggtaccaacagaggcctggccag agccccaggctcctcatctatagcacctccaacctggccagcggcatcccagccaggttcagtggcag tgggtctgggagcgactacactctcaccatcagcagcctagagcctgaagattttgcagtttattact gtcagcagcgtagcagctccccttttcacctttggcagcggcaccaaagtggaaattaaaaggacggtg gctgcaccatctgtcttcatcttcccgccatctgatgagcagttgaaatctggaactgcctctgttgt -continued

```
gtgcctgctgaataacttctatcccagagaggccaaagtacagtggaaggtggataacgccctccaat cgggtaactcccaggagagtgtcacagagcaggacagcaaggacagcacctacagcctcagcagcacc ctgacgctgagcaaagcagactacgagaaacacaaagtctacgcctgcgaagtcacccatcagggcct gagctcgcccgtcacaaagagcttcaacaggggagagtgttagtaagtttaaactctaga
```

(amino acids)

(SEQ ID NO: 108)

EF*AWATMEAPAQLLFLLLLWLPDTTGEIVLTQSPATLSLSPGERATLTCSATSSVSYIHWYQQRPGQ

SPRLLIYSTSNLASGIPARFSGSGSGSDYTLTISSLEPEDFAVYYCQQRSSSPFTFGSGTKVEIKRTV

AAPSVFIFPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC**V*TLX

Human Kappa light chain constant region sequence:
(DNA)

(SEQ ID NO: 109)

```
aggacggtggctgcaccatctgtcttcatcttcccgccatctgatgagcagttgaaatctggaactgc ctctgttgtgtgcctgctgaataacttctatcccagagaggccaaagtacagtggaaggtggataacg ccctccaatcgggtaactcccaggagagtgtcacagagcaggacagcaaggacagcacctacagcctc agcagcaccctgacgctgagcaaagcagactacgagaaacacaaagtctacgcctgcgaagtcaccca tcagggcctgagctcgcccgtcacaaagagcttcaacaggggagagtgttag
```

(amino acids)

(SEQ ID NO: 110)

RTVAAPSVFIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

Humanized E6 lambda light chain sequence:
(DNA)

(SEQ ID NO: 111)

```
gaaattgtgttgacacagtctccagccaccctgtctttgtctccaggggaaagagccaccctcacctg cagcgccaccagcagtgttagctacatccactggtaccaacagaggcctggccagagcccaggctcc tcatctatagcacctccaacctggccagcggcatcccagccaggttcagtggcagtgggtctgggagc gactacactctcaccatcagcagcctagagcctgaagattttgcagtttattactgtcagcagcgtag cagctcccctttcacctttggcagcggcaccaaagtggaaattaaaggtcagcccaaggctgccccct cggtcactctgttcccgccctcctctgaggagcttcaagccaacaaggccacactggtgtgtctcata agtgacttctacccgggagccgtgacagtggcctggaaggcagatagcagccccgtcaaggcgggagt ggagaccaccacaccctccaaacaaagcaacaacaagtacgcggccagcagctatctgagcctgacgc ctgagcagtggaagtcccacagaagctacagctgccaggtcacgcatgaagggagcaccgtggagaag acagtggcccctacagaatgttcatagtaa
```

(amino acids)

(SEQ ID NO: 112)

EIVLTQSPATLSLSPGERATLTCSATSSVSYIHWYQQRPGQSPRLLIYSTSNLASGIPARFSGSGSGS

DYTLTISSLEPEDFAVYYCQQRSSSPFTFGSGTKVEIKGQPKAAPSVTLFPPSSEELQANKATLVCLI

SDFYPGAVTVAWKADSSPVKAGVETTTPSKQSNNKYAASSYLSLTPEQWKSHRSYSCQVTHEGSTVEK

TVAPTECS**

Humanized lambda light chain constant region sequence:
(DNA)

(SEQ ID NO: 113)

```
ggtcagcccaaggctgccccctcggtcactctgttcccgccctcctctgaggagcttcaagccaacaa ggccacactggtgtgtctcataagtgacttctacccgggagccgtgacagtggcctggaaggcagata gcagccccgtcaaggcgggagtggagaccaccacaccctccaaacaaagcaacaacaagtacgcggcc
```

-continued agcagctatctgagcctgacgcctgagcagtggaagtcccacagaagctacagctgccaggtcacgca tgaagggagcaccgtggagaagacagtggcccctacagaatgttcatagtaa (amino acids)
(SEQ ID NO: 114)
GQPKAAPSVTLFPPSSEELQANKATLVCLISDFYPGAVTVAWKADSSPVKAGVETTTPSKQSNNKYAA

SSYLSLTPEQWKSHRSYSCQVTHEGSTVEKTVAPTECS**

Human lambda light chain constant region gBLOCK#3 sequence:
(DNA)
(SEQ ID NO: 115)
agcgccaccagcagtgttagctacatccactggtaccaacagaggcctggccagagccccaggctcct catctatagcacctccaacctggccagcggcatcccagccaggttcagtggcagtgggtctgggagcg actacactctcaccatcagcagcctagagcctgaagattttgcagtttattactgtcagcagcgtagc agctcccctttcacctttggcagcggcaccaaagtggaaattaaaggtcagcccaaggctgcccccct ggtcactctgttcccgccctcctctgaggagcttcaagccaacaaggccacactggtgtgtctcataa gtgacttctacccgggagccgtgacagtggcctggaaggcagatagcagcccccgtcaaggcgggagtg gagaccaccacaccctccaaacaaagcaacaacaagtacgcggccagcagctatctgagcctgacgcc tgagcagtggaagtcccacagaagctacagctgccaggtcacgcatgaagggagcaccgtggagaaga cagtggcccctacagaatgttcatagtaagtttaaacccgctgatcagcctcgactgtgccttctagt tg E6 light chain variable region overlapping sequence:
(DNA)
(SEQ ID NO: 116)
agcgccaccagcagtgttagctacatccact pCDNA3.1 V5 and pSECTag2 overlapping sequence:
(DNA)
(SEQ ID NO: 117)
ccgctgatcagcctcgactgtgccttctagttg Mouse C2 heavy chain variable region sequence:
(DNA)
(SEQ ID NO: 118)
gaggtccagctggaggagtcaggggggaggcttagtgaagcctggagggtccctgaaactctcctgtgc agcctctggattcactttcagtggctatgccatgtcttgggttcgccagactccggagaagaggctgg agtgggtcgcaaccattagtagtggtggtacttatatctactatccagacagtgtgaaggggcgattc accatctccagagacaatgccaagaacaccctgtacctgcaaatgagcagtctgaggtctgaggacac ggccatgtattactgtgcaagacttggggggataattactacgaatacttcgatgtctggggcgcag ggaccacggtcaccgtctcctccgccaaaacgacaccccccatctgtctat (amino acids)
(SEQ ID NO: 119)
EVQLEESGGGLVKPGGSLKLSCAASGFTFSGYAMSWVRQTPEKRLEWVATISSGGTYIYYPDSVKGRF

TISRDNAKNTLYLQMSSLRSEDTAMYYCARLGGDNYYEYFDVWGAGTTVTVSSAKTTPPSVY

Mouse C2 heavy chain variable framework region 1 (FWR1) sequence:
(DNA)
(SEQ ID NO: 120)
gaggtccagctggaggagtcaggggggaggcttagtgaagcctggagggtccctgaaactctcctgtgc agcctctggattcactttcagt (amino acids)
(SEQ ID NO: 121)
EVQLEESGGGLVKPGGSLKLSCAASGFTFS Mouse C2 heavy chain variable complementarity determining regions 1
(CDR1) sequence:
(DNA)
(SEQ ID NO: 122)
ggctatgccatgtct

```
(amino acids)
                                                     (SEQ ID NO: 123)
GYAMS Mouse C2 heavy chain variable framework region 2 (FWR2) sequence:
(DNA)
                                                     (SEQ ID NO: 124)
tgggttcgccagactccggagaagaggctggagtgggtcgca (amino acids)
                                                     (SEQ ID NO: 125)
WVRQTPEKRLEWVA Mouse C2 heavy chain variable complementarity determining regions 2
(CDR2) sequence:
(DNA)
                                                     (SEQ ID NO: 126)
accattagtagtggtggtacttatatctactatccagacagtgtgaagggg (amino acids)
                                                     (SEQ ID NO: 127)
TISSGGTYIYYPDSVKG Mouse C2 heavy chain variable framework region 3 (FWR3) sequence:
(DNA)
                                                     (SEQ ID NO: 128)
cgattcaccatctccagagacaatgccaagaacaccctgtacctgcaaatgagcagtctgaggtctga ggacacggccatgtattactgtgcaaga (amino acids)
                                                     (SEQ ID NO: 129)
RFTISRDNAKNTLYLQMSSLRSEDTAMYYCAR Mouse C2 heavy chain variable complementarity determining regions 3
(CDR3) sequence:
(DNA)
                                                     (SEQ ID NO: 130)
cttggggggataattactacgaatacttcgatgtc (amino acids)
                                                     (SEQ ID NO: 131)
LGGDNYYEYFDV IGHV3-21*04 heavy chain variable region sequence:
(DNA)
                                                     (SEQ ID NO: 132)
gaggtgcagctggtggagtctgggggaggcctggtcaagcctggggggtccctgagactctcctgtgc agcctctggattcaccttcagtagctatagcatgaactgggtccgccaggctccagggaaggggctgg agtgggtctcatccattagtagtagtagtagttacatatactacgcagactcagtgaagggccgattc accatctccagagacaacgccaagaactcactgtatctgcaaatgaacagcctgagagccgaggacac ggccgtgtattactgtgcgaga (amino acids)
                                                     (SEQ ID NO: 133)
EVQLVESGGGLVKPGGSLRLSCAASGFTFSSYSMNWVRQAPGKGLEWVSSISSSSSYIYYADSVKGRF

TISRDNAKNSLYLQMNSLRAEDTAVYYCAR

IGHV3-21*04 heavy chain variable framework region 1 (FWR1) sequence:
(DNA)
                                                     (SEQ ID NO: 134)
gaggtgcagctggtggagtctgggggaggcctggtcaagcctggggggtccctgagactctccgtg agcctctggattcaccttcagt (amino acids)
                                                     (SEQ ID NO: 135)
EVQLVESGGGLVKPGGSLRLSCAASGFTFS IGHV3-21*04 heavy chain variable complementarity determining regions
1 (CDR1) sequence:
(DNA)
                                                     (SEQ ID NO: 136)
agctatagcatgaac
```

```
(amino acids)
                                          (SEQ ID NO: 137)
SYSMN IGHV3-21*04 heavy chain variable framework region 2 (FWR2)
sequence:
(DNA)
                                          (SEQ ID NO: 138)
gggtccgccaggctccagggaaggggctggagtgggtctca (amino acids)
                                          (SEQ ID NO: 139)
WVRQAPGKGLEWVS IGHV3-21*04 heavy chain variable complementarity determining regions
2 (CDR2) sequence:
(DNA)
                                          (SEQ ID NO: 140)
tccattagtagtagtagtagttacatatactacgcagactcagtgaagggc (amino acids)
                                          (SEQ ID NO: 141)
SISSSSSYIYYADSVKG IGHV3-21*04 heavy chain variable framework region 3 (FWR3) sequence:
(DNA)
                                          (SEQ ID NO: 142)
cgattcaccatctccagagacaacgccaagaactcactgtatctgcaaatgaacagcctgagagccga ggacacggccgtgtattactgtgcgaga (amino acids)
                                          (SEQ ID NO: 143)
RFTISRDNAKNSLYLQMNSLRAEDTAVYYCAR Humanized C2 heavy chain variable region sequence:
(DNA)
                                          (SEQ ID NO: 144)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggataattactacgaatacttcgatgtctggggcaaag ggaccacggtcaccgtctcctcc (amino acids)
                                          (SEQ ID NO: 145)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSS

Humanized C2 heavy chain variable framework region 1 (FWR1)
sequence:
(DNA)
                                          (SEQ ID NO: 146)
gaggtgcagctggtggagtctgggggaggcctggtcaagcctggggggtccctgagactctcctgtg agcctctggattcaccttcagt (amino acids)
                                          (SEQ ID NO: 147)
EVQLVESGGGLVKPGGSLRLSCAASGFTFS Humanized C2 heavy chain variable complementarity determining
regions 1 (CDR1) sequence:
(DNA)
                                          (SEQ ID NO: 148)
ggctatgccatgagc (amino acids)
                                          (SEQ ID NO: 149)
GYAMS
```

-continued

Humanized C2 heavy chain variable framework region 2 (FWR2) sequence:
(DNA)
(SEQ ID NO: 150)
tgggtccgccaggctccagggaaggggctggagtgggtctcaa (amino acids)
(SEQ ID NO: 151)
WVRQAPGKGLEWVS Humanized C2 heavy chain variable complementarity determining regions 2 (CDR2) sequence:
(DNA)
(SEQ ID NO: 152)
accattagtagtggcggaacctacatatactaccccgactcagtgaagggc (amino acids)
(SEQ ID NO: 153)
TISSGGTYIYYPDSVKG Humanized C2 heavy chain variable framework region 3 (FWR3) sequence:
(DNA)
(SEQ ID NO: 154)
cgattcaccatctccagagacaacgccaagaactcactgtatctgcaaatgaacagcctgagagccga ggacacggccgtgtattactgtgcgaga (amino acids)
(SEQ ID NO: 155)
RFTISRDNAKNSLYLQMNSLRAEDTAVYYCAR Humanized C2 heavy chain variable complementarity determining regions 3 (CDR3) sequence:
(DNA)
(SEQ ID NO: 156)
cttggggggataattactacgaatacttcgatgtc (amino acids)
(SEQ ID NO: 157)
LGGDNYYEYFDV Humanized C2 IgG1 heavy chain sequence
(DNA)
(SEQ ID NO: 157)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttgggggggataattactacgaatacttcgatgtctggggcaaag ggaccacggtcaccgtctcctccgctagcaccaagggcccatcggtcttccccctggcaccctcctcc aagagcacctctgggggcacagcggccctgggctgcctggtcaaggactacttccccgaaccggtgac ggtgtcgtggaactcaggcgccctgaccagcggcgtgcacaccttcccggctgtcctacagtcctcag gactctactccctcagcagcgtggtgacagtgccctccagcagcttgggcacccagacctacatctgc aacgtgaatcacaagcccagcaacaccaaggtggacaagaaagttgagcccaaatcttgtgacaaaac tcacacatgcccaccgtgcccagcacctgaactcctggggggaccgtcagtcttcctcttccccccaa aacccaaggacaccctcatgatctcccggacccctgaggtcacatgcgtggtggtggacgtgagccac gaagaccctgaggtcaagttcaactggtacgtggacggcgtggaggtgcataatgccaagacaaagcc gcggaggagcagtacaacagcacgtaccgtgtggtcagcgtcctcaccgtcctgcaccaggactggc tgaatggcaaggagtacaagtgcaaggtctccaacaaagccctcccagcccccatcgagaaaaccatc tccaaagccaaagggcagccccgagaaccacaggtgtacaccctgcccccatcccgggaggagatgac caagaaccaggtcagcctgacctgcctggtcaaaggcttctatcccagcgacatcgccgtggagtggg agagcaatgggcagccggagaacaactacaagaccacgcctcccgtgctggactccgacggctccttc -continued

```
ttcctctacagcaagctcaccgtggacaagagcaggtggcagcaggggaacgtcttctcatgctccgt gatgcatgaggctctgcacaaccactacacgcagaagagcctctccctgtctccgggtaaatgataa
```

(amino acids)
(SEQ ID NO: 158)
```
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSASTKGPSVFPLAPSS

KSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK**
```

Humanized C2 gBLOCK#4 sequence:
(DNA)
(SEQ ID NO: 160)
```
actcactatagggagacccaagctggctagttaagcttgggccaccatggagacagacacactcctgc tatgggtactgctgctctgggttccaggttccactggtgacgaggtgcagctggtggagtctggggga ggcctggtcaagcctggggggtccctgagactctcctgtgcagcctctggattccacttcagtggcta tgccatgagctgggtccgccaggctccagggaaggggctggagtgggtctcaaccattagtagtggcg gaacctacatatactaccccgactcagtgaagggccgattcaccatctccagagacaacgccaagaac tcactgtatctgcaaatgaacagcctgagagccgaggacacggccgtgtattactgtgcgagacttgg gggggataattactacgaatacttcgatgtctggggcaaagggaccacggtcaccgtctcctccgcta gcaccaagggcccatcggtcttccccctggcaccctcctccaagagcacctctggggggcacagcggcc ctgggctgcctggtcaaggactacttccccgaaccggtgacggtgtcgtggaactcaggcgccctgac cagc
``` pCDNA3.1 V5 overlapping sequence:
(DNA)
(SEQ ID NO: 161)
```
actcactatagggagacccaagctggctagtt
```

Human IgG1 constant region overlapping sequence:
(DNA)
(SEQ ID NO: 162)
```
gacggtgtcgtggaactcaggcgccctgaccagc
```

Humanized C2 IgG2 heavy chain sequence
(DNA)
(SEQ ID NO: 163)
```
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggggataattactacgaatacttcgatgtctggggcaaag ggaccacggtcaccgtctcctccgcctccaccaagggcccatcggtcttcccctggcgccctgctcc aggagcacctccgagagcacagccgccctgggctgcctggtcaaggactacttccccgaaccggtgac ggtgtcgtggaactcaggcgctctgaccagcggcgtgcacaccttcccagctgtcctacagtcctcag gactctactccctcagcagcgtggtgaccgtgccctccagcaacttcggcacccagacctacacctgc aacgtagatcacaagcccagcaacaccaaggtggacaagacagttgagcgcaaatgttgtgtcgagtg cccaccgtgcccagcacacctgtggcaggaccgtcagtcttcctcttccccccaaaacccaaggaca cccttcatgatctcccggacccctgaggtcacgtgcgtggtggtggacgtgagccacgaagaccccgag
```

-continued

```
gtccagttcaactggtacgtggacggcgtggaggtgcataatgccaagacaaagccacgggaggagca gttcaacagcacgttccgtgtggtcagcgtcctcaccgttgtgcaccaggactggctgaacggcaagg agtacaagtgcaaggtctccaacaaaggcctcccagcccccatcgagaaaaccatctccaaaaccaaa gggcagccccgagaaccacaggtgtacaccctgcccccatcccgggaggagatgaccaagaaccaggt cagcctgacctgcctggtcaaaggcttctaccccagcgacatcgccgtggagtgggagagcaatgggc agccggagaacaactacaagaccacacctcccatgctggactccgacggctccttcttcctctacagc aagctcaccgtggacaagagcaggtggcagcaggggaacgtcttctcatgctccgtgatgcatgaggc tctgcacaaccactacacgcagaagagcctctccctgtctccgggtaaatagtaa
```

(amino acids)

(SEQ ID NO: 164)
```
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSASTKGPSVFPLAPCS

RSTSESTAALGCLVKDYFPEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPENNYKTTPPMLDSDGSFFLYS

KLTVDKSRWQQGNVFSCSVMHEALHNHYTQKSLSLSPGK**
```

Humanized C2 gBLOCK#5 sequence:
(DNA)

(SEQ ID NO: 165)
```
tgctctgggttccaggttccactggtgacgcggcccagccggccgaggtgcagctggtggagtctggg ggaggcctggtcaagcctggggggtccctgagactctcctgtgcagcctctggattcaccttcagtgg ctatgccatgagctgggtccgccaggctccagggaaggggctggagtgggtctcaaccattagtagtg gcggaacctacatatactaccccgactcagtgaagggccgattcaccatctccagagacaacgccaag aactcactgtatctgcaaatgaacagcctgagagccgaggacacggccgtgtattactgtgcgagact tggggggggataattactacgaatacttcgatgtctggggcaaagggaccacggtcaccgtctcctccg cctccaccaagggcccatcggtcttccccctggcgccctgctccaggagcacctccgagagcacagcc gccctgggctgcctggtcaaggactacttccccgaaccggtgacggtgtcgtggaactcaggcgctct gacca
``` pSEC Tag2 overlapping sequence:
(DNA)

(SEQ ID NO: 166)
```
tgctctgggttccaggttccactggtgacgc
```

Human IgG2 constant region overlapping sequence:
(DNA)

(SEQ ID NO: 167)
```
gacggtgtcgtggaactcaggcgctctgacca
```

Mouse C2 light chain variable region sequence:
(DNA)

(SEQ ID NO: 168)
```
gacattgtgatcacacagtctacagcttccttaggtgtatctctggggcagagggccaccatctcatg cagggccagcaaaagtgtcagtacatctggctatagttatatgcactggtaccaacagagaccaggac agccacccaaactcctcatctatcttgcatccaacctagaatctggggtccctgccaggttcagtggc agtgggtctgggacagacttcaccctcaacatccatcctgtggaggaggaggatgctgcaacctatta ctgtcagcacagtagggagcttccgttcacgttcggaggggggaccaagctggagataaaacgggctg atgctgcaccaactgtatcc
```

(amino acids)
(SEQ ID NO: 169)
DIVITQSTASLGVSLGQRATISCRASKSVSTSGYSYMHWYQQRPGQPPKLLIYLASNLESGVPARFSG

SGSGTDFTLNIHPVEEEDAATYYCQHSRELPFTFGGGTKLEIKRADAAPTVS

Mouse C2 light chain variable framework region 1 (FWR1) sequence:
(DNA)
(SEQ ID NO: 170)
gacattgtgatcacacagtctacagcttccttaggtgtatctctggggcagagggccaccatctcatg c (amino acids)
(SEQ ID NO: 171)
DIVITQSTASLGVSLGQRATISC Mouse C2 light chain variable complementarity determining regions 1
(CDR1) sequence:
(DNA)
(SEQ ID NO: 172)
agggccagcaaaagtgtcagtacatctggctatagttatatgcac (amino acids)
(SEQ ID NO: 173)
RASKSVSTSGYSYMH Mouse C2 light chain variable framework region 2 (FWR2) sequence:
(DNA)
(SEQ ID NO: 174)
tggtaccaacagagaccaggacagccacccaaactcctcatctat (amino acids)
(SEQ ID NO: 175)
WYQQRPGQPPKLLIY Mouse C2 light chain variable complementarity determining regions 2
(CDR2) sequence:
(DNA)
(SEQ ID NO: 176)
cttgcatccaacctagaatc (amino acids)
(SEQ ID NO: 177)
LASNLES Mouse C2 light chain variable framework region 3 (FWR3) sequence:
(DNA)
(SEQ ID NO: 178)
tggggtccctgccaggttcagtggcagtgggtctgggacagacttcaccctcaacatccatcctgtgg aggaggaggatgctgcaacctattactgt (amino acids)
(SEQ ID NO: 179)
GVPARFSGSGSGTDFTLNIHPVEEEDAATYYC Mouse C2 light chain variable complementarity determining regions 3
(CDR3) sequence:
(DNA)
(SEQ ID NO: 180)
cagcacagtagggagcttccgttcacg (amino acids)
(SEQ ID NO: 181)
QHSRELPFT IGKV7-3*01 light chain variable region sequence:
(DNA)
(SEQ ID NO: 182)
gacattgtgctgacccagtctccagcctccttggccgtgtctccaggacagagggccaccatcacctg cagagccagtgagagtgtcagtttcttgggaataaacttaattcactggtatcagcagaaaccaggac aacctcctaaactcctgatttaccaagcatccaataaagacactggggtcccagccaggttcagcggc agtgggtctgggaccgatttcaccctcacaattaatcctgtggaagctaatgatactgcaaattatta ctgtctgcagagtaagaattttcctcccaca -continued (amino acid)

(SEQ ID NO: 183)
DIVLTQSPASLAVSPGQRATITCRASESVSFLGINLIHWYQQKPGQPPKLLIYQASNKDTGVPARFSG

SGSGTDFTLTINPVEANDTANYYCLQSKNFPPT

IGKV7-3*01 light chain variable framework region 1 (FWR1) sequence:
(DNA)

(SEQ ID NO: 184)
gacattgtgctgacccagtctccagcctccttggccgtgtctccaggacagagggccaccatcacctg c (amino acids)

(SEQ ID NO: 185)
DIVLTQSPASLAVSPGQRATITC

IGKV7-3*01 light chain variable complementarity determining regions
1 (CDR1) sequence:
(DNA)

(SEQ ID NO: 186)
agagccagtgagagtgtcagtttcttgggaataaacttaattcac (amino acids)

(SEQ ID NO: 187)
RASESVSFLGINLIH

IGKV7-3*01 light chain variable framework region 2 (FWR2) sequence:
(DNA)

(SEQ ID NO: 188)
tggtatcagcagaaaccaggacaacctcctaaactcctgatttac (amino acids)

(SEQ ID NO: 189)
WYQQKPGQPPKLLIY

IGKV7-3*01 light chain variable complementarity determining regions
2 (CDR2) sequence:
(DNA)

(SEQ ID NO: 190)
caagcatccaataaagacact (amino acids)

(SEQ ID NO: 191)
QASNKDT

IGKV7-3*01 light chain variable framework region 3 (FWR3) sequence:
(DNA)

(SEQ ID NO: 192)
ggggtcccagccaggttcagcggcagtgggtctgggaccgatttcaccctcacaattaatcctgtgga agctaatgatactgcaaattattactgt (amino acids)

(SEQ ID NO: 193)
GVPARFSGSGSGTDFTLTINPVEANDTANYYC

Humanized C2 light chain variable region sequence:
(DNA)

(SEQ ID NO: 194)
gacattgtgctgacccagtctccagcctccttggccgtgtctccaggacagagggccaccatcacctg cagagccagtaagagtgtcagtaccagcggatactcctacatgcactggtatcagcagaaaccaggac aacctcctaaactcctgatttacctggcatccaatctggagagcggggtcccagccaggttcagcggc agtgggtctgggaccgatttcaccctcacaattaatcctgtggaagctaatgatactgcaaattatta ctgtcagcacagtagggagctgccttctcacattcggcggagggaccaaggtggagatcaaacgaact (amino acids)

(SEQ ID NO: 195)
DIVLTQSPASLAVSPGQRATITCRASKSVSTSGYSYMHWYQQKPGQPPKLLIYLASNLESGVPARFSG

SGSGTDFTLTINPVEANDTANYYCQHSRELPFTFGGGTKVEIKRT

Humanized C2 light chain variable framework region 1 (FWR1) acid sequence:
(DNA)
(SEQ ID NO: 196)
gacattgtgctgacccagtctccagcctccttggccgtgtctccaggacagagggccaccatcacctg c (amino acids)
(SEQ ID NO: 197)
DIVLTQSPASLAVSPGQRATITC Humanized C2 light chain variable complementarity determining regions 1 (CDR1) sequence:
(DNA)
(SEQ ID NO: 198)
agagccagtaagagtgtcagtaccagcggatactcctacatgcac (amino acids)
(SEQ ID NO: 199)
RASKSVSTSGYSYMH Humanized C2 heavy light variable framework region 2 (FWR2) acid sequence:
(DNA)
(SEQ ID NO: 200)
tggtatcagcagaaaccaggacaacctcctaaactcctgatttac (amino acids)
(SEQ ID NO: 201)
WYQQKPGQPPKLLIY Humanized C2 light chain variable complementarity determining regions 2 (CDR2) sequence:
(DNA)
(SEQ ID NO: 202)
ctggcatccaatctggagagc (amino acids)
(SEQ ID NO: 203)
LASNLES Humanized C2 light chain variable framework region 3 (FWR3) acid sequence:
(DNA)
(SEQ ID NO: 204)
ggggtcccagccaggttcagcggcagtgggtctgggaccgatttcaccctcacaattaatcctgtgga agctaatgatactgcaaattattactgt (amino acids)
(SEQ ID NO: 205)
GVPARFSGSGSGTDFTLTINPVEANDTANYYC Humanized C2 light chain variable complementarity determining regions 3 (CDR3) sequence:
(DNA)
(SEQ ID NO: 206)
cagcacagtagggagctgcctttcaca (amino acids)
(SEQ ID NO: 207)
QHSRELPFT Humanized C2 light chain variable complementarity determining regions 3 (CDR3) sequence:
(DNA)
(SEQ ID NO: 208)
ctgcagagtaagaattttcctcccaca (amino acids)
(SEQ ID NO: 209)
LQSKNFPPT Humanized C2 gBLOCK#6 sequence (Kappa light chain in pCDNA3.1 V5):
(DNA)
(SEQ ID NO: 210)
actcactatagggagacccaagctggctagttaagcttgggccaccatggagacagacacactcctgc tatgggtactgctgctctgggttccaggttccactggtgacgacattgtgctgacccagtctccagcc -continued tccttggccgtgtctccaggacagagggccaccatcacctgcagagccagtaagagtgtcagtaccag cggatactcctacatgcactggtatcagcagaaaccaggacaacctcctaaactcctgatttacctgg catccaatctggagagcggggtcccagccaggttcagcggcagtgggtctgggaccgatttcaccctc acaattaatcctgtggaagctaatgatactgcaaattattactgtcagcacagtagggagctgccttt cacattcggcggagggaccaaggtggagatcaaacgaactacggtggctgcaccatctgtcttcatct tcccgccatctgatgagcagttgaaatctggaactgcctctgttgtgtgcctgctgaataacttctat cccagagaggccaaagtacagtggaaggtggataacgccctccaatcgggtaactcccaggagagtgt cacagagcaggacagcaaggacagcacctacagcctcagcagcaccctgacgctgagcaaagcagact acgagaaacacaaagtctacgcctgcgaagtcacccatcagggcctgagctcgcccgtcacaaagagc ttcaacaggggagagtgttagtaagtttaaacccgctgatcagcctcgactgtgccttctagttg pCDNA3.1 V5 5' overlapping sequence:
(DNA)
(SEQ ID NO: 211)
actcactatagggagacccaagctggctagtt pCDNA3.1 V5 3' overlapping sequence:
(DNA)
(SEQ ID NO: 212)
ccgctgatcagcctcgactgtgccttctagttg Humanized C2 gBLOCK#7 sequence (Kappa light chain in pSEC Tag2):
(DNA)
(SEQ ID NO: 213)
tgctctgggttccaggttccactggtgacgcggcccagccggccgacattgtgctgacccagtctcca gcctccttggccgtgtctccaggacagagggccaccatcacctgcagagccagtaagagtgtcagtac cagcggatactcctacatgcactggtatcagcagaaaccaggacaacctcctaaactcctgatttacc tggcatccaatctggagagcggggtcccagccaggttcagcggcagtgggtctgggaccgatttcacc ctcacaattaatcctgtggaagctaatgatactgcaaattattactgtcagcacagtagggagctgcc tttcacattcggcggagggaccaaggtggagatcaaacgaactacggtggctgcaccatctgtcttca tcttcccgccatctgatgagcagttgaaatctggaactgcctctgttgtgtgcctgctgaataacttc tatcccagagaggccaaagtacagtggaaggtggataacgccctccaatcgggtaactcccaggagag tgtcacagagcaggacagcaaggacagcacctacagcctcagcagcaccctgacgctgagcaaagcag actacgagaaacacaaagtctacgcctgcgaagtcacccatcagggcctgagctcgcccgtcacaaag agcttcaacaggggagagtgttagtaagtttaaacccgctgatcagcctcgactgtgccttctagttg pSEC Tag2 5' overlapping sequence:
(DNA)
(SEQ ID NO: 214)
tgctctgggttccaggttccactggtgacgc pSEC Tag2 3' overlapping sequence:
(DNA)
(SEQ ID NO: 215)
ccgctgatcagcctcgactgtgccttctagttg Humanized C2 gBLOCK#8 sequence (lambda light chain in pCDNA3.1 V5):
(DNA)
(SEQ ID NO: 216)
actcactatagggagacccaagctggctagttaagcttgggccaccatggagacagacacactcctgc tatgggtactgctgctctgggttccaggttccactggtgacgacattgtgctgacccagtctccagcc tccttggccgtgtctccaggacagagggccaccatcacctgcagagccagtaagagtgtcagtaccag cggatactcctacatgcactggtatcagcagaaaccaggacaacctcctaaactcctgatttacctgg catccaatctggagagcggggtcccagccaggttcagcggcagtgggtctgggaccgatttcaccctc acaattaatcctgtggaagctaatgatactgcaaattattactgtcagcacagtagggagctgccttt -continued

```
cacattcggcggagggaccaaggtggagatcaaacgaactggtcagcccaaggctgcccctcggtca ctctgttcccgcctcctctgaggagcttcaagccaacaaggccacactggtgtgtctcataagtgac ttctacccgggagccgtgacagtggcctggaaggcagatagcagccccgtcaaggcgggagtggagac caccacaccctccaaacaaagcaacaacaagtacgcggccagcagctatctgagcctgacgcctgagc agtggaagtcccacagaagctacagctgccaggtcacgcatgaagggagcaccgtggagaagacagtg gcccctacagaatgttcatagtaagtttaaacccgctgatcagcctcgactgtgccttctagttg
``` pCDNA3.1 V5 5' overlapping sequence:
(DNA)
(SEQ ID NO: 217)
actcactatagggagacccaagctggctagtt pCDNA3.1 V5 3' overlapping sequence:
(DNA)
(SEQ ID NO: 218)
ccgctgatcagcctcgactgtgccttctagttg Humanized C2 gBLOCK#9 sequence (lambda light chain in pSEC Tag2):
(DNA)
(SEQ ID NO: 219)
```
tgctctgggttccaggttccactggtgacgcggcccagccggccgacattgtgctgacccagtctcca gcctccttggccgtgtctccaggacagagggccaccatcacctgcagagccagtaagagtgtcagtac cagcggatactcctacatgcactggtatcagcagaaaccaggacaacctcctaaactcctgatttacc tggcatccaatctggagagcggggtcccagccaggttcagcggcagtgggtctgggaccgatttcacc ctcacaattaatcctgtggaagctaatgatactgcaaattattactgtcagcacagtagggagctgcc tttcacattcggcggagggaccaaggtggagatcaaacgaactggtcagcccaaggctgcccctcgg tcactctgttcccgcctcctctgaggagcttcaagccaacaaggccacactggtgtgtctcataagt gacttctacccgggagccgtgacagtggcctggaaggcagatagcagccccgtcaaggcgggagtgga gaccaccacaccctccaaacaaagcaacaacaagtacgcggccagcagctatctgagcctgacgcctg agcagtggaagtcccacagaagctacagctgccaggtcacgcatgaagggagcaccgtggagaagaca gtggcccctacagaatgttcatagtaagtttaaacccgctgatcagcctcgactgtgccttctagttg
``` pSEC Tag2 5' overlapping sequence:
(DNA)
(SEQ ID NO: 220)
tgctctgggttccaggttccactggtgacgc pSEC Tag2 3' overlapping sequence:
(DNA)
(SEQ ID NO: 221)
ccgctgatcagcctcgactgtgccttctagttg Murine Ig kappa chain leader sequence
(DNA)
(SEQ ID NO: 222)
atggagacagacacactcctgctatgggtactgctgctctgggttccaggttccactggtgac (amino acids)
(SEQ ID NO: 223)
METDTLLLWVLLLWVPGSTGD Interleukin-2 (IL-2) leader sequence
(DNA)
(SEQ ID NO: 224)
atgtacaggatgcaactcctgtcttgcattgcactaagtcttgcacttgtcacaaacagt (amino acids)
(SEQ ID NO: 225)
MYRMQLLSCIALSLALVTNS CD33 leader sequence
(SEQ ID NO: 226)
atgcctcttctgcttctgcttcctctgctttgggctggagctcttgct (DNA)
(amino acids)

(SEQ ID NO: 227)

MPLLLLLPLLWAGALA

IGHV3-21*03 leader sequence
(DNA)

(SEQ ID NO: 228)

atggaactggggctccgctgggttttccttgttgctattttagaaggtgtccagtgt (amino acids)

(SEQ ID NO: 229)

MELGLRWVFLVAILEGVQC

IGHV3-11*02 leader sequence
(DNA)

(SEQ ID NO: 230)

atggaagccccagcgcagcttctcttcctcctgctactctggctcccagataccactgga (amino acids)

(SEQ ID NO: 231)

MEAPAQLLFLLLLWLPDTTG

Humanized E6 single chain GS3
(DNA)

(SEQ ID NO: 232)

gaggtgcagctggtggagtctggggagggcctggtcaagcctggggggtccctgagactctc ctgtgcagcctctggattcaccttcagtaggtatggcatgagctgggtccgccaggctccag ggaagaggctggagtgggtctcaaccattagtggcggaggcacctacatatactacccagac tcagtgaagggccgattcaccatctccagagacaacgccaagaacaccctgtatctgcaaat gaacagcctgagagccgaggacacggctgtgtattactgtaccagagataactatggccgca actatgattatggcatggattattggggccagggcaccctggtgaccgtgagcagcggcggt agccaccctgtctttgtctccaggggaaagagccaccctcacctgcagcgccaccagcagtg ttagctacatccactggtaccaacagaggcctggccagagccccaggctcctcatctatagc acctccaacctggccagcggcatcccagccaggttcagtggcagtgggtctgggagcgacta cactctcaccatcagcagcctagagcctgaagattttgcagtttattactgtcagcagcgta gcagctcccctttcacctttggcagcggcaccaaagtggaaattaaa (amino acids)

(SEQ ID NO: 233)

EVQLVESGGGLVKPGGSLRLSCAASGFTFSRYGMSWVRQAPGKRLEWVSTISGGGTYIYYPDSVKGRF

TISRDNAKNTLYLQMNSLRAEDTAVYYCTRDNYGRNYDYGMDYWGQGTLVTVSSGGGGSGGGGSGGGG

SEIVLTQSPATLSLSPGERATLTCSATSSVSYIHWYQQRPGQSPRLLIYSTSNLASGIPARFSGSGSG

SDYTLTISSLEPEDFAVYYCQQRSSSPFTFGSGTKVEIK

Humanized E6 single chain IgG1noC
(DNA)

(SEQ ID NO: 234)

gaggtgcagctggtggagtctggggagggcctggtcaagcctggggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacaccctgtatctgcaaatgaacagcctgagagccgaggacac ggctgtgtattactgtaccagagataactatggccgcaactatgattatggcatggattattggggcc agggcaccctggtgaccgtgagcagcgataaaacccatactaaaccgccaaaaccggcgccggaactg ctgggtggtcctggtaccggtgaaattgtgttgacacagtctccagccaccctgtctttgtctccagg ggaaagagccaccctcacctgcagcgccaccagcagtgttagctacatccactggtaccaacagaggc ctggccagagccccaggctcctcatctatagcacctccaacctggccagcggcatcccagccaggttc -continued agtggcagtgggtctgggagcgactacactctcaccatcagcagcctagagcctgaagattttgcagt ttattactgtcagcagcgtagcagctccccttcacctttggcagcggcaccaaagtggaaattaaa (amino acids)

(SEQ ID NO: 235)
EVQLVESGGGLVKPGGSLRLSCAASGFTFSRYGMSWVRQAPGKRLEWVSTISGGGTYIYYPDSVKGRF
TISRDNAKNTLYLQMNSLRAEDTAVYYCTRDNYGRNYDYGMDYWGQGTLVTVSSDKTHTKPPKPAPEL
LGGPGTGEIVLTQSPATLSLSPGERATLTCSATSSVSYIHWYQQRPGQSPRLLIYSTSNLASGIPARF
SGSGSGSDYTLTISSLEPEDFAVYYCQQRSSSPFTFGSGTKVEIK

Humanized E6 single chain X4 (linker is IgG1 and IgG2 modified hinge
region)
(DNA)

(SEQ ID NO: 236)
gaggtgcagctggtggagtctgggggaggcctggtcaagcctggggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacacccctgtatctgcaaatgaacagcctgagagccgaggacac ggctgtgtattactgtaccagagataactatggccgcaactatgattatggcatggattattggggcc agggcaccctggtgaccgtgagcagcgataaaacccatactaaaccgccaaaaccggcgccggaactg ctgggtggtcctggtaccggtactggtggtccgactattaaacctccgaaacctccgaaacctgctcc gaacctgctgggtggtccggaaattgtgttgacacagtctccagccaccctgtctttgtctccagggg aaagagccaccctcacctgcagcgccaccagcagtgttagctacatccactggtaccaacagaggcct ggccagagcccaggctcctcatctatagcacctccaacctggcagcggcatcccagccaggttcag tggcagtgggtctgggagcgactacactctcaccatcagcagcctagagcctgaagattttgcagttt attactgtcagcagcgtagcagctccccttcacctttggcagcggcaccaaagtggaaattaaa (amino acids)

(SEQ ID NO: 237)
EVQLVESGGGLVKPGGSLRLSCAASGFTFSGYGMSWVRQAPGKGLEWVSTISSGGTYIYYPDSVKGRF
TISRDNAKNTLYLQMNSLRAEDTAVYYCTRDNYGRNYDYGMDYWGQGTLVTVSSDKTHTKPPKPAPEL
LGGPGTGTGGPTIKPPKPPKPAPNLLGGPEIVLTQSPATLSLSPGERATLTCSATSSVSYIHWYQQRP
GQSPRLLIYSTSNLASGIPARFSGSGSGSDYTLTISSLEPEDFAVYYCQQRSSSPFTFGSGTKVEIK

Humanized C2 single chain GS3
(DNA)

(SEQ ID NO: 238)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttgggggggataattactacgaatacttcgatgtctggggcaaag ggaccacggtcaccgtctcctccggcggtggcggatccggcggtggcggatccggcggtggcggatcc gacattgtgctgacccagtctccagcctccttggccgtgtctccaggacagagggccaccatcacctg cagagccagtaagagtgtcagtaccagcggatactcctacatgcactggtatcagcagaaaccaggac aacctcctaaactcctgatttacctggcatccaatctggagagcggggtcccagccaggttcagcggc agtgggtctgggaccgatttcaccctcacaattaatcctgtggaagctaatgatactgcaaattatta ctgtcagcacagtagggagctgcctttcacattcggcggagggaccaaggtggagatcaaacgaact

```
(amino acids)
                                                    (SEQ ID NO: 239)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSGGGGSGGGGSGGGGS

DIVLTQSPASLAVSPGQRATITCRASKSVSTSGYSYMHWYQQKPGQPPKLLIYLASNLESGVPARFSG

SGSGTDFTLTINPVEANDTANYYCQHSRELPFTFGGGTKVEIKRT

Humanized C2 single chain IgG (no Cysteine)
(DNA)
                                                    (SEQ ID NO: 240)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggataattactacgaatacttcgatgtctggggcaaag ggaccacggtcaccgtctcctccgataaaacccatactaaaccgccaaaaccggcgccggaactgctg ggtggtcctggtaccggtgacattgtgctgacccagtctccagcctccttggccgtgtctccaggaca gagggccaccatcacctgcagagccagtaagagtgtcagtaccagcggatactcctacatgcactggt atcagcagaaaccaggacaacctcctaaactcctgatttacctggcatccaatctggagagcggggtc ccagccaggttcagcggcagtgggtctgggaccgatttcaccctcacaattaatcctgtggaagctaa tgatactgcaaattattactgtcagcacagtagggagctgcctttcacattcggcggagggaccaagg tggagatcaaacgaact (amino acids)
                                                    (SEQ ID NO: 241)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSDKTHTKPPKPAPELL

GGPGTGDIVLTQSPASLAVSPGQRATITCRASKSVSTSGYSYMHWYQQKPGQPPKLLIYLASNLESGV

PARFSGSGSGTDFTLTINPVEANDTANYYCQHSRELPFTFGGGTKVEIKRT

Humanized C2 single chain X4 (linker is IgG1 and IgG2 modified hinge
region)
(DNA)
                                                    (SEQ ID NO: 242)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggataattactacgaatacttcgatgtctggggcaaag ggaccacggtcaccgtctcctccgataaaacccatactaaaccgccaaaaccggcgccggaactgctg ggtggtcctggtaccggtactggtggtccgactattaaacctccgaaacctccgaaacctgctccgaa cctgctgggtggtccggacattgtgctgacccagtctccagcctccttggccgtgtctccaggacaga gggccaccatcacctgcagagccagtaagagtgtcagtaccagcggatactcctacatgcactggtat cagcagaaaccaggacaacctcctaaactcctgatttacctggcatccaatctggagagcggggtccc agccaggttcagcggcagtgggtctgggaccgatttcaccctcacaattaatcctgtggaagctaatg atactgcaaattattactgtcagcacagtagggagctgcctttcacattcggcggagggaccaaggtg gagatcaaacgaact
```

(amino acids)

(SEQ ID NO: 243)
EVQLVESGGGLVKPGGSLRLSCAASGFTFSGYAMSWVRQAPGKGLEWVSTISSGGTYIYYPDSVKGRF
TISRDNAKNSLYLQMNSLRAEDTAVYYCARLGGDNYYEYFDVWGKGTTVTVSSDKTHTKPPKPAPELL
GGPGTGTGGPTIKPPKPPKPAPNLLGGPDIVLTQSPASLAVSPGQRATITCRASKSVSTSGYSMHWY
QQKPGQPPKLLIYLASNLESGVPARFSGSGSGTDFTLTINPVEANDTANYYCQHSRELPFTFGGGTKV
EIKRT

Humanized C3 single chain GS3
(DNA)

(SEQ ID NO: 244)
caggttcagctggtgcagtctggagctgaggtgaagaagcctggggcctcagtgaaggtctcctgcaa
ggcttctggttacacctttaccgactacgccatgaactgggtgcgacaggcccctggacaagggcttg
agtggatgggagtgatcagcaccttcagcggtaacacaaacttcaaccagaagttcaagggcagagtc
accatgaccacagacacatccacgagcacagcctacatggagctgaggagcctgagatctgacgacac
ggccgtgtattactgtgcgagaagcgactactacggcccatacttcgactactggggccagggcacca
ccctgaccgtgtccagcggcggtggcggatccggcggtggcggatccggcggtggcggatccgatatt
gtgatgacccagactccactctctctgtccgtcacccctggacagccggcctccatctcctgcaggtc
tagtcagaccattgtccatagtaatggaaacacctatttggagtggtacctgcagaagccaggccagt
ctccacagctcctgatctataaggtttccaaccggttctctggagtgccagataggttcagtggcagc
gggtcagggacagatttcacactgaaaatcagccgggtggaggctgaggatgttggggtttattactg
cttccaaggtagccacgtgcctttcaccttcggcggagggaccaaggtggagatcaaacgaact (amino acids)

(SEQ ID NO: 245)
QVQLVQSGAEVKKPGASVKVSCKASGYTFTDYAMNWVRQAPGQGLEWMGVISTFSGNTNFNQKFKGRV
TMTTDTSTSTAYMELRSLRSDDTAVYYCARSDYYGPYFDYWGQGTTLTVSSGGGGSGGGGSGGGGSDI
VMTQTPLSLSVTPGQPASISCRSSQTIVHSNGNTYLEWYLQKPGQSPQLLIYKVSNRFSGVPDRFSGS
GSGTDFTLKISRVEAEDVGVYYCFQGSHVPFTFGGGTKVEIKRT

Humanized C3 single chain IgG1 (no Cysteine)
(DNA)

(SEQ ID NO: 246)
caggttcagctggtgcagtctggagctgaggtgaagaagcctggggcctcagtgaaggtctcctgcaa
ggcttctggttacacctttaccgactacgccatgaactgggtgcgacaggcccctggacaagggcttg
agtggatgggagtgatcagcaccttcagcggtaacacaaacttcaaccagaagttcaagggcagagtc
accatgaccacagacacatccacgagcacagcctacatggagctgaggagcctgagatctgacgacac
ggccgtgtattactgtgcgagaagcgactactacggcccatacttcgactactggggccagggcacca
ccctgaccgtgtccagcgataaaacccatactaaaccgccaaaaccggcgccggaactgctgggtggt
cctggtaccggtgatattgtgatgacccagactccactctctctgtccgtcacccctggacagccggc
ctccatctcctgcaggtctagtcagaccattgtccatagtaatggaaacacctatttggagtggtacc
tgcagaagccaggccagtctccacagctcctgatctataaggtttccaaccggttctctggagtgcca
gataggttcagtggcagcgggtcagggacagatttcacactgaaaatcagccgggtggaggctgagga
tgttggggtttattactgcttccaaggtagccacgtgcctttcaccttcggcggagggaccaaggtgg
agatcaaacgaact (amino acids)

(SEQ ID NO: 247)
QVQLVQSGAEVKKPGASVKVSCKASGYTFTDYAMNWVRQAPGQGLEWMGVISTFSGNTNFNQKFKGRV
TMTTDTSTSTAYMELRSLRSDDTAVYYCARSDYYGPYFDYWGQGTTLTVSSDKTHTKPPKPAPELLGG

PGTGDIVMTQTPLSLSVTPGQPASISCRSSQTIVHSNGNTYLEWYLQKPGQSPQLLIYKVSNRFSGVP

DRFSGSGSGTDFTLKISRVEAEDVGVYYCFQGSHVPFTFGGGTKVEIKRT

Humanized C3 single chain X4 (linker is IgG1 and IgG2 modified hinge
region)
(DNA)
(SEQ ID NO: 248)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagcgataaaacccatactaaaccgccaaaaccggcgccggaactgctgggtggt cctggtaccggtactggtggtccgactattaaacctccgaaacctccgaaacctgctccgaacctgct gggtggtccggatattgtgatgacccagactccactctctctgtccgtcacccctggacagccggcct ccatctcctgcaggtctagtcagaccattgtccatagtaatggaaacacctatttggagtggtacctg cagaagccaggccagtctccacagctcctgatctataaggtttccaaccggttctctggagtgccaga taggttcagtggcagcgggtcagggacagatttcacactgaaaatcagccgggtggaggctgaggatg ttggggtttattactgcttccaaggtagccacgtgcctttcaccttcggcggagggaccaaggtggag atcaaacgaact (amino acids)
(SEQ ID NO: 249)
QVQLVQSGAEVKKPGASVKVSCKASGYTFTDYAMNWVRQAPGQGLEWMGVISTFSGNTNFNQKFKGRV

TMTTDTSTSTAYMELRSLRSDDTAVYYCARSDYYGPYFDYWGQGTTLTVSSDKTHTKPPKPAPELLGG

PGTGTGGPTIKPPKPPKPAPNLLGGPDIVMTQTPLSLSVTPGQPASISCRSSQTIVHSNGNTYLEWYL

QKPGQSPQLLIYKVSNRFSGVPDRFSGSGSGTDFTLKISRVEAEDVGVYYCFQGSHVPFTFGGGTKVE

IKRT

Humanized C8 single chain GS3 (linker is [Gly$_4$Ser$_1$]$_3$)
(DNA)
(SEQ ID NO: 250)
agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctccggcggtggcggatccggcggtggcggatccggcggtggcggatccgacatcgtg atgacccagtctccagactccctggctgtgtctctgggcgagagggccaccatcaactgcagggccag caagagtgttagcaccagcggctacagctacatgcactggtaccagcagaaaccaggacagcctccta agctgctcatttacctggtgtctaacctggaatccggggtccctgaccgattcagtggcagcgggtct gggacagatttcactctcaccatcagcagcctgcaggctgaagatgtggcagtttattactgtcaaca cattcgggaactgaccaggagtgaattcggcggagggaccaaggtggagatcaaacgaact (amino acids)
(SEQ ID NO: 251)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSGGGGSGGGGSGGGGSDIV

MTQSPDSLAVSLGERATINCRASKSVSTSGYSYMHWYQQKPGQPPKLLIYLVSNLESGVPDRFSGSGS

GTDFTLTISSLQAEDVAVYYCQHIRELTRSEFGGGTKVEIKRT

-continued

Humanized C8 single chain IgG1 (no Cysteine)
(DNA)
(SEQ ID NO: 252)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctccgataaaacccatactaaaccgcaaaaccggcgccggaactgctgggtggtcct ggtaccggtgacatcgtgatgacccagtctccagactccctggctgtgtctctgggcgagagggccac catcaactgcagggccagcaagagtgttagcaccagcggctacagctacatgcactggtaccagcaga aaccaggacagcctcctaagctgctcatttacctggtgtctaacctggaatccggggtccctgaccga ttcagtggcagcgggtctgggacagatttcactctcaccatcagcagcctgcaggctgaagatgtggc agtttattactgtcaacacattcgggaactgaccaggagtgaattcggcggagggaccaaggtggaga tcaaacgaact (amino acids)
(SEQ ID NO: 253)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSDKTHTKPPKPAPELLGGP

GTGDIVMTQSPDSLAVSLGERATINCRASKSVSTSGYSYMHWYQQKPGQPPKLLIYLVSNLESGVPDR

FSGSGSGTDFTLTISSLQAEDVAVYYCQHIRELTRSEFGGGTKVEIKRT

Humanized C8 single chain X4 (linker is IgG1 and IgG2 modified hinge
region)
(DNA)
(SEQ ID NO: 254)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactacccagactcagtgaagggccgattc accatctccagagacaacgccaagaactcactgtatctgcaaatgaacagcctgagagccgaggacac ggccgtgtattactgtgcgagactgggcggcgacaattactatgagtattggggcaaagggaccacgg tcaccgtctcctccgataaaacccatactaaaccgccaaaaccggcgccggaactgctgggtggtcct ggtaccggtactggtggtccgactattaaacctccgaaacctccgaaacctgctccgaacctgctggg tggtccggacatcgtgatgacccagtctccagactccctggctgtgtctctgggcgagagggccacca tcaactgcagggccagcaagagtgttagcaccagcggctacagctacatgcactggtaccagcagaaa ccaggacagcctcctaagctgctcatttacctggtgtctaacctggaatccggggtccctgaccgatt cagtggcagcgggtctgggacagatttcactctcaccatcagcagcctgcaggctgaagatgtggcag tttattactgtcaacacattcgggaactgaccaggagtgaattcggcggagggaccaaggtggagatc aaacgaact (amino acids)
(SEQ ID NO: 255)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSDKTHTKPPKPAPELLGGP

GTGTGGPTIKPPKPPKPAPNLLGGPDIVMTQSPDSLAVSLGERATINCRASKSVSTSGYSYMHWYQQK

PGQPPKLLIYLVSNLESGVPDRFSGSGSGTDFTLTISSLQAEDVAVYYCQHIRELTRSEFGGGTKVEI

KRT

-continued pSECTag2 E6 scFV-FC
(DNA)
(SEQ ID NO: 256)
atggagacagacacactcctgctatgggtactgctgctctgggttccaggttccactggtga ggtccctgagactctcctgtgcagcctctggattcaccttcagtaggtatggcatgagctgg gtccgccaggctccagggaagaggctggagtgggtctcaaccattagtggcggaggcaccta catatactacccagactcagtgaagggccgattcaccatctccagagacaacgccaagaaca ccctgtatctgcaaatgaacagcctgagagccgaggacacggctgtgtattactgtaccaga gataactatggccgcaactatgattatggcatggattattggggccagggcaccctggtgac cgtgagcagcggcggtggcggatccggcggtggcggatccggcggtggcggatccgaaattg tgttgacacagtctccagccaccctgtctttgtctccaggggaaagagccaccctcacctgc agcgccaccagcagtgttagctacatccactggtaccaacagagagcctggccagagcccag gctcctcatctatagcacctccaacctggccagcggcatcccagccaggttcagtggcagtg ggtctgggagcgactacactctcaccatcagcagcctagagcctgaagattttgcagtttat tactgtcagcagcgtagcagctccccttcacctttggcagcggcaccaaagtggaaattaa agagcccaaatcttgtgacaaaactcacacatgcccaccgtgcccagcacctgaactcctgg ggggaccgtcagtcttcctcttccccccaaaacccaaggacaccctcatgatctcccggacc cctgaggtcacatgcgtggtggtggacgtgagccacgaagaccctgaggtcaagttcaactg gtacgtggacggcgtggaggtgcataatgccaagacaaagccgcgggaggagcagtacaaca gcacgtaccgtgtggtcagcgtcctcaccgtcctgcaccaggactggctgaatggcaaggag tacaagtgcaaggtctccaacaaagcccttccagcccccatcgagaaaaccatctccaaagc caaagggcagccccgagaaccacaggtgtacaccctgcccccatcccgggaggagatgacca agaaccaggtcagcctgacctgcctggtcaaaggcttctatcccagcgacatcgccgtggag tgggagagcaatgggcagccggagaacaactacaagaccacgcctcccgtgctggactccga cggctccttcttcctctacagcaagctcaccgtggacaagagcaggtggcagcaggggaacg tcttctcatgctccgtgatgcatgaggctctgcacaaccactacacgcagaagagcctctcc ctgtctccgggtaaatgataa (amino acids)
(SEQ ID NO: 257)
METDTLLLWVLLLWVPGSTGDAAQPAEVQLVESGGGLVKPGGSLRLSCAASGFTFSRYGMSW

VRQAPGKRLEWVSTISGGGTYIYYPDSVKGRFTISRDNAKNTLYLQMNSLRAEDTAVYYCTR

DNYGRNYDYGMDYWGQGTLVTVSSGGGGSGGGGSGGGGSEIVLTQSPATLSLSPGERATLTC

SATSSVSYIHWYQQRPGQSPRLLIYSTSNLASGIPARFSGSGSGSDYTLTISSLEPEDFAVY

YCQQRSSSPFTFGSGTKVEIKEPKSCDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLS

LSPGK**

E6 scFC-FC 1 gBLOCK sequence:
(SEQ ID NO: 258)
tgctctgggttccaggttccactggtgacgcggcccagccggccgaggtgcagctggtggag caccttcagtaggtatggcatgagctgggtccgccaggctccagggaagaggctggagtggg tctcaaccattagtggcggaggcacctacatatactacccagactcagtgaagggccgattc accatctccagagacaacgccaagaacaccctgtatctgcaaatgaacagcctgagagccga ggacacggctgtgtattactgtaccagagataactatggccgcaactatgattatggcatgg attattggggccagggcaccctggtgaccgtgagcagcggcggtggcggatccggcggtggc ggatccggcggtggcggatccgaaattgtgttgacacagtctccagccaccctgtctttgtc E6 scFC-FC 2 gBLOCK sequence:

(SEQ ID NO: 259)

aattgtgttgacacagtctccagccaccctgtctttgtctccaggggaaagagccaccctca cctgcagcgccaccagcagtgttagctacatccactggtaccaacagaggcctggccagagc cccaggctcctcatctatagcacctccaacctggccagcggcatcccagccaggttcagtgg cagtgggtctgggagcgactacactctcaccatcagcagcctagagcctgaagattttgcag tttattactgtcagcagcgtagcagctccccctttcacctttggcagcggcaccaaagtggaa attaaagagcccaaatcttgtgacaaaactcacacatgcccaccgtgcccagcacctgaact cctggggggaccgtcagtcttcctcttccccccaaaacccaaggacaccctcatgatctccc ggacccctgaggtcacatgcgtggtggtggacgtgagccacgaagaccctgaggtcaagttc aactggtacgtggacggcgtggaggtgcataatgccaagacaaagccgcgggaggagcagta caacagcacgtaccgtgtggtcagc pSECTag2 C2 scFV-FC
(DNA)

(SEQ ID NO: 260)

atggagacagacacactcctgctatgggtactgctgctctgggttccaggttccactggtga cgcggcccagccggccgaggtgcagctggtggagtctgggggaggcctggtcaagcctgggg ggtccctgagactctcctgtgcagcctctggattcaccttcagtggctatgccatgagctgg gtccgccaggctccagggaaggggctggagtgggtctcaaccattagtagtggcggaaccta catatactaccccgactcagtgaagggccgattcaccatctccagagacaacgccaagaact cactgtatctgcaaatgaacagcctgagagccgaggacacggccgtgtattactgtgcgaga cttgggggataattactacgaatacttcgatgtctggggcaaagggaccacggtcaccgt ctcctccggcggtggcggatccggcggtggcggatccggcggtggcggatccgacattgtgc tgacccagtctccagcctccttggccgtgtctccaggacagagggccaccatcacctgcaga gccagtaagagtgtcagtaccagcggatactcctacatgcactggtatcagcagaaaccagg acaacctcctaaactcctgatttacctggcatccaatctggagagcggggtcccagccaggt tcagcggcagtgggtctgggaccgatttcaccctcacaattaatcctgtggaagctaatgat actgcaaattattactgtcagcacagtagggagctgcctttcacattcggcggagggaccaa ggtggagatcaaacgaactgagcccaaatcttgtgacaaaactcacacatgcccaccgtgcc cagcacctgaactcctggggggaccgtcagtcttcctcttccccccaaaacccaaggacacc ctcatgatctcccggacccctgaggtcacatgcgtggtggtggacgtgagccacgaagaccc tgaggtcaagttcaactggtacgtggacggcgtggaggtgcataatgccaagacaaagccgc gggaggagcagtacaacagcacgtaccgtgtggtcagcgtcctcaccgtcctgcaccaggac tggctgaatggcaaggagtacaagtgcaaggtctccaacaaagccctcccagcccccatcga gaaaaccatctccaaagccaaagggcagccccgagaaccacaggtgtacaccctgcccccat cccgggaggagatgaccaagaaccaggtcagcctgacctgcctggtcaaaggcttctatccc agcgacatcgccgtggagtgggagagcaatgggcagccggagaacaactacaagaccacgcc tcccgtgctggactccgacggctccttcttcctctacagcaagctcaccgtggacaagagca ggtggcagcaggggaacgtcttctcatgctccgtgatgcatgaggctctgcacaaccactac acgcagaagagcctctccctgtctccgggtaaatgataa -continued (amino acids)
(SEQ ID NO: 261)
METDTLLLWVLLLWVPGSTGDAAQPAEVQLVESGGGLVKPGGSLRLSCAASGFTFSGYAMSW

VRQAPGKGLEWVSTISSGGTYIYYPDSVKGRFTISRDNAKNSLYLQMNSLRAEDTAVYYCAR

LGGDNYYEYFDVWGKGTTVTVSSGGGGSGGGGSGGGGSDIVLTQSPASLAVSPGQRATITCR

ASKSVSTSGYSYMHWYQQKPGQPPKLLIYLASNLESGVPARFSGSGSGTDFTLTINPVEAND

TANYYCQHSRELPFTFGGGTKVEIKRTEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFSCSVMHEALHNHY

TQKSLSLSPGK**

C2 scFV-FC 1 gBLOCK sequence:
(DNA)
(SEQ ID NO: 262)
tgctctgggttccaggttccactggtgacgcggcccagccggccgaggtgcagctggtggag caccttcagtggctatgccatgagctgggtccgccaggctccagggaaggggctggagtggg tgtcaaccattagtagtggcggaacctacatatactaccccgactcagtgaagggccgattc accatctccagagacaacgccaagaactcactgtatctgcaaatgaacagcctgagagccga ggacacggccgtgtattactgtgcgagacttgggggggataattactacgaatacttcgatg tctggggcaaagggaccacggtcaccgtctcctccggcggtggcggatccggcggtggcgga tccggcggtggcggatccgacattgtgctgacccagtctccagcctccttggc C2 scFV-FC 2 gBLOCK sequence:
(DNA)
(SEQ ID NO: 263)
cattgtgctgacccagtctccagcctccttggccgtgtctccaggacagagggccaccatca cctgcagagccagtaagagtgtcagtaccagcggatactcctacatgcactggtatcagcag aaaccaggacaacctcctaaactcctgatttacctggcatccaatctggagagcgggtccc agccaggttcagcggcagtgggtctgggaccgatttcaccctcacaattaatcctgtggaag ctaatgatactgcaaattattactgtcagcacagtagggagctgcctttcacattcggcgga gggaccaaggtggagatcaaacgaactgagcccaaatcttgtgacaaaactcacacatgccc accgtgcccagcacctgaactcctggggggaccgtcagtcttcctcttccccccaaaaccca aggacaccctcatgatctcccggacccctgaggtcacatgcgtggtggtggacgtgagccac gaagaccctgaggtcaagttcaactggtacgtggacggcgtggaggtgcataatgccaagac aaagccgcgggaggagcagtacaacagcacgtaccgtgtggtcagc pSECTag2 C3 scFV-FC
(DNA)
(SEQ ID NO: 264)
atggagacagacacactcctgctatgggtactgctgctctggttccaggttccactggtga cgcggcccagccggcccaggttcagctggtgcagtctggagctgaggtgaagaagcctggg cctcagtgaaggtctcctgcaaggcttctggttacacctttaccgactacgccatgaactgg gtgcgacaggcccctggacaagggcttgagtggatgggagtgatcagcacccttcagcggtaa cacaaacttcaaccagaagttcaagggcagagtcaccatgaccacagacacatccacgagca cagcctacatggagctgaggagcctgagatctgacgacacggccgtgtattactgtgcgaga agcgactactacggcccatacttcgactactggggccagggcaccaccctgaccgtgtccag agactccactctctctgtccgtcacccctggacagcggcctccatctcctgcaggtctagt cagaccattgtccatagtaatggaaacacctatttggagtggtacctgcagaagccaggcca -continued

```
gtctccacagctcctgatctataaggtttccaaccggttctctggagtgccagataggttca gtggcagcgggtcagggacagatttcacactgaaaatcagccgggtggaggctgaggatgtt ggggtttattactgcttccaaggtagccacgtgcctttcaccttcggcggagggaccaaggt ggagatcaaacgaactgagcccaaatcttgtgacaaaactcacacatgcccaccgtgcccag cacctgaactcctggggggaccgtcagtcttcctcttcccccccaaaacccaaggacaccctc atgatctcccggacccctgaggtcacatgcgtggtggtggacgtgagccacgaagaccctga ggtcaagttcaactggtacgtggacggcgtggaggtgcataatgccaagacaaagccgcggg aggagcagtacaacagcacgtaccgtgtggtcagcgtcctcaccgtcctgcaccaggactgg ctgaatggcaaggagtacaagtgcaaggtctccaacaaagcccctcccagcccccatcgagaa aaccatctccaaagccaaagggcagccccgagaaccacaggtgtacaccctgcccccatccc gggaggagatgaccaagaaccaggtcagcctgacctgcctggtcaaaggcttctatcccagc gacatcgccgtggagtgggagagcaatgggcagccggagaacaactacaagaccacgcctcc cgtgctggactccgacggctccttcttcctctacagcaagctcaccgtggacaagagcaggt ggcagcaggggaacgtcttctcatgctccgtgatgcatgaggctctgcacaaccactacacg cagaagagcctctccctgtctccgggtaaatgataa
```

(amino acids)

(SEQ ID NO: 265)

```
METDTLLLWVLLLWVPGSTGDAAQPAQVQLVQSGAEVKKPGASVKVSCKASGYTFTDYAMNWVRQAPG

QGLEWMGVISTFSGNTNFNQKFKGRVTMTTDTSTSTAYMELRSLRSDDTAVYYCARSDYYGPYFDYWG

QGTTLTVSSGGGGSGGGGSGGGGSDIVMTQTPLSLSVTPGQPASISCRSSQTIVHSNGNTYLEWYLQK

PGQSPQLLIYKVSNRFSGVPDRFSGSGSGTDFTLKISRVEAEDVGVYYCFQGSHVPFTFGGGTKVEIK

RTEPKSCDKTHTCPPCPAPELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK**
```

C3 GS scFV FC 1 gBLOCK sequence:
(DNA)

(SEQ ID NO: 266)

```
tgctctgggttccaggttccactggtgacgcggcccagccggcccaggttcagctggtgcag tctggagctgaggtgaagaagcctggggcctcagtgaaggtctcctgcaaggcttctggtta cacctttaccgactacgccatgaactgggtgcgacaggcccctggacaagggcttgagtgga tgggagtgatcagcaccttcagcggtaacacaaacttcaaccagaagttcaagggcagagtc accatgaccacagacacatccacgagcacagcctacatggagctgaggagcctgagatctga cgacacggccgtgtattactgtgcgagaagcgactactacggcccatacttcgactactggg gccagggcaccaccctgaccgtgtccagcggcggtggcggatccggcggtggcggatccggc ggtggcggatccgatattgtgatgacccagactccactctctctgt
```

C3 scFV FC2 gBLOCK sequence:
(DNA)

(SEQ ID NO: 267)

```
tattgtgatgacccagactccactctctctgtccgtcacccctggacagccggcctccatct cctgcaggtctagtcagaccattgtccatagtaatggaaacacctatttggagtggtacctg cagaagccaggccagtctccacagctcctgatctataaggtttccaaccggttctctggagt gccagataggttcagtggcagcgggtcagggacagatttcacactgaaaatcagccgggtgg aggctgaggatgttggggtttattactgcttccaaggtagccacgtgccctttcaccttcggc
```

-continued ggagggaccaaggtggagatcaaacgaactgagcccaaatcttgtgacaaaactcacacatg cccaccgtgcccagcacctgaactcctggggggaccgtcagtcttcctcttcccccaaaac ccaaggacaccctcatgatctcccggacccctgaggtcacatgcgtggtggtggacgtgagc cacgaagaccctgaggtcaagttcaactggtacgtggacggcgtggaggtgcataatgccaa gacaaagccgcgggaggagcagtacaacagcacgtaccgtgtggtcagc pSECTag2 C8 scFV-FC
(DNA)

(SEQ ID NO: 268)

atggagacagacacactcctgctatgggtactgctgctctgggttccaggttccactggtga cgcggcccagccggccgaggtgcagctggtggagtctgggggaggcctggtcaagcctgggg ggtccctgagactctcctgtgcagcctctggattcaccttcagtggctatgccatgagctgg gtccgccaggctccagggaaggggctggagtgggtctcaaccattagtagtggcggaaccta catatactaccctgactcagtgaagggccgattcaccatctccagagacaacgccaagaact cactgtatctgcaaatgaacagcctgagagccgaggacacggccgtgtattactgtgcgaga ctgggcggcgataactattatgaatattggggcaaagggaccacggtcaccgtctcctccgg ctccagactccctggctgtgtctctgggcgagagggccaccatcaactgcagggccagcaag agtgttagcaccagcggctacagctacatgcactggtaccagcagaaaccaggacagcctcc taagctgctcatttacctggtgtctaacctggaatccggggtccctgaccgattcagtggca gcgggtctgggacagatttcactctcaccatcagcagcctgcaggctgaagatgtggcagtt tattactgtcaacacattcgggaactgaccaggagtgaattcggcggagggaccaaggtgga gatcaaacgaactgagcccaaatcttgtgacaaaactcacacatgcccaccgtgcccagcac ctgaactcctggggggaccgtcagtcttcctcttccccccaaaacccaaggacaccctcatg atctcccggacccctgaggtcacatgcgtggtggtggacgtgagccacgaagaccctgaggt caagttcaactggtacgtggacggcgtggaggtgcataatgccaagacaaagccgcgggagg agcagtacaacagcacgtaccgtgtggtcagcgtcctcaccgtcctgcaccaggactggctg aatggcaaggagtacaagtgcaaggtctccaacaaagcccctcccagccccatcgagaaaac catctccaaagccaaagggcagccccgagaaccacaggtgtacaccctgcccccatcccggg aggagatgaccaagaaccaggtcagcctgacctgcctggtcaaaggcttctatcccagcgac atcgccgtggagtgggagagcaatgggcagccggagaacaactacaagaccacgcctcccgt gctggactccgacggctccttcttcctctacagcaagctcaccgtggacaagagcaggtggc agcaggggaacgtcttctcatgctccgtgatgcatgaggctctgcacaaccactacacgcag aagagcctctccctgtctccgggtaaatgataa (amino acids)

(SEQ ID NO: 269)

METDTLLLWVLLLWVPGSTGDAAQPAEVQLVESGGGLVKPGGSLRLSCAASGFTFSGYAMSWVRQAPG

KGLEWVSTISSGGTYIYYPDSVKGRFTISRDNAKNSLYLQMNSLRAEDTAVYYCARLGGDNYYEYWGK

GTTVTVSSGGGGSGGGGSGGGGSDIVMTQSPDSLAVSLGERATINCRASKSVSTSGYSYMHWYQQKPG

QPPKLLIYLVSNLESGVPDRFSGSGSGTDFTLTISSLQAEDVAVYYCQHIRELTRSEFGGGTKVEIKR

TEPKSCDKTHTCPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQ

QGNVFSCSVMHEALHNHYTQKSLSLSPGK**

-continued

C8 scFV FC 1 gBLOCK sequence:
(DNA)
(SEQ ID NO: 270)
tgctctgggttccaggttccactggtgacgcggcccagccggccgaggtgcagctggtggag caccttcagtggctatgccatgagctgggtccgccaggctccagggaaggggctggagtggg tgtcaaccattagtagtggcggaacctacatatactaccctgactcagtgaagggccgattc accatctccagagacaacgccaagaactcactgtatctgcaaatgaacagcctgagagccga ggacacggccgtgtattactgtgcgagactgggcggcgataactattatgaatattggggca aagggaccacggtcaccgtctcctccggcggtggcggatccggcggtggcggatccggcggt ggcggatccgacatcgtgatgacccagtctccagactccctgg C8 scFV FC2 gBLOCK sequence:
(DNA)
(SEQ ID NO: 271)
catcgtgatgacccagtctccagactccctggctgtgtctctgggcgagagggccaccatca actgcagggccagcaagagtgttagcaccagcggctacagctacatgcactggtaccagcag aaaccaggacagcctcctaagctgctcatttacctggtgtctaacctggaatccggggtccc tgaccgattcagtggcagcgggtctgggacagatttcactctcaccatcagcagcctgcagg ctgaagatgtggcagtttattactgtcaacacattcgggaactgaccaggagtgaattcggc ggagggaccaaggtggagatcaaacgaactgagcccaaatcttgtgacaaaactcacacatg cccaccgtgcccagcacctgaactcctggggggaccgtcagtcttcctcttccccccaaaac ccaaggacaccctcatgatctcccggacccctgaggtcacatgcgtggtggtggacgtgagc cacgaagaccctgaggtcaagttcaactggtacgtggacggcgtggaggtgcataatgccaa gacaaagccgcgggaggagcagtacaacagcacgtaccgtgtggtcagc Human IgG1 Fc sequence:
(DNA)
(SEQ ID NO: 272)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccacgcctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)
(SEQ ID NO: 273)
EPKSCDKTHTCPPCPAPELLGGPSVFLFPPKPKDTLMISRTPEVTCVVVDVSHEDPEVKFNWYVDGVE

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPGK**

Human IgG1 CH2-CH3 domain sequence:
(DNA)
(SEQ ID NO: 274)
ccgtgcccagcacctgaactcctggggggaccgtcagtcttcctcttccccccaaaacccaaggacac cctcatgatctcccggacccctgaggtcacatgcgtggtggtggacgtgagccacgaagaccctgagg -continued

```
tcaagttcaactggtacgtggacggcgtggaggtgcataatgccaagacaaagccgcgggaggagcag tacaacagcacgtaccgtgtggtcagcgtcctcaccgtcctgcaccaggactggctgaatggcaagga gtacaagtgcaaggtctccaacaaagccctcccagcccccatcgagaaaaccatctccaaagccaaag ggcagccccgagaaccacaggtgtacaccctgcccccatcccgggaggagatgaccaagaaccaggtc agcctgacctgcctggtcaaaggcttctatcccagcgacatcgccgtggagtgggagagcaatgggca gccggagaacaactacaagaccacgcctcccgtgctggactccgacggctccttcttcctctacagca agctcaccgtggacaagagcaggtggcagcaggggaacgtcttctcatgctccgtgatgcatgaggct ctgcacaaccactacacgcagaagagcctctccctgtctccgggtaaatgataa
```

(amino acids)

(SEQ ID NO: 275)

```
PCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEA
LHNHYTQKSLSLSPGK**
```

Human IgG1 CH3 domain sequence:
(DNA)

(SEQ ID NO: 276)

```
gggcagccccgagaaccacaggtgtacaccctgcccccatcccgggaggagatgaccaagaaccaggt cagcctgacctgcctggtcaaaggcttctatcccagcgacatcgccgtggagtgggagagcaatgggc agccggagaacaactacaagaccacgcctcccgtgctggactccgacggctccttcttcctctacagc aagctcaccgtggacaagagcaggtggcagcaggggaacgtcttctcatgctccgtgatgcatgaggc tctgcacaaccactacacgcagaagagcctctccctgtctccgggtaaatgataa
```

(amino acids)

(SEQ ID NO: 277)

```
GQPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK**
```

Human IgG1 Fc Y407R sequence:
(DNA)

(SEQ ID NO: 278)

```
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccacgcctcccg tgctggactccgacggctccttcttcctcaggagcaagctcaccgtggacaagagcaggtggcagcag gggaacgtcttctcatgctccgtgatgcatgaggctctgcacaaccactacacgcagaagagcctctc cctgtctccgggtaaatgataa
```

(amino acids)

(SEQ ID NO: 279)

```
EPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLRSKLTVDKSRWQQ
GNVFSCSVMHEALHNHYTQKSLSLSPGK**
```

-continued

Human IgG1 Fc F405Q sequence:
(DNA)
(SEQ ID NO: 280)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccacgcctcccg tgctggactccgacggctccttccagctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)
(SEQ ID NO: 281)
EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSD

GSFQLYSKLTVDKSRWQQGNVFSCSVMHEALHNHYTQKSLSLSPGK**

Human IgG1 Fc T394D sequence:
(DNA)
(SEQ ID NO: 282)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccgaccctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)
(SEQ ID NO: 283)
EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTDPPVLDSD

GSFFLYSKLTVDKSRWQQGNVFSCSVMHEALHNHYTQKSLSLSPGK**

Human IgG1 Fc T366W/L368W sequence:
(DNA)
(SEQ ID NO: 284)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct -continued caccgtcctgcaccaggactggctgaatggcaaggagtacaagtgcaaggtctccaacaaagccctcc cagccccatcgagaaaaccatctccaaagccaaagggcagccccgagaaccacaggtgtacaccctg cccccatcccgggaggagatgaccaagaaccaggtcagcctgtggtgctgggtcaaaggcttctatcc cagcgacatcgccgtggagtgggagagcaatgggcagccggagaacaactacaagaccacgcctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)

(SEQ ID NO: 285)
EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLWCWVKGFYPSDIAVEWESNGQPENNYKTTPPVLDSD

GSFFLYSKLTVDKSRWQQGNVFSCSVMHEALHNHYTQKSLSLSPGK**

Human IgG1 Fc T364R/L368R sequence:
(DNA)

(SEQ ID NO: 286)
gagcccaaatcttgtgacaaaactcacacatgcccaccgtgcccagcacctgaactcctgggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagccccatcgagaaaaccatctccaaagccaaagggcagccccgagaaccacaggtgtacaccctg cccccatcccgggaggagatgaccaagaaccaggtcaggctgacctgcagggtcaaaggcttctatcc cagcgacatcgccgtggagtgggagagcaatgggcagccggagaacaactacaagaccacgcctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)

(SEQ ID NO: 287)
EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVRLTCRVKGFYPSDIAVEWESNGQPENNYKTTPPVLDSD

GSFFLYSKLTVDKSRWQQGNVFSCSVMHEALHNHYTQKSLSLSPGK**

Human IgG1 Fc hingeless sequence:
(DNA)

(SEQ ID NO: 288)
gcacctgaactcctgggggaccgtcagtcttcctcttccccccaaaacccaaggacaccctcatgat ctcccggacccctgaggtcacatgcgtggtggtggacgtgagccacgaagaccctgaggtcaagttca actggtacgtggacggcgtggaggtgcataatgccaagacaaagccgcgggaggagcagtacaacagc acgtaccgtgtggtcagcgtcctcaccgtcctgcaccaggactggctgaatggcaaggagtacaagtg caaggtctccaacaaagccctcccagccccatcgagaaaaccatctccaaagccaaagggcagcccc gagaaccacaggtgtacaccctgcccccatcccgggaggagatgaccaagaaccaggtcagcctgacc tgcctggtcaaaggcttctatcccagcgacatcgccgtggagtgggagagcaatgggcagccggagaa caactacaagaccacgcctcccgtgctggactccgacggctccttcttcctctacagcaagctcaccg -continued tggacaagagcaggtggcagcaggggaacgtcttctcatgctccgtgatgcatgaggctctgcacaac cactacacgcagaagagcctctccctgtctccgggtaaatgataa (amino acids)

(SEQ ID NO: 289)

APELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSRWQQGNVFSCSVMHEALHN

HYTQKSLSLSPGK**

Human IgG1 G237A FC sequence:
(DNA)

(SEQ ID NO: 290)

gagcccaaatcttgtgacaaaactcacacatgcccaccgtgcccagcacctgaactcctggg ggccccgtcagtcttcctcttccccccaaaacccaaggacaccctcatgatctcccggaccc ctgaggtcacatgcgtggtggtggacgtgagccacgaagaccctgaggtcaagttcaactgg tacgtggacggcgtggaggtgcataatgccaagacaaagccgcgggaggagcagtacaacag cacgtaccgtgtggtcagcgtcctcaccgtcctgcaccaggactggctgaatggcaaggagt acaagtgcaaggtctccaacaaagccctcccagcccccatcgagaaaaccatctccaaagcc aaagggcagccccgagaaccacaggtgtacaccctgcccccatcccgggaggagatgaccaa gaaccaggtcagcctgacctgcctggtcaaaggcttctatcccagcgacatcgccgtggagt gggagagcaatgggcagccggagaacaactacaagaccacgcctcccgtgctggactccgac ggctccttcttcctctacagcaagctcaccgtggacaagagcaggtggcagcaggggaacgt cttctcatgctccgtgatgcatgaggctctgcacaaccactacacgcagaagagcctctccc tgtctccgggtaaa (amino acids)

(SEQ ID NO: 291)

EPKSCDKTHTCPPCPAPELLGAPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

Human IgG1 L234A/L235A FC sequence:
(DNA)

(SEQ ID NO: 292)

gagcccaaatcttgtgacaaaactcacacatgcccaccgtgcccagcacctgaagccgccgg gggaccgtcagtcttcctcttccccccaaaacccaaggacaccctcatgatctcccggaccc ctgaggtcacatgcgtggtggtggacgtgagccacgaagaccctgaggtcaagttcaactgg tacgtggacggcgtggaggtgcataatgccaagacaaagccgcgggaggagcagtacaacag cacgtaccgtgtggtcagcgtcctcaccgtcctgcaccaggactggctgaatggcaaggagt acaagtgcaaggtctccaacaaagccctcccagcccccatcgagaaaaccatctccaaagcc aaagggcagccccgagaaccacaggtgtacaccctgcccccatcccgggaggagatgaccaa gaaccaggtcagcctgacctgcctggtcaaaggcttctatcccagcgacatcgccgtggagt gggagagcaatgggcagccggagaacaactacaagaccacgcctcccgtgctggactccgac ggctccttcttcctctacagcaagctcaccgtggacaagagcaggtggcagcaggggaacgt cttctcatgctccgtgatgcatgaggctctgcacaaccactacacgcagaagagcctctccc tgtctccgggtaaa -continued (amino acids)
(SEQ ID NO: 293)
EPKSCDKTHTCPPCPAPEAAGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

CAR-T E6 CD3z sequence:
(DNA)
(SEQ ID NO: 294)
atggccctgcccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtgggggggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctcccccattcacctttgggagtgggaccaaggttgaaattaaaacgacaaccccggc ccccagaccaccaacgccagccccaccatcgccagccaaccctgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgccgcgttaagttctcccgatcagccgacgcgcctgcttacaagcagggccagaacc aactgtacaacgagctgaatctcggtagacgggaagagtacgacgtgttggacaaacggaga ggccgcgacccagaaatgggcggcaagcctcgcaggaaaaaccccaggagggactgtacaa tgagttgcagaaagataagatggcagaagcttatagcgagatcggaatgaaggggaaagga gacgagggaaaggacacgacggcctttatcagggcctgtccacagcaacaaaagatacgtat gacgccctccatatgcaggcacttccaccacggtgataa (amino acids)
(SEQ ID NO: 295)
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDI

YIWAPLAGTCGVLLLSLVITLYCRVKFSRSADAPAYKQGQNQLYNELNLGRREEYDVLDKRR

GRDPEMGGKPRRKNPQEGLYNELQKDKMAEAYSEIGMKGERRRGKGHDGLYQGLSTATKDTY

DALHMQALPPR****

-continued

CAR-T E6 CD3z gBLOCK sequence:
(DNA)
(SEQ ID NO: 296)
tggagctgtgcacacaagaggactggatttcgcctgtgatatctacatttgggccccgctcgcaggca catgtggagtgctcctcctctccctggtgattaccctgtactgccgcgttaagttctcccgatcagcc gacgcgcctgcttacaagcagggccagaaccaactgtacaacgagctgaatctcggtagacgggaaga gtacgacgtgttggacaaacggagaggccgcgacccagaaatgggcggcaagcctcgcaggaaaaacc cccaggagggactgtacaatgagttgcagaaagataagatggcagaagcttatagcgagatcggaatg aaggggggaaaggagacgagggaaaggacacgacggcctttatcagggcctgtccacagcaacaaaaga tacgtatgacgccctccatatgcaggcacttccaccacggtgataagtttaaacccgctgatcagcct cgactgtgc CAR-T E6 CD28/CD3z sequence:
(DNA)
(SEQ ID NO: 297)
atggccctgcccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaataccctgtatttgcaga tgaattctctgagagcagaggacacagctgtttactattgtacccgcgacaactatggcagg aactacgactacggtatggactattggggacaagggacattggttacagtgagcagtggcgg ccgcgactctcagtctctcacctggggaacgagctaccctgacgtgctctgctacctcctca gtgtcatatattcactggtatcagcaacggcccgggcagtccccctagattgctcatttatag tacctctaatctggcctcaggtatccctgcacgatttttctggatctggttcaggttctgatt acaccctcactatctctagcctggagcctgaagactttgccgttattactgccagcagagg tctagctccccattcacctttgggagtgggaccaaggttgaaattaaaacgacaaccccggc ccccagaccaccaacgccagccccaccatcgccagccaaccccgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgcagaagcaagcggtctcggctcctgcattctgattacatgaacatgaccccaagaa gaccaggccccaccaggaaacattaccagccctacgctccgccacgcgacttcgctgcctac cggtcccgcgttaagttctcccgatcagccgacgcgcctgcttacaagcagggccagaacca actgtacaacgagctgaatctcggtagacgggaagagtacgacgtgttggacaaacggagag gccgcgacccagaaatgggcggcaagcctcgcaggaaaaacccccaggagggactgtacaat gagttgcagaaagataagatggcagaagcttatagcgagatcggaatgaaggggggaaaggag acgagggaaaggacacgacggcctttatcagggcctgtccacagcaacaaaagatacgtatg acgccctccatatgcaggcacttccaccacggtgataa (amino acids)
(SEQ ID NO: 298)
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDI

YIWAPLAGTCGVLLLSLVITLYCRSKRSRLLHSDYMNMTPRRPGPTRKHYQPYAPPRDFAAY

RSRVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR**

CAR-T E6 CD28/CD3z g BLOCK sequence:
(DNA)

(SEQ ID NO: 299)

tggagctgtgcacacaagaggactggatttcgcctgtgatatctacatttgggcccgctcgcaggca catgtggagtgctcctcctctccctggtgattaccctgtactgcagaagcaagcggtctcggctcctg cattctgattacatgaacatgaccccaagaagaccaggccccaccaggaaacattaccagccctacgc tccgccacgcgacttcgctgcctaccggtcccgcgttaagttctcccgatcagccgacgcgcctgctt acaagcagggccagaaccaactgtacaacgagctgaatctcggtagacgggaagagtacgacgtgttg gacaaacggagaggccgcgacccagaaatgggcggcaagcctcgcaggaaaaaccccaggagggact gtacaatgagttgcagaaagataagatggcagaagcttatagcgagatcggaatgaaggggaagga gacgagggaaggacacgacggcctttatcagggcctgtccacagcaacaaaagatacgtatgacgcc ctccatatgcaggcacttccaccacggtgataagtttaaacccgctgatcagcctcgactgtgc CAR-T E6 4-1BB/CD3z sequence:
(DNA)

(SEQ ID NO: 300)

atggccctgcccgtgaccgctttgctgctcccccctggcgctgctgctgcacgccgccaggcc agaggtccagctggttgagagtggcgtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacccgtatttgcaga tgaattctctgagagcagaggacacagctgtttactattgtacccgcgacaactatggcagg aactacgactacggtatggactattggggacaagggacattggttacagtgagcagtggcgg cggggcagcggaggaggaggcagcggtgggggggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagcccccaccatcgccagccaaccctgtctctgagaccagaag cctgtaggcctgccgccggtggagctgtgcacacaagaggactggatttcgcctgtgatatc tacatttgggcccgctcgcaggcacatgtggagtgctcctcctctccctggtgattaccct gtactgcaaaaggggccgcaaaaaactcctttacatttttaagcagccttttatgaggccag tacagacgactcaagaggaagacgggtgctcatgccgctttcctgaggaggaggaaggaggg tgcgaactgcgcgttaagttctcccgatcagccgacgcgcctgcttacaagcagggccagaa ccaactgtacaacgagctgaatctcggtagacgggaagagtacgacgtgttggacaaacgga gaggccgcgacccagaaatgggcggcaagcctcgcaggaaaaaccccaggagggactgtac aatgagttgcagaaagataagatggcagaagcttatagcgagatcggaatgaaggggaaag gagacgagggaaggacacgacggcctttatcagggcctgtccacagcaacaaaagatacgt atgacgccctccatatgcaggcacttccaccacggtgataa -continued (amino acids)

(SEQ ID NO: 301)
MALPVTALLLPLALLLHAARPEVQLVESGGGLVKPGGSLRLSCAASGFTFSRYGMSWVRQAPGKRLEW

VSTISGGGTYIYYPDSVKGRFTISRDNAKNTLYLQMNSLRAEDTAVYYCTRDNYGRNYDYGMDYWGQG

TLVTVSSGGGGSGGGGSGGGGSEIVLTQSPATLSLSPGERATLTCSATSSVSYIHWYQQRPGQSPRLL

TYSTSNLASGIPARFSGSGSGSDYTLTISSLEPEDFAVYYCQQRSSSPFTFGSGTKVEIKTTTPAPRP

PTPAPTIASQPLSLRPEACRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERRRGKGHDGLYQGLSTATKDTY

DALHMQALPPR**

CAR-T E6 4-1BB/CD3z gBLOCK sequence:
(DNA)

(SEQ ID NO: 302)
tggagctgtgcacacaagaggactggatttcgcctgtgatatctacatttgggccccgctcgcaggca catgtggagtgctcctcctctccctggtgattaccctgtactgcaaaaggggccgcaaaaaactcctt tacattttaagcagccttttatgaggccagtacagacgactcaagaggaagacgggtgctcatgccg ctttcctgaggaggaggaaggagggtgcgaactgcgcgttaagttctcccgatcagccgacgcgcctg cttacaagcagggccagaaccaactgtacaacgagctgaatctcggtagacgggaagagtacgacgtg ttggacaaacgagaggccgcgacccagaaatgggcggcaagcctcgcaggaaaaaccccaggaggg actgtacaatgagttgcagaaagataagatggcagaagcttatagcgagatcggaatgaaggggaaa ggagacgagggaaaggacacgacgcctttatcagggcctgtccacagcaacaaaagatacgtatgac gccctccatatgcaggcacttccaccacggtgataagtttaaacccgctgatcagcctcgactgtgc CAR-T E6 CD28/4-1BB/CD3z sequence:
(DNA)

(SEQ ID NO: 303)
atggccctgcccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattacccccga ctcagtcaaggggagatttaccatttcacgagacaacgctaagaataccctgtatttgcaga tgaattctctgagagcagaggacacagctgtttactattgtacccgcgacaactatggcagg aactacgactacggtatggactattggggacaagggacattggttacagtgagcagtggcgg ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagccccaccatcgccagccaacccctgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgcaagaagcaagcggtctcggctcctgcattctgattacatgaacatgaccccaagaa gaccaggcccaccaggaaacattaccagccctacgctccgccacgcgacttcgctgcctac cggtccaaaaggggccgcaaaaaactcctttacattttaagcagccttttatgaggccagt acagacgactcaagaggaagacgggtgctcatgccgctttcctgaggaggaggaaggagggt

```
gcgaactgcgcgttaagttctcccgatcagccgacgcgcctgcttacaagcagggccagaac caactgtacaacgagctgaatctcggtagacgggaagagtacgacgtgttggacaaacggag aggccgcgacccagaaatgggcggcaagcctcgcaggaaaaaccccaggagggactgtaca atgagttgcagaaagataagatggcagaagcttatagcgagatcggaatgaaggggaaagg agacgagggaaaggacacgacggcctttatcagggcctgtccacagcaacaaaagatacgta tgacgccctccatatgcaggcacttccaccacggtgataa
```

(amino acids)

(SEQ ID NO: 304)

```
MALPVTALLLPLALLLHAARPEVQLVESGGGLVKPGGSLRLSCAASGFTFSRYGMSWVRQAPGKRLEW

VSTISGGGTYIYYPDSVKGRFTISRDNAKNTLYLQMNSLRAEDTAVYYCTRDNYGRNYDYGMDYWGQG

TLVTVSSGGGGSGGGGSGGGGSEIVLTQSPATLSLSPGERATLTCSATSSVSYIHWYQQRPGQSPRLL

IYSTSNLASGIPARFSGSGSGSDYTLTISSLEPEDFAVYYCQQRSSSPFTFGSGTKVEIKTTTPAPRP

PTPAPTIASQPLSLRPEACRPAAGGAVHTRGLDFACDIYIWAPLAGTCGVLLLSLVITLYCRSKRSRL

LHSDYMNMTPRRPGPTRKHYQPYAPPRDFAAYRSKRGRKKLLYIFKQPFMRPVQTTQEEDGCSCRFPE

EEEGGCELRVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR**
```

CAR-T E6 CD28/4-1BB/CD3z gBLOCK sequence:
(DNA)

(SEQ ID NO: 305)

```
atagggagacccaagctggctagttaagcttggtaccgagggccaccatggccctgcccgtg accgctttgctgctccccctggcgctgctgctgcacgccgccaggccagaggtccagctggt gatttactttcagccgatatgggatgagttgggtgcggcaagctcccgggaagaggctggaa tgggtctcaacaatctccggggggggcacttacatctattaccccgactcagtcaaggggag atttaccatttcacgagacaacgctaagaatacactgtatttgcagatgaattctctgagag cagaggacacagctgtttactattgtacccgcgacaactatggcaggaactacgactacggt atggactattggggacaagggacattggttacagtgagcagtggcggcggggcagcggagg tctcacctggggaacgagctaccctgacgtgctctgctacctcctcagtgtcatatattcac tggtatcagcaacggcccgggcagtcccctagattgctcatttatagtacctctaatctggc ctcaggtatccctgcacgattttctggatctggttcaggttctgattacaccctcactatct ctagcctggagcctgaagactttgccgtttattactgccagcagaggtctagctccccattc acctttgggagtgggaccaaggttgaaattaaaacgacaaccccggcccccagaccaccaac gccagcccccaccatcgccagccaacccctgtctctgagaccagaagcctgtaggcctgccg ccggtggagctgtgcacacaagaggactggatttcgcctgtgatatctacatttgggccccg ctcgcaggcacatgtggagtgctcctcctctccctggtgattaccctgtactgcagaagcaa gcggtctcggctcctgcattctgattacatgaacatgaccccaagaagaccaggccccacca ggaaacattaccagccctacgctccgccacgcgacttcgctgcctaccggtccaaaagggggc cgcaaaaaactcctttacatttttaagcagccttttatgaggccagtacagacgactcaaga ggaagacggtgctcatgccgctttcctgaggaggaggaaggagggtgcgaactgcgcgtta agttctcccgatcagccgacgcgcctgcttacaagcagggccagaaccaactgtacaacgag ctgaatctcggtagacgggaagagtacgacgtgttggacaaacggagaggccgcgacccaga aatgggcggcaagcctcgcaggaaaaaccccaggagggactgtacaatgagttgcagaaag ataagatggcagaagcttatagcgagatcggaatgaaggggaaaggagacgagggaaagga
```

-continued cacgacggcctttatcagggcctgtccacagcaacaaaagatacgtatgacgccctccatat gcaggcacttccaccacggtgataagtttaaacccgctgatcagcctcgactgtgc CAR-T C2 CD28/4-1BB/CD3z sequence:
(DNA)
(SEQ ID NO: 306)
atggccttgccagtgacggccctgctgctgccattggctcttctgttgcacgctgccaggcctgaagt gcagctcgtagagagtggcgggggactggtgaagcccggtggaagcctcagactcagttgcgccgcct caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggaaagggact accgtgacagtttcaagcggaggaggtggctcaggtggaggcgggtcaggggggggaggaagtgatat tgtgctcacacaatccccagcctccctggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactccccttctacgttcggcggggcacaaaggtcgaaattaagagaaccacgaca accccggcccccagaccaccaacgccagcccccaccatcgccagccaacccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaga agcaagcggtctcggctcctgcattctgattacatgaacatgaccccaagaagaccaggcccaccag gaaacattaccagccctacgctccgccacgcgacttcgctgcctaccggtccaaaaggggccgcaaaa aactcctttacattttaagcagccttttatgaggccagtacagacgactcaagaggaagacgggtgc tcatgccgctttcctgaggaggaggaaggagggtgcgaactgcgcgttaagttctcccgatcagccga cgcgcctgcttacaagcagggccagaaccaactgtacaacgagctgaatctcggtagacgggaagagt acgacgtgttggacaaacggagaggccgcgacccagaaatgggcggcaagcctcgcaggaaaaacccc caggagggactgtacaatgagttgcagaaagataagatggcagaagcttatagcgagatcggaatgaa gggggaaaggagacgagggaaaggacacgacggcctttatcagggcctgtccacagcaacaaaagata cgtatgacgccctccatatgcaggcacttccaccacggtgataa (amino acids)
(SEQ ID NO: 307)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSGGGGSGGGGSGGGGS

DIVLTQSPASLAVSPGQRATITCRASKSVSTSGYSYMHWYQQKPGQPPKLLIYLASNLESGVPARFSG

SGSGTDFTLTINPVEANDTANYYCQHSRELPFTFGGGTKVEIKRTTTTPAPRPPTPAPTIASQPLSLR

PEACRPAAGGAVHTRGLDFACDIYIWAPLAGTCGVLLLSLVITLYCRSKRSRLLHSDYMNMTPRRPGP

TRKHYQPYAPPRDFAAYRSKRGRKKLLYIFKQPFMRPVQTTQEEDGCSCRFPEEEEGGCELRVKFSRS

ADAPAYKQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

CAR-T C2-1 gBLOCK sequence:
(DNA)
(SEQ ID NO: 308)
atagggagacccaagctggctagttaagcttggtaccgagggccaccatggccttgccagtgacggcc ctgctgctgccattggctcttctgttgcacgctgccaggcctgaagtgcagctcgtagagagtggcgg gggactggtgaagcccggtggaagcctcagactcagttgcgccgcctcaggtttcacttttttcaggtt -continued acgccatgtcctgggtaagacaggcaccggggaaaggactcgagtgggtgtctactatcagctcagga ggcacttatatatattatcctgactctgtaaaaggccgatttacgatttctcgcgacaatgcaaagaa ctccctctacctccaaatgaacagtcttagggcagaagacactgctgtatactattgtgcacgcctcg gcggcgacaactactacgagtactttgacgtgtggggaaagggactaccgtgacagtttcaagcgga ggaggtggctcaggtggaggcgggtcaggggggggaggaagtgatattgtgctcacacaatccccagc ctccctggc CAR-T C2-2 gBLOCK sequence:
(DNA)

(SEQ ID NO: 309)

aagtgatattgtgctcacacaatccccagcctccctggctgtgtctcccggccaacgcgctacaatta catgtcgggcctccaaaagcgtgagcaccagcggctacagctacatgcactggtatcaacagaaacca ggacaacccccaaactgttgatttatctcgcttcaaacttggagtccggcgtgcctgcgcgcttttc agggagtgggagcggcacagattttacgctgactatcaaccccgtagaagcaaacgatacagcgaatt attattgtcaacattcccgggaactcccctttacgttcggcggggggcacaaaggtcgaaattaagaga accacgacaaccccggccccagaccaccaacgccagcccccaccatcgccagccaacccctgtctct gagaccagaagcctgtaggcctgccgccggtggagctgtgcacacaagaggactggatttcgcctgtg atatctacatttgggccccgctcgcaggcacatgtggagtgc CAR E6 Fc/8/4-1BB/CD3z sequence:
(DNA)

(SEQ ID NO: 310)

atggccctgcccgtgaccgctttgctgctcccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctcccccattcacctttgggagtgggaccaaggttgaaattaaagagcccaaatcttg tgacaaaactcacacatgcccaccgtgcccagcacctgaactcctggggggaccgtcagtct tcctcttccccccaaaacccaaggacaccctcatgatctcccggacccctgaggtcacatgc gtggtggtggacgtgagccacgaagaccctgaggtcaagttcaactggtacgtggacggcgt ggaggtgcataatgccaagacaaagccgcgggaggagcagtacaacagcacgtaccgtgtgg tcagcgtcctcaccgtcctgcaccaggactggctgaatggcaaggagtacaagtgcaaggtc tccaacaaagccctcccagcccccatcgagaaaaccatctccaaagccaaagggcagcccg agaaccacaggtgtacaccctgcccccatcccgggaggagatgaccaagaaccaggtcagcc tgacctgcctggtcaaaggcttctatcccagcgacatcgccgtggagtgggagagcaatggg cagccggagaacaactacaagaccacgcctcccgtgctggactccgacggctccttcttcct ctacagcaagctcaccgtggacaagagcaggtggcagcaggggaacgtcttctcatgctccg -continued tgatgcatgaggctctgcacaaccactacacgcagaagagcctctccctgtctccgggtaaa atctacatttgggccccgctcgcaggcacatgtggagtgctcctcctctccctggtgattac cctgtactgcaaaaggggccgcaaaaaactcctttacattttttaagcagccttttatgaggc cagtacagacgactcaagaggaagacgggtgctcatgccgctttcctgaggaggaggaagga gggtgcgaactgcgcgttaagttctcccgatcagccgacgcgcctgcttacaagcagggcca gaaccaactgtacaacgagctgaatctcggtagacgggaagagtacgacgtgttggacaaac ggagaggccgcgacccagaaatgggcggcaagcctcgcaggaaaaaccccaggagggactg tacaatgagttgcagaaagataagatggcagaagcttatagcgagatcggaatgaaggggga aaggagacgagggaaggacacgacggcctttatcagggcctgtccacagcaacaaaagata cgtatgacgccctccatatgcaggcacttccaccacggtgataa (amino acids)

(SEQ ID NO: 311)
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

IYIWAPLAGTCGVLLLSLVITLYCKRGRKKLLYIFKQPFMRPVQTTQEEDGCSCRFPEEEEG

GCELRVKFSRSADAPAYKOGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR**

E6 CAR pCDH gBLOCK sequence:
(DNA)

(SEQ ID NO: 312)
acgctgtttttgacctccatagaagattctagagctagctgtagagcttggtaccgagggcca ccatggccctgcccgtgaccgctttgctgctccccctggcgctgctgctgcacgccgccagg ccagaggtccagctggttgagagtggcggtgggctggttaagcctggcggctccctgcggct gagctgcgccgcgagtggatttactttcagccgatatgggatgagttgggtgcggcaagctc ccgggaagaggctggaatgggtctcaacaatctccggggggggcacttacatctattacccc gactcagtcaaggggagatttaccatttcacgagacaacgctaagaatacc ctgtatttgca gatgaattctctgagagcagaggacacagctgtttactattgtacccgcgacaactatggca ggaactacgactacggtatggactattggggacaaggacattggttacagtgagcagtggc acccgcgactctcagtctctcacctggggaacgagctaccctgacgtgctctgctacctcct cagtgtcatatattcactggtatcagcaacgcccgggcagtcccctagattgctcatttat agtacctctaatctggcctcaggtatccctgc E6 CAR Fc pCDH gBLOCK sequence:
(DNA)

(SEQ ID NO: 313)
agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagagcccaaatct tgtgacaaaactcacacatgcccaccgtgcccagcacctgaactcctgggggaccgtcagt cttcctcttccccccaaaacccaaggacaccctcatgatctcccggacccctgaggtcacat -continued gcgtggtggtggacgtgagccacgaagaccctgaggtcaagttcaactggtacgtggacggc gtggaggtgcataatgccaagacaaagccgcgggaggagcagtacaacagcacgtaccgtgt ggtcagcgtcctcaccgtcctgcaccaggactggctgaatggcaaggagtacaagtgcaagg tctccaacaaagccctcccagcccccatcgagaaaaccatctccaaagccaaagggcagccc cgagaaccacaggtgtacaccctgcccccatcccgggaggagatgaccaagaaccaggtcag cctgacctgcctggtcaaaggcttctatcccagcgacatcgccgtggagtgggagagcaatg ggcagccggagaacaactacaagaccacgcctcccgtgctg E6 CAR 8BB3 pCDH gBLOCK sequence:
(DNA)
(SEQ ID NO: 314)
agaacaactacaagaccacgcctcccgtgctggactccgacggctccttcttcctctacagc aagctcaccgtggacaagagcaggtggcagcaggggaacgtcttctcatgctccgtgatgca tgaggctctgcacaaccactacacgcagaagagcctctccctgtctccgggtaaaatctaca tttgggccccgctcgcaggcacatgtggagtgctcctcctctccctggtgattaccctgtac tgcaaaaggggccgcaaaaaactcctttacatttttaagcagcctttatgaggccagtaca gacgactcaagaggaagacgggtgctcatgccgctttcctgaggaggaggaaggagggtgcg aactgcgcgttaagttctcccgatcagccgacgcgcctgcttacaagcagggccagaaccaa ctgtacaacgagctgaatctcggtagacgggaagagtacgacgtgttggacaaacggagagg ccgcgacccagaaatgggcggcaagcctcgcaggaaaaaccccaggagggactgtacaatg agttgcagaaagataagatggcagaagcttatagcgagatcggaatgaaggggggaaggaga cgagggaaggacacgacggcctttatcagggcctgtccacagcaacaaaagatacgtatga cgccctccatatgcaggcacttccaccacggtgataagtttaaacccgctgatcaggcggcc gcgaaggatctgcgatcgctccggtgcccgtcag CAR E6 FCH/8/4-1BB/CD3z sequence:
(DNA)
(SEQ ID NO: 315)
atggccctgcccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagtttgggtgcggcaagctccc gggaagaggctggaatgggtctcaacaatctccgggggggggcacttacatctattacccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg cggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagcacctgaactcct cccctgaggtcacatgcgtggtggtggacgtgagccacgaagaccctgaggtcaagttcaac tggtacgtggacggcgtggaggtgcataatgccaagacaaagccgcgggaggagcagtacaa cagcacgtaccgtgtggtcagcgtcctcaccgtcctgcaccaggactggctgaatggcaagg agtacaagtgcaaggtctccaacaaagccctcccagcccccatcgagaaaaccatctccaaa -continued

```
gccaaagggcagccccgagaaccacaggtgtacaccctgcccccatcccgggaggagatgac caagaaccaggtcagcctgacctgcctggtcaaaggcttctatcccagcgacatcgccgtgg agtgggagagcaatgggcagccggagaacaactacaagaccacgcctcccgtgctggactcc gacggctccttcttcctctacagcaagctcaccgtggacaagagcaggtggcagcaggggaa cgtcttctcatgctccgtgatgcatgaggctctgcacaaccactacacgcagaagagcctct ccctgtctccgggtaaaatctacatttgggccccgctcgcaggcacatgtggagtgctcctc ctctccctggtgattaccctgtactgcaaaaggggccgcaaaaaactcctttacatttttaa gcagcctttatgaggccagtacagacgactcaagaggaagacgggtgctcatgccgctttc ctgaggaggaggaaggagggtgcgaactgcgcgttaagttctcccgatcagccgacgcgcct gcttacaagcagggccagaaccaactgtacaacgagctgaatctcggtagacgggaagagta cgacgtgttggacaaacggagaggccgcgacccagaaatgggcggcaagcctcgcaggaaaa accccaggagggactgtacaatgagttgcagaaagataagatggcagaagcttatagcgag atcggaatgaaggggaaaggagacgagggaaaggacacgacggcctttatcagggcctgtc cacagcaacaaaagatacgtatgacgccctccatatgcaggcacttccaccacggtgataa
```

(amino acids)

(SEQ ID NO: 316)

```
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKIYIWAPLAGTCGVLL

LSLVITLYCKRGRKKLLYIFKQPFMRPVQTTQEEDGCSCRFPEEEEGGCELRVKFSRSADAP

AYKQGQNQLYNELNLGRREEYDVLDKRRGRDPEMGGKPRRKNPQEGLYNELQKDKMAEAYSE

IGMKGERRRGKGHDGLYQGLSTATKDTYDALHMQALPPR**
```

E6 CAR FCH pCDH gBLOCK sequence:
(DNA)

(SEQ ID NO: 317)

```
agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagcacctgaactc ctgggggaccgtcagtcttcctcttccccccaaaacccaaggacacccctcatgatctcccg gaccccctgaggtcacatgcgtggtggtggacgtgagccacgaagaccctgaggtcaagttca actggtacgtggacggcgtggaggtgcataatgccaagacaaagccgcgggaggagcagtac aacagcacgtaccgtgtggtcagcgtcctcaccgtcctgcaccaggactggctgaatggcaa ggagtacaagtgcaaggtctccaacaaagccctcccagcccccatcgagaaaaccatctcca aagccaaagggcagccccgagaaccacaggtgtacaccctgcccccatcccgggaggagatg accaagaaccaggtcagcctgacctgcctggtcaaaggcttctatcccagcgacatcgccgt ggagtgggagagcaatgggcagccggagaacaactacaagaccacgcctcccgtgctg
```

-continued

CAR E6 Fc/4/4-1BB/CD3z sequence:
(DNA)
(SEQ ID NO: 318)
atggccctgcccgtgaccgctttgctgctccccctggcgctgctgctgcacgccgccaggcc agaggtccagctggttgagagtggcgtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagagcccaaatcttg tgacaaaactcacacatgcccaccgtgcccagcacctgaactcctggggggaccgtcagtct tcctcttccccccaaaacccaaggacaccctcatgatctcccggacccctgaggtcacatgc gtggtggtggacgtgagccacgaagaccctgaggtcaagttcaactggtacgtggacggcgt ggaggtgcataatgccaagacaaagccgcgggaggagcagtacaacagcacgtaccgtgtgg tcagcgtcctcaccgtcctgcaccaggactggctgaatggcaaggagtacaagtgcaaggtc tccaacaaagccctcccagcccccatcgagaaaaccatctccaaagccaaagggcagccccg agaaccacaggtgtacaccctgcccccatcccgggaggagatgaccaagaaccaggtcagcc tgacctgcctggtcaaaggcttctatcccagcgacatcgccgtggagtgggagagcaatggg cagccggagaacaactacaagaccacgcctcccgtgctggactccgacggctccttcttcct ctacagcaagctcaccgtggacaagagcaggtggcagcagggaacgtcttctcatgctccg tgatgcatgaggctctgcacaaccactacacgcagaagagcctctccctgtctccgggtaaa cttcaaaagggccgcaaaaaactcctttacattttttaagcagccttttatgaggccagtac agacgactcaagaggaagacgggtgctcatgccgctttcctgaggaggaggaaggagggtgc gaactgcgcgttaagttctcccgatcagccgacgcgcctgcttacaagcagggccagaacca actgtacaacgagctgaatctcggtagacgggaagagtacgacgtgttggacaaacggagag gccgcgacccagaaatgggcggcaagcctcgcaggaaaaaccccaggagggactgtacaat gagttgcagaaagataagatggcagaagcttatagcgagatcggaatgaaggggaaggag acgagggaaggacacgacggcctttatcagggcctgtccacagcaacaaaagatacgtatg acgccctccatatgcaggcacttccaccacggtgataa (amino acids)
(SEQ ID NO: 319)
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLNGKEYKCKV

-continued

SNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

MALIVLGGVAGLLLFIGLGIFFKRGRKKLLYIFKQPFMRPVQTTQEEDGCSCRFPEEEEGGC

ELRVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR**

E6 CAR 44BB3 pCDH gBLOCK sequence:
(DNA)
(SEQ ID NO: 320)

agaacaactacaagaccacgcctcccgtgctggactccgacggctccttcttcctctacagc aagctcaccgtggacaagagcaggtggcagcaggggaacgtcttctcatgctccgtgatgca tgaggctctgcacaaccactacacgcagaagagcctctccctgtctccgggtaaaatggccc aggggccgcaaaaaactcctttacattttttaagcagccttttatgaggccagtacagacgac tcaagaggaagacgggtgctcatgccgctttcctgaggaggaggaaggagggtgcgaactgc gcgttaagttctcccgatcagccgacgcgcctgcttacaagcagggccagaaccaactgtac aacgagctgaatctcggtagacgggaagagtacgacgtgttggacaaacggagaggccgcga cccagaaatgggcggcaagcctcgcaggaaaaaccccaggagggactgtacaatgagttgc agaaagataagatggcagaagcttatagcgagatcggaatgaaggggggaaaggagacgaggg aaaggacacgacggcctttatcagggcctgtccacagcaacaaaagatacgtatgacgccct ccatatgcaggcacttccaccacggtgataagtttaaacccgctgatcaggcggccgcgaag gatctgcgatcgctccggtgcccgtcag CAR E6 FCH/4/4-1BB/CD3z sequence:
(DNA)
(SEQ ID NO: 321)

atggccctgcccgtgaccgctttgctgctcccccctggcgctgctgctgcacgccgccaggcc agaggtccagctggttgagagtggcgtgggctggttaagcctggcggctccctgcggctga gctgcgccgcgagtggatttactttcagccgatatggatgagttgggtgcggcaagctccc gggaagaggctggaatgggtctcaacaatctccgggggggcacttacatctattaccccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg cgggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctcccccattcacctttgggagtgggaccaaggttgaaattaaagcacctgaactcct gggggggaccgtcagtcttcctcttcccccaaaacccaaggacaccctcatgatctcccgga cccctgaggtcacatgcgtggtggtggacgtgagccacgaagaccctgaggtcaagttcaac tggtacgtggacggcgtggaggtgcataatgccaagacaaagccgcgggaggagcagtacaa cagcacgtaccgtgtggtcagcgtcctcaccgtcctgcaccaggactggctgaatggcaagg agtacaagtgcaaggtctccaacaaagccctcccagcccccatcgagaaaaccatctccaaa gccaaagggcagccccgagaaccacaggtgtacaccctgcccccatcccgggaggagatgac caagaaccaggtcagcctgacctgcctggtcaaaggcttctatcccagcgacatcgccgtgg -continued agtgggagagcaatgggcagccggagaacaactacaagaccacgcctcccgtgctggactcc gacggctccttcttcctctacagcaagctcaccgtggacaagagcaggtggcagcaggggaa cgtcttctcatgctccgtgatgcatgaggctctgcacaaccactacacgcagaagagcctct ccctgtctccgggtaaaatggccctgattgtgctggggggcgtcgccggcctcctgcttttc attgggctaggcatcttcttcaaaaggggccgcaaaaaactcctttacattttttaagcagcc ttttatgaggccagtacagacgactcaagaggaagacgggtgctcatgccgctttcctgagg aggaggaaggagggtgcgaactgcgcgttaagttctcccgatcagccgacgcgcctgcttac aagcagggccagaaccaactgtacaacgagctgaatctcggtagacgggaagagtacgacgt gttggacaaacggagaggccgcgacccagaaatgggcggcaagcctcgcaggaaaaacccc aggagggactgtacaatgagttgcagaaagataagatggcagaagcttatagcgagatcgga atgaaggggaaggagacgagggaaaggacacgacggcctttatcagggcctgtccacagc aacaaaagatacgtatgacgccctccatatgcaggcacttccaccacggtgataa (amino acids)

(SEQ ID NO: 322)

MALPVTALLLPLALLLHAARPEVQLVESGGGLVKPGGSLRLSCAASGFTFSRYGMSWVRQAP

GKRLEWVSTISGGGTYTYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKMALIVLGGVAGLLLF

IGLGIFFKRGRKKLLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

CAR E6 IgD/8/4-1BB/CD3z sequence:
(DNA)

(SEQ ID NO: 323)

atggccctgcccgtgaccgctttgctgctcccctggcgctgctgctgcacgccgccaggccagaggt ccagctggttgagagtggcggtgggctggttaagcctggcggctccctgcgctgagctgcgccgcga gtggatttactttcagccgatatgggatgagttgggtgcggcaagctcccgggaagaggctggaatgg gtctcaacaatctccgggggggcacttacatctattaccccgactcagtcaaggggagatttaccat ttcacgagacaacgctaagaatacctgtatttgcagatgaattctctgagagcagaggacacagctg tttactattgtacccgcgacaactatggcaggaactacgactacggtatggactattggggacaaggg acattggttacagtgagcagtggcggcggggcagcggaggaggaggcagcggtggcggaggcagcga gatagtgctcacgcagtcacccgcgactctcagtctctcacctggggaacgagctaccctgacgtgct ctgctacctcctcagtgtcatatattcactggtatcagcaacggcccgggcagtcccctagattgctc atttatagtacctctaatctggcctcaggtatccctgcacgattttctggatctggttcaggttctga ttacaccctcactatctctagcctggagcctgaagactttgccgtttattactgccagcagaggtcta gctccccattcacctttgggagtgggaccaaggttgaaattaaagagtctccaaaggcacaggcctcc tcagtgcccactgcacaaccccaagcagagggcagcctcgccaaggcaaccacagccccagccaccac ccgtaacacaggaagaggcggcgaagagaagaaaaaggagaaggagaaagaggaacaagaagagagag agacaaagacaccaatctacatttgggccccgctcgcaggcacatgtggagtgctcctcctctccctg -continued

```
gtgattaccctgtactgcaaaaggggccgcaaaaaactcctttacatttttaagcagccttttatgag gccagtacagacgactcaagaggaagacgggtgctcatgccgctttcctgaggaggaggaaggagggt gcgaactgcgcgttaagttctcccgatcagccgacgcgcctgcttacaagcagggccagaaccaactg tacaacgagctgaatctcggtagacgggaagagtacgacgtgttggacaaacggagaggccgcgaccc agaaatgggcggcaagcctcgcaggaaaaaccccaggagggactgtacaatgagttgcagaaagata agatggcagaagcttatagcgagatcggaatgaaggggaaggagacgagggaaggacacgacggc ctttatcagggcctgtccacagcaacaaaagatacgtatgacgccctccatatgcaggcacttccacc acggtgataa
```

(amino acids)
(SEQ ID NO: 324)

MALPVTALLLPLALLLHAARPEVQLVESGGGLVKPGGSLRLSCAASGFTFSRYGMSWVRQAP
GKRLEWVSTISGGGTYIYYPDSVKGRFTISRDNAKNTLYLQMNSLRAEDTAVYYCTRDNYGR
NYDYGMDYWGQGTLVTVSSGGGGSGGGGSGGGGSEIVLTQSPATLSLSPGERATLTCSATSS
VSYIHWYQQRPGQSPRLLIYSTSNLASGIPARFSGSGSGSDYTLTISSLEPEDFAVYYCQQR
SSSPFTFGSGTKVEIKESPKAQASSVPTAQPQAEGSLAKATTAPATTRNTGRGGEEKKKEKE
KEEQEERETKTPIYIWAPLAGTCGVLLLSLVITLYCKRGRKKLLYIFKQPFMRPVQTTQEED
GCSCRFPEEEEGGCELRVKFSRSADAPAYKQGQNQLYNELNLGRREEYDVLDKRRGRDPEMG
GKPRRKNPQEGLYNELQKDKMAEAYSEIGMKGERRRGKGHDGLYQGLSTATKDTYDALHMQA
LPPR**

E6 CAR IgD8 pcDH gBLOCK sequence:
(DNA)
(SEQ ID NO: 325)

```
agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagagtctccaaag gcacaggcctcctcagtgcccactgcacaaccccaagcagagggcagcctcgccaaggcaac cacagccccagccaccacccgtaacacaggaagaggcggcgaagagaagaaaaaggagaagg agaaagaggaacaagaagagagagagagacaaagacaccaatctacatttgggccccgctcgca ggcacatgtggagtgctcctcctctcccctggtgattaccctgtactgcaaaaggggccgcaa aaaactcctttacatttttaagcagccttttatgaggccag
```

E6 CAR BB 3 pCDH gBLOCK sequence:
(DNA)
(SEQ ID NO: 326)

```
acattttaagcagccttttatgaggccagtacagacgactcaagaggaagacgggtgctca tgccgctttcctgaggaggaggaaggagggtgcgaactgcgcgttaagttctcccgatcagc cgacgcgcctgcttacaagcagggccagaaccaactgtacaacgagctgaatctcggtagac gggaagagtacgacgtgttggacaaacggagaggccgcgacccagaaatgggcggcaagcct cgcaggaaaaaccccaggagggactgtacaatgagttgcagaaagataagatggcagaagc ttatagcgagatcggaatgaaggggaaggagacgagggaaggacacgacggcctttatc agggcctgtccacagcaacaaaagatacgtatgacgccctccatatgcaggcacttccacca cggtgataagttttaaacccgctgatcaggcggccgcgaaggatctgcgatcgctccggtgcc cgtcag
```

-continued

CAR E6 IgD/4/4-1BB/CD3z sequence:
(DNA)
(SEQ ID NO: 327)
atggccctgccgtgaccgctttgctgctcccctggcgctgctgctgcacgccgccaggcc agaggtccagctggttgagagtggcgtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtccctagattgctcatttatag tacctctaatctggcctcaggtatccctgcacgatttctggatctggttcaggttctgatt acaccctcactatctctagcctggagcctgaagactttgccgtttattactgccagcagagg tctagctccccattcacctttgggagtgggaccaaggttgaaattaaagagtctccaaaggc acaggcctcctcagtgcccactgcacaaccccaagcagagggcagcctcgccaaggcaacca cagccccagccaccaccccgtaacacaggaagaggcggcgaagagaagaaaaaggagaaggag aaagaggaacaagaagagagagagacaaagacaccaatggccctgattgtgctgggggggcgt cgccggcctcctgcttttcattgggctaggcatcttcttcaaaaggggccgcaaaaaactcc tttacatttttaagcagccttttatgaggccagtacagacgactcaagaggaagacgggtgc tcatgccgctttcctgaggaggaggaaggagggtgcgaactgcgcgttaagttctcccgatc agccgacgcgcctgcttacaagcagggccagaaccaactgtacaacgagctgaatctcggta gacgggaagagtacgacgtgttggacaaacgagaggccgcgacccagaaatgggcggcaag cctcgcaggaaaaaccccccaggagggactgtacaatgagttgcagaaagataagatggcaga agcttatagcgagatcggaatgaaggggggaaaggagacgagggaaaggacacgacggcctttt atcagggcctgtccacagcaacaaaagatacgtatgacgccctccatatgcaggcacttcca ccacggtgataa (amino acids)
(SEQ ID NO: 328)
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKESPKAQASSVPTAQPQAEGSLAKATTAPATTRNTGRGGEEKKKEKE

KEEQEERETKTPMALIVLGGVAGLLLFIGLGIFFKRGRKKLLYIFKQPFMRPVQTTQEEDGC

SCRFPEEEEGGCELRVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR**

E6 CAR IgD4 pcDH gBLOCK sequence:
(DNA)
(SEQ ID NO: 329)
agtacctctaatctggcctcaggtatccctgcacgattttctggatctggttcaggttctga ttacaccctcactatctctagcctggagcctgaagactttgccgtttattactgccagcaga -continued ggtctagctccccattcacctttgggagtgggaccaaggttgaaattaaagagtctccaaag gcacaggcctcctcagtgcccactgcacaaccccaagcagagggcagcctcgccaaggcaac cacagccccagccaccacccgtaacacaggaagaggcggcgaagagaagaaaaaggagaagg agaaagaggaacaagaagagagagagacaaagacaccaatggccctgattgtgctgggggc gtcgccggcctcctgcttttcattgggctaggcatcttcttcaaaaggggccgcaaaaaact cctttacattttaagcagccttttatgaggccag CAR E6 X4/8/4-1BB/CD3z sequence:
(DNA)

(SEQ ID NO: 330)

atggccctgccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccgggggggcacttacatctattaccccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagacaagacgcacac caagccacctaaaccagctccagaactgctcggaggtcctggcaccggaaccggaggaccta ccatcaaaccacctaagccacctaagcctgctcctaacctgctcggaggacctatctacatt tgggccccgctcgcaggcacatgtggagtgctcctcctctccctggtgattaccctgtactg caaaaggggccgcaaaaaactccttacattttaagcagccttttatgaggccagtacaga cgactcaagaggaagacgggtgctcatgccgctttcctgaggaggaggaaggagggtgcgaa ctgcgcgttaagttctcccgatcagccgacgcgcctgcttacaagcagggccagaaccaact gtacaacgagctgaatctcggtagacgggaagagtacgacgtgttggacaaacggagaggcc gcgacccagaaatgggcggcaagcctcgcaggaaaaaccccaggagggactgtacaatgag ttgcagaaagataagatggcagaagcttatagcgagatcggaatgaagggggaaggagacg agggaaggacacgacggcctttatcagggcctgtccacagcaacaaaagatacgtatgacg ccctccatatgcaggcacttccaccacggtgataa (amino acids)

(SEQ ID NO: 331)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKDKTHTKPPKPAPELLGGPGTGTGGPTIKPPKPPKPAPNLLGGPIYI

WAPLAGTCGVLLLSLVITLYCKRGRKKLLYIFKQPFMRPVQTTQEEDGCSCRFPEEEEGGCE

LRVKFSRSADAPAYKQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR**

E6 CAR X48 pCDH gBLOCK sequence:
(DNA)

(SEQ ID NO: 332)

agtacctctaatctggcctcaggtatccctgcacgattttctggatctggttcaggttctga ttacaccctcactatctctagcctggagcctgaagactttgccgtttattactgccagcaga ggtctagctccccattcacctttggagtgggaccaaggttgaaattaaagacaagacgcac accaagccacctaaaccagctccagaactgctcggaggtcctggcaccggaaccggaggacc taccatcaaaccacctaagccacctaagcctgctcctaacctgctcggaggacctatctaca tttgggccccgctcgcaggcacatgtggagtgctcctcctctcccctggtgattaccctgtac tgcaaaagggggccgcaaaaaactcctttacattttttaagcagccttttatgaggccag CAR E6 X4/4-1BB/CD3z sequence:
(DNA)

(SEQ ID NO: 333)

atggccctgccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccgggggggggcacttacatctattacccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg ccgcgactctcagtctctcacctggggaacgagctaccctgacgtgctctgctacctcctca gtgtcatatattcactggtatcagcaacggcccgggcagtccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagacaagacgcacac caagccacctaaaccagctccagaactgctcggaggtcctggcaccggaaccggaggaccta ccatcaaaccacctaagccacctaagcctgctcctaacctgctcggaggacctatggccctg attgtgctgggggggcgtcgccggcctcctgcttttcattgggctaggcatcttcttcaaag gggccgcaaaaaactcctttacattttttaagcagccttttatgaggccagtacagacgactc aagaggaagacgggtgctcatgccgctttcctgaggaggaggaaggagggtgcgaactgcgc gttaagttctcccgatcagccgacgcgcctgcttacaagcagggccagaaccaactgtacaa cgagctgaatctcggtagacgggaagagtacgacgtgttggacaaacggagaggccgcgacc cagaaatgggcggcaagcctcgcaggaaaaaccccccaggaggggactgtacaatgagttgcag aaagataagatggcagaagcttatagcgagatcggaatgaaggggggaaggagacgaggaaa aggacacgacggcctttatcagggcctgtccacagcaacaaaagatacgtatgacgccctcc atatgcaggcacttccaccacggtgataa (amino acids)

(SEQ ID NO: 334)

MALPVTALLLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKDKTHTKPPKPAPELLGGPGTGTGGPTIKPPKPPKPAPNLLGGPMAL

IVLGGVAGLLLFIGLGIFFKRGRKKLLYIFKQPFMRPVQTTQEEDGCSCRFPEEEEGGCELR

VKFSRSADAPAYKQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR**

E6 CAR X44 pCDH gBLOCK sequence:
(DNA)
(SEQ ID NO: 335)
agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagacaagacgcac accaagccacctaaaccagctccagaactgctcggaggtcctggcaccggaaccggaggacc taccatcaaaccacctaagccacctaagcctgctcctaacctgctcggaggacctatggccc aggggccgcaaaaaactcctttacattttttaagcagccttttatgaggccag CAR E6 8+4/4/4-1BB/CD3z sequence:
(DNA)
(SEQ ID NO: 336)
atggccctgccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccgggggggcacttacatctattaccccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg ccgcgactctcagtctctcacctggggaacgagctacccctgacgtgctctgctacctcctca gtgtcatatattcactggtatcagcaacggcccgggcagtccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagcccccaccatcgccagccaacccctgtctctgagaccagaag cctgtaggcctgccgccggtggagctgtgcacacaagaggactggatttcgcctgtgatatg caaaaggggccgcaaaaaactcctttacattttttaagcagccttttatgaggccagtacaga cgactcaagaggaagacgggtgctcatgccgctttcctgaggaggaggaaggagggtgcgaa ctgcgcgttaagttctcccgatcagccgacgcgcctgcttacaagcagggccagaaccaact gtacaacgagctgaatctcggtagacgggaagagtacgacgtgttggacaaacggagaggcc gcgacccagaaatgggcggcaagcctcgcaggaaaaaccccaggagggactgtacaatgag ttgcagaaagataagatggcagaagcttatagcgagatcggaatgaaggggaaggagacg agggaaggacacgacggcctttatcagggcctgtccacagcaacaaaagatacgtatgacg ccctccatatgcaggcacttccaccacggtgataa (amino acids)
(SEQ ID NO: 337)
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDM

ALIVLGGVAGLLLFIGLGIFFKRGRKKLLYIFKQPFMRPVQTTQEEDGCSCRFPEEEEGGCE

LRVKFSRSADAPAYKQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR**

E6 CAR CD844 pCDH gBLOCK sequence:
(DNA)
(SEQ ID NO: 338)
agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaaacgacaaccccg gcccccagaccaccaacgccagcccccaccatcgccagccaaccccgtgtctctgagaccaga agcctgtaggcctgccgccggtggagctgtgcacacaagaggactggatttcgcctgtgata ttcaaaaggggccgcaaaaaactcctttacattttttaagcagccttttatgaggccag Humanized C2 scFV sequence in CAR:
(DNA)
(SEQ ID NO: 339)
gagggccaccatggccttgccagtgacggccctgctgctgccattggctcttctgttgcacgctgcca ggcctgaagtgcagctcgtagagagtggcgggggactggtgaagcccgtggaagcctcagactcagt tgcgccgcctcaggttttcacttttcaggttacgccatgtcctgggtaagacaggcaccggggaaagg actcgagtgggtgtctactatcagctcaggaggcacttatatatattatcctgactctgtaaaaggcc gatttacgatttctcgcgacaatgcaaagaactccctctacctccaaatgaacagtcttagggcagaa gacactgctgtatactattgtgcacgcctcggcggcgacaactactacgagtactttgacgtgtgggg gaaagggactaccgtgacagtttcaagcggaggaggtggctcaggtggaggcgggtcaggggggggag gaagtgatattgtgctcacacaatcccagcctcctggctgtgtctcccggccaacgcgctacaatt acatgtcgggcctccaaaagcgtgagcaccagcggctacagctacatgcactggtatcaacagaaacc aggacaaccccccaaactgttgatttatctcgcttcaaacttggagtccggcgtgcctgcgcgcttt cagggagtgggagcggcacagattttacgctgactatcaaccccgtagaagcaaacgatacagcgaat tattattgtcaacattcccgggaactccccttttacgttcggcggggggcacaaaggtcgaaattaagag aacc (amino acids)
(SEQ ID NO: 340)
EVQLVESGGGLVKPGGSLRLSCAASGFTFSGYAMSWVRQAPGKGLEWVSTISSGGTYIYYPD

SVKGRFTISRDNAKNSLYLQMNSLRAEDTAVYYCARLGGDNYYEYFDVWGKGTTVTVSSGGG

GSGGGGSGGGGSDIVLTQSPASLAVSPGQRATITCRASKSVSTSGYSYMHWYQQKPGQPPKL

LIYLASNLESGVPARFSGSGSGTDFTLTINPVEANDTANYYCQHSRELPFTFGGGTKVEIKR

T

Humanized E6 scFV sequence in CAR:
(DNA)
(SEQ ID NO: 341)
gaggtccagctggttgagagtggcggtgggctggttaagcctggcggctccctgcggctgag ctgcgccgcgagtggatttactttcagccgatatgggatgagttgggtgcggcaagctcccg ggaagaggctggaatgggtctcaacaatctccgggggggcacttacatctattaccccgac tcagtcaaggggagatttaccatttcacgagacaacgctaagaatacctgtatttgcagat gaattctctgagagcagaggacacagctgtttactattgtacccgcgacaactatggcagga actacgactacggtatggactattggggacaagggacattggttacagtgagcagtggcggc cgcgactctcagtctctcacctggggaacgagctaccctgacgtgctctgctacctcctcag tgtcatatattcactggtatcagcaacggcccgggcagtcccctagattgctcatttatagt acctctaatctggcctcaggtatccctgcacgattttctggatctggttcaggttctgatta -continued caccctcactatctctagcctggagcctgaagactttgccgtttattactgccagcagaggt ctagctccccattcacctttgggagtgggaccaaggttgaaattaaa (amino acids)
(SEQ ID NO: 342)
EVQLVESGGGLVKPGGSLRLSCAASGFTFSGYAMSWVRQAPGKGLEWVSTISSGGTYIYYPD

SVKGRFTISRDNAKNTLYLQMNSLRAEDTAVYYCTRDNYGRNYDYGMDYWGQGTLVTVSSGG

GGSGGGGSGGGGSEIVLTQSPATLSLSPGERATLTCSATSSVSYIHWYQQRPGQSPRLLIYS

TSNLASGIPARFSGSGSGSDYTLTISSLEPEDFAVYYCQQRSSSPFTFGSGTKVEIK

CD8 leader sequence:
(DNA)
(SEQ ID NO: 343)
atggccctgccvgtgaccgctttgctgctccccctggcgctgctgctgcacgccgccaggcc a (amino acids)
(SEQ ID NO: 344)
MALPVTALLLPLALLLHAARP CD8 hinge domain sequence:
(DNA)
(SEQ ID NO: 345)
acgacaaccccggcccccagaccaccaacgccagcccccaccatcgccagccaaccccctgtc tctgagaccagaagcctgtaggcctgccgccggtggagctgtgcacacaagaggactggatt tcgcctgtgat (amino acids)
(SEQ ID NO: 346)
TTTPAPRPPTPAPTIASQPLSLRPEACRPAAGGAVHTRGLDFACD CD4 hinge domain sequence:
(DNA)
(SEQ ID NO: 347)
tcgggacaggtcctgctggaatccaacatcaaggttctgcccacatggtccaccccggtgca gcca (amino acids)
(SEQ ID NO: 348)
SGQVLLESNIKVLPTWSTPVQP CD28 hinge domain sequence:
(DNA)
(SEQ ID NO: 349)
aaacacctttgtccaagtccctatttcccggaccttctaagccc (amino acids)
(SEQ ID NO: 350)
KHLCPSPLFPGPSKP CD8+CD4 hinge domain sequence:
(DNA)
(SEQ ID NO: 351)
acgacaaccccggcccccagaccaccaacgccagcccccaccatcgccagccaaccccctgtc tctgagaccagaagcctgtaggcctgccgccggtggagctgtgcacacaagaggactggatt tcgcctgtgattcgggacaggtcctgctggaatccaacatcaaggttctgcccacatggtcc accccggtgcagcca (amino acids)
(SEQ ID NO: 352)
TTTPAPRPPTPAPTIASQPLSLRPEACRPAAGGAVHTRGLDFACDSGQVLLESNIKVLPTWS

TPVQP

-continued

CD8+CD28 hinge domain sequence:
(DNA)

(SEQ ID NO: 353)
acgacaaccccggcccccagaccaccaacgccagcccccaccatcgccagccaacccctgtc tctgagaccagaagcctgtaggcctgccgccggtggagctgtgcacacaagaggactggatt tcgcctgtgataaacacctttgtccaagtcccctatttcccggaccttctaagccc (amino acids)

(SEQ ID NO: 354)
TTTPAPRPPTPAPTIASQPLSLRPEACRPAAGGAVHTRGLDFACDKHLCPSPLFPGPSKP

CD28+CD4 hinge domain sequence:
(DNA)

(SEQ ID NO: 355)
aaacacctttgtccaagtcccctatttcccggaccttctaagccctcgggacaggtcctgct ggaatccaacatcaaggttctgcccacatggtccaccccggtgcagcca (amino acids)

(SEQ ID NO: 356)
KHLCPSPLFPGPSKPSGQVLLESNIKVLPTWSTPVQP

Human IgD hinge domain sequence:
(DNA)

(SEQ ID NO: 357)
gagtctccaaaggcacaggcctcctcagtgcccactgcacaaccccaagcagagggcagcct cgccaaggcaaccacagccccagccaccacccgtaacacaggaagaggcggcgaagagaaga aaaggagaaggagaaagaggaacaagaagagagagagacaaagacacca (amino acids)

(SEQ ID NO: 358)
ESPKAQASSVPTAQPQAEGSLAKATTAPATTRNTGRGGEEKKKEKEKEEQEERETKTP

X4 linker (IgG1 and IgG2 modified hinge region) sequence:
(DNA)

(SEQ ID NO: 359)
gacaagacgcacaccaagccacctaaaccagctccagaactgctcggaggtcctggcaccgg aaccggaggacctaccatcaaaccacctaagccacctaagcctgctcctaacctgctcggag gacct (amino acids)

(SEQ ID NO: 360)
DKTHTKPPKPAPELLGGPGTGTGGPTIKPPKPPKPAPNLLGGP

CD3 zeta transmembrane domain sequence:
(DNA)

(SEQ ID NO: 361)
ctctgctacctgctggatggaatcctcttcatctatggtgtcattctcactgccttgttcct g (amino acids)

(SEQ ID NO: 362)
LCYLLDGILFIYGVILTALFL

CD8 transmembrane domain sequence:
(DNA)

(SEQ ID NO: 363)
atctacatttgggccccgctcgcaggcacatgtggagtgctcctcctctcccctggtgattac cctgtactgc (amino acids)

(SEQ ID NO: 364)
IYIWAPLAGTCGVLLLSLVITLYC

CD4 transmembrane domain sequence:
(DNA)

(SEQ ID NO: 365)
cttc (amino acids)

(SEQ ID NO: 366)
MALIVLGGVAGLLLFIGLGIFF

-continued

```
CD28 transmembrane domain sequence:
(DNA)
                                                      (SEQ ID NO: 367)
ctttattattttctgggtg (amino acids)
                                                      (SEQ ID NO: 368)
FWVLVVVGGVLACYSLLVTVAFIIFWV 4-1BB transmembrane domain sequence:
(DNA)
                                                      (SEQ ID NO: 369)
atcatctccttctttcttgcgctgacgtcgactgcgttgctcttcctgctgttcttcctcac gctccgtttctctgttgtt (amino acids)
                                                      (SEQ ID NO: 370)
IISFFLALTSTALLFLLFFLTLRFSVV OX40 transmembrane domain sequence:
(DNA)
                                                      (SEQ ID NO: 371)
gttgccgccatcctgggcctgggcctggtgctggggggg ggccctgtacctgctc (amino acids)
                                                      (SEQ ID NO: 372)
VAAILGLGLVLGLLGPLAILLALYLL CD3 zeta domain sequence:
(DNA)
                                                      (SEQ ID NO: 373)
cgcgttaagttctcccgatcagccgacgcgcctgcttacaagcagggccagaaccaactgta caacgagctgaatctcggtagacgggaagagtacgacgtgttggacaaacggagaggccgcg acccagaaatgggcggcaagcctcgcaggaaaaaccccagagggactgtacaatgagttg cagaaagataagatggcagaagcttatagcgagatcggaatgaaggggaaaggagacgagg gaaaggacacgacggcctttatcagggcctgtccacagcaacaaaagatacgtatgacgccc tccatatgcaggcacttccaccacgg (amino acids)
                                                      (SEQ ID NO: 374)
RVKFSRSADAPAYKQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

CD3 zeta domain variant sequence:
(DNA)
                                                      (SEQ ID NO: 375)
agagtgaagttcagcaggagcgcagacgcccccgcgtaccagcagggccagaaccagctcta taacgagctcaatctaggacgaagagaggagtacgatgttttggacaagagacgtggccggg accctgagatggggggaaagccgagaaggaagaaccctcaggaaggcctgtacaatgaactg cagaaagataagatggcggaggcctacagtgagattgggatgaaaggcgagcgccggaggg caaggggcacgatggccttaccagggtctcagtacagccaccaaggacacctacgacgccc ttcacatgcaggccctgcccctcgc (amino acids)
                                                      (SEQ ID NO: 376)
RVKFSRSADAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

CD28 domain sequence:
(DNA)
                                                      (SEQ ID NO: 377)
agaagcaagcggtctcggctcctgcattctgattacatgaacatgaccccaagaagaccagg ccccaccaggaaacattaccagccctacgctccgccacgcgacttcgctgcctaccggtcc
```

```
(amino acids)
                                                      (SEQ ID NO: 378)
RSKRSRLLHSDYMNMTPRRPGPTRKHYQPYAPPRDFAAYRS 4-1BB domain sequence:
(DNA)
                                                      (SEQ ID NO: 379)
aaaaggggccgcaaaaaactcctttacatttttaagcagccttttatgaggccagtacagac gactcaagaggaagacgggtgctcatgccgctttcctgaggaggaggaaggagggtgcgaac tg (amino acids)
                                                      (SEQ ID NO: 380)
KRGRKKLLYIFKQPFMRPVQTTQEEDGCSCRFPEEEEGGCEL OX40 domain sequence:
(DNA)
                                                      (SEQ ID NO: 381)
cggagggaccagaggctgcccccgatgcccacaagcccctgggggaggcagtttccggac ccccatccaagaggagcaggccgacgcccactccaccctggccaagatc (amino acids)
                                                      (SEQ ID NO: 382)
RRDQRLPPDAHKPPGGGSFRTPIQEEQADAHSTLAKI Humanized anti CD3 scFV clone 12F6 (VH-VL) sequence:
(DNA)
                                                      (SEQ ID NO: 383)
caggtgcagctggtgcagagcggaggtggagtggtccaacctggaagatctctgagactgag ctgtaaggctagcgggtacacgttcacatcttacacgatgcactgggtgaggcaagcccccg gtaagggcctggaatggatcggatatataaacccagctcagggtataccaaatataatcag aagttcaaagatcggttcacgatttctgctgataaaagtaagtccaccgctttcctgcagat ggactcactcaggccagaagatactggtgtttatttctgtgcaaggtggcaggactacgacg tgtactttgactattgggggcaggggacgcctgtaacagtatcaagcggcggtggcggatcc gagcgcgagcgtgggcgatcgcgtgaccatgacctgccgcgcgagcagcagcgtgagctata tgcattggtatcagcagaccccgggcaaagcgccgaaaccgtggatttatgcgaccagcaac ctggcgagcggcgtgccgagccgctttagcggcagcggcagcggcaccgattataccctgac cattagcagcctgcagccggaagatattgcgacctattattgccagcagtggagcagcaacc cgccgacctttggccagggcaccaaactgcagattacccgc (amino acids)
                                                      (SEQ ID NO: 384)
QVQLVQSGGGVVQPGRSLRLSCKASGYTFTSYTMHWVRQAPGKGLEWIGYINPSSGYTKYNQ

KFKDRFTISADKSKSTAFLQMDSLRPEDTGVYFCARWQDYDVYFDYWGQGTPVTVSSGGGGS

GGGGSGGGGSDIQMTQSPSSLSASVGDRVTMTCRASSSVSYMHWYQQTPGKAPKPWIYATSN

LASGVPSRFSGSGSGTDYTLTISSLQPEDIATYYCQQWSSNPPTFGQGTKLQITR

Humanized anti CD3 scFV clone 12F6 (VL-VH) sequence:
(DNA)
                                                      (SEQ ID NO: 385)
gatattcagatgacccagagcccgagcagcctgagcgcgagcgtgggcgatcgcgtgaccat gacctgccgcgcgagcagcagcgtgagctatatgcattggtatcagcagaccccgggcaaag cgccgaaaccgtggatttatgcgaccagcaacctggcgagcggcgtgccgagccgctttagc ggcagcggcagcggcaccgattataccctgaccattagcagcctgcagccggaagatattgc gacctattattgccagcagtggagcagcaacccgccgacctttggccagggcaccaaactgc cagctggtgcagagcggaggtggagtggtccaacctggaagatctctgagactgagctgtaa ggctagcgggtacacgttcacatcttacacgatgcactgggtgaggcaagccccggtaagg gcctggaatggatcggatatataaacccagctcagggtataccaaatataatcagaagttc
```

-continued

```
aaagatcggttcacgatttctgctgataaaagtaagtccaccgctttcctgcagatggactc actcaggccagaagatactggtgtttatttctgtgcaaggtggcaggactacgacgtgtact ttgactattgggggcaggggacgcctgtaacagtatcaagc
```

(amino acids)

(SEQ ID NO: 386)

```
DIQMTQSPSSLSASVGDRVTMTCRASSSVSYMHWYQQTPGKAPKPWIYATSNLASGVPSRFS

GSGSGTDYTLTISSLQPEDIATYYCQQWSSNPPTFGQGTKLQITRGGGGSGGGGSGGGGSQV

QLVQSGGGVVQPGRSLRLSCKASGYTFTSYTMHWVRQAPGKGLEWIGYINPSSGYTKYNQKF

KDRFTISADKSKSTAFLQMDSLRPEDTGVYFCARWQDYDVYFDYWGQGTPVTVSS
```

Humanized anti CD3 scFV clone OKT3 (VH-VL) sequence:
(DNA)

(SEQ ID NO: 387)

```
caggtgcagctggtgcagagcggaggcggagtggtgcagcctggaagaagcctgcgcctgag ctgcaaagcgagcggctatacctttacccgctataccatgcattgggtgcgccaggcgccgg gcaaaggcctggaatggattggctatattaacccgagccgcggctataccaactataaccag aaagtgaaagatcgctttaccattagcaccgataaaagcaaaagcaccgcgtttctgcagat ggatagcctgcgcccggaagataccgcggtgtattattgcgcgcgctattatgatgatcatt attgcctggattattggggccagggcaccaccctgaccgtgagcagcggcggtggcggatcc gagcgcgagcgtgggcgatcgcgtgaccattacctgcagcgcgagcagcagcgtgagctata tgaactggtatcagcagaccccgggcaaagcgccgaaacgctggatttatgataccagcaaa ctggcgagcggcgtgccgagccgctttagcggcagcggcagcggcaccgattataccttta cattagcagcctgcagccggaagatattgcgacctattattgccagcagtggagcagcaacc cgtttacctttggccagggcaccaaactgcagattacccgc
```

(amino acids)

(SEQ ID NO: 388)

```
QVQLVQSGGGVVQPGRSLRLSCKASGYTFTRYTMHWVRQAPGKGLEWIGYINPSRGYTNYNQ

KVKDRFTISTDKSKSTAFLQMDSLRPEDTAVYYCARYYDDHYCLDYWGQGTTLTVSSGGGGS

GGGGSGGGGSDIQMTQSPSSLSASVGDRVTITCSASSSVSYMNWYQQTPGKAPKRWIYDTSK

LASGVPSRFSGSGSGTDYTFTISSLQPEDIATYYCQQWSSNPFTFGQGTKLQITR
```

Humanized anti CD3 scFV clone OKT3 (VH-VL) sequence:
(DNA)

(SEQ ID NO: 389)

```
gatattcagatgacccagagcccgagcagcctgagcgcgagcgtgggcgatcgcgtgaccat tacctgcagcgcgagcagcagcgtgagctatatgaactggtatcagcagaccccgggcaaag cgccgaaacgctggatttatgataccagcaaactggcgagcggcgtgccgagccgctttagc ggcagcggcagcggcaccgattatacctttaccattagcagcctgcagccggaagatattgc gacctattattgccagcagtggagcagcaacccgtttacctttggccagggcaccaaactgc agattacccgcggcggtggcggatccggcggtggcggatccggcggtggcggatcccaggtg cagctggtgcagagcggaggcggagtggtgcagcctggaagaagcctgcgcctgagctgcaa agcgagcggctatacctttacccgctataccatgcattgggtgcgccaggcgccgggcaaag gcctggaatggattggctatattaacccgagccgcggctataccaactataaccagaaagtg aaagatcgctttaccattagcaccgataaaagcaaaagcaccgcgtttctgcagatggatag cctgcgcccggaagataccgcggtgtattattgcgcgcgctattatgatgatcattattgcc tggattattggggccagggcaccaccctgaccgtgagcagc
```

-continued (amino acids)
(SEQ ID NO: 390)
DIQMTQSPSSLSASVGDRVTITCSASSSVSYMNWYQQTPGKAPKRWIYDTSKLASGVPSRFS

GSGSGTDYTFTISSLQPEDIATYYCQQWSSNPFTFGQGTKLQITRGGGGSGGGGSGGGGSQV

QLVQSGGGVVQPGRSLRLSCKASGYTFTRYTMHWVRQAPGKGLEWIGYINPSRGYTNYNQKV

KDRFTISTDKSKSTAFLQMDSLRPEDTAVYYCARYYDDHYCLDYWGQGTTLTVSS

HumanizeE6 scFV (VH-VL) sequence:
(DNA)
(SEQ ID NO: 391)
gaggtgcagctggtggagtctgggggaggcctggtcaagcctgggggtccctgagactctc ctgtgcagcctctggattcaccttcagtaggtatggcatgagctgggtccgccaggctccag ggaagaggctggagtgggtctcaaccattagtggcggaggcacctacatatactacccagac tcagtgaagggccgattcaccatctccagagacaacgccaagaacaccctgtatctgcaaat gaacagcctgagagccgaggacacggctgtgtattactgtaccagagataactatggccgca actatgattatggcatggattattggggccagggcaccctggtgaccgtgagcagcggcggt agccaccctgtctttgtctccaggggaaagagccaccctcacctgcagcgccaccagcagtg ttagctacatccactggtaccaacagaggcctggccagagccccaggctcctcatctatagc acctccaacctggccagcggcatcccagccaggttcagtggcagtgggtctgggagcgacta cactctcaccatcagcagcctagagcctgaagattttgcagtttattactgtcagcagcgta gcagctcccctttcacctttggcagcggcaccaaagtggaaattaaa (amino acids)
(SEQ ID NO: 392)
EVQLVESGGGLVKPGGSLRLSCAASGFTFSGYAMSWVRQAPGKGLEWVSTISSGGTYIYYPD

SVKGRFTISRDNAKNTLYLQMNSLRAEDTAVYYCTRDNYGRNYDYGMDYWGQGTLVTVSSGG

GGSGGGGSGGGGSEIVLTQSPATLSLSPGERATLTCSATSSVSYIHWYQQRPGQSPRLLIYS

TSNLASGIPARFSGSGSGSDYTLTISSLEPEDFAVYYCQQRSSSPFTFGSGTKVEIK

HumanizeE6 scFV (VL-VH) sequence:
(DNA)
(SEQ ID NO: 393)
gaaattgtgttgacacagtctccagccaccctgtctttgtctccaggggaaagagccaccct cacctgcagcgccaccagcagtgttagctacatccactggtaccaacagaggcctggccaga gccccaggctcctcatctatagcacctccaacctggccagcggcatcccagccaggttcagt ggcagtgggtctgggagcgactacactctcaccatcagcagcctagagcctgaagattttgc agtttattactgtcagcagcgtagcagctcccctttcacctttggcagcggcaccaaagtgg aaattaaaggcggtggcggatccggcggtggcggatccggcggtggcggatccgaggtgcag ctctggattcaccttcagtaggtatggcatgagctgggtccgccaggctccaggaagaggc tggagtgggtctcaaccattagtggcggaggcacctacatatactacccagactcagtgaag ggccgattcaccatctccagagacaacgccaagaacaccctgtatctgcaaatgaacagcct gagagccgaggacacggctgtgtattactgtaccagagataactatggccgcaactatgatt atggcatggattattggggccagggcaccctggtgaccgtgagcagc (amino acids)
(SEQ ID NO: 394)
EIVLTQSPATLSLSPGERATLTCSATSSVSYIHWYQQRPGQSPRLLIYSTSNLASGIPARFS

GSGSGSDYTLTISSLEPEDFAVYYCQQRSSSPFTFGSGTKVEIKGGGGSGGGGSGGGGSEVQ

LVESGGGLVKPGGSLRLSCAASGFTFSRYGMSWVRQAPGKRLEWVSTISGGGTYIYYPDSVK

GRFTISRDNAKNTLYLQMNSLRAEDTAVYYCTRDNYGRNYDYGMDYWGQGTLVTVSS

HumanizeC2 scFV (VH-VL) sequence:
(DNA)

(SEQ ID NO: 395)
gaggtgcagctggtggagtctggggaggcctggtcaagcctggggggtccctgagactctc ctgtgcagcctctggattcaccttcagtggctatgccatgagctgggtccgccaggctcag ggaaggggctggagtgggtctcaaccattagtagtggcggaacctacatatactaccccgac tcagtgaagggccgattcaccatctccagagacaacgccaagaactcactgtatctgcaaat gaacagcctgagagccgaggacacggccgtgtattactgtgcgagacttgggggggataatt actacgaatacttcgatgtctggggcaaagggaccacggtcaccgtctcctccggcggtggc ctccttggccgtgtctccaggacagagggccaccatcacctgcagagccagtaagagtgtca gtaccagcggatactcctacatgcactggtatcagcagaaaccaggacaacctcctaaactc ctgatttacctggcatccaatctggagagcggggtcccagccaggttcagcggcagtgggtc tgggaccgatttcaccctcacaattaatcctgtggaagctaatgatactgcaaattattact gtcagcacagtagggagctgccttttcacattcggcggagggaccaaggtggagatcaaacga act (amino acids)

(SEQ ID NO: 396)
EVQLVESGGGLVKPGGSLRLSCAASGFTFSGYAMSWVRQAPGKGLEWVSTISSGGTYIYYPD

SVKGRFTISRDNAKNSLYLQMNSLRAEDTAVYYCARLGGDNYYEYFDVWGKGTTVTVSSGGG

GSGGGGSGGGGSDIVLTQSPASLAVSPGQRATITCRASKSVSTSGYSYMHWYQQKPGQPPKL

LIYLASNLESGVPARFSGSGSGTDFTLTINPVEANDTANYYCQHSRELPFTFGGGTKVEIKR

T

HumanizeE6 scFV (VL-VH) sequence:
(DNA)

(SEQ ID NO: 397)
gacattgtgctgacccagtctccagcctccttggccgtgtctccaggacagagggccaccat cacctgcagagccagtaagagtgtcagtaccagcggatactcctacatgcactggtatcagc agaaaccaggacaacctcctaaactcctgatttacctggcatccaatctggagagcggggtc ccagccaggttcagcggcagtgggtctgggaccgatttcaccctcacaattaatcctgtgga agctaatgatactgcaaattattactgtcagcacagtagggagctgccttttcacattcggcg gagggaccaaggtggagatcaaacgaactggcggtggcggatccggcggtggcggatccggc ggtggcggatccgaggtgcagctggtggagtctggggaggcctggtcaagcctggggggtc cctgagactctcctgtgcagcctctggattcaccttcagtggctatgccatgagctgggtcc gccaggctccagggaaggggctggagtgggtctcaaccattagtagtggcggaacctacata tactaccccgactcagtgaagggccgattcaccatctccagagacaacgccaagaactcact gtatctgcaaatgaacagcctgagagccgaggacacggccgtgtattactgtgcgagacttg ggggggataattactacgaatacttcgatgtctggggcaaagggaccacggtcaccgtctcc tcc (amino acids)

(SEQ ID NO: 398)
DIVLTQSPASLAVSPGQRATITCRASKSVSTSGYSYMHWYQQKPGQPPKLLIYLASNLESGV

PARFSGSGSGTDFTLTINPVEANDTANYYCQHSRELPFTFGGGTKVEIKRTGGGGSGGGGSG

GGGSEVQLVESGGGLVKPGGSLRLSCAASGFTFSGYAMSWVRQAPGKGLEWVSTISSGGTYI

YYPDSVKGRFTISRDNAKNSLYLQMNSLRAEDTAVYYCARLGGDNYYEYFDVWGKGTTVTVS

S

G4S1 linker sequence:
(DNA)
(SEQ ID NO: 399)
ggcggtggcggatcc (amino acids)
(SEQ ID NO: 400)
GGGGS

[G4S1]x3 linker sequence:
(DNA)
(SEQ ID NO: 401)
ggcggtggcggatccggcggtggcggatccggcggtggcggatcc (amino acids)
(SEQ ID NO: 402)
GGGGSGGGGSGGGGS 8 aa GS linker sequence:
(DNA)
(SEQ ID NO: 403)
ggcggttccggcggtggatccgga (amino acids)
(SEQ ID NO: 404)
GGSGGGSG 12 aa GS linker sequence:
(DNA)
(SEQ ID NO: 405)
ggcggttccggcggtggatccggggggggat (amino acids)
(SEQ ID NO: 406)
GGSGGGSGGGSG 13 aa GS linker sequence:
(DNA)
(SEQ ID NO: 407)
ggcggtggatccggcggtggggatccggggg (amino acids)
(SEQ ID NO: 408)
GGGSGGGGSGGGS 22 aa GS linker sequence:
(DNA)
(SEQ ID NO: 409)
tgga (amino acids)
(SEQ ID NO: 4110)
GGGSGGGGSGSGGSGGGGSGGG 24 aa GS linker sequence:
(DNA)
(SEQ ID NO: 411)
ggcggttccggcggtggatccggcggtggcggatccggaggcggttccggcggtggatccg cggtggcggatccgga (amino acids)
(SEQ ID NO: 412)
GGSGGGSGGGSGGGSGGGSGGGSG Mouse C3 Heavy chain variable region sequence:
(DNA)
(SEQ ID NO: 413)
caggtccagctgcagcagtctgggcctgagctggtgaggcctggggtctcagtgaagatttcctgcaa gggttccggctacagattcactgattatgctatgaactgggtgaagcagagtcatgcaaagagtctag agtggattggagttattagtactttctctggtaatacaaacttcaaccagaagtttaagggcaaggcc acaatgactgtagacaaatcctccagcacagcctatatggaacttgccagattgacatctgaggattc tgccatgtattactgtgcaagatcggattactacggcccatactttgactactggggccaaggcacca ctctcacagtctcctca (amino acids)

(SEQ ID NO: 414)
QVQLQQSGPELVRPGVSVKISCKGSGYRFTDYAMNWVKQSHAKSLEWIGVISTFSGNTNFNQKFKGKA

TMTVDKSSSTAYMELARLTSEDSAMYYCARSDYYGPYFDYWGQGTTLTVSS

Mouse C3 heavy chain variable framework region 1 (FWR1) sequence:
(DNA)

(SEQ ID NO: 415)
caggtccagctgcagcagtctgggcctgagctggtgaggcctggggtctcagtgaagatttcctgcaa gggttccggctacagattcact (amino acids)

(SEQ ID NO: 416)
QVQLQQSGPELVRPGVSVKISCKGSGYRFT

Mouse C3 heavy chain variable complementarity determining regions 1
(CDR1) sequence:
(DNA)

(SEQ ID NO: 417)
gattatgctatgaac (amino acids)

(SEQ ID NO: 418)
DYAMN

Mouse C3 heavy chain variable framework region 2 (FWR2) sequence:
(DNA)

(SEQ ID NO: 419)
tgggtgaagcagagtcatgcaaagagtctagagtggattgga (amino acids)

(SEQ ID NO: 420)
WVKQSHAKSLEWIG

Mouse C3 heavy chain variable complementarity determining regions 2
(CDR2) sequence:
(DNA)

(SEQ ID NO: 421)
gttattagtacttctctggtaatacaaacttcaaccagaagtttaagggc (amino acids)

(SEQ ID NO: 422)
VISTFSGNTNFNQKFKG

Mouse C3 heavy chain variable framework region 3 (FWR3) acid
sequence:
(DNA)

(SEQ ID NO: 423)
aaggccacaatgactgtagacaaatcctccagcacagcctatatggaacttgccagattgacatctga ggattctgccatgtattactgtgcaaga (amino acids)

(SEQ ID NO: 424)
KATMTVDKSSSTAYMELARLTSEDSAMYYCAR

Mouse C3 heavy chain variable complementarity determining regions 3
(CDR3) sequence:
(DNA)

(SEQ ID NO: 425)
tcggattactacggcccatactttgactac (amino acids)

(SEQ ID NO: 426)
SDYYGPYFDY

IGHV1-18*04 heavy chain variable region sequence:
(DNA)

(SEQ ID NO: 427)
caggttcagctggtgcagtctggagctgaggtgaagaagcctggggcctcagtgaaggtctc ctgcaaggcttctggttacacctttaccagctacggtatcagctgggtgcgacaggcccctg gacaagggcttgagtggatgggatggatcagcgcttacaatggtaacacaaactatgcacag aagctccagggcagagtcaccatgaccacagacacatccacgagcacagcctacatggagct gaggagcctgagatctgacgacacggccgtgtattactgtgcgagaga (amino acids)

(SEQ ID NO: 428)
QVQLVQSGAEVKKPGASVKVSCKASGYTFTSYGISWVRQAPGQGLEWMGWISAYNGNTNYAQKLQGRV

TMTTDTSTSTAYMELRSLRSDDTAVYYCAR

IGHV1-18*04 heavy chain variable framework region 1 (FWR1) sequence:
(DNA)

(SEQ ID NO: 429)
caggttcagctggtgcagtctggagctgaggtgaagaagcctggggcctcagtgaaggtctcctgcaa ggcttctggttacacctttacc (amino acids)

(SEQ ID NO: 430)
QVQLVQSGAEVKKPGASVKVSCKASGYTFT

IGHV1-18*04 heavy chain variable complementarity determining regions
1 (CDR1) sequence:
(DNA)

(SEQ ID NO: 431)
agctacggtatcagc (amino acids)

(SEQ ID NO: 432)
SYGIS

IGHV1-18*04 heavy chain variable framework region 2 (FWR2) sequence:
(DNA)

(SEQ ID NO: 433)
tgggtgcgacaggcccctggacaagggcttgagtggatggga (amino acids)

(SEQ ID NO: 434)
WVRQAPGQGLEWMG

IGHV1-18*04 heavy chain variable complementarity determining regions
2 (CDR2) sequence:
(DNA)

(SEQ ID NO: 435)
tggatcagcgcttacaatggtaacacaaactatgcacagaagctccagggc (amino acids)

(SEQ ID NO: 436)
WISAYNGNTNYAQKLQG

IGHV1-18*04 heavy chain variable framework region 3 (FWR3) sequence:
(DNA)

(SEQ ID NO: 437)
agagtcaccatgaccacagacacatccacgagcacagcctacatggagctgaggagcctgagatctga cgacacggccgtgtattactgtgcgaga (amino acids)

(SEQ ID NO: 438)
RVTMTTDTSTSTAYMELRSLRSDDTAVYYCAR

Humanized C3 heavy chain variable region sequence:
(DNA)

(SEQ ID NO: 439)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagc (amino acids)

(SEQ ID NO: 440)
QVQLVQSGAEVKKPGASVKVSCKASGYTFTDYAMNWVRQAPGQGLEWMGVISTFSGNTNFNQKFKGRV

TMTTDTSTSTAYMELRSLRSDDTAVYYCARSDYYGPYFDYWGQGTTLTVSS

Humanized C3 heavy chain variable framework region 1 (FWR1) acid sequence:
(DNA)
(SEQ ID NO: 441)
caggttcagctggtgcagtctggagctgaggtgaagaagcctggggcctcagtgaaggtctcctgcaa ggcttctggttacacctttacc (amino acids)
(SEQ ID NO: 442)
QVQLVQSGAEVKKPGASVKVSCKASGYTFT Humanized C3 heavy chain variable complementarity determining regions 1 (CDR1) sequence:
(DNA)
(SEQ ID NO: 443)
gactacgccatgaac (amino acids)
(SEQ ID NO: 444)
DYAMN Humanized C3 heavy chain variable framework region 2 (FWR2) acid sequence:
(DNA)
(SEQ ID NO: 445)
tgggtgcgacaggcccctggacaagggcttgagtggatggga (amino acids)
(SEQ ID NO: 446)
WVRQAPGQGLEWMG Humanized C3 heavy chain variable complementarity determining regions 2 (CDR2) sequence:
(DNA)
(SEQ ID NO: 447)
gtgatcagcaccttcagcggtaacacaaacttcaaccagaagttcaagggc (amino acids)
(SEQ ID NO: 448)
VISTFSGNTNFNQKFKG Humanized C3 heavy chain variable framework region 3 (FWR3) acid sequence:
(DNA)
(SEQ ID NO: 449)
agagtcaccatgaccacagacacatccacgagcacagcctacatggagctgaggagcctgagatctga cgacacggccgtgtattactgtgcgaga (amino acids)
(SEQ ID NO: 450)
RVTMTTDTSTSTAYMELRSLRSDDTAVYYCAR Humanized C3 heavy chain variable complementarity determining regions 3 (CDR3) sequence:
(DNA)
(SEQ ID NO: 451)
agcgactactacggcccatacttcgactac (amino acids)
(SEQ ID NO: 452)
SDYYGPYFDY Humanized C3 IgG1 heavy chain sequence
(DNA)
(SEQ ID NO: 453)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagcgctagcaccaagggcccatcggtcttccccctggcaccctcctccaagagc acctctggggcacagcggccctgggctgcctggtcaaggactacttccccgaaccggtgacggtgtc -continued

```
gtggaactcaggcgccctgaccagcggcgtgcacaccttcccggctgtcctacagtcctcaggactct actccctcagcagcgtggtgacagtgccctccagcagcttgggcacccagacctacatctgcaacgtg aatcacaagcccagcaacaccaaggtggacaagaaagttgagcccaaatcttgtgacaaaactcacac atgcccaccgtgcccagcacctgaactcctggggggaccgtcagtcttcctcttccccccaaaaccca aggacaccctcatgatctcccggacccctgaggtcacatgcgtggtggtggacgtgagccacgaagac cctgaggtcaagttcaactggtacgtggacggcgtggaggtgcataatgccaagacaaagccgcggga ggagcagtacaacagcacgtaccgtgtggtcagcgtcctcaccgtcctgcaccaggactggctgaatg gcaaggagtacaagtgcaaggtctccaacaaagcccteeceageeeceategagaaaaceatetecaaa gccaaagggcagccccgagaaccacaggtgtacaccctgcccccatcccgggaggagatgaccaagaa ccaggtcagcctgacctgcctggtcaaaggcttctatcccagcgacatcgccgtggagtgggagagca atgggcagccggagaacaactacaagaccacgcctcccgtgctggactccgacggctccttcttcctc tacagcaagctcaccgtggacaagagcaggtggcagcaggggaacgtcttctcatgctccgtgatgca tgaggctctgcacaaccactacacgcagaagagcctctccctgtctccgggtaaatgataa
```

(amino acids)

(SEQ ID NO: 454)

QVQLVQSGAEVKKPGASVKVSCKASGYTFTDYAMNWVRQAPGQGLEWMGVISTFSGNTNFNQKFKGRV

TMTTDTSTSTAYMELRSLRSDDTAVYYCARSDYYGPYFDYWGQGTTLTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPGK**

Humanized C3 IgG2 heavy chain sequence
(DNA)

(SEQ ID NO: 455)

```
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagcgcctccaccaagggcccatcggtcttccccctggcgccctgctccaggagc acctccgagagcacagccgccctgggctgcctggtcaaggactacttccccgaaccggtgacggtgtc gtggaactcaggcgctctgaccagcggcgtgcacaccttcccagctgtcctacagtcctcaggactct actccctcagcagcgtggtgaccgtgccctccagcaacttcggcacccagacctacacctgcaacgta gatcacaagcccagcaacaccaaggtggacaagacagttgagcgcaaatgttgtgtcgagtgcccacc gtgcccagcaccacctgtggcaggaccgtcagtcttcctcttccccccaaaacccaaggacaccctca tgatctcccggacccctgaggtcacgtgcgtggtggtggacgtgagccacgaagaccccgaggtccag ttcaactggtacgtggacggcgtggaggtgcataatgccaagacaaagccacgggaggagcagttcaa cagcacgttccgtgtggtcagcgtcctcaccgttgtgcaccaggactggctgaacggcaaggagtaca agtgcaaggtctccaacaaaggcctcccagccccatcgagaaaaccatctccaaaaccaaagggcag ccccgagaaccacaggtgtacaccctgcccccatcccgggaggagatgaccaagaaccaggtcagcct gacctgcctggtcaaaggcttctaccccagcgacatcgccgtggagtgggagagcaatgggcagccgg agaacaactacaagaccacacctcccatgctggactccgacggctccttcttcctctacagcaagctc
```

-continued

```
accgtggacaagagcaggtggcagcaggggaacgtcttctcatgctccgtgatgcatgaggctctgca caaccactacacgcagaagagcctctccctgtctccgggtaaatagtaa
```

(amino acids)

(SEQ ID NO: 456)

```
QVQLVQSGAEVKKPGASVKVSCKASGYTFTDYAMNWVRQAPGQGLEWMGVISTFSGNTNFNQKFKGRV

TMTTDTSTSTAYMELRSLRSDDTAVYYCARSDYYGPYFDYWGQGTTLTVSSASTKGPSVFPLAPCSRS

TSESTAALGCLVKDYFPEPVTVSWNSGALTSGVHTFPAVLQSSGLYSLSSVVTVPSSNFGTQTYTCNV

DHKPSNTKVDKTVERKCCVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSNKGLPAPIEKTISKTKGQ

PREPQVYTLPPSREEMTKNQVSLTCLVKGFYPSDIAVEWESNGQPENNYKTTPPMLDSDGSFFLYSKL

TVDKSRWQQGNVFSCSVMHEALHNHYTQKSLSLSPGK**
```

Humanized C3 heavy chain IgG1 gBLOCK sequence:
(DNA)

(SEQ ID NO: 457)

```
tgctctgggttccaggttccactggtgacgcggcccagccggcccaggttcagctggtgcagtctgga gctgaggtgaagaagcctggggcctcagtgaaggtctcctgcaaggcttctggttacacctttaccga ctacgccatgaactgggtgcgacaggcccctggacaagggcttgagtggatgggagtgatcagcacct tcagcggtaacacaaacttcaaccagaagttcaagggcagagtcaccatgaccacagacacatccacg agcacagcctacatggagctgaggagcctgagatctgacgacacggccgtgtattactgtgcgagaag cgactactacggcccatacttcgactactggggccagggcaccaccctgaccgtgtccagcgctagca ccaagggcccatcggtcttccccctggcaccctcctccaagagcacctctggggcacagcggccctg ggctgcctggtcaaggactacttccccgaaccggtgacggtgtcgtggaactcaggcgccctgaccag c
```

Mouse C3 Light Chain variable region sequence:
(DNA)

(SEQ ID NO: 458)

```
gatgttttgatgacccaaactccactctccctgcctgtcagtcttggagatcaagcctccatctcttg cagatctagtcagaccattgtacatagtaatggaaacacctatttagaatggtacctgcagaaaccag gccagtctccaaagctcctgatctacaaagtttccaaccgattttctggggtcccagacaggttcagt ggcagtggatcagggacagatttcacactcaagatcaacagagtggaggctgaggatctgggagttta ttactgctttcaaggttcacatgttccattcacgttcggctcggggacaaagttggaaataaaa
```

(amino acids)

(SEQ ID NO: 459)

```
DVLMTQTPLSLPVSLGDQASISCRSSQTIVHSNGNTYLEWYLQKPGQSPKLLIYKVSNRFSGVPDRFS

GSGSGTDFTLKINRVEAEDLGVYYCFQGSHVPFTFGSGTKLEIK
```

Mouse C3 light chain variable framework region 1 (FWR1) sequence:
(DNA)

(SEQ ID NO: 460)

```
gatgttttgatgacccaaactccactctccctgcctgtcagtcttggagatcaagcctccatctcttg c
```

(amino acids)

(SEQ ID NO: 461)

DVLMTQTPLSLPVSLGDQASISC

Mouse C3 light chain variable complementarity determining regions 1
(CDR1) sequence:
(DNA)

(SEQ ID NO: 462)

agatctagtcagaccattgtacatagtaatggaaacacctatttagaa (amino acids)

(SEQ ID NO: 463)

RSSQTIVHSNGNTYLE

Mouse C3 light chain variable framework region 2 (FWR2) sequence:
(DNA)
(SEQ ID NO: 464)
tggtacctgcagaaaccaggccagtctccaaagctcctgatctac (amino acids)
(SEQ ID NO: 465)
WYLQKPGQSPKLLIY Mouse C3 light chain variable complementarity determining regions 2 (CDR2) sequence:
(DNA)
(SEQ ID NO: 466)
aaagtttccaaccgattttct (amino acids)
(SEQ ID NO: 467)
KVSNRFS Mouse C3 light chain variable framework region 3 (FWR3) sequence:
(DNA)
(SEQ ID NO: 468)
ggggtcccagacaggttcagtggcagtggatcagggacagatttcacactcaagatcaacagagtgga ggctgaggatctgggagtttattactgc (amino acids)
(SEQ ID NO: 469)
GVPDRFSGSGSGTDFTLKINRVEAEDLGVYYC Mouse C3 light chain variable complementarity determining regions 3 (CDR3) sequence:
(DNA)
(SEQ ID NO: 470)
tttcaaggttcacatgttccattcacg (amino acids)
(SEQ ID NO: 471)
FQGSHVPFT IGKV2-29*03 light chain variable region sequence:
(DNA)
(SEQ ID NO: 472)
gatattgtgatgacccagactccactctctctgtccgtcacccctggacagccggcctccatctcctg caagtctagtcagagcctcctgcatagtgatggaaagacctatttgtattggtacctgcagaagccag gccagtctccacagctcctgatctatgaagtttccagccggttctctggagtgccagataggttcagt ggcagcgggtcagggacagatttcacactgaaaatcagccgggtggaggctgaggatgttggggttta ttactgcatgcaaggtatacaccttcct (amino acids)
(SEQ ID NO: 473)
DIVMTQTPLSLSVTPGQPASISCKSSQSLLHSDGKTYLYWYLQKPGQSPQLLIYEVSSRFSGVPDRFS

GSGSGTDFTLKISRVEAEDVGVYYCMQGIHLP

IGKV2-29*03 light chain variable framework region 1 (FWR1) acid sequence:
(DNA)
(SEQ ID NO: 474)
gatattgtgatgacccagactccactctctctgtccgtcaccccttggacagccggcctccatctcctg c (amino acids)
(SEQ ID NO: 475)
DIVMTQTPLSLSVTPGQPASISC IGKV2-29*03 light chain variable complementarity determining regions 1 (CDR1) sequence:
(DNA)
(SEQ ID NO: 476)
aagtctagtcagagcctcctgcatagtgatggaaagacctatttgtat (amino acids)
(SEQ ID NO: 477)
KSSQSLLHSDGKTYLY IGKV2-29*03 light chain variable framework region 2 (FWR2) sequence:
(DNA)
(SEQ ID NO: 478)
tggtacctgcagaagccaggccagtctccacagctcctgatctat (amino acids)
(SEQ ID NO: 479)
WYLQKPGQSPQLLIY IGKV2-29*03 light chain variable complementarity determining regions
2 (CDR2) sequence:
(DNA)
(SEQ ID NO: 480)
gaagtttccagccggttc (amino acids)
(SEQ ID NO: 481)
EVSSRFS IGKV2-29*03 light chain variable framework region 3 (FWR3) sequence:
(DNA)
(SEQ ID NO: 482)
ggagtgccagataggttcagtggcagcgggtcagggacagatttcacactgaaaatcagccgggtgga ggctgaggatgttggggtttattactgc (amino acids)
(SEQ ID NO: 483)
GVPDRFSGSGSGTDFTLKISRVEAEDVGVYYC IGKV2-29*03 light chain variable complementarity determining
regions3 (CDR3) sequence:
(DNA)
(SEQ ID NO: 484)
atgcaaggtatacaccttcct (amino acids)
(SEQ ID NO: 485)
MQGIHLP Humanized C3 light chain variable region sequence:
(DNA)
(SEQ ID NO: 486)
gatattgtgatgacccagactccactctctctgtccgtcacccctggacagccggcctccat ctcctgcaggtctagtcagaccattgtccatagtaatggaaacacctatttggagtggtacc tgcagaagccaggccagtctccacagctcctgatctataaggtttccaaccggttctctgga gtgccagataggttcagtggcagcgggtcagggacagatttcacactgaaaatcagccggt ggaggctgaggatgttggggtttattactgcttccaaggtagccacgtgcctttcaccttcg gcggagggaccaaggtggagatcaaacgaact (amino acids)
(SEQ ID NO: 487)
DIVMTQTPLSLSVTPGQPASISCRSSQTIVHSNGNTYLEWYLQKPGQSPQLLIYKVSNRFSG

VPDRFSGSGSGTDFTLKISRVEAEDVGVYYCFQGSHVPFTFGGGTKVEIKRT

Humanized C3 light chain variable framework region 1 (FWR1)
acid sequence:
(DNA)
(SEQ ID NO: 488)
gatattgtgatgacccagactccactctctctgtccgtcacccctggacagccggcctccat ctcctgc (amino acids)
(SEQ ID NO: 489)
DIVMTQTPLSLSVTPGQPASISC Humanized C3 light chain variable complementarity determining
regions 1 (CDR1) sequence:
(DNA)
(SEQ ID NO: 490)
ggtctagtcagaccattgtccatagtaatggaaacacctatttggag -continued (amino acids) (SEQ ID NO: 491)
RSSQTIVHSNGNTYLE Humanized C3 light chain variable framework region 2 (FWR2) acid
sequence:
(DNA)
(SEQ ID NO: 492)
tggtacctgcagaagccaggccagtctccacagctcctgatctat (amino acids) (SEQ ID NO: 493)
WYLQKPGQSPQLLIY Humanized C3 light chain variable complementarity determining
regions 2 (CDR2) sequence:
(DNA)
(SEQ ID NO: 494)
aaggtttccaaccggttctct (amino acids) (SEQ ID NO: 495)
KVSNRFS Humanized C3 light chain variable framework region 3 (FWR3) acid
sequence:
(DNA)
(SEQ ID NO: 496)
ggagtgccagataggttcagtggcagcgggtcagggacagatttcacactgaaaatcagccgggtgga ggctgaggatgttggggtttattactgc (amino acids) (SEQ ID NO: 497)
GVPDRFSGSGSGTDFTLKISRVEAEDVGVYYC Humanized C3 light chain variable complementarity determining
regions 3 (CDR3) sequence:
(DNA)
(SEQ ID NO: 498)
ttccaaggtagccacgtgcctttcacc (amino acids) (SEQ ID NO: 499)
FQGSHVPFT Humanized C3 lambda light chain sequence
(DNA)
(SEQ ID NO: 500)
gatattgtgatgacccagactccactctctctgtccgtcacccctggacagccggcctccatctcctg caggtctagtcagaccattgtccatagtaatggaaacacctatttggagtggtacctgcagaagccag gccagtctccacagctcctgatctataaggtttccaaccggttctctggagtgccagataggttcagt ggcagcgggtcagggacagatttcacactgaaaatcagccgggtggaggctgaggatgttggggttta ttactgcttccaaggtagccacgtgcctttcaccttcggcggagggaccaaggtggagatcaaacgaa ctggtcagcccaaggctgccccctcggtcactctgttcccgccctcctctgaggagcttcaagccaac aaggccacactggtgtgtctcataagtgacttctacccgggagccgtgacagtggcctggaaggcaga tagcagccccgtcaaggcgggagtggagaccaccacaccctccaaacaaagcaacaacaagtacgcgg ccagcagctatctgagcctgacgcctgagcagtggaagtcccacagaagctacagctgccaggtcacg catgaagggagcaccgtggagaagacagtggcccctacagaatgttcatagtaa (amino acids) (SEQ ID NO: 501)
DIVMTQTPLSLSVTPGQPASISCRSSQTIVHSNGNTYLEWYLQKPGQSPQLLIYKVSNRFSGVPDRFS

GSGSGTDFTLKISRVEAEDVGVYYCFQGSHVPFTFGGGTKVEIKRTGQPKAAPSVTLFPPSSEELQAN

KATLVCLISDFYPGAVTVAWKADSSPVKAGVETTTPSKQSNNKYAASSYLSLTPEQWKSHRSYSCQVT

HEGSTVEKTVAPTECS**

-continued

Humanized C3 Kappa light chain
(DNA)
(SEQ ID NO: 502)
gatattgtgatgacccagactccactctctctgtccgtcacccctggacagccggcctccatctcctg caggtctagtcagaccattgtccatagtaatggaaacacctatttggagtggtacctgcagaagccag gccagtctccacagctcctgatctataaggtttccaaccggttctctggagtgccagataggttcagt ggcagcgggtcagggacagatttcacactgaaaatcagccgggtggaggctgaggatgttgggg ttta ttactgcttccaaggtagccacgtgccttt caccttcggcggagggaccaaggtggagatcaaacgaa ctacggtggctgcaccatctgtcttcatcttcccgccatctgatgagcagttgaaatctggaactgcc tctgttgtgtgcctgctgaataacttctatcccagagaggccaaagtacagtggaaggtggataacgc cctccaatcgggtaactcccaggagagtgtcacagagcaggacagcaaggacagcacctacagcctca gcagcaccctgacgctgagcaaagcagactacgagaaacacaaagtctacgcctgcgaagtcacccat cagggcctgagctcgcccgtcacaaagagcttcaacaggggagagtgttagtaa (amino acids)
(SEQ ID NO: 503)
DIVMTQTPLSLSVTPGQPASISCRSSQTIVHSNGNTYLEWYLQKPGQSPQLLIYKVSNRFSGVPDRFS

GSGSGTDFTLKISRVEAEDVGVYYCFQGSHVPFTFGGGTKVEIKRTTVAAPSVFIFPPSDEQLKSGTA

SVVCLLNNFYPREAKVQWKVDNALQSGNSQESVTEQDSKDSTYSLSSTLTLSKADYEKHKVYACEVTH

QGLSSPVTKSFNRGEC**

Humanized C3 Kappa light gBLOCK sequence:
(DNA)
(SEQ ID NO: 504)
agctggctaggtaagcttggtaccgagctcggatccacgccaccatggagacagacacactc ctgctatgggtactgctgctctggttccaggttccactggtgacgatattgtgatgaccca gactccactctctctgtccgtcacccctggacagccggcctccatctcctgcaggtctagtc agaccattgtccatagtaatggaaacacctatttggagtggtacctgcagaagccaggccag tctccacagctcctgatctataaggtttccaaccggttctctggagtgccagataggttcag tggcagcgggtcagggacagatttcacactgaaaatcagccgggtggaggctgaggatgttg gggtttattactgcttccaaggtagccacgtgccttt caccttcggcggagggaccaaggtg gagatcaaacgaactacggtggctgcaccatctgtcttcatcttcccgccatctgatgagca gttgaaatctggaactgcctctgttgtgtgcctgctgaataacttctatcccagagaggcca aagtacagtggaaggtggataacgccctccaatcgggtaactcccaggagagtgtcacagag caggacagcaaggacagcacctacagcctcagcagcaccctgacgctgagcaaagcagacta cgagaaacacaaagtctacgcctgcgaagtcacccatcagggcctgagctcgcccgtcacaa agagcttcaacaggggagagtgttagtaagtttaaacccgctgatcagcctcgactgtgcct tctagttgc Mouse C8 heavy chain variable region sequence
(DNA)
(SEQ ID NO: 505)
gaagtgatggtcgtggaaagcggcggtggtctggtaaagccggggggatcccttaagctttc ttgcgccgcatccgggttcacgttctccggctatgccatgtcctgggtccgacagactcccg aaaagcgcttggaatgggtggccactatctcctcggggggacgtacatctactaccccgac agtgtgaaaggaagatttacaatatctcgcgacaacgcaaaaaataccttgtatcttcaaat gagctccctgcggtcagaggacactgccatgtactattgcgcccgcctgggcggcgacaatt actatgagtat -continued (amino acids)

(SEQ ID NO: 506)
EVMVVESGGGLVKPGGSLKLSCAASGFTFSGYAMSWVRQTPEKRLEWVATISSGGTYIYYPDS

VKGRFTISRDNAKNTLYLQMSSLRSEDTAMYYCARLGGDNYYEY

Mouse C8 heavy chain variable complementarity determining region 1
(CDR1) sequence:
(DNA)

(SEQ ID NO: 507)
ggctatgccatgtcc (amino acids)

(SEQ ID NO: 508)
GYAMS

Mouse C8 heavy chain variable complementarity determining region 2
(CDR2) sequence:
(DNA)

(SEQ ID NO: 509)
actatctcctccggggggacgtacatctactaccccgacagtgtgaaagga (amino acids)

(SEQ ID NO: 510)
TISSGGTYIYYPDSVKG

Mouse C8 heavy chain variable complementarity determining region 3
(CDR3) sequence:
(DNA)

(SEQ ID NO: 511)
ctgggcggcgacaattactatgagtat (amino acids)

(SEQ ID NO: 512)
LGGDNYYEY

IGHV3-21*04 heavy chain variable region sequence:
(DNA)

(SEQ ID NO: 513)
gaggtgcagctggtggagtctgggggaggcctggtcaagcctggggggtccctgagactctc ctgtgcagcctctggattcaccttcagtagctatagcatgaactgggtccgccaggctccag ggaaggggctggagtgggtctcatccattagtagtagtagtagttacatatactacgcagac tcagtgaagggccgattcaccatctccagagacaacgccaagaactcactgtatctgcaaat gaacagcctgagagccgaggacacggccgtgtattactgtgcga (amino acids)

(SEQ ID NO: 514)
EVQLVESGGGLVKPGGSLRLSCAASGFTFSSYSMNWVRQAPGKGLEWVSSISSSSSYIYYADSVKGRF

TISRDNAKNSLYLQMNSLRAEDTAVYYCAR

IGHV3-21*04 heavy chain variable framework region 1 (FWR1) sequence:
(DNA)

(SEQ ID NO: 515)
gaggtgcagctggtggagtctgggggaggcctggtcaagcctggggggtccctgagactctcctgtg agcctctggattcaccttcagt (amino acids)

(SEQ ID NO: 516)
EVQLVESGGGLVKPGGSLRLSCAASGFTFS

IGHV3-21*04 heavy chain variable complementarity determining regions
1 (CDR1) sequence:
(DNA)

(SEQ ID NO: 517)
agctatagcatgaac (amino acids)

(SEQ ID NO: 518)
SYSMN

IGHV3-21*04 heavy chain variable framework region 2 (FWR2) sequence:
(DNA)

(SEQ ID NO: 519)
tgggtccgccaggctccagggaaggggctggagtgggtc (amino acids)
(SEQ ID NO: 520)
WVRQAPGKGLEWV IGHV3-21*04 heavy chain variable complementarity determining regions
2 (CDR2) sequence:
(DNA)
(SEQ ID NO: 521)
tcatccattagtagtagtagtagttacatatactacgcagactcagtgaagggc (amino acids)
(SEQ ID NO: 522)
SSISSSSSYIYYADSVKG IGHV3-21*04 heavy chain variable framework region 3 (FWR3) sequence:
(DNA)
(SEQ ID NO: 523)
cgattcaccatctccagagacaacgccaagaactcactgtatctgcaaatgaacagcctgagagccga ggacacggccgtgtattactgtgcga (amino acids)
(SEQ ID NO: 524)
RFTISRDNAKNSLYLQMNSLRAEDTAVYYCAR Humanized C8 heavy chain variable region sequence:
(DNA)
(SEQ ID NO: 525)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctcc (amino acids)
(SEQ ID NO: 526)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSS

Humanized C8 heavy chain variable framework region 1 (FWR1)
sequence:
(DNA)
(SEQ ID NO: 527)
gaggtgcagctggtggagtctgggggaggcctggtcaagcctggggggtccctgagactctcctgtg agcctctggattcaccttcagt (amino acids)
(SEQ ID NO: 528)
EVQLVESGGGLVKPGGSLRLSCAASGFTFS Humanized C8 heavy chain variable complementarity determining region
1 (CDR1) sequence:
(DNA)
(SEQ ID NO: 529)
ggctatgccatgagc (amino acids)
(SEQ ID NO: 530)
GYAMS Humanized C8 sequence: heavy chain variable framework
(DNA)
(SEQ ID NO: 531)
tgggtccgccaggctccagggaaggggctggagtgggtctca (amino acids)
(SEQ ID NO: 532)
WVRQAPGKGLEWVS -continued Humanized C8 heavy chain variable complementarity determining region
2 (CDR2) sequence:
(DNA)
(SEQ ID NO: 533)
accattagtagtggcggaacctacatatactaccctgactcagtgaagggc (amino acids)
(SEQ ID NO: 534)
TISSGGTYIYYPDSVKG Humanized C8 heavy chain variable framework region 3 (FWR3)
sequence:
(DNA)
(SEQ ID NO: 535)
cgattcaccatctccagagacaacgccaagaactcactgtatctgcaaatgaacagcctgagagccga ggacacggccgtgtattactgtgcgaga (amino acids)
(SEQ ID NO: 536)
RFTISRDNAKNSLYLQMNSLRAEDTAVYYCAR Humanized C8 heavy chain variable complementarity determining region
3 (CDR3) sequence:
(DNA)
(SEQ ID NO: 537)
ctgggcggcgataactattatgaatat (amino acids)
(SEQ ID NO: 538)
LGGDNYYEY Humanized C8 IgG1 heavy chain sequence
(DNA)
(SEQ ID NO: 539)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctcgctagcaccaagggcccatcggtcttccccctggcaccctcctccaagagcacc tctgggggcacagcggccctgggctgcctggtcaaggactacttccccgaaccggtgacggtgtcgtg gaactcaggcgccctgaccagcggcgtgcacaccttcccggctgtcctacagtcctcaggactctact ccctcagcagcgtggtgacagtgccctccagcagcttgggcacccagacctacatctgcaacgtgaat cacaagcccagcaacaccaaggtggacaagaaagttgagcccaaatcttgtgacaaaactcacacatg cccaccgtgcccagcacctgaactcctggggggaccgtcagtcttcctcttccccccaaaacccaagg acaccctcatgatctcccggacccctgaggtcacatgcgtggtggtggacgtgagccacgaagaccct gaggtcaagttcaactggtacgtggacggcgtggaggtgcataatgccaagacaaagccgcgggagga gcagtacaacagcacgtaccgtgtggtcagcgtcctcaccgtcctgcaccaggactggctgaatggca aggagtacaagtgcaaggtctccaacaaagcccteccagcccccatcgagaaaaccatctccaaagcc aaagggcagccccgagaaccacaggtgtacaccctgcccccatcccgggaggagatgaccaagaacca ggtcagcctgacctgcctggtcaaaggcttctatcccagcgacatcgccgtggagtgggagagcaatg ggcagccggagaacaactacaagaccacgcctcccgtgctggactccgacggctccttcttcctctac agcaagctcaccgtggacaagagcaggtggcagcaggggaacgtcttctcatgctccgtgatgcatga ggctctgcacaaccactacacgcagaagagcctctccctgtctccgggtaaatgataa (amino acids)
(SEQ ID NO: 540)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSASTKGPSVFPLAPSSKST

-continued

SGGTAALGCLVKDYFPEPVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSDGSFFLY

SKLTVDKSRWQQGNVFSCSVMHEALHNHYTQKSLSLSPGK**

Humanized C8 IgG2 heavy chain sequence
(DNA)
(SEQ ID NO: 541)
gaggtgcagctggtggagtctgggggaggcctggtcaagcctggggggtccctgagactctcctgtgc agcctctggattcaccttcagtggctatgccatgagctgggtccgccaggctccaggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctccgcctccaccaagggcccatcggtcttccccctggcgccctgctccaggagcacc tccgagagcacagccgccctgggctgcctggtcaaggactacttccccgaaccggtgacggtgtcgtg gaactcaggcgctctgaccagcggcgtgcacaccttcccagctgtcctacagtcctcaggactctact ccctcagcagcgtggtgaccgtgccctccagcaacttcggcacccagacctacacctgcaacgtagat cacaagcccagcaacaccaaggtggacaagacagttgagcgcaaatgttgtgtcgagtgcccaccgtg cccagcaccacctgtggcaggaccgtcagtcttcctcttccccccaaaacccaaggacaccctcatga tctcccggacccctgaggtcacgtgcgtggtggtggacgtgagccacgaagaccccgaggtccagttc aactggtacgtggacggcgtggaggtgcataatgccaagacaaagccacgggaggagcagttcaacag cacgttccgtgtggtcagcgtcctcaccgttgtgcaccaggactggctgaacggcaaggagtacaagt gcaaggtctccaacaaaggcctcccagcccccatcgagaaaaccatctccaaaaccaaagggcagccc cgagaaccacaggtgtacaccctgcccccatcccgggaggagatgaccaagaaccaggtcagcctgac ctgcctggtcaaaggcttctaccccagcgacatcgccgtggagtgggagagcaatgggcagccggaga acaactacaagaccacacctcccatgctggactccgacggctccttcttcctctacagcaagctcacc gtggacaagagcaggtggcagcaggggaacgtcttctcatgctccgtgatgcatgaggctctgcacaa ccactacacgcagaagagcctctccctgtctccgggtaaatagtaa (amino acids)
(SEQ ID NO: 542)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSASTKGPSVFPLAPCSRST

SESTAALGCLVKDYFPEPVTVSWNSGALTSGVHTFPAVLQSSGLYSLSSVVTVPSSNFGTQTYTCNVD

HKPSNTKVDKTVERKCCVECPPCPAPPVAGPSVFLFPPKPKDTLMISRTPEVTCVVVDVSHEDPEVQF

NWYVDGVEVHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGSFFLYSKLT

VDKSRWQQGNVFSCSVMHEALHNHYTQKSLSLSPGK**

Mouse C8 light chain variable region sequence
(DNA)
(SEQ ID NO: 543)
gacatcgtcattacgcagacccctgccagtcttgccgtttctctgggccagagggccactatcagtta cagggcgagtaagtctgtgagtaccagcggctatagttacatgcattggaaccagcagaaaccgggac agccaccacgcctgcttatttatctggtgtctaatcttgagtccggggtgcccgccaggttcagcggc -continued agcggctctgggaccgacttcacactcaacattcatccagtggaagaagaggacgctgctacatacta ctgtcaacacattcgggaactgaccaggagtgaa (amino acids)
(SEQ ID NO: 544)
DIVITQTPASLAVSLGQRATISYRASKSVSTSGYSYMHWNQQKPGQPPRLLIYLVSNLESGV

PARFSGSGSGTDFTLNIHPVEEEDAATYYCQHIRELTRSE

Mouse C8 light chain variable complementarity determining region 1
(CDR1) sequence:
(DNA)
(SEQ ID NO: 545)
agggcgagtaagtctgtgagtaccagcggctatagttacatgcat (amino acids)
(SEQ ID NO: 546)
RASKSVSTSGYSYMH Mouse C8 light chain variable complementarity determining region 2
(CDR2) sequence:
(DNA)
(SEQ ID NO: 547)
ctggtgtctaatcttgagtcc (amino acids)
(SEQ ID NO: 548)
LVSNLES Mouse C8 light chain variable complementarity determining region 3
(CDR3) sequence:
(DNA)
(SEQ ID NO: 549)
caacacattcgggaactgaccaggagtgaa (amino acids)
(SEQ ID NO: 550)
QHIRELTRSE NCBI germline z00023 light chain variable region sequence:
(DNA)
(SEQ ID NO: 551)
gacatcgtgatgacccagtctccagactccctggctgtgtctctgggcgagagggccaccatcaactg caagtccagccagagtgttttatacagctccaacaataagaactacttagcttggtaccagcagaaac caggacagcctcctaagctgctcatttactgggcatctacccgggaatccggggtccctgaccgattc agtggcagcgggtctgggacagatttcactctcaccatcagcagcctgcaggctgaagatgtggcagt ttattactgtcagcaatattatagtactcct (amino acids)
(SEQ ID NO: 552)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQYYSTP

NCBI germline z00023 light chain variable framework region 1 (FWR1)
acid sequence:
(DNA)
(SEQ ID NO: 553)
gacatcgtgatgacccagtctccagactccctggctgtgtctctgggcgagagggccaccatcaactg c (amino acids)
(SEQ ID NO: 554)
DIVMTQSPDSLAVSLGERATINC NCBI germline z00023 light chain variable complementarity
determining regions 1 (CDR1) sequence:
(DNA)
(SEQ ID NO: 555)
aagtccagccagagtgttttatacagctccaacaataagaactacttagct (amino acids)
(SEQ ID NO: 556)
KSSQSVLYSSNNKNYLA

```
NCBI germline z00023 light chain variable framework region 2 (FWR2)
sequence:
(DNA)
                                                         (SEQ ID NO: 557)
tggtaccagcagaaaccaggacagcctcctaagctgctcatttac (amino acids)
                                                         (SEQ ID NO: 558)
WYQQKPGQPPKLLIY NCBI germline z00023 light chain variable complementarity
determining regions 2 (CDR2) sequence:
(DNA)
                                                         (SEQ ID NO: 559)
tgggcatctacccgggaatcc (amino acids)
                                                         (SEQ ID NO: 560)
WASTRES NCBI germline z00023 light chain variable framework region 3 (FWR3)
sequence:
(DNA)
                                                         (SEQ ID NO: 561)
ggggtccctgaccgattcagtggcagcgggtctgggacagatttcactctcaccatcagcagcctgca ggctgaagatgtggcagtttattactgt (amino acids)
                                                         (SEQ ID NO: 562)
GVPDRFSGSGSGTDFTLTISSLQAEDVAVYYC NCBI germline z00023 light chain variable complementarity
determining regions3 (CDR3) sequence:
(DNA)
                                                         (SEQ ID NO: 563)
cagcaatattatagtactcct (amino acids)
                                                         (SEQ ID NO: 564)
QQYYSTP Humanized C8 light chain variable region sequence
(DNA)
                                                         (SEQ ID NO: 565)
gacatcgtgatgacccagtctccagactccctggctgtgtctctgggcgagagggccaccat caactgcagggccagcaagagtgttagcaccagcggctacagctacatgcactggtaccagc agaaaccaggacagcctcctaagctgctcatttacctggtgtctaacctggaatccggggtc cctgaccgattcagtggcagcgggtctgggacagatttcactctcaccatcagcagcctgca ggctgaagatgtggcagtttattactgtcaacacattcgggaactgaccaggagtgaattcg gcggagggaccaaggtggagatcaaacgaact (amino acids)
                                                         (SEQ ID NO: 566)
DIVMTQSPDSLAVSLGERATINCRASKSVSTSGYSYMHWYQQKPGQPPKLLIYLVSNLESGV

PDRFSGSGSGTDFTLTISSLQAEDVAVYYCQHIRELTRSEFGGGTKVEIKRT

Humanized C8 light chain variable framework region 1 (FWR1)
sequence:
(DNA)
                                                         (SEQ ID NO: 567)
gacatcgtgatgacccagtctccagactccctggctgtgtctctgggcgagagggccaccat caactgc (amino acids)
                                                         (SEQ ID NO: 568)
DIVMTQSPDSLAVSLGERATINC Humanized C8 light chain variable complementarity determining region
1 (CDR1) sequence:
(DNA)
                                                         (SEQ ID NO: 569)
agggccagcaagagtgttagcaccagcggctacagctacatg
```

-continued (amino acids)

(SEQ ID NO: 570)

RASKSVSTSGYSYM

Humanized C8 light chain variable framework region 2 (FWR2) sequence:
(DNA)

(SEQ ID NO: 571)

cactggtaccagcagaaaccaggacagcctcctaagctgctcatttac (amino acids)

(SEQ ID NO: 572)

HWYQQKPGQPPKLLIY

Humanized C8 light chain variable complementarity determining region 2 (CDR2) sequence:
(DNA)

(SEQ ID NO: 573)

ctggtgtctaacctggaatcc (amino acids)

(SEQ ID NO: 574)

LVSNLES

Humanized C8 light chain variable framework region 3 (FWR3) sequence:
(DNA)

(SEQ ID NO: 575)

ggggtccctgaccgattcagtggcagcgggtctgggacagatttcactctcaccatcagcagcctgca ggctgaagatgtggcagtttattactgt (amino acids)

(SEQ ID NO: 576)

GVPDRFSGSGSGTDFTLTISSLQAEDVAVYYC

Humanized C8 light chain variable complementarity determining region 3 (CDR3) sequence:
(DNA)

(SEQ ID NO: 577)

caacacattcgggaactgaccaggagtgaa (amino acids)

(SEQ ID NO: 578)

QHIRELTRSE

Humanized C8 Lambda light chain sequence
(DNA)

(SEQ ID NO: 579)

gacatcgtgatgacccagtctccagactccctggctgtgtctctgggcgagagggccaccatcaactg cagggccagcaagagtgttagcaccagcggctacagctacatgcactggtaccagcagaaaccaggac agcctcctaagctgctcatttacctggtgtctaacctggaatccggggtccctgaccgattcagtggc agcgggtctgggacagatttcactctcaccatcagcagcctgcaggctgaagatgtggcagtttatta ctgtcaacacattcgggaactgaccaggagtgaattcggcggagggaccaaggtggagatcaaacgaa ctggtcagcccaaggctgccccctcggtcactctgttcccgccctcctctgaggagcttcaagccaac aaggccacactggtgtgtctcataagtgacttctacccgggagccgtgacagtggcctggaaggcaga tagcagccccgtcaaggcgggagtggagaccaccacaccctccaaacaaagcaacaacaagtacgcgg ccagcagctatctgagcctgacgcctgagcagtggaagtcccacagaagctacagctgccaggtcacg catgaagggagcaccgtggagaagacagtggcccctacagaatgttcatagtaa (amino acids)

(SEQ ID NO: 580)

DIVMTQSPDSLAVSLGERATINCRASKSVSTSGYSYMHWYQQKPGQPPKLLIYLVSNLESGVPDRFSG

SGSGTDFTLTISSLQAEDVAVYYCQHIRELTRSEFGGGTKVEIKRTGQPKAAPSVTLFPPSSEELQAN

KATLVCLISDFYPGAVTVAWKADSSPVKAGVETTTPSKQSNNKYAASSYLSLTPEQWKSHRSYSCQVT

HEGSTVEKTVAPTECS**

Humanized C8 Kappa light chain sequence
(DNA)
(SEQ ID NO: 581)
gacatcgtgatgacccagtctccagactccctggctgtgtctctgggcgagagggccaccatcaactg cagggccagcaagagtgttagcaccagcggctacagctacatgcactggtaccagcagaaaccaggac agcctcctaagctgctcatttacctggtgtctaacctggaatccggggtccctgaccgattcagtggc agcgggtctgggacagatttcactctcaccatcagcagcctgcaggctgaagatgtggcagtttatta ctgtcaacacattcgggaactgaccaggagtgaattcggcggagggaccaaggtggagatcaaacgaa ctacggtggctgcaccatctgtcttcatcttcccgccatctgatgagcagttgaaatctggaactgcc tctgttgtgtgcctgctgaataacttctatcccagagaggccaaagtacagtggaaggtggataacgc cctccaatcgggtaactcccaggagagtgtcacagagcaggacagcaaggacagcacctacagcctca gcagcaccctgacgctgagcaaagcagactacgagaaacacaaagtctacgcctgcgaagtcacccat cagggcctgagctcgcccgtcacaaagagcttcaacaggggagagtgttagtaa (amino acids)
(SEQ ID NO: 582)
DIVMTQSPDSLAVSLGERATINCRASKSVSTSGYSYMHWYQQKPGQPPKLLIYLVSNLESGVPDRFSG

SGSGTDFTLTISSLQAEDVAVYYCQHIRELTRSEFGGGTKVEIKRTTVAAPSVFIFPPSDEQLKSGTA

SVVCLLNNFYPREAKVQWKVDNALQSGNSQESVTEQDSKDSTYSLSSTLTLSKADYEKHKVYACEVTH

QGLSSPVTKSFNRGEC**

Humanized C8 Kappa light chain gBLOCK sequence:
(DNA)
(SEQ ID NO: 583)
agctggctaggtaagcttggtaccgagctcggatccacgccaccatggagacagacacactcctgcta tgggtactgctgctctgggttccaggttccactggtgacgacatcgtgatgacccagtctccagactc cctggctgtgtctctgggcgagagggccaccatcaactgcagggccagcaagagtgttagcaccagcg gctacagctacatgcactggtaccagcagaaaccaggacagcctcctaagctgctcatttacctggtg tctaacctggaatccggggtccctgaccgattcagtggcagcgggtctgggacagatttcactctcac catcagcagcctgcaggctgaagatgtggcagtttattactgtcaacacattcgggaactgaccagga gtgaattcggcggagggaccaaggtggagatcaaacgaactacggtggctgcaccatctgtcttcatc ttcccgccatctgatgagcagttgaaatctggaactgcctctgttgtgtgcctgctgaataacttcta tcccagagaggccaaagtacagtggaaggtggataacgccctccaatcgggtaactcccaggagagtg tcacagagcaggacagcaaggacagcacctacagcctcagcagcaccctgacgctgagcaaagcagac tacgagaaacacaaagtctacgcctgcgaagtcacccatcagggcctgagctcgcccgtcacaaagag cttcaacaggggagagtgttagtaagtttaaacccgctgatcagcctcgactgtgccttctagttgc CAR-T E6 CD8 sequence:
(DNA)
(SEQ ID NO: 584)
gaggtccagctggttgagagtggcggtgggctggttaagcctggcggctccctgcggctgagctgcgc cgcgagtggatttactttcagccgatatgggatgagttgggtgcggcaagctcccgggaagaggctgg aatgggtctcaacaatctccggggggggcacttacatctattaccccgactcagtcaaggggagattt accatttcacgagacaacgctaagaatacctgtatttgcagatgaattctctgagagcagaggacac agctgtttactattgtacccgcgacaactatggcaggaactacgactacggtatggactattgggac aagggacattggttacagtgagcagtggcggcggggggcagcggaggaggaggcagcggtgggggggc agcgagatagtgctcacgcagtcacccgcgactctcagtctctcacctggggaacagctaccctgac gtgctctgctacctcctcagtgtcatatattcactggtatcagcaacggccggcagtcccctagat tgctcatttatagtacctctaatcggcctcaggtatccctgcacgattttctggatctggttcaggt tctgattacaccctcactatctctagcctggagcctgaagactttgccgtttattactgccagcagag -continued

```
gtctagctccccattcacctttgggagtgggaccaaggttgaaattaaaacgacaaccccggccccca gaccaccaacgccagccccaccatcgccagccaacccctgtctctgagaccagaagcctgtaggcct gccgccggtggagctgtgcacacaagaggactggatttcgcctgtgatatctacatttgggccccgct cgcaggcacatgtggagtgctcctcctctccctggtgattaccctgtactgctgataa
```

(amino acids)

(SEQ ID NO: 585)
EVQLVESGGGLVKPGGSLRLSCAASGFTFSRYGMSWVRQAPGKGLEWVSTISSGGTYIYYPD
SVKGRFTISRDNAKNTLYLQMNSLRAEDTAVYYCTRDNYGRNYDYGMDYWGQGTLVTVSSGG
GGSGGGGSGGGGSEIVLTQSPATLSLSPGERATLTCSATSSVSYIHWYQQRPGQSPRLLIYS
TSNLASGIPARFSGSGSGSDYTLTISSLEPEDFAVYYCQQRSSSPFTFGSGTKVEIKTTTPA
PRPPTPAPTIASQPLSRPEACRPAAGGAVHTRGLDFACDIYIWAPLAGTCGVLLLSLVITL
YC**

CAR-T C2 CD8 sequence:
(DNA)

(SEQ ID NO: 586)
```
gaagtgcagctcgtagagagtggcgggggactggtgaagcccggtggaagcctcagactcag ttgcgccgcctcaggtttcacttttcaggttacgccatgtcctgggtaagacaggcaccgg ggaaaggactcgagtgggtgtctactatcagctcaggaggcacttatatatattatcctgac totgtaaaaggccgatttacgatttctcgcgacaatgcaaagaactccctctacctccaaat gaacagtcttagggcagaagacactgctgtatactattgtgcacgcctcggcggcgacaact actacgagtactttgacgtgtggggggaaagggactaccgtgacagtttcaagcggaggaggt ggctcaggtggaggcgggtcaggggggggaggaagtgatattgtgctcacacaatccccagc ctccctggctgtgtctcccggccaacgcgctacaattacatgtcgggcctccaaaagcgtga gcaccagcggctacagctacatgcactggtatcaacagaaaccaggacaaccccccaaactg ttgatttatctcgcttcaaacttggagtccggcgtgcctgcgcgcttttcagggagtgggag cggcacagattttacgctgactatcaaccccgtagaagcaaacgatacagcgaattattatt gtcaacattcccgggaactcccctttacgttcggcgggggcacaaaggtcgaaattaagaga accacgacaaccccggcccccagaccaccaacgccagcccccaccatcgccagccaacccc gtctctgagaccagaagcctgtaggcctgccgccggtggagctgtgcacacaagaggactgg atttcgcctgtgatatctacatttgggccccgctcgcaggcacatgtggagtgctcctcctc tccctggtgattaccctgtactgctgataa
```

(amino acids)

(SEQ ID NO: 587)
EVQLVESGGGLVKPGGSLRLSCAASGFTFSGYAMSWVRQAPGKGLEWVSTISSGGTYIYYPD
SVKGRFTISRDNAKNSLYLQMNSLRAEDTAVYYCARLGGDNYYEYFDVWGKGTTVTVSSGGG
GSGGGGSGGGGSDIVLTQSPASLAVSPGQRATITCRASKSVSTSGYSYMHWYQQKPGQPPKL
LIYLASNLESGVPARFSGSGSGTDFTLTINPVEANDTANYYCQHSRELPFTFGGGTKVEIKR
TTTTPAPRPPTPAPTIASQPLSLRPEACRPAAGGAVHTRGLDFACDIYIWAPLAGTCGVLLL
SLVITLYC**

CD8/4-1BB sequence
(DNA)

(SEQ ID NO: 588)
```
acgacaaccccggcccccagaccaccaacgccagcccccaccatcgccagccaacccctgtc totgagaccagaagcctgtaggcctgccgccggtggagctgtgcacacaagaggactggatt tcgcctgtgatatctacatttgggccccgctcgcaggcacatgtggagtgctcctcctctcc
```

-continued ctggtgattaccctgtactgcaaaaggggccgcaaaaaactcctttacattttttaagcagcc ttttatgaggccagtacagacgactcaagaggaagacgggtgctcatgccgctttcctgagg aggaggaaggagggtgcgaactgtgataa (amino acids)

(SEQ ID NO: 589)
TTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCEL**

CD8/CD28 sequence
(DNA)

(SEQ ID NO: 590)
acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattaccctgtactgcagaagcaagcggtctcggctcctgcattctgattacatgaa catgaccccaagaagaccaggccccaccaggaaacattaccagccctacgctccgccacgcg acttcgctgcctaccggtcctgataa (amino acids)

(SEQ ID NO: 591)
TTTPAPRPPTPAPTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRS**

CD8/CD3z sequence:
(DNA)

(SEQ ID NO: 592)
acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattaccctgtactgccgcgttaagttctcccgatcagccgacgcgcctgcttacaa gcagggccagaaccaactgtacaacgagctgaatctcggtagacgggaagagtacgacgtgt tggacaaacggagaggccgcgacccagaaatgggcggcaagcctcgcaggaaaaaccccag gagggactgtacaatgagttgcagaaagataagatggcagaagcttatagcgagatcggaat gaaggggggaaggagacgagggaaaggacacgacggcctttatcagggcctgtccacagcaa caaaagatacgtatgacgccctccatatgcaggcacttccaccacggtgataa (amino acids)

(SEQ ID NO: 593)
TTTPAPRPPTPAPTIASQPLSLRPEACRPAAGGAVHTRGLDFACDIYIWAPLAGTCGVLLLS

LVITLYCRVKFSRSADAPAYKQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR**

CD8/CD28/CD3z sequence:
(DNA)

(SEQ ID NO: 594)
acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattaccctgtactgcagaagcaagcggtctcggctcctgcattctgattacatgaa catgaccccaagaagaccaggccccaccaggaaacattaccagccctacgctccgccacgcg acttcgctgcctaccggtcctgcgttaagttctcccgatcagccgacgcgcctgcttacaag cagggccagaaccaactgtacaacgagctgaatctcggtagacgggaagagtacgacgtgtt ggacaaacggagaggccgcgacccagaaatgggcggcaagcctcgcaggaaaaaccccagg -continued agggactgtacaatgagttgcagaaagataagatggcagaagcttatagcgagatcggaatg aagggggaaaggagacgagggaaaggacacgacggcctttatcagggcctgtccacagcaac aaaagatacgtatgacgccctccatatgcaggcacttccaccacggtgataa (amino acids)

(SEQ ID NO: 595)
TTTPAPRPPTPAPTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRSRVKFSRSADAPAYK

QGQNQLYNELNLGRREEYDVLDKRRGRDPEMGGKPRRKNPQEGLYNELQKDKMAEAYSEIGM

KGERRRGKGHDGLYQGLSTATKDTYDALHMQALPPR**

CD8/4-1BB/CD3z sequence:
(DNA)

(SEQ ID NO: 596)
acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctcatttgggccccgctcgcaggcacatgtggagtgctcctcctctcc ctggtgattaccctgtactgcaaaaggggccgcaaaaaactcctttacattttttaagcagcc ttttatgaggccagtacagacgactcaagaggaagacgggtgctcatgccgctttcctgagg aggaggaaggagggtgcgaactgcgcgttaagttctcccgatcagccgacgcgcctgcttac aagcagggccagaaccaactgtacaacgagctgaatctcggtagacgggaagagtacgacgt gttggacaaacggagaggccgcgacccagaaatgggvggcaagcctcgcaggaaaaacccc aggagggactgtacaatgagttgcagaaagataagatggcagaagcttatagcgagatcgga atgaaggggggaaaggagacgagggaaaggacacgacggcctttatcagggcctgtccacagc aacaaaagatacgtatgacgccctccatatgcaggcacttccaccacggtgataa (amino acids)

(SEQ ID NO: 597)
TTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

CD8/CD28/4-1BB/CD3z sequence:
(DNA)

(SEQ ID NO: 598)
acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattaccctgtactgcagaagcaagcggtctcggctcctgcattctgattacatgaa catgacccccaagaagaccaggccccaccaggaaacattaccagccctacgctccgccacgcg acttcgctgcctaccggtccaaaaggggccgcaaaaaactcctttacattttttaagcagcct tttatgaggccagtacagacgactcaagaggaagacgggtgctcatgccgctttcctgagga ggaggaaggagggtgcgaactgcgcgttaagttctcccgatcagccgacgcgcctgcttaca agcagggccagaaccaactgtacaacgagctgaatctcggtagacgggaagagtacgacgtg ttggacaaacggagaggccgcgacccagaaatgggcggcaagcctcgcaggaaaaaccccca ggagggactgtacaatgagttgcagaaagataagatggcagaagcttatagcgagatcggaa tgaaggggggaaaggagacgagggaaaggacacgacggcctttatcagggcctgtccacagca acaaaagatacgtatgacgccctccatatgcaggcacttccaccacggtgataa (amino acids)

(SEQ ID NO: 599)

TTTPAPRPPTPAPTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRSKRGRKKLLYIFKQP

FMRPVQTTQEEDGCSCRFPEEEEGGCELRVKFSRSADAPAYKQGQNQLYNELNLGRREEYDV

LDKRRGRDPEMGGKPRRKNPQEGLYNELQKDKMAEAYSEIGMKGERRRGKHDGLYQGLSTA

TKDTYDALHMQALPPR**

CAR-T C3 4-1BB/CD3z sequence:
(DNA)

(SEQ ID NO: 600)

atggccctgcccgtgaccgctttgctgctcccactggcgctgctgctgcacgccgccaggcc acaggttcagctggtgcagtctggagctgaggtgaagaagcctggggcctcagtgaaggtct cctgcaaggcttctggttacaccttaccgactacgccatgaactgggtgcgacaggcccct ggacaagggcttgagtggatgggagtgatcagcaccttcagcggtaacacaaacttcaacca gaagttcaagggcagagtcaccatgaccacagacacatccacgagcacagcctacatggagc tgaggagcctgagatctgacgacacggccgtgtattactgtgcgagaagcgactactacggc ccatacttcgactactggggccagggcaccaccctgaccgtgtccagcggcggtggcggatc tgtccgtcacccctggacagccggcctccatctcctgcaggtctagtcagaccattgtccat agtaatggaaacacctatttggagtggtacctgcagaagccaggccagtctccacagctcct gatctataaggtttccaaccggttctctggagtgccagataggttcagtggcagcgggtcag ggacagatttcacactgaaaatcagccgggtggaggctgaggatgttggggtttattactgc ttccaaggtagccacgtgccttttcaccttcggcggagggaccaaggtggagatcaaacgaac tacgacaaccccggccccccagaccaccaacgccagccccaccatcgccagccaaccccctgt ctctgagaccagaagcctgtaggcctgccgccggtggagctgtgcacacaagaggactggat ttcgcctgtgatatctacatttgggccccgctcgcaggcacatgtggagtgctcctcctctc cctggtgattaccctgtactgcaaaaggggccgcaaaaaactccttacatttttaagcagc cttttatgaggccagtacagacgactcaagaggaagacgggtgctcatgccgctttcctgag gaggaggaaggagggtgcgaactgcgcgttaagttctcccgatcagccgacgcgcctgctta caagcagggccagaaccaactgtacaacgagctgaatctcggtagacgggaagagtacgacg tgttggacaaacgagaggccgcgacccagaaatgggcggcaagcctcgcaggaaaaaccccc caggagggactgtacaatgagttgcagaaagataagatggcagaagcttatagcgagatcgg aatgaaggggaaggagacgagggaaaggacacgacggcctttatcagggcctgtccacag caacaaaagatacgtatgacgccctccatatgcaggcacttccaccacggtgataa (amino acids)

(SEQ ID NO: 601)

QVQLVQSGAEVKKPGASVKVSCKASGYTFTDYAMNWVRQAPGQGLEWMGVISTFSGNTNFNQ

KFKGRVTMTTDTSTSTAYMELRSLRSDDTAVYYCARSDYYGPYFDYWGQGTTLTVSSGGGGS

GGGGSGGGGSDIVMTQTPLSLSVTPGQPASISCRSSQTIVHSNGNTYLEWYLQKPGQSPQLL

IYKVSNRFSGVPDRFSGSGSGTDFTLKISRVEAEDVGVYYCFQGSHVPFTFGGGTKVEIKRT

TTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNELQKDKMAEAYSEIG

MKGERRRGKHDGLYQGLSTATKDTYDALHMQALPPR**

C3 CAR gBLOCK 1 sequence:
(DNA)
(SEQ ID NO: 602)
atccacgctgttttgacctccatagaagattctagagctagctgtagagcttggtaccgagg gccaccatggccctgcccgtgaccgctttgctgctcccctggcgctgctgctgcacgccgc caggccacaggttcagctggtgcagtctggagctgaggtgaagaagcctggggcctcagtga aggtctcctgcaaggcttctggttacacctttaccgactacgccatgaactgggtgcgacag gcccctggacaagggcttgagtggatgggagtgatcagcaccttcagcggtaacacaaactt caaccagaagttcaagggcagagtcaccatgaccacagacacatccacgagcacagcctaca tggagctgaggagcctgagatctgacgacacggccgtgtattactgtgcgagaagcgactac tacggcccatacttcgactactggggccaggcaccaccctgaccgtgtccagcggcggtgg cggatccggcggtggcggatccggggggggatccgatattgtgatgacccagactccac tctctctgt C3 CAR gBLOCK 2 sequence:
(DNA)
(SEQ ID NO: 603)
tattgtgatgacccagactccactctctctgtccgtcaccctggacagccggcctccatct cctgcaggtctagtcagaccattgtccatagtaatggaaacacctatttggagtggtacctg cagaagccaggccagtctccacagctcctgatctataaggtttccaaccggttctctggagt gccagataggttcagtggcagcgggtcagggacagatttcacactgaaaatcagccgggtgg aggctgaggatgttggggtttattactgcttccaaggtagccacgtgccttccaccttcggc ggagggaccaaggtggagatcaaacgaactacgacaaccccggccccagaccaccaacgcc agcccccaccatcgccagccaacccctgtctctgagaccagaagcctgtaggcctgccgccg gtggagctgtgcacacaagaggactggatttcgcctgtgatatctacatttgggccccgctc gcaggcacatgtg E6 scFV gBLOCK 1 sequence:
(DNA)
(SEQ ID NO: 604)
tgctctgggttccaggttccactggtgacgcggcccagccggccgaggtgcagctggtggag caccttcagtaggtatggcatgagctgggtccgccaggctccagggaagaggctggagtggg tctcaaccattagtggcggaggcacctacatatactacccagactcagtgaagggccgattc accatctccagagacaacgccaagaacaccctgtatctgcaaatgaacagcctgagagccga ggacacggctgtgtattactgtaccagagataactatggccgcaactatgattatggcatgg attattggggccagggcaccctggtgaccgtgagcagcggcggtggcggatccggcggtggc ggatccggcggtggcggatcc E6 scFV gBLOCK 2 sequence:
(DNA)
(SEQ ID NO: 605)
ggcggtggcggatccggcggtggcggatccggcggtggcggatccgaaattgtgttgacaca gtctccagccaccctgtctttgtctccaggggaaagagccaccctcacctgcagcgccacca gcagtgttagctacatccactggtaccaacagaggcctggccagagcccaggctcctcatc tatagcacctccaacctggccagcggcatcccagccaggttcagtggcagtgggtctgggag cgactacactctcaccatcagcagcctagagcctgaagattttgcagtttattactgtcagc agcgtagcagctccccctttcacctttggcagcggcaccaaagtggaaattaaaaccggtcat catcaccatcaccactgataagtttaaaccgctgatcagcctcgactgtgccttctagt -continued CAR-T C2 CD3z sequence:
(DNA)
(SEQ ID NO: 606)
atggccttgccagtgacggccctgctgctgccattggctcttctgttgcacgctgccaggcctgaagt gcagctcgtagagagtggcgggggactggtgaagcccggtggaagcctcagactcagttgcgccgcct caggtttcacttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggggaaagggact accgtgacagtttcaagcggaggaggtggctcaggtggaggcgggtcagggggggaggaagtgatat tgtgctcacacaatccccagcctcctggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactccccttttacgttcggcggggggcacaaaggtcgaaattaagagaaccacgaca accccggccccagaccaccaacgccagccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgccgc gttaagttctcccgatcagccgacgcgcctgcttacaagcagggccagaaccaactgtacaacgagct gaatctcggtagacgggaagagtacgacgtgttggacaaacggagaggccgcgacccagaaatgggcg gcaagcctcgcaggaaaaaccccaggagggactgtacaatgagttgcagaaagataagatggcagaa gcttatagcgagatcggaatgaaggggggaaaggagacgagggaaaggacacgacggcctttatcaggg cctgtccacagcaacaaaagatacgtatgacgcccctccatatgcaggcacttccaccacggtgataa (amino acids)
(SEQ ID NO: 607)
MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRVKFSRSADAPAYKQGQNQLYNELNLGRREEYD

VLDKRRGRDPEMGGKPRRKNPQEGLYNELQKDMAEAYSEIGMKGERRRGKGHDGLYQGLST

ATKDTYDALHMQALPPR**

CAR-T C2 CD28/CD3z sequence:
(DNA)
(SEQ ID NO: 608)
atggccttgccagtgacggccctgctgctgccattggctcttctgttgcacgctgccaggcctgaagt gcagctcgtagagagtggcgggggactggtgaagcccggtggaagcctcagactcagttgcgccgcct caggtttcacttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggggaaagggact accgtgacagtttcaagcggaggaggtggctcaggtggaggcgggtcagggggggaggaagtgatat tgtgctcacacaatccccagcctcctggctgtgtctcccggccaacgcgctacaattacatgtcggg -continued

```
cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactcccctttacgttcggcggggcacaaaggtcgaaattaagagaaccacgaca accccggccccagaccaccaacgccagccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaga agcaagcggtctcggctcctgcattctgattacatgaacatgaccccaagaagaccaggccccaccag gaaacattaccagccctacgctccgccacgcgacttcgctgcctaccggtcccgcgttaagttctccc gatcagccgacgcgcctgcttacaagcagggccagaaccaactgtacaacgagctgaatctcggtaga cgggaagagtacgacgtgttggacaaacgagaggccgcgacccagaaatgggcggcaagcctcgcag gaaaaaccccaggagggactgtacaatgagttgcagaaagataagatggcagaagcttatagcgaga tcggaatgaaggggaaggagacgagggaaggacacgacggcctttatcagggcctgtccacagca acaaaagatacgtatgacgccctccatatgcaggcacttccaccacggtgataa
```

(amino acids)
(SEQ ID NO: 609)
MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRSKRSRLLHSDYMNMTPRRPGPTRKHYQPYAPP

RDFAAYRSRVKFSRSADAPAYKQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR**

CAR-T C2 4-1BB/CD3z sequence:
(DNA)
(SEQ ID NO: 610)
```
atggccttgccagtgacggccctgctgctgccattggctcttctgttgcacgctgccaggcctgaagt gcagctcgtagagagtggcggggggactggtgaagcccggtggaagcctcagactcagttgcgccgcct caggtttcacttttcaggttacgccatgtcctgggtaagacaggcaccggggaaaggactcgagtgg gtgtctactatcagctcaggaggcacttatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggaagggact accgtgacagtttcaagcggaggaggtggctcaggtggaggcgggtcaggggggggaggaagtgatat tgtgctcacacaatccccagcctcctggctgtgtctcccggcaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactcccctttacgttcggcggggcacaaaggtcgaaattaagagaaccacgaca accccggccccagaccaccaacgccagccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaaa agggggccgcaaaaaactccttttacattttttaagcagccttttatgaggccagtacagacgactcaaga
```

-continued

```
ggaagacgggtgctcatgccgcttcctgaggaggaggaaggagggtgcgaactgcgcgttaagttct cccgatcagccgacgcgcctgcttacaagcagggccagaaccaactgtacaacgagctgaatctcggt agacgggaagagtacgacgtgttggacaaacggagaggccgcgacccagaaatgggcggcaagcctcg caggaaaaaccccaggagggactgtacaatgagttgcagaaagataagatggcagaagcttatagcg agatcggaatgaaggggaaaggagacgagggaaaggacacgacggcctttatcagggcctgtccaca gcaacaaaagatacgtatgacgccctccatatgcaggcacttccaccacggtgataa
```

(amino acids)

(SEQ ID NO: 611)
MALPVTALLLPLALLLHAARPEVQLVESGGGLVKPGGSLRLSCAASGFTFSGYAMSWVRQAP

GKGLEWVSTISSGGTYTYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFP

EEEEGGCELRVKFSRSADAPAYKOGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR**

CAR-T C2 OX40/CD3z sequence:
(DNA)

(SEQ ID NO: 612)
```
atggccttgccagtgacggccctgctgctgccattggctcttctgttgcacgctgccaggcctgaagt gcagctcgtagagagtggcgggggactggtgaagcccggtggaagcctcagactcagttgcgccgcct caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtgggggaaagggact accgtgacagttcaagcgcggaggaggtggctcaggtggaggcgggtcaggggggggaggaagtgatat tgtgctcacacaatccccagcctcctggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactcccctttacgttcggcgggggcacaaaggtcgaaattaagagaaccacgaca accccggcccccagaccaccaacgccagcccccaccatcgccagccaaccccgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgccgg agggaccagaggctgccccccgatgcccacaagcccctgggggaggcagtttccggaccccatcca agaggagcaggccgacgcccactccaccctggccaagatccgcgttaagttctcccgatcagccgacg cgcctgcttacaagcagggccagaaccaactgtacaacgagctgaatctcggtagacgggaagagtac gacgtgttggacaaacggagaggccgcgacccagaaatgggcggcaagcctcgcaggaaaaaccccca ggagggactgtacaatgagttgcagaaagataagatggcagaagcttatagcgagatcggaatgaagg gggaaaggagacgagggaaaggacacgacggcctttatcagggcctgtccacagcaacaaaagatacg tatgacgccctccatatgcaggcacttccaccacggtgataa
```

-continued (amino acids)

(SEQ ID NO: 613)

MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRRDQRLPPDAHKPPGGGSFRTPIQEEQADAHST

LAKIRVKFSRSADAPAYKQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR**

CAR-T C2 CD28/OX40/CD3z sequence:
(DNA)

(SEQ ID NO: 614)

atggccttgccagtgacggccctgctgctgccattggctcttctgttgcacgctgccaggcctgaagt gcagctcgtagagagtggcggggggactggtgaagcccggtggaagcctcagactcagttgcgccgcct caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtgggggaaagggact accgtgacagtttcaagcggaggaggtggctcaggtggaggcgggtcagggggggaggaagtgatat tgtgctcacacaatccccagcctccctggctgtgtctcccggcaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactccccttttacgttcggcgggggcacaaaggtcgaaattaagagaaccacgaca accccggcccccagaccaccaacgccagcccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaga agcaagcggtctcggctcctgcattctgattacatgaacatgaccccaagaagaccaggccccaccag gaaacattaccagccctacgctccgccacgcgacttcgctgcctaccggtcccggagggaccagaggc tgcccccgatgcccacaagcccctgggggaggcagtttccggaccccatccaagaggagcaggcc gacgcccactccaccctggccaagatccgcgttaagttctcccgatcagccgacgcgcctgcttacaa gcagggccagaaccaactgtacaacgagctgaatctcggtagacgggaagagtacgacgtgttggaca aacggagaggccgcgacccagaaatgggcggcaagcctcgcaggaaaaaccccaggagggactgtac aatgagttgcagaaagataagatggcagaagcttatagcgagatcggaatgaaggggaaaggagacg agggaaaggacacgacggcctttatcagggcctgtccacagcaacaaaagatacgtatgacgccctcc atatgcaggcacttccaccacggtgataa (amino acids)

(SEQ ID NO: 615)

MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

-continued

DFACDIYIWAPLAGTCGVLLLSLVITLYCRSKRSRLLHSDYMNMTPRRPGPTRKHYQPYAPP
RDFAAYRSRRDQRLPPDAHKPPGGGSFRTPIQEEQADAHSTLAKIRVKFSRSADAPAYKQGQ
NQLYNELNLGRREEYDVLDKRRGRDPEMGGKPRRKNPQEGLYNELQKDKMAEAYSEIGMKGE
RRRGKGHDGLYQGLSTATKDTYDALHMQALPPR**

CAR-T E6 OX40/CD3z sequence:
(DNA)
(SEQ ID NO: 616)

atggccctgcccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacccgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggggggggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctcccccattcacctttgggagtgggaccaaggttgaaattaaaaacgacaaccccggc ccccagaccaccaacgccagcccccaccatcgccagccaaccccgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgccggagggaccagaggctgccccccgatgcccacaagcccctggggaggcagtt tccggacccccatccaagaggagcaggccgacgcccactccaccctggccaagatccgcgtt aagttctcccgatcagccgacgcgcctgcttacaagcagggccagaaccaactgtacaacga gctgaatctcggtagacgggaagagtacgacgtgttggacaaacggagaggccgcgacccag aaatgggcggcaagcctcgcaggaaaaaccccagggaggactgtacaatgagttgcagaaa gataagatggcagaagcttatagcgagatcggaatgaaggggggaaaggagacgagggaaagg acacgacggcctttatcagggcctgtccacagcaacaaaagatacgtatgacgccctccata tgcaggcacttccaccacggtgataa (amino acids)
(SEQ ID NO: 617)

MALPVTALLLPLALLLHAARPEVQLVESGGGLVKPGGSLRLSCAASGFTFSGYAMSWVRQAP
GKRLEWVSTISGGGTYIYYPDSVKGRFTISRDNAKNTLYLQMNSLRAEDTAVYYCTRDNYGR
NYDYGMDYWGQGTLVTVSSGGGGSGGGGSGGGGSEIVLTQSPATLSLSPGERATLTCSATSS
VSYIHWYQQRPGQSPRLLIYSTSNLASGIPARFSGSGSGSDYTLTISSLEPEDFAVYYCQQR
SSSPFTFGSGTKVEIKTTTPAPRPPTPAPTIASQPLSLRPEACRPAAGGAVHTRGLDFACDI
YIWAPLAGTCGVLLLSLVITLYCRRDQRLPPDAHKPPGGGSFRTPIQEEQADAHSTLAKIRV
KFSRSADAPAYKQGQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR**

-continued

CAR-T E6 CD28/OX40/CD3z sequence:

(DNA)

(SEQ ID NO: 618)

atggccctgcccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattacccccga ctcagtcaaggggagatttaccatttcacgagacaacgctaagaatacc ctgtatttgcaga tgaattctctgagagcagaggacacagctgtttactattgtacccgcgacaactatggcagg aactacgactacggtatggactattggggacaagggacattggttacagtgagcagtggcgg ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagcccccaccatcgccagccaacccctgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgcagaagcaagcggtctcggctcctgcattctgattacatgaacatgaccccaagaa gaccaggccccaccaggaaacattaccagccctacgctccgccacgcgacttcgctgcctac cggtcccggagggaccagaggctgccccccgatgcccacaagccccctgggggaggcagttt ccggaccccatccaagaggagcaggccgacgcccactccaccctggccaagatccgcgtta agttctcccgatcagccgacgcgcctgcttacaagcagggccagaaccaactgtacaacgag ctgaatctcggtagacgggaagagtacgacgtgttggacaaacggagaggccgcgacccaga aatgggcggcaagcctcgcaggaaaaaccccaggagggactgtacaatgagttgcagaaag ataagatggcagaagcttatagcgagatcggaatgaaggggggaaaggagacgagggaagga cacgacggcctttatcagggcctgtccacagcaacaaaagatacgtatgacgccctccatat gcaggcacttccaccacggtgataa (amino acids)

(SEQ ID NO: 619)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDI

YIWAPLAGTCGVLLLSLVITLYCRSKRSRLLHSDYMNMTPRRPGPTRKHYQPYAPPRDFAAY

RSRRDQRLPPDAHKPPGGGSFRTPIQEEQADAHSTLAKIRVKFSRSADAPAYKQGQNQLYNE

LNLGRREEYDVLDKRRGRDPEMGGKPRRKNPQEGLYNELQKDKMAEAYSEIGMKGERRRGKG

HDGLYQGLSTATKDTYDALHMQALPPR\*\*

MUC1 truncated cytoplasmic sequence
(amino acids)

(SEQ ID NO: 620)

SNIKFRPGSVVVQLTLAFREGTINVHDVETQFNQYKTEAASRY

```
MUC1 truncated cytoplasmic sequence
(amino acids)
                                                        (SEQ ID NO: 621)
SVVVQLTLAFREGTINVHDVETQFNQYKTEAASRY MUC1 truncated cytoplasmic sequence
(amino acids)
                                                        (SEQ ID NO: 622)
VQLTLAFREGTINVHDVETQFNQY MUC1 truncated cytoplasmic sequence
(amino acids)
                                                        (SEQ ID NO: 623)
SNIKFRPGSVVVQLTLAFREGTIN Primers
                                                        (SEQ ID NO: 624)
attctaagcttgggccaccatggaactg (SEQ ID NO: 625)
tctagagtttaaacttactatttacccggagacagggagag (SEQ ID NO: 626)
agtatggcccagccggccgaggtgcagctggtggagtctgg (SEQ ID NO: 627)
tagaaggcacagtcgaggctgatcag (SEQ ID NO: 628)
attctaagcttgggccaccatggaagc (SEQ ID NO: 629)
tctagagtttaaacttactaacactctcccctgttgaagc (SEQ ID NO: 630)
agtatggcccagccggccgaaattgtgttgacacagtctccag (SEQ ID NO: 631)
tagaaggcacagtcgaggctgatcag (SEQ ID NO: 632)
actgtcatatggaggtgcagctggtggagtctg (SEQ ID NO: 633)
actgtctcgagtttaatttccactttggtgccgctgc (SEQ ID NO: 634)
actgtcatatggaggtgcagctggtggagtctg (SEQ ID NO: 635)
actgtaccggttttaatttccactttggtgccgctgc (SEQ ID NO: 636)
cttcttcctcaggagcaagctcaccgtgg (SEQ ID NO: 637)
gagccgtcggagtccagc (SEQ ID NO: 638)
gcacctgaactcctgggg (SEQ ID NO: 639)
tttaatttccactttggtgccg (SEQ ID NO: 640)
cgcggctagcttaagcttggtaccgagggcca (SEQ ID NO: 641)
cgcggcggccgcctgatcaggggttaaactatc
```

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—ELISA Competition with NME1 and NME7

PSMGFR peptide was covalently coupled to BSA using Imject Maleimide activated BSA kit (Thermo Fisher). PSMGFR peptide coupled BSA was diluted to 7.5 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and NME1 or NME7, diluted in PBS-T+ 1% BSA, was added at saturating concentration. After 1 h at RT the plate was washed 3× with PBS-T and anti-MUC1* antibody (or antibody fragments), diluted in PBS-T+1% BSA, was added (5× molar excess comapred to NME1/NME7). After 1 h at RT the plate was washed 3× with PBS-T and goat anti HisTag-HRP, diluted in PBS-T+1% BSA, was added at 1/10000 dilution. After 1 h at RT the plate was washed 3× with PBS-T and remaining NME1 or NME7 bound to the PSMGFR peptide was measured at 415 nm using a ABTS solution (Thermo Fisher).

Example 2—Humanization of Anti-MUC1* Extracellular Domain Monoclonal Antibodies We generated humanized antibodies that bind to the extracellular domain of MUC1* by a process called complementarity determining region, 'CDR', grafting. First, homology searches were performed to independently align the heavy chain variable region and light chain variable region nucleotides sequences of mouse monoclonal anti-MUC1* antibody (E6 HC SEQ ID NOS:12-13; LC SEQ ID NOS:65-66 and MN-C2 HC SEQ ID NO:118-119; LC SEQ ID NO: 168-169) against a repertoire of human antibody sequences (IMGT, the international ImMunoGeneTics information system). The sequences with the highest homology were selected. IGHV3-21*01 is a human IgG heavy chain variable region sequence with 82.9% (DNA) and 74.5% (amino acids) identity to MouseMN-E6 heavy chain variable region. IGKV3-11*02 is a human IgG light chain variable region sequence with 68.8% (DNA) and 61.1% (amino acids) identity to MouseMN-E6 light chain variable region. IGHV3-21*04 is a human IgG heavy chain variable region sequence with 85% (DNA) and 81.6% (amino acids) identity to Mouse MN-C2 heavy chain variable region. IGKV7-3*01 is a human IgG light chain variable region sequence with 76.9% (DNA) and 71.3% (amino acids) identity to Mouse MN-C2 light chain variable region. Second, a model of the mouse scFv was generated to select and keep the mouse residues important for the stability of the CDR and framework. Finally, CDRs from the human germlines were replaced by the corresponding mouse CDRs.

Humanized MN-E6 Ig2G2 Heavy Chain Cloning

The Kozak consensus sequence followed by the IGHV3-21*03 leader sequence, the humanizedMN-E6 heavy chain variable region and the constant region of human IgG2 was synthesized by our request by GenScript, NJ (SEQ ID NOS:52-53. The cDNA was amplified by polymerase chain reaction (PCR) using the following primer: 5'-ATTCTAAGCTTGGGCCACCATGGAACTG-3' (SEQ ID NO:624) and 5'-TCTAGAGTTTAAACTTACTATT-TACCCGGAGACAGGGAGAG-3' (SEQ ID NO:625). After digestion with HindIII and PmeI restriction enzymes (New England Biolabs), the purified fragment was cloned into the pCDNA 3.1 V5 vector (Life Technologies) digested with the same restriction enzymes.

Humanized MN-E6 heavy chain cDNA was amplified by polymerase chain reaction (PCR) using the following primer: 5'-AGTATGGCCCAGCCGGCCGAGGTGCAG-CTGGTGGAGTCTGG-3' (SEQ ID NO:626) and 5'-TAGAAGGCACAGTCGAGGCTGATCAG-3' (SEQ ID NO:627). After digestion with SfiI and PmeI restriction enzymes (New England Biolabs), the purified fragment was cloned into the pSECTag2 vector (Life Technologies) digested with the same restriction enzymes.

Humanized MN-E6 Kappa Light Chain Cloning

The Kozak consensus sequence followed by the IGHV3-11*02 leader sequence, the humanizedMN-E6 light chain variable region and the constant region of human Kappa light chain was synthesized by our request by GenScript, NJ (SEQ ID NOS: 107-108). The cDNA was amplified by polymerase chain reaction (PCR) using the following primer: 5'-ATTCTAAGCTTGGGCCACCATGGAAGC-3' (SEQ ID NO:628) and 5'-TCTAGAGTTTAAACT-TACTAACACTCTCCCCTGTTGAAGC-3' (SEQ ID NO:629). After digestion with HindIII and PmeI restriction enzymes (New England Biolabs), the purified fragment was cloned into the pCDNA 3.1 V5 vector (Life Technologies) digested with the same restriction enzymes.

HumanizedMN-E6 light chain cDNA was amplified by polymerase chain reaction (PCR) using the following primer: 5'-AGTATGGCCCAGCCGGCCGAAATTGTGT-TGACACAGTCTCCAG-3' (SEQ ID NO:630) and 5'-TAGAAGGCACAGTCGAGGCTGATCAG-3' (SEQ ID NO:631). After digestion with SfiI and PmeI restriction enzymes (New England Biolabs), the purified fragment was cloned into the pSECTag2 vector (Life Technologies) digested with the same restriction enzymes.

Humanized MN-E6 IgG1 Heavy Chain Cloning

HumanizedMN-E6 IgG2 constructs (pCDNA 3.1 V5 and pSECTag2) were digested with BstEII and PmeI (New England Biolabs) to remove the IgG2 heavy chain constant region. The vector with humanizedMN-E6 heavy chain variable region was purified. Human IgG1 heavy chain constant region was synthesized by our request by IDT, IA (SEq ID NOS: 60-61). Both gBLOCKS and the purified vector with humanizedMN-E6 variable region were ligated using the Gibson assembly cloning kit (New England Biolabs).

HumanizedMN-E6 Lambda Light Chain Cloning

HumanizedMN-E6 kappa light chain constructs (pCDNA 3.1 V5 vector and pSECTag2 vector) were digested with KpnI and PmeI (New England Biolabs) to remove the kappa light chain constant region. The vector with humanizedMN-E6 light chain variable region was purified. Human lambda light chain constant region was synthesized by our request by IDT, IA (SEQ ID NO: 115). Both, gBLOCK and the purified vector with humanizedMN-E6 light chain variable region were ligated using the Gibson assembly cloning kit (New England Biolabs).

Humanized MN-C2 IgG1 and IgG2 Heavy Chain Cloning

HumanizedMN-E6 IgG1 and IgG2 heavy chain in pSEC-Tag2 were digested with SfiI and AgeI to remove the MN-E6 variable region. HumanizedMN-E6 IgG1 and IgG2 heavy chain in pCDNA 3.1 V5 were digested with HindIII and AgeI to remove the MN-E6 variable region The vectors with human IgG1 or IgG2 constant region were purified. Humanized MN-C2 heavy chains were synthesized by our request by IDT, IA (SEQ ID NOS:160 and 165). Sequence to be cloned into pCDNA 3.1 V5 contains in 5' the murine Ig kappa chain leader sequence (SEQ ID NO 160). Both, gBLOCK and purified vector with human IgG1 or IgG2 constant region were ligated using the Gibson assembly cloning kit (New England Biolabs).

Humanized MN-C2 Kappa/Lambda Light Chain Cloning

Two humanized MN-C2 variable region fused to the kappa light chain constant region and two humanized MN-C2 variable region fused to the lambda light chain constant region were synthesized by our request by IDT, IA (SEQ ID NOS: 210 and 213 and SEQ ID NOS: 216 and 219, respectively). pCDNA 3.1 V5 was digested with HindIII and PmeI restriction enzymes (New England Biolabs) and pSEC Tag2 was digested with SfiI and PmeI restriction enzymes (New England Biolabs). Both plasmids were then purified. SEQ ID NOS: 210 and 216 were ligated into digested pCDNA 3.1 V5 and SEQ ID NOS: 213 and 219 were ligated into digested pSEC Tag2 using the Gibson assembly cloning kit (New England Biolabs).

Humanized C3 IgG1 Heavy Chain Cloning

Humanized E6 IgG1 construct (pSECTag2) was digested with SfiI and AgeI (New England Biolabs) to remove the E6 heavy chain variable region. The vector without humanized E6 heavy chain variable region was purified. Humanized C3 heavy chain variable region was synthesized by our request by IDT, IA (SEQ ID NO:457). gBLOCK and the purified vector were ligated using the Gibson assembly cloning kit (New England Biolabs).

Humanized C3 Kappa Light Chain Cloning pEF V5-His was digested with BamHI and PmeI (New England Biolabs) and purified. Humanized C3 kappa light chain was synthesized by our request by IDT, IA (SEq ID NO:504). Both, gBLOCK and the purified vector were ligated using the Gibson assembly cloning kit (New England Biolabs).

Humanized C8 Kappa Light Chain Cloning pEF V5-His was digested with BamHI and PmeI (New England Biolabs) and purified. Humanized C8 kappa light chain was synthesized by our request by IDT, IA (SEq ID NO:583). Both, gBLOCK and the purified vector were ligated using the Gibson assembly cloning kit (New England Biolabs).

Example 3—Cloning of Humanized scFV of Anti-MUC1* Extracellular Domain Antibodies Humanized E6 scFV Cloning:

pSEC Tag2 was digested with SfiI and PmeI (New England Biolabs) and purified. Humanized E6 scFV gBLOCKS were synthesized by our request by IDT, IA (SEQ ID NOS: 604-605). Both, gBLOCKs and the purified vector were ligated using the Gibson assembly cloning kit (New England Biolabs).

Humanized E6 scFV cDNA was amplified by polymerase chain reaction (PCR) using the following primers: 5-ACTGTCATATGGAGGTGCAGCTGGTGGAGTCTG-3' (SEQ ID NO:632) and 5'-ACTGTCTCGAGTTTAAT-TTCCACTTTGGTGCCGCTGC-3' (SEQ ID NO:633). After digestion with NdeI and XhoI restriction enzymes (New England Biolabs), the purified fragment was cloned into the pET21b vector (Novagen) digested with the same restriction enzymes. Humanized E6 scFV cDNA was cloned 5' of the Histidine Tag for protein purification.

Humanized E6 scFV cDNA was amplified by polymerase chain reaction (PCR) using the following primers: 5-ACTGTCATATGGAGGTGCAGCTGGTGGAGTCTG-3' (SEQ ID NO:634) and 5'-ACTGTACCGGTTTTAAT-TTCCACTTTGGTGCCGCTGC-3' (SEQ ID NO:635). After digestion with NdeI and AgeI restriction enzymes (New England Biolabs), the purified fragment was cloned into a modified pET21b vector (Novagen) digested with the same restriction enzymes. The vector was modified to include the StrepTag2 sequence followed by 2 stop codons 5' of the Histidine Tag. Humanized E6 scFV cDNA was cloned 5' of the StrepTag2 for protein purification.

Humanized E6, C2, C3 and C8 scFV-Fc Cloning

Humanized E6 IgG1 construct (pSECTag2) was digested with SfiI and SacII (New England Biolabs) to remove the E6 heavy chain variable region and part of the IgG1 heavy chain constant region. The vector without humanized E6 heavy chain variable region was purified. Humanized E6, C2, C3 and C8 scFV gBLOCKS were synthesized by our request by IDT, IA (SEQ ID NO:258-259, 262-263, 266-267 and 270-271). E6, C2, C3 and C8 gBLOCKS and the purified vector were ligated using the Gibson assembly cloning kit (New England Biolabs) to assemble the corresponding scFV in frame of the human IgG1 Fc region.

Humanized E6 scFV-Fc Y407R Cloning

Humanized E6 scFV-Fc tyrosine 407 was mutated to an arginine (Y407R) by site directed mutagenesis. The Q5 site directed mutagenesis kit (NEB) was used with the following primers: 5'-CTTCTTCCTCAGGAGCAAGCTCACCG-TGG-3' (SEQ ID NO:636) and 5'-GAGCCGTCG-GAGTCCAGC-3' (SEQ ID NO:637)

Humanized E6 scFV-Fc Hingeless Cloning

Hinge region of humanized E6 scFV-Fc was removed by site directed mutagenesis. The Q5 site directed mutagenesis kit (NEB) was used with the following primers: 5'-GCACCTGAACTCCTGGGG-3' (SEQ ID NO:638) and 5'-TTTAATTTCCACTTTGGTGCCG-3' (SEQ ID NO:639)

Example 4—Cloning of CAR-T of Anti-MUC1* Extracellular Domain Antibodies

Car E6 CD28/4-1BB/CD3z Cloning:

pCDNA 3.1 V5 was digested with KpnI and PmeI (New England Biolabs) and purified. Full CAR-T E6 (CD8/CD28/4-1BB/CD3z) gBLOCK was synthesized by our request by IDT, IA (SEq ID NO:305). Both, gBLOCK and the purified vector were ligated using the Gibson assembly cloning kit (New England Biolabs).

Car E6 CD3z Cloning:

pCDNA 3.1 V5 CAR-T E6 CD8/CD28/4-1BB/CD3z was digested with EcoRV and PmeI (New England Biolabs) to remove cytoplasmic domains. The vector without cytoplasmic domains was purified. CAR-T E6 CD8/CD3z gBLOCK was synthesized by our request by IDT, IA (SEq ID NO:296). Both, gBLOCK and the purified vector were ligated using the Gibson assembly cloning kit (New England Biolabs).

Car E6 CD28/CD3z Cloning:

pCDNA 3.1 V5 CAR-T E6 CD8/CD28/4-1BB/CD3z was digested with EcoRV and PmeI (New England Biolabs) to remove cytoplasmic domains. The vector without cytoplasmic domains was purified. CAR-T E6 CD8/CD28/CD3z gBLOCK was synthesized by our request by IDT, IA (SEq ID NO:299). Both, gBLOCK and the purified vector were ligated using the Gibson assembly cloning kit (New England Biolabs).

Car E6 4-1BB/CD3z Cloning:

pCDNA 3.1 V5 CAR-T E6 CD8/CD28/4-1BB/CD3z was digested with EcoRV and PmeI (New England Biolabs) to remove cytoplasmic domains. The vector without cytoplasmic domains was purified. CAR-T E6 CD8/4-1BB/CD3z gBLOCK was synthesized by our request by IDT, IA (SEq ID NO:302). Both, gBLOCK and the purified vector were ligated using the Gibson assembly cloning kit (New England Biolabs).

Car C2 CD28/4-1BB/CD3z Cloning:

pCDNA 3.1 V5 CAR-T E6 CD8/CD28/4-1BB/CD3z was digested with KpnI and EcoRV (New England Biolabs) E6 scFV. The vector without E6 scFV was purified. CAR-T C2 gBLOCKs were synthesized by our request by IDT, IA (SEq ID NOS: 308-309). Both, gBLOCKs and the purified vector were ligated using the Gibson assembly cloning kit (New England Biolabs).

CAR Sub-Cloning into Lentiviral Vectors:

All pcDNA 3.1 V5 CAR cDNAs were amplified by polymerase chain reaction (PCR) using the following primers: 5-CGCGGCTAGCTTAAGCTTGGTACCGAGGG-CCA-3' (SEQ ID NO:640) and 5'-CGCGGCGGCCGCCT-GATCAGCGGGTTTAAACTTATC-3' (SEQ ID NO:641). After digestion with NheI and NotI restriction enzymes (New England Biolabs), the purified fragments were cloned into lentiviral vectors (pCDH-EF1-MCS-IRES GFP and pCDH-CMV-MCS-EF1-copGFP+puro, SBI) digested with the same restriction enzymes.

Car-E6-Fc/8/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 313 and 314). The gBLOCKs and the purified vector were ligated using the Gibson assembly cloning kit (New England Biolabs).

Car-E6-FcH/8/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 317 and 314). The gBLOCKs and the purified vector were ligated using the Gibson assembly cloning kit (New England Biolabs).

Car-E6-Fc-4-41BB-CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 313 and 320). The gBLOCKs and the purified vector were ligated using the Gibson assembly cloning kit (New England Biolabs).

Car-E6 FcH/4/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 317 and 320). The gBLOCKs and the purified vector were ligated using the Gibson assembly cloning kit (New England Biolabs).

Car-E6 IgD/8/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 325 and 326). The gBLOCKs and the purified vector were ligated using the Gibson assembly cloning kit (New England Biolabs).

Car-E6 IgD/4/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 329 and 326). The gBLOCKs and the purified vector were ligated using the Gibson assembly cloning kit (New England Biolabs).

Car-E6 X4/8/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 332 and 326). The gBLOCKs and the purified vector were ligated using the Gibson assembly cloning kit (New England Biolabs).

Car-E6 X4/4/41BB/CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 335 and 326). The gBLOCKs and the purified vector were ligated using the Gibson assembly cloning kit (New England Biolabs).

Car E6-8+4-4-41BB-CD3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 338 and 326). The gBLOCKs and the purified vector were ligated using the Gibson assembly cloning kit (New England Biolabs).

Example 5—Lentivirus Production

HEK 293T cells (ATCC) were used to produce lentivirus. The day prior transfection plates (6well plate) were coated with poly-D-lysine and cells seeded so that cell density reaches 90-95% at the time of transfection and cultures in a 5% CO2 atmosphere. The next daycells were transfected with Lipofectamine 3000 (life technologies) and Opti-MEM® I Reduced Serum Medium according to the manufacturer instructions (0.75 ug of lentiviral expression vecotr and 2.25 ug of pPACKH1 packaging mix was used). After 6 h incubation, the media was changed and media containing lentivirus was harvested after 24 and 48 hours. Lentivirus was concentrated with Lenti-X concentrator (Clontech) and titer was calculated using the Lenti-X p@4 Rapid Titer Kit (Clontech). Lentivirus was store at −80C in single-use aliquots.

Example 6—Lipofectamine Transient Expression

HEK 293T cells (ATCC) were used to test expression of humanized IgG. The night before transfection, cells were passed at 1/3 dilution (6well plate) and cultures in a 5% CO2 atmosphere. The next day, 1 hour before transfection, the media was change to complete media without antibiotics (DMEM high glucose from ATCC containing 10% fetal calf serum). For transfection, we used Lipofectamine 3000 (life technologies) and Opti-MEM® I Reduced Serum Medium according to the manufacturer instructions. 1.25 ug of the heavy chain construct and 1.25 ug of the light chain construct or 2.5 ug of Fc-fusion constructs was used. After 48 h incubation, the media was collected, cleared by centrifugation and used in an ELISA assay to quantify the level of humanized IgG expression and binding to PSMGFR peptide.

Example 7—Polyethylenimine (PEI) Large Scale Transient Expression

HEK 293T cells (ATCC) were used for large scale expression of Fc-fusion protein. The night before transfection, cells were passed (6.5×10$^6$ cells in 150 mm dish) and cultures in a 5% CO2 atmosphere. The next day, 1 hour before transfection, cell were washed once with PBS pH 7.4 and the media was change to complete media without antibiotics (DMEM high glucose from ATCC containing 10% ultra low IgG fetal calf serum). For transfection, we used Polyethylenimine "Max" (PEI "Max", Polysciences) and Opti- MEM® I Reduced Serum Medium (25 ug of Fc-fusion constructs+250 ug of PEI). After 72 h incubation, the media was collected and stored at −20° C. or cleared by centrifugation/filtration for purification.

Example 8—Jurkat Cells Lentivirus Transduction

Protocol #1: A 50/50 solution (2 mL) of lentivirus was prepared in fresh media, supplemented with 8 ug/mL of polybrene and added to a well of a 6 well plate. Jurkat E6-1 cells (ATCC, TIB-152) were pelleted at 1200 rpm for 5 min at RT and resuspended in fresh media (RPMI containing 10% fetal calf serum and 1% penicillin/streptomycin/amphotericin b). Cells were counted and add $2 \times 10^5$ cells to the well containing the virus+Polybrene solution. Incubate for 24-48 h and add fresh media and/or split the cells. After 72 h, start growing cells with antibiotic selection (puromycin).

Protocol #2: Jurkat E6-1 cells (ATCC, TIB-152) were pelleted at 1200 rpm for 5 min at RT and resuspended in fresh media (RPMI containing 10% fetal calf serum and 1% penicillin/streptomycin/amphotericin b) at $2.5 \times 10^5$ cells/mL. Add 2 mL of cells to a 15 mL sterile conical tube, add 1× of Transdux infection reagent (1×, SBI) and lentivirus. Mix gently and incubate at RT for 20 min. Centrifuge cells at 1900 rpm for 30 min at 32° C., remove supernatant, resuspend cells in 2 mL of fresh media and transfer cells to a well of a 6 well plate. Inspect cells for GFP expression after 48 h.

Example 9—T Cells Lentivirus Transduction

Highly purified T cells (AllCells) were pelleted at 200×g for 5 min at RT and resuspended at $1 \times 10^6$ cells/mL in fresh media (RPMI1640 containing 10% fetal calf serum and 1% penicillin/streptomycin). Add CD3/CD28 activator Dynabeads (Thermo Fisher, 25 uL for $1 \times 10^6$ cells) and seed 24 well plate with 1 mL of cells and add IL2 (Thermo Fisher). Monitor cells daily and split cells if needed. The day before the transduction coat a plate with Retronectin (Takara) and store it overnight at 4° C. The next, remove the Retronectin solution add add a blocking solution (2% BSA in PBS) and incubate 30 min at RT. Remove BSA solution add add PBS until cells are ready. Collect activated T cells and resuspend them at $0.5 \times 10^6$ cells/mL in fresh media. Add 1 mL of cells to the retronectin treated plate, 1 mL of lentivirus solution and IL2. Cells were spinoculated by centrifugation of the pate at 1000×g for 90 min at RT. The plate was return to the incubator overnight. Next, remove 1 mL of media, add 1 mL of virus and repeat spinoculation. Monitor cells and split them if necessarry at a density of $0.5-1 \times 10^6$ cells/mL. T cells can be used for cytokine release assay or cytotoxicity assay 48 h post transduction.

Example 10—IL2 Detection

IL-2 secretion in media was measured using a human IL-2 ELISA kit (Thermo Fisher). Plates were coated with and anti-IL-2 antibody (coating antibody, 1/100 in PBS). After overnight incubation at 4° C., the plate was wash 3 times with PBS-T and a 4% BSA solution was added to block remaining binding site on the well. After 1 h at RT the plate was washed once with PBS-T and conditioned media (CM) and IL-2 standard diluted in PBS+4% BSA, was added. After 2 h at RT the plate was washed 3× with PBS-T and anti-human IL-2 (detection antibody) diluted in PBS+4% BSA ($1/100$), was added. After 2 h at RT the plate was washed 5× with PBS-T and Streptavidin-HRP ($1/400$) was added. After 30 min at RT, the plate was washed 7× with PBS-T (soak 1 min each wash) and. substrate solution was added. The reaction was stopped after 20 min by adding the stop solution and absorbance was read at 450 nm (minus absorbance at 550 nm) within 30 min of stopping.

Example 11—IFN-γ Detection

IFN-γ secretion in media was measured using a human IFN-γ ELISA kit (Biolegend). Plates were coated with and anti-IFN-γ antibody (capture antibody, 1× in coating buffer). After overnight incubation at 4° C., the plate was washed 4 times with PBS-T and blocking solution was added to block remaining binding site on the well. After 1 h at RT (shaking at 500 rpm) the plate was washed 4 times with PBS-T and conditioned media (CM) and IFN-γ standard, was added. After 2 h at RT with shaking, the plate was washed 4 times with PBS-T and detection antibody (1×), was added. After 1 h at RT with shaking, the plate was washed 4 times with PBS-T and Avidin-HRP (lx) was added. After 30 min at RT with shaking, the plate was washed 5 times with PBS-T (soak 1 min each wash) and TMB substrate solution was added. The reaction was stopped after 20 min by adding the stop solution and absorbance was read at 450 nm (minus absorbance at 570 nm) within 15 min of stopping.

Example 12—CAR T Cytotoxicity Assay

Human T cells were isolated from whole blood according to standard protocols. The T cells were then separately transduced twice with lenti virus bearing the CAR constructs, wherein the CAR constructs bear a GFP tag. Following 2-3 days of culture in RPMI 10% FBS and IL-2, the cells were stained with F(ab')2 to label surface expression of MN-E6, MN-C2, MN-C3 and MN-C8. Cells were then sorted by flow cytometry for Fab-positive, GFP-positive cells. That means that the double positive population had a CAR inserted and that the CAR exposed the correct antibody fragment. The CAR T cells were then ready to be mixed with the MUC1* negative control cells or the target MUC1* positive cancer cells.

The target cells were prepared as follows: Harvest target cells and resuspend cells in serum-free medium containing 15 uM of CMTMr dye (Cell Tracker Orange, 5-and-6-4-chloromethyl benzoyl amino tetramethylrhodamine, Thermo Fisher) at $1-1.5 \times 10^6$ cells/mL. Incubate 30 min under growth conditions appropriate to particular cell type. Wash in culture media and transfer stained cells to a new tube and incubate the cells 60 min in media. Wash 2 more times in culture media to get rid of all excess dye. Set up the assay in 24 well plates with 0.5 ml media total volume. Resuspend the target cells (and control target cells) so that there are always 20,000 cells per well (20,000 cells/250 ul). Plate 250 ul in each well. Add 250 ul of the T cells so that the ratio of T cell: target cells=20:1, 10:1, 5:1 or 1:1. Analyse cells after 24 h and 72 h. For suspension target cells, take off the 0.5 ml media from the well and place in tube, wash the well with 0.5 ml media or PBS. For adherent target cells, take off the 0.5 ml media from the well and place in tube, wash the well with 0.5 ml PBS. Add the PBS to the same tube and add 120 ul trypsin to the well. Incubate for 4 min then add 0.5 ml media to neutralize trypsin and place that in the tube as well. Spin cells and resuspend pellet in 100 ul FACS buffer. Spin cells again. Resuspend cells in 100 ul buffer+5 ul anti-CD3 antibody, for 30 min on ice (to stain T cells). After 30 min, wash stained cells 2× with FACS buffer and resuspend in 250 ul buffer. Run the cells through the filter cap of the FACS tube. 10 min prior to analysis, add 10 ul 7AAD dye to each tube and analyze with Fortessa under the Cytotoxicity template.

Example 13—ELISA Expression Level of Humanized IgG

Figure 9:
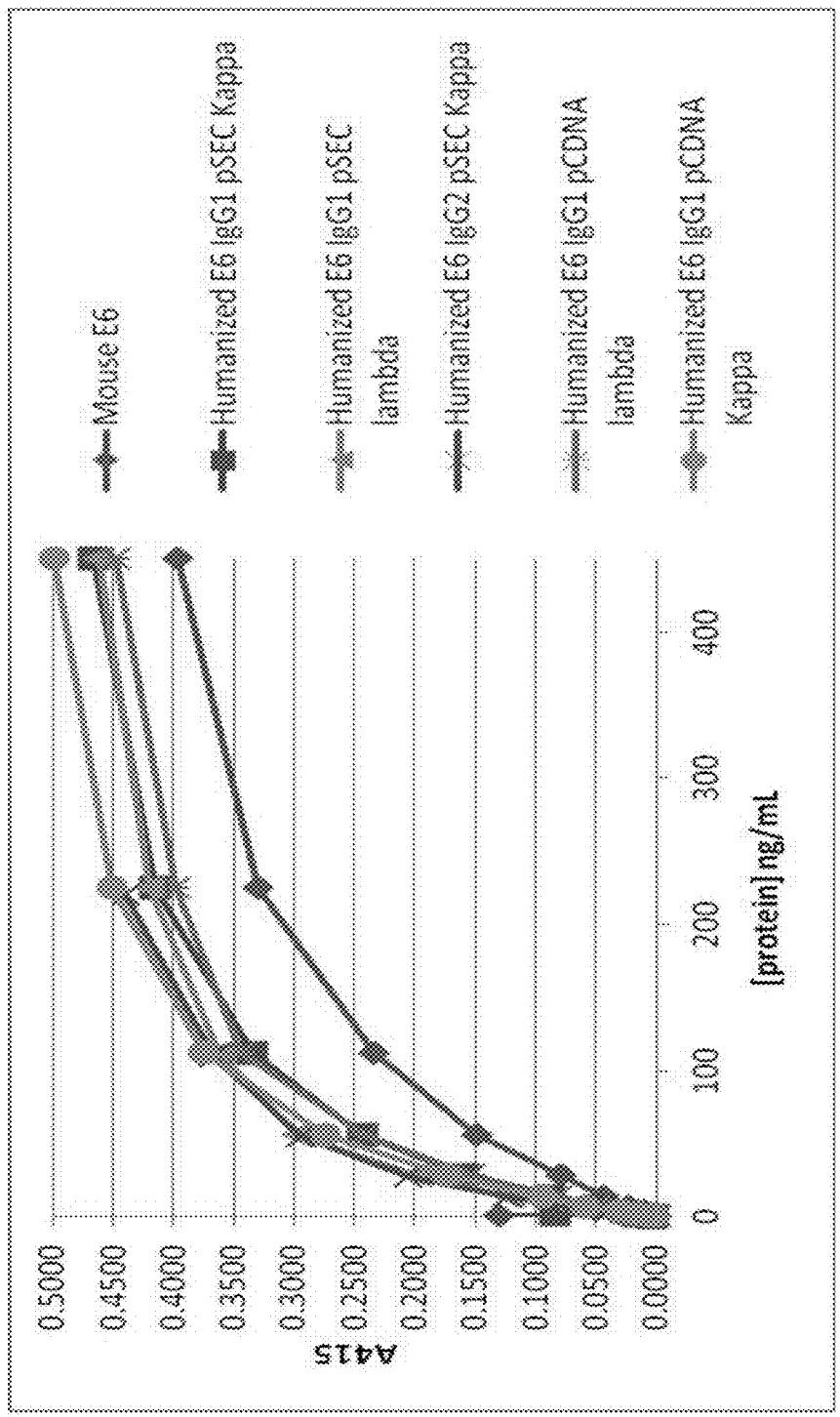
FIG. 9 is a graph of an ELISA assay comparing the binding of the parent mouseMN-E6 antibody to the humanized versions of the MN-E6 antibody to a surface presenting the PSMGFR peptide derived from the MUC1* extracellular domain.
Figure 11:
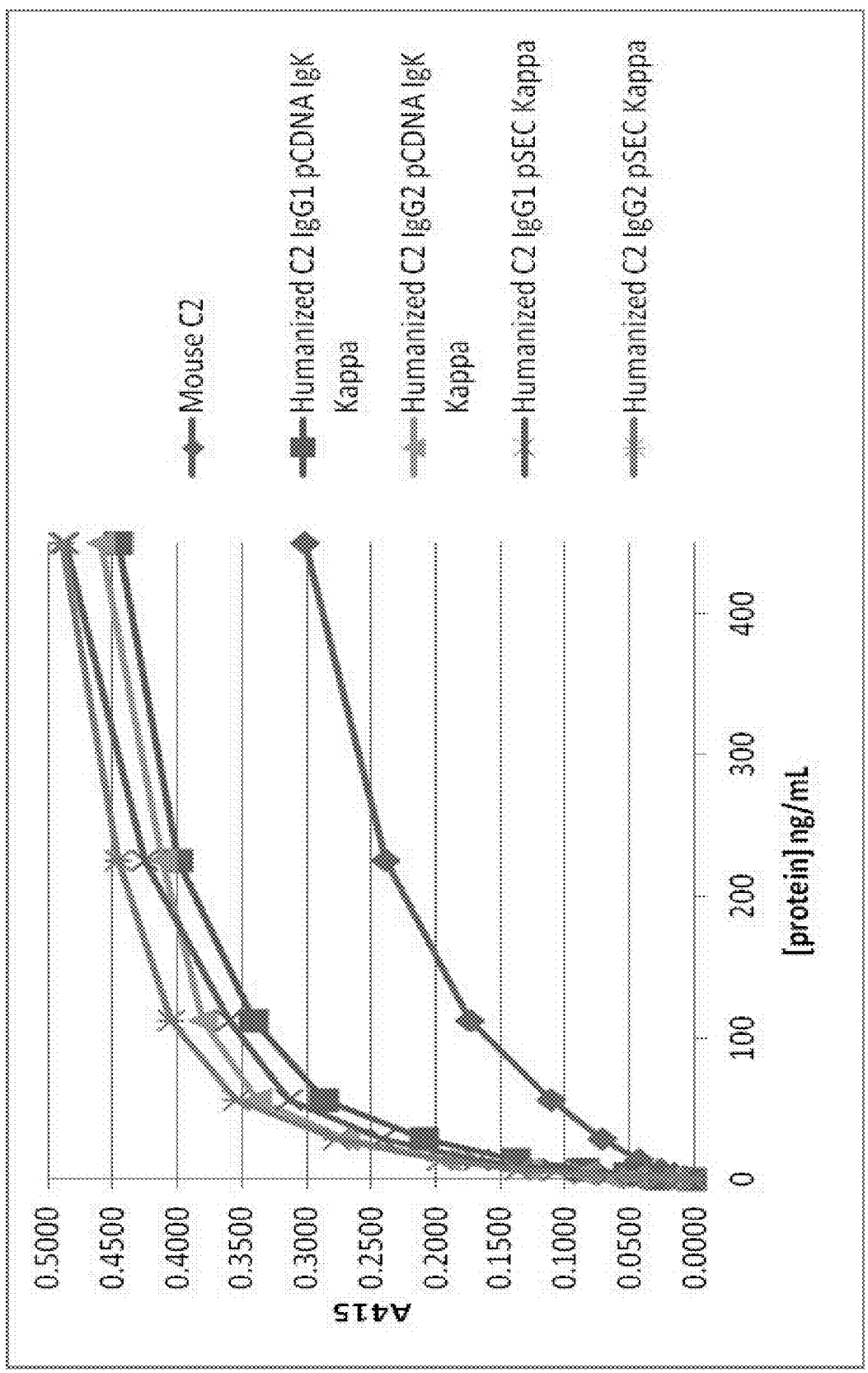
FIG. 11 is a graph of an ELISA assay comparing the binding of the parent mouse MN-C2 antibody to the humanized versions of the MN-C2 antibody to a surface presenting the PSMGFR peptide derived from the MUC1* extracellular domain.
Figure 12:
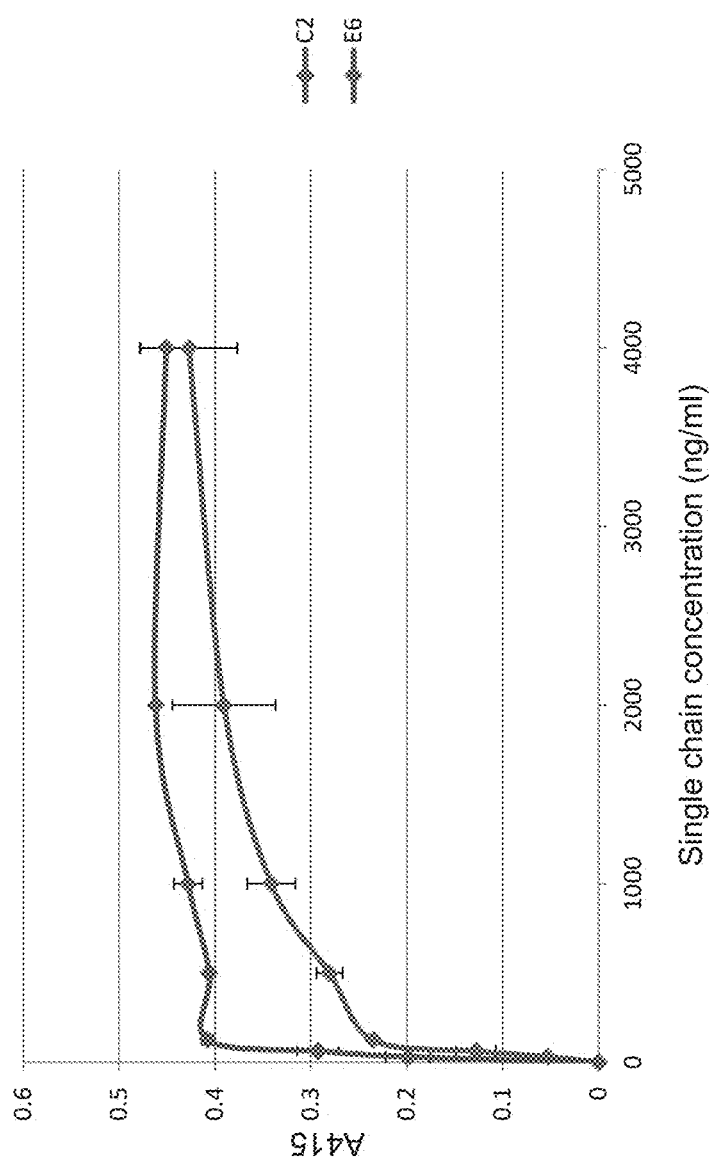
FIG. 12 is a graph of an ELISA assay showing binding of humanized single chain (scFv) MN-C2 and MN-E6 antibodies binding to a surface presenting the PSMGFR peptide derived from the MUC1* extracellular domain.

Goat Anti-human Fc specific antibody was diluted to 5 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and conditioned media (CM), diluted in PBS-T+1% BSA, was added at different concentrations. Also, purified human IgG (life technologies), diluted in PBS-T+1% BSA, was added at different concentrations to make a standard curve for determination of the expression level of the humanized IgG or Fc-fusion protein. After 1 h at RT the plate was washed 3× with PBS-T and anti-human (H+L) HRP (life technologies) diluted in PBS-T+1% BSA, was added at 1/2500. After 1 h at RT the plate was washed 3× with PBS-T and binding of human IgG and humanized IgG was measured at 415 nm using a ABTS solution (ThermoFisher) (FIG. 9 (MN-E6) and FIG. 11 (MN-C2)).

Figure 8:
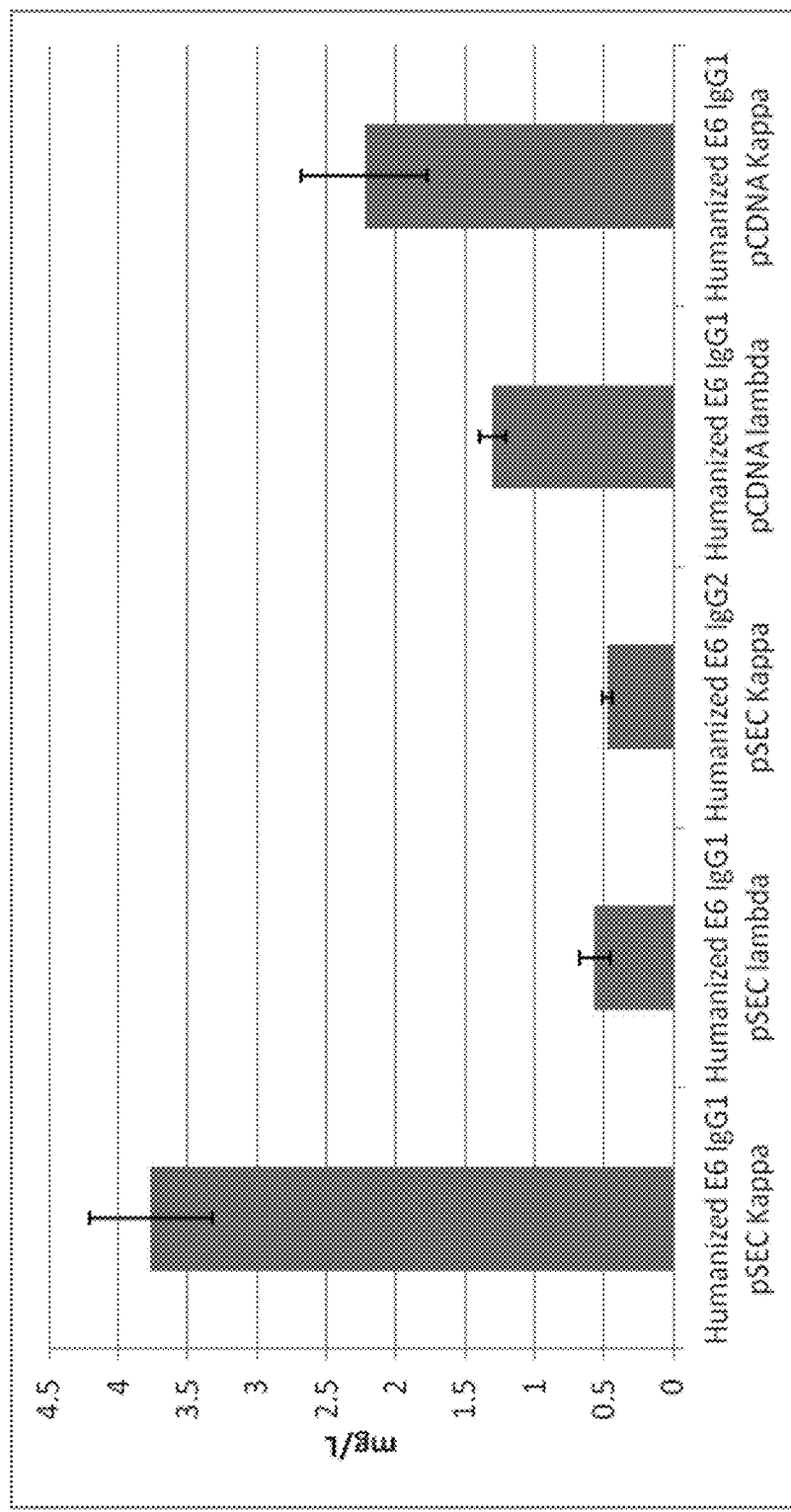
FIG. 8 is a graph of an ELISA assay showing differing levels of expression of humanizedMN-E6 anti-MUC1* antibody depending on whether the light chain was kappa or lambda and whether the variable portion was fused to a human IgG1 or IgG2.

Example 14—ELISA Humanized IgG Binding to PSMGFR Peptide of the MUC1* Extracellular Domain A synthetic peptide of sequence PSMGFR was covalently coupled to BSA using Imject Maleimide activated BSA kit (Thermo Fisher). PSMGFR coupled BSA was diluted to 7.5 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and conditioned media (CM), diluted in PBS-T+1% BSA, was added at different concentrations. At the same time corresponding mouse IgG was diluted in PBS-T+1% BSA and added at different concentrations as binding control. After 1 h at RT the plate was washed 3× with PBS-T and anti-human (H+L) HRP (life technologies) diluted in PBS-T+1% BSA, was added at 1/5000 to detect binding of humanized IgG. Anti-Mouse HRP (life technologies) diluted in PBS-T+1% BSA, was added at 1/2500 to detect binding of mouse IgG. After 1 h at RT the plate was washed 3× with PBS-T and binding was measured at 415 nm using a ABTS solution (ThermoFisher) (FIG. 8 (MN-E6) and FIG. 10 (MN-C2)).

Example 15—Stable Cell Lines Generation

CHO-K1 cells (ATCC) were used to create stable cell lines expressing high level of humanized IgG. HEK293 cells (ATCC) were used to create stable cell lines expressing high level of Fc-fusion proteins. The night before transfection, cells were passed at 1/3 dilution (6well plate) and cultures in a 5% CO2 atmosphere. The next day, 1 hour before transfection, the media was change to complete media without antibiotics (F12K or DMEM containing 10% fetal calf serum). For transfection, we used Lipofectamine 3000 (life technologies) and Opti-MEM® I Reduced Serum Medium according to the manufacturer instructions. 1.25 ug of the heavy chain construct and 1.25 ug of the light chain construct or 2.5 ug of Fc-fusion constructs was used. After 24 h, cells were trypsinized and plated into a T75 flask (in F12K or DMEM containing 10% fetal calf serum). After 24 h, cells were trypsinized, diltuted to 100 cells/mL and 1000 cells/mL in F12K or DMEM containing 10% FCS and selection agent (Zeocin for pSECTag2 or G418 for pCDNA 3.1 V5), plated in 96 well plate (100 uL per well) and cultures in a 5% CO2 atmosphere. After 2-3 weeks, the culture media from single clones were collected, cleared by centrifugation and used in an ELISA assay to quantify the level of humanized IgG expression and binding to PSMGFR peptide. The clones with the highest expression and PSMGFR binding were expanded for large scale expression.

Example 16—scFV Expression pET21b E6 scFV plasmid (with HisTag or StrepTagII) was transformed into Shuffle T7 express competent cells (NEB). TB broth (Terrific broth) was inoculated with 1/100 of an overnight culture (LB broth–30° C.-200 rpm) and cultured at 30° C./200 rpm. When OD600 reached ~1, temperature was reduced to 20° C. and growth was continued. After 2 h, recombinant protein expression was induced with 0.2 mM Isopropyl-β-D-thio-galactoside (IPTG, Gold Biotechnology) and culture was stopped after 22 h. After harvesting the cells by centrifugation (6000 rpm for 10 min at 4° C.), cell pellet was resupended with running buffer. For Histag protein buffer was: 50 mM Tris pH8.0, 300 mM NaCl and 5 mM imidazole. For StrepTagII protein buffer was 100 mM Tris pH 8.0 and 150 mM NaCl.

Example 17—HisTag EscFV Purification

MgCl2 (0.5 mM), DNAse (0.5 ug/mL, Sigma), PMSF (1 mM, Gold Bitotechnology) and BugBuster (1×, Novagen) was added. Cell suspension was incubated on a rotating platform for 20 min at RT. Insoluble cell debris was removed by centrifugation (20000 rpm for 30 min at 4° C.). The cleared lysate was then applied to a Ni-NTA column (Qiagen) equilibrated with the running buffer. The column was washed before eluting the protein off the column with the running buffer supplemented with 495 mM imidazole. The protein was further purified by size exclusion chromatography (Superdex 200). The fractions containing the protein were pooled, aliquoted and stored at −80° C.

Example 18—StrepTagII EscFV Purification

MgCl2 (0.5 mM), DNAse (0.5 ug/mL, Sigma), PMSF (1 mM, Gold Bitotechnology) and BugBuster (1×, Novagen) was added. Cell suspension was incubated on a rotating platform for 20 min at RT. Insoluble cell debris was removed by centrifugation (20000 rpm for 30 min at 4° C.). The cleared lysate was then applied to a Strep-Tactin column (IBA) equilibrated with the running buffer. The column was washed before eluting the protein off the column with the running buffer supplemented with 5 mM d-Desthiobiotin. The protein was further purified by size exclusion chromatography (Superdex 200). The fractions containing the protein were pooled, aliquoted and stored at −80° C.

Example 19—Humanize IgG/Fc-Fusion Purification

Condition media (from transient transfection or stable cell line) was collected, cleared by centrifugation and filtered (0.2 um). The media was then loaded on a protein A (Genscript) or CaptureSelect FcXL (Thermo Fisher) and the protein purified according to manufacturer instructions using acid condition for elution. The eluted protein was then dialyzed against PBS pH 7.4 and further purified by size exclusion chromatography (Superdex 200). The fractions containing the protein were pooled, aliquoted and stored at −80° C.

Example 20—Immunohistochemistry

Human tissue specimens were purchased from Biomax. The tissues were either normal or cancerous as determined by a board certified pathologist. Tissues were anonymized but were labeled with a number, tissue type, stage of cancer and if available, a TNM tumor grading designation. TNM grading is as follows: T is primary tumor. Tx is primary tumor cannot be assessed. T0 is no evidence of a tumor. This is carcinoma in situ, intraepithelial or invasion of *Lamina propia*. T1 is tumor invades submucosa. T2 is tumor invades muscularis propia. T3 is tumor invades through muscularis propia into subserosa or into non-peritonealized pericolic or perirectal tissues. T4 is tumor directly invades other organs or structures and/or perforate visceral peritoneum. N is regional lymph nodes. N0 is no regional lymph node metastasis. N1 is metastasis in 1 to 3 regional lymph nodes. N2 is metastatic in 4 or more regional lymph nodes. M is for distant metastasis. M0 means no distant metastasis. M1 is distant metastasis.

Tissues were stained with a primary anti-MUC1* antibody mouse monoclonal MN-C2, MN-E6, humanized MN-E6 scFv-Fc, or humanized MN-E6 scFv-Fc-biotin. If the primary were a mouse monoclonal antibody, then the secondary antibody used was a rabbit anti-mouse HRP-conjugated antibody. If the primary were a humanized antibody, then the secondary was a goat-anti-human HRP conjugated antibody antibody. If the primary were a biotinylated antibody, then the secondary was a streptavidin HRP conjugated antibody.

Tissue specimens were de-paraffinized using xylene and ethanol according to standard protocols. An antigen retrieval procedure was used for some tissues which involved 10 mM Sodium Citrate-0.05% Tween pH 6 buffer (pre boil buffer, keep warm) boil 10', cool down 20' in rice cooker, then rinse cold tap water 5 minutes then two 5 min. washes in TBS. Tissues were blocked for 1 hr at RT in 10% NGS plus 5% BSA in TBS. If the primary antibody used was humanized MN-E6scFv, which was conjugated to biotin so that it could be visualized by a secondary antibody, the tissues were pre-blocked with an avidin solution then a biotin solution. Primary antibodies were incubated with tissues overnight at 4 degrees C. in 1% BSA-TBS with gentle orbital rotation. Tissues were rinsed with TBS-T for 5 minutes with gentle rocking. For HRP-conjugate detection only, mounted tissues were incubated in 3% $H_2O_2$ in TBS for 15 minutes at RT. For tissues incubated with biotinylated primary antibodies, they were then bathed in StreptAvidin for 10 min with Streptavidin-HRP label (Biocare Cat #: HP604 G, H, L), then washed 3 times for 5 minutes at RT in TBS-T with gentle rocking. They were then developed with chromogen (DAB—1 mL diluent; 1 drop DAB substrate) for 5 minutes at RT, then rinsed with running tap water for 5 minutes. They were then counterstained for 1 second hematoxylin then brief dip in 0.08% NH4OH 'bluing reagent' followed by 5 minutes in running water. Tissues were then dehydrated and mounted with Cytoseal XYL (1 drop/section) and cover-slipped.

All of the references cited herein are incorporated by reference in their entirety.

\* \* \* \* \*

Those skilled in the art will recognize, or be able to ascertain using no more than routine experimentation, many equivalents to the specific embodiments of the invention specifically described herein.

The invention claimed is:

1. A chimeric antigen receptor (CAR) comprising
(a) an anti-MUC1* antibody fragment wherein the anti-MUC1* antibody fragment comprises a heavy chain variable region and a light chain variable region that has complementarity determining regions (CDRs) in the heavy chain variable region and the light chain variable region as follows:
CDR1 heavy chain SEQ ID NO: 123,
CDR1 light chain SEQ ID NO: 173,
CDR2 heavy chain SEQ ID NO: 127,
CDR2 light chain SEQ ID NO: 177,
CDR3 heavy chain SEQ ID NO: 131, and
CDR3 light chain SEQ ID NO: 181; and
(b) a T cell receptor co-stimulatory domain.

2. The chimeric antigen receptor of claim 1, wherein the heavy chain variable region comprises an amino acid sequence that has at least 90% sequence identity to SEQ ID NO: 145 and the light chain variable region comprises an amino acid sequence that has at least 90% sequence identity to SEQ ID NO: 195.

3. The chimeric antigen receptor of claim 1, wherein the heavy chain variable region comprises an amino acid sequence that has at least 95% sequence identity to SEQ ID NO: 145 and the light chain variable region comprises an amino acid sequence that has at least 95% sequence identity to SEQ ID NO: 195.

4. The chimeric antigen receptor of claim 1, wherein the heavy chain variable region comprises an amino acid sequence that has at least 98% sequence identity to SEQ ID NO: 145 and the light chain variable region comprises an amino acid sequence that has at least 98% sequence identity to SEQ ID NO: 195.

5. The chimeric antigen receptor of claim 1, wherein the heavy chain variable region comprises the amino acid sequence according to SEQ ID NO: 145 and the light chain variable region comprises the amino acid sequence according to SEQ ID NO: 195.

6. The chimeric antigen receptor of claim 1, wherein the heavy chain variable region and the light chain variable region are connected by a linker.

7. The chimeric antigen receptor of claim 6, wherein the linker comprises the amino acid sequence according to SEQ ID NO: 402.

8. The chimeric antigen receptor of claim 1, wherein the anti-MUC1* antibody fragment comprises a single chain variable fragment (scFv).

9. The chimeric antigen receptor of claim 8, wherein the scFv comprises an amino acid sequence that has at least 90% sequence identity to any one of SEQ ID NOs: 239, 241, 243, or 398.

10. The chimeric antigen receptor of claim 8, wherein the scFv comprises an amino acid sequence that has at least 95% sequence identity to any one of SEQ ID NOs: 239, 241, 243, or 398.

11. The chimeric antigen receptor of claim 8, wherein the scFv comprises an amino acid sequence that has at least 98% sequence identity to any one of SEQ ID NOs: 239, 241, 243, or 398.

12. The chimeric antigen receptor of claim 8, wherein the scFv comprises an amino acid sequence according to any one of SEQ ID NOs: 239, 241, 243, or 398.

13. The chimeric antigen receptor of claim 1, wherein the T cell receptor co-stimulatory domain comprises a cytoplasmic domain of CD3-zeta, CD27, CD28, 4-1BB, OX40, CD30, CD40, PD-1, ICAM-1, LFA-1, ICOS, CD2, CD5, CD7, or Fc receptor gamma domain.

14. The chimeric antigen receptor of claim 1, wherein the T cell receptor co-stimulatory domain comprises a cytoplasmic domain of CD3-zeta.

15. The chimeric antigen receptor of claim 1, wherein the T cell receptor co-stimulatory domain comprises a cytoplasmic domain of 4-1BB.

16. The chimeric antigen receptor of claim 1, wherein the T cell receptor co-stimulatory domain comprises a cytoplasmic domain of CD3-zeta and a cytoplasmic domain of 4-1BB.

17. The chimeric antigen receptor of claim 16, wherein the cytoplasmic domain of CD3-zeta comprises an amino acid sequence with at least 95% sequence identity to SEQ ID NO: 374.

18. The chimeric antigen receptor of claim 16, wherein the cytoplasmic domain of 4-1BB comprises an amino acid sequence with at least 95% sequence identity to SEQ ID NO: 380.

19. The chimeric antigen receptor of claim 16, wherein the T cell receptor co-stimulatory domain comprises the amino acid sequences of SEQ ID NO: 374 and SEQ ID NO: 380.

20. The chimeric antigen receptor of claim 16, wherein the CAR comprises an amino acid sequence that has at least 90% sequence identity to SEQ ID NO: 611.

21. The chimeric antigen receptor of claim 16, wherein the CAR comprises an amino acid sequence that has at least 95% sequence identity to SEQ ID NO: 611.

22. The chimeric antigen receptor of claim 16, wherein the CAR comprises an amino acid sequence that has at least 98% sequence identity to SEQ ID NO: 611.

23. The chimeric antigen receptor of claim 8, wherein the scFv binds to a MUC1* peptide, wherein the MUC1* peptide comprises the amino acid sequence of SEQ ID NO: 2, SEQ ID NO: 620, or SEQ ID NO: 621.

24. The chimeric antigen receptor of claim 8, wherein the scFv binds to a MUC1* positive cancer cell or a MUC1* transfected cell.

25. The chimeric antigen receptor of claim 24, wherein the MUC1* positive cancer cell is a MUC1* positive breast cancer cell.

26. The chimeric antigen receptor of claim 24, wherein the MUC1* positive cancer cell is a MUC1* positive prostate cancer cell.

27. The chimeric antigen receptor of claim 8, wherein the scFv inhibits growth of a MUC1* positive cancer cell.

28. The chimeric antigen receptor of claim 27, wherein the MUC1* positive cancer cell is a MUC1* positive breast cancer cell.

29. A cell comprising the CAR of claim 1.

30. The cell of claim 29, wherein the cell comprises a T cell, a dendritic cell, or a mast cell.

* * * * *

SEQUENCE LISTING

```
Sequence total quantity: 643
SEQ ID NO: 1            moltype = AA  length = 1255
FEATURE                 Location/Qualifiers
REGION                  1..1255
                        note = MUC1 Receptor
source                  1..1255
                        mol_type = protein
                        organism = synthetic construct
SEQUENCE: 1
MTPGTQSPFF LLLLLTVLTV VTGSGHASST PGGEKETSAT QRSSVPSSTE KNAVSMTSSV   60
LSSHSPGSGS STTQGQDVTL APATEPASGS AATWGQDVTS VPVTRPALGS TTPPAHDVTS  120
APDNKPAPGS TAPPAHGVTS APDTRPAPGS TAPPAHGVTS APDTRPAPGS TAPPAHGVTS  180
APDTRPAPGS TAPPAHGVTS APDTRPAPGS TAPPAHGVTS APDTRPAPGS TAPPAHGVTS  240
APDTRPAPGS TAPPAHGVTS APDTRPAPGS TAPPAHGVTS APDTRPAPGS TAPPAHGVTS  300
APDTRPAPGS TAPPAHGVTS APDTRPAPGS TAPPAHGVTS APDTRPAPGS TAPPAHGVTS  360
APDTRPAPGS TAPPAHGVTS APDTRPAPGS TAPPAHGVTS APDTRPAPGS TAPPAHGVTS  420
APDTRPAPGS TAPPAHGVTS APDTRPAPGS TAPPAHGVTS APDTRPAPGS TAPPAHGVTS  480
APDTRPAPGS TAPPAHGVTS APDTRPAPGS TAPPAHGVTS APDTRPAPGS TAPPAHGVTS  540
APDTRPAPGS TAPPAHGVTS APDTRPAPGS TAPPAHGVTS APDTRPAPGS TAPPAHGVTS  600
APDTRPAPGS TAPPAHGVTS APDTRPAPGS TAPPAHGVTS APDTRPAPGS TAPPAHGVTS  660
APDTRPAPGS TAPPAHGVTS APDTRPAPGS TAPPAHGVTS APDTRPAPGS TAPPAHGVTS  720
APDTRPAPGS TAPPAHGVTS APDTRPAPGS TAPPAHGVTS APDTRPAPGS TAPPAHGVTS  780
APDTRPAPGS TAPPAHGVTS APDTRPAPGS TAPPAHGVTS APDTRPAPGS TAPPAHGVTS  840
APDTRPAPGS TAPPAHGVTS APDTRPAPGS TAPPAHGVTS APDTRPAPGS TAPPAHGVTS  900
APDTRPAPGS TAPPAHGVTS APDTRPAPGS TAPPAHGVTS APDNRPALGS TAPPVHNVTS  960
ASGSASGSAS TLVHNGTSAR ATTTPASKST PFSIPSHHSD TPTTLASHST KTDASSTHHS  1020
SVPPLTSSNH STSPQLSTGV SFFFLSFHIS NLQFNSSLED PSTDYYQELQ RDISEMFLQI  1080
YKQGGFLGLS NIKFRPGSVV VQLTLAFREG TINVHDVETQ FNQYKTEAAS RYNLTISDVS  1140
VSDVPFPFSA QSGAGVPGWG IALLVLVCVL VALAIVYLIA LAVCQCRRKN YGQLDIFPAR  1200
DTYHPMSEYP TYHTHGRYVP PSSTDRSPYE KVSAGNGGSS LSYTNPAVAA ASANL       1255
```

```
SEQ ID NO: 2              moltype = AA   length = 45
FEATURE                   Location/Qualifiers
REGION                    1..45
                          note = PSMGFR
source                    1..45
                          mol_type = protein
                          organism = synthetic construct
SEQUENCE: 2
GTINVHDVET QFNQYKTEAA SRYNLTISDV SVSDVPFPFS AQSGA                  45

SEQ ID NO: 3              moltype = DNA   length = 459
FEATURE                   Location/Qualifiers
misc_feature              1..459
                          note = Human NME1
source                    1..459
                          mol_type = other DNA
                          organism = synthetic construct
SEQUENCE: 3
atggccaact gtgagcgtac cttcattgcg atcaaaccag atggggtcca gcggggtctt   60
gtgggagaga ttatcaagcg ttttgagcag aaaggattcc gccttgttgg tctgaaattc  120
atgcaagctt ccgaagatct tctcaaggaa cactacgttg acttgaagga ccgtccattc  180
tttgccggcc tggtgaaata catgcactca gggccggtag ttgccatggt ctggagggg   240
ctgaatgtgg tgaagacggg ccgagtcatg ctcgggggaga ccaaccctgc agactccaag  300
cctgggacca tccgtggaga cttctgcata caagttggca ggaacattat acatggcagt  360
gattctgtgg agagtgcaga aggagatc ggcttgtggt ttcaccctga ggaactggta   420
gattacacga gctgtgctca gaactggatc tatgaatga                         459

SEQ ID NO: 4              moltype = AA   length = 152
FEATURE                   Location/Qualifiers
REGION                    1..152
                          note = Human NME1
source                    1..152
                          mol_type = protein
                          organism = synthetic construct
SEQUENCE: 4
MANCERTFIA IKPDGVQRGL VGEIIKRFEQ KGFRLVGLKF MQASEDLLKE HYVDLKDRPF   60
FAGLVKYMHS GPVVAMVWEG LNVVKTGRVM LGETNPADSK PGTIRGDFCI QVGRNIIHGS  120
DSVESAEKEI GLWFHPEELV DYTSCAQNWI YE                                152

SEQ ID NO: 5              moltype = DNA   length = 1131
FEATURE                   Location/Qualifiers
misc_feature              1..1131
                          note = Human NME7
source                    1..1131
                          mol_type = other DNA
                          organism = synthetic construct
SEQUENCE: 5
atgaatcata gtgaaagatt cgttttcatt gcagagtggt atgatccaaa tgcttcactt   60
cttcgacgtt atgagctttt atttacccca ggggatggat ctgttgaaat gcatgatgta  120
aagaatcatc gcacctttt aaagcggacc aaatatgata acctgcactt ggaagattta  180
tttataggca acaaagtgaa tgtctttct cgacaactgg tattaattga ctatggggat  240
caatatacag ctcgccagct gggcagtagg aagaaaaaa cgctagccct aattaaacca  300
gatgcaatat caaaggctgg agaaataatt gaaataataa caaagctgg atttactata  360
accaaactca aaatgatgat gctttcaagg aagaagcat tggattttca tgtagatcac  420
cagtcaagac ccttttttcaa tgagctgatc cagttttata caactggtcc tattattgcc  480
atggagattt taagagatga tgctatatgt gaatggaaaa gactgctggg acctgcaaac  540
tctggagtgg cacgcacaga tgcttctgaa agcattagag ccctctttgg aacagatggc  600
ataagaaatg cagcgcatgg ccctgattct tttgcttctg cggccagaga aatggagttg  660
ttttttcctt caagtggagg ttgtgggccg gcaaacactg ctaaatttac taattgtacc  720
tgttgcattg ttaaacccca tgctgtcagt gaaggactgt tgggaaagat cctgatggct  780
atccgagatg caggttttga aatctcagct atgcagatgt caatatggaa tcgggttaat  840
gttgaggaat tctatgaagt ttataaagga gtagtgaccg aatatcatga catggtgaca  900
gaaatgtatt ctggcccttg tgtagcaatg gagattcaac agaatagtc tacaaagaca  960
tttcgagaat tttgtggacc tgctgatcct gaaattgccc ggcatttacg ccctggaact 1020
ctcagagcaa tctttggtaa aactaagatc cagaatgctt tcactgtac tgatctgcca 1080
gaggatggcc tattagaggt tcaatacttc ttcaagatct ggataatta g           1131

SEQ ID NO: 6              moltype = AA   length = 376
FEATURE                   Location/Qualifiers
REGION                    1..376
                          note = Human NME7
source                    1..376
                          mol_type = protein
                          organism = synthetic construct
SEQUENCE: 6
MNHSERFVFI AEWYDPNASL LRRYELLFYP GDGSVEMHDV KNHRTFLKRT KYDNLHLEDL   60
FIGNKVNVFS RQLVLIDYGD QYTARQLGSR KEKTLALIKP DAISKAGEII EIINKAGFTI  120
TKLKMMMLSR KEALDFHVDH QSRPFFNELI QFITTGPIIA MEILRDDAIC EWKRLLGPAN  180
```

```
SGVARTDASE SIRALFGTDG IRNAAHGPDS FASAAREMEL FFPSSGGCGP ANTAKFTNCT    240
CCIVKPHAVS EGLLGKILMA IRDAGFEISA MQMFNMDRVN VEEFYEVYKG VVTEYHDMVT    300
EMYSGPCVAM EIQQNNATKT FREFCGPADP EIARHLRPGT LRAIFGKTKI QNAVHCTDLP    360
EDGLLEVQYF FKILDN                                                    376

SEQ ID NO: 7            moltype = AA   length = 16
FEATURE                 Location/Qualifiers
REGION                  1..16
                        note = NME7 peptide 1 (A domain)
source                  1..16
                        mol_type = protein
                        organism = synthetic construct
SEQUENCE: 7
MLSRKEALDF HVDHQS                                                     16

SEQ ID NO: 8            moltype = AA   length = 11
FEATURE                 Location/Qualifiers
REGION                  1..11
                        note = NME7A peptide 2 (A domain)
source                  1..11
                        mol_type = protein
                        organism = synthetic construct
SEQUENCE: 8
SGVARTDASE S                                                          11

SEQ ID NO: 9            moltype = AA   length = 20
FEATURE                 Location/Qualifiers
REGION                  1..20
                        note = NME7B peptide 1 (B domain)
source                  1..20
                        mol_type = protein
                        organism = synthetic construct
SEQUENCE: 9
DAGFEISAMQ MFNMDRVNVE                                                 20

SEQ ID NO: 10           moltype = AA   length = 16
FEATURE                 Location/Qualifiers
REGION                  1..16
                        note = NME7B peptide 2 (B domain)
source                  1..16
                        mol_type = protein
                        organism = synthetic construct
SEQUENCE: 10
EVYKGVVTEY HDMVTE                                                     16

SEQ ID NO: 11           moltype = AA   length = 29
FEATURE                 Location/Qualifiers
REGION                  1..29
                        note = NME7B peptide 3 (B domain)
source                  1..29
                        mol_type = protein
                        organism = synthetic construct
SEQUENCE: 11
AIFGKTKIQN AVHCTDLPED GLLEVQYFF                                       29

SEQ ID NO: 12           moltype = DNA   length = 366
FEATURE                 Location/Qualifiers
misc_feature            1..366
                        note = Mouse E6 Heavy chain variable region sequence
source                  1..366
                        mol_type = other DNA
                        organism = synthetic construct
SEQUENCE: 12
gaggtgaagg tggtggagtc tgggggagac ttagtgaagc ctggagggtc cctgaaactc     60
tcctgtgtag tctctggatt cactttcagt agatatggca tgtcttgggt tcgccagact    120
ccaggcaaga ggctggagtg ggtcgcaacc attagtggtg gcgtactta catctactat     180
ccagacagtg tgaaggggcg attcaccatc tccagagaca atgccaagaa caccctgtac    240
ctgcaaatga gcagtctgaa gtctgaggac acagccatgt atcactgtac aagggataac    300
tacggtagga actacgacta cggtatggac tactgggtc aaggaacctc agtcaccgtc    360
tcctca                                                                366

SEQ ID NO: 13           moltype = AA   length = 122
FEATURE                 Location/Qualifiers
REGION                  1..122
                        note = Mouse E6 Heavy chain variable region sequence
source                  1..122
                        mol_type = protein
                        organism = synthetic construct
SEQUENCE: 13
```

```
EVKVVESGGD LVKPGGSLKL SCVVSGFTFS RYGMSWVRQT PGKRLEWVAT ISGGGTYIYY    60
PDSVKGRFTI SRDNAKNTLY LQMSSLKSED TAMYHCTRDN YGRNYDYGMD YWGQGTSVTV   120
SS                                                                 122

SEQ ID NO: 14           moltype = DNA  length = 75
FEATURE                 Location/Qualifiers
misc_feature            1..75
                        note = Mouse E6 heavy chain variable framework region 1
                        (FWR1) sequence
source                  1..75
                        mol_type = other DNA
                        organism = synthetic construct
SEQUENCE: 14
gaggtgaagg tggtggagtc tgggggagac ttagtgaagc ctggagggtc cctgaaactc    60
tcctgtgtag tctct                                                    75

SEQ ID NO: 15           moltype = AA  length = 30
FEATURE                 Location/Qualifiers
REGION                  1..30
                        note = Mouse E6 heavy chain variable framework region 1
                        (FWR1) sequence
source                  1..30
                        mol_type = protein
                        organism = synthetic construct
SEQUENCE: 15
EVKVVESGGD LVKPGGSLKL SCVVSGFTFS                                    30

SEQ ID NO: 16           moltype = DNA  length = 30
FEATURE                 Location/Qualifiers
misc_feature            1..30
                        note = Mouse E6 heavy chain variable complementarity
                        determining regions1 (CDR1) sequence
source                  1..30
                        mol_type = other DNA
                        organism = synthetic construct
SEQUENCE: 16
ggattcactt tcagtagata tggcatgtct                                    30

SEQ ID NO: 17           moltype = AA  length = 5
FEATURE                 Location/Qualifiers
REGION                  1..5
                        note = Mouse E6 heavy chain variable complementarity
                        determining regions1 (CDR1) sequence
source                  1..5
                        mol_type = protein
                        organism = synthetic construct
SEQUENCE: 17
RYGMS                                                               5

SEQ ID NO: 18           moltype = DNA  length = 42
FEATURE                 Location/Qualifiers
misc_feature            1..42
                        note = Mouse E6 heavy chain variable framework region 2
                        (FWR2) sequence
source                  1..42
                        mol_type = other DNA
                        organism = synthetic construct
SEQUENCE: 18
tggguttcgcc agactccagg caagaggctg gagtgggtcg ca                     42

SEQ ID NO: 19           moltype = AA  length = 14
FEATURE                 Location/Qualifiers
REGION                  1..14
                        note = Mouse E6 heavy chain variable framework region 2
                        (FWR2) sequence
source                  1..14
                        mol_type = protein
                        organism = synthetic construct
SEQUENCE: 19
WVRQTPGKRL EWVA                                                     14

SEQ ID NO: 20           moltype = DNA  length = 51
FEATURE                 Location/Qualifiers
misc_feature            1..51
                        note = Mouse E6 heavy chain variable complementarity
                        determining regions2 (CDR2) sequence
source                  1..51
                        mol_type = other DNA
                        organism = synthetic construct
```

```
SEQUENCE: 20
accattagtg gtggcggtac ttacatctac tatccagaca gtgtgaaggg g           51

SEQ ID NO: 21              moltype = AA  length = 17
FEATURE                    Location/Qualifiers
REGION                     1..17
                           note = Mouse E6 heavy chain variable complementarity
                            determining regions2 (CDR2) sequence
source                     1..17
                           mol_type = protein
                           organism = synthetic construct
SEQUENCE: 21
TISGGGTYIY YPDSVKG                                                 17

SEQ ID NO: 22              moltype = DNA  length = 96
FEATURE                    Location/Qualifiers
misc_feature               1..96
                           note = Mouse E6 heavy chain variable framework region 3
                            (FWR3) acidsequence
source                     1..96
                           mol_type = other DNA
                           organism = synthetic construct
SEQUENCE: 22
cgattcacca tctccagaga caatgccaag aacaccctgt acctgcaaat gagcagtctg  60
aagtctgagg acacagccat gtatcactgt acaagg                            96

SEQ ID NO: 23              moltype = AA  length = 32
FEATURE                    Location/Qualifiers
REGION                     1..32
                           note = Mouse E6 heavy chain variable framework region 3
                            (FWR3) acidsequence
source                     1..32
                           mol_type = protein
                           organism = synthetic construct
SEQUENCE: 23
RFTISRDNAK NTLYLQMSSL KSEDTAMYHC TR                                32

SEQ ID NO: 24              moltype = DNA  length = 39
FEATURE                    Location/Qualifiers
misc_feature               1..39
                           note = Mouse E6 heavy chain variable complementarity
                            determining regions3 (CDR3) sequence
source                     1..39
                           mol_type = other DNA
                           organism = synthetic construct
SEQUENCE: 24
gataactacg gtaggaacta cgactacggt atggactac                         39

SEQ ID NO: 25              moltype = AA  length = 13
FEATURE                    Location/Qualifiers
REGION                     1..13
                           note = Mouse E6 heavy chain variable complementarity
                            determining regions3 (CDR3) sequence
source                     1..13
                           mol_type = protein
                           organism = synthetic construct
SEQUENCE: 25
DNYGRNYDYG MDY                                                     13

SEQ ID NO: 26              moltype = DNA  length = 294
FEATURE                    Location/Qualifiers
misc_feature               1..294
                           note = IGHV3-21*03 heavy chain variable region sequence
source                     1..294
                           mol_type = other DNA
                           organism = synthetic construct
SEQUENCE: 26
gaggtgcagc tggtggagtc tgggggaggc ctggtcaagc ctggggggtc cctgagactc  60
tcctgtgcag cctctggatt caccttcagt agctatagca tgaactgggt ccgccaggct  120
ccagggaagg ggctggagtg ggtctcatcc attagtagta gtagtagtta catatactac  180
gcagactcag tgaagggccg attcaccatc tccagagaca cgccaagaa ctcactgtat  240
ctgcaaatga acagcctgag agccgaggac acggctgtgt attactgtgc gaga        294

SEQ ID NO: 27              moltype = AA  length = 98
FEATURE                    Location/Qualifiers
REGION                     1..98
                           note = IGHV3-21*03 heavy chain variable region sequence
source                     1..98
                           mol_type = protein
```

```
                                organism = synthetic construct
SEQUENCE: 27
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCAR                           98

SEQ ID NO: 28              moltype = DNA   length = 90
FEATURE                    Location/Qualifiers
misc_feature               1..90
                           note = IGHV3-21*01 heavy chain variable framework region 1
                           (FWR1)sequence
source                     1..90
                           mol_type = other DNA
                           organism = synthetic construct
SEQUENCE: 28
gaggtgcagc tggtggagtc tgggggaggc ctggtcaagc ctggggggtc cctgagactc    60
tcctgtgcag cctctggatt caccttcagt                                     90

SEQ ID NO: 29              moltype = AA   length = 30
FEATURE                    Location/Qualifiers
REGION                     1..30
                           note = IGHV3-21*01 heavy chain variable framework region 1
                           (FWR1)sequence
source                     1..30
                           mol_type = protein
                           organism = synthetic construct
SEQUENCE: 29
EVQLVESGGG LVKPGGSLRL SCAASGFTFS                                     30

SEQ ID NO: 30              moltype = DNA   length = 15
FEATURE                    Location/Qualifiers
misc_feature               1..15
                           note = IGHV3-21*01 heavy chain variable complementarity
                           determiningregions 1 (CDR1) sequence
source                     1..15
                           mol_type = other DNA
                           organism = synthetic construct
SEQUENCE: 30
agctatagca tgaac                                                     15

SEQ ID NO: 31              moltype = AA   length = 5
FEATURE                    Location/Qualifiers
REGION                     1..5
                           note = IGHV3-21*01 heavy chain variable complementarity
                           determiningregions 1 (CDR1) sequence
source                     1..5
                           mol_type = protein
                           organism = synthetic construct
SEQUENCE: 31
SYSMN                                                                 5

SEQ ID NO: 32              moltype = DNA   length = 42
FEATURE                    Location/Qualifiers
misc_feature               1..42
                           note = IGHV3-21*01 heavy chain variable framework region 2
                           (FWR2)sequence
source                     1..42
                           mol_type = other DNA
                           organism = synthetic construct
SEQUENCE: 32
tgggtccgcc aggctccagg gaaggggctg gagtgggtct ca                        42

SEQ ID NO: 33              moltype = AA   length = 14
FEATURE                    Location/Qualifiers
REGION                     1..14
                           note = IGHV3-21*01 heavy chain variable framework region 2
                           (FWR2)sequence
source                     1..14
                           mol_type = protein
                           organism = synthetic construct
SEQUENCE: 33
WVRQAPGKGL EWVS                                                      14

SEQ ID NO: 34              moltype = DNA   length = 51
FEATURE                    Location/Qualifiers
misc_feature               1..51
                           note = IGHV3-21*01 heavy chain variable complementarity
                           determiningregions 2 (CDR2) sequence
source                     1..51
                           mol_type = other DNA
```

```
                        organism = synthetic construct
SEQUENCE: 34
tccattagta gtagtagtag ttacatatac tacgcagact cagtgaaggg c        51

SEQ ID NO: 35           moltype = AA   length = 17
FEATURE                 Location/Qualifiers
REGION                  1..17
                        note = IGHV3-21*01 heavy chain variable complementarity
                         determiningregions 2 (CDR2) sequence
source                  1..17
                        mol_type = protein
                        organism = synthetic construct
SEQUENCE: 35
SISSSSSYIY YADSVKG                                              17

SEQ ID NO: 36           moltype = DNA   length = 96
FEATURE                 Location/Qualifiers
misc_feature            1..96
                        note = IGHV3-21*01 heavy chain variable framework region 3
                         (FWR3)sequence
source                  1..96
                        mol_type = other DNA
                        organism = synthetic construct
SEQUENCE: 36
cgattcacca tctccagaga caacgccaag aactcactgt atctgcaaat gaacagcctg  60
agagccgagg acacggctgt gtattactgt gcgaga                           96

SEQ ID NO: 37           moltype = AA   length = 32
FEATURE                 Location/Qualifiers
REGION                  1..32
                        note = IGHV3-21*01 heavy chain variable framework region 3
                         (FWR3)sequence
source                  1..32
                        mol_type = protein
                        organism = synthetic construct
SEQUENCE: 37
RFTISRDNAK NSLYLQMNSL RAEDTAVYYC AR                              32

SEQ ID NO: 38           moltype = DNA   length = 366
FEATURE                 Location/Qualifiers
misc_feature            1..366
                        note = Humanized E6 heavy chain variable region sequence
source                  1..366
                        mol_type = other DNA
                        organism = synthetic construct
SEQUENCE: 38
gaggtgcagc tggtggagtc tgggggaggc ctggtcaagc ctgggggtc cctgagactc   60
tcctgtgcag cctctggatt caccttcagt aggtatggca tgagctgggt ccgccaggct  120
ccagggaaga ggctgagtg gtctcaacc attagtggcg aggcaccta catatactac    180
ccagactcag tgaagggccg attcaccatc tccagagaca cgccaagaa caccctgtat  240
ctgcaaatga cagcctgag agccgaggac acggctgtgt attactgtac cagagataac  300
tatggccgca actatgatta tggcatggat tattgggcc agggcaccct ggtgaccgtg  360
agcagc                                                            366

SEQ ID NO: 39           moltype = AA   length = 122
FEATURE                 Location/Qualifiers
REGION                  1..122
                        note = Humanized E6 heavy chain variable region sequence
source                  1..122
                        mol_type = protein
                        organism = synthetic construct
SEQUENCE: 39
EVQLVESGGG LVKPGGSLRL SCAASGFTFS RYGMSWVRQA PGKRLEWVST ISGGGTYIYY  60
PDSVKGRFTI SRDNAKNTLY LQMNSLRAED TAVYYCTRDN YGRNYDYGMD YWGQGTLVTV 120
SS                                                                122

SEQ ID NO: 40           moltype = DNA   length = 90
FEATURE                 Location/Qualifiers
misc_feature            1..90
                        note = Humanized E6 heavy chain variable framework region 1
                         (FWR1) acidsequence
source                  1..90
                        mol_type = other DNA
                        organism = synthetic construct
SEQUENCE: 40
gaggtgcagc tggtggagtc tgggggaggc ctggtcaagc ctgggggtc cctgagactc   60
tcctgtgcag cctctggatt caccttcagt                                  90

SEQ ID NO: 41           moltype = AA   length = 30
```

```
FEATURE              Location/Qualifiers
REGION               1..30
                     note = Humanized E6 heavy chain variable framework region 1
                     (FWR1) acidsequence
source               1..30
                     mol_type = protein
                     organism = synthetic construct
SEQUENCE: 41
EVQLVESGGG LVKPGGSLRL SCAASGFTFS                                       30

SEQ ID NO: 42        moltype = DNA  length = 15
FEATURE              Location/Qualifiers
misc_feature         1..15
                     note = Humanized E6 heavy chain variable complementarity
                     determiningregions 1 (CDR1) sequence
source               1..15
                     mol_type = other DNA
                     organism = synthetic construct
SEQUENCE: 42
aggtatggca tgagc                                                      15

SEQ ID NO: 43        moltype = AA  length = 5
FEATURE              Location/Qualifiers
REGION               1..5
                     note = Humanized E6 heavy chain variable complementarity
                     determiningregions 1 (CDR1) sequence
source               1..5
                     mol_type = protein
                     organism = synthetic construct
SEQUENCE: 43
RYGMS                                                                  5

SEQ ID NO: 44        moltype = DNA  length = 42
FEATURE              Location/Qualifiers
misc_feature         1..42
                     note = Humanized E6 heavy chain variable framework region 2
                     (FWR2) acidsequence
source               1..42
                     mol_type = other DNA
                     organism = synthetic construct
SEQUENCE: 44
tgggtccgcc aggctccagg gaagaggctg gagtgggtct ca                        42

SEQ ID NO: 45        moltype = AA  length = 14
FEATURE              Location/Qualifiers
REGION               1..14
                     note = Humanized E6 heavy chain variable framework region 2
                     (FWR2) acidsequence
source               1..14
                     mol_type = protein
                     organism = synthetic construct
SEQUENCE: 45
WVRQAPGKRL EWVS                                                       14

SEQ ID NO: 46        moltype = DNA  length = 51
FEATURE              Location/Qualifiers
misc_feature         1..51
                     note = Humanized E6 heavy chain variable complementarity
                     determiningregions 2 (CDR2) sequence
source               1..51
                     mol_type = other DNA
                     organism = synthetic construct
SEQUENCE: 46
accattagtg gcggaggcac ctacatatac tacccagact cagtgaaggg c              51

SEQ ID NO: 47        moltype = AA  length = 17
FEATURE              Location/Qualifiers
REGION               1..17
                     note = Humanized E6 heavy chain variable complementarity
                     determiningregions 2 (CDR2) sequence
source               1..17
                     mol_type = protein
                     organism = synthetic construct
SEQUENCE: 47
TISGGGTYIY YPDSVKG                                                    17

SEQ ID NO: 48        moltype = DNA  length = 96
FEATURE              Location/Qualifiers
misc_feature         1..96
```

```
                        note = Humanized E6 heavy chain variable framework region 3
                            (FWR3) acidsequence
source                  1..96
                        mol_type = other DNA
                        organism = synthetic construct
SEQUENCE: 48
cgattcacca tctccagaga caacgccaag aacaccctgt atctgcaaat gaacagcctg      60
agagccgagg acacggctgt gtattactgt accaga                               96

SEQ ID NO: 49           moltype = AA   length = 32
FEATURE                 Location/Qualifiers
REGION                  1..32
                        note = Humanized E6 heavy chain variable framework region 3
                            (FWR3) acidsequence
source                  1..32
                        mol_type = protein
                        organism = synthetic construct
SEQUENCE: 49
RFTISRDNAK NTLYLQMNSL RAEDTAVYYC TR                                   32

SEQ ID NO: 50           moltype = DNA   length = 39
FEATURE                 Location/Qualifiers
misc_feature            1..39
                        note = Humanized E6 heavy chain variable complementarity
                            determiningregions 3 (CDR3) sequence
source                  1..39
                        mol_type = other DNA
                        organism = synthetic construct
SEQUENCE: 50
gataactatg gccgcaacta tgattatggc atggattat                            39

SEQ ID NO: 51           moltype = AA   length = 13
FEATURE                 Location/Qualifiers
REGION                  1..13
                        note = Humanized E6 heavy chain variable complementarity
                            determiningregions 3 (CDR3) sequence
source                  1..13
                        mol_type = protein
                        organism = synthetic construct
SEQUENCE: 51
DNYGRNYDYG MDY                                                        13

SEQ ID NO: 52           moltype = DNA   length = 1442
FEATURE                 Location/Qualifiers
misc_feature            1..1442
                        note = Humanized E6 IgG2 heavy chain synthesized by
                            Genescript
source                  1..1442
                        mol_type = other DNA
                        organism = synthetic construct
SEQUENCE: 52
gaattctaag cttgggccac catggaactg gggctccgct gggttttcct tgttgctatt      60
ttagaaggtg tccagtgtga ggtgcagctg gtggagtctg ggggaggcct ggtcaagcct     120
ggggggtccc tgagactctc ctgtgcagcc tctggattca ccttcagtag gtatggcatg     180
agctgggtcc gccaggctcc agggaagagg ctggagtggg tctcaaccat tagtggcgga     240
ggcacctaca tatactaccc agactcagtg aagggccgat tcaccatctc cagagacaac     300
gccaagaaca ccctgtatct gcaaatgaac agcctgagag ccgaggacac ggctgtgtat     360
tactgtacca gagataacta tggccgcaac tatgattatg gcatggatta ttggggccag     420
ggcaccctgg tgaccgtgag cagcgcctcc accaagggcc catcggtctt ccccctggcg     480
cctgctcca ggagcacctc cgagagcaca gccgccctgg gctgcctggt caaggactac     540
ttccccgaac cggtgacggt gtcgtggaac tcaggcgctc tgaccagcgg cgtgcacacc     600
ttcccagctg tcctacagtc ctcaggactc tactccctca gcagcgtggt gaccgtgccc     660
tccagcaact tcggcaccca gacctacacc tgcaacgtag atcacaagcc cagcaacacc     720
aaggtggaca gacagttgag gcgcaaatgt tgtgtcgagt gcccaccgtg cccagcacca     780
cctgtggcag gaccgtcagt cttcctcttc ccccaaaaac ccaaggacac cctcatgatc     840
tcccggaccc ctgaggtcac gtgcgtggtg gtggacgtga gccacgaaga ccccgaggtc     900
cagttcaact ggtacgtgga cggcgtggag gtgcataatg ccaagacaaa gccacgggag     960
gagcagttca acagcacgtt ccgtgtggtc agcgtcctca ccgttgtgca ccaggactgg    1020
ctgaacggca aggagtacaa gtgcaaggtc tccaacaaag gcctcccagc ccccatcgag    1080
aaaaccatct ccaaaaccaa agggcagccc cgagaaccac aggtgtacac cctgccccca    1140
tcccgggagg agatgaccaa gaaccaggtc agcctgacct gcctggtcaa aggcttctac    1200
cccagcgaca tcgccgtgga gtgggagagc aatgggcagc cggagaacaa ctacaagacc    1260
acacctccca tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cgcagaagag cctctccctg tctccgggta aatagtaagt ttaaactcta    1440
ga                                                                   1442

SEQ ID NO: 53           moltype = AA   length = 477
FEATURE                 Location/Qualifiers
```

```
REGION                  1..477
                        note = Humanized E6 IgG2 heavy chain synthesized by
                         Genescript
SITE                    477
                        note = misc_feature - Xaa can be any naturally occurring
                         amino acid
source                  1..477
                        mol_type = protein
                        organism = synthetic construct
SEQUENCE: 53
EFAWATMELG LRWVFLVAIL EGVQCEVQLV ESGGGLVKPG GSLRLSCAAS GFTFSRYGMS   60
WVRQAPGKRL EWVSTISGGG TYIYYPDSVK GRFTISRDNA KNTLYLQMNS LRAEDTAVYY  120
CTRDNYGRNY DYGMDYWGQG TLVTVSSAST KGPSVFPLAP CSRSTSESTA ALGCLVKDYF  180
PEPVTVSWNS GALTSGVHTF PAVLQSSGLY SLSSVVTVPS SNFGTQTYTC NVDHKPSNTK  240
VDKTVERKCC VECPPCPAPP VAGPSVFLFP PKPKDTLMIS RTPEVTCVVV DVSHEDPEVQ  300
FNWYVDGVEV HNAKTKPREE QFNSTFRVVS VLTVVHQDWL NGKEYKCKVS NKGLPAPIEK  360
TISKTKGQPR EPQVYTLPPS REEMTKNQVS LTCLVKGFYP SDIAVEWESN GQPENNYKTT  420
PPMLDSDGSF FLYSKLTVDK SRWQQGNVFS CSVMHEALHN HYTQKSLSLS PGKVTLX     477

SEQ ID NO: 54           moltype = DNA  length = 981
FEATURE                 Location/Qualifiers
misc_feature            1..981
                        note = Human IgG2 heavy chain constant region sequence
source                  1..981
                        mol_type = other DNA
                        organism = synthetic construct
SEQUENCE: 54
gcctccacca agggcccatc ggtcttcccc ctggcgccct gctccaggag cacctccgag   60
agcacagccg ccctgggctg cctggtcaag gactacttcc ccgaaccggt gacggtgtcg  120
tggaactcag gcgctctgac cagcggcgtg cacaccttcc cagctgtcct acagtcctca  180
ggactctact ccctcagcag cgtggtgacc gtgccctcca gcaacttcgg cacccagacc  240
tacacctgca acgtagatca caagcccagc aacaccaagg tggacaagac agttgagcgc  300
aaatgttgtg tcgagtgccc accgtgccca gcaccacctg tggcaggacc gtcagtcttc  360
ctcttccccc caaaacccaa ggacaccctc atgatctccc ggacccctga ggtcacgtgc  420
gtggtggtgg acgtgagcca cgaagacccc gaggtccagt tcaactggta cgtggacggc  480
gtggaggtgc ataatgccaa gacaaagcca cgggaggagc agttcaacag cacgttccgt  540
gtggtcagcg tcctcaccgt tgtgcaccag gactggctga acggcaagga gtacaagtgc  600
aaggtctcca acaaaggcct cccagccccc atcgagaaaa ccatctccaa aaccaaaggg  660
cagccccgag aaccacaggt gtacaccctg cccccatccc gggaggagat gaccaagaac  720
caggtcagcc tgacctgcct ggtcaaaggc ttctacccca gcgacatcgc cgtggagtgg  780
gagagcaatg gcagccggag aacaactac aagaccacac ctcccatgct ggactccgac  840
ggctccttct tcctctacag caagctcacc gtggacaaga gcaggtggca gcaggggaac  900
gtcttctcat gctccgtgat gcatgaggct ctgcacaacc actacacgca gaagagcctc  960
tccctgtctc cgggtaaata g                                            981

SEQ ID NO: 55           moltype = AA  length = 326
FEATURE                 Location/Qualifiers
REGION                  1..326
                        note = Human IgG2 heavy chain constant region sequence
source                  1..326
                        mol_type = protein
                        organism = synthetic construct
SEQUENCE: 55
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 56           moltype = DNA  length = 1362
FEATURE                 Location/Qualifiers
misc_feature            1..1362
                        note = Humanized E6 IgG1 heavy chain sequence
source                  1..1362
                        mol_type = other DNA
                        organism = synthetic construct
SEQUENCE: 56
gaggtgcagc tggtggagtc tgggggaggc ctggtcaagc ctgggggtc cctgagactc    60
tcctgtgcag cctctggatt cacctttcagt aggtatggca tgagctgggt ccgccaggct  120
ccagggaaga ggctgagtg gtctcaacc attagtggcg gaggcaccta catatactac    180
ccagactcag tgaagggccg attcaccatc tccagagaca cgccaagaa cccactgtat  240
ctgcaaatga acagcctgag agccgaggac acggctgtgt attactgtcc cagagataac  300
tatggccgca actatgatta tggcatggat tattgggcc aggcacccc tggtcaccgtc  360
agcagcgcta gcaccaaggg cccatcggtc ttccccctgg cacctcctc caagagcacc  420
tctgggggca gcggccct gggctgcctg gtcaaggact acttcccga accggtgacg   480
gtgtcgtgga actcaggcgc cctgaccagc ggcgtgcaca ccttcccggc tgtcctacag  540
tcctcaggac tctactccct cagcagcgtg gtgacagtgc cctccagcag cttgggcacc  600
cagacctaca tctgcaacgt gaatcacaag cccagcaaca ccaaggtgga caagaaagtt  660
```

```
gagcccaaat cttgtgacaa aactcacaca tgcccaccgt gcccagcacc tgaactcctg   720
gggggaccgt cagtcttcct cttccccca aacccaagg acaccctcat gatctcccgg   780
accctgagg tcacatgcgt ggtggtggac gtgagccacg aagacccga ggtcaagttc   840
aactggtacg tggacggcgt ggaggtgcat aatgccaaga caaagccgcg ggaggagcag   900
tacaacagca cgtaccgtgt ggtcagcgtc ctcaccgtcc tgcaccagga ctggctgaat   960
ggcaaggagt acaagtgcaa ggtctccaac aaagccctcc cagccccat cgagaaaacc  1020
atctccaaag ccaaagggca gccccgagaa ccacaggtgt acaccctgcc cccatcccgg  1080
gaggagatga ccaagaacca ggtcagcctg acctgcctgg tcaaaggctt ctatcccagc  1140
gacatcgccg tggagtggga gagcaatggg cagccggaga acaactacaa gaccacgcct  1200
cccgtgctgg actccgacgg ctccttcttc ctctacagca agctcaccgt ggacaagagc  1260
aggtggcagc aggggaacgt cttctcatgc tccgtgatgc atgaggctct gcacaaccac  1320
tacacgcaga gagcctctc cctgtctccg ggtaaatgat aa                     1362
```

```
SEQ ID NO: 57          moltype = AA   length = 452
FEATURE                Location/Qualifiers
REGION                 1..452
                       note = Humanized E6 IgG1 heavy chain sequence
source                 1..452
                       mol_type = protein
                       organism = synthetic construct
SEQUENCE: 57
EVQLVESGGG LVKPGGSLRL SCAASGFTFS RYGMSWVRQA PGKRLEWVST ISGGGTYIYY    60
PDSVKGRFTI SRDNAKNPLY LQMNSLRAED TAVYYCPRDN YGRNYDYGMD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 58          moltype = DNA   length = 996
FEATURE                Location/Qualifiers
misc_feature           1..996
                       note = Human IgG1 heavy chain constant region sequence
source                 1..996
                       mol_type = other DNA
                       organism = synthetic construct
SEQUENCE: 58
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgaca gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagcccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagc tctccctgtc tccgggtaaa tgataa                             996

SEQ ID NO: 59          moltype = AA   length = 330
FEATURE                Location/Qualifiers
REGION                 1..330
                       note = Human IgG1 heavy chain constant region sequence
source                 1..330
                       mol_type = protein
                       organism = synthetic construct
SEQUENCE: 59
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 60          moltype = DNA   length = 560
FEATURE                Location/Qualifiers
misc_feature           1..560
                       note = Human IgG1 heavy chain constant region gBLOCK#1
                          sequence
source                 1..560
                       mol_type = other DNA
                       organism = synthetic construct
```

```
SEQUENCE: 60
atggcatgga ttattggggc cagggcaccc tggtgaccgt gagcagcgct agcaccaagg    60
gcccatcggt cttccccctg gcaccctcct ccaagagcac ctctgggggc acagcggccc   120
tgggctgcct ggtcaaggac tacttccccg aaccggtgac ggtgtcgtgg aactcaggcg   180
ccctgaccag cggcgtgcac accttcccgg ctgtcctaca gtcctcagga ctctactccc   240
tcagcagcgt ggtgacagtg ccctccagca gcttgggcac ccagacctac atctgcaacg   300
tgaatcacaa gcccagcaac accaaggtgg acaagaaagt tgagcccaaa tcttgtgaca   360
aaactcacac atgcccaccg tgcccagcac ctgaactcct ggggggaccg tcagtcttcc   420
tcttcccccc aaaacccaag gacaccctca tgatctcccg gacccctgag gtcacatgcg   480
tggtggtgga cgtgagccac gaagaccctg aggtcaagtt caactggtac gtggacggcg   540
tggaggtgca taatgccaag                                              560

SEQ ID NO: 61          moltype = DNA   length = 557
FEATURE                Location/Qualifiers
misc_feature           1..557
                       note = Human IgG1 heavy chain constant region gBLOCK#2
                       sequence
source                 1..557
                       mol_type = other DNA
                       organism = synthetic construct
SEQUENCE: 61
tacgtggacg gcgtggaggt gcataatgcc aagacaaagc cgcgggagga gcagtacaac    60
agcacgtacc gtgtggtcag cgtcctcacc gtcctgcacc aggactggct gaatggcaag   120
gagtacaagt gcaaggtctc caacaaagcc ctcccagccc ccatcgagaa aaccatctcc   180
aaagccaaag ggcagccccg agaaccacag gtgtacaccc tgcccccatc ccgggaggag   240
atgaccaaga accaggtcag cctgacctgc ctggtcaaag gcttctatcc cagcgacatc   300
gccgtggagt gggagagcaa tgggcagccg gagaacaact acaagaccac gcctcccgtg   360
ctggactccg acggctcctt cttcctctac agcaagctca ccgtggacaa gagcaggtgg   420
cagcagggga acgtcttctc atgctccgtg atgcatgagg ctctgcacaa ccactacacg   480
cagaagagcc tctccctgtc tccgggtaaa tgataagttt aaacccgctg atcagcctcg   540
actgtgcctt ctagttg                                                 557

SEQ ID NO: 62          moltype = DNA   length = 31
FEATURE                Location/Qualifiers
misc_feature           1..31
                       note = E6 heavy chain variable region overlapping sequence
source                 1..31
                       mol_type = other DNA
                       organism = synthetic construct
SEQUENCE: 62
atggcatgga ttattggggc cagggcaccc t                                  31

SEQ ID NO: 63          moltype = DNA   length = 33
FEATURE                Location/Qualifiers
misc_feature           1..33
                       note = IgG1 heavy chain constant region overlapping region
                       sequence
source                 1..33
                       mol_type = other DNA
                       organism = synthetic construct
SEQUENCE: 63
tacgtggacg gcgtggaggt gcataatgcc aag                                33

SEQ ID NO: 64          moltype = DNA   length = 33
FEATURE                Location/Qualifiers
misc_feature           1..33
                       note = pCDNA3.1 V5 and pSECTag2 overlapping sequence
source                 1..33
                       mol_type = other DNA
                       organism = synthetic construct
SEQUENCE: 64
ccgctgatca gcctcgactg tgccttctag ttg                                33

SEQ ID NO: 65          moltype = DNA   length = 318
FEATURE                Location/Qualifiers
misc_feature           1..318
                       note = Mouse E6 Light Chain variable region sequence
source                 1..318
                       mol_type = other DNA
                       organism = synthetic construct
SEQUENCE: 65
caaattgttc tcacccagtc tccagcaatc atgtctgcat ctccagggga ggaggtcacc    60
ctaacctgca gtgccacctc aagtgtaagt tacatacact ggttccagca gaggccaggc   120
acttctccca aactctggat ttatagcaca tccaacctgg cttctggagt ccctgttcgc   180
ttcagtggca gtggatatgg gacctcttac tctctcacaa tcagccgaat ggaggctgaa   240
gatgctgcca cttattactg ccagcaaagg agtagttccc cattcacgtt cggctcgggg   300
acaaagttgg aaataaaa                                                318

SEQ ID NO: 66          moltype = AA    length = 106
```

```
FEATURE              Location/Qualifiers
REGION               1..106
                     note = Mouse E6 Light Chain variable region sequence
source               1..106
                     mol_type = protein
                     organism = synthetic construct
SEQUENCE: 66
QIVLTQSPAI MSASPGEEVT LTCSATSSVS YIHWFQQRPG TSPKLWIYST SNLASGVPVR     60
FSGSGYGTSY SLTISRMEAE DAATYYCQQR SSSPFTFGSG TKLEIK                  106

SEQ ID NO: 67        moltype = DNA  length = 69
FEATURE              Location/Qualifiers
misc_feature         1..69
                     note = Mouse E6 light chain variable framework region 1
                     (FWR1) sequence
source               1..69
                     mol_type = other DNA
                     organism = synthetic construct
SEQUENCE: 67
caaattgttc tcacccagtc tccagcaatc atgtctgcat ctccagggga ggaggtcacc     60
ctaacctgc                                                            69

SEQ ID NO: 68        moltype = AA  length = 23
FEATURE              Location/Qualifiers
REGION               1..23
                     note = Mouse E6 light chain variable framework region 1
                     (FWR1) sequence
source               1..23
                     mol_type = protein
                     organism = synthetic construct
SEQUENCE: 68
QIVLTQSPAI MSASPGEEVT LTC                                            23

SEQ ID NO: 69        moltype = DNA  length = 30
FEATURE              Location/Qualifiers
misc_feature         1..30
                     note = Mouse E6 light chain variable complementarity
                     determining regions1 (CDR1) sequence
source               1..30
                     mol_type = other DNA
                     organism = synthetic construct
SEQUENCE: 69
agtgccacct caagtgtaag ttacatacac                                     30

SEQ ID NO: 70        moltype = AA  length = 10
FEATURE              Location/Qualifiers
REGION               1..10
                     note = Mouse E6 light chain variable complementarity
                     determining regions1 (CDR1) sequence
source               1..10
                     mol_type = protein
                     organism = synthetic construct
SEQUENCE: 70
SATSSVSYIH                                                           10

SEQ ID NO: 71        moltype = DNA  length = 45
FEATURE              Location/Qualifiers
misc_feature         1..45
                     note = Mouse E6 light chain variable framework region 2
                     (FWR2) sequence
source               1..45
                     mol_type = other DNA
                     organism = synthetic construct
SEQUENCE: 71
tggttccagc agaggccagg cacttctccc aaactctgga tttat                    45

SEQ ID NO: 72        moltype = AA  length = 15
FEATURE              Location/Qualifiers
REGION               1..15
                     note = Mouse E6 light chain variable framework region 2
                     (FWR2) sequence
source               1..15
                     mol_type = protein
                     organism = synthetic construct
SEQUENCE: 72
WFQQRPGTSP KLWIY                                                     15

SEQ ID NO: 73        moltype = DNA  length = 21
FEATURE              Location/Qualifiers
```

```
misc_feature            1..21
                        note = Mouse E6 light chain variable complementarity
                         determining regions2 (CDR2) sequence
source                  1..21
                        mol_type = other DNA
                        organism = synthetic construct
SEQUENCE: 73
agcacatcca acctggcttc t                                             21

SEQ ID NO: 74           moltype = AA  length = 7
FEATURE                 Location/Qualifiers
REGION                  1..7
                        note = Mouse E6 light chain variable complementarity
                         determining regions2 (CDR2) sequence
source                  1..7
                        mol_type = protein
                        organism = synthetic construct
SEQUENCE: 74
STSNLAS                                                              7

SEQ ID NO: 75           moltype = DNA  length = 96
FEATURE                 Location/Qualifiers
misc_feature            1..96
                        note = Mouse E6 light chain variable framework region 3
                         (FWR3) sequence
source                  1..96
                        mol_type = other DNA
                        organism = synthetic construct
SEQUENCE: 75
ggagtccctg ttcgcttcag tggcagtgga tatgggacct cttactctct cacaatcagc   60
cgaatggagg ctgaagatgc tgccacttat tactgc                             96

SEQ ID NO: 76           moltype = AA  length = 32
FEATURE                 Location/Qualifiers
REGION                  1..32
                        note = Mouse E6 light chain variable framework region 3
                         (FWR3) sequence
source                  1..32
                        mol_type = protein
                        organism = synthetic construct
SEQUENCE: 76
GVPVRFSGSG YGTSYSLTIS RMEAEDAATY YC                                 32

SEQ ID NO: 77           moltype = DNA  length = 27
FEATURE                 Location/Qualifiers
misc_feature            1..27
                        note = Mouse E6 light chain variable complementarity
                         determining regions3 (CDR3) sequence
source                  1..27
                        mol_type = other DNA
                        organism = synthetic construct
SEQUENCE: 77
cagcaaagga gtagttcccc attcacg                                       27

SEQ ID NO: 78           moltype = AA  length = 9
FEATURE                 Location/Qualifiers
REGION                  1..9
                        note = Mouse E6 light chain variable complementarity
                         determining regions3 (CDR3) sequence
source                  1..9
                        mol_type = protein
                        organism = synthetic construct
SEQUENCE: 78
QQRSSSPFT                                                            9

SEQ ID NO: 79           moltype = DNA  length = 287
FEATURE                 Location/Qualifiers
misc_feature            1..287
                        note = IGKV3-11*02 light chain variable region sequence
source                  1..287
                        mol_type = other DNA
                        organism = synthetic construct
SEQUENCE: 79
gaaattgtgt tgacacagtc tccagccacc ctgtctttgt ctccagggga aagagccacc   60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggagagac ttcactctca ccatcagcag cctagagcct  240
gaagattttg cagtttatta ctgtcagcag cgtagcaact ggcctcc                287
```

```
SEQ ID NO: 80              moltype = AA  length = 96
FEATURE                    Location/Qualifiers
REGION                     1..96
                           note = IGKV3-11*02 light chain variable region sequence
source                     1..96
                           mol_type = protein
                           organism = synthetic construct
SEQUENCE: 80
EIVLTQSPAT LSLSPGERAT LSCRASQSVS SYLAWYQQKP GQAPRLLIYD ASNRATGIPA     60
RFSGSGSGRD FTLTISSLEP EDFAVYYCQQ RSNWPP                               96

SEQ ID NO: 81              moltype = DNA  length = 69
FEATURE                    Location/Qualifiers
misc_feature               1..69
                           note = IGKV3-11*02 light chain variable framework region 1
                           (FWR1) acidsequence
source                     1..69
                           mol_type = other DNA
                           organism = synthetic construct
SEQUENCE: 81
gaaattgtgt tgacacagtc tccagccacc ctgtctttgt ctccagggga aagagccacc     60
ctctcctgc                                                             69

SEQ ID NO: 82              moltype = AA  length = 23
FEATURE                    Location/Qualifiers
REGION                     1..23
                           note = IGKV3-11*02 light chain variable framework region 1
                           (FWR1) acidsequence
source                     1..23
                           mol_type = protein
                           organism = synthetic construct
SEQUENCE: 82
EIVLTQSPAT LSLSPGERAT LSC                                             23

SEQ ID NO: 83              moltype = DNA  length = 33
FEATURE                    Location/Qualifiers
misc_feature               1..33
                           note = IGKV3-11*02 light chain variable complementarity
                           determiningregions 1 (CDR1) sequence
source                     1..33
                           mol_type = other DNA
                           organism = synthetic construct
SEQUENCE: 83
agggccagtc agagtgttag cagctactta gcc                                  33

SEQ ID NO: 84              moltype = AA  length = 11
FEATURE                    Location/Qualifiers
REGION                     1..11
                           note = IGKV3-11*02 light chain variable complementarity
                           determiningregions 1 (CDR1) sequence
source                     1..11
                           mol_type = protein
                           organism = synthetic construct
SEQUENCE: 84
RASQSVSSYL A                                                          11

SEQ ID NO: 85              moltype = DNA  length = 45
FEATURE                    Location/Qualifiers
misc_feature               1..45
                           note = IGKV3-11*02 light chain variable framework region 2
                           (FWR2)sequence
source                     1..45
                           mol_type = other DNA
                           organism = synthetic construct
SEQUENCE: 85
tggtaccaac agaaacctgg ccaggctccc aggctcctca tctat                     45

SEQ ID NO: 86              moltype = AA  length = 15
FEATURE                    Location/Qualifiers
REGION                     1..15
                           note = IGKV3-11*02 light chain variable framework region 2
                           (FWR2)sequence
source                     1..15
                           mol_type = protein
                           organism = synthetic construct
SEQUENCE: 86
WYQQKPGQAP RLLIY                                                      15

SEQ ID NO: 87              moltype = DNA  length = 21
```

```
FEATURE                 Location/Qualifiers
misc_feature            1..21
                        note = IGKV3-11*02 light chain variable complementarity
                          determiningregions 2 (CDR2) sequence
source                  1..21
                        mol_type = other DNA
                        organism = synthetic construct
SEQUENCE: 87
gatgcatcca acagggccac t                                               21

SEQ ID NO: 88           moltype = AA  length = 7
FEATURE                 Location/Qualifiers
REGION                  1..7
                        note = IGKV3-11*02 light chain variable complementarity
                          determiningregions 2 (CDR2) sequence
source                  1..7
                        mol_type = protein
                        organism = synthetic construct
SEQUENCE: 88
DASNRAT                                                                7

SEQ ID NO: 89           moltype = DNA  length = 96
FEATURE                 Location/Qualifiers
misc_feature            1..96
                        note = IGKV3-11*02 light chain variable framework region 3
                          (FWR3)sequence
source                  1..96
                        mol_type = other DNA
                        organism = synthetic construct
SEQUENCE: 89
ggcatcccag ccaggttcag tggcagtggg tctgggagag acttcactct caccatcagc     60
agcctagagc ctgaagattt tgcagtttat tactgt                               96

SEQ ID NO: 90           moltype = AA  length = 32
FEATURE                 Location/Qualifiers
REGION                  1..32
                        note = IGKV3-11*02 light chain variable framework region 3
                          (FWR3)sequence
source                  1..32
                        mol_type = protein
                        organism = synthetic construct
SEQUENCE: 90
GIPARFSGSG SGTDFTLTIS SLEPEDFAVY YC                                   32

SEQ ID NO: 91           moltype = DNA  length = 23
FEATURE                 Location/Qualifiers
misc_feature            1..23
                        note = IGKV3-11*02 light chain variable complementarity
                          determiningregions3 (CDR3) sequence
source                  1..23
                        mol_type = other DNA
                        organism = synthetic construct
SEQUENCE: 91
cagcagcgta gcaactggcc tcc                                             23

SEQ ID NO: 92           moltype = AA  length = 8
FEATURE                 Location/Qualifiers
REGION                  1..8
                        note = IGKV3-11*02 light chain variable complementarity
                          determiningregions3 (CDR3) sequence
source                  1..8
                        mol_type = protein
                        organism = synthetic construct
SEQUENCE: 92
QQRSNWPP                                                               8

SEQ ID NO: 93           moltype = DNA  length = 318
FEATURE                 Location/Qualifiers
misc_feature            1..318
                        note = Humanized E6 light chain variable region sequence
source                  1..318
                        mol_type = other DNA
                        organism = synthetic construct
SEQUENCE: 93
gaaattgtgt tgacacagtc tccagccacc ctgtctttgt ctccagggga aagagccacc     60
ctcacctgca gcgccaccag cagtgttagc tacatccact ggtaccaaca gaggcctggc    120
cagagcccca ggctcctcat ctatagcacc tccaacctgg ccagcggcat cccagccagg    180
ttcagtggca gtgggtctgg gagcgactac actctcacca tcagcagcct agagcctgaa    240
gattttgcag tttattactg tcagcagcgt agcaactccc ctttcacctt tggcagcggc    300
```

```
accaaagtgg aaattaaa                                                   318

SEQ ID NO: 94           moltype = AA   length = 106
FEATURE                 Location/Qualifiers
REGION                  1..106
                        note = Humanized E6 light chain variable region sequence
source                  1..106
                        mol_type = protein
                        organism = synthetic construct
SEQUENCE: 94
EIVLTQSPAT LSLSPGERAT LTCSATSSVS YIHWYQQRPG QSPRLLIYST SNLASGIPAR    60
FSGSGSGSDY TLTISSLEPE DFAVYYCQQR SSSPFTFGSG TKVEIK                  106

SEQ ID NO: 95           moltype = DNA   length = 69
FEATURE                 Location/Qualifiers
misc_feature            1..69
                        note = Humanized E6 light chain variable framework region 1
                        (FWR1) acidsequence
source                  1..69
                        mol_type = other DNA
                        organism = synthetic construct
SEQUENCE: 95
gaaattgtgt tgacacagtc tccagccacc ctgtctttgt ctccagggga aagagccacc    60
ctcacctgc                                                            69

SEQ ID NO: 96           moltype = AA   length = 23
FEATURE                 Location/Qualifiers
REGION                  1..23
                        note = Humanized E6 light chain variable framework region 1
                        (FWR1) acidsequence
source                  1..23
                        mol_type = protein
                        organism = synthetic construct
SEQUENCE: 96
EIVLTQSPAT LSLSPGERAT LTC                                             23

SEQ ID NO: 97           moltype = DNA   length = 30
FEATURE                 Location/Qualifiers
misc_feature            1..30
                        note = Humanized E6 light chain variable complementarity
                        determiningregions 1 (CDR1) sequence
source                  1..30
                        mol_type = other DNA
                        organism = synthetic construct
SEQUENCE: 97
agcgccacca gcagtgttag ctacatccac                                      30

SEQ ID NO: 98           moltype = AA   length = 10
FEATURE                 Location/Qualifiers
REGION                  1..10
                        note = Humanized E6 light chain variable complementarity
                        determiningregions 1 (CDR1) sequence
source                  1..10
                        mol_type = protein
                        organism = synthetic construct
SEQUENCE: 98
SATSSVSYIH                                                            10

SEQ ID NO: 99           moltype = DNA   length = 45
FEATURE                 Location/Qualifiers
misc_feature            1..45
                        note = Humanized E6 heavy light variable framework region 2
                        (FWR2) acidsequence
source                  1..45
                        mol_type = other DNA
                        organism = synthetic construct
SEQUENCE: 99
tggtaccaac agaggcctgg ccagagcccc aggctcctca tctat                     45

SEQ ID NO: 100          moltype = AA   length = 15
FEATURE                 Location/Qualifiers
REGION                  1..15
                        note = Humanized E6 heavy light variable framework region 2
                        (FWR2) acidsequence
source                  1..15
                        mol_type = protein
                        organism = synthetic construct
SEQUENCE: 100
WYQQRPGQSP RLLIY                                                      15
```

| SEQ ID NO: 101 | moltype = DNA  length = 21 |
|---|---|
| FEATURE | Location/Qualifiers |
| misc_feature | 1..21 |
| | note = Humanized E6 light chain variable complementarity determiningregions 2 (CDR2) sequence |
| source | 1..21 |
| | mol_type = other DNA |
| | organism = synthetic construct |

SEQUENCE: 101
agcacctcca acctggccag c                                              21

| SEQ ID NO: 102 | moltype = AA  length = 7 |
|---|---|
| FEATURE | Location/Qualifiers |
| REGION | 1..7 |
| | note = Humanized E6 light chain variable complementarity determiningregions 2 (CDR2) sequence |
| source | 1..7 |
| | mol_type = protein |
| | organism = synthetic construct |

SEQUENCE: 102
STSNLAS                                                              7

| SEQ ID NO: 103 | moltype = DNA  length = 96 |
|---|---|
| FEATURE | Location/Qualifiers |
| misc_feature | 1..96 |
| | note = Humanized E6 light chain variable framework region 3 (FWR3) acidsequence |
| source | 1..96 |
| | mol_type = other DNA |
| | organism = synthetic construct |

SEQUENCE: 103
ggcatcccag ccaggttcag tggcagtggg tctgggagcg actacactct caccatcagc    60
agcctagagc ctgaagattt tgcagtttat tactgt                              96

| SEQ ID NO: 104 | moltype = AA  length = 32 |
|---|---|
| FEATURE | Location/Qualifiers |
| REGION | 1..32 |
| | note = Humanized E6 light chain variable framework region 3 (FWR3) acidsequence |
| source | 1..32 |
| | mol_type = protein |
| | organism = synthetic construct |

SEQUENCE: 104
GIPARFSGSG SGSDYTLTIS SLEPEDFAVY YC                                   32

| SEQ ID NO: 105 | moltype = DNA  length = 27 |
|---|---|
| FEATURE | Location/Qualifiers |
| misc_feature | 1..27 |
| | note = Humanized E6 light chain variable complementarity determiningregions 3 (CDR3) sequence |
| source | 1..27 |
| | mol_type = other DNA |
| | organism = synthetic construct |

SEQUENCE: 105
cagcagcgta gcagctcccc tttcacc                                        27

| SEQ ID NO: 106 | moltype = AA  length = 9 |
|---|---|
| FEATURE | Location/Qualifiers |
| REGION | 1..9 |
| | note = Humanized E6 light chain variable complementarity determiningregions 3 (CDR3) sequence |
| source | 1..9 |
| | mol_type = protein |
| | organism = synthetic construct |

SEQUENCE: 106
QQRSSSPFT                                                            9

| SEQ ID NO: 107 | moltype = DNA  length = 740 |
|---|---|
| FEATURE | Location/Qualifiers |
| misc_feature | 1..740 |
| | note = Humanized E6 Kappa light chain synthesized by Genescript |
| source | 1..740 |
| | mol_type = other DNA |
| | organism = synthetic construct |

SEQUENCE: 107
gaattctaag cttgggccac catggaagcc cagcgcagc ttctcttcct cctgctactc      60
tggctcccag ataccactgg agaaattgtg ttgacacagt ctccagccac cctgtctttg    120

```
tctccagggg aaagagccac cctcacctgc agcgccacca gcagtgttag ctacatccac    180
tggtaccaac agaggcctgg ccagagcccc aggctcctca tctatagcac ctccaacctg    240
gccagcggca tcccagccag gttcagtggc agtgggtctg ggagcgacta cactctcacc    300
atcagcagcc tagagcctga agattttgca gtttattact gtcagcagcg tagcagctcc    360
cctttcacct ttggcagcgg caccaaagtg gaaattaaaa gacggtggc tgcaccatct    420
gtcttcatct tcccgccatc tgatgagcag ttgaaatctg gaactgcctc tgttgtgtgt    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tagtaagttt aaactctaga                                                740

SEQ ID NO: 108         moltype = AA  length = 243
FEATURE                Location/Qualifiers
REGION                 1..243
                       note = Humanized E6 Kappa light chain synthesized by
                       Genescript
SITE                   243
                       note = misc_feature - Xaa can be any naturally occurring
                       amino acid
source                 1..243
                       mol_type = protein
                       organism = synthetic construct
SEQUENCE: 108
EFAWATMEAP AQLLFLLLLW LPDTTGEIVL TQSPATLSLS PGERATLTCS ATSSVSYIHW    60
YQQRPGQSPR LLIYSTSNLA SGIPARFSGS GSGSDYTLTI SSLEPEDFAV YYCQQRSSSP   120
FTFGSGTKVE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGECV   240
TLX                                                                 243

SEQ ID NO: 109         moltype = DNA  length = 324
FEATURE                Location/Qualifiers
misc_feature           1..324
                       note = Human Kappa light chain constant region sequence
source                 1..324
                       mol_type = other DNA
                       organism = synthetic construct
SEQUENCE: 109
aggacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                          324

SEQ ID NO: 110         moltype = AA  length = 107
FEATURE                Location/Qualifiers
REGION                 1..107
                       note = Human Kappa light chain constant region sequence
source                 1..107
                       mol_type = protein
                       organism = synthetic construct
SEQUENCE: 110
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 111         moltype = DNA  length = 642
FEATURE                Location/Qualifiers
misc_feature           1..642
                       note = Humanized E6 lambda light chain sequence
source                 1..642
                       mol_type = other DNA
                       organism = synthetic construct
SEQUENCE: 111
gaaattgtgt tgacacagtc tccagccacc ctgtctttgt ctccagggga aagagccacc    60
ctcacctgca gcgccaccag cagtgttagc tacatccact ggtaccaaca gaggcctggc   120
cagagcccca ggctcctcat ctatagcacc tccaacctgg ccagcggcat cccagccagg   180
ttcagtggca gtgggtctgg gagcgactac actctcacca tcagcagcct agagcctgaa   240
gattttgcag tttattactg tcagcagcgt agcagctccc ctttcacctt tggcagcggc   300
accaaagtgg aaattaaagg tcagcccaag gctgccccct cggtcactct gttcccgccc   360
tcctctgagg agcttcaagc caacaaggcc acactggtgt gtctcataag tgacttctac   420
ccgggagccg tgacagtggc ctggaaggca gatagcagcc ccgtcaaggc gggagtggag   480
accaccacac cctccaaaca aagcaacaac aagtacgcgg ccagcagcta tctgagcctg   540
acgcctgagc agtggaagtc cacacagagc tacgctgcag aggtcacgca tgaagggagc   600
accgtggaga gacagtggc cctacagaa tgttcatagt aa                        642

SEQ ID NO: 112         moltype = AA  length = 212
FEATURE                Location/Qualifiers
REGION                 1..212
```

|  |  |  |
|---|---|---|
|  | note = Humanized E6 lambda light chain sequence | |
| source | 1..212 | |
|  | mol_type = protein | |
|  | organism = synthetic construct | |

SEQUENCE: 112
```
EIVLTQSPAT LSLSPGERAT LTCSATSSVS YIHWYQQRPG QSPRLLIYST SNLASGIPAR    60
FSGSGSGSDY TLTISSLEPE DFAVYYCQQR SSSPFTFGSG TKVEIKGQPK AAPSVTLFPP   120
SSEELQANKA TLVCLISDFY PGAVTVAWKA DSSPVKAGVE TTTPSKQSNN KYAASSYLSL   180
TPEQWKSHRS YSCQVTHEGS TVEKTVAPTE CS                                 212
```

|  |  |  |
|---|---|---|
| SEQ ID NO: 113 | moltype = DNA   length = 324 | |
| FEATURE | Location/Qualifiers | |
| misc_feature | 1..324 | |
|  | note = Humanized lambda light chain constant region sequence | |
| source | 1..324 | |
|  | mol_type = other DNA | |
|  | organism = synthetic construct | |

SEQUENCE: 113
```
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac ccctccaaa    180
caaagcaaca caagtacgc ggccagcagc tatctgagcc tgacgcctga gcagtggaag   240
tcccacagaa gctacagctg ccaggtcacg catgaaggga gcaccgtgga gaagacagtg   300
gcccctacag aatgttcata gtaa                                          324
```

|  |  |  |
|---|---|---|
| SEQ ID NO: 114 | moltype = AA   length = 106 | |
| FEATURE | Location/Qualifiers | |
| REGION | 1..106 | |
|  | note = Humanized lambda light chain constant region sequence | |
| source | 1..106 | |
|  | mol_type = protein | |
|  | organism = synthetic construct | |

SEQUENCE: 114
```
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106
```

|  |  |  |
|---|---|---|
| SEQ ID NO: 115 | moltype = DNA   length = 614 | |
| FEATURE | Location/Qualifiers | |
| misc_feature | 1..614 | |
|  | note = Human lambda light chain constant region gBLOCK#3 sequence | |
| source | 1..614 | |
|  | mol_type = other DNA | |
|  | organism = synthetic construct | |

SEQUENCE: 115
```
agcgccacca gcagtgttag ctacatccac tggtaccaac agaggcctgg ccagagcccc    60
aggctcctca tctatagcac ctccaacctg gccagccagca tcccagccag gttcagtggc   120
agtgggtctg ggagcgacta cactctcacc atcagcagcc tagagcctga agattttgca   180
gtttattact gtcagcagcg tagcagctcc ccttttcacct ttggcagcgg caccaaagtg   240
gaaattaaag gtcagcccaa ggctgccccc tcggtcactc tgttcccgcc ctcctctgag   300
gagcttcaag ccaacaaggc cacactggtg tgtctcataa gtgacttcta cccgggagcc   360
gtgacagtgg cctggaaggc agatagcagc cccgtcaagg cgggagtgga gaccaccaca   420
ccctccaaac aaagcaacaa caagtacgcg gccagcagct atctgagcct gacgcctgag   480
cagtggaagt cccacagaag ctacagctgc caggtcacgc atgaagggag caccgtggag   540
aagacagtgg cccctacaga atgttcatag taagtttaaa cccgctgatc agcctcgact   600
gtgccttcta gttg                                                    614
```

|  |  |  |
|---|---|---|
| SEQ ID NO: 116 | moltype = DNA   length = 31 | |
| FEATURE | Location/Qualifiers | |
| misc_feature | 1..31 | |
|  | note = E6 light chain variable region overlapping sequence | |
| source | 1..31 | |
|  | mol_type = other DNA | |
|  | organism = synthetic construct | |

SEQUENCE: 116
```
agcgccacca gcagtgttag ctacatccac t                                   31
```

|  |  |  |
|---|---|---|
| SEQ ID NO: 117 | moltype = DNA   length = 33 | |
| FEATURE | Location/Qualifiers | |
| misc_feature | 1..33 | |
|  | note = pCDNA3.1 V5 and pSECTag2 overlapping sequence | |
| source | 1..33 | |
|  | mol_type = other DNA | |
|  | organism = synthetic construct | |

SEQUENCE: 117
```
ccgctgatca gcctcgactg tgccttctag ttg                                 33
```

|  |  |  |
|---|---|---|
| SEQ ID NO: 118 | moltype = DNA   length = 390 | |
| FEATURE | Location/Qualifiers | |

| | |
|---|---|
| misc_feature | 1..390<br>note = Mouse C2 heavy chain variable region sequence |
| source | 1..390<br>mol_type = other DNA<br>organism = synthetic construct |

SEQUENCE: 118

```
gaggtccagc tggaggagtc agggggaggc ttagtgaagc ctggagggtc cctgaaactc   60
tcctgtgcag cctctggatt cactttcagt ggctatgcca tgtcttgggt tcgccagact  120
ccggagaaga ggctggagtg ggtcgcaacc attagtagtg gtggtactta tatctactat  180
ccagacagtg tgaagggcg attcaccatc tccagagaca atgccaagaa caccctgtac  240
ctgcaaatga gcagtctgag gtctgaggac acggccatgt attactgtgc aagacttggg  300
ggggataatt actacgaata cttcgatgtc tggggcgcag ggaccacggt caccgtctcc  360
tccgccaaaa cgacaccccc atctgtctat                                   390
```

| | |
|---|---|
| SEQ ID NO: 119 | moltype = AA  length = 130 |
| FEATURE | Location/Qualifiers |
| REGION | 1..130<br>note = Mouse C2 heavy chain variable region sequence |
| source | 1..130<br>mol_type = protein<br>organism = synthetic construct |

SEQUENCE: 119

```
EVQLEESGGG LVKPGGSLKL SCAASGFTFS GYAMSWVRQT PEKRLEWVAT ISSGGTYIYY   60
PDSVKGRFTI SRDNAKNTLY LQMSSLRSED TAMYYCARLG GDNYYEYFDV WGAGTTVTVS  120
SAKTTPPSVY                                                         130
```

| | |
|---|---|
| SEQ ID NO: 120 | moltype = DNA  length = 90 |
| FEATURE | Location/Qualifiers |
| misc_feature | 1..90<br>note = Mouse C2 heavy chain variable framework region 1<br>(FWR1) sequence |
| source | 1..90<br>mol_type = other DNA<br>organism = synthetic construct |

SEQUENCE: 120

```
gaggtccagc tggaggagtc agggggaggc ttagtgaagc ctggagggtc cctgaaactc   60
tcctgtgcag cctctggatt cactttcagt                                    90
```

| | |
|---|---|
| SEQ ID NO: 121 | moltype = AA  length = 30 |
| FEATURE | Location/Qualifiers |
| REGION | 1..30<br>note = Mouse C2 heavy chain variable framework region 1<br>(FWR1) sequence |
| source | 1..30<br>mol_type = protein<br>organism = synthetic construct |

SEQUENCE: 121

```
EVQLEESGGG LVKPGGSLKL SCAASGFTFS                                    30
```

| | |
|---|---|
| SEQ ID NO: 122 | moltype = DNA  length = 15 |
| FEATURE | Location/Qualifiers |
| misc_feature | 1..15<br>note = Mouse C2 heavy chain variable complementarity<br>determining regions1 (CDR1) sequence |
| source | 1..15<br>mol_type = other DNA<br>organism = synthetic construct |

SEQUENCE: 122

```
ggctatgcca tgtct                                                    15
```

| | |
|---|---|
| SEQ ID NO: 123 | moltype = AA  length = 5 |
| FEATURE | Location/Qualifiers |
| REGION | 1..5<br>note = Mouse C2 heavy chain variable complementarity<br>determining regions1 (CDR1) sequence |
| source | 1..5<br>mol_type = protein<br>organism = synthetic construct |

SEQUENCE: 123

```
GYAMS                                                               5
```

| | |
|---|---|
| SEQ ID NO: 124 | moltype = DNA  length = 42 |
| FEATURE | Location/Qualifiers |
| misc_feature | 1..42<br>note = Mouse C2 heavy chain variable framework region 2<br>(FWR2) sequence |
| source | 1..42<br>mol_type = other DNA<br>organism = synthetic construct |

```
SEQUENCE: 124
tgggttcgcc agactccgga gaagaggctg gagtgggtcg ca                    42

SEQ ID NO: 125          moltype = AA   length = 14
FEATURE                 Location/Qualifiers
REGION                  1..14
                        note = Mouse C2 heavy chain variable framework region 2
                         (FWR2) sequence
source                  1..14
                        mol_type = protein
                        organism = synthetic construct
SEQUENCE: 125
WVRQTPEKRL EWVA                                                   14

SEQ ID NO: 126          moltype = DNA   length = 51
FEATURE                 Location/Qualifiers
misc_feature            1..51
                        note = Mouse C2 heavy chain variable complementarity
                         determining regions2 (CDR2) sequence
source                  1..51
                        mol_type = other DNA
                        organism = synthetic construct
SEQUENCE: 126
accattagta gtggtggtac ttatatctac tatccagaca gtgtgaaggg g          51

SEQ ID NO: 127          moltype = AA   length = 17
FEATURE                 Location/Qualifiers
REGION                  1..17
                        note = Mouse C2 heavy chain variable complementarity
                         determining regions2 (CDR2) sequence
source                  1..17
                        mol_type = protein
                        organism = synthetic construct
SEQUENCE: 127
TISSGGTYIY YPDSVKG                                                17

SEQ ID NO: 128          moltype = DNA   length = 96
FEATURE                 Location/Qualifiers
misc_feature            1..96
                        note = Mouse C2 heavy chain variable framework region 3
                         (FWR3) sequence
source                  1..96
                        mol_type = other DNA
                        organism = synthetic construct
SEQUENCE: 128
cgattcacca tctccagaga caatgccaag aacaccctgt acctgcaaat gagcagtctg 60
aggtctgagg acacggccat gtattactgt gcaaga                          96

SEQ ID NO: 129          moltype = AA   length = 32
FEATURE                 Location/Qualifiers
REGION                  1..32
                        note = Mouse C2 heavy chain variable framework region 3
                         (FWR3) sequence
source                  1..32
                        mol_type = protein
                        organism = synthetic construct
SEQUENCE: 129
RFTISRDNAK NTLYLQMSSL RSEDTAMYYC AR                               32

SEQ ID NO: 130          moltype = DNA   length = 36
FEATURE                 Location/Qualifiers
misc_feature            1..36
                        note = Mouse C2 heavy chain variable complementarity
                         determining regions3 (CDR3) sequence
source                  1..36
                        mol_type = other DNA
                        organism = synthetic construct
SEQUENCE: 130
cttgggggggg ataattacta cgaatacttc gatgtc                          36

SEQ ID NO: 131          moltype = AA   length = 12
FEATURE                 Location/Qualifiers
REGION                  1..12
                        note = Mouse C2 heavy chain variable complementarity
                         determining regions3 (CDR3) sequence
source                  1..12
                        mol_type = protein
                        organism = synthetic construct
SEQUENCE: 131
```

LGGDNYYEYF DV                                                                12

SEQ ID NO: 132          moltype = DNA   length = 294
FEATURE                 Location/Qualifiers
misc_feature            1..294
                        note = IGHV3-21*04 heavy chain variable region sequence
source                  1..294
                        mol_type = other DNA
                        organism = synthetic construct
SEQUENCE: 132
gaggtgcagc tggtgagtc tgggggaggc ctggtcaagc ctgggggtc cctgagactc    60
tcctgtgcag cctctggatt caccttcagt agctatagca tgaactgggt ccgccaggct  120
ccagggaagg ggctggagtg ggtctcatcc attagtagta gtagtagtta catatactac  180
gcagactcag tgaagggccg attcaccatc tccagagaca cgccaagaa ctcactgtat   240
ctgcaaatga acagcctgag agccgaggac acggccgtgt attactgtgc gaga         294

SEQ ID NO: 133          moltype = AA    length = 98
FEATURE                 Location/Qualifiers
REGION                  1..98
                        note = IGHV3-21*04 heavy chain variable region sequence
source                  1..98
                        mol_type = protein
                        organism = synthetic construct
SEQUENCE: 133
EVQLVESGGG LVKPGGSLRL SCAASGFTFS SYSMNWVRQA PGKGLEWVSS ISSSSSYIYY   60
ADSVKGRFTI SRDNAKNSLY LQMNSLRAED TAVYYCAR                           98

SEQ ID NO: 134          moltype = DNA   length = 90
FEATURE                 Location/Qualifiers
misc_feature            1..90
                        note = IGHV3-21*04 heavy chain variable framework region 1
                        (FWR1) sequence
source                  1..90
                        mol_type = other DNA
                        organism = synthetic construct
SEQUENCE: 134
gaggtgcagc tggtggagtc tgggggaggc ctggtcaagc ctgggggtc cctgagactc    60
tcctgtgcag cctctggatt caccttcagt                                    90

SEQ ID NO: 135          moltype = AA    length = 30
FEATURE                 Location/Qualifiers
REGION                  1..30
                        note = IGHV3-21*04 heavy chain variable framework region 1
                        (FWR1) sequence
source                  1..30
                        mol_type = protein
                        organism = synthetic construct
SEQUENCE: 135
EVQLVESGGG LVKPGGSLRL SCAASGFTFS                                    30

SEQ ID NO: 136          moltype = DNA   length = 15
FEATURE                 Location/Qualifiers
misc_feature            1..15
                        note = IGHV3-21*04 heavy chain variable complementarity
                        determiningregions 1 (CDR1) sequence
source                  1..15
                        mol_type = other DNA
                        organism = synthetic construct
SEQUENCE: 136
agctatagca tgaac                                                    15

SEQ ID NO: 137          moltype = AA    length = 5
FEATURE                 Location/Qualifiers
REGION                  1..5
                        note = IGHV3-21*04 heavy chain variable complementarity
                        determiningregions 1 (CDR1) sequence
source                  1..5
                        mol_type = protein
                        organism = synthetic construct
SEQUENCE: 137
SYSMN                                                               5

SEQ ID NO: 138          moltype = DNA   length = 41
FEATURE                 Location/Qualifiers
misc_feature            1..41
                        note = IGHV3-21*04 heavy chain variable framework region 2
                        (FWR2) sequence
source                  1..41
                        mol_type = other DNA

|   |   |
|---|---|
| | organism = synthetic construct |
| SEQUENCE: 138 | | gggtccgcca ggctccaggg aagggggctgg agtgggtctc a 41

| SEQ ID NO: 139 | moltype = AA  length = 14 |
|---|---|
| FEATURE | Location/Qualifiers |
| REGION | 1..14 |
| | note = IGHV3-21*04 heavy chain variable framework region 2 (FWR2) sequence |
| source | 1..14 |
| | mol_type = protein |
| | organism = synthetic construct |
| SEQUENCE: 139 | |

WVRQAPGKGL EWVS 14

| SEQ ID NO: 140 | moltype = DNA  length = 51 |
|---|---|
| FEATURE | Location/Qualifiers |
| misc_feature | 1..51 |
| | note = IGHV3-21*04 heavy chain variable complementarity determiningregions 2 (CDR2) sequence |
| source | 1..51 |
| | mol_type = other DNA |
| | organism = synthetic construct |
| SEQUENCE: 140 | | tccattagta gtagtagtag ttacatatac tacgcagact cagtgaaggg c 51

| SEQ ID NO: 141 | moltype = AA  length = 17 |
|---|---|
| FEATURE | Location/Qualifiers |
| REGION | 1..17 |
| | note = IGHV3-21*04 heavy chain variable complementarity determiningregions 2 (CDR2) sequence |
| source | 1..17 |
| | mol_type = protein |
| | organism = synthetic construct |
| SEQUENCE: 141 | |

SISSSSSYIY YADSVKG 17

| SEQ ID NO: 142 | moltype = DNA  length = 96 |
|---|---|
| FEATURE | Location/Qualifiers |
| misc_feature | 1..96 |
| | note = IGHV3-21*04 heavy chain variable framework region 3 (FWR3) sequence |
| source | 1..96 |
| | mol_type = other DNA |
| | organism = synthetic construct |
| SEQUENCE: 142 | | cgattcacca tctccagaga caacgccaag aactcactgt atctgcaaat gaacagcctg 60
agagccgagg acacggccgt gtattactgt gcgaga 96

| SEQ ID NO: 143 | moltype = AA  length = 32 |
|---|---|
| FEATURE | Location/Qualifiers |
| REGION | 1..32 |
| | note = IGHV3-21*04 heavy chain variable framework region 3 (FWR3) sequence |
| source | 1..32 |
| | mol_type = protein |
| | organism = synthetic construct |
| SEQUENCE: 143 | |

RFTISRDNAK NSLYLQMNSL RAEDTAVYYC AR 32

| SEQ ID NO: 144 | moltype = DNA  length = 363 |
|---|---|
| FEATURE | Location/Qualifiers |
| misc_feature | 1..363 |
| | note = Humanized C2 heavy chain variable region sequence |
| source | 1..363 |
| | mol_type = other DNA |
| | organism = synthetic construct |
| SEQUENCE: 144 | | gaggtgcagc tggtggagtc tgggggaggc ctggtcaagc ctgggggggtc cctgagactc 60
tcctgtgcag cctctggatt cacccttcagt ggctatgcca tgagctgggt ccgccaggct 120
ccagggaagg ggctggagtg ggtctcaacc attagtagtg gcggaaccta catatactac 180
cccgactcag tgaagggccg attcaccatc tccagagaca acgccaagaa ctcactgtat 240
ctgcaaatga acagcctgag agccgaggac acggccgtgt attactgtgc gagacttggg 300
ggggataatt actacgaata cttcgatgtc tggggcaaag gaccacggt caccgtctcc 360
tcc 363

| SEQ ID NO: 145 | moltype = AA  length = 121 |
|---|---|
| FEATURE | Location/Qualifiers |
| REGION | 1..121 |

```
                              note = Humanized C2 heavy chain variable region sequence
source                        1..121
                              mol_type = protein
                              organism = synthetic construct
SEQUENCE: 145
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYFDV WGKGTTVTVS   120
S                                                                   121

SEQ ID NO: 146                moltype = DNA   length = 90
FEATURE                       Location/Qualifiers
misc_feature                  1..90
                              note = Humanized C2 heavy chain variable framework region 1
                                (FWR1) sequence
source                        1..90
                              mol_type = other DNA
                              organism = synthetic construct
SEQUENCE: 146
gaggtgcagc tggtggagtc tgggggaggc ctggtcaagc ctggggggtc cctgagactc    60
tcctgtgcag cctctggatt caccttcagt                                     90

SEQ ID NO: 147                moltype = AA    length = 30
FEATURE                       Location/Qualifiers
REGION                        1..30
                              note = Humanized C2 heavy chain variable framework region 1
                                (FWR1) sequence
source                        1..30
                              mol_type = protein
                              organism = synthetic construct
SEQUENCE: 147
EVQLVESGGG LVKPGGSLRL SCAASGFTFS                                     30

SEQ ID NO: 148                moltype = DNA   length = 15
FEATURE                       Location/Qualifiers
misc_feature                  1..15
                              note = Humanized C2 heavy chain variable complementarity
                                determiningregions 1 (CDR1) sequence
source                        1..15
                              mol_type = other DNA
                              organism = synthetic construct
SEQUENCE: 148
ggctatgcca tgagc                                                     15

SEQ ID NO: 149                moltype = AA    length = 5
FEATURE                       Location/Qualifiers
REGION                        1..5
                              note = Humanized C2 heavy chain variable complementarity
                                determiningregions 1 (CDR1) sequence
source                        1..5
                              mol_type = protein
                              organism = synthetic construct
SEQUENCE: 149
GYAMS                                                                 5

SEQ ID NO: 150                moltype = DNA   length = 43
FEATURE                       Location/Qualifiers
misc_feature                  1..43
                              note = Humanized C2 heavy chain variable framework region 2
                                (FWR2) sequence
source                        1..43
                              mol_type = other DNA
                              organism = synthetic construct
SEQUENCE: 150
tgggtccgcc aggctccagg gaagggctg gagtgggtct caa                       43

SEQ ID NO: 151                moltype = AA    length = 14
FEATURE                       Location/Qualifiers
REGION                        1..14
                              note = Humanized C2 heavy chain variable framework region 2
                                (FWR2) sequence
source                        1..14
                              mol_type = protein
                              organism = synthetic construct
SEQUENCE: 151
WVRQAPGKGL EWVS                                                      14

SEQ ID NO: 152                moltype = DNA   length = 51
FEATURE                       Location/Qualifiers
misc_feature                  1..51
```

|  | note = Humanized C2 heavy chain variable complementarity determiningregions 2 (CDR2) sequence |
|---|---|
| source | 1..51 |
|  | mol_type = other DNA |
|  | organism = synthetic construct |

SEQUENCE: 152
accattagta gtggcggaac ctacatatac taccccgact cagtgaaggg c                51

| SEQ ID NO: 153 | moltype = AA   length = 17 |
|---|---|
| FEATURE | Location/Qualifiers |
| REGION | 1..17 |
|  | note = Humanized C2 heavy chain variable complementarity determiningregions 2 (CDR2) sequence |
| source | 1..17 |
|  | mol_type = protein |
|  | organism = synthetic construct |

SEQUENCE: 153
TISSGGTYIY YPDSVKG                                                       17

| SEQ ID NO: 154 | moltype = DNA   length = 96 |
|---|---|
| FEATURE | Location/Qualifiers |
| misc_feature | 1..96 |
|  | note = Humanized C2 heavy chain variable framework region 3 (FWR3)sequence |
| source | 1..96 |
|  | mol_type = other DNA |
|  | organism = synthetic construct |

SEQUENCE: 154
cgattcacca tctccagaga caacgccaag aactcactgt atctgcaaat gaacagcctg        60
agagccgagg acacggccgt gtattactgt gcgaga                                  96

| SEQ ID NO: 155 | moltype = AA   length = 32 |
|---|---|
| FEATURE | Location/Qualifiers |
| REGION | 1..32 |
|  | note = Humanized C2 heavy chain variable framework region 3 (FWR3)sequence |
| source | 1..32 |
|  | mol_type = protein |
|  | organism = synthetic construct |

SEQUENCE: 155
RFTISRDNAK NSLYLQMNSL RAEDTAVYYC AR                                      32

| SEQ ID NO: 156 | moltype = DNA   length = 36 |
|---|---|
| FEATURE | Location/Qualifiers |
| misc_feature | 1..36 |
|  | note = Humanized C2 heavy chain variable complementarity determiningregions 3 (CDR3) sequence |
| source | 1..36 |
|  | mol_type = other DNA |
|  | organism = synthetic construct |

SEQUENCE: 156
cttggggggg ataattacta cgaatacttc gatgtc                                  36

| SEQ ID NO: 157 | moltype = AA   length = 12 |
|---|---|
| FEATURE | Location/Qualifiers |
| REGION | 1..12 |
|  | note = Humanized C2 heavy chain variable complementarity determiningregions 3 (CDR3) sequence |
| source | 1..12 |
|  | mol_type = protein |
|  | organism = synthetic construct |

SEQUENCE: 157
LGGDNYYEYF DV                                                            12

| SEQ ID NO: 158 | moltype = DNA   length = 1359 |
|---|---|
| FEATURE | Location/Qualifiers |
| misc_feature | 1..1359 |
|  | note = Humanized C2 IgG1 heavy chain sequence |
| source | 1..1359 |
|  | mol_type = other DNA |
|  | organism = synthetic construct |

SEQUENCE: 158
gaggtgcagc tggtggagtc tgggggaggc ctggtcaagc ctggggggtc cctgagactc        60
tcctgtgcag cctctggatt caccttcagt ggctatgcca tgagctgggt ccgccaggct       120
ccagggaagg ggctggagtg ggtctcaacc attagtagtg gcggaaccta catatactac       180
cccgactcag tgaagggccg attcaccatc tccagagaca acgccaagaa ctcactgtat       240
ctgcaaatga acagcctgag agccgaggac acggccgtgt attactgtgc gagacttggg       300
ggggataatt actacgaata cttcgatgtc tgggcaaagg gaccacggt caccgtctcc       360
tccgctagca ccaagggccc atcggtcttc ccctggcac cctcctccaa gagcacctct       420

```
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg acagtgccct ccagcagctt gggcaccag     600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gcccteccag cccccatcga gaaaaccatc   1020
tccaaagcca aagggcagcc ccgagaacca caggtgtaca ccctgccccc atcccgggag   1080
gagatgacca gaaccaggtc agcctgacct gcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatgataa                          1359

SEQ ID NO: 159           moltype = AA   length = 451
FEATURE                  Location/Qualifiers
REGION                   1..451
                         note = Humanized C2 IgG1 heavy chain sequence
source                   1..451
                         mol_type = protein
                         organism = synthetic construct
SEQUENCE: 159
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 160           moltype = DNA   length = 616
FEATURE                  Location/Qualifiers
misc_feature             1..616
                         note = Humanized C2 gBLOCK#4 sequence
source                   1..616
                         mol_type = other DNA
                         organism = synthetic construct
SEQUENCE: 160
actcactata gggagaccca agctggctag ttaagcttgg gccaccatgg agacagacac     60
actcctgcta tgggtactgc tgctctgggt tccaggttcc actggtgacg aggtgcagct    120
ggtggagtct gggggaggcc tggtcaagcc tgggggtcc ctgagactct cctgtgcagc     180
ctctggatte accttcagtg gctatgccat gagctgggtc cgccaggctc cagggaaggg    240
gctggagtgg gtctcaacca ttagtagtgg cggaacctac atatactacc ccgactcagt    300
gaagggccga ttcaccatct ccagagacaa cgccaagaac tcactgtatc tgcaaatgaa    360
cagcctgaga gccgaggaca cggccgtgta ttactgtgcg agacttgggg gggataatta    420
ctacgaatac ttcgatgtct ggggcaaagg gaccacggtc accgtctcct ccgctagcac    480
caagggccca tcggtcttcc ccctggcacc ctcctccaag agcacctctg ggggcacagc    540
ggccctgggc tgcctggtca aggactactt ccccgaaccg gtgacggtgt cgtggaactc    600
aggcgccctg accagc                                                    616

SEQ ID NO: 161           moltype = DNA   length = 32
FEATURE                  Location/Qualifiers
misc_feature             1..32
                         note = pCDNA3.1 V5 overlapping sequence
source                   1..32
                         mol_type = other DNA
                         organism = synthetic construct
SEQUENCE: 161
actcactata gggagaccca agctggctag tt                                   32

SEQ ID NO: 162           moltype = DNA   length = 34
FEATURE                  Location/Qualifiers
misc_feature             1..34
                         note = Human IgG1 constant region overlapping sequence
source                   1..34
                         mol_type = other DNA
                         organism = synthetic construct
SEQUENCE: 162
gacggtgtcg tggaactcag gcgccctgac cagc                                 34

SEQ ID NO: 163           moltype = DNA   length = 1347
FEATURE                  Location/Qualifiers
misc_feature             1..1347
                         note = Humanized C2 IgG2 heavy chain sequence
source                   1..1347
```

```
                            mol_type = other DNA
                            organism = synthetic construct
SEQUENCE: 163
gaggtgcagc tggtggagtc tgggggaggc ctggtcaagc ctgggggtc  cctgagactc    60
tcctgtgcag cctctggatt caccttcagt ggctatgcca tgagctgggt ccgccaggct   120
ccagggaagg ggctggagtg ggtctcaacc attagtagtg gcggaaccta catatactac   180
cccgactcag tgaagggccg attcaccatc tccagagaca acgccaagaa ctcactgtat   240
ctgcaaatga acagcctgag agccgaggac acggccgtgt attactgtgc gagacttggg   300
ggggataatt actacgaata cttcgatgtc tggggcaaag ggaccacggt caccgtctcc   360
tccgcctcca ccaagggccc atcggtcttc cccctggcgc cctgctccag gagcacctcc   420
gagagcacag ccgccctggg ctgcctggtc aaggactact ccccgaaacc ggtgacggtg   480
tcgtggaact caggcgctct gaccagcggc gtgcacacct tcccagctgt cctacagtcc   540
tcaggactct actccctcag cagcgtggtg accgtgccct ccagcaactt cggcacccag   600
acctacacct gcaacgtaga tcacaagccc agcaacacca aggtggacaa gacagttgag   660
cgcaaatgtt gtgtcgagtg cccaccgtgc ccagcaccac ctgtggcagg accgtcagtc   720
ttcctcttcc ccccaaaacc caaggacacc ctcatgatct cccggacccc tgaggtcacg   780
tgcgtggtgg tggacgtgag ccacgaagac cccgaggtcc agttcaactg gtacgtggac   840
ggcgtggagg tgcataatgc caagacaaag ccacgggagg agcagttcaa cagcacgttc   900
cgtgtggtca gcgtcctcac cgttgtgcac caggactggc tgaacggcaa ggagtacaag   960
tgcaaggtct ccaacaaagg cctcccagcc cccatcgaga aaaccatctc caaaaccaaa  1020
gggcagcccc gagaaccaca ggtgtacacc ctgcccccat cccgggagga gatgaccaag  1080
aaccaggtca gcctgacctg cctggtcaaa ggcttctacc ccagcgacat cgccgtggag  1140
tgggagagca atgggcagcc ggagaacaac tacaagacca cacctcccat gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa atagtaa                                      1347

SEQ ID NO: 164              moltype = AA  length = 447
FEATURE                     Location/Qualifiers
REGION                      1..447
                            note = Humanized C2 IgG2 heavy chain sequence
source                      1..447
                            mol_type = protein
                            organism = synthetic construct
SEQUENCE: 164
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYFDV WGKGTTVTVS   120
SASTKGPSVF PLAPCSRSTS ESTAALGCLV KDYFPEPVTV SWNSGALTSG VHTFPAVLQS   180
SGLYSLSSVV TVPSSNFGTQ TYTCNVDHKP SNTKVDKTVE RKCCVECPPC PAPPVAGPSV   240
FLFPPKPKDT LMISRTPEVT CVVVDVSHED PEVQFNWYVD GVEVHNAKTK PREEQFNSTF   300
RVVSVLTVVH QDWLNGKEYK CKVSNKGLPA PIEKTISKTK GQPREPQVYT LPPSREEMTK   360
NQVSLTCLVK GFYPSDIAVE WESNGQPENN YKTTPPMLDS DGSFFLYSKL TVDKSRWQQG   420
NVFSCSVMHE ALHNHYTQKS LSLSPGK                                      447

SEQ ID NO: 165              moltype = DNA  length = 549
FEATURE                     Location/Qualifiers
misc_feature                1..549
                            note = Humanized C2 gBLOCK#5 sequence
source                      1..549
                            mol_type = other DNA
                            organism = synthetic construct
SEQUENCE: 165
tgctctgggt tccaggttcc actggtgacg cggcccagcc ggccgaggtg cagctggtgg    60
agtctggggg aggcctggtc aagcctgggg ggtccctgag actctcctgt gcagcctctg   120
gattcacctt cagtggctat gccatgagct gggtccgcca ggctccaggg aaggggctgg   180
agtgggtctc aaccattagt agtggcggaa cctacatata ctaccccgac tcagtgaagg   240
gccgattcac catctccaga gacaacgcca agaactcact gtatctgcaa atgaacagcc   300
tgagagccga ggacacggcc gtgtattact gtgcgagact tgggggggat aattactacg   360
aatacttcga tgtctggggc aaagggacca cggtcaccgt ctcctccgcc tccaccaagg   420
gcccatcggt cttccccctg gcgccctgct ccaggagcac ctccgagagc acagccgccc   480
tgggctgcct ggtcaaggac tacttcccg  aaccggtgac ggtgtcgtgg aactcaggcg   540
ctctgacca                                                           549

SEQ ID NO: 166              moltype = DNA  length = 31
FEATURE                     Location/Qualifiers
misc_feature                1..31
                            note = pSEC Tag2 overlapping sequence
source                      1..31
                            mol_type = other DNA
                            organism = synthetic construct
SEQUENCE: 166
tgctctgggt tccaggttcc actggtgacg c                                   31

SEQ ID NO: 167              moltype = DNA  length = 32
FEATURE                     Location/Qualifiers
misc_feature                1..32
                            note = Human IgG2 constant region overlapping sequence
source                      1..32
                            mol_type = other DNA
```

```
                        organism = synthetic construct
SEQUENCE: 167
gacggtgtcg tggaactcag gcgctctgac ca                              32

SEQ ID NO: 168          moltype = DNA  length = 360
FEATURE                 Location/Qualifiers
misc_feature            1..360
                        note = Mouse C2 light chain variable region sequence
source                  1..360
                        mol_type = other DNA
                        organism = synthetic construct
SEQUENCE: 168
gacattgtga tcacacagtc tacagcttcc ttaggtgtat ctctggggca gagggccacc  60
atctcatgca gggccagcaa aagtgtcagt acatctggct atagttatat gcactggtac 120
caacagagac caggacagcc acccaaactc ctcatctatc ttgcatccaa cctagaatct 180
ggggtccctg ccaggttcag tggcagtggg tctgggacag acttcaccct caacatccat 240
cctgtggagg aggaggatgc tgcaacctat tactgtcagc acagtaggga gcttccgttc 300
acgttcggag gggggaccaa gctggagata aaacgggctg atgctgcacc aactgtatcc 360

SEQ ID NO: 169          moltype = AA   length = 120
FEATURE                 Location/Qualifiers
REGION                  1..120
                        note = Mouse C2 light chain variable region sequence
source                  1..120
                        mol_type = protein
                        organism = synthetic construct
SEQUENCE: 169
DIVITQSTAS LGVSLGQRAT ISCRASKSVS TSGYSYMHWY QQRPGQPPKL LIYLASNLES  60
GVPARFSGSG SGTDFTLNIH PVEEEDAATY YCQHSRELPF TFGGGTKLEI KRADAAPTVS 120

SEQ ID NO: 170          moltype = DNA   length = 69
FEATURE                 Location/Qualifiers
misc_feature            1..69
                        note = Mouse C2 light chain variable framework region 1
                        (FWR1) sequence
source                  1..69
                        mol_type = other DNA
                        organism = synthetic construct
SEQUENCE: 170
gacattgtga tcacacagtc tacagcttcc ttaggtgtat ctctggggca gagggccacc  60
atctcatgc                                                         69

SEQ ID NO: 171          moltype = AA   length = 23
FEATURE                 Location/Qualifiers
REGION                  1..23
                        note = Mouse C2 light chain variable framework region 1
                        (FWR1) sequence
source                  1..23
                        mol_type = protein
                        organism = synthetic construct
SEQUENCE: 171
DIVITQSTAS LGVSLGQRAT ISC                                         23

SEQ ID NO: 172          moltype = DNA   length = 45
FEATURE                 Location/Qualifiers
misc_feature            1..45
                        note = Mouse C2 light chain variable complementarity
                        determining regions1 (CDR1) sequence
source                  1..45
                        mol_type = other DNA
                        organism = synthetic construct
SEQUENCE: 172
agggccagca aaagtgtcag tacatctggc tatagttata tgcac                 45

SEQ ID NO: 173          moltype = AA   length = 15
FEATURE                 Location/Qualifiers
REGION                  1..15
                        note = Mouse C2 light chain variable complementarity
                        determining regions1 (CDR1) sequence
source                  1..15
                        mol_type = protein
                        organism = synthetic construct
SEQUENCE: 173
RASKSVSTSG YSYMH                                                  15

SEQ ID NO: 174          moltype = DNA   length = 45
FEATURE                 Location/Qualifiers
misc_feature            1..45
                        note = Mouse C2 light chain variable framework region 2
```

```
                        (FWR2) sequence
source                  1..45
                        mol_type = other DNA
                        organism = synthetic construct
SEQUENCE: 174
tggtaccaac agagaccagg acagccaccc aaactcctca tctat               45

SEQ ID NO: 175          moltype = AA  length = 15
FEATURE                 Location/Qualifiers
REGION                  1..15
                        note = Mouse C2 light chain variable framework region 2
                        (FWR2) sequence
source                  1..15
                        mol_type = protein
                        organism = synthetic construct
SEQUENCE: 175
WYQQRPGQPP KLLIY                                                15

SEQ ID NO: 176          moltype = DNA  length = 20
FEATURE                 Location/Qualifiers
misc_feature            1..20
                        note = Mouse C2 light chain variable complementarity
                        determining regions2 (CDR2) sequence
source                  1..20
                        mol_type = other DNA
                        organism = synthetic construct
SEQUENCE: 176
cttgcatcca acctagaatc                                           20

SEQ ID NO: 177          moltype = AA  length = 7
FEATURE                 Location/Qualifiers
REGION                  1..7
                        note = Mouse C2 light chain variable complementarity
                        determining regions2 (CDR2) sequence
source                  1..7
                        mol_type = protein
                        organism = synthetic construct
SEQUENCE: 177
LASNLES                                                         7

SEQ ID NO: 178          moltype = DNA  length = 97
FEATURE                 Location/Qualifiers
misc_feature            1..97
                        note = Mouse C2 light chain variable framework region 3
                        (FWR3) sequence
source                  1..97
                        mol_type = other DNA
                        organism = synthetic construct
SEQUENCE: 178
tggggtccct gccaggttca gtggcagtgg gtctgggaca gacttcaccc tcaacatcca  60
tcctgtggag gaggaggatg ctgcaaccta ttactgt                          97

SEQ ID NO: 179          moltype = AA  length = 32
FEATURE                 Location/Qualifiers
REGION                  1..32
                        note = Mouse C2 light chain variable framework region 3
                        (FWR3) sequence
source                  1..32
                        mol_type = protein
                        organism = synthetic construct
SEQUENCE: 179
GVPARFSGSG SGTDFTLNIH PVEEEDAATY YC                              32

SEQ ID NO: 180          moltype = DNA  length = 27
FEATURE                 Location/Qualifiers
misc_feature            1..27
                        note = Mouse C2 light chain variable complementarity
                        determining regions3 (CDR3) sequence
source                  1..27
                        mol_type = other DNA
                        organism = synthetic construct
SEQUENCE: 180
cagcacagta gggagcttcc gttcacg                                    27

SEQ ID NO: 181          moltype = AA  length = 9
FEATURE                 Location/Qualifiers
REGION                  1..9
                        note = Mouse C2 light chain variable complementarity
                        determining regions3 (CDR3) sequence
```

```
source                          1..9
                                mol_type = protein
                                organism = synthetic construct
SEQUENCE: 181
QHSRELPFT                                                              9

SEQ ID NO: 182                  moltype = DNA   length = 303
FEATURE                         Location/Qualifiers
misc_feature                    1..303
                                note = IGKV7-3*01 light chain variable region sequence
source                          1..303
                                mol_type = other DNA
                                organism = synthetic construct
SEQUENCE: 182
gacattgtgc tgacccagtc tccagcctcc ttggccgtgt ctccaggaca gagggccacc    60
atcacctgca gagccagtga gagtgtcagt ttcttgggaa taaacttaat tcactggtat   120
cagcagaaac aggacaaacc tcctaaactc ctgatttacc aagcatccaa taaagacact   180
ggggtcccag ccaggttcag cggcagtggg tctgggaccg atttcaccct cacaattaat   240
cctgtggaag ctaatgatac tgcaaattat tactgtctgc agagtaagaa ttttcctccc   300
aca                                                                303

SEQ ID NO: 183                  moltype = AA   length = 101
FEATURE                         Location/Qualifiers
REGION                          1..101
                                note = IGKV7-3*01 light chain variable region sequence
source                          1..101
                                mol_type = protein
                                organism = synthetic construct
SEQUENCE: 183
DIVLTQSPAS LAVSPGQRAT ITCRASESVS FLGINLIHWY QQKPGQPPKL LIYQASNKDT    60
GVPARFSGSG SGTDFTLTIN PVEANDTANY YCLQSKNFPP T                       101

SEQ ID NO: 184                  moltype = DNA   length = 69
FEATURE                         Location/Qualifiers
misc_feature                    1..69
                                note = IGKV7-3*01 light chain variable framework region 1
                                 (FWR1) sequence
source                          1..69
                                mol_type = other DNA
                                organism = synthetic construct
SEQUENCE: 184
gacattgtgc tgacccagtc tccagcctcc ttggccgtgt ctccaggaca gagggccacc    60
atcacctgc                                                            69

SEQ ID NO: 185                  moltype = AA   length = 23
FEATURE                         Location/Qualifiers
REGION                          1..23
                                note = IGKV7-3*01 light chain variable framework region 1
                                 (FWR1) sequence
source                          1..23
                                mol_type = protein
                                organism = synthetic construct
SEQUENCE: 185
DIVLTQSPAS LAVSPGQRAT ITC                                             23

SEQ ID NO: 186                  moltype = DNA   length = 45
FEATURE                         Location/Qualifiers
misc_feature                    1..45
                                note = IGKV7-3*01 light chain variable complementarity
                                 determiningregions 1 (CDR1) sequence
source                          1..45
                                mol_type = other DNA
                                organism = synthetic construct
SEQUENCE: 186
agagccagtg agagtgtcag tttcttggga ataaacttaa ttcac                     45

SEQ ID NO: 187                  moltype = AA   length = 15
FEATURE                         Location/Qualifiers
REGION                          1..15
                                note = IGKV7-3*01 light chain variable complementarity
                                 determiningregions 1 (CDR1) sequence
source                          1..15
                                mol_type = protein
                                organism = synthetic construct
SEQUENCE: 187
RASESVSFLG INLIH                                                      15

SEQ ID NO: 188                  moltype = DNA   length = 45
FEATURE                         Location/Qualifiers
```

```
misc_feature               1..45
                           note = IGKV7-3*01 light chain variable framework region 2
                              (FWR2)sequence
source                     1..45
                           mol_type = other DNA
                           organism = synthetic construct
SEQUENCE: 188
tggtatcagc agaaaccagg acaacctcct aaactcctga tttac            45

SEQ ID NO: 189             moltype = AA   length = 15
FEATURE                    Location/Qualifiers
REGION                     1..15
                           note = IGKV7-3*01 light chain variable framework region 2
                              (FWR2)sequence
source                     1..15
                           mol_type = protein
                           organism = synthetic construct
SEQUENCE: 189
WYQQKPGQPP KLLIY                                              15

SEQ ID NO: 190             moltype = DNA   length = 21
FEATURE                    Location/Qualifiers
misc_feature               1..21
                           note = IGKV7-3*01 light chain variable complementarity
                              determiningregions 2 (CDR2) sequence
source                     1..21
                           mol_type = other DNA
                           organism = synthetic construct
SEQUENCE: 190
caagcatcca ataaagacac t                                       21

SEQ ID NO: 191             moltype = AA   length = 7
FEATURE                    Location/Qualifiers
REGION                     1..7
                           note = IGKV7-3*01 light chain variable complementarity
                              determiningregions 2 (CDR2) sequence
source                     1..7
                           mol_type = protein
                           organism = synthetic construct
SEQUENCE: 191
QASNKDT                                                       7

SEQ ID NO: 192             moltype = DNA   length = 96
FEATURE                    Location/Qualifiers
misc_feature               1..96
                           note = IGKV7-3*01 light chain variable framework region 3
                              (FWR3)sequence
source                     1..96
                           mol_type = other DNA
                           organism = synthetic construct
SEQUENCE: 192
ggggtcccag ccaggttcag cggcagtggg tctgggaccg atttcaccct cacaattaat   60
cctgtggaag ctaatgatac tgcaaattat tactgt                             96

SEQ ID NO: 193             moltype = AA   length = 32
FEATURE                    Location/Qualifiers
REGION                     1..32
                           note = IGKV7-3*01 light chain variable framework region 3
                              (FWR3)sequence
source                     1..32
                           mol_type = protein
                           organism = synthetic construct
SEQUENCE: 193
GVPARFSGSG SGTDFTLTIN PVEANDTANY YC                           32

SEQ ID NO: 194             moltype = DNA   length = 339
FEATURE                    Location/Qualifiers
misc_feature               1..339
                           note = Humanized C2 light chain variable region sequence
source                     1..339
                           mol_type = other DNA
                           organism = synthetic construct
SEQUENCE: 194
gacattgtgc tgacccagtc tccagcctcc ttggccgtgt ctccaggaca gagggccacc   60
atcacctgca gagccagtaa gagtgtcagt accagcggat actcctacat gcactggtat  120
cagcagaaac caggacaacc tcctaaactc ctgatttacc tggcatccaa tctgagagc   180
ggggtcccag ccaggttcag cggcagtggg tctgggaccg atttcaccct cacaattaat  240
cctgtggaag ctaatgatac tgcaaattat tactgtcagc acagtaggga gctgcctttc  300
acattcggcg agggaccaa ggtggagatc aaacgaact                          339
```

```
SEQ ID NO: 195          moltype = AA   length = 113
FEATURE                 Location/Qualifiers
REGION                  1..113
                        note = Humanized C2 light chain variable region sequence
source                  1..113
                        mol_type = protein
                        organism = synthetic construct
SEQUENCE: 195
DIVLTQSPAS LAVSPGQRAT ITCRASKSVS TSGYSYMHWY QQKPGQPPKL LIYLASNLES    60
GVPARFSGSG SGTDFTLTIN PVEANDTANY YCQHSRELPF TFGGGTKVEI KRT          113

SEQ ID NO: 196          moltype = DNA   length = 69
FEATURE                 Location/Qualifiers
misc_feature            1..69
                        note = Humanized C2 light chain variable framework region 1
                        (FWR1) acidsequence
source                  1..69
                        mol_type = other DNA
                        organism = synthetic construct
SEQUENCE: 196
gacattgtgc tgacccagtc tccagcctcc ttggccgtgt ctccaggaca gagggccacc    60
atcacctgc                                                            69

SEQ ID NO: 197          moltype = AA   length = 23
FEATURE                 Location/Qualifiers
REGION                  1..23
                        note = Humanized C2 light chain variable framework region 1
                        (FWR1) acidsequence
source                  1..23
                        mol_type = protein
                        organism = synthetic construct
SEQUENCE: 197
DIVLTQSPAS LAVSPGQRAT ITC                                            23

SEQ ID NO: 198          moltype = DNA   length = 45
FEATURE                 Location/Qualifiers
misc_feature            1..45
                        note = Humanized C2 light chain variable complementarity
                         determiningregions 1 (CDR1) sequence
source                  1..45
                        mol_type = other DNA
                        organism = synthetic construct
SEQUENCE: 198
agagccagta agagtgtcag taccagcgga tactcctaca tgcac                    45

SEQ ID NO: 199          moltype = AA   length = 15
FEATURE                 Location/Qualifiers
REGION                  1..15
                        note = Humanized C2 light chain variable complementarity
                         determiningregions 1 (CDR1) sequence
source                  1..15
                        mol_type = protein
                        organism = synthetic construct
SEQUENCE: 199
RASKSVSTSG YSYMH                                                     15

SEQ ID NO: 200          moltype = DNA   length = 45
FEATURE                 Location/Qualifiers
misc_feature            1..45
                        note = Humanized C2 heavy light variable framework region 2
                        (FWR2) acidsequence
source                  1..45
                        mol_type = other DNA
                        organism = synthetic construct
SEQUENCE: 200
tggtatcagc agaaaccagg acaacctcct aaactcctga tttac                    45

SEQ ID NO: 201          moltype = AA   length = 15
FEATURE                 Location/Qualifiers
REGION                  1..15
                        note = Humanized C2 heavy light variable framework region 2
                        (FWR2) acidsequence
source                  1..15
                        mol_type = protein
                        organism = synthetic construct
SEQUENCE: 201
WYQQKPGQPP KLLIY                                                     15
```

```
SEQ ID NO: 202          moltype = DNA  length = 21
FEATURE                 Location/Qualifiers
misc_feature            1..21
                        note = Humanized C2 light chain variable complementarity
                        determiningregions 2 (CDR2) sequence
source                  1..21
                        mol_type = other DNA
                        organism = synthetic construct
SEQUENCE: 202
ctggcatcca atctggagag c                                              21

SEQ ID NO: 203          moltype = AA  length = 7
FEATURE                 Location/Qualifiers
REGION                  1..7
                        note = Humanized C2 light chain variable complementarity
                        determiningregions 2 (CDR2) sequence
source                  1..7
                        mol_type = protein
                        organism = synthetic construct
SEQUENCE: 203
LASNLES                                                              7

SEQ ID NO: 204          moltype = DNA  length = 96
FEATURE                 Location/Qualifiers
misc_feature            1..96
                        note = Humanized C2 light chain variable framework region 3
                        (FWR3) acidsequence
source                  1..96
                        mol_type = other DNA
                        organism = synthetic construct
SEQUENCE: 204
ggggtcccag ccaggttcag cggcagtggg tctgggaccg atttcaccct cacaattaat    60
cctgtggaag ctaatgatac tgcaaattat tactgt                              96

SEQ ID NO: 205          moltype = AA  length = 32
FEATURE                 Location/Qualifiers
REGION                  1..32
                        note = Humanized C2 light chain variable framework region 3
                        (FWR3) acidsequence
source                  1..32
                        mol_type = protein
                        organism = synthetic construct
SEQUENCE: 205
GVPARFSGSG SGTDFTLTIN PVEANDTANY YC                                  32

SEQ ID NO: 206          moltype = DNA  length = 27
FEATURE                 Location/Qualifiers
misc_feature            1..27
                        note = Humanized C2 light chain variable complementarity
                        determiningregions 3 (CDR3) sequence
source                  1..27
                        mol_type = other DNA
                        organism = synthetic construct
SEQUENCE: 206
cagcacagta gggagctgcc tttcaca                                        27

SEQ ID NO: 207          moltype = AA  length = 9
FEATURE                 Location/Qualifiers
REGION                  1..9
                        note = Humanized C2 light chain variable complementarity
                        determiningregions 3 (CDR3) sequence
source                  1..9
                        mol_type = protein
                        organism = synthetic construct
SEQUENCE: 207
QHSRELPFT                                                            9

SEQ ID NO: 208          moltype = DNA  length = 27
FEATURE                 Location/Qualifiers
misc_feature            1..27
                        note = Humanized C2 light chain variable complementarity
                        determiningregions 3 (CDR3) sequence
source                  1..27
                        mol_type = other DNA
                        organism = synthetic construct
SEQUENCE: 208
ctgcagagta agaattttcc tcccaca                                        27

SEQ ID NO: 209          moltype = AA  length = 9
```

```
FEATURE                 Location/Qualifiers
REGION                  1..9
                        note = Humanized C2 light chain variable complementarity
                         determiningregions 3 (CDR3) sequence
source                  1..9
                        mol_type = protein
                        organism = synthetic construct
SEQUENCE: 209
LQSKNFPPT                                                                  9

SEQ ID NO: 210          moltype = DNA   length = 813
FEATURE                 Location/Qualifiers
misc_feature            1..813
                        note = Humanized C2 gBLOCK#6 sequence (Kappa light chain in
                         pCDNA3.1 V5)
source                  1..813
                        mol_type = other DNA
                        organism = synthetic construct
SEQUENCE: 210
actcactata gggagaccca agctggctag ttaagcttgg gccaccatgg agacagacac    60
actcctgcta tgggtactgc tgctctgggt tccaggttcc actggtgacg acattgtgct   120
gacccagtct ccagcctcct tggccgtgtc tccaggacag agggccacca tcacctgcag   180
agccagtaag agtgtcagta ccagcggata ctcctacatg cactggtatc agcagaaacc   240
aggacaacct cctaaactcc tgatttacct ggcatccaat ctggagagcg ggtcccagc    300
caggttcagc ggcagtgggt ctgggaccga tttcaccctc acaattaatc ctgtggaagc   360
taatgatact gcaaattatt actgtcagca cagtaggggg gtgccttttca cattcggcgg   420
agggaccaag gtggagatca aacgaactac ggtggctgca ccatctgtct tcatcttccc   480
gccatctgat gagcagttga aatctggaac tgcctctgtt gtgtgcctgc tgaataactt   540
ctatcccaga gaggccaaag tacagtggaa ggtggataac gccctccaat cgggtaactc   600
ccaggagagt gtcacagagc aggacagcaa ggacagcacc tacagcctca gcagcacct    660
gacgctgagc aaagcagact acgagaaaca caaagtctac gcctgcgaag tcacccatca   720
gggcctgagc tcgcccgtca caaagagctt caacagggga gagtgttagt aagtttaaac   780
ccgctgatca gcctcgactg tgccttctag ttg                                 813

SEQ ID NO: 211          moltype = DNA   length = 32
FEATURE                 Location/Qualifiers
misc_feature            1..32
                        note = pCDNA3.1 V5 5' overlapping sequence
source                  1..32
                        mol_type = other DNA
                        organism = synthetic construct
SEQUENCE: 211
actcactata gggagaccca agctggctag tt                                   32

SEQ ID NO: 212          moltype = DNA   length = 33
FEATURE                 Location/Qualifiers
misc_feature            1..33
                        note = pCDNA3.1 V5 3' overlapping sequence
source                  1..33
                        mol_type = other DNA
                        organism = synthetic construct
SEQUENCE: 212
ccgctgatca gcctcgactg tgccttctag ttg                                  33

SEQ ID NO: 213          moltype = DNA   length = 748
FEATURE                 Location/Qualifiers
misc_feature            1..748
                        note = Humanized C2 gBLOCK#7 sequence (Kappa light chain in
                         pSEC Tag2)
source                  1..748
                        mol_type = other DNA
                        organism = synthetic construct
SEQUENCE: 213
tgctctgggt tccaggttcc actggtgacg cggcccagcc ggccgacatt gtgctgaccc    60
agtctccagc ctccttggcc gtgtctccag gacagagggc caccatcacc tgcagagcca   120
gtaagagtgt cagtaccagc ggatactcct acatgcactg gtatcagcag aaaccaggac   180
aacctcctaa actcctgatt tacctggcat ccaatctgga gagcgggtc ccagccaggt    240
tcagcggcag tgggtctggg accgatttca ccctcacaat taatcctgtg gaagctaatg   300
atactgcaaa ttattactgt cagcacagta gggagctgcc tttcacattc ggcggaggga   360
ccaaggtgga gatcaaacga actacgtggg ctgcaccatc tgtcttcatc ttcccgccat   420
ctgatgagca gttgaaatct ggaactgcct ctgttgtgtg cctgctgaat aacttctatc   480
ccagagaggc caaagtacag tggaaggtgg ataacgccct ccaatcgggt aactcccagg   540
agagtgtcac agagcaggac agcaaggaca gcacctacag cctcagcagc acctgacgc    600
tgagcaaagc agactacgag aaacacaaag tctacgcctg cgaagtcacc catcagggcc   660
tgagctcgcc cgtcacaaag agcttcaaca ggggagagtg ttagtaagtt taaacccgct   720
gatcagcctc gactgtgcct tctagttg                                       748

SEQ ID NO: 214          moltype = DNA   length = 31
FEATURE                 Location/Qualifiers
```

```
misc_feature           1..31
                       note = pSEC Tag2 5' overlapping sequence
source                 1..31
                       mol_type = other DNA
                       organism = synthetic construct
SEQUENCE: 214
tgctctgggt tccaggttcc actggtgacg c                                    31

SEQ ID NO: 215         moltype = DNA  length = 33
FEATURE                Location/Qualifiers
misc_feature           1..33
                       note = pSEC Tag2 3' overlapping sequence
source                 1..33
                       mol_type = other DNA
                       organism = synthetic construct
SEQUENCE: 215
ccgctgatca gcctcgactg tgccttctag ttg                                  33

SEQ ID NO: 216         moltype = DNA  length = 813
FEATURE                Location/Qualifiers
misc_feature           1..813
                       note = Humanized C2 gBLOCK#8 sequence (lambda light chain
                        in pCDNA3.1V5)
source                 1..813
                       mol_type = other DNA
                       organism = synthetic construct
SEQUENCE: 216
actcactata gggagaccca agctggctag ttaagcttgg gccaccatgg agacagacac      60
actcctgcta tgggtactgc tgctctgggt tccaggttcc actggtgacg acattgtgct     120
gacccagtct ccagcctcct tggccgtgtc tccaggagca ggggccacca tcacctgcag     180
agccagtaag agtgtcagta ccagcggata ctcctacatg cactggtatc agcagaaacc     240
aggacaacct cctaaactcc tgatttacct ggcatccaat ctggagagcg ggtcccagc      300
caggttcagc ggcagtgggt ctgggaccga tttcaccctc acaattaatc ctgtggaagc     360
taatgatact gcaaattatt actgtcagca gtagggag ctgcctttca cattcggcgg      420
agggaccaag gtggagatca aacgaactgg tcagcccaag gctgccccct cggtcactct     480
gttcccgccc tcctctgagg agcttcaagc caacaaggcc acactggtgt gtctcataag     540
tgacttctac ccgggagccg tgacagtggc ctggaaggca gatagcagcc ccgtcaaggc     600
gggagtggag accaccacac cctccaaaca aagcaacaac aagtacgcgg ccagcagcta     660
tctgagcctg acgcctgagc agtggaagtc ccacagaagc tacagctgcc aggtcacgca     720
tgaagggagc accgtggaga gacagtggcc cctacagaa tgttcatagt aagtttaaac      780
ccgctgatca gcctcgactg tgccttctag ttg                                 813

SEQ ID NO: 217         moltype = DNA  length = 32
FEATURE                Location/Qualifiers
misc_feature           1..32
                       note = pCDNA3.1 V5 5' overlapping sequence
source                 1..32
                       mol_type = other DNA
                       organism = synthetic construct
SEQUENCE: 217
actcactata gggagaccca agctggctag tt                                   32

SEQ ID NO: 218         moltype = DNA  length = 33
FEATURE                Location/Qualifiers
misc_feature           1..33
                       note = pCDNA3.1 V5 3' overlapping sequence
source                 1..33
                       mol_type = other DNA
                       organism = synthetic construct
SEQUENCE: 218
ccgctgatca gcctcgactg tgccttctag ttg                                  33

SEQ ID NO: 219         moltype = DNA  length = 748
FEATURE                Location/Qualifiers
misc_feature           1..748
                       note = Humanized C2 gBLOCK#9 sequence (lambda light chain
                        in pSEC Tag2)
source                 1..748
                       mol_type = other DNA
                       organism = synthetic construct
SEQUENCE: 219
tgctctgggt tccaggttcc actggtgacg cggcccagcc ggccgacatt gtgctgaccc      60
agtctccagc ctccttggcc gtgtctccag gacagagggc caccatcacc tgcagagcca    120
gtaagagtgt cagtaccagc ggatactcct acatgcactg gtatcagcag aaaccaggac    180
aacctcctaa actcctgatt tacctggcat ccaatctgga gagcgggtc ccagccaggt    240
tcagcggcag tgggtctggg accgatttca ccctcacaat taatcctgtg gaagctaatg    300
atactgcaaa ttattactgt cagcacagta gggagctgcc tttcacattc ggcggaggga    360
ccaaggtgga gatcaaacga actggtcagc ccaaggctgc ccctcggtc actctgttcc    420
cgcccctcctc tgaggagctt caagccaaca aggccacact ggtgtgtctc ataagtgact    480
```

```
tctacccggg agccgtgaca gtggcctgga aggcagatag cagccccgtc aaggcgggag    540
tggagaccac cacaccctcc aaacaaagca caacaagta cgcggccagc agctatctga     600
gcctgacgcc tgagcagtgg aagtcccaca gaagctacag ctgccaggtc acgcatgaag    660
ggagcaccgt ggagaagaca gtggccccta cagaatgttc atagtaagtt taaacccgct   720
gatcagcctc gactgtgcct tctagttg                                       748

SEQ ID NO: 220          moltype = DNA   length = 31
FEATURE                 Location/Qualifiers
misc_feature            1..31
                        note = pSEC Tag2 5' overlapping sequence
source                  1..31
                        mol_type = other DNA
                        organism = synthetic construct
SEQUENCE: 220
tgctctgggt tccaggttcc actggtgacg c                                   31

SEQ ID NO: 221          moltype = DNA   length = 33
FEATURE                 Location/Qualifiers
misc_feature            1..33
                        note = pSEC Tag2 3' overlapping sequence
source                  1..33
                        mol_type = other DNA
                        organism = synthetic construct
SEQUENCE: 221
ccgctgatca gcctcgactg tgccttctag ttg                                 33

SEQ ID NO: 222          moltype = DNA   length = 63
FEATURE                 Location/Qualifiers
misc_feature            1..63
                        note = Murine Ig kappa chain leader sequence
source                  1..63
                        mol_type = other DNA
                        organism = synthetic construct
SEQUENCE: 222
atggagacag acacactcct gctatgggta ctgctgctct gggttccagg ttccactggt    60
gac                                                                  63

SEQ ID NO: 223          moltype = AA    length = 21
FEATURE                 Location/Qualifiers
REGION                  1..21
                        note = Murine Ig kappa chain leader sequence
source                  1..21
                        mol_type = protein
                        organism = synthetic construct
SEQUENCE: 223
METDTLLLWV LLLWVPGSTG D                                              21

SEQ ID NO: 224          moltype = DNA   length = 60
FEATURE                 Location/Qualifiers
misc_feature            1..60
                        note = Interleukin-2 (IL-2) leader sequence
source                  1..60
                        mol_type = other DNA
                        organism = synthetic construct
SEQUENCE: 224
atgtacagga tgcaactcct gtcttgcatt gcactaagtc ttgcacttgt cacaaacagt    60

SEQ ID NO: 225          moltype = AA    length = 20
FEATURE                 Location/Qualifiers
REGION                  1..20
                        note = Interleukin-2 (IL-2) leader sequence
source                  1..20
                        mol_type = protein
                        organism = synthetic construct
SEQUENCE: 225
MYRMQLLSCI ALSLALVTNS                                                20

SEQ ID NO: 226          moltype = DNA   length = 48
FEATURE                 Location/Qualifiers
misc_feature            1..48
                        note = CD33 leader sequence
source                  1..48
                        mol_type = other DNA
                        organism = synthetic construct
SEQUENCE: 226
atgccttctc tgcttctgct tcctctgctt tgggctggag ctcttgct                 48

SEQ ID NO: 227          moltype = AA    length = 16
FEATURE                 Location/Qualifiers
```

| | |
|---|---|
| REGION | 1..16<br>note = CD33 leader sequence |
| source | 1..16<br>mol_type = protein<br>organism = synthetic construct |

SEQUENCE: 227
MPLLLLLPLL WAGALA                                                16

| | |
|---|---|
| SEQ ID NO: 228 | moltype = DNA  length = 57 |
| FEATURE | Location/Qualifiers |
| misc_feature | 1..57<br>note = IGHV3-21*03 leader sequence |
| source | 1..57<br>mol_type = other DNA<br>organism = synthetic construct |

SEQUENCE: 228
atggaactgg ggctccgctg ggttttcctt gttgctattt tagaaggtgt ccagtgt    57

| | |
|---|---|
| SEQ ID NO: 229 | moltype = AA  length = 19 |
| FEATURE | Location/Qualifiers |
| REGION | 1..19<br>note = IGHV3-21*03 leader sequence |
| source | 1..19<br>mol_type = protein<br>organism = synthetic construct |

SEQUENCE: 229
MELGLRWVFL VAILEGVQC                                             19

| | |
|---|---|
| SEQ ID NO: 230 | moltype = DNA  length = 60 |
| FEATURE | Location/Qualifiers |
| misc_feature | 1..60<br>note = IGHV3-11*02 leader sequence |
| source | 1..60<br>mol_type = other DNA<br>organism = synthetic construct |

SEQUENCE: 230
atggaagccc cagcgcagct tctcttcctc ctgctactct ggctcccaga taccactgga  60

| | |
|---|---|
| SEQ ID NO: 231 | moltype = AA  length = 20 |
| FEATURE | Location/Qualifiers |
| REGION | 1..20<br>note = IGHV3-11*02 leader sequence |
| source | 1..20<br>mol_type = protein<br>organism = synthetic construct |

SEQUENCE: 231
MEAPAQLLFL LLLWLPDTTG                                            20

| | |
|---|---|
| SEQ ID NO: 232 | moltype = DNA  length = 729 |
| FEATURE | Location/Qualifiers |
| misc_feature | 1..729<br>note = Humanized E6 single chain GS3 |
| source | 1..729<br>mol_type = other DNA<br>organism = synthetic construct |

SEQUENCE: 232
gaggtgcagc tggtggagtc tgggggaggc ctggtcaagc ctgggggggtc cctgagactc  60
tcctgtgcag cctctggatt caccttcagt aggtatggca tgagctgggt ccgccaggct 120
ccagggaaga ggctggagtg ggtctcaacc attagtggcg gaggcaccta catatactac 180
ccagactcag tgaagggccg attcaccatc tccagagaca cgcaagaa cacccctgtat 240
ctgcaaatga acagcctgag agccgaggac acggctgtgt attactgtac cagagataac 300
tatgccgcca actatgatta tggcatggat tattgggggcc agggcaccct ggtgaccgtg 360
agcagcggcg gtgtcggatc cggcggtggc ggatccggcg gtgcggatc cgaaattgtg 420
ttgacacagt ctccagccac cctgtctttg tctccagggg aaagagccac cctcacctgc 480
agcgccacca gcagtgttag ctacatccac tggtaccaac agaggcctgg ccagagcccc 540
aggctcctca tctatagcac ctccaacctg gccagcggca tcccagccag gttcagtggc 600
agtgggtctg ggagcgacta cactctcacc atcagcagcc tagagcctga agattttgca 660
gtttattact gtcagcagcg tagcagctcc cctttcacct ttggcagcgg caccaaagtg 720
gaaattaaa                                                       729

| | |
|---|---|
| SEQ ID NO: 233 | moltype = AA  length = 243 |
| FEATURE | Location/Qualifiers |
| REGION | 1..243<br>note = Humanized E6 single chain GS3 |
| source | 1..243<br>mol_type = protein<br>organism = synthetic construct |

SEQUENCE: 233
EVQLVESGGG LVKPGGSLRL SCAASGFTFS RYGMSWVRQA PGKRLEWVST ISGGGTYIYY  60

```
PDSVKGRFTI SRDNAKNTLY LQMNSLRAED TAVYYCTRDN YGRNYDYGMD YWGQGTLVTV    120
SSGGGGSGGG GSGGGGSEIV LTQSPATLSL SPGERATLTC SATSSVSYIH WYQQRPGQSP    180
RLLIYSTSNL ASGIPARFSG SGSGSDYTLT ISSLEPEDFA VYYCQQRSSS PFTFGSGTKV    240
EIK                                                                  243

SEQ ID NO: 234             moltype = DNA   length = 747
FEATURE                    Location/Qualifiers
misc_feature               1..747
                           note = Humanized E6 single chain IgG1noC
source                     1..747
                           mol_type = other DNA
                           organism = synthetic construct
SEQUENCE: 234
gaggtgcagc tggtggagtc tgggggaggc ctggtcaagc ctggggggtc cctgagactc     60
tcctgtgcag cctctggatt caccttcagt aggtatggca tgagctgggt ccgccaggct    120
ccagggaaga ggctggagtg ggtctcaacc attagtggcg gaggcaccta catatactac    180
ccagactcag tgaagggccg attcaccatc tccagagaca cgccaagaa caccctgtat     240
ctgcaaatga acagcctgag agccgaggac acggctgtga ttactgtac cagagataac    300
tatggccgca actatgatta tggcatggat tattgggggcc agggcaccct ggtgaccgtg   360
agcagcgata aaacccatac taaaccgcca aaaccggcgc cggaactgct gggtggtcct    420
ggtaccggtg aaattgtgtt gacacagtct ccagccacc tgtctttgtc tccagggga     480
agagccaccc tcacctgcag cgccaccagc agtgttagtt acatcccact gtaccaacag    540
aggcctggcc agagccccag gctcctcatc tatagcacct ccaacctggc cagcggcatc    600
ccagccaggt tcagtggcag tgggtctggg acagactaca ctctcaccat cagcagccta    660
gagcctgaag attttgcagt ttattactgt cagcagcgta gcagctcccc tttcaccttt    720
ggcagcggca ccaaagtgga aattaaa                                         747

SEQ ID NO: 235             moltype = AA   length = 249
FEATURE                    Location/Qualifiers
REGION                     1..249
                           note = Humanized E6 single chain IgG1noC
source                     1..249
                           mol_type = protein
                           organism = synthetic construct
SEQUENCE: 235
EVQLVESGGG LVKPGGSLRL SCAASGFTFS RYGMSWVRQA PGKRLEWVST ISGGGTYIYY     60
PDSVKGRFTI SRDNAKNTLY LQMNSLRAED TAVYYCTRDN YGRNYDYGMD YWGQGTLVTV    120
SSDKTHTKPP KPAPELLGGP GTGEIVLTQS PATLSLSPGE RATLTCSATS SVSYIHWYQQ    180
RPGQSPRLLI YSTSNLASGI PARFSGSGSG SDYTLTISSL EPEDFAVYYC QQRSSSPFTF    240
GSGTKVEIK                                                            249

SEQ ID NO: 236             moltype = DNA   length = 813
FEATURE                    Location/Qualifiers
misc_feature               1..813
                           note = Humanized E6 single chain X4 (linker is IgG1 and
                           IgG2 modifiedhinge region)
source                     1..813
                           mol_type = other DNA
                           organism = synthetic construct
SEQUENCE: 236
gaggtgcagc tggtggagtc tgggggaggc ctggtcaagc ctggggggtc cctgagactc     60
tcctgtgcag cctctggatt caccttcagt aggtatggca tgagctgggt ccgccaggct    120
ccagggaaga ggctggagtg ggtctcaacc attagtggcg gaggcaccta catatactac    180
ccagactcag tgaagggccg attcaccatc tccagagaca cgccaagaa caccctgtat     240
ctgcaaatga acagcctgag agccgaggac acggctgtgt attactgtac cagagataac    300
tatggccgca actatgatta tggcatggat tattgggggcc agggcaccct ggtgaccgtg   360
agcagcgata aaacccatac taaaccgcca aaaccggcgc cggaactgct gggtggtcct    420
ggtaccggta ctggtggtcc gactattaaa cctccgaaac tccgaaacc tgctccgaac    480
ctgctgggtg gtccggaaat tgtgttgaca gtctccag ccaccctgtc tttgtctcca     540
ggggaaagag ccacctcac ctgcagcgcc accagcagtg ttagctacat ccactgttca    600
caacagaggc ctggcagag ccccaggctc tcatctata gcacctccaa cctgccagc      660
ggcatcccag ccaggttcag tggcagtggg tctgggagcg actacactct caccatcagc    720
agcctagagc ctgaagattt tgcagtttat tactgtcagc agcgtagcag ctccccttc    780
accttttggca gcggcaccaa agtggaaatt aaa                                 813

SEQ ID NO: 237             moltype = AA   length = 271
FEATURE                    Location/Qualifiers
REGION                     1..271
                           note = Humanized E6 single chain X4 (linker is IgG1 and
                           IgG2 modifiedhinge region)
source                     1..271
                           mol_type = protein
                           organism = synthetic construct
SEQUENCE: 237
EVQLVESGGG LVKPGGSLRL SCAASGFTFS RYGMSWVRQA PGKRLEWVST ISGGGTYIYY     60
PDSVKGRFTI SRDNAKNTLY LQMNSLRAED TAVYYCTRDN YGRNYDYGMD YWGQGTLVTV    120
SSDKTHTKPP KPAPELLGGP GTGTGGPTIK PPKPPKPAPN LLGGPEIVLT QSPATLSLSP    180
GERATLTCSA TSSVSYIHWY QQRPGQSPRL LIYSTSNLAS GIPARFSGSG SGSDYTLTIS    240
SLEPEDFAVY YCQQRSSSPF TFGSGTKVEI K                                    271
```

```
SEQ ID NO: 238            moltype = DNA  length = 747
FEATURE                   Location/Qualifiers
misc_feature              1..747
                          note = Humanized C2 single chain GS3
source                    1..747
                          mol_type = other DNA
                          organism = synthetic construct
SEQUENCE: 238
gaggtgcagc tggtggagtc tgggggaggc ctggtcaagc ctggggggtc cctgagactc   60
tcctgtgcag cctctggatt caccttcagt ggctatgcca tgagctgggt ccgccaggct  120
ccagggaagg gctggagtg gtctcaacc attagtagtg gcggaaccta catatactac   180
cccgactcag tgaagggccg attcaccatc tccagagaca cgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccggcggtg gcggatccgg cggtggcgga tccggcggtg gcggatccga cattgtgctg  420
acccagtctc cagcctcctt ggccgtgtct ccaggacaga gggccaccat cacctgcaga  480
gccagtaaga gtgtcagtac cagcggatac tcctacatgc actggtatca gcagaaacca  540
ggacaacctc ctaaactcct gatttacctg catccaatc tggagagcgg ggtcccagcc  600
aggttcagcg gcagtgggtc tgggaccgat ttcaccctca caattaatcc tgtggaagct  660
aatgatactg caaattatta ctgtcagcac agtagggagc tgccttcac attcggcgga  720
gggaccaagg tggagatcaa acgaact                                     747

SEQ ID NO: 239            moltype = AA  length = 249
FEATURE                   Location/Qualifiers
REGION                    1..249
                          note = Humanized C2 single chain GS3
source                    1..249
                          mol_type = protein
                          organism = synthetic construct
SEQUENCE: 239
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRT                                                          249

SEQ ID NO: 240            moltype = DNA  length = 765
FEATURE                   Location/Qualifiers
misc_feature              1..765
                          note = Humanized C2 single chain IgG (no Cysteine)
source                    1..765
                          mol_type = other DNA
                          organism = synthetic construct
SEQUENCE: 240
gaggtgcagc tggtggagtc tgggggaggc ctggtcaagc ctggggggtc cctgagactc   60
tcctgtgcag cctctggatt caccttcagt ggctatgcca tgagctgggt ccgccaggct  120
ccagggaagg gctggagtg gtctcaacc attagtagtg gcggaaccta catatactac   180
cccgactcag tgaagggccg attcaccatc tccagagaca cgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tccgataaaa cccatactaa accgccaaaa ccggcgccgg aactgctggg tggtcctggt  420
accggtgaca ttgtgctgac ccagtctcca gcctccttgg ccgtgtctcc aggacagagg  480
gccaccatca cctgcagagc cagtaagagt gtcagtacca gcggatactc ctacatgcac  540
tggtatcagc agaaaccagg acaacctcct aaactcctga tttacctggc atccaatctg  600
gagagcgggg tcccagccag gttcagcggc agtgggtctg ggaccgattt caccctcaca  660
attaatcctg tggaagccta atgatactgca aattattact gtcagcacag tagggagctg  720
cctttcacat tcggcggagg gaccaaggtg gagatcaaac gaact                 765

SEQ ID NO: 241            moltype = AA  length = 255
FEATURE                   Location/Qualifiers
REGION                    1..255
                          note = Humanized C2 single chain IgG (no Cysteine)
source                    1..255
                          mol_type = protein
                          organism = synthetic construct
SEQUENCE: 241
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYFDV WGKGTTVTVS  120
SDKTHTKPPK PAPELLGGPG TGDIVLTQSP ASLAVSPGQR ATITCRASKS VSTSGYSYMH  180
WYQQKPGQPP KLLIYLASNL ESGVPARFSG SGSGTDFTLT INPVEANDTA NYYCQHSREL  240
PFTFGGGTKV EIKRT                                                   255

SEQ ID NO: 242            moltype = DNA  length = 831
FEATURE                   Location/Qualifiers
misc_feature              1..831
                          note = Humanized C2 single chain X4 (linker is IgG1 and
                          IgG2 modifiedhinge region)
source                    1..831
```

```
                        mol_type = other DNA
                        organism = synthetic construct
SEQUENCE: 242
gaggtgcagc tggtggagtc tggggggaggc ctggtcaagc ctgggggggtc cctgagactc    60
tcctgtgcag cctctggatt cacccttcagt ggctatgcca tgagctgggt ccgccaggct   120
ccagggaagg ggctggagtg ggtctcaacc attagtagtg gcggaaccta catatactac   180
cccgactcag tgaagggccg attcaccatc tccagagaca cgccaagaa ctcactgtat   240
ctgcaaatga acagcctgag agccgaggac acggccgtgt attactgtgc gagacttggg   300
ggggataatt actacgaata cttcgatgtc tgggggcaaag ggaccacggt caccgtctcc   360
tccgataaaa cccatactaa accgccaaaa ccggcgccaaa aactgctggg tggtcctggt   420
accggtactg tggtccgac tattaaacct ccgaaacctc cgaaacctgc tccgaacctg   480
ctgggtggtc cggacattgt gctgacccag tctccagcct ccttggccgt gtctccagga   540
cagagggcca ccatcacctg cagagccagt aagagtgtca gtaccagcgg atactcctac   600
atgcactggt atcagcagaa accaggacaa cctcctaaac tcctgattta cctggcatcc   660
aatctggaga gcggggtccc agccaggttc agcggcagtg ggtctgggac cgatttcacc   720
ctcacaatta tcctgtgga agctaatgat actgcaaatt attactgtca gcacagtagg   780
gagctgcctt tcacattcgg cggagggacc aaggtggaga tcaaacgaac t            831

SEQ ID NO: 243          moltype = AA  length = 277
FEATURE                 Location/Qualifiers
REGION                  1..277
                        note = Humanized C2 single chain X4 (linker is IgG1 and
                        IgG2 modifiedhinge region)
source                  1..277
                        mol_type = protein
                        organism = synthetic construct
SEQUENCE: 243
EVQLVESGGG LVKPGGSLRL SCAASGFTFS GYAMSWVRQA PGKGLEWVST ISSGGTYIYY      60
PDSVKGRFTI SRDNAKNSLY LQMNSLRAED TAVYYCARLG GDNYYEYFDV WGKGTTVTVS    120
SDKTHTKPPK PAPELLGGPG TGTGGPTIKP PKPPKPAPNL LGGPDIVLTQ SPASLAVSPG    180
QRATITCRAS KSVSTSGYSY MHWYQQKPGQ PPKLLIYLAS NLESGVPARF SGSGSGTDFT    240
LTINPVEAND TANYYCQHSR ELPFTFGGGT KVEIKRT                             277

SEQ ID NO: 244          moltype = DNA  length = 744
FEATURE                 Location/Qualifiers
misc_feature            1..744
                        note = Humanized C3 single chain GS3
source                  1..744
                        mol_type = other DNA
                        organism = synthetic construct
SEQUENCE: 244
caggttcagc tggtgcagtc tggagctgag gtgaagaagc ctggggcctc agtgaaggtc     60
tcctgcaagg cttctggtta cacctttacc gactacgcca tgaactgggt gcgacaggcc   120
cctggacaag gcttgagtg gatgggagtg atcagcacct tcagcggtaa cacaaacttc   180
aaccagaagt tcaagggcag agtcaccatg accacagaca catccacgag cacagcctac   240
atggagctga ggagcctgag atctgacgac acggccgtgt attactgtgc gagaagcgac   300
tactacggcc catacttcga ctactggggc cagggcacca cctgaccgt gtccagcggc   360
ggtggcggat ccggcggtgg cggatccggc ggtggcggat ccgatattgt gatgacccag   420
actccactct ctctgtccgt cacccctgga cagccggcct ccatctcctg caggtctagt   480
cagaccattg tccatagtaa tggaaacacc tatttggagt ggtacctgca aagccaggc   540
cagtctccac agctcctgat ctataaggtt tccaacctt tctctggagt gccagatagg   600
ttcagtggca gcgggtcagg gacagatttc acactgaaaa tcagccggt ggaggctgag   660
gatgttgggg tttattactg cttccaaggt agcacgtgc ctttcacctt cggcgaggg   720
accaaggtgg agatcaaacg aact                                          744

SEQ ID NO: 245          moltype = AA  length = 248
FEATURE                 Location/Qualifiers
REGION                  1..248
                        note = Humanized C3 single chain GS3
source                  1..248
                        mol_type = protein
                        organism = synthetic construct
SEQUENCE: 245
QVQLVQSGAE VKKPGASVKV SCKASGYTFT DYAMNWVRQA PGQGLEWMGV ISTFSGNTNF      60
NQKFKGRVTM TTDTSTSTAY MELRSLRSDD TAVYYCARSD YYGPYFDYWG QGTTLTVSSG    120
GGGSGGGGSG GGGSDIVMTQ TPLSLSVTPG QPASISCRSS QTIVHSNGNT YLEWYLQKPG    180
QSPQLLIYKV SNRFSGVPDR FSGSGSGTDF TLKISRVEAE DVGVYYCFQG SHVPFTFGGG    240
TKVEIKRT                                                             248

SEQ ID NO: 246          moltype = DNA  length = 762
FEATURE                 Location/Qualifiers
misc_feature            1..762
                        note = Humanized C3 single chain IgG1 (no Cysteine)
source                  1..762
                        mol_type = other DNA
                        organism = synthetic construct
SEQUENCE: 246
caggttcagc tggtgcagtc tggagctgag gtgaagaagc ctggggcctc agtgaaggtc     60
tcctgcaagg cttctggtta cacctttacc gactacgcca tgaactgggt gcgacaggcc   120
```

```
cctggacaag ggcttgagtg gatgggagtg atcagcacct tcagcggtaa cacaaacttc   180
aaccagaagt tcaagggcag agtcaccatg accacagaca catccacgag cacagcctac   240
atggagctga ggagcctgag atctgacgac acggccgtgt attactgtgc gagaagcgac   300
tactacggcc catacttcga ctactggggc cagggcacca ccctgaccgt gtccagcgat   360
aaacccata ctaaaccgcc aaaaccggcg ccggaactgc tgggtggtcc tggtaccggt   420
gatattgtga tgacccagac tccactctct ctgtccgtca cccctggaca gccggcctcc   480
atctcctgca ggtctagtca gaccattgtc catagtaatg gaaacaccta tttggagtgg   540
tacctgcaga agccaggcca gtctccacag ctcctgatct ataaggtttc caaccggttc   600
tctggagtgc cagataggtt cagtggcagc gggtcaggga cagatttcac actgaaaatc   660
agccgggtgg aggctgagga tgttggggtt tattactgct tccaaggtag ccacgtgcct   720
ttcacccttcg gcggaggac caaggtggag atcaaacgaa ct                     762

SEQ ID NO: 247        moltype = AA   length = 254
FEATURE               Location/Qualifiers
REGION                1..254
                      note = Humanized C3 single chain IgG1 (no Cysteine)
source                1..254
                      mol_type = protein
                      organism = synthetic construct
SEQUENCE: 247
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSSD   120
KTHTKPPKPA PELLGGPGTG DIVMTQTPLS LSVTPGQPAS ISCRSSQTIV HSNGNTYLEW   180
YLQKPGQSPQ LLIYKVSNRF SGVPDRFSGS GSGTDFTLKI SRVEAEDVGV YYCFQGSHVP   240
FTFGGGTKVE IKRT                                                    254

SEQ ID NO: 248        moltype = DNA   length = 828
FEATURE               Location/Qualifiers
misc_feature          1..828
                      note = Humanized C3 single chain X4 (linker is IgG1 and
                      IgG2 modifiedhinge region)
source                1..828
                      mol_type = other DNA
                      organism = synthetic construct
SEQUENCE: 248
caggttcagc tggtgcagtc tggagctgag gtgaagaagc ctggggcctc agtgaaggtc   60
tcctgcaagg cttctggtta cacctttacc gactacgcca tgaactgggt gcgacaggcc   120
cctggacaag ggcttgagtg gatgggagtg atcagcacct tcagcggtaa cacaaacttc   180
aaccagaagt tcaagggcag agtcaccatg accacagaca catccacgag cacagcctac   240
atggagctga ggagcctgag atctgacgac acggccgtgt attactgtgc gagaagcgac   300
tactacggcc catacttcga ctactggggc cagggcacca ccctgaccgt gtccagcgat   360
aaacccata ctaaaccgcc aaaaccggcg ccggaactgc tgggtggtcc tggtaccggt   420
actggtggtc cgactattaa acctccgaaa cctccgaaac ctgctgggt                480
ggtccggata ttgtgatgac ccagactcca ctctctctgt ccgtcacccc tggacagccg   540
gcctccatct cctgcaggtc tagtcagacc attgtccata gtaatggaaa cacctatttg   600
gagtggtacc tgcagaagcc aggccagtct ccacagctcc tgatctataa ggtttccaac   660
cggttctctg gagtgccaga taggttcagt ggcagcgggt cagggacaga tttcacactg   720
aaaatcagcc gggtggaggc tgaggatgtt ggggtttatt actgcttcca aggtagccac   780
gtgcctttca ccttcggcgg agggaccaag gtggagatca aacgaact               828

SEQ ID NO: 249        moltype = AA   length = 276
FEATURE               Location/Qualifiers
REGION                1..276
                      note = Humanized C3 single chain X4 (linker is IgG1 and
                      IgG2 modifiedhinge region)
source                1..276
                      mol_type = protein
                      organism = synthetic construct
SEQUENCE: 249
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSSD   120
KTHTKPPKPA PELLGGPGTG TGGPTIKPPK PPKPAPNLLG GPDIVMTQTP LSLSVTPGQP   180
ASISCRSSQT IVHSNGNTYL EWYLQKPGQS PQLLIYKVSN RFSGVPDRFS GSGSGTDFTL   240
KISRVEAEDV GVYYCFQGSH VPFTFGGGTK VEIKRT                            276

SEQ ID NO: 250        moltype = DNA   length = 741
FEATURE               Location/Qualifiers
misc_feature          1..741
                      note = Humanized C8 single chain GS3 (linker is [Gly4Ser1]3)
source                1..741
                      mol_type = other DNA
                      organism = synthetic construct
SEQUENCE: 250
gaggtgcagc tggtggagtc tgggggaggc ctggtcaagc ctggggggtc cctgagactc   60
tcctgtgcag cctctggatt caccttcagt ggctatgcca tgagctgggt ccgccaggct   120
ccagggaagg gctggagtg gtgtccaacc attagtagtg gcggaaccta catatactac   180
cctgactcag tgaagggccg attcaccatc tccagagaca acgccaagaa ctcactgtat   240
ctgcaaatga acagcctgag agccgaggac acggccgtgt attactgtgc gagactgggc   300
ggcgataact attatgaata ttggggcaaa gggaccacgg tcaccgtctc ctcgggcggt   360
```

```
ggcggatccg gcggtggcgg atccggcggt ggcggatccg acatcgtgat gacccagtct   420
ccagactccc tggctgtgtc tctgggcgag agggccacca tcaactgcag ggccagcaag   480
agtgttagca ccagcggcta cagctacatg cactggtacc agcagaaacc aggacagcct   540
cctaagctgc tcatttacct ggtgtctaac ctggaatccg gggtccctga ccgattcagt   600
ggcagcgggt ctgggacaga tttcactctc accatcagca gcctgcaggc tgaagatgtg   660
gcagtttatt actgtcaaca cattcgggaa ctgaccagga gtgaattcgg cggagggacc   720
aaggtggaga tcaaacgaac t                                             741
```

```
SEQ ID NO: 251          moltype = AA   length = 247
FEATURE                 Location/Qualifiers
REGION                  1..247
                        note = Humanized C8 single chain GS3 (linker is [Gly4Ser1]3)
source                  1..247
                        mol_type = protein
                        organism = synthetic construct
SEQUENCE: 251
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSSGG   120
GGSGGGGSGG GGSDIVMTQS PDSLAVSLGE RATINCRASK SVSTSGYSYM HWYQQKPGQP   180
PKLLIYLVSN LESGVPDRFS GSGSGTDFTL TISSLQAEDV AVYYCQHIRE LTRSEFGGGT   240
KVEIKRT                                                             247
```

```
SEQ ID NO: 252          moltype = DNA   length = 759
FEATURE                 Location/Qualifiers
misc_feature            1..759
                        note = Humanized C8 single chain IgG1 (no Cysteine)
source                  1..759
                        mol_type = other DNA
                        organism = synthetic construct
SEQUENCE: 252
gaggtgcagc tggtggagtc tgggggaggc ctggtcaagc ctgggggtc cctgagactc     60
tcctgtgcag cctctggatt caccttcagt ggctatgcca tgagctgggt ccgccaggct   120
ccagggaagg ggctggagtg ggtctcaacc attagtagtg gcggaaccta catatactac   180
cctgactcag tgaagggccg attcaccatc tccagagaca cgccaagaa ctcactgtat    240
ctgcaaatga acagcctgag agccgaggac acggccgtgt attactgtgc gagactgggc   300
ggcgataact attatgaata ttggggcaaa gggaccacgg tcaccgtctc ctccgataaa   360
acccatacta aaccgccaaa accggcgccg gaactgctgg gtggtcctgg taccggtgac   420
atcgtgatga cccagtctcc agactccctg gctgtgtctc tgggcgagag gccaccatc    480
aactgcagg ccagcaagag tgttagcacc agcggctaca gctacatgca ctggtaccag    540
cagaaaccag gacagcctcc taagctgctc atttacctgg tgtctaacct ggaatccggg   600
gtccctgacc gattcagtgg cagcgggtct gggacagatt tcactctcac catcagcagc   660
ctgcaggctg aagatgtggc agtttattac tgtcaacaca ttcgggaact gaccaggagt   720
gaattcggcg gagggaccaa ggtggagatc aaacgaact                          759
```

```
SEQ ID NO: 253          moltype = AA   length = 253
FEATURE                 Location/Qualifiers
REGION                  1..253
                        note = Humanized C8 single chain IgG1 (no Cysteine)
source                  1..253
                        mol_type = protein
                        organism = synthetic construct
SEQUENCE: 253
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSSDK   120
THTKPPKPAP ELLGGPGTGD IVMTQSPDSL AVSLGERATI NCRASKSVST SGYSYMHWYQ   180
QKPGQPPKLL IYLVSNLESG VPDRFSGSGS GTDFTLTISS LQAEDVAVYY CQHIRELTRS   240
EFGGGTKVEI KRT                                                      253
```

```
SEQ ID NO: 254          moltype = DNA   length = 825
FEATURE                 Location/Qualifiers
misc_feature            1..825
                        note = Humanized C8 single chain X4 (linker is IgG1 and
                        IgG2 modifiedhinge region)
source                  1..825
                        mol_type = other DNA
                        organism = synthetic construct
SEQUENCE: 254
gaggtgcagc tggtggagtc tgggggaggc ctggtcaagc ctgggggtc cctgagactc     60
tcctgtgcag cctctggatt caccttcagt ggctatgcca tgagctgggt ccgccaggct   120
ccagggaagg ggctggagtg ggtctcaacc attagtagtg gcggaaccta catatactac   180
ccagactcag tgaagggccg attcaccatc tccagagaca cgccaagaa ctcactgtat    240
ctgcaaatga acagcctgag agccgaggac acggccgtgt attactgtgc gagactgggc   300
ggcgacaatt actatgagta ttggggcaaa gggaccacgg tcaccgtctc ctccgataaa   360
acccatacta aaccgccaaa accggcgccg gaactgctgg gtggtcctgg taccggtact   420
ggtggtccga ctattaaacc tcgaaacct ccgaaacctg ctccgaacct gctgggtggt   480
ccggacatcg tgatgaccca gtctccagac tccctggctg tgtctctggg cgagagggcc   540
accatcaact gcagggccag caagagtgtt agcaccagcg gctacagcta catgcactgg   600
taccagcaga aaccaggaca gcctcctaag ctgctcattt acctggtgtc taacctggaa   660
tccggggtcc ctgaccgatt cagtggcagc gggtctggga cagatttcac tctcaccatc   720
```

```
agcagcctgc aggctgaaga gtgtggcagtt tattactgtc aacacattcg ggaactgacc   780
aggagtgaat tcggcggagg gaccaaggtg gagatcaaac gaact                    825

SEQ ID NO: 255         moltype = AA   length = 275
FEATURE                Location/Qualifiers
REGION                 1..275
                       note = Humanized C8 single chain X4 (linker is IgG1 and
                       IgG2 modifiedhinge region)
source                 1..275
                       mol_type = protein
                       organism = synthetic construct
SEQUENCE: 255
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYWGK GTTVTVSSDK  120
THTKPPKPAP ELLGGPGTGT GGPTIKPPKP PKPAPNLLGG PDIVMTQSPD SLAVSLGERA  180
TINCRASKSV STSGYSYMHW YQQKPGQPPK LLIYLVSNLE SGVPDRFSGS GSGTDFTLTI  240
SSLQAEDVAV YYCQHIRELT RSEFGGGTKV EIKRT                             275

SEQ ID NO: 256         moltype = DNA   length = 1509
FEATURE                Location/Qualifiers
misc_feature           1..1509
                       note = pSECTag2 E6 scFV-FC
source                 1..1509
                       mol_type = other DNA
                       organism = synthetic construct
SEQUENCE: 256
atggagacag acacactcct gctatgggta ctgctgctct ggttccagg ttccactggt    60
gacgcggccc agccggccga ggtgcagctg gtggagtctg ggggaggcct ggtcaagcct  120
gggggggtccc tgagactctc ctgtgcagcc tctggattca ccttcagtag gtatggcatg  180
agctgggtcc gccaggctcc agggaagagg ctggagtggg tctcaaccat tagtggcggt  240
ggcacctaca tatactaccc agactcagtg aagggccgat tcaccatctc cagagacaac  300
gccaagaaca ccctgtatct gcaaatgaac agcctgagag ccgaggacac ggctgtgtat  360
tactgtacca gagataacta tggccgcaac tatgattatg catggattag ttggggccag  420
ggcaccctgg tgaccgtgag cagcggcggt ggcggatccg gcgtggcgg atccggcggt  480
ggcgatccg aaattgtgtt gacacagtct ccagccaccc tgtctttgtc tccagggaa    540
agagccaccc tcacctgcag cgccaccagc agtgttagct acatccactg gtaccaacag  600
aggcctggcc agagcccag gctcctcatc tatagccct ccaacctggc cagcggcatc   660
ccagccaggt tcagtggcag tgggtctggg acagactaca ctctcaccat cagcagccta  720
gagcctgaag attttgcagt ttattactgt cagcagcgta gcagctcccc tttcaccttt  780
ggcagcggca ccaaagtgga aattaaagag cccaaatctt gtgacaaaac tcacacatgc  840
ccaccgtgcc cagcacctga actcctgggg ggaccgtcag tcttcctctt ccccccaaaa  900
cccaaggaca cctctcatgat ctcccggacc cctgaggtca catgcgtggt ggtggacgtg  960
agccacgaag accctgaggt caagttcaac tggtacgtgg acggcgtgga ggtgcataat 1020
gccaagacaa agccgcggga ggagcagtac aacagcacgt accgtgtggt cagcgtcctc 1080
accgtcctgc accaggactg gctgaatggc aaggagtaca gtgcaaggt ctccaacaaa  1140
gccctcccag ccccatcga gaaaaccatc tccaaagcca agggcagcc ccgagaacca   1200
caggtgtaca ccctgccccc atcccggag gagatgacca agaaccaggt cagcctgacc  1260
tgcctggtca aaggcttcta tcccagcgac atcgccgtgg agtgggagag caatgggcag  1320
ccggagaaca actacaagac cacgcctccc gtgctggact ccgacggctc cttcttcctc  1380
tacagcaagc tcaccgtgga caagagcagg tggcagcagg ggaacgtctt ctcatgctcc  1440
gtgatgcatg aggctctgca caaccactac acgcagaaga gcctctccct gtctccgggt  1500
aaatgataa                                                         1509

SEQ ID NO: 257         moltype = AA   length = 501
FEATURE                Location/Qualifiers
REGION                 1..501
                       note = pSECTag2 E6 scFV-FC
source                 1..501
                       mol_type = protein
                       organism = synthetic construct
SEQUENCE: 257
METDTLLLWV LLLWVPGSTG DAAQPAEVQL VESGGGLVKP GGSLRLSCAA SGFTFSRYGM   60
SWVRQAPGKR LEWVSTISGG GTYIYYPDSV KGRFTISRDN AKNTLYLQMN SLRAEDTAVY  120
YCTRDNYGRN YDYGMDYWGQ GTLVTVSSGG GGSGGGGSGG GGSEIVLTQS PATLSLSPGE  180
RATLTCSATS SVSYIHWYQQ RPGQSPRLLI YSTSNLASGI PARFSGSGSG SDYTLTISSL  240
EPEDFAVYYC QQRSSSPFTF GSGTKVEIKE PKSCDKTHTC PPCPAPELLG GPSVFLFPPK  300
PKDTLMISRT PEVTCVVVDV SHEDPEVKFN WYVDGVEVHN AKTKPREEQY NSTYRVVSVL  360
TVLHQDWLNG KEYKCKVSNK ALPAPIEKTI SKAKGQPREP QVYTLPPSRE EMTKNQVSLT  420
CLVKGFYPSD IAVEWESNGQ PENNYKTTPP VLDSDGSFFL YSKLTVDKSR WQQGNVFSCS  480
VMHEALHNHY TQKSLSLSPG K                                            501

SEQ ID NO: 258         moltype = DNA   length = 496
FEATURE                Location/Qualifiers
misc_feature           1..496
                       note = E6 scFC-FC 1 gBLOCk sequence
source                 1..496
                       mol_type = other DNA
                       organism = synthetic construct
SEQUENCE: 258
```

```
tgctctgggt tccaggttcc actggtgacg cggcccagcc ggccgaggtg cagctggtgg    60
agtctggggg aggcctggtc aagcctgggg ggtccctgag actctcctgt gcagcctctg   120
gattcacctt cagtaggtat ggcatgagct gggtccgcca ggctccaggg aagaggctgg   180
agtgggtctc aaccattagt ggcggaggca cctacatata ctacccagac tcagtgaagg   240
gccgattcac catctccaga gacaacgcca agaacacgct gtatctgcaa atgaacagcc   300
tgagagccga ggacacggct gtgtattact gtaccagaga taactatggc cgcaactatg   360
attatggcat ggattattgg ggccaggca ccctggtgac cgtgagcagc ggcggtggcg    420
gatccggcgt tggcggatcc ggcggtggcg atccgaaat tgtgttgaca cagtctccag    480
ccaccctgtc tttgtc                                                   496

SEQ ID NO: 259          moltype = DNA  length = 583
FEATURE                 Location/Qualifiers
misc_feature            1..583
                        note = E6 scFC-FC 2 gBLOCk sequence
source                  1..583
                        mol_type = other DNA
                        organism = synthetic construct
SEQUENCE: 259
aattgtgttg acacagtctc cagccaccct gtctttgtct ccaggggaaa gagccaccct    60
cacctgcagc gccaccagca gtgttagcta catccactgg taccaacaga ggcctggcca   120
gagcccagg ctcctcatct atagcaccctc caacctggcc agcggcatcc cagccaggtt   180
cagtggcagt gggtctggga cgactacac tctcaccatc agcagcctag agcctgaaga   240
ttttgcagtt tattactgtc agcagcgtag cagctcccct ttcacctttg gcagcggcac   300
caaagtggaa attaaagagc ccaaatcttg tgacaaaact cacacatgcc caccgtgccc   360
agcacctgaa ctcctggggg gaccgtcagt cttcctcttc ccccaaaaac ccaaggacac   420
cctcatgatc tcccggaccc ctgaggtcac atgcgtggtg gtggacgtga gccacgaaga   480
ccctgaggtc aagttcaact ggtacgtgga cggcgtggag gtgcataatg ccaagacaaa   540
gccgcgggag gagcagtaca acagcacgta ccgtgtggtc agc                     583

SEQ ID NO: 260          moltype = DNA  length = 1527
FEATURE                 Location/Qualifiers
misc_feature            1..1527
                        note = pSECTag2 C2 scFV-FC
source                  1..1527
                        mol_type = other DNA
                        organism = synthetic construct
SEQUENCE: 260
atggagacag acacactcct gctatgggta ctgctgctct gggttccagg ttccactggt    60
gacgcggccc agccggccga ggtgcagctg gtggagtctg ggggaggcct ggtcaagcct   120
gggggggtccc tgagactctc ctgtgcagcc tctggattca ccttcagtgg ctatgccatg   180
agctgggtcc gccaggctcc agggaagggg ctggagtggg tctcaaccat tagtagtggc   240
ggaacctaca tatactaccc cgactcagtg aagggccgat tcaccatctc cagagacaac   300
gccaagaact cactgtatct gcaaatgaac agcctgagac ccgaggacac ggctgtgtat   360
tactgtgcga gacttggggg ggataattac tacgaatact cgatgtctg gggcaaaggg    420
accacggtca ccgtctcctc cggcggtggc ggatccggcg tggcggatc cggcggtggc   480
ggatccgaca ttgtgctgac ccagtctcca gcctccttgg ccgtgtctcc aggacagagg   540
gccaccatca cctgcagagc cagtaagagt gtcagtacca gcggatactc ctacatgcac   600
tggtatcagc agaaaccagg acaacctcct aaactcctga tttacctggc atccaatctg   660
gagagcgggg tcccagccag gttcagcgga agtgggtctg ggaccgattt cacctctcaca   720
attaatcctg tggaagctaa tgatactgca attattact gtcagcacag tagggagctg    780
cctttcacat tcggcggagg gaccaaggtg gagatcaagc gaaatcttgt                840
gacaaaactc acacatgccc accgtgccca gcacctgaac tcctgggggg accgtcagtc    900
ttcctcttcc cccaaaaccc aaggacacc tcatgatctc cccggaccccc tgaggtcaca   960
tgcgtggtgg tggacgtgag ccacgaagac cctgaggtca agttcaactg gtacgtggac   1020
ggcgtggagg tgcataatgc caagacaaag ccgcggagg agcagtacaa cagcacgtac   1080
cgtgtggtca gcgtcctcac cgtcctgcac caggactggc tgaatggcaa ggagtacaag   1140
tgcaaggtct ccaacaaagc cctcccagcc cccatcgaga aaaccatctc caaagccaaa   1200
gggcagcccc gagaaccaca ggtgtacacc ctgcccccat cccgggagga gatgaccaag   1260
aaccaggtca gcctgacctg cctggtcaaa ggcttctatc ccagcgacat cgccgtggag   1320
tgggagagca atgggcagcc ggagaacaac tacaagacca cgcctcccgt gctggactcc   1380
gacggctcct tcttcctcta cagcaagctc accgtggaca agagcaggtg gcagcagggg   1440
aacgtcttct catgctccgt gatgcatgag gctctgcaca accactacac gcagaagagc   1500
ctctccctgt ctccgggtaa atgataa                                        1527

SEQ ID NO: 261          moltype = AA  length = 507
FEATURE                 Location/Qualifiers
REGION                  1..507
                        note = pSECTag2 C2 scFV-FC
source                  1..507
                        mol_type = protein
                        organism = synthetic construct
SEQUENCE: 261
METDTLLLWV LLLWVPGSTG DAAQPAEVQL VESGGGLVKP GGSLRLSCAA SGFTFSGYAM    60
SWVRQAPGKG LEWVSTISSG GTYIYYPDSV KGRFTISRDN AKNSLYLQMN SLRAEDTAVY   120
YCARLGGDNY YEYFDVWGKG TTVTVSSGGG GSGGGGSGGG GSDIVLTQSP ASLAVSPGQR   180
ATITCRASKS VSTSGYSYMH WYQQKPGQPP KLLIYLASNL ESGVPARFSG SGSGTDFTLT   240
INPVEANDTA NYYCQHSREL PFTFGGGTKV EIKRTEPKSC DKTHTCPPCP APELLGGPSV   300
FLFPPKPKDT LMISRTPEVT CVVVDVSHED PEVKFNWYVD GVEVHNAKTK PREEQYNSTY   360
RVVSVLTVLH QDWLNGKEYK CKVSNKALPA PIEKTISKAK GQPREPQVYT LPPSREEMTK   420
```

```
NQVSLTCLVK GFYPSDIAVE WESNGQPENN YKTTPPVLDS DGSFFLYSKL TVDKSRWQQG   480
NVFSCSVMHE ALHNHYTQKS LSLSPGK                                       507

SEQ ID NO: 262            moltype = DNA   length = 487
FEATURE                   Location/Qualifiers
misc_feature              1..487
                          note = C2 scFV-FC 1 gBLOCk sequence
source                    1..487
                          mol_type = other DNA
                          organism = synthetic construct
SEQUENCE: 262
tgctctgggt tccaggttcc actggtgacg cggcccagcc ggccgaggtg cagctggtgg    60
agtctggggg aggcctggtc aagcctgggg ggtccctgag actctcctgt gcagcctctg   120
gattcacctt cagtggctat gccatgagct gggtccgcca ggctccaggg aaggggctgg   180
agtgggtctc aaccattagt agtggcgaa cctacatata ctaccccgac tcagtgaagg    240
gccgattcac catctccaga gacaacgcca agaactcact gtatctgcaa atgaacagcc   300
tgagagccga ggacacggcc gtgtattact gtgcagact ggggggat aattactacg      360
aatacttcga tgtctgggc aaagggacca cggtcaccgt ctcctccggc ggtggcggat    420
ccggcggtgg cggatccggc ggtggcggat ccgacattgt gctgacccag tctccagcct   480
ccttggc                                                             487

SEQ ID NO: 263            moltype = DNA   length = 604
FEATURE                   Location/Qualifiers
misc_feature              1..604
                          note = C2 scFV-FC 2 gBLOCk sequence
source                    1..604
                          mol_type = other DNA
                          organism = synthetic construct
SEQUENCE: 263
cattgtgctg acccagtctc cagcctcctt ggccgtgtct ccaggacaga gggccaccat    60
cacctgcaga gccagtaaga gtgtcagtac cagcggatac tcctacatgc actggtatca   120
gcagaaacca ggacaacctc ctaaactcct gatttacctg gcatccaatc tggagagcgg   180
ggtcccagcc aggttcagcg gcagtgggtc tgggaccgat ttcaccctca caattaatcc   240
tgtggaagct aatgatactg caaattatta ctgtcagcac agtagggagc tgcctttcac   300
attcggccag gggaccaagg tggagatcaa acgaactgag cccaaatctt gtgacaaaac   360
tcacacatgc ccaccgtgcc cagcacctga actcctgggg ggaccgtcag tcttcctctt   420
cccccaaaa cccaaggaca ccctcatgat ctcccggacc cctgaggtca catgcgtggt    480
ggtggacgtg agccacgaag accctgaggt caagttcaac tggtacgtgg acggcgtgga   540
ggtgcataat gccaagacaa agccgcggga ggagcagtac aacagcacgt accgtgtggt   600
cagc                                                                604

SEQ ID NO: 264            moltype = DNA   length = 1524
FEATURE                   Location/Qualifiers
misc_feature              1..1524
                          note = pSECTag2 C3 scFV-FC
source                    1..1524
                          mol_type = other DNA
                          organism = synthetic construct
SEQUENCE: 264
atggagacag acacactcct gctatgggta ctgctgctct gggttccagg ttccactggt    60
gacgcggccc agccggccca ggttcagctg gtgcagtctg gagctgaggt gaagaagcct   120
ggggcctcag tgaaggtctc ctgcaaggct tctggttaca cctttaccga ctacgccatg   180
aactgggtgc gacaggcccc tggacaaggg cttgagtgga tgggagtgat cagcaccttc   240
agcggtaaca caaacttcaa ccagaagttc aagggcagag tcaccatgac cacagacaca   300
tccacgagca cagcctacat ggagctgagg agcctgagat ctgacgacac ggccgtgtat   360
tactgtgcga aagcgactac tacggcccca tacttcgact actggggcca gggcaccacc   420
ctgaccgtgt ccagcggcgg tggcggatcc ggcggtggcg gatccggcgg tggcggatcc   480
gatattgtga tgacccagac tccactctct ctgtccgtca cccctggaca gccggcctcc   540
atctcctgca ggtctagtca gaccattgtc catagtaatg gaaacaccta tttggagtgg   600
tacctgcaga agccaggcca gtctccacag ctcctgatct ataaggtttc caaccggttc   660
tctggagtgc cagataggtt cagtggcagc gggtcaggga cagatttcac actgaaaatc   720
agccgggtgg aggctgagga tgttggggtt tattactgct tccaaggtag ccacgtgcct   780
ttcaccttcg gcgagggac caaggtggag atcaaacgaa ctgagcccaa atcttgtgac   840
aaaactcaca catgcccacc gtgcccagca cctgaactcc tggggggacc gtcagtcttc   900
ctcttccccc caaaacccaa ggacaccctc atgatctccc ggaccctga ggtcacatgc    960
gtggtggtgg acgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtctcca acaaagccct cccagccccc atcgagaaaa ccatctccaa agccaaaggg   1200
cagccccgag aaccacaggt gtacaccctg cccccatccc gggaggagat gaccaagaac   1260
caggtcagcc tgacctgcct ggtcaaaggc ttctatccca gcgacatcgc cgtggagtgg   1320
gagagcaatg gcagccggga gaacaactac aagaccacgc ctcccgtgct ggactccgac   1380
ggctccttct tcctctacag caagctcacc gtggacaaga gcaggtggca gcaggggaac   1440
gtcttctcat gctccgtgat gcatgaggct ctgcacaacc actacacgca gaagagcctc   1500
tccctgtctc cgggtaaatg ataa                                         1524

SEQ ID NO: 265            moltype = AA   length = 506
FEATURE                   Location/Qualifiers
REGION                    1..506
```

|  | note = pSECTag2 C3 scFV-FC |  |
| --- | --- | --- |
| source | 1..506 |  |
|  | mol_type = protein |  |
|  | organism = synthetic construct |  |

SEQUENCE: 265

```
METDTLLLWV LLLWVPGSTG DAAQPAQVQL VQSGAEVKKP GASVKVSCKA SGYTFTDYAM  60
NWVRQAPGQG LEWMGVISTF SGNTNFNQKF KGRVTMTTDT STSTAYMELR SLRSDDTAVY  120
YCARSDYYGP YFDYWGQGTT LTVSSGGGGS GGGGSGGGGS DIVMTQTPLS LSVTPGQPAS  180
ISCRSSQTIV HSNGNTYLEW YLQKPGQSPQ LLIYKVSNRF SGVPDRFSGS GSGTDFTLKI  240
SRVEAEDVGV YYCFQGSHVP FTFGGGTKVE IKRTEPKSCD KTHTCPPCPA PELLGGPSVF  300
LFPPKPKDTL MISRTPEVTC VVVDVSHEDP EVKFNWYVDG VEVHNAKTKP REEQYNSTYR  360
VVSVLTVLHQ DWLNGKEYKC KVSNKALPAP IEKTISKAKG QPREPQVYTL PPSREEMTKN  420
QVSLTCLVKG FYPSDIAVEW ESNGQPENNY KTTPPVLDSD GSFFLYSKLT VDKSRWQQGN  480
VFSCSVMHEA LHNHYTQKSL SLSPGK                                     506
```

|  |  |
| --- | --- |
| SEQ ID NO: 266 | moltype = DNA length = 480 |
| FEATURE | Location/Qualifiers |
| misc_feature | 1..480 |
|  | note = C3 GS scFV FC 1 gBLOCk sequence |
| source | 1..480 |
|  | mol_type = other DNA |
|  | organism = synthetic construct |

SEQUENCE: 266

```
tgctctgggt tccaggttcc actggtgacg cggcccagcc ggcccaggtt cagctggtgc   60
agtctggagc tgaggtgaag aagcctgggg cctcagtgaa ggtctcctgc aaggcttctg  120
gttacaccct taccgactac gccatgaact gggtgcgaca agggcttg              180
agtggatggg agtgatcagc accttcagcg gtaacacaaa cttcaaccag aagttcaagg  240
gcagagtcac catgaccaca gacacatcca cgagcacagc ctacatggag ctgaggagcc  300
tgagatctga cgacacggcc gtgtattact gtgcgagaag cgactactac ggcccatact  360
tcgactactg gggccagggc accaccctga ccgtgtccag cggcggtggc ggatccggcg  420
gtggcggatc cggcggtggc ggatccgata tgtgatgac ccagactcca ctctctctgt  480
```

|  |  |
| --- | --- |
| SEQ ID NO: 267 | moltype = DNA length = 607 |
| FEATURE | Location/Qualifiers |
| misc_feature | 1..607 |
|  | note = C3 scFV FC2 gBLOCk sequence |
| source | 1..607 |
|  | mol_type = other DNA |
|  | organism = synthetic construct |

SEQUENCE: 267

```
tattgtgatg acccagactc cactctctct gtccgtcacc cctggacagc cggcctccat   60
ctcctgcagg tctagtcaga ccattgtcca tagtaatgga acacctattt ggagtggta  120
cctgcagaag ccaggccagt ctccacagct cctgatctat aaggtttcca accggttctc  180
tggagtgcca gataggttca gtggcagcgg gtcaggaca gatttcacac tgaaaatcag  240
ccgggtggag gctgaggatg ttgggggttta ttactgcttc caaggtagcc acgtgccttt  300
cacccttcggc ggagggacca aggtggagat caaacgaact gagcccaaat cttgtgacaa  360
aactcacaca tgcccaccgt gcccagcacc tgaactcctg ggggaccgt cagtcttcct  420
cttcccccca aaacccaagg acaccctcat gatctcccgg acccctgagg tcacatgcgt  480
ggtggtggac gtgagccacg aagaccctga ggtcaagttc aactggtacg tggacggcgt  540
ggaggtgcat aatgccaaga caaagccgcg ggaggagcag tacaacagca cgtaccgtgt  600
ggtcagc                                                          607
```

|  |  |
| --- | --- |
| SEQ ID NO: 268 | moltype = DNA length = 1521 |
| FEATURE | Location/Qualifiers |
| misc_feature | 1..1521 |
|  | note = pSECTag2 C8 scFV-FC |
| source | 1..1521 |
|  | mol_type = other DNA |
|  | organism = synthetic construct |

SEQUENCE: 268

```
atggagacag acacactcct gctatgggta ctgctgctct gggttccagg ttccactggt   60
gacgcggccc agccggccga ggtgcagctg gtggagtctg ggggaggcct ggtcaagcct  120
gggggggtccc tgagactctc ctgtgcagcc tctggattca ccttcagtgg ctatgccatg  180
agctgggtcc gccaggctcc agggaagggg ctggagtggg tctcaaccat tagtagtgga  240
ggaacctaca tatactaccc tgactcagtg aagggccgat tcaccatctc cagagacaac  300
gccaagaact cactgtatct gcaaatgaac agcctgagag ccgaggacac ggccgtgtat  360
tactgtgcga gactggcgg cgataactat tatgaatatt gggcaaagg gaccacggtc  420
accgtctcct ccggcggtgg cggatccggc ggtggcggat ccggcggtgg cggatccgac  480
atcgtgatga cccagtctcc agactccctg gctgtgtctc tgggcgagag ggccaccatc  540
aactgcaggg ccagcaagag tgttagcacc agcggctaca gctacatgca ctggtaccag  600
cagaaaccag gacagcctcc taagctgctc atttacctgg tgtctaacct ggaatccggg  660
gtccctgacc gattcagtgg cagcgggtct gggacagatt tcactctcac catcagcagc  720
ctgcaggctg aagatgtggc agtttattac tgtcaacaca ttcgggaact gaccaggagt  780
gaattgacg gagggaccaa ggtggagatc aaacgaactg agcccaaatc ttgtgacaaa  840
actcacacat gcccaccgtg cccagcacct gaactcctgg ggggaccgtc agtcttcctc  900
ttccccccaa aacccaagga caccctcatg atctcccgga cccctgaggt cacatgcgtg  960
gtggtggacg tgagccacga agaccctgag gtcaagttca actggtacgt ggacggcgtg 1020
gaggtgcata atgccaagac aaagccgcgg gaggagcagt acaacagcac gtaccgtgtg 1080
gtcagcgtcc tcaccgtcct gcaccaggac tggctgaatg gcaaggagta caagtgcaag 1140
```

```
gtctccaaca aagccctccc agcccccatc gagaaaacca tctccaaagc caaagggcag   1200
ccccgagaac cacaggtgta caccctgccc ccatcccggg aggagatgac caagaaccag   1260
gtcagcctga cctgcctggt caaaggcttc tatcccagcg acatcgccgt ggagtgggag   1320
agcaatggtg agccggagaa caactacaag accacgcctc ccgtgctgga ctccgacggc   1380
tccttcttcc tctacagcaa gctcaccgtg gacaagagca ggtggcagca ggggaacgtc   1440
ttctcatgct ccgtgatgca tgaggctctg cacaaccact acacgcagaa gagcctctcc   1500
ctgtctccgg gtaaatgata a                                              1521

SEQ ID NO: 269           moltype = AA  length = 505
FEATURE                  Location/Qualifiers
REGION                   1..505
                         note = pSECTag2 C8 scFV-FC
source                   1..505
                         mol_type = protein
                         organism = synthetic construct
SEQUENCE: 269
METDTLLLWV LLLWVPGSTG DAAQPAEVQL VESGGGLVKP GGSLRLSCAA SGFTFSGYAM    60
SWVRQAPGKG LEWVSTISSG GTYIYYPDSV KGRFTISRDN AKNSLYLQMN SLRAEDTAVY   120
YCARLGGDNY YEYWGKGTTV TVSSGGGGSG GGGSGGGGSD IVMTQSPDSL AVSLGERATI   180
NCRASKSVST SGYSYMHWYQ QKPGQPPKLL IYLVSNLESG VPDRFSGSGS GTDFTLTISS   240
LQAEDVAVYY CQHIRELTRS EFGGGTKVEI KRTEPKSCDK THTCPPCPAP ELLGGPSVFL   300
FPPKPKDTLM ISRTPEVTCV VVDVSHEDPE VKFNWYVDGV EVHNAKTKPR EEQYNSTYRV   360
VSVLTVLHQD WLNGKEYKCK VSNKALPAPI EKTISKAKGQ PREPQVYTLP PSREEMTKNQ   420
VSLTCLVKGF YPSDIAVEWE SNGQPENNYK TTPPVLDSDG SFFLYSKLTV DKSRWQQGNV   480
FSCSVMHEAL HNHYTQKSLS LSPGK                                        505

SEQ ID NO: 270           moltype = DNA  length = 477
FEATURE                  Location/Qualifiers
misc_feature             1..477
                         note = C8 scFV FC 1 gBLOCk sequence
source                   1..477
                         mol_type = other DNA
                         organism = synthetic construct
SEQUENCE: 270
tgctctgggt tccaggttcc actggtgacg cggcccagcc ggccgaggtg cagctggtgg    60
agtctggggg aggcctggtc aagcctgggg ggtccctgag actctcctgt gcagcctctg   120
gattcacctt cagtggctat gccatgagct gggtccgcca ggctcaggga aggggctga   180
agtgggtctc aaccattagt agtggcggaa cctacatata ctacccggac tcagtgaagg   240
gccgattcac catctccaga gacaacgcca agaactcact gtatctgcaa atgaacagcc   300
tgagagccga ggacacggcc gtgtattact gtgcgagact ggggcggcgat aactattatg   360
aatattgggg caagggacc acggtcaccg tctcctccgg cggtggcgga tccggccgtg   420
gcggatccgg cgtggcgga tccgacatcg tgatgaccca gtctccagac tccctgg      477

SEQ ID NO: 271           moltype = DNA  length = 607
FEATURE                  Location/Qualifiers
misc_feature             1..607
                         note = C8 scFV FC2 gBLOCk sequence
source                   1..607
                         mol_type = other DNA
                         organism = synthetic construct
SEQUENCE: 271
catcgtgatg acccagtctc cagactccct ggctgtgtct ctgggcgaga gggccaccat    60
caactgcagg gccagcaaga gtgttagcac cagcggctac agctacatgc actggtacca   120
gcagaaacca ggacagcctc ctaagctgct catttacctg tgtctaaacc tggaatccgg   180
ggtccctgac cgattcagtg gcagcgggtc tgggacagat ttcactctca ccatcagcag   240
cctgcaggct gaagatgtgg cagtttatta ctgtcaacaa attcgggaac tgaccaggag   300
tgaattcggc ggagggacca aggtggagat caaacgaact gagcccaaat cttgtgacaa   360
aactcacaca tgcccaccgt gcccagcacc tgaactcctg ggggaccgt cagtcttcct   420
cttcccccca aaacccaagg acaccctcat gatctcccgg acccctgagg tcacatgcgt   480
ggtggtggac gtgagccacg aagaccctga ggtcaagttc aactggtacg tggacggcgt   540
ggaggtgcat aatgccaaga caaagccgcg ggaggagcag tacaacagca cgtaccgtgt   600
ggtcagc                                                             607

SEQ ID NO: 272           moltype = DNA  length = 702
FEATURE                  Location/Qualifiers
misc_feature             1..702
                         note = Human IgG1 Fc sequence
source                   1..702
                         mol_type = other DNA
                         organism = synthetic construct
SEQUENCE: 272
gagcccaaat cttgtgacaa aactcacaca tgcccaccgt gcccagcacc tgaactcctg    60
gggggaccgt cagtcttcct cttcccccca aaacccaagg acaccctcat gatctcccgg   120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
```

```
gacatcgccg tggagtggga gagcaatggg cagccggaga acaactacaa gaccacgcct  540
cccgtgctgg actccgacgg ctccttcttc ctctacagca agctcaccgt ggacaagagc  600
aggtggcagc aggggaacgt cttctcatgc tccgtgatgc atgaggctct gcacaaccac  660
tacacgcaga gagcctctcc cctgtctccg ggtaaatgat aa                     702

SEQ ID NO: 273           moltype = AA  length = 232
FEATURE                  Location/Qualifiers
REGION                   1..232
                         note = Human IgG1 Fc sequence
source                   1..232
                         mol_type = protein
                         organism = synthetic construct
SEQUENCE: 273
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 274           moltype = DNA  length = 666
FEATURE                  Location/Qualifiers
misc_feature             1..666
                         note = Human IgG1 CH2-CH3 domain sequence
source                   1..666
                         mol_type = other DNA
                         organism = synthetic construct
SEQUENCE: 274
ccgtgcccag cacctgaact cctgggggga ccgtcagtct tcctcttccc cccaaaaccc   60
aaggacaccc tcatgatctc ccggacccct gaggtcacat gcgtggtggt ggacgtgagc  120
cacgaagacc ctgaggtcaa gttcaactgg tacgtggacg gcgtggaggt gcataatgcc  180
aagacaaagc cgcgggagga gcagtacaac agcacgtacc gtgtggtcag cgtcctcacc  240
gtcctgcacc aggactggct gaatggcaag gagtacaagt gcaaggtctc caacaaagcc  300
ctcccagccc ccatcgagaa aaccatctcc aaagccaaag gcagccccg agaaccacag  360
gtgtacaccc tgcccccatc ccgggaggag atgaccaaga accaggtcag cctgacctgc  420
ctggtcaaag gcttctatcc cagcgacatc gccgtggagt gggagagcaa tgggcagccg  480
gagaacaact acaagaccac gcctcccgtg ctggactccg acggctcctt cttcctctac  540
agcaagctca ccgtggacaa gagcaggtgg cagcagggga acgtcttctc atgctccgtg  600
atgcatgagg ctctgcacaa ccactacacg cagaagagcc tctccctgtc tccgggtaaa  660
tgataa                                                             666

SEQ ID NO: 275           moltype = AA  length = 220
FEATURE                  Location/Qualifiers
REGION                   1..220
                         note = Human IgG1 CH2-CH3 domain sequence
source                   1..220
                         mol_type = protein
                         organism = synthetic construct
SEQUENCE: 275
PCPAPELLGG PSVFLFPPKP KDTLMISRTP EVTCVVVDVS HEDPEVKFNW YVDGVEVHNA   60
KTKPREEQYN STYRVVSVLT VLHQDWLNGK EYKCKVSNKA LPAPIEKTIS KAKGQPREPQ  120
VYTLPPSREE MTKNQVSLTC LVKGFYPSDI AVEWESNGQP ENNYKTTPPV LDSDGSFFLY  180
SKLTVDKSRW QQGNVFSCSV MHEALHNHYT QKSLSLSPGK                        220

SEQ ID NO: 276           moltype = DNA  length = 327
FEATURE                  Location/Qualifiers
misc_feature             1..327
                         note = Human IgG1 CH3 domain sequence
source                   1..327
                         mol_type = other DNA
                         organism = synthetic construct
SEQUENCE: 276
gggcagcccc gagaaccaca ggtgtacacc ctgcccccat cccgggagga gatgaccaag   60
aaccaggtca gcctgacctg cctggtcaaa ggcttctatc ccagcgacat cgccgtggag  120
tgggagagca atgggcagcc ggagaacaac tacaagacca cgcctcccgt gctggactcc  180
gacggctcct tcttcctcta cagcaagctc accgtggaca agagcaggtg gcagcagggg  240
aacgtcttct catgctccgt gatgcatgag gctctgcaca accactacac gcagaagagc  300
ctctccctgt ctccgggtaa atgataa                                      327

SEQ ID NO: 277           moltype = AA  length = 107
FEATURE                  Location/Qualifiers
REGION                   1..107
                         note = Human IgG1 CH3 domain sequence
source                   1..107
                         mol_type = protein
                         organism = synthetic construct
SEQUENCE: 277
GQPREPQVYT LPPSREEMTK NQVSLTCLVK GFYPSDIAVE WESNGQPENN YKTTPPVLDS   60
DGSFFLYSKL TVDKSRWQQG NVFSCSVMHE ALHNHYTQKS LSLSPGK                107

SEQ ID NO: 278           moltype = DNA  length = 702
```

| FEATURE | Location/Qualifiers |
|---|---|
| misc_feature | 1..702 |
| | note = Human IgG1 Fc Y407R sequence |
| source | 1..702 |
| | mol_type = other DNA |
| | organism = synthetic construct |

SEQUENCE: 278

```
gagcccaaat cttgtgacaa aactcacaca tgcccaccgt gcccagcacc tgaactcctg    60
gggggaccgt cagtcttcct cttccccccca aaacccaagg acaccctcat gatctcccgg   120
accccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
gacatcgccg tggagtggga gagcaatggg cagccggaga acaactacaa gaccacgcct   540
cccgtgctgg actccgacgg ctccttcttc ctcaggagca agctcaccgt ggacaagagc   600
aggtggcagc aggggaacgt cttctcatgc tccgtgatgc atgaggctct gcacaaccac   660
tacacgcaga agagcctctc cctgtctccg ggtaaatgat aa                      702
```

| SEQ ID NO: 279 | moltype = AA length = 232 |
|---|---|
| FEATURE | Location/Qualifiers |
| REGION | 1..232 |
| | note = Human IgG1 Fc Y407R sequence |
| source | 1..232 |
| | mol_type = protein |
| | organism = synthetic construct |

SEQUENCE: 279

```
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LRSKLTVDKS RWQQGNVFSC SVMHEALHNH YTQKSLSLSP GK           232
```

| SEQ ID NO: 280 | moltype = DNA length = 702 |
|---|---|
| FEATURE | Location/Qualifiers |
| misc_feature | 1..702 |
| | note = Human IgG1 Fc F405Q sequence |
| source | 1..702 |
| | mol_type = other DNA |
| | organism = synthetic construct |

SEQUENCE: 280

```
gagcccaaat cttgtgacaa aactcacaca tgcccaccgt gcccagcacc tgaactcctg    60
gggggaccgt cagtcttcct cttccccccca aaacccaagg acaccctcat gatctcccgg   120
accccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
gacatcgccg tggagtggga gagcaatggg cagccggaga acaactacaa gaccacgcct   540
cccgtgctgg actccgacgg ctccttccag tctctacaga agctcaccgt ggacaagagc   600
aggtggcagc aggggaacgt cttctcatgc tccgtgatgc atgaggctct gcacaaccac   660
tacacgcaga agagcctctc cctgtctccg ggtaaatgat aa                      702
```

| SEQ ID NO: 281 | moltype = AA length = 232 |
|---|---|
| FEATURE | Location/Qualifiers |
| REGION | 1..232 |
| | note = Human IgG1 Fc F405Q sequence |
| source | 1..232 |
| | mol_type = protein |
| | organism = synthetic construct |

SEQUENCE: 281

```
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFQ LYSKLTVDKS RWQQGNVFSC SVMHEALHNH YTQKSLSLSP GK           232
```

| SEQ ID NO: 282 | moltype = DNA length = 702 |
|---|---|
| FEATURE | Location/Qualifiers |
| misc_feature | 1..702 |
| | note = Human IgG1 Fc T394D sequence |
| source | 1..702 |
| | mol_type = other DNA |
| | organism = synthetic construct |

SEQUENCE: 282

```
gagcccaaat cttgtgacaa aactcacaca tgcccaccgt gcccagcacc tgaactcctg    60
gggggaccgt cagtcttcct cttccccccca aaacccaagg acaccctcat gatctcccgg   120
accccctgagg tcacatgcgt ggtggtggac gtgagccacg aagaccctga ggtcaagttc   180
aactggtacg tggacggcgt ggaggtgcat aatgccaaga caaagccgcg ggaggagcag   240
```

```
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
gacatcgccg tggagtggga gagcaatggg cagccggaga caactacaa gaccgaccct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga gagcctctcc cctgtctccg ggtaaatgat aa                      702

SEQ ID NO: 283          moltype = AA    length = 232
FEATURE                 Location/Qualifiers
REGION                  1..232
                        note = Human IgG1 Fc T394D sequence
source                  1..232
                        mol_type = protein
                        organism = synthetic construct
SEQUENCE: 283
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTDP   180
PVLDSDGSFF LYSKLTVDKS RWQQGNVFSC SVMHEALHNH YTQKSLSLSP GK           232

SEQ ID NO: 284          moltype = DNA    length = 702
FEATURE                 Location/Qualifiers
misc_feature            1..702
                        note = Human IgG1 Fc T366W/L368W sequence
source                  1..702
                        mol_type = other DNA
                        organism = synthetic construct
SEQUENCE: 284
gagcccaaat cttgtgacaa aactcacaca tgcccaccgt gcccagcacc tgaactcctg    60
gggggaccgt cagtcttcct cttcccccca aaacccaagg acaccctcat gatctcccgg   120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg tggtgctggg tcaaaggctt ctatcccagc   480
gacatcgccg tggagtggga gagcaatggg cagccggaga caactacaa gaccacgcct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga gagcctctcc cctgtctccg ggtaaatgat aa                      702

SEQ ID NO: 285          moltype = AA    length = 232
FEATURE                 Location/Qualifiers
REGION                  1..232
                        note = Human IgG1 Fc T366W/L368W sequence
source                  1..232
                        mol_type = protein
                        organism = synthetic construct
SEQUENCE: 285
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL WCWVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 286          moltype = DNA    length = 702
FEATURE                 Location/Qualifiers
misc_feature            1..702
                        note = Human IgG1 Fc T364R/L368R sequence
source                  1..702
                        mol_type = other DNA
                        organism = synthetic construct
SEQUENCE: 286
gagcccaaat cttgtgacaa aactcacaca tgcccaccgt gcccagcacc tgaactcctg    60
gggggaccgt cagtcttcct cttcccccca aaacccaagg acaccctcat gatctcccgg   120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcaggctg acctgcaggg tcaaaggctt ctatcccagc   480
gacatcgccg tggagtggga gagcaatggg cagccggaga caactacaa gaccacgcct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga gagcctctcc cctgtctccg ggtaaatgat aa                      702

SEQ ID NO: 287          moltype = AA    length = 232
FEATURE                 Location/Qualifiers
```

```
REGION                      1..232
                            note = Human IgG1 Fc T364R/L368R sequence
source                      1..232
                            mol_type = protein
                            organism = synthetic construct
SEQUENCE: 287
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVRL TCRVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 288              moltype = DNA  length = 657
FEATURE                     Location/Qualifiers
misc_feature                1..657
                            note = Human IgG1 Fc hingeless sequence
source                      1..657
                            mol_type = other DNA
                            organism = synthetic construct
SEQUENCE: 288
gcacctgaac tcctgggggg accgtcagtc ttcctcttcc cccaaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa gggcagcccc gagaaccaca ggtgtacacc   360
ctgcccccat cccgggagga tgaccaag aaccaggtca gcctgacctg cctggtcaaa    420
ggcttctatc ccagcgacat cgccgtggag tgggagagca atgggcagcc ggagaacaac   480
tacaagacca cgcctcccgt gctggactcc gacggctcct tcttcctcta cagcaagctc   540
accgtggaca agagcaggtg gcagcagggg aacgtcttct catgctccgt gatgcatgag   600
gctctgcaca accactacac gcagaagagc ctctccctgt ctccgggtaa atgataa      657

SEQ ID NO: 289              moltype = AA  length = 217
FEATURE                     Location/Qualifiers
REGION                      1..217
                            note = Human IgG1 Fc hingeless sequence
source                      1..217
                            mol_type = protein
                            organism = synthetic construct
SEQUENCE: 289
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNHYTQKS LSLSPGK                            217

SEQ ID NO: 290              moltype = DNA  length = 696
FEATURE                     Location/Qualifiers
misc_feature                1..696
                            note = Human IgG1 G237A FC sequence
source                      1..696
                            mol_type = other DNA
                            organism = synthetic construct
SEQUENCE: 290
gagcccaaat cttgtgacaa aactcacaca tgcccaccgt gcccagcacc tgaactcctg    60
gggggcccgt cagtcttcct cttcccccca aaacccaagg acaccctcat gatctcccgg   120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
gacatcgccg tggagtggga gagcaatggg cagccggaga caactacaa gaccacgcct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga gagcctctc cctgtctccg ggtaaa                              696

SEQ ID NO: 291              moltype = AA  length = 232
FEATURE                     Location/Qualifiers
REGION                      1..232
                            note = Human IgG1 G237A FC sequence
source                      1..232
                            mol_type = protein
                            organism = synthetic construct
SEQUENCE: 291
EPKSCDKTHT CPPCPAPELL GAPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 292              moltype = DNA  length = 696
```

```
FEATURE                 Location/Qualifiers
misc_feature            1..696
                        note = Human IgG1 L234A/L235A FC sequence
source                  1..696
                        mol_type = other DNA
                        organism = synthetic construct
SEQUENCE: 292
gagcccaaat cttgtgacaa aactcacaca tgcccaccgt gcccagcacc tgaagccgcc    60
gggggaccgt cagtcttcct cttccccccca aaacccaagg acaccctcat gatctcccgg   120
accccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagcccctcc cagcccccat cgagaaaacc   360
atctccaaag ccaaagggca gccccgagaa ccacaggtgt acaccctgcc cccatcccga   420
gaggagatga ccaagaacca ggtcagcctg acctgcctgg tcaaaggctt ctatcccagc   480
gacatcgccg tggagtggga gagcaatggg cagccggaga acaactacaa gaccacgcct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga gagcctctc cctgtctccg ggtaaa                                696

SEQ ID NO: 293          moltype = AA  length = 232
FEATURE                 Location/Qualifiers
REGION                  1..232
                        note = Human IgG1 L234A/L235A FC sequence
source                  1..232
                        mol_type = protein
                        organism = synthetic construct
SEQUENCE: 293
EPKSCDKTHT CPPCPAPEAA GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR EEMTKNQVSL TCLVKGFYPS DIAVEWESNG QPENNYKTTP    180
PVLDSDGSFF LYSKLTVDKS RWQQGNVFSC SVMHEALHNH YTQKSLSLSP GK             232

SEQ ID NO: 294          moltype = DNA  length = 1341
FEATURE                 Location/Qualifiers
misc_feature            1..1341
                        note = CAR-T E6 CD3z sequence
source                  1..1341
                        mol_type = other DNA
                        organism = synthetic construct
SEQUENCE: 294
atggccctgc ccgtgaccgc tttgctgctc ccctggcgc tgctgctgca cgccgccagg      60
ccagagtcc agctggttga gagtggcggt gggctggcg tcccctgcgg                120
ctgagctgcg ccgcgagtgg atttactttc agccgatatg ggatgagttg ggtgcggcaa    180
gctcccggga gaggctggaa atgggtctca caatctccgg gggggggcac ttacatctat    240
taccccgact cagtcaaggg gagatttacc atttcacgag acaacgctaa gaatacccctg   300
tatttgcaga tgaattctct gagagcagag gacacagctg tttactattg tacccgcgac   360
aactatggca ggaactacga ctacggtatg gactattggg gacaagggac attggttaca   420
gtgagcagtg gcggcggggg cagcggagga ggaggcagcg gtgggggggg cagcgagata   480
gtgctcacgc agtcacccgc gactctcagt ctctcacctg gggaacgagc taccctgacg   540
tgctctgcta cctcctcagt gtcatatatt cactggtatc agcaacgccc aggcagtcc    600
cctagattgc tcatttatag tacctctaat ctggcctcag gtatccctgc acgattttct    660
ggatctggtt caggttctga ttacaccctc actatctcta gcctggagcc tgaagactttc   720
gccgtttatt actgccagca gaggtctagc tcccccattca cctttgggag tgggaccaag   780
gttgaaatta aaacgacaac cccggccccc agaccaccaa cgccagcccc caccatcgcc    840
agccaacccc tgtctctgag accagaagcc tgtaggcctg ccgccggtgg agctgtgcac    900
acaagaggac tggatttcgc ctgtgatatc tacatttggg ccccgctcgc aggcacatgt    960
ggagtgctcc tcctctccct ggtgattacc ctgtactgcc gcgttaagtt ctcccgatca   1020
gccgacgcgc ctgcttacaa gcagggccag aaccaactgt acaacgagct gaatctcggt   1080
agacgggaag agtacgacgt gttggacaaa cggagaggcc gcgacccaga aatgggcggt   1140
aagcctcgca ggaaaaaccc ccaggaggga ctgtacaatg agttgcagaa agataagatg   1200
gcagaagctt atagcgagat cggaatgaag ggggaaagga cgagggaa aggacacgac   1260
ggcctttatc agggcctgtc cacagcaaca aaagatacgt atgacgccct ccatatgcag   1320
gcacttccac cacggtgata a                                            1341

SEQ ID NO: 295          moltype = AA  length = 445
FEATURE                 Location/Qualifiers
REGION                  1..445
                        note = CAR-T E6 CD3z sequence
source                  1..445
                        mol_type = protein
                        organism = synthetic construct
SEQUENCE: 295
MALPVTALLL PLALLLHAAR PEVQLVESGG GLVKPGGSLR LSCAASGFTF SRYGMSWVRQ     60
APGKRLEWVS TISGGGTYIY YPDSVKGRFT ISRDNAKNTL YLQMNSLRAE DTAVYYCTRD    120
NYGRNYDYGM DYWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF    240
AVYYCQQRSS SPFTFGSGTK VEIKTTTPAP RPPTPAPTIA SQPLSLRPEA CRPAAGGAVH    300
TRGLDFACDI YIWAPLAGTC GVLLLSLVIT LYCRVKFSRS ADAPAYKQGQ NQLYNELNLG    360
```

```
RREEYDVLDK RRGRDPEMGG KPRRKNPQEG LYNELQKDKM AEAYSEIGMK GERRRGKGHD   420
GLYQGLSTAT KDTYDALHMQ ALPPR                                        445

SEQ ID NO: 296           moltype = DNA   length = 485
FEATURE                  Location/Qualifiers
misc_feature             1..485
                         note = CAR-T E6 CD3z gBLOCK sequence
source                   1..485
                         mol_type = other DNA
                         organism = synthetic construct
SEQUENCE: 296
tggagctgtg cacacaagag gactggattt cgcctgtgat atctacattt gggccccgct    60
cgcaggcaca tgtggagtgc tcctcctctc cctggtgatt accctgtact gccgcgttaa   120
gttctcccga tcagccgacg cgcctgctta aagcagggc cagaaccaac tgtacaacga   180
gctgaatctc ggtagacggg aagagtacga cgtgttggac aaacggagag gccgcgaccc   240
agaaatgggc ggcaagcctc gcaggaaaaa ccccaggag ggactgtaca atgagttgca   300
gaaagataag atgcagaag cttatagcga gatcggaatg aaggggaaa ggagacgagg   360
gaaaggacac gacggccttt atcagggcct gtccacagca acaaaagata cgtatgacgc   420
cctccatatg caggcacttc caccacggtg ataagtttaa acccgctgat cagcctcgac   480
tgtgc                                                              485

SEQ ID NO: 297           moltype = DNA   length = 1464
FEATURE                  Location/Qualifiers
misc_feature             1..1464
                         note = CAR-T E6 CD28/CD3z sequence
source                   1..1464
                         mol_type = other DNA
                         organism = synthetic construct
SEQUENCE: 297
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgtatg ggatgagttg ggtgcggcaa   180
gctcccggga gaggctgga atgggtctca acaatctccg ggggggggcac ttacatctat   240
taccccgact cagtcaaggg gagatttacc atttcacgag acaacgctaa gaataccctg   300
tatttgcaga tgaattctct gagagcagag gacacagctg tttactattg tacccgcgca   360
aactatggca ggaactacga ctacggtatg gactattggg gacaagggac attggttaca   420
gtgagcagtg gcggcggggg cagcggagga ggaggcagcg gtgggggggg cagcgagata   480
gtgctcacgc agtcaccgc gactctcagt ctctcacctg gggaacgagc taccctgacg   540
tgctctgcta cctcctcagt gtcatatatt cactggtatc agcaacggcc cgggcagtcc   600
cctagattgc tcatttatag tacctctaat ctggcctcag gtatccctgc acgattttct   660
ggatctggtt caggttctga ttacaccctc actatctcta gcctggagcc tgaagacttt   720
gccgtttatt actgccagca gaggtctagc tccccattca cctttgggag tgggaccaag   780
gttgaaatta aacgacaac cccggcccc agaccaccaa ccacatcgcc                840
agccaacccc tgtctctgag accagaagcc tgtaggcctg ccgccggtgg agctgtgcac   900
acaagaggac tggatttcgc ctgtgatatc tacatttggg ccccgctcgc aggcacatgt   960
ggagtgctcc tcctctcct ggtgattacc ctgtactgca agcaagcg gtctcggctc   1020
ctgcattctg attacatgaa catgacccca agaagaccag gaaacattac                1080
cagcccctacg ctccgccacg cgacttcgct gcctaccggt cccgcgttaa gttctcccga  1140
tcagccgacg cgcctgctta aagcaggggc cagaaccaac tgtacaacga gctgaatctc  1200
ggtagacggg aagagtacga cgtgttggac aaacggagag gccgcgaccc agaaatgggc  1260
ggcaagcctc gcaggaaaaa ccccaggag ggactgtaca atgagttgca gaaagataag  1320
atgcagaag cttatagcga gatcggaatg aaggggaaa ggagacgagg gaaaggacac  1380
gacggccttt atcagggcct gtccacagca acaaaagata cgtatgacgc cctccatatg  1440
caggcacttc caccacggtg ataa                                        1464

SEQ ID NO: 298           moltype = AA   length = 486
FEATURE                  Location/Qualifiers
REGION                   1..486
                         note = CAR-T E6 CD28/CD3z sequence
source                   1..486
                         mol_type = protein
                         organism = synthetic construct
SEQUENCE: 298
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKTTTPAP RPPTPAPTIA SQPLSLRPEA CRPAAGGAVH   300
TRGLDFACDI YIWAPLAGTC GVLLLSLVIT LYCRSKRSRL LHSDYMNMTP RRPGPTRKHY   360
QPYAPPRDFA AYRSRVKFSR SADAPAYKQG NQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                             486

SEQ ID NO: 299           moltype = DNA   length = 608
FEATURE                  Location/Qualifiers
misc_feature             1..608
                         note = CAR-T E6 CD28/CD3z g BLOCK sequence
source                   1..608
                         mol_type = other DNA
```

```
                        organism = synthetic construct
SEQUENCE: 299
tggagctgtg cacacaagag gactggattt cgcctgtgat atctacattt gggccccgct    60
cgcaggcaca tgtggagtgc tcctcctctc cctggtgatt accctgtact gcagaagcaa   120
gcggtctcgg ctcctgcatt ctgattacat gaacatgacc ccaagaagac caggccccac   180
caggaaacat taccagccct acgctccgcc acgcgacttc gctgcctacc ggtcccgcgt   240
taagttctcc cgatcagccg acgcgcctgc ttacaagcag gccagaacc aactgtacaa    300
cgagctgaat ctcggtagac gggaagagta cgacgtgttg gacaaacgga gaggccgcga   360
cccagaaatg ggcggcaagc ctcgcaggaa aaacccccag gagggactgt acaatgagtt   420
gcagaaagat aagatggcag aagcttatag cgagatcgga atgaaggggg aaaggagacg   480
agggaaagga cacgacggcc tttatcaggg cctgtccaca gcaacaaaag atacgtatga   540
cgccctccat atgcaggcac ttccaccacg gtgataagtt taaacccgct gatcagcctc   600
gactgtgc                                                           608

SEQ ID NO: 300          moltype = DNA  length = 1467
FEATURE                 Location/Qualifiers
misc_feature            1..1467
                        note = CAR-T E6 4-1BB/CD3z sequence
source                  1..1467
                        mol_type = other DNA
                        organism = synthetic construct
SEQUENCE: 300
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg gatgagttg ggtgcggcaa    180
gctcccggga agaggctgga atgggtctca acaatctcga gggggggctac ttacatctat   240
taccccgact cagtcaaggg gagatttacc atttcacgag acaacgctaa gaataccctg   300
tatttgcaga tgaattctct gagagcagag gacacagctg tttactattg tacccgcgac   360
aactatggca ggaactacga ctacggtatg gactattggg gacaagggac attggttaca   420
gtgagcagtg gcggcgggg cagcggagga ggaggcgtg gtgggggggg cagcagata    480
gtgctcacgc agtcaccgc gactctcagt ctctcacctg ggaacgagc tacctgacg    540
tgctctgcta cctcctcagt gtcatatatt cactggtatc agcaacgcc cgggcagtcc    600
cctagattgc tcatttatag tacctctaat ctggcctcag gtatccctgc acgattttct   660
ggatctggtt caggttctga ttacaccctc actatctcta gcctggagc tgaagacttt   720
gccgtttatt actgccagca gaggtctagc tccccattca cctttgggag tgggaccaag   780
gttgaaatta aaacgacaac cccggccccc agaccaccaa cgccagcccc caccatcgcc   840
agccaacccc tgtctctgag accagaagcc tgtaggcctg ccgccggtgg agctgtgcac   900
acaagaggac tggatttcgc ctgtgatatc tacatttggg ccccgctcgc aggcacatgt   960
ggagtgctcc tcctctccct ggtgattacc ctgtactgca aaggggccg caaaaactc   1020
ctttacattt ttaagcagcc ttttatgagg ccagtacaa cgactcaaga ggaagacggg   1080
tgctcatgcc gctttcctga ggaggaggaa ggagggtgcg aactgcgcgt taagttctcc   1140
cgatcagccg acgcgcctgc ttacaagcag gccagaacc aactgtacaa cgagctgaat    1200
ctcggtagac gggaagagta cgacgtgttg gacaaacgga gaggccgcga cccagaaatg   1260
ggcggcaagc ctcgcaggaa aaacccccag gagggactgt acaatgagtt gcagaaagat   1320
aagatggcag aagcttatag cgagatcgga atgaaggggg aaaggagacg agggaaagga   1380
cacgacggcc tttatcaggg cctgtccaca gcaacaaaag atacgtatga cgccctccat   1440
atgcaggcac ttccaccacg gtgataa                                      1467

SEQ ID NO: 301          moltype = AA  length = 487
FEATURE                 Location/Qualifiers
REGION                  1..487
                        note = CAR-T E6 4-1BB/CD3z sequence
source                  1..487
                        mol_type = protein
                        organism = synthetic construct
SEQUENCE: 301
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYKQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                            487

SEQ ID NO: 302          moltype = DNA  length = 611
FEATURE                 Location/Qualifiers
misc_feature            1..611
                        note = CAR-T E6 4-1BB/CD3z gBLOCK sequence
source                  1..611
                        mol_type = other DNA
                        organism = synthetic construct
SEQUENCE: 302
tggagctgtg cacacaagag gactggattt cgcctgtgat atctacattt gggccccgct    60
cgcaggcaca tgtggagtgc tcctcctctc cctggtgatt accctgtact gcaaaggggg   120
ccgcaaaaaa ctcctttaca ttttaagca gccttttatg aggccagtac agacgactca   180
agaggaagac gggtgctcat gccgctttcc tgaggaggag gaaggagggt gcgaactgcg   240
cgttaagttc tcccgatcag ccgacgcgcc tgcttacaag cagggccaga accaactgta   300
```

```
caacgagctg aatctcggta gacgggaaga gtacgacgtg ttggacaaac ggagaggccg   360
cgacccagaa atgggcggca agcctcgcag gaaaaacccc caggagggac tgtacaatga   420
gttgcagaaa gataagatgg cagaagctta tagcgagatc ggaatgaagg gggaaaggag   480
acgagggaaa ggacacgacg gcctttatca gggcctgtcc acagcaacaa aagatacgta   540
tgacgccctc catatgcagg cacttccacc acggtgataa gtttaaaccc gctgatcagc   600
ctcgactgtg c                                                       611

SEQ ID NO: 303          moltype = DNA  length = 1590
FEATURE                 Location/Qualifiers
misc_feature            1..1590
                        note = CAR-T E6 CD28/4-1BB/CD3z sequence
source                  1..1590
                        mol_type = other DNA
                        organism = synthetic construct
SEQUENCE: 303
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg ggatgagttg ggtgcggcaa   180
gctcccggga agaggctgga atgggtctca acaatctccg ggggggggcac ttacatctat   240
taccccgact cagtcaaggg gagatttacc atttcacgag acaacgctaa gaatacccctg   300
tatttgcaga tgaattctct gagagcagag gacacagctg tttactattg taccccgcgac   360
aactatggca ggaactacga ctacggtatg gactattggg gacaagggac attggttaca   420
gtgagcagtg gcggcgggggg cagcggagga ggaggcagcg gtggggggggg cagcgagata   480
gtgctcacgc agtcacccgc gactctcagt ctctcacctg ggaacgagcc tacccctgacg   540
tgctctgcta cctcctcagt gtcatatatt cactggtatc agcaacggcc cgggcagtcc   600
cctagattgc tcatttatag tacctctaat ctggcctcag gtgatccctgc acgatttttct   660
ggatctggtt caggttctga ttacacccctc actatctcta gcctggagcc tgaagacttt   720
gccgtttatt actgccagca gaggtctagc tccccattca cctttgggag tgggaccaag   780
gttgaaatta aaacgacaac cccggccccc agaccaccaa cgccagcccc caccatcgcc   840
agccaaccc tgtctctgag accagaagcc tgtaggcctg gacgccggtgg agctgtgcac   900
acaagaggac tggatttcgc ctgtgatatc tacattgggc cccgctcgc aggcacatgt   960
ggagtgctcc tcctctccct ggtgattacc ctgtactgca gaagcaagcg gtctcggctc  1020
ctgcattctg attacatgaa catgaccccca gaagaccagg ccccaccagg aaacattac  1080
cagccctacg ctccgccacg cgacttcgct gcctaccggg caaaagggg ccgcaaaaaa  1140
ctcctttaca ttttaagca gcctttttatg aggcagtac agacgactca agaggaagac  1200
gggtgctcat gccgctttcc tgaggaggag gaaggagggt gcgaactgcg cgttaagttc  1260
tcccgatcag ccgacgcgcc tgcttacaag cagggccaga accaactgta caacgagctg  1320
aatctcggta gacgggaaga gtacgacgtg ttggacaaac ggagaggccg cgacccagaa  1380
atgggcggca agcctcgcag gaaaaacccc caggagggac tgtacaatga gttgcagaaa  1440
gataagatgg cagaagctta tagcgagatc ggaatgaagg gggaaaggag acgagggaaa  1500
ggacacgacg gcctttatca gggcctgtcc acagcaacaa aagatacgta tgacgccctc  1560
catatgcagg cacttccacc acggtgataa                                   1590

SEQ ID NO: 304          moltype = AA  length = 528
FEATURE                 Location/Qualifiers
REGION                  1..528
                        note = CAR-T E6 CD28/4-1BB/CD3z sequence
source                  1..528
                        mol_type = protein
                        organism = synthetic construct
SEQUENCE: 304
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKTTTPAP RPPTPAPTIA SQPLSLRPEA CRPAAGGAVH   300
TRGLDFACDI YIWAPLAGTC GVLLLSLVIT LYCRSKRSRL LHSDYMNMTP RRPGPTRKHY   360
QPYAPPRDFA AYRSKRGRKK LLYIFKQPFM RPVQTTQEED GCSCRFPEEE EGGCELRVKF   420
SRSADAPAYK QGQNQLYNEL NLGRREEYDV LDKRRGRDPE MGGKPRRKNP QEGLYNELQK   480
DKMAEAYSEI GMKGERRRGK GHDGLYQGLS TATKDTYDAL HMQALPPR               528

SEQ ID NO: 305          moltype = DNA  length = 1668
FEATURE                 Location/Qualifiers
misc_feature            1..1668
                        note = CAR-T E6 CD28/4-1BB/CD3z gBLOCK sequence
source                  1..1668
                        mol_type = other DNA
                        organism = synthetic construct
SEQUENCE: 305
atagggagac ccaagctggc tagttaagct tggtaccgag gccaccatg gccctgcccg    60
tgaccgcttt gctgctcccc ctggcgctgc tgctgcacgc cgccaggcca gaggtccagc   120
tggttgagag tggcggtggg ctggttaagc ctggcggctc cctgcggctg agctgcgccg   180
cgagtggatt tactttcagc cgatatggga tgagttgggt gcggcaagct cccgggaaga   240
ggctggaatg ggtctcaaca atctccgggg ggcacttaca tctattaccc cgactcagtc   300
aaggggagat ttaccattt cacgagacaa cgctaagaa taccctgtat ttgcagatga   360
attctctgag agcagaggac acagctgttt actattgtac ccgcgacaac tatggcagga   420
actacgacta cggtatggac tattggggac aagggacatt ggttacagtg agcagtggcg   480
gcgggggcag cggaggagga ggcagcgtg ggggggcag cgagatagtg ctcacgcagt   540
cacccgcgac tctcagtctc tcacctgggg aacgagctac cctgacgtgc tctgctacct   600
```

-continued

```
cctcagtgtc atatattcac tggtatcagc aacggcccgg gcagtcccct agattgctca    660
tttatagtac ctctaatctg gcctcaggta tccctgcacg attttctgga tctggttcag    720
gttctgatta caccctcact atctctagcc tggagcctga agactttgcc gtttattact    780
gccagcagag gtctagctcc ccattcacct ttgggagtgg gaccaaggtt gaaattaaaa    840
cgacaacccc ggcccccaga ccaccaacgc cagcccccac catcgccagc caacccctgt    900
ctctgagacc agaagcctgt aggcctgccg ccggtggagc tgtgcacaca agaggactgg    960
atttcgcctg tgatatctac atttgggccc cgctcgcagg cacatgtgga gtgctcctcc   1020
tctccctggt gattaccctg tactgcagaa gcaagcggtc tcggctcctg cattctgatt   1080
acatgaacat gaccccaaga agaccaggcc ccaccaggaa acattaccag ccctacgctc   1140
cgccacgcga cttcgctgcc taccggtcca aaagggccg caaaaaactc ctttacattt    1200
ttaagcagcc ttttatgagg ccagtacaga cgactcaaga ggaagacggg tgctcatgcc   1260
gctttcctga ggaggaggaa ggagggtgcg aactgcgcgt taagttctcc cgatcagccg   1320
acgcgcctgc ttacaagcag ggccagaacc aactgtacaa cgagctgaat ctcggtagac   1380
gggaagagta cgacgttgtt gacaaacgga gaggccgcaa cccagaaatg ggcggcaagc   1440
ctcgcaggaa aaaccccag gagggactgt acaatgagtt gcagaaagat aagatggcag   1500
aagcttatag cgagatcgga atgaaggggg aaggagacg agggaaagga cacgacggcc   1560
tttatcaggg cctgtccaca gcaacaaaag atacgtatga cgccctccat atgcaggcac   1620
ttccaccacg gtgataagtt taaacccgct gatcagcctc gactgtgc                1668

SEQ ID NO: 306            moltype = DNA  length = 1608
FEATURE                   Location/Qualifiers
misc_feature              1..1608
                          note = CAR-T C2 CD28/4-1BB/CD3z sequence
source                    1..1608
                          mol_type = other DNA
                          organism = synthetic construct
SEQUENCE: 306
atggccttgc cagtgacggc cctgctgctg ccattggctc ttctgttgca cgctgccagg     60
cctgaagtgc agctcgtaga gagtggcggg ggactggtga agcccggtgg aagcctcaga    120
ctcagttgcg ccgcctcagg tttcactttt tcaggttacg ccatgtcctg ggtaagacag    180
gcaccgggga aaggactcga gtgggtgtct actatcagtc caggaggcac ttatatatat    240
tatcctgact ctgtaaaagg ccgatttacg atttctcgcg acaatgcaaa gaactccctc    300
tacctccaaa tgaacagtct tagggcagaa gacactgctg tatactattg tgcacgcctc    360
ggcggcgaca actactacga gtactttgac gtgtggggga aagggactac cgtgacagtt    420
tcaagcggag gaggtggctc aggtggaggc gggtcaggg ggggaggaag tgatattgtg    480
ctcacacaat cccagcctc cctggctgtg tctcccggcc aacgcgctac aattacatgt    540
cgggcctcca aaagcgtgag caccagcggc tacagctaca tgcactggta tcaacagaaa    600
ccaggacaac cccccaaact gttgatttat ctcgcttcaa acttggagtc cggcgtgcct    660
gcgcgctttt cagggagtgg gagcggcaca gattttacgc tgactatcaa ccccgtagaa    720
gcaaacgata cagcgaatta ttattgtcaa cattcccggg aactccccttt acgttcggc   780
ggggggcacaa aggtcgaaat taagagaacc acgacaaccc cggcccccag accaccaacg    840
ccagccccca ccatcgccag caacccctgt ctctgagacc agaagcctgt aggcctgcc     900
gccgtggag ctgtgcacac aagaggactg gatttcgcct gtgatatcta catttgggcc     960
ccgctcgcag gcacatgtgg agtgctcctc ctctccctgg tgattaccct gtactgcaga   1020
agcaagcggt ctcggctcct gcattctgat tacatgaaca tgaccccaag aagaccaggc   1080
cccaccagga acattaccag ccctacgct ccgccacgcg acttcgctgc ctaccggtcc    1140
aaaagggcc gcaaaaaact cctttacatt tttaagcagc ctttttatgag gccagtacag   1200
acgactcaag aggaagacgg gtgctcatgc cgctttcctg aggaggagga aggggtgc    1260
gaactgcgcg ttaagttctc ccgatcagcc gacgcgcctg cttacaagca gggccagaac   1320
caactgtaca acgagctgaa tctcggtaga cgggaagagt acgacgtgtt ggacaaacgg   1380
agaggccgcg acccagaaat gggcggcaag cctcgcagga aaaaccccca ggagggactg   1440
tacaatgagt tgcagaaaga taagatggca gaagcttata gcgagatcgg aatgaagggt   1500
gaaggagac gagggaaagg acacgacggc ctttatcagg gcctgtccac agcaacaaaa   1560
gatacgtatg acgccctcca tatgcaggca cttccaccac ggtgataa               1608

SEQ ID NO: 307            moltype = AA  length = 513
FEATURE                   Location/Qualifiers
REGION                    1..513
                          note = CAR-T C2 CD28/4-1BB/CD3z sequence
source                    1..513
                          mol_type = protein
                          organism = synthetic construct
SEQUENCE: 307
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS    120
SGGGGSGGGG SGGGGSDIVL TQSPASLAVS PGQRATITCR ASKSVSTSGY SYMHWYQQKP    180
GQPPKLLIYL ASNLESGVPA RFSGSGSGTD FTLTINPVEA NDTANYYCQH SRELPFTFGG    240
GTKVEIKRTT TPAPRPPTP APTIASQPLS LRPEACRPAA GGAVHTRGLD FACDIYIWAP    300
LAGTCGVLLL SLVITLYCRS KRSRLLHSDY MNMTPRRPGP TRKHYQPYAP PRDFAAYRSK    360
RGRKKLLYIF KQPFMRPVQT TQEEDGCSCR FPEEEEGGCE LRVKFSRSAD APAYKQGQNQ    420
LYNELNLGRR EEYDVLDKRR GRDPEMGGKP RRKNPQEGLY NELQKDKMAE AYSEIGMKGE    480
RRRGKGHDGL YQGLSTATKD TYDALHMQAL PPR                                 513

SEQ ID NO: 308            moltype = DNA  length = 553
FEATURE                   Location/Qualifiers
misc_feature              1..553
                          note = CAR-T C2-1 gBLOCK sequence
source                    1..553
                          mol_type = other DNA
```

```
                        organism = synthetic construct
SEQUENCE: 308
ataqqqaqac ccaaqctqqc taqttaaqct tqqtaccqaq qqccaccatq qccttqccaq    60
tqacqqccct qctqctqcca ttqqctcttc tqttqcacqc tqccaqqcct qaaqtqcaqc   120
tcqtaqaqaq tqqcqqqqqa ctqqtqaaqc ccqqtqaaqq cctcaqactc aqttqcqccq   180
cctcaqqttt cactttttca qqttacqcca tqtcctqqqt aaqacaqqca ccqqqqaaaq   240
qactcqaqtq qqtqtctact atcaqctcaq qaqqcactta tatatattat cctqactctq   300
taaaaqqccq atttacqatt tctcqcqaca atqcaaaqaa ctccctctac ctccaaatqa   360
acaqtcttaq qqcaqaaqac actqctqtat actattqtqc acqcctcqqc qqcqacaact   420
actacqaqta ctttqacqtq tqqqqqaaaq qqactaccqt qacaqtttca aqcqqaqqaq   480
qtqqctcaqq tqqaqqcqqq tcaqqqqqqq qaqqaaqtqa tattqtqctc acacaatccc   540
caqcctccct qqc                                                      553

SEQ ID NO: 309          moltype = DNA  length = 518
FEATURE                 Location/Qualifiers
misc_feature            1..518
                        note = CAR-T C2-2 gBLOCK sequence
source                  1..518
                        mol_type = other DNA
                        organism = synthetic construct
SEQUENCE: 309
aaqtqatatt qtqctcacac aatccccaqc ctccctqqct qtqtctcccq qccaacqcqc    60
tacaattaca tqtcqqqcct ccaaaaaqcqt qaqcaccaqc qqctacaqct acatqcactq   120
qtatcaacaq aaaccaqqac aaccccccaa actqttqatt tatctcqctt caaacttqqa   180
qtccqqcqtq cctqcqcqct tttcaqqqaq tqqqaqcqqc acaqatttta cqctqactat   240
caacccqqta qaaqcaaacq atacaqcqaa ttattattqt caacattccc qqqaactccc   300
ctttacqttc qqcqqqqqca caaaqqtcqa aattaaqaqa accacqacaa ccccqqcccc   360
caqaccacca acqccaqccc ccaccatcqc caqccaaccc ctqtctctqa qccaqaaqc    420
ctqtaqqcct qccqccqqtq qaqctqtqca caaqaqqaqa ctqqatttcq cctqtqatat   480
ctacatttqq qccccqctcq caqqcacatq tqqaqtqc                           518

SEQ ID NO: 310          moltype = DNA  length = 2028
FEATURE                 Location/Qualifiers
misc_feature            1..2028
                        note = CAR E6 Fc/8/4-1BB/CD3z sequence
source                  1..2028
                        mol_type = other DNA
                        organism = synthetic construct
SEQUENCE: 310
atqqccctqc ccqtqaccqc tttqctqctc cccctqqcqc tqctqctqca cqccqccaqq    60
ccaqaqqtcc aqctqqttqa qaqtqqcqqt qqqctqqtta aqcctqqcqq ctccctqcqq   120
ctqaqctqcq ccqcqaqtqq atttactttc aqccqatatq qqatqaqttq qqtqcqqcaa   180
qctcccqqqa aqaqqctqqa atqqqtctca caaatctcqt aqqqqqcac ttacatctat   240
taccccqact caqtcaaqqq qaqatttacc atttcacqaq acaacqctaa qaataccctq   300
tatttqcaqa tqaattctct qaqaqcaqaq qacacaqctq tttactattq taccccqcqac   360
aactatqqca qqaactacqa ctacqqtatq qactattqqq qacaaqqqac attqqttaca   420
qtqaqcaqtq qcqqcqqqqq caqcqqaqqa qqaqqcaqc qtqqcqqaqq caqcqaqata   480
qtqctcacqc aqtcacccqc qactctcaqt ctctcacctq qqaacqaqc taccctqacq    540
tqctctqcta cctcctcaqt qtcatatatt cactqqtatc aqcaacqqcc cqqqcaqtcc   600
cctaqattqc tcatttataq tacctctaat ctqqcctcaq qtatccctqc acqatttcct   660
qqatctqqtt caqqttctqa ttacaccctc actatctcta qcctqaqqc tqaaqactct   720
qccqtttatt actqccaqca qaqqtctaqc tccccattca cctttqqqaq tqqqaccaaq   780
qttqaaatta aaqaqcccaa atctqtqaca aaaactcaca catqcccacc qtqcccaqca   840
cctqaactcc tqqqqqqacc qtcaqtcttc ctcttccccc caaaacccaa qqacaccctc   900
atqatctccc qqacccctqa qqtcacatqc qtqqtqqtqq acqtqaqcca cqaaqaccct   960
qaqqtcaaqt tcaactqqta cqtqqacqqc qtqqaqqtqc ataatqccaa qacaaaqccq  1020
cqqqaqqaqc aqtacaacaq cacqtaccqt qtqqtcaqcq tcctcaccqt cctqcaccaq  1080
qactqqctqa atqqcaaqqa qtacaaqtqc aaqqtctcca caaaqccct cccaqccccc  1140
atcqaqaaaa ccatctccaa aqccaaaqqq caqccccqaq aaccacaqqt qtacaccctq  1200
cccccatccc qqqaqqaqat qaccaaqaac caqqtcaqcc tqacctqcct qqtcaaaqqc  1260
ttctatccca qcqacatcqc cqtqqaqtqq qaqaqcaatq qqcaqccqqa qaacaactac  1320
aaqaccacqc ctcccqtqct qqactccqac qqctccttct tcctctacaq caaqctcacc  1380
qtqqacaaqa qcaqqtqqca qcaqqqqaac qtcttctcat qctccqtqat qcatqaqqct  1440
ctqcacaacc actacacqca qaaqaqcctc tccctqtctc cqqqtaaaat ctacatttqq  1500
qccccqctcq caqqcacatq tqqaqtqctc ctcctctccc tqqtqattac cctqtactqc  1560
aaaaqqqqcc qcaaaaaact cctttacatt tttaaqcaqc ctttctqqaq qccaqtacaq  1620
acqactcaaq aqqaaqacqq tqtqctcatq cqctttcctq aqqaqqaqqa aqqaqqqtqc  1680
qaactqcqcq ttaaqttctc ccqatcaqcc qacqcqcctq cttacaaqqa qqqccaqaac  1740
caactqtaca acqaqctqaa tctcqqtaqa cqqaaaqaqt acqacqtqtt qqacaaaqqq  1800
aqaqqccqcq acccaqaaat qqqcqqcaaq cctcqcaqqa aaaccccca qqaqqqactq  1860
tacaatqaqt tqcaqaaaqa taaqatqqca qaaqcttata cqcaqatcqq aatqaaqqqq  1920
qaaaqqaqac qaqqqaaaqq qacacqacqq ctttatcaqq qcctqccac aqcaacaaaa  1980
qatacqtatq acqccctcca tatqcaqqca cttccaccac qqtqataa               2028

SEQ ID NO: 311          moltype = AA  length = 674
FEATURE                 Location/Qualifiers
REGION                  1..674
                        note = CAR E6 Fc/8/4-1BB/CD3z sequence
source                  1..674
```

```
                         mol_type = protein
                         organism = synthetic construct
SEQUENCE: 311
MALPVTALLL PLALLLHAAR PEVQLVESGG GLVKPGGSLR LSCAASGFTF SRYGMSWVRQ       60
APGKRLEWVS TISGGGTYIY YPDSVKGRFT ISRDNAKNTL YLQMNSLRAE DTAVYYCTRD      120
NYGRNYDYGM DYWGQGTLVT VSSGGGGSGG GGSGGGGSEI VLTQSPATLS LSPGERATLT      180
CSATSSVSYI HWYQQRPGQS PRLLIYSTSN LASGIPARFS GSGSGSDYTL TISSLEPEDF      240
AVYYCQQRSS SPFTFGSGTK VEIKEPKSCD KTHTCPPCPA PELLGGPSVF LFPPKPKDTL      300
MISRTPEVTC VVVDVSHEDP EVKFNWYVDG VEVHNAKTKP REEQYNSTYR VVSVLTVLHQ      360
DWLNGKEYKC KVSNKALPAP IEKTISKAKG QPREPQVYTL PPSREEMTKN QVSLTCLVKG      420
FYPSDIAVEW ESNGQPENNY KTTPPVLDSD GSFFLYSKLT VDKSRWQQGN VFSCSVMHEA      480
LHNHYTQKSL SLSPGKIYIW APLAGTCGVL LLSLVITLYC KRGRKKLLYI FKQPFMRPVQ      540
TTQEEDGCSC RFPEEEEGGC ELRVKFSRSA DAPAYKQGQN QLYNELNLGR REEYDVLDKR      600
RGRDPEMGGK PRRKNPQEGL YNELQKDKMA EAYSEIGMKG ERRRGKGHDG LYQGLSTATK      660
DTYDALHMQA LPPR                                                       674

SEQ ID NO: 312           moltype = DNA  length = 714
FEATURE                  Location/Qualifiers
misc_feature             1..714
                         note = E6 CAR pCDH gBLOCK sequence
source                   1..714
                         mol_type = other DNA
                         organism = synthetic construct
SEQUENCE: 312
acgctgttttt gacctccata gaagattcta gagctagctg tagagcttgg taccgagggc     60
caccatggcc ctgcccgtga ccgctttgct gctccccctg cacgccgccc ctgaacacgc    120
caggccagag gtccagctgg ttgagagtgg cggtgggctg gttaagcctg gcggctccct    180
gcggctgagc tgcgccgcga gtggatttac tttcagccga tatgggatga gttgggtgcg    240
gcaagctccc gggaagaggc tggaatgggt ctcaacaatc tccggggggg gcacttacat    300
ctattacccc gactcagtca aggggagatt taccatttca cgagacaacg ctaagaatac    360
cctgtatttg cagatgaatt ctctgagagc agaggacaca gctgtttact attgtacccg    420
cgacaactat ggcaggaact acgactacgg tatggactat ggggacaagg gacattggt     480
tacagtgagc agtggcggcg ggggcagcgg aggaggaggc agcggtggcg gaggcagcga    540
gatagtgctc acgcagtcac ccgcgactct cagtctcctca cctggggaac gagctaccct    600
gacgtgctct gctacctcct cagtgtcata tattcagcaa ggcccgggca                660
gtccctaga ttgctcattt atagtaccct taatctggcc tcaggtatcc ctgc            714

SEQ ID NO: 313           moltype = DNA  length = 723
FEATURE                  Location/Qualifiers
misc_feature             1..723
                         note = E6 CAR Fc pCDH gBLOCK sequence
source                   1..723
                         mol_type = other DNA
                         organism = synthetic construct
SEQUENCE: 313
agtacctcta atctggcctc aggtatccct gcacgatttt ctggatctgg ttcaggttct      60
gattacaccc tcactatctc tagcctggag cctgaagact tgcgtttta ttactgccag     120
cagaggtcta gctccccatt caccttggg agtgggacca aggttgaaat taaagagccc     180
aaatcttgtg acaaaactca cacatgccca ccgtgcccag cacctgaact cctgggggga    240
ccgtcagtct tcctcttccc cccaaaaccc aaggacaccc tcatgatctc ccggaccct     300
gaggtcacat gcgtggtggt ggacgtgagc cacgaagacc ctgaggtcaa gttcaactgg    360
tacgtggacg gcgtggaggt gcataatgcc aagacaaagc cgcgggagga gcagtacaac    420
agcacgtacc gtgtggtcag cgtcctcacc gtcctgcacc aggactggct gaatggcaag    480
gagtacaagt gcaaggtctc caacaaagcc ctcccagccc ccatcgagaa aaccatctcc    540
aaagccaaag ggcagccccg agaaccacag gtgtacaccc tgcccccatc ccgggaggag    600
atgaccaaga accaggtcag cctgacctgc ctggtcaaag gcttctatcc cagcgacatc    660
gccgtggagt gggagagcaa tgggcagccg gagaacaact acaagaccac gcctcccgtg    720
ctg                                                                   723

SEQ ID NO: 314           moltype = DNA  length = 778
FEATURE                  Location/Qualifiers
misc_feature             1..778
                         note = E6 CAR 8BB3 pCDH gBLOCK sequence
source                   1..778
                         mol_type = other DNA
                         organism = synthetic construct
SEQUENCE: 314
agaacaacta caagaccacg cctcccgtgc tggactccga cggctccttc ttcctctaca      60
gcaagctcac cgtggacaag agcaggtggc agcagggga cgtcttctca tgctccgtga    120
tgcatgaggc tctgcacaac cactacacgc agaagagcct ctccctgtct ccgggtaaaa    180
tctacatttg gccccgctc gcaggcacat tggagtgct ctcctctcc ctggtgatta       240
ccctgtactg caaagggggc cgcaaaaaac tcctttacat tttaagcag cctttatga      300
ggccagtaca gacgactcaa gaggaagacg ggtgctcatg ccgctttcct gaggaggagg    360
aaggagggtg cgaactcgc gttaagtttct ccgatccgaa gcgcgcct gcttacaaga     420
agggccagaa ccaactgtac aacgagctga atctcggtag acgggaagag tacgacgtgt    480
tggacaaacg gagaggccgc gacccagaaa tgggcggcaa gcctcgcagg aaaaacccc     540
aggagggact gtacaatgag ttgcagaaag ataagatggc agaagcttat agcgagatcg    600
gaatgaaggg ggaaaggaga cgaggaaag gacacgacgg cctttatcag ggcctgtcca    660
cagcaacaaa agatacgtat gacgccctcc atatgcaggc acttccacca cggtgataag    720
```

```
tttaaacccg ctgatcaggc ggccgcgaag gatctgcgat cgctccggtg cccgtcag      778

SEQ ID NO: 315           moltype = DNA   length = 1983
FEATURE                  Location/Qualifiers
misc_feature             1..1983
                         note = CAR E6 FcH/8/4-1BB/CD3z sequence
source                   1..1983
                         mol_type = other DNA
                         organism = synthetic construct
SEQUENCE: 315
atggccctgc ccgtgaccgc tttgctgctc cccctggcgc tgctgctgca cgccgccagg      60
ccagaggtcc agctggttga gagtggcggt gggctggtta agcctggcgg ctccctgcgg     120
ctgagctgcg ccgcgagtgg atttactttc agccgatatg gatgagttg ggtgcggcaa     180
gctcccggga agaggctgga atgggtctca acaatctccg ggggggcac ttacatctat     240
taccccgact cagtcaaggg agatttacc atttcacgag acaacgctaa gaataccctg     300
tatttgcaga tgaattctct gagagcgag gacacagctg tttactattg tacccgcgac     360
aactatggca ggaactacga ctacggtatg gactattggg acaagggac attggttaca     420
gtgagcagtg gcggcggggg cagcggagga ggaggcgg gtggcggagg cagcagata     480
gtgctcacgc agtcacccgc gactctcagt ctctcacctg ggaacgagc tacccctacg     540
tgctctgcta cctcctcagt gtcatatatt cactggtatc agcaacggcc cgggcagtcc     600
cctagattgc tcatttatag tacctctaat ctggcctcag gtatccctgc acgatttct     660
ggatctggtt caggttctga ttacaccctc actatctca gcctggagcc tgaagactt     720
gccgtttatt actgccagca gaggtctagc tccccattca cctttgggag tgggaccaag     780
gttgaaatta agcacctga actcctgggg gaccgtcag tcttcctctt ccccccaaaa     840
cccaaggaca ccctcatgat ctcccggacc ctgaggtca catgcgtggt ggtggacgtg     900
agccacgaag accctgaggt caagttcaac tggtacgtgg acggcgtgga ggtgcataat     960
gccaagacaa agccgcggga ggagcagtac aacagcacgt accgtgtgt cagcgtcctc    1020
accgtcctgc accaggactg gctgaatggc aaggagtaca agtgcaaggt ctccaacaaa    1080
gccctcccag cccccatcga gaaaccatc tccaaagcca agggcagcc ccgagaacca    1140
caggtgtaca ccctgccccc atcccgggag gagatgacca agaaccaggt cagcctgacc    1200
tgcctggtca aaggcttcta tcccagcgac atcgccgtgg agtgggagag caatgggcag    1260
ccggagaaca actacaagac cacgcctccc gtgctggact ccgacggctc cttcttcctc    1320
tacagcaagc tcaccgtgga caagagcagg tggcagcagg ggaacgtctt ctcatgctcc    1380
gtgatgcatg aggctctgca caaccactac acgcagaaga gcctctccct gtctccgggt    1440
aaaatctaca tttgggcccc gctcgcaggc acatgtggag tgctcctcct ctccctggtg    1500
attaccctgt actgcaaaag gggccgcaaa aaactccttt acattttaa gcagcctttt    1560
atgaggccag tacagacgac tcaagaggaa gacgggtgct catgccgctt cctgaggag    1620
gaggaaggag ggtgcgaact gcgcgttaag ttctcccgat cagccgacgc gcctgcttac    1680
aagcaggcc agaaccaact gtacaacgag ctgaatctcg gtagacggga agatacgac    1740
gtgttggaca acggagagg ccgcgaccca gaaatgggcg gcaagcctcg caggaaaaac    1800
ccccaggagg gactgtacaa tgagttgcag aagataaga tggcagaagc ttatagcgag    1860
atcggaatga aggggaaag gagacgaggg aaggacacg acggccttta tcagggcctg    1920
tccacagcaa caaaagatac gtatgacgcc ctccatatgc aggcacttcc accacggtga    1980
taa                                                                 1983

SEQ ID NO: 316           moltype = AA   length = 659
FEATURE                  Location/Qualifiers
REGION                   1..659
                         note = CAR E6 FcH/8/4-1BB/CD3z sequence
source                   1..659
                         mol_type = protein
                         organism = synthetic construct
SEQUENCE: 316
MALPVTALLL PLALLLHAAR PEVQLVESGG GLVKPGGSLR LSCAASGFTF SRYGMSWVRQ      60
APGKRLEWVS TISGGGTYIY YPDSVKGRFT ISRDNAKNTL YLQMNSLRAE DTAVYYCTRD     120
NYGRNYDYGM DYWGQGTLVT VSSGGGGSGG GGSGGGGSEI VLTQSPATLS LSPGERATLT     180
CSATSSVSYI HWYQQRPGQS PRLLIYSTSN LASGIPARFS GSGSGSDYTL TISSLEPEDF     240
AVYYCQQRSS SPFTFGSGTK VEIKAPELLG GPSVFLFPPK PKDTLMISRT PEVTCVVVDV     300
SHEDPEVKFN WYVDGVEVHN AKTKPREEQY NSTYRVVSVL TVLHQDWLNG KEYKCKVSNK     360
ALPAPIEKTI SKAKGQPREP QVYTLPPSRE EMTKNQVSLT CLVKGFYPSD IAVEWESNGQ     420
PENNYKTTPP VLDSDGSFFL YSKLTVDKSR WQQGNVFSCS VMHEALHNHY TQKSLSLSPG     480
KIYIWAPLAG TCGVLLLSLV ITLYCKRGRK KLLYIFKQPF MRPVQTTQEE DGCSCRFPEE     540
EEGGCELRVK FSRSADAPAY KQGQNQLYNE LNLGRREEYD VLDKRRGRDP EMGGKPRRKN     600
PQEGLYNELQ KDKMAEAYSE IGMKGERRRG KGHDGLYQGL STATKDTYDA LHMQALPPR      659

SEQ ID NO: 317           moltype = DNA   length = 678
FEATURE                  Location/Qualifiers
misc_feature             1..678
                         note = E6 CAR FcH pCDH gBLOCK sequence
source                   1..678
                         mol_type = other DNA
                         organism = synthetic construct
SEQUENCE: 317
agtaccctcta atctggcctc aggtatccct gcacgatttt ctggatctgg ttcaggttct      60
gattacaccc tcactatctc tagcctggag cctgaagact tgccgtttta ttactgccag     120
cagaggtcta gctccccatt cacctttggg agtgggacca aggttgaaat taagcacct     180
gaactcctgg gggaccgtc agtcttcctc ttccccccaa aacccaagga cacctcatg     240
atctcccgga cccctgaggt cacatgcgtg gtggtggacg tgagccacga agaccctgag     300
gtcaagttca ctggtacgt ggacggcgtg gaggtgcata atgccaagac aaagccgcgg     360
```

```
gaggagcagt acaacagcac gtaccgtgtg gtcagcgtcc tcaccgtcct gcaccaggac  420
tggctgaatg gcaaggagta caagtgcaag gtctccaaca aagccctccc agccccatc   480
gagaaaacca tctccaaagc caagggcag ccccgagaac acaggtgta caccctgccc    540
ccatcccggg aggagatgac caagaaccag gtcagcctga cctgcctggt caaaggcttc  600
tatcccagcg acatcgccgt ggagtgggag agcaatgggc agccggagaa caactacaag  660
accacgcctc ccgtgctg                                                678

SEQ ID NO: 318          moltype = DNA   length = 2022
FEATURE                 Location/Qualifiers
misc_feature            1..2022
                        note = CAR E6 Fc/4/4-1BB/CD3z sequence
source                  1..2022
                        mol_type = other DNA
                        organism = synthetic construct
SEQUENCE: 318
atggccctgc ccgtgaccgc tttgctgctc cccctggcgc tgctgctgca cgccgccagg  60
ccagaggtcc agctggttga gagtggcggt gggctggtta gcctggcgg ctccctgcgg   120
ctgagctgcg ccgcgagtgg atttactttc agccgatatg ggatgagttg ggtgcggcaa  180
gctcccggga gaggctgga atgggtctca acaatctccg ggggggcac ttacatctat   240
taccccgact cagtcaaggg gagatttacc atttcacgag acaacgctaa gaatacctg   300
tatttgcaga tgaattctct gagagcagag gacacagctg tttactattg taccgcgac   360
aactatggca ggaactacga ctacggtatg gactattgg gacaagggac attggttaca  420
gtgagcagtg gcggcggggg cagcggagga ggaggcagcg gtggcggagg cagcgagata  480
gtgctcacgc agtcacccgc gactctcagt ctctccacctg gggaacgagc taccctgacg  540
tgctctgcta cctcctcagt gtcatatatt cactggtatc agcaacggcc cgggcagtcc  600
cctagattgc tcatttatag tacctctaat ctggcctcag gtatccctgc acgatttct   660
ggatctggtt caggttctga ttacaccctc actatctcta gcctggagcc tgaagacttt  720
gccgtttatt actgccagca gaggtctagc tccccattca cctttgggag tgggaccaag  780
gttgaaatta aagagcccaa atcttgtgac aaaactcaca catgcccacc gtgcccagca  840
cctgaactcc tgggggggacc gtcagtcttc ctcttccccc caaaacccaa ggacacctc   900
atgatctccc ggaccctga ggtcacatgc gtggtggtgg acgtgagcca cgaagaccct    960
gaggtcaagt tcaactggta cgtggacggc gtggaggtgc ataatgccaa gacaaagccg  1020
cgggaggagc agtacaacag cacgtaccgt gtggtcagcg tcctcaccgt cctgcaccag  1080
gactggctga atggcaagga gtacaagtgc aaggtctcca acaaagccct cccagcccc   1140
atcgagaaaa ccatctccaa agccaaaggg cagccccgag aaccacaggt gtacaccctg  1200
cccccatccc gggaggagat gaccaagaac caggtcagcc tgacctgcct ggtcaaaggc  1260
ttctatccca gcgacatcgc cgtggagtgg gagagcaatg ggcagccgga gaacaactac  1320
aagaccacgc ctcccgtgct ggactccgac ggctccttct cctctacag caagctcacc  1380
gtggacaaga gcaggtggca gcaggggaac gtcttctcat gctccgtgat gcatgaggct  1440
ctgcacaacc actacacgca gaagagcctc tccctgtctc cgggtaaaat ggccctgatt  1500
gtgctggggg gcgtcgccgg cctcctgctt ttcattgggc taggcatctt cttcaaaagg  1560
ggccgcaaaa aactcctta catttttaag cagccttta tgaggccagt acagacgact   1620
caagaggaag acggggtgct atgccgcttt cctgaggagg aggaaggagg tgcgaactg   1680
cgcgttaagt tctcccgatc agccgacgcg cctgcttaca gcagggcca gaaccaactg   1740
tacaacagct gaatctcgg tagacgggaa gagtacgacg tgttggacaa acggagaggc  1800
cgcgaccag aaatggcgg caagcctcgc aggaaaaacc cccaggaggg actgtacaat   1860
gagttgcaa aagataagat ggcagaagct tatagcgaga tcggaatgaa ggggggaaagg  1920
agacgaggga aaggacacga cggcctttat cagggcctgt ccacagcaac aaaagatacg  1980
tatgacgccc tccatatgca ggcacttcca ccacggtgat aa                    2022

SEQ ID NO: 319          moltype = AA   length = 672
FEATURE                 Location/Qualifiers
REGION                  1..672
                        note = CAR E6 Fc/4/4-1BB/CD3z sequence
source                  1..672
                        mol_type = protein
                        organism = synthetic construct
SEQUENCE: 319
MALPVTALLL PLALLLHAAR PEVQLVESGG GLVKPGGSLR LSCAASGFTF SRYGMSWVRQ  60
APGKRLEWVS TISGGGTYIY YPDSVKGRFT ISRDNAKNTL YLQMNSLRAE DTAVYYCTRD  120
NYGRNYDYGM DYWGQGTLVT VSSGGGGSGG GGSGGGGSEI VLTQSPATLS LSPGERATLT  180
CSATSSVSYI HWYQQRPGQS PRLLIYSTSN LASGIPARFS GSGSGSDYTL TISSLEPEDF  240
AVYYCQQRSS SPFTFGSGTK VEIKEPKSCD KTHTCPPCPA PELLGGPSVF LFPPKPKDTL  300
MISRTPEVTC VVVDVSHEDP EVKFNWYVDG VEVHNAKTKP REEQYNSTYR VVSVLTVLHQ  360
DWLNGKEYKC KVSNKALPAP IEKTISKAKG QPREPQVYTL PPSREEMTKN QVSLTCLVKG  420
FYPSDIAVEW ESNGQPENNY KTTPPVLDSD GSFFLYSKLT VDKSRWQQGN VFSCSVMHEA  480
LHNHYTQKSL SLSPGKMALI VLGGVAGLLL FIGLGIFFKR GRKKLLYIFK QPFMRPVQTT  540
QEEDGCSCRF PEEEEGGCEL RVKFSRSADA PAYKQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                     672

SEQ ID NO: 320          moltype = DNA   length = 772
FEATURE                 Location/Qualifiers
misc_feature            1..772
                        note = E6 CAR 44BB3 pCDH gBLOCK sequence
source                  1..772
                        mol_type = other DNA
                        organism = synthetic construct
SEQUENCE: 320
```

-continued

```
agaacaacta caagaccacg cctcccgtgc tggactccga cggctccttc ttcctctaca    60
gcaagctcac cgtggacaag agcaggtggc agcaggggaa cgtcttctca tgctccgtga   120
tgcatgaggc tctgcacaac cactacacgc agaagagcct ctccctgtct ccgggtaaaa   180
tggccctgat tgtgctgggg ggcgtcgccg gcctcctgct tttcattggg ctaggcatct   240
tcttcaaaag gggccgcaaa aaactccttt acatttttaa gcagccttt atgaggccaa    300
tacagacgac tcaagaggaa gacggtgctc atgccgcctt tcctgaggag gaggaaggag   360
ggtgcgaact cgcgcgttaag ttctcccgat cagccgacgc gcctgcttac aagcagggcc  420
agaaccaact gtacaacgag ctgaatctcg gtagacggga agagtacgac gtgttggaca   480
aacggagagg ccgcgaccca gaaatgggcg gcaagcctcg caggaaaaac cccaggagg    540
gactgtacaa tgagttgcag aaagataaga tggcagaagc ttatagcgag atcgaatga   600
agggggaaag gagacgaggg aaaggacacg acggccttta tcagggcctg tccacagcaa   660
caaaagatac gtatgacgcc ctccatatgc aggcacttcc accacggtga taagtttaaa   720
cccgctgatc aggcggccgc gaaggatctg cgatcgctcc ggtgcccgtc ag           772

SEQ ID NO: 321        moltype = DNA length = 1977
FEATURE               Location/Qualifiers
misc_feature          1..1977
                      note = CAR E6 FcH/4/4-1BB/CD3z sequence
source                1..1977
                      mol_type = other DNA
                      organism = synthetic construct
SEQUENCE: 321
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg gatgagttg ggtgcggcaa    180
gctcccggga agaggctgga atgggtctca acaatctccg ggggggcta ttacatctat   240
taccccgact cagtcaaggg agatttacc atttcacgag acaacgctaa gaataccctg   300
tatttgcaga tgaattctct gagagcagag gacacagctg tttactattg taccgcgac    360
aactatggca ggaactacga ctacggtatg gactattggg gacaagggac attggttaca   420
gtgagcagtg gcggcggggg cagcggagga ggaggcggcg gtggcggagg cagcgagata   480
gtgctcacgc agtcacccgc gactctcagt ctctcacctg ggaacgagc taccctgacg   540
tgctctgcta cctcctcagt gtcatatatt cactggtatc agcaacggcc cggcagtcc    600
cctagattgc tcatttatag tacctctaat ctggcctcag gtatccctgc acgattttct   660
ggatctggtt caggttctga ttacaccctc actatctcta gcctgagcc tgaagcttt    720
gccgttatt actgccagca gaggtctagc tccccattca cctttgggag tgggaccaag   780
gttgaaatta agcacctga actcctgggg ggaccgtcag tcttcctctt cccccccaaaa   840
cccaaggaca ccctcatgat ctcccggacc cctgaggtca catgcgtggt ggtggacgtg   900
agccacgaag accctgaggt caagttcaac tggtacgtgg acggcgtgga ggtgcataat   960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag ccccatcga gaaaccatc tccaaagcca agggcagcc cgagaaccca   1140
caggtgtaca ccctgccccc atcccgggag gagatgacca gaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg gaacgtcttc tcatgctcc   1380
gtgatgcatg aggctctgca caaccactac acgcagaaga gcctctccct gtctccgggt  1440
aaaatggccc tgattgtgct ggggggcgtc gccggcctcc tgcttttcat tgggctaggc  1500
atcttcttca aaaggggccg caaaaaactc ctttacattt ttaagcagcc ttttatgagg  1560
ccagtacaga cgactcaaga ggaagacggg tgctcatgcc gctttcctga ggaggaggaa  1620
ggagggtgcg aactgcgcgt taagttctcc cgatcagccg acgcgcctgc ttacaagcag  1680
ggccagaacc aactgtacaa cgagctgaat ctcggtagac gggaagagta cgacgtgttg  1740
gacaaacgga gaggccgcga cccagaaatg ggcggcaagc ctcgcaggaa aaaccccag   1800
gagggactgt acaatgagtt gcagaaagat aagatggcag aagcttatag cgagatcgga  1860
atgaaggggg aaaggagacg agggaaagga cacgacggcc tttatcaggg cctgtccaca  1920
gcaacaaaag atacgtatga cgccctccat atgcaggcac ttccaccacg gtgataa     1977

SEQ ID NO: 322        moltype = AA length = 657
FEATURE               Location/Qualifiers
REGION                1..657
                      note = CAR E6 FcH/4/4-1BB/CD3z sequence
source                1..657
                      mol_type = protein
                      organism = synthetic construct
SEQUENCE: 322
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF   240
AVYYCQQRSS SPFTFGSGTK VEIKAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRE EMTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
KMALIVLGGV AGLLLFIGLG IFFKRGRKKL LYIFKQPFMR PVQTTQEEDG CSCRFPEEEE   540
GGCELRVKFS RSADAPAYKQ GQNQLYNELN LGRREEYDVL DKRRGRDPEM GGKPRRKNPQ   600
EGLYNELQKD KMAEAYSEIG MKGERRRGKG HDGLYQGLST ATKDTYDALH MQALPPR      657

SEQ ID NO: 323        moltype = DNA length = 1506
FEATURE               Location/Qualifiers
misc_feature          1..1506
```

```
                        note = CAR E6 IgD/8/4-1BB/CD3z sequence
source                  1..1506
                        mol_type = other DNA
                        organism = synthetic construct
SEQUENCE: 323
atggccctgc ccgtgaccgc tttgctgctc cccctggcgc tgctgctgca cgccgccagg   60
ccagaggtcc agctggttga gagtggcggt gggctggtta agcctggcgg ctccctgcgg  120
ctgagctgcg ccgcgagtgg atttactttc agccgatatg ggatgagttg ggtgcggcaa  180
gctcccggga gaggctggaa atgggtctca caaatcccg gggggggcac ttacatctat   240
taccccgact cagtcaaggg gagatttacc atttcacgag acaacgctaa gaataccctg  300
tatttgcaga tgaattctct gagagcagag gacacagctg tttactattg taccgcgac   360
aactatggca ggaactacga ctacggtatg gactattggg acaagggac attggttaca   420
gtgagcagtg gcggcggggg cagcggagga ggaggcagcg gtggcggagg cagcgagata  480
gtgctcacgc agtcacccgc gactctcagt ctctcacctg ggaacgagc tacccctgacg  540
tgctctgcta cctcctcagt gtcatatatt cactggtatc agcaacggcc cgggcagtcc  600
cctagattgc tcatttatag tacctctaat ctggcctcag gtatccctgc acgatttct   660
ggatctggtt caggttctga ttcacccctc actatctcta gcctggagcc tgaagacttt  720
gccgtttatt actgccagca gaggtctagc tccccattca cctttgggag tgggaccaag  780
gttgaaatta aagagtctcc aaaggcacag gcctcctcag tgcccactgc acaacccaa   840
gcagagggca gcctcgccaa ggcaaccaca gccccagcca ccaccgtaa cacaggaaga  900
ggcggcgaag agaagaaaaa ggagaaggag aagaggaac aagaagagag agacaaag    960
acaccaatct acatttgggc cccgctcga ggcacatgt gagtgctcct cctctccctg   1020
gtgattaccc tgtactgcaa aaggggccgc aaaaaactcc tttacatttt taagcagcct 1080
tttatgaggc cagtacagac gactcaagag gaagacgggt gctcatgccg ctttcctgag 1140
gaggaggaag gagggtgcga actgcgcgtt aagttctccc gatcagccga cgcgcctgct 1200
tacacaggg gccagaacca actgtacaac gagctgaatc tcggtagacg ggaagagtac 1260
gacgtgttgg acaaacggag aggccgcgac ccagaaatgg gcggcaagcc tcgcaggaaa 1320
aaccccag g gggactgta caatgagttg cagaaagata agatggcaga agcttatagc 1380
gagatcggaa tgaaggggga aggagacga gggaaggac acgacggcct ttatcagggc 1440
ctgtccacag caacaaaaga tacgtatgac gccctccata tgcaggcact tccaccacgg 1500
tgataa                                                             1506

SEQ ID NO: 324          moltype = AA  length = 500
FEATURE                 Location/Qualifiers
REGION                  1..500
                        note = CAR E6 IgD/8/4-1BB/CD3z sequence
source                  1..500
                        mol_type = protein
                        organism = synthetic construct
SEQUENCE: 324
MALPVTALLL PLALLLHAAR PEVQLVESGG GLVKPGGSLR LSCAASGFTF SRYGMSWVRQ   60
APGKRLEWVS TISGGGTYIY YPDSVKGRFT ISRDNAKNTL YLQMNSLRAE DTAVYYCTRD  120
NYGRNYDYGM DYWGQGTLVT VSSGGGGSGG GGSGGGGSEI VLTQSPATLS LSPGERATLT  180
CSATSSVSYI HWYQQRPGQS PRLLIYSTSN LASGIPARFS GSGSGSDYTL TISSLEPEDF  240
AVYYCQQRSS SPFTFGSGTK VEIKESPKAQ ASSVPTAQPQ AEGSLAKATT APATTRNTGR  300
GGEEKKKEKE KEEQEERETK TPIYIWAPLA GTCGVLLLSL VITLYCKRGR KKLLYIFKQP  360
FMRPVQTTQE EDGCSCRFPE EEEGGCELRV KFSRSADAPA YKQGQNQLYN ELNLGRREEY  420
DVLDKRRGRD PEMGGKPRRK NPQEGLYNEL QKDKMAEAYS EIGMKGERRR GKGHDGLYQG  480
LSTATKDTYD ALHMQALPPR                                              500

SEQ ID NO: 325          moltype = DNA  length = 475
FEATURE                 Location/Qualifiers
misc_feature            1..475
                        note = E6 CAR IgD8 pCDH gBLOCK sequence
source                  1..475
                        mol_type = other DNA
                        organism = synthetic construct
SEQUENCE: 325
agtacctcta atctggcctc aggtatccct gcacgatttt ctggatctgg ttcaggttct   60
gattacaccc tcactatctc tagcctggag cctgaagact tgccgttta ttactgccag  120
cagaggtcta gctccccatt cacctttggg agtgggacca aggttgaaat taaagagtct  180
ccaaaggcac aggcctcctc agtgcccact gcacaacccc aagcagaggg cagcctcgcc  240
aaggcaacca gcccagc caccaccgt aacacaggg gaggcggcg agagaagaa          300
aaggagaagg agaaagagga acaagaagag agagacaccaat ctacatttgg            360
gccccgctcg caggcacatg tggagtgctc ctcctctccc tggtgattac cctgtactgc  420
aaaaggggcc gcaaaaaact cctttacatt tttaagcagc cttttatgag gccag        475

SEQ ID NO: 326          moltype = DNA  length = 502
FEATURE                 Location/Qualifiers
misc_feature            1..502
                        note = E6 CAR BB 3 pCDH gBLOCK sequence
source                  1..502
                        mol_type = other DNA
                        organism = synthetic construct
SEQUENCE: 326
acatttttaa gcagcctttt atgaggccag tacagacgac tcaagaggaa gacgggtgct   60
catgccgctt tcctgaggag gaggaaggag ggtgcgaact gcgcgttaag ttctcccgat  120
cagccgacgc gcctgcttac aagcagggcc agaaccaact gtacaacgag ctgaatctcg  180
gtagacggga agagtacgac gtgttggaca aacggagagg ccgcgaccca gaaatgggcg  240
```

```
gcaagcctcg caggaaaaac ccccaggagg gactgtacaa tgagttgcag aaagataaga   300
tggcagaagc ttatagcgag atcggaatga aggggaaag  gagacagggg aaaggacacg   360
acggccttta tcagggcctg tccacagcaa caaaagatac gtatgacgcc ctccatatgc   420
aggcacttcc accacggtga taagtttaaa cccgctgatc aggcggccgc gaaggatctg   480
cgatcgctcc ggtgcccgtc ag                                            502

SEQ ID NO: 327          moltype = DNA  length = 1500
FEATURE                 Location/Qualifiers
misc_feature            1..1500
                        note = CAR E6 IgD/4/4-1BB/CD3z sequence
source                  1..1500
                        mol_type = other DNA
                        organism = synthetic construct
SEQUENCE: 327
atggccctgc ccgtgaccgc tttgctgctc cccctggcgc tgctgctgca cgccgccagg    60
ccagaggtcc agctggttga gagtggcggt gggctggtta gcctggcgg  ctccctgcgg   120
ctgagctgcg ccgcgagtgg atttactttc agccgatatg gatgagttg  ggtgcggcaa   180
gctcccggga agaggctgga atgggtctca acaatcccg  ggggggcac ttacatctat    240
taccccgact cagtcaaggg gagatttacc atttcacgag acaacgctaa gaataccctg    300
tatttgcaga tgaattctct gagagcagag gacacagctg tttactattg taccgcgac    360
aactatggca ggaactacga ctacggtatg gactattggg gacaagggac attggttaca    420
gtgagcagtg gcggcggggg cagcggagga ggaggcggcg gttggcggga cagcagata    480
gtgctcacgc agtcacccgc gactctcagt ctctcacctg ggaacgagc  taccctgacg   540
tgctctgcta cctcctcagt gtcatatatt cactggtatc agcaacgcc  cgggcagtcc   600
cctagattgc tcatttatag tacctctaat ctggcctcag gtatccctgc acgattttct   660
ggatctggtt caggttctga ttacaccctc actatctca  gcctgagcc  tgaagactt   720
gccgtttatt actgccagca gaggtctagc tccccattca cctttgggag tgggaccaag   780
gttgaaatta aagagtctcc aaaggcacag gcctcctcag tgcccactgc acaaccccaa   840
gcagagggca gcctcgccaa gcaaccaca  gccccagcca ccaccgtaa  cacaggaaga   900
ggcggcgaag aagagaaaaa ggagaaggag aagaggaac  aagagagag  agagaacaa   960
acaccaatgg ccctgattgt gctgggggc  gtcgccggcc tcctgctttt cattgggcta  1020
ggcatcttct tcaaaagggg ccgcaaaaaa ctcctttaca tttttaagca gccttttatg  1080
aggccagtac agacgactca gaggaagac  gggtgctcat gccgctttcc tgaggaggag  1140
gaaggagggt gcgaactgcg cgttaagttc tcccgatcag ccgacgcgcc tgcttacaag  1200
cagggccaga accaactgta caacgagctg aatctcggta gacgggaaga gtacgacgtg  1260
ttggacaaac ggagaggccg cgacccagaa atgggcggca agcctcgcag gaaaaacccc  1320
caggagggac tgtacaatga gttgcagaaa gataagatgg cagaagctta tagcgagatc  1380
ggaatgaagg gggaaggag  acgagggaaa ggacacgacg gcctttatca gggcctgtcc  1440
acagcaacaa aagatacgta tgacgccctc catatgcagg cacttccacc acggtgataa  1500

SEQ ID NO: 328          moltype = AA  length = 498
FEATURE                 Location/Qualifiers
REGION                  1..498
                        note = CAR E6 IgD/4/4-1BB/CD3z sequence
source                  1..498
                        mol_type = protein
                        organism = synthetic construct
SEQUENCE: 328
MALPVTALLL PLALLLHAAR PEVQLVESGG GLVKPGGSLR LSCAASGFTF SRYGMSWVRQ     60
APGKRLEWVS TISGGGTYIY YPDSVKGRFT ISRDNAKNTL YLQMNSLRAE DTAVYYCTRD    120
NYGRNYDYGM DYWGQGTLVT VSSGGGSGG  GGSGGGGSEI VLTQSPATLS LSPGERATLT    180
CSATSSVSYI HWYQQRPGQS PRLLIYSTSN LASGIPARFS GSGSGSDYTL TISSLEPEDF    240
AVYYCQQRSS SPFTFGSGTK VEIKESPKAQ ASSVPTAQPQ AEGSLAKATT APATTRNTGR    300
GGEEKKKEKE KEEQEERETK TPMALIVLGG VAGLLLFIGL GIFFKRGRKK LLYIFKQPFM    360
RPVQTTQEED GCSCRFPEEE EGGCELRVKF SRSADAPAYK QGQNQLYNEL NLGRREEYDV    420
LDKRRGRDPE MGGKPRRKNP QEGLYNELQK DKMAEAYSEI GMKGERRGK  GHDGLYQGLS    480
TATKDTYDAL HMQALPPR                                                  498

SEQ ID NO: 329          moltype = DNA  length = 469
FEATURE                 Location/Qualifiers
misc_feature            1..469
                        note = E6 CAR IgD4 pcDH gBLOCK sequence
source                  1..469
                        mol_type = other DNA
                        organism = synthetic construct
SEQUENCE: 329
agtacctcta atctggcctc aggtatccct gcacgatttt ctggatctgg ttcaggttct     60
gattacaccc tcactatctc tagcctggag cctgaagact ttgccgttta ttactgccag    120
cagaggtcta gctccccatt cacctttggg agtgggacca aggttgaaat taaagagtct    180
ccaaaggcac aggcctcctc agtgcccact gcacaacccc aagcagaggg cagcctcgcc    240
aaggcaacca gccccagcca ccaccccgt  aacacaggaa gaggcggcga agaagaaaa    300
aaggagaagg agaaagagga caagaagag  agagagacaa agacaccaat ggccctgatt    360
gtgctggggg gcgtcgccgg cctcctgctt ttcattgggc taggcatctt cttcaaaagg    420
ggccgcaaaa aactccttta catttttaag cagccttta  tgaggccag                469

SEQ ID NO: 330          moltype = DNA  length = 1461
FEATURE                 Location/Qualifiers
misc_feature            1..1461
                        note = CAR E6 X4/8/4-1BB/CD3z sequence
```

```
source                  1..1461
                        mol_type = other DNA
                        organism = synthetic construct
SEQUENCE: 330
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg ggatgagttg ggtgcggcaa   180
gctcccggga agaggctgga atgggtctca acaatctccg gggggggcac ttacatctat   240
taccccgact cagtcaaggg gagatttacc atttcacgag acaacgctaa gaatacccta   300
tatttgcaga tgaattctct gagagcagag gacacagctg tttactattg taccgcgcga   360
aactatggca ggaactacga ctacggtatg gactattggg gacaagggac attggttaca   420
gtgagcagtg gcggcggggg cagcggagga ggaggcagcg gtggcggagg cagcgagata   480
gtgctcacgc agtcacccgc gactctcagt ctctcacctg gggaacgagc taccctgacg   540
tgctctgcta cctcctcagt gtcatatatt cactggtatc agcaacggca gcggcagtcc   600
cctagattgc tcatttatag tacctctaat ctggcctcag gtatccctgc acgattttct   660
ggatctggtt caggttctga ttacaccctc actatctcta gcctggagcc tgaagacttt   720
gccgtttatt actgccagca gaggtctagc tccccattca cctttgggag tgggaccaag   780
gttgaaatta agacaagac gcacaccaag ccacctaaac cagctccaga actgctcgga   840
ggtcctggca ccggaaccgg aggacctacc atcaaaccac ctaagccacc taagcctgct   900
cctaacctgc tcggaggacc tatctacatt tgggccccgc tcgcaggcac atgtggagtg   960
ctcctcctct ccctggtgat tacccttgtac tgcaaagggg ccgcaaaaa actcctttac  1020
atttttaagc agccttttat gaggccagta cagacgacta aagaggaaga cgggtgctca  1080
tgccgctttc ctgaggagga ggaaggaggg tgcgaactgc gcgttaagtt ctcccgatca  1140
gccgacgcgc tgcttacaa gcagggccag aaccaactgt acaacgagct gaatctcggt  1200
agacgggaag agtacgacgt gttggacaaa cggagaggcc gcgacccaga aatgggcggc  1260
aagcctcgca ggaaaaaccc caggaggga ctgtacgaac tgttgcagaa agataagatg  1320
gcagaagctt atagcgagat cggaatgaag gggaaaggaa gacgagggaa aggacacgac  1380
ggcctttatc agggcctgtc cacagcaaca aaagatacgt atgacgccct ccatatgcag  1440
gcacttccac cacggtgata a                                             1461

SEQ ID NO: 331          moltype = AA    length = 485
FEATURE                 Location/Qualifiers
REGION                  1..485
                        note = CAR E6 X4/8/4-1BB/CD3z sequence
source                  1..485
                        mol_type = protein
                        organism = synthetic construct
SEQUENCE: 331
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKDKTHTK PPKPAPELLG GPGTGTGGPT IKPPKPPKPA   300
PNLLGGPIYI WAPLAGTCGV LLLSLVITLY CKRGRKKLLY IFKQPFMRPV QTTQEEDGCS   360
CRFPEEEEGG CELRVKFSRS ADAPAYKQGQ NQLYNELNLG RREEYDVLDK RRGRDPEMGG   420
KPRRKNPQEG LYNELQKDKM AEAYSEIGMK GERRRGKGHD GLYQGLSTAT KDTYDALHMQ   480
ALPPR                                                               485

SEQ ID NO: 332          moltype = DNA   length = 430
FEATURE                 Location/Qualifiers
misc_feature            1..430
                        note = E6 CAR X48 pCDH gBLOCK sequence
source                  1..430
                        mol_type = other DNA
                        organism = synthetic construct
SEQUENCE: 332
agtacctcta atctggcctc aggtatccct gcacgatttt ctggatctgg ttcaggttct    60
gattacaccc tcactatctc tagcctggag cctgaagact ttgccgttta ttactgccag   120
cagaggtcta gctcccccatt cacctttggg agtgggacca aggttgaaat taaagacaag   180
acgcacacca agccacctaa accagctcca gaactgctcg gaggtcctgg caccggaacc   240
ggaggaccta ccatcaaacc acctaagcca cctaagcctg ctcctaacct gctcggagga   300
cctatctaca tttgggcccc gctcgcaggc acatgtggag tgctcctcct ctccctggtg   360
attacccttgt actgcaaaag gggccgcaaa aaactccttt acatttttaa gcagcctttt   420
atgaggccag                                                          430

SEQ ID NO: 333          moltype = DNA   length = 1455
FEATURE                 Location/Qualifiers
misc_feature            1..1455
                        note = CAR E6 X4/4/4-1BB/CD3z sequence
source                  1..1455
                        mol_type = other DNA
                        organism = synthetic construct
SEQUENCE: 333
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg ggatgagttg ggtgcggcaa   180
gctcccggga agaggctgga atgggtctca acaatctccg gggggggcac ttacatctat   240
taccccgact cagtcaaggg gagatttacc atttcacgag acaacgctaa gaatacccta   300
tatttgcaga tgaattctct gagagcagag gacacagctg tttactattg taccgcgac   360
```

```
aactatggca ggaactacga ctacggtatg gactattggg gacaagggac attggttaca    420
gtgagcagtg gcggcggggg cagcggagga ggaggcagcg gtgcggagg  cagcgagata    480
gtgctcacgc agtcacccgc gactctcagt ctctcacctg gggaacgagc taccctgacg    540
tgctctgcta cctcctcagt gtcatatatt cactggtatc agcaacggcc cgggcagtcc    600
cctagattgc tcatttatag tacctctaat ctggcctcag gtatccctgc acgattttct    660
ggatctggtt caggttctga ttacaccctc actatctcta gcctggagcc tgaagacttt    720
gccgtttatt actgccagca gaggtctagc tccccattca cctttgggag tgggaccaag    780
gttgaaatta agacaagac  gcacaccaag ccacctaaac cagctccaga actgctcgga    840
ggtcctggca ccggaaccgg aggacctacc atcaaaccac ctaagccacc taagcctgct    900
cctaacctgc tcggaggacc tatggccctg attgtgctgg ggggcgtcgc cggcctcctg    960
cttttcattg ggctaggcat cttcttcaaa aggggccgca aaaaactcct ttacattttt   1020
aagcagcctt ttatgaggcc agtacagacg actcaagagg aagacgggtg tcatgccgc    1080
tttcctgagg aggaggaagg agggtgcgaa ctgcgcgtta agttctcccg atcagccgac   1140
gcgcctgctt acaagcaggg ccagaaccaa ctgtacaacg agctgaatct cggtagacgg   1200
gaagagtacg acgtgttgga caaacgggaga ggccgcgacc cagaaatggg cggcaagcct  1260
cgcaggaaaa accccaggga gggactgtac aatgagttgc agaaagataa gatggcagaa   1320
gcttatagcg agatcggaat gaaggggaa  aggagacgag ggaaaggaca cgacggcctt   1380
tatcagggcc tgtccacagc aacaaaagat acgtatgacg ccctccatat gcaggcactt   1440
ccaccacggt gataa                                                    1455

SEQ ID NO: 334         moltype = AA  length = 483
FEATURE                Location/Qualifiers
REGION                 1..483
                       note = CAR E6 X4/4/4-1BB/CD3z sequence
source                 1..483
                       mol_type = protein
                       organism = synthetic construct
SEQUENCE: 334
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKDKTHTK PPKAPELLG  GPGTGTGGPT IKPPKPPKPA   300
PNLLGGPMAL IVLGGVAGLL LFIGLGIFFK RGRKKLLYIF KQPFMRPVQT TQEEDGCSCR   360
FPEEEEGGCE LRVKFSRSAD APAYKQGQNQ LYNELNLGRR EEYDVLDKRR GRDPEMGGKP   420
RRKNPQEGLY NELQKDKMAE AYSEIGMKGE RRRGKGHDGL YQGLSTATKD TYDALHMQAL   480
PPR                                                                483

SEQ ID NO: 335         moltype = DNA  length = 424
FEATURE                Location/Qualifiers
misc_feature           1..424
                       note = E6 CAR X44 pCDH gBLOCK sequence
source                 1..424
                       mol_type = other DNA
                       organism = synthetic construct
SEQUENCE: 335
agtacctcta atctggcctc aggtatccct gcacgatttt ctggatctgg ttcaggttct    60
gattacaccc tcactatctc tagcctggag cctgaagact ttgccgttta ttactgccag   120
cagaggtcta gctccccatt cacctttggg agtgggacca aggttgaaat taagacaag   180
acgcacacca agccacctaa accagctcca gaactgctcg gaggtcctgg caccggaacc   240
ggaggaccta ccatcaaacc acctaagcca cctaagcctg ctcctaacct gctcggagga   300
cctatggccc tgattgtgct gggggggcgtc gccggcctcc tgcttttcat tgggctaggc   360
atcttcttca aaaggggccg caaaaaactc ctttacattt ttaagcagcc ttttatgagg   420
ccag                                                               424

SEQ ID NO: 336         moltype = DNA  length = 1461
FEATURE                Location/Qualifiers
misc_feature           1..1461
                       note = CAR E6 8+4/4/4-1BB/CD3z sequence
source                 1..1461
                       mol_type = other DNA
                       organism = synthetic construct
SEQUENCE: 336
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg gatgagttg  ggtgcggcaa   180
gctcccggga agaggctgga atgggtctca acaatctccg gggggggcac ttacatctat   240
taccccgact cagtcaaggg gagatttacc atttcacgag acaacgctaa gaatacctca   300
tatttgcaga tgaattctct gagagcagag gacacagtcg tttactattg taccegcgca   360
aactatggca ggaactacga ctacggtatg gactattggg gacaagggac attggttaca   420
gtgagcagtg gcggcggggg cagcggagga ggaggcagcg gtgcggagg  cagcgagata   480
gtgctcacgc agtcacccgc gactctcagt ctctcacctg gggaacgagc taccctgacg   540
tgctctgcta cctcctcagt gtcatatatt cactggtatc agcaacggcc cgggcagtcc   600
cctagattgc tcatttatag tacctctaat ctggcctcag gtatccctgc acgattttct   660
ggatctggtt caggttctga ttacaccctc actatctcta gcctggagcc tgaagacttt   720
gccgtttatt actgccagca gaggtctagc tccccattca cctttgggag tgggaccaag   780
gttgaaatta aaacgacaac cccggccccc agaccaccaa cgccagcccc caccatcgcc   840
agccaacccc tgtctctgag accagaagcc tgtaggcctg ccgccggtgg agctgtgcac   900
acaagaggac tggattcgc  ctgtgatatg gcccctgatt gctgggggg  cgtcgccggc   960
```

```
ctcctgcttt tcattgggct aggcatcttc ttcaaaaggg gccgcaaaaa actcctttac  1020
atttttaagc agccttttat gaggccagta cagacgactc aagaggaaga cgggtgctca  1080
tgccgctttc ctgaggagga ggaaggaggg tgcgaactgc gcgttaagtt ctcccgatca  1140
gccgacgcgc ctgcttacaa gcagggccag aaccaactgt acaacgagct gaatctcggt  1200
agacgggaag agtacgacgt gttggacaaa cggagagcgc cgacccaga aatgggcggc  1260
aagcctcgca ggaaaaaccc ccaggaggga ctgtacaatg agttgcagaa agataagatg  1320
gcagaagctt atagcgagat cggaatgaag gggaaagga gacgaggaa aggacacgac  1380
ggcctttatc agggcctgtc cacagcaaca aaagatacgt atgacgccct ccatatgcag  1440
gcacttccac cacggtgata a                                           1461

SEQ ID NO: 337          moltype = AA  length = 485
FEATURE                 Location/Qualifiers
REGION                  1..485
                        note = CAR E6 8+4/4/4-1BB/CD3z sequence
source                  1..485
                        mol_type = protein
                        organism = synthetic construct
SEQUENCE: 337
MALPVTALLL PLALLLHAAR PEVQLVESGG GLVKPGGSLR LSCAASGFTF SRYGMSWVRQ   60
APGKRLEWVS TISGGGTYIY YPDSVKGRFT ISRDNAKNTL YLQMNSLRAE DTAVYYCTRD  120
NYGRNYDYGM DYWGQGTLVT VSSGGGGSGG GGSGGGGSEI VLTQSPATLS LSPGERATLT  180
CSATSSVSYI HWYQQRPGQS PRLLIYSTSN LASGIPARFS GSGSGSDYTL TISSLEPEDF  240
AVYYCQQRSS SPFTFGSGTK VEIKTTTPAP RPPTPAPTIA SQPLSLRPEA CRPAAGGAVH  300
TRGLDFACDM ALIVLGGVAG LLLFIGLGIF FKRGRKKLLY IFKQPFMRPV QTTQEEDGCS  360
CRFPEEEEGG CELRVKFSRS ADAPAYKQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                              485

SEQ ID NO: 338          moltype = DNA  length = 430
FEATURE                 Location/Qualifiers
misc_feature            1..430
                        note = E6 CAR CD844 pCDH gBLOCK sequence
source                  1..430
                        mol_type = other DNA
                        organism = synthetic construct
SEQUENCE: 338
agtacctcta atctgcctc aggtatccct gcacgatttt ctggatctgg ttcaggttct   60
gattacaccc tcactatctc tagcctggag cctgaagact ttgccgttta ttactgccag  120
cagaggtcta gctccccatt caccttgg agtgggaca aggttgaaat taaaacgaca  180
accccggccc ccagaccacc aacgccagcc ccaccatcg ccagccaacc cctgtctctg   240
agaccagaag cctgtaggcc tgccgccggt ggagctgtgc acacaagagg actggatttc  300
gcctgtgata tggccctgat tgtgctgggg ggcgtcgccg gctcctgct tttcattggg  360
ctaggcatct tcttcaaaag ggccgcaaa aaactccttt acatttttaa gcagcctttt  420
atgaggccag                                                         430

SEQ ID NO: 339          moltype = DNA  length = 820
FEATURE                 Location/Qualifiers
misc_feature            1..820
                        note = Humanized C2 scFV sequence in CAR
source                  1..820
                        mol_type = other DNA
                        organism = synthetic construct
SEQUENCE: 339
gagggccacc atggccttgc cagtgacggc cctgctgctg ccattggctc ttctgttgca   60
cgctgccagg cctgaagtgc agctcgtaga gagtggcggg ggactggtga agcccggtag  120
aagcctcaga ctcagttgcg ccgcctcagg tttcactttt tcaggttacg ccatgtcctg  180
ggtaagacag gcaccgggga aaggactcga gtgggtgtct actatcagct caggaggcac  240
ttatatatat tatcctgact ctgtaaaagg ccgatttacg atttctcgcg acaatgcaaa  300
gaactccctc tacctccaaa tgaacagtct tagggcagaa gacactgctg tatactattg  360
tgcacgcctc ggcggcgaca actactacga gtactttgac gtgtggggga aagggactac  420
cgtgacagtt tcaagcggag aggtggctc aggtggaggc gggtcagggg ggggaggaag  480
tgatattgtg ctcacacaat cccagcctc cctggctgtg tctcccggcc aacgcgctac  540
aattacatgt cgggcctcca aaagcgtgag caccagcggc tacagctaca tgcactggta  600
tcaacagaaa ccaggacaac cccccaaact gttgatttat tcgcttcaa acttggagtc  660
cggcgtgcct gcgcgctttt cagggagtgg gagcggcaca gattttacgc tgactatcaa  720
ccccgtagaa gcaaacgata cagcgaatta ttattgtcaa cattcccggg aactccccttt  780
tacgttcggc gggggcacaa aggtcgaaat taagagaacc                        820

SEQ ID NO: 340          moltype = AA  length = 249
FEATURE                 Location/Qualifiers
REGION                  1..249
                        note = Humanized C2 scFV sequence in CAR
source                  1..249
                        mol_type = protein
                        organism = synthetic construct
SEQUENCE: 340
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
```

```
GQPPKLLIYL ASNLESGVPA RFSGSGSGTD FTLTINPVEA NDTANYYCQH SRELPFTFGG   240
GTKVEIKRT                                                          249

SEQ ID NO: 341          moltype = DNA  length = 729
FEATURE                 Location/Qualifiers
misc_feature            1..729
                        note = Humanized E6 scFV sequence in CAR
source                  1..729
                        mol_type = other DNA
                        organism = synthetic construct
SEQUENCE: 341
gaggtccagc tggttgagag tggcggtggg ctggttaagc ctggcggctc cctgcggctg   60
agctgcgccg cgagtggatt tactttcagc cgatatggga tgagttgggt gcggcaagct  120
cccggggaaga ggctggaatg ggtctcaaca atctccggga ggggcactta catctattac  180
cccgactcag tcaaggggag atttaccatt tcacgagaca acgctaagaa tacccctgtat 240
ttgcagatga attctctgag agcagaggac acagctgttt actattgtac ccgcgacaac  300
tatggcagga actacgacta cggtatggac tattgggac aagggacatt ggttacagtg   360
agcagtgggcg gcggggggcag cggaggagga ggcagcgtg ggggggcag cgagatagtg   420
ctcacgcagt caccccgcgac tctcagtctc tcacctgggg aacgagctac cctgacgtgc  480
tctgctacct cctcagtgtc atatattcac tggtatcagc aacggcccgg gcagtccct   540
agattgctca tttatagtac ctctaatctg gcctcaggta tccctgcacg attttctgga  600
tctggttcag gttctgatta cccctcact atctctagcc tggagcctga agactttgcc   660
gtttattact gccagcagag gtctagctcc ccattcacct ttgggagtgg gaccaaggtt  720
gaaattaaa                                                          729

SEQ ID NO: 342          moltype = AA  length = 243
FEATURE                 Location/Qualifiers
REGION                  1..243
                        note = Humanized E6 scFV sequence in CAR
source                  1..243
                        mol_type = protein
                        organism = synthetic construct
SEQUENCE: 342
EVQLVESGGG LVKPGGSLRL SCAASGFTFS RYGMSWVRQA PGKRLEWVST ISGGGTYIYY   60
PDSVKGRFTI SRDNAKNTLY LQMNSLRAED TAVYYCTRDN YGRNYDYGMD YWGQGTLVTV  120
SSGGGGSGGG GSGGGGSEIV LTQSPATLSL SPGERATLTC SATSSVSYIH WYQQRPGQSP  180
RLLIYSTSNL ASGIPARFSG SGSGSDYTLT ISSLEPEDFA VYYCQQRSSS PFTFGSGTKV  240
EIK                                                                243

SEQ ID NO: 343          moltype = DNA  length = 63
FEATURE                 Location/Qualifiers
misc_feature            1..63
                        note = CD8 leader sequence
source                  1..63
                        mol_type = other DNA
                        organism = synthetic construct
SEQUENCE: 343
atggccctgc ccgtgaccgc tttgctgctc cccctggcgc tgctgctgca cgccgccagg   60
cca                                                                63

SEQ ID NO: 344          moltype = AA  length = 21
FEATURE                 Location/Qualifiers
REGION                  1..21
                        note = CD8 leader sequence
source                  1..21
                        mol_type = protein
                        organism = synthetic construct
SEQUENCE: 344
MALPVTALLL PLALLLHAAR P                                             21

SEQ ID NO: 345          moltype = DNA  length = 135
FEATURE                 Location/Qualifiers
misc_feature            1..135
                        note = CD8 hinge domain sequence
source                  1..135
                        mol_type = other DNA
                        organism = synthetic construct
SEQUENCE: 345
acgacaaccc cggcccccag accaccaacg ccagccccca ccatcgccag ccaaccctg    60
tctctgagac cagaagcctg taggcctgcc gccggtggag ctgtgcacac aagaggactg  120
gatttcgcct gtgat                                                   135

SEQ ID NO: 346          moltype = AA  length = 45
FEATURE                 Location/Qualifiers
REGION                  1..45
                        note = CD8 hinge domain sequence
source                  1..45
                        mol_type = protein
                        organism = synthetic construct
```

```
SEQUENCE: 346
TTTPAPRPPT PAPTIASQPL SLRPEACRPA AGGAVHTRGL DFACD                45

SEQ ID NO: 347              moltype = DNA   length = 66
FEATURE                     Location/Qualifiers
misc_feature                1..66
                            note = CD4 hinge domain sequence
source                      1..66
                            mol_type = other DNA
                            organism = synthetic construct
SEQUENCE: 347
tcgggacagg tcctgctgga atccaacatc aaggttctgc ccacatggtc accccggtg    60
cagcca                                                              66

SEQ ID NO: 348              moltype = AA   length = 22
FEATURE                     Location/Qualifiers
REGION                      1..22
                            note = CD4 hinge domain sequence
source                      1..22
                            mol_type = protein
                            organism = synthetic construct
SEQUENCE: 348
SGQVLLESNI KVLPTWSTPV QP                                            22

SEQ ID NO: 349              moltype = DNA   length = 45
FEATURE                     Location/Qualifiers
misc_feature                1..45
                            note = CD28 hinge domain sequence
source                      1..45
                            mol_type = other DNA
                            organism = synthetic construct
SEQUENCE: 349
aaacaccttt gtccaagtcc cctatttccc ggaccttcta agccc                   45

SEQ ID NO: 350              moltype = AA   length = 15
FEATURE                     Location/Qualifiers
REGION                      1..15
                            note = CD28 hinge domain sequence
source                      1..15
                            mol_type = protein
                            organism = synthetic construct
SEQUENCE: 350
KHLCPSPLFP GPSKP                                                    15

SEQ ID NO: 351              moltype = DNA   length = 201
FEATURE                     Location/Qualifiers
misc_feature                1..201
                            note = CD8+CD4 hinge domain sequence
source                      1..201
                            mol_type = other DNA
                            organism = synthetic construct
SEQUENCE: 351
acgacaaccc cggcccccag accaccaacg ccagccccca ccatcgccag ccaacccctg   60
tctctgagac cagaagcctg taggcctgcc gccggtggag ctgtgcacac aagaggactg  120
gatttcgcct gtgattcggg acaggtcctg ctggaatcca acatcaaggt tctgcccaca  180
tggtccaccc cggtgcagcc a                                            201

SEQ ID NO: 352              moltype = AA   length = 67
FEATURE                     Location/Qualifiers
REGION                      1..67
                            note = CD8+CD4 hinge domain sequence
source                      1..67
                            mol_type = protein
                            organism = synthetic construct
SEQUENCE: 352
TTTPAPRPPT PAPTIASQPL SLRPEACRPA AGGAVHTRGL DFACDSGQVL LESNIKVLPT   60
WSTPVQP                                                             67

SEQ ID NO: 353              moltype = DNA   length = 180
FEATURE                     Location/Qualifiers
misc_feature                1..180
                            note = CD8+CD28 hinge domain sequence
source                      1..180
                            mol_type = other DNA
                            organism = synthetic construct
SEQUENCE: 353
acgacaaccc cggcccccag accaccaacg ccagccccca ccatcgccag ccaacccctg   60
tctctgagac cagaagcctg taggcctgcc gccggtggag ctgtgcacac aagaggactg  120
gatttcgcct gtgataaaca cctttgtcca agtccctat ttcccggacc ttctaagccc  180
```

```
SEQ ID NO: 354           moltype = AA  length = 60
FEATURE                  Location/Qualifiers
REGION                   1..60
                         note = CD8+CD28 hinge domain sequence
source                   1..60
                         mol_type = protein
                         organism = synthetic construct
SEQUENCE: 354
TTTPAPRPPT PAPTIASQPL SLRPEACRPA AGGAVHTRGL DFACDKHLCP SPLFPGPSKP    60

SEQ ID NO: 355           moltype = DNA  length = 111
FEATURE                  Location/Qualifiers
misc_feature             1..111
                         note = CD28+CD4 hinge domain sequence
source                   1..111
                         mol_type = other DNA
                         organism = synthetic construct
SEQUENCE: 355
aaacacctttt gtccaagtcc cctatttccc ggaccttcta agccctcggg acaggtcctg    60
ctggaatcca acatcaaggt tctgcccaca tggtccaccc cggtgcagcc a             111

SEQ ID NO: 356           moltype = AA  length = 37
FEATURE                  Location/Qualifiers
REGION                   1..37
                         note = CD28+CD4 hinge domain sequence
source                   1..37
                         mol_type = protein
                         organism = synthetic construct
SEQUENCE: 356
KHLCPSPLFP GPSKPSGQVL LESNIKVLPT WSTPVQP                              37

SEQ ID NO: 357           moltype = DNA  length = 174
FEATURE                  Location/Qualifiers
misc_feature             1..174
                         note = Human IgD hinge domain sequence
source                   1..174
                         mol_type = other DNA
                         organism = synthetic construct
SEQUENCE: 357
gagtctccaa aggcacaggc ctcctcagtg cccactgcac aacccaagc agagggcagc     60
ctcgccaagg caaccacagc cccagccacc acccgtaaca caggaagagg cggcgaagag   120
aagaaaaagg agaaggagaa agaggaacaa gaagagagag agacaaagac acca          174

SEQ ID NO: 358           moltype = AA  length = 58
FEATURE                  Location/Qualifiers
REGION                   1..58
                         note = Human IgD hinge domain sequence
source                   1..58
                         mol_type = protein
                         organism = synthetic construct
SEQUENCE: 358
ESPKAQASSV PTAQPQAEGS LAKATTAPAT TRNTGRGGEE KKKEKEKEEQ EERETKTP       58

SEQ ID NO: 359           moltype = DNA  length = 129
FEATURE                  Location/Qualifiers
misc_feature             1..129
                         note = X4 linker (IgG1 and IgG2 modified hinge region)
                         sequence
source                   1..129
                         mol_type = other DNA
                         organism = synthetic construct
SEQUENCE: 359
gacaagacgc acaccaagcc acctaaacca gctccagaac tgctcggagg tcctggcacc     60
ggaaccggag gacctaccat caaaccacct aagccaccta agcctgctcc taacctgctc    120
ggaggacct                                                             129

SEQ ID NO: 360           moltype = AA  length = 43
FEATURE                  Location/Qualifiers
REGION                   1..43
                         note = X4 linker (IgG1 and IgG2 modified hinge region)
                         sequence
source                   1..43
                         mol_type = protein
                         organism = synthetic construct
SEQUENCE: 360
DKTHTKPPKP APELLGGPGT GTGGPTIKPP KPPKPAPNLL GGP                        43

SEQ ID NO: 361           moltype = DNA  length = 63
```

| FEATURE | Location/Qualifiers |
|---|---|
| misc_feature | 1..63 |
| | note = CD3 zeta transmembrane domain sequence |
| source | 1..63 |
| | mol_type = other DNA |
| | organism = synthetic construct |

SEQUENCE: 361
ctctgctacc tgctggatgg aatcctcttc atctatggtg tcattctcac tgccttgttc    60
ctg                                                                 63

| SEQ ID NO: 362 | moltype = AA   length = 21 |
|---|---|
| FEATURE | Location/Qualifiers |
| REGION | 1..21 |
| | note = CD3 zeta transmembrane domain sequence |
| source | 1..21 |
| | mol_type = protein |
| | organism = synthetic construct |

SEQUENCE: 362
LCYLLDGILF IYGVILTALF L                                             21

| SEQ ID NO: 363 | moltype = DNA   length = 72 |
|---|---|
| FEATURE | Location/Qualifiers |
| misc_feature | 1..72 |
| | note = CD8 transmembrane domain sequence |
| source | 1..72 |
| | mol_type = other DNA |
| | organism = synthetic construct |

SEQUENCE: 363
atctacattt gggccccgct cgcaggcaca tgtggagtgc tcctcctctc cctggtgatt    60
accctgtact gc                                                       72

| SEQ ID NO: 364 | moltype = AA   length = 24 |
|---|---|
| FEATURE | Location/Qualifiers |
| REGION | 1..24 |
| | note = CD8 transmembrane domain sequence |
| source | 1..24 |
| | mol_type = protein |
| | organism = synthetic construct |

SEQUENCE: 364
IYIWAPLAGT CGVLLLSLVI TLYC                                          24

| SEQ ID NO: 365 | moltype = DNA   length = 66 |
|---|---|
| FEATURE | Location/Qualifiers |
| misc_feature | 1..66 |
| | note = CD4 transmembrane domain sequence |
| source | 1..66 |
| | mol_type = other DNA |
| | organism = synthetic construct |

SEQUENCE: 365
atggccctga ttgtgctggg gggcgtcgcc ggcctcctgc ttttcattgg gctaggcatc    60
ttcttc                                                              66

| SEQ ID NO: 366 | moltype = AA   length = 22 |
|---|---|
| FEATURE | Location/Qualifiers |
| REGION | 1..22 |
| | note = CD4 transmembrane domain sequence |
| source | 1..22 |
| | mol_type = protein |
| | organism = synthetic construct |

SEQUENCE: 366
MALIVLGGVA GLLLFIGLGI FF                                            22

| SEQ ID NO: 367 | moltype = DNA   length = 81 |
|---|---|
| FEATURE | Location/Qualifiers |
| misc_feature | 1..81 |
| | note = CD28 transmembrane domain sequence |
| source | 1..81 |
| | mol_type = other DNA |
| | organism = synthetic construct |

SEQUENCE: 367
ttttgggtgc tggtggtggt tggtggagtc ctggcttgct atagcttgct agtaacagtg    60
gcctttatta ttttctgggt g                                             81

| SEQ ID NO: 368 | moltype = AA   length = 27 |
|---|---|
| FEATURE | Location/Qualifiers |
| REGION | 1..27 |
| | note = CD28 transmembrane domain sequence |
| source | 1..27 |
| | mol_type = protein |

```
                        organism = synthetic construct
SEQUENCE: 368
FWVLVVVGGV LACYSLLVTV AFIIFWV                                          27

SEQ ID NO: 369          moltype = DNA  length = 81
FEATURE                 Location/Qualifiers
misc_feature            1..81
                        note = 4-1BB transmembrane domain sequence
source                  1..81
                        mol_type = other DNA
                        organism = synthetic construct
SEQUENCE: 369
atcatctcct tctttcttgc gctgacgtcg actgcgttgc tcttcctgct gttcttcctc      60
acgctccgtt tctctgttgt t                                                81

SEQ ID NO: 370          moltype = AA  length = 27
FEATURE                 Location/Qualifiers
REGION                  1..27
                        note = 4-1BB transmembrane domain sequence
source                  1..27
                        mol_type = protein
                        organism = synthetic construct
SEQUENCE: 370
IISFFLALTS TALLFLLFFL TLRFSVV                                          27

SEQ ID NO: 371          moltype = DNA  length = 78
FEATURE                 Location/Qualifiers
misc_feature            1..78
                        note = OX40 transmembrane domain sequence
source                  1..78
                        mol_type = other DNA
                        organism = synthetic construct
SEQUENCE: 371
gttgccgcca tcctgggcct gggcctggtg ctggggctgc tgggccccct ggccatcctg      60
ctggccctgt acctgctc                                                    78

SEQ ID NO: 372          moltype = AA  length = 26
FEATURE                 Location/Qualifiers
REGION                  1..26
                        note = OX40 transmembrane domain sequence
source                  1..26
                        mol_type = protein
                        organism = synthetic construct
SEQUENCE: 372
VAAILGLGLV LGLLGPLAIL LALYLL                                           26

SEQ ID NO: 373          moltype = DNA  length = 336
FEATURE                 Location/Qualifiers
misc_feature            1..336
                        note = CD3 zeta domain sequence
source                  1..336
                        mol_type = other DNA
                        organism = synthetic construct
SEQUENCE: 373
cgcgttaagt tctcccgatc agccgacgcg cctgcttaca agcagggcca gaaccaactg      60
tacaacgagc tgaatctcgg tagacgggaa gagtacgacg tgttggacaa acggagaggc     120
cgcgacccag aaatgggcgg caagcctcgc aggaaaaaac cccaggaggg actgtacaat     180
gagttgcaga agataagat ggcagaagct tatagcgaga tcggaatgaa gggggaaagg      240
agacgaggga aaggacacga cggcctttat cagggcctgt ccacagcaac aaaagatacg     300
tatgacgccc tccatatgca ggcacttcca ccacgg                               336

SEQ ID NO: 374          moltype = AA  length = 112
FEATURE                 Location/Qualifiers
REGION                  1..112
                        note = CD3 zeta domain sequence
source                  1..112
                        mol_type = protein
                        organism = synthetic construct
SEQUENCE: 374
RVKFSRSADA PAYKQGQNQL YNELNLGRRE EYDVLDKRRG RDPEMGGKPR RKNPQEGLYN       60
ELQKDKMAEA YSEIGMKGER RRGKGHDGLY QGLSTATKDT YDALHMQALP PR              112

SEQ ID NO: 375          moltype = DNA  length = 336
FEATURE                 Location/Qualifiers
misc_feature            1..336
                        note = CD3 zeta domain variant sequence
source                  1..336
                        mol_type = other DNA
                        organism = synthetic construct
```

| | | |
|---|---|---|
| SEQUENCE: 375 | | |
| agagtgaagt tcagcaggag cgcagacgcc cccgcgtacc agcagggcca gaaccagctc | | 60 |
| tataacgagc tcaatctagg acgaagagag gagtacgatg tttggacaa gagacgtggc | | 120 |
| cgggaccctg agatggggg aaagccgaga aggaagaacc ctcaggaagg cctgtacaat | | 180 |
| gaactgcaga aagataagat ggcggaggcc tacagtgaga ttgggatgaa aggcgagcgc | | 240 |
| cggaggggca aggggcacga tggccttac caggttctca gtacagccac caaggacacc | | 300 |
| tacgacgccc ttcacatgca ggccctgccc cctcgc | | 336 |

| | |
|---|---|
| SEQ ID NO: 376 | moltype = AA   length = 112 |
| FEATURE | Location/Qualifiers |
| REGION | 1..112 |
| | note = CD3 zeta domain variant sequence |
| source | 1..112 |
| | mol_type = protein |
| | organism = synthetic construct |

| | | |
|---|---|---|
| SEQUENCE: 376 | | |
| RVKFSRSADA PAYQQGQNQL YNELNLGRRE EYDVLDKRRG RDPEMGGKPR RKNPQEGLYN | | 60 |
| ELQKDKMAEA YSEIGMKGER RRGKGHDGLY QGLSTATKDT YDALHMQALP PR | | 112 |

| | |
|---|---|
| SEQ ID NO: 377 | moltype = DNA   length = 123 |
| FEATURE | Location/Qualifiers |
| misc_feature | 1..123 |
| | note = CD28 domain sequence |
| source | 1..123 |
| | mol_type = other DNA |
| | organism = synthetic construct |

| | | |
|---|---|---|
| SEQUENCE: 377 | | |
| agaagcaagc ggtctcggct cctgcattct gattacatga acatgacccc aagaagacca | | 60 |
| ggccccacca ggaaacatta ccagccctac gctccgccac gcgacttcgc tgcctaccgg | | 120 |
| tcc | | 123 |

| | |
|---|---|
| SEQ ID NO: 378 | moltype = AA   length = 41 |
| FEATURE | Location/Qualifiers |
| REGION | 1..41 |
| | note = CD28 domain sequence |
| source | 1..41 |
| | mol_type = protein |
| | organism = synthetic construct |

| | | |
|---|---|---|
| SEQUENCE: 378 | | |
| RSKRSRLLHS DYMNMTPRRP GPTRKHYQPY APPRDFAAYR S | | 41 |

| | |
|---|---|
| SEQ ID NO: 379 | moltype = DNA   length = 126 |
| FEATURE | Location/Qualifiers |
| misc_feature | 1..126 |
| | note = 4-1BB domain sequence |
| source | 1..126 |
| | mol_type = other DNA |
| | organism = synthetic construct |

| | | |
|---|---|---|
| SEQUENCE: 379 | | |
| aaaagggggcc gcaaaaaact cctttacatt tttaagcagc cttttatgag gccagtacag | | 60 |
| acgactcaag aggaagacgg gtgctcatgc cgctttcctg aggaggagga aggggtgc | | 120 |
| gaactg | | 126 |

| | |
|---|---|
| SEQ ID NO: 380 | moltype = AA   length = 42 |
| FEATURE | Location/Qualifiers |
| REGION | 1..42 |
| | note = 4-1BB domain sequence |
| source | 1..42 |
| | mol_type = protein |
| | organism = synthetic construct |

| | | |
|---|---|---|
| SEQUENCE: 380 | | |
| KRGRKKLLYI FKQPFMRPVQ TTQEEDGCSC RFPEEEEGGC EL | | 42 |

| | |
|---|---|
| SEQ ID NO: 381 | moltype = DNA   length = 111 |
| FEATURE | Location/Qualifiers |
| misc_feature | 1..111 |
| | note = OX40 domain sequence |
| source | 1..111 |
| | mol_type = other DNA |
| | organism = synthetic construct |

| | | |
|---|---|---|
| SEQUENCE: 381 | | |
| cggagggacc agaggctgcc ccccgatgcc cacaagcccc ctgggggagg cagtttccgg | | 60 |
| accccccatcc aagaggagca ggccgacgcc cactccaccc tggccaagat c | | 111 |

| | |
|---|---|
| SEQ ID NO: 382 | moltype = AA   length = 37 |
| FEATURE | Location/Qualifiers |
| REGION | 1..37 |
| | note = OX40 domain sequence |
| source | 1..37 |

```
                         mol_type = protein
                         organism = synthetic construct
SEQUENCE: 382
RRDQRLPPDA HKPPGGGSFR TPIQEEQADA HSTLAKI                         37

SEQ ID NO: 383           moltype = DNA    length = 723
FEATURE                  Location/Qualifiers
misc_feature             1..723
                         note = Humanized anti CD3 scFV clone 12F6 (VH-VL) sequence
source                   1..723
                         mol_type = other DNA
                         organism = synthetic construct
SEQUENCE: 383
caggtgcagc tggtgcagag cggaggtgga gtggtccaac ctggaagatc tctgagactg   60
agctgtaagg ctagcgggta cacgttcaca tcttacacga tgcactgggt gaggcaagcc  120
cccggtaagg gcctggaatg gatcggatat ataaaccccca gctcagggta taccaaatat  180
aatcagaagt tcaaagatcg gttcacgatt tctgctgata aaagtaagtc caccgctttc  240
ctgcagatgg actcactcag gccagaagat actggtgttt atttctgtgc aaggtggcag  300
gactacgacg tgtactttga ctattggggg caggggacgc ctgtaacagt atcaagcggc  360
ggtggcggat ccggcggtgg cggatccggc ggtggcggat ccgatattca gatgacccag  420
agcccgagca gcctgagcgc gagcgtgggc gatcgcgtga ccatgacctg ccgcgcgagc  480
agcagcgtga gctatatgca ttggtatcag cagacccccg gcaaagcgcc gaaaccgtgg  540
atttatgcga ccagcaacct ggcgagcggc gtgccgagcc gctttagcgg cagcggcagc  600
ggcaccgatt atccctgac cattagcagc ctgcagccgg aagatattgc gacctattat  660
tgccagcagt ggagcagcaa cccgccgacc tttggccagg gcaccaaact gcagattacc  720
cgc                                                                723

SEQ ID NO: 384           moltype = AA    length = 241
FEATURE                  Location/Qualifiers
REGION                   1..241
                         note = Humanized anti CD3 scFV clone 12F6 (VH-VL) sequence
source                   1..241
                         mol_type = protein
                         organism = synthetic construct
SEQUENCE: 384
QVQLVQSGGG VVQPGRSLRL SCKASGYTFT SYTMHWVRQA PGKGLEWIGY INPSSGYTKY   60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
R                                                                 241

SEQ ID NO: 385           moltype = DNA    length = 723
FEATURE                  Location/Qualifiers
misc_feature             1..723
                         note = Humanized anti CD3 scFV clone 12F6 (VL-VH) sequence
source                   1..723
                         mol_type = other DNA
                         organism = synthetic construct
SEQUENCE: 385
gatattcaga tgacccagag cccgagcagc ctgagcgcga gcgtgggcga tcgcgtgacc   60
atgacctgcc gcgcgagcag cagcgtgagc tatatgcatt ggtatcagca gacccccggg  120
aaagcgccga aaccgtggat ttatgcgacc agcaacctgg cgagcggcgt gccgagccgc  180
tttagcggca gcggcagcgg caccgattat accctgacca ttagcagcct gcagccggaa  240
gatattgcga cctattattg ccagcagtgg agcagcaacc cgccgacctt tggccagggc  300
accaaactgc agattacccg cggcggtggc ggatccggcg gtggcggatc cggcggtggc  360
ggatcccagg tgcagctggt gcagagcgga ggtggagtgg tccaacctgg aagatctctg  420
agactgagct gtaaggctag cgggtacacg ttcacatctt acacgatgca ctgggtgagg  480
caagcccccg gtaagggcct ggaatggatc ggatatataa accccagctc agggtatacc  540
aaatataatc agaagttcaa agatcggttc acgatttctg ctgataaaag taagtccacc  600
gctttcctgc agatggactc actcaggcca gaagatactg gtgtttattt ctgtgcaagg  660
tggcaggact acgacgtgta ctttgactat tgggggcagg ggacgcctgt aacagtatca  720
agc                                                                723

SEQ ID NO: 386           moltype = AA    length = 241
FEATURE                  Location/Qualifiers
REGION                   1..241
                         note = Humanized anti CD3 scFV clone 12F6 (VL-VH) sequence
source                   1..241
                         mol_type = protein
                         organism = synthetic construct
SEQUENCE: 386
DIQMTQSPSS LSASVGDRVT MTCRASSSVS YMHWYQQTPG KAPKPWIYAT SNLASGVPSR   60
FSGSGSGTDY TLTISSLQPE DIATYYCQQW SSNPPTFGQG TKLQITRGGG GSGGGGSGGG  120
GSQVQLVQSG GGVVQPGRSL RLSCKASGYT FTSYTMHWVR QAPGKGLEWI GYINPSSGYT  180
KYNQKFKDRF TISADKSKST AFLQMDSLRP EDTGVYFCAR WQDYDVYFDY WGQGTPVTVS  240
S                                                                 241

SEQ ID NO: 387           moltype = DNA    length = 723
FEATURE                  Location/Qualifiers
```

```
misc_feature            1..723
                        note = Humanized anti CD3 scFV clone OKT3 (VH-VL) sequence
source                  1..723
                        mol_type = other DNA
                        organism = synthetic construct
SEQUENCE: 387
caggtgcagc tggtgcagag cggaggcgga gtggtgcagc ctggaagaag cctgcgcctg    60
agctgcaaaa cgagcggcta tacctttacc cgctatacca tgcattgggt gcgccaggcg   120
ccgggcaaag gcctggaatg gattggctat attaacccga gccgcggcta taccaactat   180
aaccagaaag tgaaagatcg ctttaccatt agcaccgata aaagcaaaag caccgcgttt   240
ctgcagatgg atagcctgcg cccggaagat accgcggtgt attattgcgc gcgctattat   300
gatgatcatt attgcctgga ttattggggc cagggcacca ccctgaccgt gagcagcggc   360
ggtggcggat ccggcggtgg cggatccggc ggtggcggat ccgatattca gatgacccag   420
agcccgagca gcctgagcgc gagcgtgggc gatcgcgtga ccattacctg cagcgcgagc   480
agcagcgtga gctatatgaa ctggtatcag cagaccccgg gcaaagcgcc gaaacgctgg   540
atttatgata ccagcaaact ggcgagcggc gtgccgagcc gctttagcgg cagcggcagc   600
ggcaccgatt ataccttttac cattagcagc ctgcagccgg aagatattgc gacctattat   660
tgccagcagt ggagcagcaa cccgtttacc tttggccagg gcaccaaact gcagattacc   720
cgc                                                                 723

SEQ ID NO: 388          moltype = AA  length = 241
FEATURE                 Location/Qualifiers
REGION                  1..241
                        note = Humanized anti CD3 scFV clone OKT3 (VH-VL) sequence
source                  1..241
                        mol_type = protein
                        organism = synthetic construct
SEQUENCE: 388
QVQLVQSGGG VVQPGRSLRL SCKASGYTFT RYTMHWVRQA PGKGLEWIGY INPSRGYTNY    60
NQKVKDRFTI STDKSKSTAF LQMDSLRPED TAVYYCARYY DDHYCLDYWG QGTTLTVSSG   120
GGGSGGGGSG GGGSDIQMTQ SPSSLSASVG DRVTITCSAS SSVSYMNWYQ QTPGKAPKRW   180
IYDTSKLASG VPSRFSGSGS GTDYTFTISS LQPEDIATYY CQQWSSNPFT FGQGTKLQIT   240
R                                                                   241

SEQ ID NO: 389          moltype = DNA  length = 723
FEATURE                 Location/Qualifiers
misc_feature            1..723
                        note = Humanized anti CD3 scFV clone OKT3 (VH-VL) sequence
source                  1..723
                        mol_type = other DNA
                        organism = synthetic construct
SEQUENCE: 389
gatattcaga tgacccagag cccgagcagc ctgagcgcga gcgtgggcga tcgcgtgacc    60
attacctgca gcgcgagcag cagcgtgagc tatatgaact ggtatcagca gaccccgggc   120
aaagcgccga acgctggat ttatgatacc agcaaactgg cgagcggcgt gccgagccgc   180
tttagcggca gcggcagcgg caccgattat acctttacca ttagcagcct gcagccggaa   240
gatattgcga cctattattg ccagcagtgg agcagcaacc cgtttacctt tggccagggc   300
accaaactgc agattacccg cggcggtggc ggatccggcg gtggcggatc cggcggtggc   360
ggatcccagg tgcagctggt gcagagcgga ggcggagtgg tgcagcctgg aagaagcctg   420
cgcctgagct gcaaagcgag cggctatacc tttacccgct ataccatgca ttgggtgcgc   480
caggcgccgg gcaaaggcct ggaatggatt ggctatatta acccgagccg cggctatacc   540
aactataacc agaaagtgaa agatcgcttt accattagca ccgataaaag caaaagcacc   600
gcgtttctgc agatggatag cctgcgcccg gaagataccg cggtgtatta ttgcgcgcgc   660
tattatgatg atcattattg cctggattat tggggccagg gcaccaccct gaccgtgagc   720
agc                                                                 723

SEQ ID NO: 390          moltype = AA  length = 241
FEATURE                 Location/Qualifiers
REGION                  1..241
                        note = Humanized anti CD3 scFV clone OKT3 (VH-VL) sequence
source                  1..241
                        mol_type = protein
                        organism = synthetic construct
SEQUENCE: 390
DIQMTQSPSS LSASVGDRVT ITCSASSSVS YMNWYQQTPG KAPKRWIYDT SKLASGVPSR    60
FSGSGSGTDY TFTISSLQPE DIATYYCQQW SSNPFTFGQG TKLQITRGGG GSGGGGSGGG   120
GSQVQLVQSG GGVVQPGRSL RLSCKASGYT FTRYTMHWVR QAPGKGLEWI GYINPSRGYT   180
NYNQKVKDRF TISTDKSKST AFLQMDSLRP EDTAVYYCAR YYDDHYCLDY WGQGTTLTVS   240
S                                                                   241

SEQ ID NO: 391          moltype = DNA  length = 729
FEATURE                 Location/Qualifiers
misc_feature            1..729
                        note = HumanizeE6 scFV (VH-VL) sequence
source                  1..729
                        mol_type = other DNA
                        organism = synthetic construct
SEQUENCE: 391
gaggtgcagc tggtggagtc tgggggaggc ctggtcaagc ctggggggtc cctgagactc    60
```

```
tcctgtgcag cctctggatt caccttcagt aggtatggca tgagctgggt ccgccaggct  120
ccagggaaga ggctggagtg ggtctcaacc attagtggcg gaggcaccta catatactac  180
ccagactcag tgaagggccg attcaccatc tccagagaca acgccaagaa cacccctgtat 240
ctgcaaatga acagcctgag agccgaggac acggctgtgt attactgtac cagagataac  300
tatgccgcca actatgatta tggcatggat tattgggggcc agggcaccct ggtgaccgtg  360
agcagcggcg gtggcggatc cggcggtggc ggatccggcg gtggcggatc cgaaattgtg  420
ttgacacagt ctccagccac cctgtctttg tctccagggg aaagagccac cctcacctgc  480
agcgccacca gcagtgttag ctacatccac tggtaccaac agaggcctgg ccagagcccc  540
aggctcctca tctatagcac ctccaacctg gccagcggga tcccagccag gttcagtggc  600
agtgggtctg ggagcgacta cactctcacc atcagcagcc tagagcctga agattttgca  660
gtttattact gtcagcagcg tagcagctcc cctttcacct tggcagcggg caccaaagtg  720
gaaattaaa                                                            729

SEQ ID NO: 392         moltype = AA   length = 243
FEATURE                Location/Qualifiers
REGION                 1..243
                       note = HumanizeE6 scFV (VH-VL) sequence
source                 1..243
                       mol_type = protein
                       organism = synthetic construct
SEQUENCE: 392
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV   120
SSGGGGSGGG GSGGGGSEIV LTQSPATLSL SPGERATLTC SATSSVSYIH WYQQRPGQSP   180
RLLIYSTSNL ASGIPARFSG SGSGSDYTLT ISSLEPEDFA VYYCQQRSSS PFTFGSGTKV   240
EIK                                                                 243

SEQ ID NO: 393         moltype = DNA   length = 729
FEATURE                Location/Qualifiers
misc_feature           1..729
                       note = HumanizeE6 scFV (VL-VH) sequence
source                 1..729
                       mol_type = other DNA
                       organism = synthetic construct
SEQUENCE: 393
gaaattgtgt tgacacagtc tccagccacc ctgtctttgt ctccagggga aagagccacc   60
ctcacctgca gcgccaccag cagtgttagc tacatccact ggtaccaaca gaggcctggc  120
cagagcccca ggctcctcat ctatagcacc tccaacctgg ccagcggcat cccagccagg  180
ttcagtggca gtgggtctgg gagcgactac actctcacca tcagcagcct agagcctgaa  240
gattttgcag tttattactg tcagcagcgt agcagctccc ctttcacctt ggcagcggc   300
accaaagtgg aaattaaagg cggtggcgga tccggcggtg cggatccgg cggtggcgga  360
tccgaggtgc agctggtgga gtctggggga ggcctggtca agcctggggg gtccctgaga  420
ctctcctgtg cagcctctgg attcaccttc agtaggtatg gcatgagctg ggtccgccag  480
gctccaggga gaggctgga gtgggtctca accattagtg gcggaggcac ctacatatac  540
tacccagact cagtgaaggg ccgattcacc atctccagag acaacgccaa gaacaccctg  600
tatctgcaaa tgaacagcct gagagccgag gacacggctg tgtattactg taccagagat  660
aactatgcc aactatgat tatggcatg gattattggg gccagggcac cctggtgacc  720
gtgagcagc                                                           729

SEQ ID NO: 394         moltype = AA   length = 243
FEATURE                Location/Qualifiers
REGION                 1..243
                       note = HumanizeE6 scFV (VL-VH) sequence
source                 1..243
                       mol_type = protein
                       organism = synthetic construct
SEQUENCE: 394
EIVLTQSPAT LSLSPGERAT LTCSATSSVS YIHWYQQRPG QSPRLLIYST SNLASGIPAR    60
FSGSGSGSDY TLTISSLEPE DFAVYYCQQR SSSPFTFGSG TKVEIKGGGG SGGGGSGGGG   120
SEVQLVESGG GLVKPGGSLR LSCAASGFTF SRYGMSWVRQ APGKRLEWVS TISGGGTYIY   180
YPDSVKGRFT ISRDNAKNTL YLQMNSLRAE DTAVYYCTRD NYGRNYDYGM DYWGQGTLVT   240
VSS                                                                 243

SEQ ID NO: 395         moltype = DNA   length = 747
FEATURE                Location/Qualifiers
misc_feature           1..747
                       note = HumanizeC2 scFV (VH-VL) sequence
source                 1..747
                       mol_type = other DNA
                       organism = synthetic construct
SEQUENCE: 395
gaggtgcagc tggtggagtc tgggggaggc ctggtcaagc ctggggggtc cctgagactc   60
tcctgtgcag cctctggatt caccttcagt ggctatgcca tgagctgggt ccgccaggct  120
ccagggaagg ggctggagtg ggtctcaacc attagtggcg gaaccta catatactac  180
cccgactcag tgaagggccg attcaccatc tccagagaca acgccaagaa ctcactgtat  240
ctgcaaatga acagcctgag agccgaggac acggccgtgt attactgtgc gagacttggg  300
ggggataatt actacgaata cttcgatgtc tggggcaaag gaccacggt caccgtctcc  360
tccggcggtg gcggatccgg cggtggcgga tccggcggtg gcggatccga cattgtgctg  420
acccagtctc cagcctcctt ggccgtgtct caggacagag ggccaccat cacctgcaga  480
```

```
gccagtaaga gtgtcagtac cagcggatac tcctacatgc actggtatca gcagaaacca    540
ggacaacctc ctaaactcct gatttacctg gcatccaatc tggagagcgg ggtcccagcc    600
aggttcagcg gcagtgggtc tgggaccgat ttcaccctca caattaatcc tgtggaagct    660
aatgatactg caaattatta ctgtcagcac agtagggagc tgcctttcac attcggcgga    720
gggaccaagg tggagatcaa acgaact                                        747

SEQ ID NO: 396            moltype = AA   length = 249
FEATURE                   Location/Qualifiers
REGION                    1..249
                          note = HumanizeC2 scFV (VH-VL) sequence
source                    1..249
                          mol_type = protein
                          organism = synthetic construct
SEQUENCE: 396
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS    120
SGGGGSGGGG SGGGGSDIVL TQSPASLAVS PGQRATITCR ASKSVSTSGY SYMHWYQQKP    180
GQPPKLLIYL ASNLESGVPA RFSGSGSGTD FTLTINPVEA NDTANYYCQH SRELPFTFGG    240
GTKVEIKRT                                                            249

SEQ ID NO: 397            moltype = DNA   length = 747
FEATURE                   Location/Qualifiers
misc_feature              1..747
                          note = HumanizeE6 scFV (VL-VH) sequence
source                    1..747
                          mol_type = other DNA
                          organism = synthetic construct
SEQUENCE: 397
gacattgtgc tgacccagtc tccagcctcc ttggccgtgt ctccaggaca gagggccacc     60
atcacctgca gagccagtaa gagtgtcagt accagcggat actcctacat gcactggtat    120
cagcagaaac caggacaacc tcctaaactc ctgatttacc tggcatccaa tctgggagag    180
ggggtcccag ccaggttcag cggcagtggg tctgggaccg atttcaccct cacaattaat    240
cctgtggaag ctaatgatac tgcaaattat tactgtcagc acagtaggga gctgcctttc    300
acattcggcg gagggaccaa ggtggagatc aaacgaactg gcggtggcgg atccggcggt    360
ggcggatccg gcggtggcgg atcctctgag gtccagctgg tagagtctgg gggaggcctg    420
gtaagcctgg ggggtccctg agactctcctgt gcagcctctg gattcacctt cagtggctat    480
gccatgagct gggtccgcca ggctccaggg aaggggctgg agtgggtctc aaccattagt    540
agtggcggaa cctacatata ctaccccgac tcagtgaagg gccgattcac catctccaga    600
gacaacgcca agaactcact gtatctgcaa atgaacagcc tgagagccga ggacacggcc    660
gtgtattact gtgcgagact tgggggggat aattactacg aatacttcga tgtctgggc    720
aaagggacca cggtcaccgt ctcctcc                                        747

SEQ ID NO: 398            moltype = AA   length = 249
FEATURE                   Location/Qualifiers
REGION                    1..249
                          note = HumanizeE6 scFV (VL-VH) sequence
source                    1..249
                          mol_type = protein
                          organism = synthetic construct
SEQUENCE: 398
DIVLTQSPAS LAVSPGQRAT ITCRASKSVS TSGYSYMHWY QQKPGQPPKL LIYLASNLES     60
GVPARFSGSG SGTDFTLTIN PVEANDTANY YCQHSRELPF TFGGGTKVEI KRTGGGGSGG    120
GGSGGGGSEV QLVESGGGLV KPGGSLRLSC AASGFTFSGY AMSWVRQAPG KGLEWVSTIS    180
SGGTYIYYPD SVKGRFTISR DNAKNSLYLQ MNSLRAEDTA VYYCARLGGD NYYEYFDVWG    240
KGTTVTVSS                                                            249

SEQ ID NO: 399            moltype = DNA   length = 15
FEATURE                   Location/Qualifiers
misc_feature              1..15
                          note = G4S1 linker sequence
source                    1..15
                          mol_type = other DNA
                          organism = synthetic construct
SEQUENCE: 399
ggcggtggcg gatcc                                                      15

SEQ ID NO: 400            moltype = AA   length = 5
FEATURE                   Location/Qualifiers
REGION                    1..5
                          note = G4S1 linker sequence
source                    1..5
                          mol_type = protein
                          organism = synthetic construct
SEQUENCE: 400
GGGGS                                                                  5

SEQ ID NO: 401            moltype = DNA   length = 45
FEATURE                   Location/Qualifiers
misc_feature              1..45
```

```
                        note = [G4S1]x3 linker sequence
source                  1..45
                        mol_type = other DNA
                        organism = synthetic construct
SEQUENCE: 401
ggcggtggcg gatccggcgg tggcggatcc ggcggtggcg gatcc          45

SEQ ID NO: 402          moltype = AA  length = 15
FEATURE                 Location/Qualifiers
REGION                  1..15
                        note = [G4S1]x3 linker sequence
source                  1..15
                        mol_type = protein
                        organism = synthetic construct
SEQUENCE: 402
GGGGSGGGGS GGGGS                                           15

SEQ ID NO: 403          moltype = DNA  length = 24
FEATURE                 Location/Qualifiers
misc_feature            1..24
                        note = 8 aa GS linker sequence
source                  1..24
                        mol_type = other DNA
                        organism = synthetic construct
SEQUENCE: 403
ggcggttccg gcggtggatc cgga                                 24

SEQ ID NO: 404          moltype = AA  length = 8
FEATURE                 Location/Qualifiers
REGION                  1..8
                        note = 8 aa GS linker sequence
source                  1..8
                        mol_type = protein
                        organism = synthetic construct
SEQUENCE: 404
GGSGGGSG                                                   8

SEQ ID NO: 405          moltype = DNA  length = 39
FEATURE                 Location/Qualifiers
misc_feature            1..39
                        note = 12 aa GS linker sequence
source                  1..39
                        mol_type = other DNA
                        organism = synthetic construct
SEQUENCE: 405
ggcggttccg gcggtggatc cggcggtggc ggatccgga                 39

SEQ ID NO: 406          moltype = AA  length = 12
FEATURE                 Location/Qualifiers
REGION                  1..12
                        note = 12 aa GS linker sequence
source                  1..12
                        mol_type = protein
                        organism = synthetic construct
SEQUENCE: 406
GGSGGGSGGG SG                                              12

SEQ ID NO: 407          moltype = DNA  length = 39
FEATURE                 Location/Qualifiers
misc_feature            1..39
                        note = 13 aa GS linker sequence
source                  1..39
                        mol_type = other DNA
                        organism = synthetic construct
SEQUENCE: 407
ggcggtggat ccggcggtgg cggatccggc ggtggatcc                 39

SEQ ID NO: 408          moltype = AA  length = 13
FEATURE                 Location/Qualifiers
REGION                  1..13
                        note = 13 aa GS linker sequence
source                  1..13
                        mol_type = protein
                        organism = synthetic construct
SEQUENCE: 408
GGGSGGGGSG GGS                                             13

SEQ ID NO: 409          moltype = DNA  length = 66
FEATURE                 Location/Qualifiers
```

```
misc_feature          1..66
                      note = 22 aa GS linker sequence
source                1..66
                      mol_type = other DNA
                      organism = synthetic construct
SEQUENCE: 409
ggcggtggaa gcggcggtgg cggatccggc agcggcggaa gcggcggtgg cggatccggc    60
ggtgga                                                                66

SEQ ID NO: 410        moltype = AA   length = 22
FEATURE               Location/Qualifiers
REGION                1..22
                      note = 22 aa GS linker sequence
source                1..22
                      mol_type = protein
                      organism = synthetic construct
SEQUENCE: 410
GGGSGGGGSG SGGSGGGGSG GG                                              22

SEQ ID NO: 411        moltype = DNA   length = 78
FEATURE               Location/Qualifiers
misc_feature          1..78
                      note = 24 aa GS linker sequence
source                1..78
                      mol_type = other DNA
                      organism = synthetic construct
SEQUENCE: 411
ggcggttccg gcggtggatc cggcggtggc ggatccggag gcggttccgg cggtggatcc    60
ggcggtggcg gatccgga                                                   78

SEQ ID NO: 412        moltype = AA   length = 24
FEATURE               Location/Qualifiers
REGION                1..24
                      note = 24 aa GS linker sequence
source                1..24
                      mol_type = protein
                      organism = synthetic construct
SEQUENCE: 412
GGSGGGSGGG SGGGSGGGSG GGSG                                            24

SEQ ID NO: 413        moltype = DNA   length = 357
FEATURE               Location/Qualifiers
misc_feature          1..357
                      note = Mouse C3 Heavy chain variable region sequence
source                1..357
                      mol_type = other DNA
                      organism = synthetic construct
SEQUENCE: 413
caggtccagc tgcagcagtc tgggcctgag ctggtgaggc ctggggtctc agtgaagatt    60
tcctgcaagg gttccggcta cagattcact gattatgcta tgaactgggt gaagcagagt   120
catgcaaaga gtctagagtg gattggagtt attagtactt ctctctggtaa tacaaacttc   180
aaccagaagt ttaagggcaa ggccacaatg actgtagaca atcctccag cacagcctat    240
atggaacttg ccagattgac atctgaggat tctgccatgt attactgtgc aagatcggat   300
tactacggcc catactttga ctactggggc caaggcacca ctctcacagt ctcctca      357

SEQ ID NO: 414        moltype = AA   length = 119
FEATURE               Location/Qualifiers
REGION                1..119
                      note = Mouse C3 Heavy chain variable region sequence
source                1..119
                      mol_type = protein
                      organism = synthetic construct
SEQUENCE: 414
QVQLQQSGPE LVRPGVSVKI SCKGSGYRFT DYAMNWVKQS HAKSLEWIGV ISTFSGNTNF    60
NQKFKGKATM TVDKSSSTAY MELARLTSED SAMYYCARSD YYGPYFDYWG QGTTLTVSS    119

SEQ ID NO: 415        moltype = DNA   length = 90
FEATURE               Location/Qualifiers
misc_feature          1..90
                      note = Mouse C3 heavy chain variable framework region 1
                        (FWR1) sequence
source                1..90
                      mol_type = other DNA
                      organism = synthetic construct
SEQUENCE: 415
caggtccagc tgcagcagtc tgggcctgag ctggtgaggc ctggggtctc agtgaagatt    60
tcctgcaagg gttccggcta cagattcact                                      90

SEQ ID NO: 416        moltype = AA   length = 30
```

```
FEATURE                 Location/Qualifiers
REGION                  1..30
                        note = Mouse C3 heavy chain variable framework region 1
                         (FWR1) sequence
source                  1..30
                        mol_type = protein
                        organism = synthetic construct
SEQUENCE: 416
QVQLQQSGPE LVRPGVSVKI SCKGSGYRFT                                         30

SEQ ID NO: 417          moltype = DNA  length = 15
FEATURE                 Location/Qualifiers
misc_feature            1..15
                        note = Mouse C3 heavy chain variable complementarity
                         determining regions1 (CDR1) sequence
source                  1..15
                        mol_type = other DNA
                        organism = synthetic construct
SEQUENCE: 417
gattatgcta tgaac                                                         15

SEQ ID NO: 418          moltype = AA  length = 5
FEATURE                 Location/Qualifiers
REGION                  1..5
                        note = Mouse C3 heavy chain variable complementarity
                         determining regions1 (CDR1) sequence
source                  1..5
                        mol_type = protein
                        organism = synthetic construct
SEQUENCE: 418
DYAMN                                                                    5

SEQ ID NO: 419          moltype = DNA  length = 42
FEATURE                 Location/Qualifiers
misc_feature            1..42
                        note = Mouse C3 heavy chain variable framework region 2
                         (FWR2) sequence
source                  1..42
                        mol_type = other DNA
                        organism = synthetic construct
SEQUENCE: 419
tgggtgaagc agagtcatgc aaagagtcta gagtggattg ga                           42

SEQ ID NO: 420          moltype = AA  length = 14
FEATURE                 Location/Qualifiers
REGION                  1..14
                        note = Mouse C3 heavy chain variable framework region 2
                         (FWR2) sequence
source                  1..14
                        mol_type = protein
                        organism = synthetic construct
SEQUENCE: 420
WVKQSHAKSL EWIG                                                          14

SEQ ID NO: 421          moltype = DNA  length = 51
FEATURE                 Location/Qualifiers
misc_feature            1..51
                        note = Mouse C3 heavy chain variable complementarity
                         determining regions2 (CDR2) sequence
source                  1..51
                        mol_type = other DNA
                        organism = synthetic construct
SEQUENCE: 421
gttattagta ctttctctgg taatacaaac ttcaaccaga agtttaaggg c                 51

SEQ ID NO: 422          moltype = AA  length = 17
FEATURE                 Location/Qualifiers
REGION                  1..17
                        note = Mouse C3 heavy chain variable complementarity
                         determining regions2 (CDR2) sequence
source                  1..17
                        mol_type = protein
                        organism = synthetic construct
SEQUENCE: 422
VISTFSGNTN FNQKFKG                                                       17

SEQ ID NO: 423          moltype = DNA  length = 96
FEATURE                 Location/Qualifiers
misc_feature            1..96
```

```
                        note = Mouse C3 heavy chain variable framework region 3
                           (FWR3) acidsequence
source                  1..96
                        mol_type = other DNA
                        organism = synthetic construct
SEQUENCE: 423
aaggccacaa tgactgtaga caaatcctcc agcacagcct atatgaaact tgccagattg   60
acatctgagg attctgccat gtattactgt gcaaga                            96

SEQ ID NO: 424          moltype = AA  length = 32
FEATURE                 Location/Qualifiers
REGION                  1..32
                        note = Mouse C3 heavy chain variable framework region 3
                           (FWR3) acidsequence
source                  1..32
                        mol_type = protein
                        organism = synthetic construct
SEQUENCE: 424
KATMTVDKSS STAYMELARL TSEDSAMYYC AR                                 32

SEQ ID NO: 425          moltype = DNA  length = 30
FEATURE                 Location/Qualifiers
misc_feature            1..30
                        note = Mouse C3 heavy chain variable complementarity
                           determining regions3 (CDR3) sequence
source                  1..30
                        mol_type = other DNA
                        organism = synthetic construct
SEQUENCE: 425
tcggattact acggcccata ctttgactac                                    30

SEQ ID NO: 426          moltype = AA  length = 10
FEATURE                 Location/Qualifiers
REGION                  1..10
                        note = Mouse C3 heavy chain variable complementarity
                           determining regions3 (CDR3) sequence
source                  1..10
                        mol_type = protein
                        organism = synthetic construct
SEQUENCE: 426
SDYYGPYFDY                                                          10

SEQ ID NO: 427          moltype = DNA  length = 296
FEATURE                 Location/Qualifiers
misc_feature            1..296
                        note = IGHV1-18*04 heavy chain variable region sequence
source                  1..296
                        mol_type = other DNA
                        organism = synthetic construct
SEQUENCE: 427
caggttcagc tggtgcagtc tggagctgag gtgaagaagc ctggggcctc agtgaaggtc   60
tcctgcaagg cttctggtta cacctttacc agctacggta tcagctgggt gcgacaggcc  120
cctggacaag ggcttgagtg gatgggatgg atcagcgctt acaatggtaa cacaaactat  180
gcacagaagc tccagggcag agtcaccatg accacagaca catccacgag cacagcctac  240
atggagctga ggagcctgag atctgacgac acggccgtgt attactgtgc gagaga      296

SEQ ID NO: 428          moltype = AA  length = 98
FEATURE                 Location/Qualifiers
REGION                  1..98
                        note = IGHV1-18*04 heavy chain variable region sequence
source                  1..98
                        mol_type = protein
                        organism = synthetic construct
SEQUENCE: 428
QVQLVQSGAE VKKPGASVKV SCKASGYTFT SYGISWVRQA PGQGLEWMGW ISAYNGNTNY   60
AQKLQGRVTM TTDTSTSTAY MELRSLRSDD TAVYYCAR                          98

SEQ ID NO: 429          moltype = DNA  length = 90
FEATURE                 Location/Qualifiers
misc_feature            1..90
                        note = IGHV1-18*04 heavy chain variable framework region 1
                           (FWR1)sequence
source                  1..90
                        mol_type = other DNA
                        organism = synthetic construct
SEQUENCE: 429
caggttcagc tggtgcagtc tggagctgag gtgaagaagc ctggggcctc agtgaaggtc   60
tcctgcaagg cttctggtta cacctttacc                                   90
```

-continued

```
SEQ ID NO: 430            moltype = AA  length = 30
FEATURE                   Location/Qualifiers
REGION                    1..30
                          note = IGHV1-18*04 heavy chain variable framework region 1
                          (FWR1)sequence
source                    1..30
                          mol_type = protein
                          organism = synthetic construct
SEQUENCE: 430
QVQLVQSGAE VKKPGASVKV SCKASGYTFT                                       30

SEQ ID NO: 431            moltype = DNA  length = 15
FEATURE                   Location/Qualifiers
misc_feature              1..15
                          note = IGHV1-18*04 heavy chain variable complementarity
                          determiningregions 1 (CDR1) sequence
source                    1..15
                          mol_type = other DNA
                          organism = synthetic construct
SEQUENCE: 431
agctacggta tcagc                                                       15

SEQ ID NO: 432            moltype = AA  length = 5
FEATURE                   Location/Qualifiers
REGION                    1..5
                          note = IGHV1-18*04 heavy chain variable complementarity
                          determiningregions 1 (CDR1) sequence
source                    1..5
                          mol_type = protein
                          organism = synthetic construct
SEQUENCE: 432
SYGIS                                                                  5

SEQ ID NO: 433            moltype = DNA  length = 42
FEATURE                   Location/Qualifiers
misc_feature              1..42
                          note = IGHV1-18*04 heavy chain variable framework region 2
                          (FWR2)sequence
source                    1..42
                          mol_type = other DNA
                          organism = synthetic construct
SEQUENCE: 433
tgggtgcgac aggcccctgg acaagggctt gagtggatgg ga                         42

SEQ ID NO: 434            moltype = AA  length = 14
FEATURE                   Location/Qualifiers
REGION                    1..14
                          note = IGHV1-18*04 heavy chain variable framework region 2
                          (FWR2)sequence
source                    1..14
                          mol_type = protein
                          organism = synthetic construct
SEQUENCE: 434
WVRQAPGQGL EWMG                                                        14

SEQ ID NO: 435            moltype = DNA  length = 51
FEATURE                   Location/Qualifiers
misc_feature              1..51
                          note = IGHV1-18*04 heavy chain variable complementarity
                          determiningregions 2 (CDR2) sequence
source                    1..51
                          mol_type = other DNA
                          organism = synthetic construct
SEQUENCE: 435
tggatcagcg cttacaatgg taacacaaac tatgcacaga agctccaggg c                51

SEQ ID NO: 436            moltype = AA  length = 17
FEATURE                   Location/Qualifiers
REGION                    1..17
                          note = IGHV1-18*04 heavy chain variable complementarity
                          determiningregions 2 (CDR2) sequence
source                    1..17
                          mol_type = protein
                          organism = synthetic construct
SEQUENCE: 436
WISAYNGNTN YAQKLQG                                                     17

SEQ ID NO: 437            moltype = DNA  length = 96
FEATURE                   Location/Qualifiers
```

| | |
|---|---|
| misc_feature | 1..96<br>note = IGHV1-18*04 heavy chain variable framework region 3 (FWR3)sequence |
| source | 1..96<br>mol_type = other DNA<br>organism = synthetic construct |

SEQUENCE: 437
```
agatcacca tgaccacaga cacatccacg agcacagcct acatggagct gaggagcctg   60
agatctgacg acacggccgt gtattactgt gcgaga                            96
```

| | |
|---|---|
| SEQ ID NO: 438 | moltype = AA  length = 32 |
| FEATURE | Location/Qualifiers |
| REGION | 1..32<br>note = IGHV1-18*04 heavy chain variable framework region 3 (FWR3)sequence |
| source | 1..32<br>mol_type = protein<br>organism = synthetic construct |

SEQUENCE: 438
```
RVTMTTDTST STAYMELRSL RSDDTAVYYC AR                                32
```

| | |
|---|---|
| SEQ ID NO: 439 | moltype = DNA  length = 357 |
| FEATURE | Location/Qualifiers |
| misc_feature | 1..357<br>note = Humanized C3 heavy chain variable region sequence |
| source | 1..357<br>mol_type = other DNA<br>organism = synthetic construct |

SEQUENCE: 439
```
caggttcagc tggtgcagtc tggagctgag gtgaagaagc ctggggcctc agtgaaggtc   60
tcctgcaagg cttctggtta cacctttacc gactacgcca tgaactgggt gcgacaggcc  120
cctggacaag ggcttgagtg gatgggagtg atcagcacct cagcggtaa cacaaacttc  180
aaccagaagt tcaagggcag agtcaccatg accacagaca catccacgag cacagcctac  240
atggagctga ggagcctgag atctgacgac acggccgtgt attactgtgc gagaagcgac  300
tactacggcc catacttcga ctactggggc cagggcacca ccctgaccgt gtccagc    357
```

| | |
|---|---|
| SEQ ID NO: 440 | moltype = AA  length = 119 |
| FEATURE | Location/Qualifiers |
| REGION | 1..119<br>note = Humanized C3 heavy chain variable region sequence |
| source | 1..119<br>mol_type = protein<br>organism = synthetic construct |

SEQUENCE: 440
```
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSS  119
```

| | |
|---|---|
| SEQ ID NO: 441 | moltype = DNA  length = 90 |
| FEATURE | Location/Qualifiers |
| misc_feature | 1..90<br>note = Humanized C3 heavy chain variable framework region 1 (FWR1) acidsequence |
| source | 1..90<br>mol_type = other DNA<br>organism = synthetic construct |

SEQUENCE: 441
```
caggttcagc tggtgcagtc tggagctgag gtgaagaagc ctggggcctc agtgaaggtc   60
tcctgcaagg cttctggtta cacctttacc                                   90
```

| | |
|---|---|
| SEQ ID NO: 442 | moltype = AA  length = 30 |
| FEATURE | Location/Qualifiers |
| REGION | 1..30<br>note = Humanized C3 heavy chain variable framework region 1 (FWR1) acidsequence |
| source | 1..30<br>mol_type = protein<br>organism = synthetic construct |

SEQUENCE: 442
```
QVQLVQSGAE VKKPGASVKV SCKASGYTFT                                   30
```

| | |
|---|---|
| SEQ ID NO: 443 | moltype = DNA  length = 15 |
| FEATURE | Location/Qualifiers |
| misc_feature | 1..15<br>note = Humanized C3 heavy chain variable complementarity determiningregions 1 (CDR1) sequence |
| source | 1..15<br>mol_type = other DNA<br>organism = synthetic construct |

SEQUENCE: 443 gactacgcca tgaac                                                      15

SEQ ID NO: 444            moltype = AA   length = 5
FEATURE                   Location/Qualifiers
REGION                    1..5
                          note = Humanized C3 heavy chain variable complementarity
                          determiningregions 1 (CDR1) sequence
source                    1..5
                          mol_type = protein
                          organism = synthetic construct
SEQUENCE: 444
DYAMN                                                                 5

SEQ ID NO: 445            moltype = DNA   length = 42
FEATURE                   Location/Qualifiers
misc_feature              1..42
                          note = Humanized C3 heavy chain variable framework region 2
                          (FWR2) acidsequence
source                    1..42
                          mol_type = other DNA
                          organism = synthetic construct
SEQUENCE: 445
tgggtgcgac aggcccctgg acaagggctt gagtggatgg ga                        42

SEQ ID NO: 446            moltype = AA   length = 14
FEATURE                   Location/Qualifiers
REGION                    1..14
                          note = Humanized C3 heavy chain variable framework region 2
                          (FWR2) acidsequence
source                    1..14
                          mol_type = protein
                          organism = synthetic construct
SEQUENCE: 446
WVRQAPGQGL EWMG                                                       14

SEQ ID NO: 447            moltype = DNA   length = 51
FEATURE                   Location/Qualifiers
misc_feature              1..51
                          note = Humanized C3 heavy chain variable complementarity
                          determiningregions 2 (CDR2) sequence
source                    1..51
                          mol_type = other DNA
                          organism = synthetic construct
SEQUENCE: 447
gtgatcagca ccttcagcgg taacacaaac ttcaaccaga agttcaaggg c               51

SEQ ID NO: 448            moltype = AA   length = 17
FEATURE                   Location/Qualifiers
REGION                    1..17
                          note = Humanized C3 heavy chain variable complementarity
                          determiningregions 2 (CDR2) sequence
source                    1..17
                          mol_type = protein
                          organism = synthetic construct
SEQUENCE: 448
VISTFSGNTN FNQKFKG                                                    17

SEQ ID NO: 449            moltype = DNA   length = 96
FEATURE                   Location/Qualifiers
misc_feature              1..96
                          note = Humanized C3 heavy chain variable framework region 3
                          (FWR3) acidsequence
source                    1..96
                          mol_type = other DNA
                          organism = synthetic construct
SEQUENCE: 449
agagtcacca tgaccacaga cacatccacg agcacagcct acatggagct gaggagcctg     60
agatctgacg acacggccgt gtattactgt gcgaga                               96

SEQ ID NO: 450            moltype = AA   length = 32
FEATURE                   Location/Qualifiers
REGION                    1..32
                          note = Humanized C3 heavy chain variable framework region 3
                          (FWR3) acidsequence
source                    1..32
                          mol_type = protein
                          organism = synthetic construct
SEQUENCE: 450
RVTMTTDTST STAYMELRSL RSDDTAVYYC AR                                   32

```
SEQ ID NO: 451            moltype = DNA  length = 30
FEATURE                   Location/Qualifiers
misc_feature              1..30
                          note = Humanized C3 heavy chain variable complementarity
                          determiningregions 3 (CDR3) sequence
source                    1..30
                          mol_type = other DNA
                          organism = synthetic construct
SEQUENCE: 451
agcgactact acggcccata cttcgactac                                           30

SEQ ID NO: 452            moltype = AA  length = 10
FEATURE                   Location/Qualifiers
REGION                    1..10
                          note = Humanized C3 heavy chain variable complementarity
                          determiningregions 3 (CDR3) sequence
source                    1..10
                          mol_type = protein
                          organism = synthetic construct
SEQUENCE: 452
SDYYGPYFDY                                                                 10

SEQ ID NO: 453            moltype = DNA  length = 1353
FEATURE                   Location/Qualifiers
misc_feature              1..1353
                          note = Humanized C3 IgG1 heavy chain sequence
source                    1..1353
                          mol_type = other DNA
                          organism = synthetic construct
SEQUENCE: 453
caggttcagc tggtgcagtc tggagctgag gtgaagaagc ctggggcctc agtgaaggtc          60
tcctgcaagg cttctggtta cacctttacc gactacgcca tgaactgggt gcgacaggcc        120
cctggacaag ggcttgagtg gatgggagtg atcagcacct tcagcggtaa cacaaacttc        180
aaccagaagt tcaagggcag agtcaccatg accacagaca tccacgcgag cacagcctac        240
atggagctga ggagcctgag atctgacgac acggccgtgt attactgtgc gagaagcgac        300
tactacggcc catacttcga ctactggggc cagggcacca ccctgaccgt gtccagcgct        360
agcaccaagg gcccatcggt cttccccctg gcaccctcct ccaagagcac ctctggggc         420
acagcggccc tgggctgcct ggtcaaggac tacttccccg aaccggtgac ggtgtcgtgg        480
aactcaggcg ccctgaccag cggcgtgcac accttcccgg ctgtcctaca gtcctcagga        540
ctctactccc tcagcagcgt ggtgacagtg ccctccagca gcttgggcac ccagacctac        600
atctgcaacg tgaatcacaa gcccagcaac accaaggtgg acaagaaagt tgagcccaaa        660
tcttgtgaca aaactcacac atgcccaccg tgcccagcac ctgaactcct ggggggaccg        720
tcagtcttcc tcttcccccc aaaacccaag gacaccctca tgatctcccg gacccctgag        780
gtcacatgcg tggtggtgga cgtgagccac gaagaccctg aggtcaagtt caactggtac        840
gtggacggcg tggaggtgca taatgccaag acaaagccgc gggaggagca gtacaacagc        900
acgtaccgtg tggtcagcgt cctcaccgtc ctgcaccagg actggctgaa tggcaaggag        960
tacaagtgca aggtctccaa caaagccctc ccagccccca tcgagaaaac catctccaaa       1020
gccaaagggc agccccgaga accacaggtg tacaccctgc ccccatcccg ggaggagatg       1080
accaagaacc aggtcagcct gacctgcctg gtcaaaggct tctatcccag cgacatcgcc       1140
gtggagtggg agagcaatgg gcagccggag aacaactaca agaccacgcc tcccgtgctg       1200
gactccgacg gctccttctt cctctacagc aagctcaccg tggacaagag caggtggcag       1260
caggggaacg tcttctcatg ctccgtgatg catgaggctc tgcacaacca ctacacgcag       1320
aagagcctct ccctgtctcc gggtaaatga taa                                    1353

SEQ ID NO: 454            moltype = AA  length = 449
FEATURE                   Location/Qualifiers
REGION                    1..449
                          note = Humanized C3 IgG1 heavy chain sequence
source                    1..449
                          mol_type = protein
                          organism = synthetic construct
SEQUENCE: 454
QVQLVQSGAE VKKPGASVKV SCKASGYTFT DYAMNWVRQA PGQGLEWMGV ISTFSGNTNF          60
NQKFKGRVTM TTDTSTSTAY MELRSLRSDD TAVYYCARSD YYGPYFDYWG QGTTLTVSSA        120
STKGPSVFPL APSSKSTSGG TAALGCLVKD YFPEPVTVSW NSGALTSGVH TFPAVLQSSG        180
LYSLSSVVTV PSSSLGTQTY ICNVNHKPSN TKVDKKVEPK SCDKTHTCPP CPAPELLGGP        240
SVFLFPPKPK DTLMISRTPE VTCVVVDVSH EDPEVKFNWY VDGVEVHNAK TKPREEQYNS        300
TYRVVSVLTV LHQDWLNGKE YKCKVSNKAL PAPIEKTISK AKGQPREPQV YTLPPSREEM        360
TKNQVSLTCL VKGFYPSDIA VEWESNGQPE NNYKTTPPVL DSDGSFFLYS KLTVDKSRWQ        420
QGNVFSCSVM HEALHNHYTQ KSLSLSPGK                                          449

SEQ ID NO: 455            moltype = DNA  length = 1341
FEATURE                   Location/Qualifiers
misc_feature              1..1341
                          note = Humanized C3 IgG2 heavy chain sequence
source                    1..1341
                          mol_type = other DNA
                          organism = synthetic construct
```

-continued

```
SEQUENCE: 455
caggttcagc tggtgcagtc tggagctgag gtgaagaagc ctggggcctc agtgaaggtc   60
tcctgcaagg cttctggtta cacctttacc gactacgcca tgaactgggt gcgacaggcc  120
cctggacaag gcttgagtg gatgggagtg atcagcacct tcagcggtaa cacaaacttc  180
aaccagaagt tcaagggcag agtcaccatg accacagaca tctccacgac cacagcctac  240
atggagctga ggagcctgag atctgacgac acggccgtgt attactgtgc gagaagcgac  300
tactacggcc catacttcga ctactggggc cagggcacca ccctgaccgt gtccagcgcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ctctgaccag cggcgtgcac accttcccgg ctgtcctaca gtcctcagga  540
ctctactccc tcagcagcgt ggtgaccgtg ccctccagca acttcggcac ccagacctac  600
acctgcaacg tagatcacaa gcccagcaac accaaggtgg acaagacagt tgagcgcaaa  660
tgttgtgtcg agtgcccacc gtgcccagca ccacctgtgg caggaccgtc agtcttcctc  720
ttccccccaa aacccaagga caccctcatg atctcccgga cccctgaggt cacgtgcgtg  780
gtggtggacg tgagccacga agaccccgag gtccagttca actggtacgt ggacggcgtg  840
gaggtgcata atgccaagac aaagccacgg gaggagcagt tcaacagcac gttccgtgtg  900
gtcagcgtcc tcaccgttgt gcaccaggac tggctgaacg gcaaggagta caagtgcaag  960
gtctccaaca aagcctccc agcccccatc gagaaaacca tctccaaaac caaagggcag 1020
ccccgagaac cacaggtgta caccctgccc ccatcccggg aggagatgac caagaaccag 1080
gtcagcctga cctgcctggt caaaggcttc taccccagcg acatcgccgt ggagtgggag 1140
agcaatgggc agccggagaa caactacaag accacacctc ccatgctgga ctccgacggc 1200
tccttcttcc tctacagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtaaatagta a                                          1341

SEQ ID NO: 456          moltype = AA   length = 445
FEATURE                 Location/Qualifiers
REGION                  1..445
                        note = Humanized C3 IgG2 heavy chain sequence
source                  1..445
                        mol_type = protein
                        organism = synthetic construct
SEQUENCE: 456
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGK                                      445

SEQ ID NO: 457          moltype = DNA   length = 545
FEATURE                 Location/Qualifiers
misc_feature            1..545
                        note = Humanized C3 heavy chain IgG1 gBLOCK sequence
source                  1..545
                        mol_type = other DNA
                        organism = synthetic construct
SEQUENCE: 457
tgctctgggt tccaggttcc actggtgacg cggcccagcc ggcccaggtt cagctggtgc   60
agtctggagc tgaggtgaag aagcctgggg cctcagtgaa ggtctcctgc aaggcttctg  120
gttacacctt taccgactac gccatgaact gggtgcgaca ggcccctgga caagggcttg  180
agtggatggg agtgatcagc accttcagcg gtaacacaaa cttcaaccag aagttcaagg  240
gcagagtcac catgaccaca gacacatcca gcacacacta catggagctg aggagcctga  300
gatctgacga cacggccgtg tattactgtg cgagaagcga ctactacggc ccatactttc  360
gactactgg ggccaggc accaccctga ccgtgtccag cgctagcacc aagggccat  420
cggtcttccc cctggcaccc tcctccaaga gcacctctgg gggcacagcg gccctgggct  480
gcctggtcaa ggactacttc cccgaaccgg tgacggtgtc gtggaactca ggcgccctga  540
ccagc                                                             545

SEQ ID NO: 458          moltype = DNA   length = 336
FEATURE                 Location/Qualifiers
misc_feature            1..336
                        note = Mouse C3 Light Chain variable region sequence
source                  1..336
                        mol_type = other DNA
                        organism = synthetic construct
SEQUENCE: 458
gatgttttga tgacccaaac tccactctcc ctgcctgtca gtcttggaga tcaagcctcc   60
atctcttgca gatctagtca gaccattgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
aacagagtgg aggctgagga tctgggagtt tattactgct tcaaggttc acatgttcca  300
ttcacgttcg gctcggggac aaagttggaa ataaaa                           336

SEQ ID NO: 459          moltype = AA   length = 112
FEATURE                 Location/Qualifiers
REGION                  1..112
```

```
                         note = Mouse C3 Light Chain variable region sequence
source                   1..112
                         mol_type = protein
                         organism = synthetic construct
SEQUENCE: 459
DVLMTQTPLS LPVSLGDQAS ISCRSSQTIV HSNGNTYLEW YLQKPGQSPK LLIYKVSNRF   60
SGVPDRFSGS GSGTDFTLKI NRVEAEDLGV YYCFQGSHVP FTFGSGTKLE IK          112

SEQ ID NO: 460           moltype = DNA  length = 69
FEATURE                  Location/Qualifiers
misc_feature             1..69
                         note = Mouse C3 light chain variable framework region 1
                         (FWR1) sequence
source                   1..69
                         mol_type = other DNA
                         organism = synthetic construct
SEQUENCE: 460
gatgttttga tgacccaaac tccactctcc ctgcctgtca gtcttggaga tcaagcctcc   60
atctcttgc                                                          69

SEQ ID NO: 461           moltype = AA  length = 23
FEATURE                  Location/Qualifiers
REGION                   1..23
                         note = Mouse C3 light chain variable framework region 1
                         (FWR1) sequence
source                   1..23
                         mol_type = protein
                         organism = synthetic construct
SEQUENCE: 461
DVLMTQTPLS LPVSLGDQAS ISC                                           23

SEQ ID NO: 462           moltype = DNA  length = 48
FEATURE                  Location/Qualifiers
misc_feature             1..48
                         note = Mouse C3 light chain variable complementarity
                         determining regions1 (CDR1) sequence
source                   1..48
                         mol_type = other DNA
                         organism = synthetic construct
SEQUENCE: 462
agatctagtc agaccattgt acatagtaat ggaaacacct atttagaa                48

SEQ ID NO: 463           moltype = AA  length = 16
FEATURE                  Location/Qualifiers
REGION                   1..16
                         note = Mouse C3 light chain variable complementarity
                         determining regions1 (CDR1) sequence
source                   1..16
                         mol_type = protein
                         organism = synthetic construct
SEQUENCE: 463
RSSQTIVHSN GNTYLE                                                   16

SEQ ID NO: 464           moltype = DNA  length = 45
FEATURE                  Location/Qualifiers
misc_feature             1..45
                         note = Mouse C3 light chain variable framework region 2
                         (FWR2) sequence
source                   1..45
                         mol_type = other DNA
                         organism = synthetic construct
SEQUENCE: 464
tggtacctgc agaaaccagg ccagtctcca aagctcctga tctac                   45

SEQ ID NO: 465           moltype = AA  length = 15
FEATURE                  Location/Qualifiers
REGION                   1..15
                         note = Mouse C3 light chain variable framework region 2
                         (FWR2) sequence
source                   1..15
                         mol_type = protein
                         organism = synthetic construct
SEQUENCE: 465
WYLQKPGQSP KLLIY                                                    15

SEQ ID NO: 466           moltype = DNA  length = 21
FEATURE                  Location/Qualifiers
misc_feature             1..21
                         note = Mouse C3 light chain variable complementarity
```

```
                        determining regions2 (CDR2) sequence
source                  1..21
                        mol_type = other DNA
                        organism = synthetic construct
SEQUENCE: 466
aaagtttcca accgattttc t                                                   21

SEQ ID NO: 467          moltype = AA   length = 7
FEATURE                 Location/Qualifiers
REGION                  1..7
                        note = Mouse C3 light chain variable complementarity
                        determining regions2 (CDR2) sequence
source                  1..7
                        mol_type = protein
                        organism = synthetic construct
SEQUENCE: 467
KVSNRFS                                                                    7

SEQ ID NO: 468          moltype = DNA   length = 96
FEATURE                 Location/Qualifiers
misc_feature            1..96
                        note = Mouse C3 light chain variable framework region 3
                        (FWR3) sequence
source                  1..96
                        mol_type = other DNA
                        organism = synthetic construct
SEQUENCE: 468
ggggtcccag acaggttcag tggcagtgga tcagggacag atttcacact caagatcaac    60
agagtggagg ctgaggatct gggagtttat tactgc                              96

SEQ ID NO: 469          moltype = AA   length = 32
FEATURE                 Location/Qualifiers
REGION                  1..32
                        note = Mouse C3 light chain variable framework region 3
                        (FWR3) sequence
source                  1..32
                        mol_type = protein
                        organism = synthetic construct
SEQUENCE: 469
GVPDRFSGSG SGTDFTLKIN RVEAEDLGVY YC                                        32

SEQ ID NO: 470          moltype = DNA   length = 27
FEATURE                 Location/Qualifiers
misc_feature            1..27
                        note = Mouse C3 light chain variable complementarity
                        determining regions3 (CDR3) sequence
source                  1..27
                        mol_type = other DNA
                        organism = synthetic construct
SEQUENCE: 470
tttcaaggtt cacatgttcc attcacg                                             27

SEQ ID NO: 471          moltype = AA   length = 9
FEATURE                 Location/Qualifiers
REGION                  1..9
                        note = Mouse C3 light chain variable complementarity
                        determining regions3 (CDR3) sequence
source                  1..9
                        mol_type = protein
                        organism = synthetic construct
SEQUENCE: 471
FQGSHVPFT                                                                  9

SEQ ID NO: 472          moltype = DNA   length = 300
FEATURE                 Location/Qualifiers
misc_feature            1..300
                        note = IGKV2-29*03 light chain variable region sequence
source                  1..300
                        mol_type = other DNA
                        organism = synthetic construct
SEQUENCE: 472
gatattgtga tgacccagac tccactctct ctgtccgtca cccctggaca gccggcctcc    60
atctcctgca agtctagtca gagcctcctg catagtgatg aaagaccta tttgtattgg   120
tacctgcaga agccaggcca gtctccacag ctcctgatct atgaagtttc cagccggttc   180
tctggagtgc cagataggtt cagtggcagc gggtcaggga cagatttcac actgaaaatc   240
agccgggtgg aggctgagga tgttggggtt tattactgca tgcaaggtat acaccttcct   300

SEQ ID NO: 473          moltype = AA   length = 100
FEATURE                 Location/Qualifiers
```

```
REGION                      1..100
                            note = IGKV2-29*03 light chain variable region sequence
source                      1..100
                            mol_type = protein
                            organism = synthetic construct
SEQUENCE: 473
DIVMTQTPLS LSVTPGQPAS ISCKSSQSLL HSDGKTYLYW YLQKPGQSPQ LLIYEVSSRF   60
SGVPDRFSGS GSGTDFTLKI SRVEAEDVGV YYCMQGIHLP                        100

SEQ ID NO: 474              moltype = DNA  length = 69
FEATURE                     Location/Qualifiers
misc_feature                1..69
                            note = IGKV2-29*03 light chain variable framework region 1
                             (FWR1) acidsequence
source                      1..69
                            mol_type = other DNA
                            organism = synthetic construct
SEQUENCE: 474
gatattgtga tgacccagac tccactctct ctgtccgtca ccctggaca gccggcctcc    60
atctcctgc                                                          69

SEQ ID NO: 475              moltype = AA  length = 23
FEATURE                     Location/Qualifiers
REGION                      1..23
                            note = IGKV2-29*03 light chain variable framework region 1
                             (FWR1) acidsequence
source                      1..23
                            mol_type = protein
                            organism = synthetic construct
SEQUENCE: 475
DIVMTQTPLS LSVTPGQPAS ISC                                          23

SEQ ID NO: 476              moltype = DNA  length = 49
FEATURE                     Location/Qualifiers
misc_feature                1..49
                            note = IGKV2-29*03 light chain variable complementarity
                             determiningregions 1 (CDR1) sequence
source                      1..49
                            mol_type = other DNA
                            organism = synthetic construct
SEQUENCE: 476
aagtctagtc agagcctcct gcatagtgat ggaaagacct atttsgtat               49

SEQ ID NO: 477              moltype = AA  length = 16
FEATURE                     Location/Qualifiers
REGION                      1..16
                            note = IGKV2-29*03 light chain variable complementarity
                             determiningregions 1 (CDR1) sequence
source                      1..16
                            mol_type = protein
                            organism = synthetic construct
SEQUENCE: 477
KSSQSLLHSD GKTYLY                                                   16

SEQ ID NO: 478              moltype = DNA  length = 45
FEATURE                     Location/Qualifiers
misc_feature                1..45
                            note = IGKV2-29*03 light chain variable framework region 2
                             (FWR2)sequence
source                      1..45
                            mol_type = other DNA
                            organism = synthetic construct
SEQUENCE: 478
tggtacctgc agaagccagg ccagtctcca cagctcctga tctat                   45

SEQ ID NO: 479              moltype = AA  length = 15
FEATURE                     Location/Qualifiers
REGION                      1..15
                            note = IGKV2-29*03 light chain variable framework region 2
                             (FWR2)sequence
source                      1..15
                            mol_type = protein
                            organism = synthetic construct
SEQUENCE: 479
WYLQKPGQSP QLLIY                                                    15

SEQ ID NO: 480              moltype = DNA  length = 18
FEATURE                     Location/Qualifiers
misc_feature                1..18
```

```
                        note = IGKV2-29*03 light chain variable complementarity
                            determiningregions 2 (CDR2) sequence
source                  1..18
                        mol_type = other DNA
                        organism = synthetic construct
SEQUENCE: 480
gaagtttcca gccggttc                                                       18

SEQ ID NO: 481          moltype = AA  length = 7
FEATURE                 Location/Qualifiers
REGION                  1..7
                        note = IGKV2-29*03 light chain variable complementarity
                            determiningregions 2 (CDR2) sequence
source                  1..7
                        mol_type = protein
                        organism = synthetic construct
SEQUENCE: 481
EVSSRFS                                                                    7

SEQ ID NO: 482          moltype = DNA  length = 96
FEATURE                 Location/Qualifiers
misc_feature            1..96
                        note = IGKV2-29*03 light chain variable framework region 3
                            (FWR3)sequence
source                  1..96
                        mol_type = other DNA
                        organism = synthetic construct
SEQUENCE: 482
ggagtgccag ataggttcag tggcagcggg tcagggacag atttcacact gaaaatcagc        60
cggtggagg ctgaggatgt tggggtttat tactgc                                    96

SEQ ID NO: 483          moltype = AA  length = 32
FEATURE                 Location/Qualifiers
REGION                  1..32
                        note = IGKV2-29*03 light chain variable framework region 3
                            (FWR3)sequence
source                  1..32
                        mol_type = protein
                        organism = synthetic construct
SEQUENCE: 483
GVPDRFSGSG SGTDFTLKIS RVEAEDVGVY YC                                        32

SEQ ID NO: 484          moltype = DNA  length = 21
FEATURE                 Location/Qualifiers
misc_feature            1..21
                        note = IGKV2-29*03 light chain variable complementarity
                            determiningregions3 (CDR3) sequence
source                  1..21
                        mol_type = other DNA
                        organism = synthetic construct
SEQUENCE: 484
atgcaaggta taccttcc t                                                     21

SEQ ID NO: 485          moltype = AA  length = 7
FEATURE                 Location/Qualifiers
REGION                  1..7
                        note = IGKV2-29*03 light chain variable complementarity
                            determiningregions3 (CDR3) sequence
source                  1..7
                        mol_type = protein
                        organism = synthetic construct
SEQUENCE: 485
MQGIHLP                                                                    7

SEQ ID NO: 486          moltype = DNA  length = 342
FEATURE                 Location/Qualifiers
misc_feature            1..342
                        note = Humanized C3 light chain variable region sequence
source                  1..342
                        mol_type = other DNA
                        organism = synthetic construct
SEQUENCE: 486
gatattgtga tgacccagac tccactctct ctgtccgtca cccctggaca gccggcctcc        60
atctcctgca ggtctagtca gaccattgtc catagtaatg gaaacaccta tttggagtgg       120
tacctgcaga agccaggcca gtctccacac ctcctgatct ataaggtttc caaccggttc       180
tctggagtgc cagataggtt cagtggcagc gggtcaggga cagatttcac actgaaaatc       240
agccgggtgg aggctgagga tgttggggtt tattactgct cccaaggtag ccacgtgcct       300
ttcaccttcg gcggagggac caaggtggag atcaaacgaa ct                          342
```

| | |
|---|---|
| SEQ ID NO: 487 | moltype = AA   length = 114 |
| FEATURE | Location/Qualifiers |
| REGION | 1..114 |
| | note = Humanized C3 light chain variable region sequence |
| source | 1..114 |
| | mol_type = protein |
| | organism = synthetic construct |

SEQUENCE: 487
DIVMTQTPLS LSVTPGQPAS ISCRSSQTIV HSNGNTYLEW YLQKPGQSPQ LLIYKVSNRF  60
SGVPDRFSGS GSGTDFTLKI SRVEAEDVGV YYCFQGSHVP FTFGGGTKVE IKRT       114

| | |
|---|---|
| SEQ ID NO: 488 | moltype = DNA   length = 69 |
| FEATURE | Location/Qualifiers |
| misc_feature | 1..69 |
| | note = Humanized C3 light chain variable framework region 1 (FWR1) acidsequence |
| source | 1..69 |
| | mol_type = other DNA |
| | organism = synthetic construct |

SEQUENCE: 488
gatattgtga tgacccagac tccactctct ctgtccgtca cccctggaca gccggcctcc  60
atctcctgc                                                         69

| | |
|---|---|
| SEQ ID NO: 489 | moltype = AA   length = 23 |
| FEATURE | Location/Qualifiers |
| REGION | 1..23 |
| | note = Humanized C3 light chain variable framework region 1 (FWR1) acidsequence |
| source | 1..23 |
| | mol_type = protein |
| | organism = synthetic construct |

SEQUENCE: 489
DIVMTQTPLS LSVTPGQPAS ISC                                          23

| | |
|---|---|
| SEQ ID NO: 490 | moltype = DNA   length = 47 |
| FEATURE | Location/Qualifiers |
| misc_feature | 1..47 |
| | note = Humanized C3 light chain variable complementarity determiningregions 1 (CDR1) sequence |
| source | 1..47 |
| | mol_type = other DNA |
| | organism = synthetic construct |

SEQUENCE: 490
ggtctagtca gaccattgtc catagtaatg gaaacaccta tttggag                47

| | |
|---|---|
| SEQ ID NO: 491 | moltype = AA   length = 16 |
| FEATURE | Location/Qualifiers |
| REGION | 1..16 |
| | note = Humanized C3 light chain variable complementarity determiningregions 1 (CDR1) sequence |
| source | 1..16 |
| | mol_type = protein |
| | organism = synthetic construct |

SEQUENCE: 491
RSSQTIVHSN GNTYLE                                                  16

| | |
|---|---|
| SEQ ID NO: 492 | moltype = DNA   length = 45 |
| FEATURE | Location/Qualifiers |
| misc_feature | 1..45 |
| | note = Humanized C3 light chain variable framework region 2 (FWR2) acidsequence |
| source | 1..45 |
| | mol_type = other DNA |
| | organism = synthetic construct |

SEQUENCE: 492
tggtacctgc agaagccagg ccagtctcca cagctcctga tctat                  45

| | |
|---|---|
| SEQ ID NO: 493 | moltype = AA   length = 15 |
| FEATURE | Location/Qualifiers |
| REGION | 1..15 |
| | note = Humanized C3 light chain variable framework region 2 (FWR2) acidsequence |
| source | 1..15 |
| | mol_type = protein |
| | organism = synthetic construct |

SEQUENCE: 493
WYLQKPGQSP QLLIY                                                   15

| | |
|---|---|
| SEQ ID NO: 494 | moltype = DNA   length = 21 |

```
FEATURE                  Location/Qualifiers
misc_feature             1..21
                         note = Humanized C3 light chain variable complementarity
                            determiningregions 2 (CDR2) sequence
source                   1..21
                         mol_type = other DNA
                         organism = synthetic construct
SEQUENCE: 494
aaggtttcca accggttctc t                                             21

SEQ ID NO: 495           moltype = AA  length = 7
FEATURE                  Location/Qualifiers
REGION                   1..7
                         note = Humanized C3 light chain variable complementarity
                            determiningregions 2 (CDR2) sequence
source                   1..7
                         mol_type = protein
                         organism = synthetic construct
SEQUENCE: 495
KVSNRFS                                                              7

SEQ ID NO: 496           moltype = DNA  length = 96
FEATURE                  Location/Qualifiers
misc_feature             1..96
                         note = Humanized C3 light chain variable framework region 3
                            (FWR3) acidsequence
source                   1..96
                         mol_type = other DNA
                         organism = synthetic construct
SEQUENCE: 496
ggagtgccag ataggttcag tggcagcggg tcagggacag atttcacact gaaaatcagc   60
cgggtggagg ctgaggatgt tggggtttat tactgc                             96

SEQ ID NO: 497           moltype = AA  length = 32
FEATURE                  Location/Qualifiers
REGION                   1..32
                         note = Humanized C3 light chain variable framework region 3
                            (FWR3) acidsequence
source                   1..32
                         mol_type = protein
                         organism = synthetic construct
SEQUENCE: 497
GVPDRFSGSG SGTDFTLKIS RVEAEDVGVY YC                                  32

SEQ ID NO: 498           moltype = DNA  length = 27
FEATURE                  Location/Qualifiers
misc_feature             1..27
                         note = Humanized C3 light chain variable complementarity
                            determiningregions 3 (CDR3) sequence
source                   1..27
                         mol_type = other DNA
                         organism = synthetic construct
SEQUENCE: 498
ttccaaggta gccacgtgcc tttcacc                                        27

SEQ ID NO: 499           moltype = AA  length = 9
FEATURE                  Location/Qualifiers
REGION                   1..9
                         note = Humanized C3 light chain variable complementarity
                            determiningregions 3 (CDR3) sequence
source                   1..9
                         mol_type = protein
                         organism = synthetic construct
SEQUENCE: 499
FQGSHVPFT                                                             9

SEQ ID NO: 500           moltype = DNA  length = 666
FEATURE                  Location/Qualifiers
misc_feature             1..666
                         note = Humanized C3 lambda light chainsequence
source                   1..666
                         mol_type = other DNA
                         organism = synthetic construct
SEQUENCE: 500
gatattgtga tgacccagac tccactctct ctgtccgtca cccctggaca gccggcctcc   60
atctcctgca ggtctagtca gaccattgtc catagtaatg aaacaccta tttggagtgg   120
tacctgcaga agccaggcca gtctccacag ctcctgatct ataaggtttc caaccggttc   180
tctggagtgc cagataggtt cagtggcagc gggtcaggga cagatttcac actgaaaatc   240
agccgggtgg aggctgagga tgttggggtt tattactgct tccaaggtag ccacgtgcct   300
```

```
ttcaccttcg gcggagggac caaggtggag atcaaacgaa ctggtcagcc caaggctgcc    360
ccctcggtca ctctgttccc gccctcctct gaggagcttc aagccaacaa ggccacactg    420
gtgtgtctca taagtgactt ctacccggga gccgtgacag tggcctggaa ggcagatagc    480
agccccgtca aggcgggagt ggagaccacc acaccctcca acaaagcaa caacaagtac    540
gcggccagca gctatctgag cctgacgcct gagcagtgga agtcccacag aagctacagc    600
tgccaggtca cgcatgaagg gagcaccgtg gagaagacag tggcccctac agaatgttca    660
tagtaa                                                                666

SEQ ID NO: 501              moltype = AA  length = 220
FEATURE                     Location/Qualifiers
REGION                      1..220
                            note = Humanized C3 lambda light chainsequence
source                      1..220
                            mol_type = protein
                            organism = synthetic construct
SEQUENCE: 501
DIVMTQTPLS LSVTPGQPAS ISCRSSQTIV HSNGNTYLEW YLQKPGQSPQ LLIYKVSNRF     60
SGVPDRFSGS GSGTDFTLKI SRVEAEDVGV YYCFQGSHVP FTFGGGTKVE IKRTGQPKAA    120
PSVTLFPPSS EELQANKATL VCLISDFYPG AVTVAWKADS SPVKAGVETT TPSKQSNNKY    180
AASSYLSLTP EQWKSHRSYS CQVTHEGSTV EKTVAPTECS                          220

SEQ ID NO: 502              moltype = DNA  length = 666
FEATURE                     Location/Qualifiers
misc_feature                1..666
                            note = Humanized C3 Kappa light chain
source                      1..666
                            mol_type = other DNA
                            organism = synthetic construct
SEQUENCE: 502
gatattgtga tgacccagac tccactctct ctgtccgtca cccctggaca gccggcctcc     60
atctcctgca ggtctagtca gaccattgtc catagtaatg gaaacaccta tttggagtgg    120
tacctgcaga agccaggcca gtctccacag ctcctgatct ataaggtttc caaccggttc    180
tctggagtgc cagataggtt cagtggcagc gggtcaggga cagatttcac actgaaaatc    240
agccgggtgg aggctgagga tgttggggtt tattactgct tccaaggtag ccacgtgcct    300
ttcaccttcg gcggagggac caaggtggag atcaaacgaa ctacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tagtaa                                                                666

SEQ ID NO: 503              moltype = AA  length = 220
FEATURE                     Location/Qualifiers
REGION                      1..220
                            note = Humanized C3 Kappa light chain
source                      1..220
                            mol_type = protein
                            organism = synthetic construct
SEQUENCE: 503
DIVMTQTPLS LSVTPGQPAS ISCRSSQTIV HSNGNTYLEW YLQKPGQSPQ LLIYKVSNRF     60
SGVPDRFSGS GSGTDFTLKI SRVEAEDVGV YYCFQGSHVP FTFGGGTKVE IKRTTVAAPS    120
VFIFPPSDEQ LKSGTASVVC LLNNFYPREA KVQWKVDNAL QSGNSQESVT EQDSKDSTYS    180
LSSTLTLSKA DYEKHKVYAC EVTHQGLSSP VTKSFNRGEC                          220

SEQ ID NO: 504              moltype = DNA  length = 815
FEATURE                     Location/Qualifiers
misc_feature                1..815
                            note = Humanized C3 Kappa light gBLOCK sequence
source                      1..815
                            mol_type = other DNA
                            organism = synthetic construct
SEQUENCE: 504
agctggctag gtaagcttgg taccgagctc ggatccacgc caccatggag acagacacac     60
tcctgctatg ggtactgctg ctctgggttc caggttccac tggtgacgat attgtgatga    120
cccagactcc actctctctg tccgtcaccc ctggacagcc ggcctccatc tcctgcaggt    180
ctagtcagac cattgtccat agtaatgaaa cacctatttg gagtggtac ctgcagaagc    240
caggccagtc tccacagctc ctgatctata aggtttccaa ccggttctct ggagtgcag    300
ataggttcag tggcagcggg tcagggacag atttcacact gaaaatcagc cgggtggag    360
ctgaggatgt tggggtttat tactgcttcc aaggtagcca cgtgcctttc accttcggcg    420
gagggaccaa ggtggagatc aaacgaacta cggtggctgc accatctgtc ttcatcttcc    480
cgccatctga tgagcagttg aaatctggaa ctgcctctgt tgtgtgcctg ctgaataact    540
tctatcccag agaggccaaa gtacagtgga aggtggataa cgccctccaa tcgggtaact    600
cccaggagag tgtcacagag caggacagca aggacagcac ctacagcctc agcagcaccc    660
tgacgctgag caaagcagac tacgagaaac acaaagtcta cgcctgcgaa gtcacccatc    720
agggcctgag ctcgcccgtc acaaagagct tcaacagggg agagtgttag taagtttaaa    780
cccgctgatc agcctcgact gtgccttcta gttgc                               815

SEQ ID NO: 505              moltype = DNA  length = 321
```

```
FEATURE                 Location/Qualifiers
misc_feature            1..321
                        note = Mouse C8 heavy chain variable region sequence
source                  1..321
                        mol_type = other DNA
                        organism = synthetic construct
SEQUENCE: 505
gaagtgatgg tcgtggaaag cggcggtggt ctggtaaagc cggggggatc ccttaagctt    60
tcttgcgccg catccgggtt cacgttctcc ggctatgcca tgtcctgggt ccgacagact   120
cccgaaaagc gcttggaatg ggtggccact atctcctccg ggggacgta catctactac    180
cccgacagtg tgaaaggaag atttacaata tctcgcgaca acgcaaaaaa taccttgtat   240
cttcaaatga gctccctgcg gtcagaggac actgccatgt actattgcgc cgcctgggc    300
ggcgacaatt actatgagta t                                             321

SEQ ID NO: 506          moltype = AA  length = 107
FEATURE                 Location/Qualifiers
REGION                  1..107
                        note = Mouse C8 heavy chain variable region sequence
source                  1..107
                        mol_type = protein
                        organism = synthetic construct
SEQUENCE: 506
EVMVVESGGG LVKPGGSLKL SCAASGFTFS GYAMSWVRQT PEKRLEWVAT ISSGGTYIYY    60
PDSVKGRFTI SRDNAKNTLY LQMSSLRSED TAMYYCARLG GDNYYEY                 107

SEQ ID NO: 507          moltype = DNA  length = 15
FEATURE                 Location/Qualifiers
misc_feature            1..15
                        note = Mouse C8 heavy chain variable complementarity
                        determining region1 (CDR1) sequence
source                  1..15
                        mol_type = other DNA
                        organism = synthetic construct
SEQUENCE: 507
ggctatgcca tgtcc                                                     15

SEQ ID NO: 508          moltype = AA  length = 5
FEATURE                 Location/Qualifiers
REGION                  1..5
                        note = Mouse C8 heavy chain variable complementarity
                        determining region1 (CDR1) sequence
source                  1..5
                        mol_type = protein
                        organism = synthetic construct
SEQUENCE: 508
GYAMS                                                                 5

SEQ ID NO: 509          moltype = DNA  length = 51
FEATURE                 Location/Qualifiers
misc_feature            1..51
                        note = Mouse C8 heavy chain variable complementarity
                        determining region2 (CDR2) sequence
source                  1..51
                        mol_type = other DNA
                        organism = synthetic construct
SEQUENCE: 509
actatctcct ccgggggac gtacatctac taccccgaca gtgtgaaagg a               51

SEQ ID NO: 510          moltype = AA  length = 17
FEATURE                 Location/Qualifiers
REGION                  1..17
                        note = Mouse C8 heavy chain variable complementarity
                        determining region2 (CDR2) sequence
source                  1..17
                        mol_type = protein
                        organism = synthetic construct
SEQUENCE: 510
TISSGGTYIY YPDSVKG                                                   17

SEQ ID NO: 511          moltype = DNA  length = 27
FEATURE                 Location/Qualifiers
misc_feature            1..27
                        note = Mouse C8 heavy chain variable complementarity
                        determining region3 (CDR3) sequence
source                  1..27
                        mol_type = other DNA
                        organism = synthetic construct
SEQUENCE: 511
ctgggcggcg acaattacta tgagtat                                        27
```

| | | |
|---|---|---|
| SEQ ID NO: 512 | moltype = AA   length = 9 | |
| FEATURE | Location/Qualifiers | |
| REGION | 1..9 | |
| | note = Mouse C8 heavy chain variable complementarity determining region3 (CDR3) sequence | |
| source | 1..9 | |
| | mol_type = protein | |
| | organism = synthetic construct | |
| SEQUENCE: 512 | | |
| LGGDNYYEY | | 9 |

| | | |
|---|---|---|
| SEQ ID NO: 513 | moltype = DNA   length = 292 | |
| FEATURE | Location/Qualifiers | |
| misc_feature | 1..292 | |
| | note = IGHV3-21*04 heavy chain variable region sequence | |
| source | 1..292 | |
| | mol_type = other DNA | |
| | organism = synthetic construct | |

SEQUENCE: 513
```
gaggtgcagc tggtggagtc tgggggaggc ctggtcaagc ctgggggtc cctgagactc    60
tcctgtgcag cctctggatt caccttcagt agctatagca tgaactgggt ccgccaggct   120
ccagggaagg gctgagtg gtctcatcc attagtagta gtagtagtta catatactac    180
gcagactcag tgaagggccg attcaccatc tccagagaca acgccaagaa ctcactgtat   240
ctgcaaatga acagcctgag agccgaggac acggccgtgt attactgtgc ga            292
```

| | | |
|---|---|---|
| SEQ ID NO: 514 | moltype = AA   length = 98 | |
| FEATURE | Location/Qualifiers | |
| REGION | 1..98 | |
| | note = IGHV3-21*04 heavy chain variable region sequence | |
| source | 1..98 | |
| | mol_type = protein | |
| | organism = synthetic construct | |

SEQUENCE: 514
```
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCAR                            98
```

| | | |
|---|---|---|
| SEQ ID NO: 515 | moltype = DNA   length = 90 | |
| FEATURE | Location/Qualifiers | |
| misc_feature | 1..90 | |
| | note = IGHV3-21*04 heavy chain variable framework region 1 (FWR1) sequence | |
| source | 1..90 | |
| | mol_type = other DNA | |
| | organism = synthetic construct | |

SEQUENCE: 515
```
gaggtgcagc tggtggagtc tgggggaggc ctggtcaagc ctgggggtc cctgagactc    60
tcctgtgcag cctctggatt caccttcagt                                     90
```

| | | |
|---|---|---|
| SEQ ID NO: 516 | moltype = AA   length = 30 | |
| FEATURE | Location/Qualifiers | |
| REGION | 1..30 | |
| | note = IGHV3-21*04 heavy chain variable framework region 1 (FWR1) sequence | |
| source | 1..30 | |
| | mol_type = protein | |
| | organism = synthetic construct | |

SEQUENCE: 516
EVQLVESGGG LVKPGGSLRL SCAASGFTFS                                     30

| | | |
|---|---|---|
| SEQ ID NO: 517 | moltype = DNA   length = 15 | |
| FEATURE | Location/Qualifiers | |
| misc_feature | 1..15 | |
| | note = IGHV3-21*04 heavy chain variable complementarity determiningregions 1 (CDR1) sequence | |
| source | 1..15 | |
| | mol_type = other DNA | |
| | organism = synthetic construct | |

SEQUENCE: 517
agctatagca tgaac                                                     15

| | | |
|---|---|---|
| SEQ ID NO: 518 | moltype = AA   length = 5 | |
| FEATURE | Location/Qualifiers | |
| REGION | 1..5 | |
| | note = IGHV3-21*04 heavy chain variable complementarity determiningregions 1 (CDR1) sequence | |
| source | 1..5 | |
| | mol_type = protein | |
| | organism = synthetic construct | |

```
SEQUENCE: 518
SYSMN                                                                            5

SEQ ID NO: 519           moltype = DNA  length = 39
FEATURE                  Location/Qualifiers
misc_feature             1..39
                         note = IGHV3-21*04 heavy chain variable framework region 2
                         (FWR2)sequence
source                   1..39
                         mol_type = other DNA
                         organism = synthetic construct
SEQUENCE: 519
tgggtccgcc aggctccagg gaaggggctg gagtgggtc                                       39

SEQ ID NO: 520           moltype = AA  length = 13
FEATURE                  Location/Qualifiers
REGION                   1..13
                         note = IGHV3-21*04 heavy chain variable framework region 2
                         (FWR2)sequence
source                   1..13
                         mol_type = protein
                         organism = synthetic construct
SEQUENCE: 520
WVRQAPGKGL EWV                                                                   13

SEQ ID NO: 521           moltype = DNA  length = 54
FEATURE                  Location/Qualifiers
misc_feature             1..54
                         note = IGHV3-21*04 heavy chain variable complementarity
                         determiningregions 2 (CDR2) sequence
source                   1..54
                         mol_type = other DNA
                         organism = synthetic construct
SEQUENCE: 521
tcatccatta gtagtagtag tagttacata tactacgcag actcagtgaa gggc                      54

SEQ ID NO: 522           moltype = AA  length = 18
FEATURE                  Location/Qualifiers
REGION                   1..18
                         note = IGHV3-21*04 heavy chain variable complementarity
                         determiningregions 2 (CDR2) sequence
source                   1..18
                         mol_type = protein
                         organism = synthetic construct
SEQUENCE: 522
SSISSSSYI YYADSVKG                                                               18

SEQ ID NO: 523           moltype = DNA  length = 94
FEATURE                  Location/Qualifiers
misc_feature             1..94
                         note = IGHV3-21*04 heavy chain variable framework region 3
                         (FWR3)sequence
source                   1..94
                         mol_type = other DNA
                         organism = synthetic construct
SEQUENCE: 523
cgattcacca tctccagaga caacgccaag aactcactgt atctgcaaat gaacagcctg                60
agagccgagg acacggccgt gtattactgt gcga                                            94

SEQ ID NO: 524           moltype = AA  length = 32
FEATURE                  Location/Qualifiers
REGION                   1..32
                         note = IGHV3-21*04 heavy chain variable framework region 3
                         (FWR3)sequence
source                   1..32
                         mol_type = protein
                         organism = synthetic construct
SEQUENCE: 524
RFTISRDNAK NSLYLQMNSL RAEDTAVYYC AR                                              32

SEQ ID NO: 525           moltype = DNA  length = 354
FEATURE                  Location/Qualifiers
misc_feature             1..354
                         note = Humanized C8 heavy chain variable region sequence
source                   1..354
                         mol_type = other DNA
                         organism = synthetic construct
SEQUENCE: 525
gaggtgcagc tggtggagtc tgggggaggc ctggtcaagc ctggggggtc cctgagactc                60
```

```
tcctgtgcag cctctggatt caccttcagt ggctatgcca tgagctgggt ccgccaggct    120
ccagggaagg ggctggagtg ggtctcaacc attagtagtg gcggaaccta catatactac    180
cctgactcag tgaagggccg attcaccatc tccagagaca acgccaagaa ctcactgtat    240
ctgcaaatga acagcctgag agccgaggac acggccgtgt attactgtgc gagactgggc    300
ggcgataact attatgaata ttggggcaaa gggaccacgg tcaccgtctc ctcc          354
```

```
SEQ ID NO: 526          moltype = AA   length = 118
FEATURE                 Location/Qualifiers
REGION                  1..118
                        note = Humanized C8 heavy chain variable region sequence
source                  1..118
                        mol_type = protein
                        organism = synthetic construct
SEQUENCE: 526
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYWGK GTTVTVSS      118

SEQ ID NO: 527          moltype = DNA   length = 90
FEATURE                 Location/Qualifiers
misc_feature            1..90
                        note = Humanized C8 heavy chain variable framework region 1
                        (FWR1) sequence
source                  1..90
                        mol_type = other DNA
                        organism = synthetic construct
SEQUENCE: 527
gaggtgcagc tggtggagtc tgggggaggc ctggtcaagc ctgggggtc cctgagactc      60
tcctgtgcag cctctggatt caccttcagt                                     90

SEQ ID NO: 528          moltype = AA   length = 30
FEATURE                 Location/Qualifiers
REGION                  1..30
                        note = Humanized C8 heavy chain variable framework region 1
                        (FWR1) sequence
source                  1..30
                        mol_type = protein
                        organism = synthetic construct
SEQUENCE: 528
EVQLVESGGG LVKPGGSLRL SCAASGFTFS                                      30

SEQ ID NO: 529          moltype = DNA   length = 15
FEATURE                 Location/Qualifiers
misc_feature            1..15
                        note = Humanized C8 heavy chain variable complementarity
                        determiningregion 1 (CDR1) sequence
source                  1..15
                        mol_type = other DNA
                        organism = synthetic construct
SEQUENCE: 529
ggctatgcca tgagc                                                     15

SEQ ID NO: 530          moltype = AA   length = 5
FEATURE                 Location/Qualifiers
REGION                  1..5
                        note = Humanized C8 heavy chain variable complementarity
                        determiningregion 1 (CDR1) sequence
source                  1..5
                        mol_type = protein
                        organism = synthetic construct
SEQUENCE: 530
GYAMS                                                                 5

SEQ ID NO: 531          moltype = DNA   length = 42
FEATURE                 Location/Qualifiers
misc_feature            1..42
                        note = Humanized C8 heavy chain variable framework region 2
                        (FWR2) sequence
source                  1..42
                        mol_type = other DNA
                        organism = synthetic construct
SEQUENCE: 531
tgggtccgcc aggctccagg gaaggggctg gagtgggtct ca                       42

SEQ ID NO: 532          moltype = AA   length = 14
FEATURE                 Location/Qualifiers
REGION                  1..14
                        note = Humanized C8 heavy chain variable framework region 2
                        (FWR2) sequence
source                  1..14
```

```
                              mol_type = protein
                              organism = synthetic construct
SEQUENCE: 532
WVRQAPGKGL EWVS                                                           14

SEQ ID NO: 533         moltype = DNA   length = 51
FEATURE                Location/Qualifiers
misc_feature           1..51
                       note = Humanized C8 heavy chain variable complementarity
                         determiningregion 2 (CDR2) sequence
source                 1..51
                       mol_type = other DNA
                       organism = synthetic construct
SEQUENCE: 533
accattagta gtggcggaac ctacatatac taccctgact cagtgaaggg c                  51

SEQ ID NO: 534         moltype = AA    length = 17
FEATURE                Location/Qualifiers
REGION                 1..17
                       note = Humanized C8 heavy chain variable complementarity
                         determiningregion 2 (CDR2) sequence
source                 1..17
                       mol_type = protein
                       organism = synthetic construct
SEQUENCE: 534
TISSGGTYIY YPDSVKG                                                        17

SEQ ID NO: 535         moltype = DNA   length = 96
FEATURE                Location/Qualifiers
misc_feature           1..96
                       note = Humanized C8 heavy chain variable framework region 3
                         (FWR3)sequence
source                 1..96
                       mol_type = other DNA
                       organism = synthetic construct
SEQUENCE: 535
cgattcacca tctccagaga caacgccaag aactcactgt atctgcaaat gaacagcctg         60
agagccgagg acacggccgt gtattactgt gcgaga                                   96

SEQ ID NO: 536         moltype = AA    length = 32
FEATURE                Location/Qualifiers
REGION                 1..32
                       note = Humanized C8 heavy chain variable framework region 3
                         (FWR3)sequence
source                 1..32
                       mol_type = protein
                       organism = synthetic construct
SEQUENCE: 536
RFTISRDNAK NSLYLQMNSL RAEDTAVYYC AR                                       32

SEQ ID NO: 537         moltype = DNA   length = 27
FEATURE                Location/Qualifiers
misc_feature           1..27
                       note = Humanized C8 heavy chain variable complementarity
                         determiningregion 3 (CDR3) sequence
source                 1..27
                       mol_type = other DNA
                       organism = synthetic construct
SEQUENCE: 537
ctgggcggcg ataactatta tgaatat                                             27

SEQ ID NO: 538         moltype = AA    length = 9
FEATURE                Location/Qualifiers
REGION                 1..9
                       note = Humanized C8 heavy chain variable complementarity
                         determiningregion 3 (CDR3) sequence
source                 1..9
                       mol_type = protein
                       organism = synthetic construct
SEQUENCE: 538
LGGDNYYEY                                                                 9

SEQ ID NO: 539         moltype = DNA   length = 1350
FEATURE                Location/Qualifiers
misc_feature           1..1350
                       note = Humanized C8 IgG1 heavy chain sequence
source                 1..1350
                       mol_type = other DNA
                       organism = synthetic construct
```

```
SEQUENCE: 539
gaggtgcagc tggtggagtc tgggggaggc ctggtcaagc ctgggggtc cctgagactc      60
tcctgtgcag cctctggatt caccttcagt ggctatgcca tgagctgggt ccgccaggct    120
ccagggaagg ggctggagtg gtctcaacc attagtagtg gcggaaccta catatactac    180
cctgactcag tgaagggccg attcaccatc tccagagaca cgccaagaa ctcactgtat    240
ctgcaaatga acagcctgag agccgaggac acggccgtgt attactgtgc gagactgggc    300
ggcgataact attatgaata ttggggcaaa gggaccacgg tcaccgtctc ctccgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gacagtgccc tccagcagct tgggcaccca gacctacatc    600
tgcaacgtga atcacaagcc cagcaacacc aaggtggaca gaaagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaatgataa                                    1350

SEQ ID NO: 540          moltype = AA   length = 448
FEATURE                 Location/Qualifiers
REGION                  1..448
                        note = Humanized C8 IgG1 heavy chain sequence
source                  1..448
                        mol_type = protein
                        organism = synthetic construct
SEQUENCE: 540
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYWGK GTTVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                      448

SEQ ID NO: 541          moltype = DNA   length = 1338
FEATURE                 Location/Qualifiers
misc_feature            1..1338
                        note = Humanized C8 IgG2 heavy chain sequence
source                  1..1338
                        mol_type = other DNA
                        organism = synthetic construct
SEQUENCE: 541
gaggtgcagc tggtggagtc tgggggaggc ctggtcaagc ctgggggtc cctgagactc      60
tcctgtgcag cctctggatt caccttcagt ggctatgcca tgagctgggt ccgccaggct    120
ccagggaagg ggctggagtg gtctcaacc attagtagtg gcggaaccta catatactac    180
cctgactcag tgaagggccg attcaccatc tccagagaca cgccaagaa ctcactgtat    240
ctgcaaatga acagcctgag agccgaggac acggccgtgt attactgtgc gagactgggc    300
ggcgataact attatgaata ttggggcaaa gggaccacgg tcaccgtctc ctccgcctcc    360
accaagggcc catcggtctt ccccctggcg ccctgctcca ggagcacctc cgagagcaca    420
gccgccctgg gctgcctggt caaggactac ttccccgaac cggtgacggt gtcgtggaac    480
tcaggcgctc tgaccagcgg cgtgcacacc ttcccagctg tcctacagtc ctcaggactc    540
tactccctca gcagcgtggt gaccgtgccc tccagcaact tcggcaccca gacctacacc    600
tgcaacgtag atcacaagcc cagcaacacc aaggtggaca gacagttga gcgcaaatgt    660
tgtgtcgagt gcccaccgtg cccagcacca cctgtggcag accgtcagt cttcctcttc    720
cccccaaaac ccaaggacac cctcatgatc tcccggaccc ctgaggtcac gtgcgtggtg    780
gtggacgtga gccacgaaga cccgaggtc agttcaact ggtacgtgga cggcgtggag    840
gtgcataatg ccaagacaaa gccgcggag gagcagttca acagcacgtt ccgtgtggtc    900
agcgtcctca ccgttgtgca ccaggactgg ctgaacggca aggagtacaa gtgcaaggtc    960
tccaacaaag gcctcccagc ccccatcgag aaaaccatct ccaaaccaa agggcagccc   1020
cgagaaccac aggtgtacac cctgcccca tcccgggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acacctccca tgctggactc cgacggctcc   1200
ttcttcctct acagcaagct caccgtggac aagagcaggt ggcagcaggg gaacgtcttc   1260
tcatgctccg tgatgcatga ggctctgcac aaccactaca cgcagaagag cctctccctg   1320
tctccgggta aatagtaa                                                 1338

SEQ ID NO: 542          moltype = AA   length = 444
FEATURE                 Location/Qualifiers
REGION                  1..444
                        note = Humanized C8 IgG2 heavy chain sequence
source                  1..444
```

```
                           mol_type = protein
                           organism = synthetic construct
SEQUENCE: 542
EVQLVESGGG LVKPGGSLRL SCAASGFTFS GYAMSWVRQA PGKGLEWVST ISSGGTYIYY      60
PDSVKGRFTI SRDNAKNSLY LQMNSLRAED TAVYYCARLG GDNYYEYWGK GTTVTVSSAS     120
TKGPSVFPLA PCSRSTSEST AALGCLVKDY FPEPVTVSWN SGALTSGVHT FPAVLQSSGL     180
YSLSSVVTVP SSNFGTQTYT CNVDHKPSNT KVDKTVERKC CVECPPCPAP PVAGPSVFLF     240
PPKPKDTLMI SRTPEVTCVV VDVSHEDPEV QFNWYVDGVE VHNAKTKPRE EQFNSTFRVV     300
SVLTVVHQDW LNGKEYKCKV SNKGLPAPIE KTISKTKGQP REPQVYTLPP SREEMTKNQV     360
SLTCLVKGFY PSDIAVEWES NGQPENNYKT TPPMLDSDGS FFLYSKLTVD KSRWQQGNVF     420
SCSVMHEALH NHYTQKSLSL SPGK                                            444

SEQ ID NO: 543             moltype = DNA  length = 306
FEATURE                    Location/Qualifiers
misc_feature               1..306
                           note = Mouse C8 light chain variable region sequence
source                     1..306
                           mol_type = other DNA
                           organism = synthetic construct
SEQUENCE: 543
gacatcgtca ttacgcagac ccctgccagt cttgccgttt ctctgggcca gagggccact      60
atcagttaca gggcgagtaa gtctgtgagt accagcggct atagttacat gcattggaac     120
cagcagaaac cgggacagcc accacgcctg cttatttatc tggtgtctaa tcttgagtcc     180
ggggtgcccg ccaggttcag cggcagcggc tctgggaccg acttcacact caacattcat     240
ccagtggaag aagaggacgc tgctacatac tactgtcaac acattcggga actgaccagg     300
agtgaa                                                                306

SEQ ID NO: 544             moltype = AA  length = 102
FEATURE                    Location/Qualifiers
REGION                     1..102
                           note = Mouse C8 light chain variable region sequence
source                     1..102
                           mol_type = protein
                           organism = synthetic construct
SEQUENCE: 544
DIVITQTPAS LAVSLGQRAT ISYRASKSVS TSGYSYMHWN QQKPGQPPRL LIYLVSNLES      60
GVPARFSGSG SGTDFTLNIH PVEEEDAATY YCQHIRELTR SE                        102

SEQ ID NO: 545             moltype = DNA  length = 45
FEATURE                    Location/Qualifiers
misc_feature               1..45
                           note = Mouse C8 light chain variable complementarity
                           determining region1 (CDR1) sequence
source                     1..45
                           mol_type = other DNA
                           organism = synthetic construct
SEQUENCE: 545
agggcgagta agtctgtgag taccagcggc tatagttaca tgcat                      45

SEQ ID NO: 546             moltype = AA  length = 15
FEATURE                    Location/Qualifiers
REGION                     1..15
                           note = Mouse C8 light chain variable complementarity
                           determining region1 (CDR1) sequence
source                     1..15
                           mol_type = protein
                           organism = synthetic construct
SEQUENCE: 546
RASKSVSTSG YSYMH                                                       15

SEQ ID NO: 547             moltype = DNA  length = 21
FEATURE                    Location/Qualifiers
misc_feature               1..21
                           note = Mouse C8 light chain variable complementarity
                           determining region2 (CDR2) sequence
source                     1..21
                           mol_type = other DNA
                           organism = synthetic construct
SEQUENCE: 547
ctggtgtcta atcttgagtc c                                                21

SEQ ID NO: 548             moltype = AA  length = 7
FEATURE                    Location/Qualifiers
REGION                     1..7
                           note = Mouse C8 light chain variable complementarity
                           determining region2 (CDR2) sequence
source                     1..7
                           mol_type = protein
                           organism = synthetic construct
```

```
SEQUENCE: 548
LVSNLES                                                                  7

SEQ ID NO: 549          moltype = DNA   length = 30
FEATURE                 Location/Qualifiers
misc_feature            1..30
                        note = Mouse C8 light chain variable complementarity
                        determining region3 (CDR3) sequence
source                  1..30
                        mol_type = other DNA
                        organism = synthetic construct
SEQUENCE: 549
caacacattc gggaactgac caggagtgaa                                         30

SEQ ID NO: 550          moltype = AA    length = 10
FEATURE                 Location/Qualifiers
REGION                  1..10
                        note = Mouse C8 light chain variable complementarity
                        determining region3 (CDR3) sequence
source                  1..10
                        mol_type = protein
                        organism = synthetic construct
SEQUENCE: 550
QHIRELTRSE                                                              10

SEQ ID NO: 551          moltype = DNA   length = 303
FEATURE                 Location/Qualifiers
misc_feature            1..303
                        note = NCBI germline z00023 light chain variable region
                        sequence
source                  1..303
                        mol_type = other DNA
                        organism = synthetic construct
SEQUENCE: 551
gacatcgtga tgacccagtc tccagactcc ctggctgtgt ctctgggcga gagggccacc         60
atcaactgca agtccagcca gagtgtttta tacagctcca acaataagaa ctacttagct        120
tggtaccagc agaaaccagg acagcctcct aagctgctca tttactgggc atctacccgg        180
gaatccgggg tccctgaccg attcagtggc agcgggtctg ggacagattt cactctcacc        240
atcagcagcc tgcaggctga agatgtggca gtttattact gtcagcaata ttatagtact        300
cct                                                                    303

SEQ ID NO: 552          moltype = AA    length = 101
FEATURE                 Location/Qualifiers
REGION                  1..101
                        note = NCBI germline z00023 light chain variable region
                        sequence
source                  1..101
                        mol_type = protein
                        organism = synthetic construct
SEQUENCE: 552
DIVMTQSPDS LAVSLGERAT INCKSSQSVL YSSNNKNYLA WYQQKPGQPP KLLIYWASTR         60
ESGVPDRFSG SGSGTDFTLT ISSLQAEDVA VYYCQQYYST P                           101

SEQ ID NO: 553          moltype = DNA   length = 69
FEATURE                 Location/Qualifiers
misc_feature            1..69
                        note = NCBI germline z00023 light chain variable framework
                        region 1(FWR1) acid sequence
source                  1..69
                        mol_type = other DNA
                        organism = synthetic construct
SEQUENCE: 553
gacatcgtga tgacccagtc tccagactcc ctggctgtgt ctctgggcga gagggccacc         60
atcaactgc                                                               69

SEQ ID NO: 554          moltype = AA    length = 23
FEATURE                 Location/Qualifiers
REGION                  1..23
                        note = NCBI germline z00023 light chain variable framework
                        region 1(FWR1) acid sequence
source                  1..23
                        mol_type = protein
                        organism = synthetic construct
SEQUENCE: 554
DIVMTQSPDS LAVSLGERAT INC                                               23

SEQ ID NO: 555          moltype = DNA   length = 51
FEATURE                 Location/Qualifiers
misc_feature            1..51
```

```
                        note = NCBI germline z00023 light chain variable
                            complementaritydetermining regions 1 (CDR1) sequence
source                  1..51
                        mol_type = other DNA
                        organism = synthetic construct
SEQUENCE: 555
aagtccagcc agagtgtttt atacagctcc aacaataaga actacttagc t            51

SEQ ID NO: 556          moltype = AA  length = 17
FEATURE                 Location/Qualifiers
REGION                  1..17
                        note = NCBI germline z00023 light chain variable
                            complementaritydetermining regions 1 (CDR1) sequence
source                  1..17
                        mol_type = protein
                        organism = synthetic construct
SEQUENCE: 556
KSSQSVLYSS NNKNYLA                                                   17

SEQ ID NO: 557          moltype = DNA  length = 45
FEATURE                 Location/Qualifiers
misc_feature            1..45
                        note = NCBI germline z00023 light chain variable framework
                            region 2(FWR2) sequence
source                  1..45
                        mol_type = other DNA
                        organism = synthetic construct
SEQUENCE: 557
tggtaccagc agaaaccagg acagcctcct aagctgctca tttac                    45

SEQ ID NO: 558          moltype = AA  length = 15
FEATURE                 Location/Qualifiers
REGION                  1..15
                        note = NCBI germline z00023 light chain variable framework
                            region 2(FWR2) sequence
source                  1..15
                        mol_type = protein
                        organism = synthetic construct
SEQUENCE: 558
WYQQKPGQPP KLLIY                                                     15

SEQ ID NO: 559          moltype = DNA  length = 21
FEATURE                 Location/Qualifiers
misc_feature            1..21
                        note = NCBI germline z00023 light chain variable
                            complementaritydetermining regions 2 (CDR2) sequence
source                  1..21
                        mol_type = other DNA
                        organism = synthetic construct
SEQUENCE: 559
tgggcatcta cccgggaatc c                                              21

SEQ ID NO: 560          moltype = AA  length = 7
FEATURE                 Location/Qualifiers
REGION                  1..7
                        note = NCBI germline z00023 light chain variable
                            complementaritydetermining regions 2 (CDR2) sequence
source                  1..7
                        mol_type = protein
                        organism = synthetic construct
SEQUENCE: 560
WASTRES                                                               7

SEQ ID NO: 561          moltype = DNA  length = 96
FEATURE                 Location/Qualifiers
misc_feature            1..96
                        note = NCBI germline z00023 light chain variable framework
                            region 3(FWR3) sequence
source                  1..96
                        mol_type = other DNA
                        organism = synthetic construct
SEQUENCE: 561
ggggtccctg accgattcag tggcagcggg tctgggacag atttcactct caccatcagc    60
agcctgcagg ctgaagatgt ggcagtttat tactgt                              96

SEQ ID NO: 562          moltype = AA  length = 32
FEATURE                 Location/Qualifiers
REGION                  1..32
                        note = NCBI germline z00023 light chain variable framework
```

```
                           region 3(FWR3) sequence
source                  1..32
                        mol_type = protein
                        organism = synthetic construct
SEQUENCE: 562
GVPDRFSGSG SGTDFTLTIS SLQAEDVAVY YC                                     32

SEQ ID NO: 563          moltype = DNA  length = 21
FEATURE                 Location/Qualifiers
misc_feature            1..21
                        note = NCBI germline z00023 light chain variable
                          complementaritydetermining regions3 (CDR3) sequence
source                  1..21
                        mol_type = other DNA
                        organism = synthetic construct
SEQUENCE: 563
cagcaatatt atagtactcc t                                                 21

SEQ ID NO: 564          moltype = AA  length = 7
FEATURE                 Location/Qualifiers
REGION                  1..7
                        note = NCBI germline z00023 light chain variable
                          complementaritydetermining regions3 (CDR3) sequence
source                  1..7
                        mol_type = protein
                        organism = synthetic construct
SEQUENCE: 564
QQYYSTP                                                                  7

SEQ ID NO: 565          moltype = DNA  length = 342
FEATURE                 Location/Qualifiers
misc_feature            1..342
                        note = Humanized C8 light chain variable region sequence
source                  1..342
                        mol_type = other DNA
                        organism = synthetic construct
SEQUENCE: 565
gacatcgtga tgacccagtc tccagactcc ctggctgtgt ctctgggcga gagggccacc       60
atcaactgca gggccagcaa gagtgttagc accagcggct acagctacat gcactggtac      120
cagcagaaac caggacagcc tcctaagctg ctcatttacc tggtgtctaa cctggaatcc      180
ggggtccctg accgattcag tggcagcggg tctgggacag atttcactct caccatcagc      240
agcctgcagg ctgaagatgt ggcagtttat tactgtcaac acattcggga actgaccagg      300
agtgaattcg gcgagggac caaggtggag atcaaacgaa ct                          342

SEQ ID NO: 566          moltype = AA  length = 114
FEATURE                 Location/Qualifiers
REGION                  1..114
                        note = Humanized C8 light chain variable region sequence
source                  1..114
                        mol_type = protein
                        organism = synthetic construct
SEQUENCE: 566
DIVMTQSPDS LAVSLGERAT INCRASKSVS TSGYSYMHWY QQKPGQPPKL LIYLVSNLES       60
GVPDRFSGSG SGTDFTLTIS SLQAEDVAVY YCQHIRELTR SEFGGGTKVE IKRT            114

SEQ ID NO: 567          moltype = DNA  length = 69
FEATURE                 Location/Qualifiers
misc_feature            1..69
                        note = Humanized C8 light chain variable framework region 1
                          (FWR1)sequence
source                  1..69
                        mol_type = other DNA
                        organism = synthetic construct
SEQUENCE: 567
gacatcgtga tgacccagtc tccagactcc ctggctgtgt ctctgggcga gagggccacc       60
atcaactgc                                                               69

SEQ ID NO: 568          moltype = AA  length = 23
FEATURE                 Location/Qualifiers
REGION                  1..23
                        note = Humanized C8 light chain variable framework region 1
                          (FWR1)sequence
source                  1..23
                        mol_type = protein
                        organism = synthetic construct
SEQUENCE: 568
DIVMTQSPDS LAVSLGERAT INC                                               23

SEQ ID NO: 569          moltype = DNA  length = 42
```

```
FEATURE                 Location/Qualifiers
misc_feature            1..42
                        note = Humanized C8 light chain variable complementarity
                         determiningregion 1 (CDR1) sequence
source                  1..42
                        mol_type = other DNA
                        organism = synthetic construct
SEQUENCE: 569
agggccagca agagtgttag caccagcggc tacagctaca tg                    42

SEQ ID NO: 570          moltype = AA  length = 14
FEATURE                 Location/Qualifiers
REGION                  1..14
                        note = Humanized C8 light chain variable complementarity
                         determiningregion 1 (CDR1) sequence
source                  1..14
                        mol_type = protein
                        organism = synthetic construct
SEQUENCE: 570
RASKSVSTSG YSYM                                                   14

SEQ ID NO: 571          moltype = DNA  length = 48
FEATURE                 Location/Qualifiers
misc_feature            1..48
                        note = Humanized C8 light chain variable framework region 2
                         (FWR2)sequence
source                  1..48
                        mol_type = other DNA
                        organism = synthetic construct
SEQUENCE: 571
cactggtacc agcagaaacc aggacagcct cctaagctgc tcatttac              48

SEQ ID NO: 572          moltype = AA  length = 16
FEATURE                 Location/Qualifiers
REGION                  1..16
                        note = Humanized C8 light chain variable framework region 2
                         (FWR2)sequence
source                  1..16
                        mol_type = protein
                        organism = synthetic construct
SEQUENCE: 572
HWYQQKPGQP PKLLIY                                                 16

SEQ ID NO: 573          moltype = DNA  length = 21
FEATURE                 Location/Qualifiers
misc_feature            1..21
                        note = Humanized C8 light chain variable complementarity
                         determiningregion 2 (CDR2) sequence
source                  1..21
                        mol_type = other DNA
                        organism = synthetic construct
SEQUENCE: 573
ctggtgtcta acctggaatc c                                           21

SEQ ID NO: 574          moltype = AA  length = 7
FEATURE                 Location/Qualifiers
REGION                  1..7
                        note = Humanized C8 light chain variable complementarity
                         determiningregion 2 (CDR2) sequence
source                  1..7
                        mol_type = protein
                        organism = synthetic construct
SEQUENCE: 574
LVSNLES                                                           7

SEQ ID NO: 575          moltype = DNA  length = 96
FEATURE                 Location/Qualifiers
misc_feature            1..96
                        note = Humanized C8 light chain variable framework region 3
                         (FWR3)sequence
source                  1..96
                        mol_type = other DNA
                        organism = synthetic construct
SEQUENCE: 575
ggggtccctg accgattcag tggcagcggg tctgggacag atttcactct caccatcagc 60
agcctgcagg ctgaagatgt ggcagtttat tactgt                           96

SEQ ID NO: 576          moltype = AA  length = 32
FEATURE                 Location/Qualifiers
```

| | |
|---|---|
| REGION | 1..32<br>note = Humanized C8 light chain variable framework region 3<br>(FWR3)sequence |
| source | 1..32<br>mol_type = protein<br>organism = synthetic construct |

SEQUENCE: 576
```
GVPDRFSGSG SGTDFTLTIS SLQAEDVAVY YC                                      32
```

| | |
|---|---|
| SEQ ID NO: 577 | moltype = DNA  length = 30 |
| FEATURE | Location/Qualifiers |
| misc_feature | 1..30<br>note = Humanized C8 light chain variable complementarity<br>determiningregion 3 (CDR3) sequence |
| source | 1..30<br>mol_type = other DNA<br>organism = synthetic construct |

SEQUENCE: 577
```
caacacattc gggaactgac caggagtgaa                                         30
```

| | |
|---|---|
| SEQ ID NO: 578 | moltype = AA  length = 10 |
| FEATURE | Location/Qualifiers |
| REGION | 1..10<br>note = Humanized C8 light chain variable complementarity<br>determiningregion 3 (CDR3) sequence |
| source | 1..10<br>mol_type = protein<br>organism = synthetic construct |

SEQUENCE: 578
```
QHIRELTRSE                                                               10
```

| | |
|---|---|
| SEQ ID NO: 579 | moltype = DNA  length = 666 |
| FEATURE | Location/Qualifiers |
| misc_feature | 1..666<br>note = Humanized C8 Lambda light chain sequence |
| source | 1..666<br>mol_type = other DNA<br>organism = synthetic construct |

SEQUENCE: 579
```
gacatcgtga tgacccagtc tccagactcc ctggctgtgt ctctgggcga gagggccacc        60
atcaactgca gggccagcaa gagtgttagc accagcggct acagctacat gcactggtac       120
cagcagaaac aggacagcc tcctaagctg ctcatttacc tggtgtctaa cctgaatcc         180
ggggtccctg accgattcag tggcagcggg tctgggacag atttcactct caccatcagc       240
agcctgcagg ctgaagatgt ggcagtttat tactgtcaac acattcggga actgaccagg       300
agtgaattcg gcggagggac caaggtggag atcaaacgaa ctggtcagcc caaggctgcc       360
ccctcggtca ctctgttccc gccctcctct gaggagcttc aagccaacaa ggccacactg       420
gtgtgtctca taagtgactt ctacccggga gccgtgacag tggcctggaa ggcagatagc       480
agccccgtca aggcgggagt ggagaccacc acaccctcca aacaaagcaa caacaagtac       540
gcggccagca gctatctgag cctgacgcct gagcagtgga agtcccacag aagctacagc       600
tgccaggtca cgcatgaagg gagcaccgtg gagaagacag tggcccctac agaatgttca       660
tagtaa                                                                  666
```

| | |
|---|---|
| SEQ ID NO: 580 | moltype = AA  length = 220 |
| FEATURE | Location/Qualifiers |
| REGION | 1..220<br>note = Humanized C8 Lambda light chain sequence |
| source | 1..220<br>mol_type = protein<br>organism = synthetic construct |

SEQUENCE: 580
```
DIVMTQSPDS LAVSLGERAT INCRASKSVS TSGYSYMHWY QQKPGQPPKL LIYLVSNLES        60
GVPDRFSGSG SGTDFTLTIS SLQAEDVAVY YCQHIRELTR SEFGGGTKVE IKRTGQPKAA       120
PSVTLFPPSS EELQANKATL VCLISDFYPG AVTVAWKADS SPVKAGVETT TPSKQSNNKY       180
AASSYLSLTP EQWKSHRSYS CQVTHEGSTV EKTVAPTECS                             220
```

| | |
|---|---|
| SEQ ID NO: 581 | moltype = DNA  length = 666 |
| FEATURE | Location/Qualifiers |
| misc_feature | 1..666<br>note = Humanized C8 Kappa light chain sequence |
| source | 1..666<br>mol_type = other DNA<br>organism = synthetic construct |

SEQUENCE: 581
```
gacatcgtga tgacccagtc tccagactcc ctggctgtgt ctctgggcga gagggccacc        60
atcaactgca gggccagcaa gagtgttagc accagcggct acagctacat gcactggtac       120
cagcagaaac aggacagcc tcctaagctg ctcatttacc tggtgtctaa cctgaatcc         180
ggggtccctg accgattcag tggcagcggg tctgggacag atttcactct caccatcagc       240
agcctgcagg ctgaagatgt ggcagtttat tactgtcaac acattcggga actgaccagg       300
agtgaattcg gcggagggac caaggtggag atcaaacgaa ctacgtggc tgcaccatct       360
```

```
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600
gaagtcaccc atcagggcct gagctcgccc gtcacaaaga gcttcaacag gggagagtgt    660
tagtaa                                                                666
```

| SEQ ID NO: 582 | moltype = AA  length = 220 |
| --- | --- |
| FEATURE | Location/Qualifiers |
| REGION | 1..220 |
| | note = Humanized C8 Kappa light chain sequence |
| source | 1..220 |
| | mol_type = protein |
| | organism = synthetic construct |

SEQUENCE: 582

```
DIVMTQSPDS LAVSLGERAT INCRASKSVS TSGYSYMHWY QQKPGQPPKL LIYLVSNLES    60
GVPDRFSGSG SGTDFTLTIS SLQAEDVAVY YCQHIRELTR SEFGGGTKVE IKRTTVAAPS    120
VFIFPPSDEQ LKSGTASVVC LLNNFYPREA KVQWKVDNAL QSGNSQESVT EQDSKDSTYS    180
LSSTLTLSKA DYEKHKVYAC EVTHQGLSSP VTKSFNRGEC                          220
```

| SEQ ID NO: 583 | moltype = DNA  length = 815 |
| --- | --- |
| FEATURE | Location/Qualifiers |
| misc_feature | 1..815 |
| | note = Humanized C8 Kappa light chain gBLOCk sequence |
| source | 1..815 |
| | mol_type = other DNA |
| | organism = synthetic construct |

SEQUENCE: 583

```
agctggctag gtaagcttgg taccgagctc ggatccacgc caccatggag acagacacac    60
tcctgctatg ggtactgctg ctctgggttc caggttccac tggtgacgac atcgtgatga    120
cccagtctcc agactccctg gctgtgtctc tgggcgagag ggccaccatc aactgcaggg    180
ccagcaagag tgttagcacc agcggctaca gctacatgca ctggtaccag cagaaaccag    240
gacagcctcc taagctgctc atttacctgg tgtctaacct ggaatccggg gtccctgacc    300
gattcagtgg cagcgggtct gggacagatt tcactctcac catcagcagc ctgcaggctg    360
aagatgtggc agtttattac tgtcaacaca ttcgggaact gaccaggagt gaattcgggg    420
gagggaccaa ggtggagatc aaacgaacta cggtggctgc accatctgtc ttcatcttcc    480
cgccatctga tgagcagttg aaatctggaa ctgcctctgt tgtgtgcctg ctgaataact    540
tctatcccag agaggccaaa gtacagtgga aggtggataa cgcctccaa tcgggtaact    600
cccaggagag tgtcacagag caggacagca aggacagcac ctacagcctc agcagcaccc    660
tgacgctgag caaagcagac tacgagaaac acaaagtcta cgcctgcgaa gtcacccatc    720
agggcctgag ctcgcccgtc acaaagagct caacagggg agagtgttag taagtttaaa    780
cccgctgatc agcctcgact gtgccttcta gttgc                                815
```

| SEQ ID NO: 584 | moltype = DNA  length = 942 |
| --- | --- |
| FEATURE | Location/Qualifiers |
| misc_feature | 1..942 |
| | note = CAR-T E6 CD8 sequence |
| source | 1..942 |
| | mol_type = other DNA |
| | organism = synthetic construct |

SEQUENCE: 584

```
gaggtccagc tggttgagag tggcggtggg ctggttaagc ctggcggctc cctgcggctg    60
agctgcgccg cgagtggatt tactttcagc cgatatggga tgagttgggt gcggcaagct    120
cccgggaaga ggctggaatg ggtctcaaca atctccgggg gggcactta catctattac    180
cccgactcag tcaaggggag atttaccatt tcacgcgata agaataccct gtat           240
ttgcagatga attctctgag agcagaggac acagctgttt actattgtac ccgcgacaac    300
tatggcagga actacgacta cggtatggac tattggggac aagggacatt ggttacagtg    360
agcagtggcg gcggggcag cggaggagga ggcagcggtg ggggggcag cgagatagtg    420
ctcacgcagt caccgcgac tctcagtctc tcacctgggg aacgagctac cctgacgtgc    480
tctgctacct cctcagtgtc atatattcac tggtatcagc aacggcccgg gcagtcccct    540
agattgctca tttatagtac ctctaatctg gcctcaggta tccctgcacg attttctgga    600
tctggttcag ttctgattca cccctcact atctctagcc tggagcctga agactttgcc    660
gtttattact gccagcagag gtctagctcc ccattcacct ttgggagtgg gaccaaggtt    720
gaaattaaaa cgacaacccc ggcccccaga ccaccaacgc caccacccgc catcgccagc    780
caaccctgt ctctgagacc agaagctgt aggcctgccg ccggtggagc tgtgcacaca    840
agaggactgg atttcgcctg tgatatctac atttgggccc cgctcgcagg cacatgtgga    900
gtgctcctcc tctcccctggt gattacctg tactgctgat aa                        942
```

| SEQ ID NO: 585 | moltype = AA  length = 312 |
| --- | --- |
| FEATURE | Location/Qualifiers |
| REGION | 1..312 |
| | note = CAR-T E6 CD8 sequence |
| source | 1..312 |
| | mol_type = protein |
| | organism = synthetic construct |

SEQUENCE: 585

```
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV    120
SSGGGGSGGG GSGGGGSEIV LTQSPATLSL SPGERATLTC SATSSVSYIH WYQQRPGQSP    180
```

```
RLLIYSTSNL ASGIPARFSG SGSGSDYTLT ISSLEPEDFA VYYCQQRSSS PFTFGSGTKV    240
EIKTTTPAPR PPTPAPTIAS QPLSLRPEAC RPAAGGAVHT RGLDFACDIY IWAPLAGTCG    300
VLLLSLVITL YC                                                        312

SEQ ID NO: 586          moltype = DNA   length = 960
FEATURE                 Location/Qualifiers
misc_feature            1..960
                        note = CAR-T C2 CD8 sequence
source                  1..960
                        mol_type = other DNA
                        organism = synthetic construct
SEQUENCE: 586
gaagtgcagc tcgtagagag tggcggggga ctggtgaagc ccggtggaag cctcagactc     60
agttgcgccg cctcaggttt cacttttca ggttacgcca tgtcctgggt aagacaggca    120
ccggggaaag gactcgagtg ggtgtctact atcagctcag gaggcactta tatatattat   180
cctgactctg taaaaggccg atttacgatt tctcgcgaca atgcaaagaa ctccctctac   240
ctccaaatga acagtcttag ggcagaagac actgctgtat actattgtgc acgcctcggc   300
ggcgacaact actacgagta ctttgacgtg tgggggaaag gcactaccgt gacagtttca   360
agcggaggag gtggctcagg tggaggcggg tcagggggg gaggaagtga tattgtgctc   420
acacaatccc cagcctccct ggctgtgtct cccggccaac gcgctacaat tacatgtcgg   480
gcctccaaaa gcgtgagcac cagcggctac agctacatgc actggtatca acagaaacca   540
ggacaacccc ccaaactgtt gatttatctc gcttcaaact tggagtccgg gcctgcctgc   600
cgcttttcag ggagtgggag cggcacagat tttacgctga ctatcaaccc cgtagaagca   660
aacgatacag cgaattatta ttgtcaacat tcccgggaac tccccttta gttcggcggg   720
ggcacaaagg tcgaaattaa gagaaccacg acaaccccgg cccccagacc accaacgcca   780
gccccacca tcgccagcca acccctgtct ctgagaccag aagcctgtag gcctgccgcc   840
ggtggagctg tgcacacaag aggactggat ttcgcctgtg atatctacat ttgggcccc   900
ctcgcaggca catgtggagt gctcctcctc ccctggtga ttaccctgta ctgctgataa   960

SEQ ID NO: 587          moltype = AA   length = 318
FEATURE                 Location/Qualifiers
REGION                  1..318
                        note = CAR-T C2 CD8 sequence
source                  1..318
                        mol_type = protein
                        organism = synthetic construct
SEQUENCE: 587
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS    120
SGGGGSGGGG SGGGGSDIVL TQSPASLAVS PGQRATITCR ASKSVSTSGY SYMHWYQQKP    180
GQPPKLLIYL ASNLESGVPA RFSGSGSGTD FTLTINPVEA NDTANYYCQH SRELPFTFGG    240
GTKVEIKRTT TTPAPRPPTP APTIASQPLS LRPEACRPAA GGAVHTRGLD FACDIYIWAP    300
LAGTCGVLLL SLVITLYC                                                  318

SEQ ID NO: 588          moltype = DNA   length = 339
FEATURE                 Location/Qualifiers
misc_feature            1..339
                        note = CD8/4-1BB sequence
source                  1..339
                        mol_type = other DNA
                        organism = synthetic construct
SEQUENCE: 588
acgacaaccc cggcccccag accaccaacg ccagccccca ccatcgccag ccaacccctg     60
tctctgagac cagaagcctg taggcctgcc gccggtggag ctgtgcacac aagaggactg    120
gatttcgcct gtgatatcta catttgggcc cgctcgcag gcacatgttca agtgctcctc   180
ctctccctgg tgattaccct gtactgcaaa aggggccgca aaaaactcct ttacattttt   240
aagcagcctt ttatgaggcc agtacagacg actcaagagg aagacgggtg ctcatgccgc   300
tttcctgagg aggaggaagg agggtgcgaa ctgtgataa                           339

SEQ ID NO: 589          moltype = AA   length = 111
FEATURE                 Location/Qualifiers
REGION                  1..111
                        note = CD8/4-1BB sequence
source                  1..111
                        mol_type = protein
                        organism = synthetic construct
SEQUENCE: 589
TTTPAPRPPT PAPTIASQPL SLRPEACRPA AGGAVHTRGL DFACDIYIWA PLAGTCGVLL     60
LSLVITLYCK RGRKKLLYIF KQPFMRPVQT TQEEDGCSCR FPEEEEGGCE L             111

SEQ ID NO: 590          moltype = DNA   length = 336
FEATURE                 Location/Qualifiers
misc_feature            1..336
                        note = CD8/CD28 sequence
source                  1..336
                        mol_type = other DNA
                        organism = synthetic construct
SEQUENCE: 590
acgacaaccc cggcccccag accaccaacg ccagccccca ccatcgccag ccaacccctg     60
```

```
tctctgagac cagaagcctg taggcctgcc gccggtggag ctgtgcacac aagaggactg    120
gatttcgcct gtgatatcta catttgggcc ccgctcgcag gcacatgtgg agtgctcctc    180
ctctccctgg tgattaccct gtactgcaga agcaagcggt ctcggctcct gcattctgat    240
tacatgaaca tgaccccaag aagaccaggc cccaccagga acattacca gccctacgct     300
ccgccacgcg acttcgctgc ctaccggtcc tgataa                              336

SEQ ID NO: 591            moltype = AA  length = 110
FEATURE                   Location/Qualifiers
REGION                    1..110
                          note = CD8/CD28 sequence
source                    1..110
                          mol_type = protein
                          organism = synthetic construct
SEQUENCE: 591
TTTPAPRPPT PAPTIASQPL SLRPEACRPA AGGAVHTRGL DFACDIYIWA PLAGTCGVLL      60
LSLVITLYCR SKRSRLLHSD YMNMTPRRPG PTRKHYQPYA PPRDFAAYRS                110

SEQ ID NO: 592            moltype = DNA  length = 549
FEATURE                   Location/Qualifiers
misc_feature              1..549
                          note = CD8/CD3z sequence
source                    1..549
                          mol_type = other DNA
                          organism = synthetic construct
SEQUENCE: 592
acgacaaccc cggcccccag accaccaacg ccagccccca ccatcgccag ccaacccctg     60
tctctgagac cagaagcctg taggcctgcc gccggtggag ctgtgcacac aagaggactg    120
gatttcgcct gtgatatcta catttgggcc ccgctcgcag gcacatgtgg agtgctcctc    180
ctctccctgg tgattaccct gtactgccgc gttaagttct cccgatcagc cgacgcgcct   240
gcttacaagc agggccagaa ccaactgtac aacgagctga atctcggtag acggaagag    300
tacgacgtgt tggacaaacg gagaggccgc gacccagaaa tgggcggcaa gcctcgcagg   360
aaaaacccc aggagggact gtacaatgag ttgcagaaag ataagatggc agaagcttat    420
agcgagatcg gaatgaaggg ggaaaggaga cgagggaaag gacacgacgg cctttatcag   480
ggcctgtcca cagcaacaaa agatacgtat gacgccctcc atatgcaggc acttccacca   540
cggtgataa                                                            549

SEQ ID NO: 593            moltype = AA  length = 181
FEATURE                   Location/Qualifiers
REGION                    1..181
                          note = CD8/CD3z sequence
source                    1..181
                          mol_type = protein
                          organism = synthetic construct
SEQUENCE: 593
TTTPAPRPPT PAPTIASQPL SLRPEACRPA AGGAVHTRGL DFACDIYIWA PLAGTCGVLL      60
LSLVITLYCR VKFSRSADAP AYKQGQNQLY NELNLGRREE YDVLDKRRGR DPEMGGKPRR    120
KNPQEGLYNE LQKDKMAEAY SEIGMKGERR RGKGHDGLYQ GLSTATKDTY DALHMQALPP    180
R                                                                    181

SEQ ID NO: 594            moltype = DNA  length = 672
FEATURE                   Location/Qualifiers
misc_feature              1..672
                          note = CD8/CD28/CD3z sequence
source                    1..672
                          mol_type = other DNA
                          organism = synthetic construct
SEQUENCE: 594
acgacaaccc cggcccccag accaccaacg ccagccccca ccatcgccag ccaacccctg     60
tctctgagac cagaagcctg taggcctgcc gccggtggag ctgtgcacac aagaggactg    120
gatttcgcct gtgatatcta catttgggcc ccgctcgcag gcacatgtgg agtgctcctc    180
ctctccctgg tgattaccct gtactgcaga agcaagcggt ctcggctcct gcattctgat    240
tacatgaaca tgaccccaag aagaccaggc cccaccagga acattacca gccctacgct     300
ccgccacgcg acttcgctgc ctaccggtcc cgcgttaagt tctcccgatc agccgacgcg    360
cctgcttaca agcagggcca gaaccaactg tacaacgagc tgaatctcgg tagacgggaa   420
gagtacgacg tgttggacaa acggagaggc cgcgacccag aaatgggcgg caagcctcgc    480
aggaaaaaacc cccaggaggg actgtacaat gagttgcaga agataagat ggcagaagct    540
tatagcgaga tcggaatgaa gggggaaagg agacgaggga aggacacga cggcctttat    600
cagggcctgt ccagcaacaa aaagatacg tatgacgccc tccatatgca ggcacttcca    660
ccacggtgat aa                                                        672

SEQ ID NO: 595            moltype = AA  length = 222
FEATURE                   Location/Qualifiers
REGION                    1..222
                          note = CD8/CD28/CD3z sequence
source                    1..222
                          mol_type = protein
                          organism = synthetic construct
SEQUENCE: 595
TTTPAPRPPT PAPTIASQPL SLRPEACRPA AGGAVHTRGL DFACDIYIWA PLAGTCGVLL      60
```

```
LSLVITLYCR SKRSRLLHSD YMNMTPRRPG PTRKHYQPYA PPRDFAAYRS RVKFSRSADA  120
PAYKQGQNQL YNELNLGRRE EYDVLDKRRG RDPEMGGKPR RKNPQEGLYN ELQKDKMAEA  180
YSEIGMKGER RRGKGHDGLY QGLSTATKDT YDALHMQALP PR                    222

SEQ ID NO: 596          moltype = DNA   length = 675
FEATURE                 Location/Qualifiers
misc_feature            1..675
                        note = CD8/4-1BB/CD3z sequence
source                  1..675
                        mol_type = other DNA
                        organism = synthetic construct
SEQUENCE: 596
acgacaaccc cggcccccag accaccaacg ccagccccca ccatcgccag ccaacccctg   60
tctctgagac cagaagcctg taggcctgcc gccggtggag ctgtgcacac aagaggactg  120
gatttcgcct gtgatatcta catttgggcc ccgctcgcag gcacatgtgg agtgctcctc  180
ctctccctgg tgattaccct gtactgcaaa aggggccgca aaaaactcct ttacattttt  240
aagcagcctt ttatgaggcc agtacagacg actcaagagg aagacgggtg ctcatgccgc  300
tttcctgagg aggaggaagg agggtgcgaa ctgcgcgtta agttctcccg atcagccgac  360
gcgcctgctt acaagcaggg ccagaaccaa ctgtacaacg agctgaatct cggtagacgg  420
gaagagtacg acgtgttgga caaacggaga ggccgcgacc cagaaatggg cggcaagcct  480
cgcaggaaaa accccaggag gggactgtac aatgagttgc agaaagataa gatggcagaa  540
gcttatagcg agatcggaat gaaggggaa aggagacgag ggaaggaca cgacggcctt  600
tatcagggcc tgtccacagc aacaaagat acgtatgacg ccctccatat gcaggcactt  660
ccaccacggt gataa                                                  675

SEQ ID NO: 597          moltype = AA   length = 223
FEATURE                 Location/Qualifiers
REGION                  1..223
                        note = CD8/4-1BB/CD3z sequence
source                  1..223
                        mol_type = protein
                        organism = synthetic construct
SEQUENCE: 597
TTTPAPRPPT PAPTIASQPL SLRPEACRPA AGGAVHTRGL DFACDIYIWA PLAGTCGVLL   60
LSLVITLYCK RGRKKLLYIF KQPFMRPVQT TQEEDGCSCR FPEEEEGGCE LRVKFSRSAD  120
APAYKQGQNQ LYNELNLGRR EEYDVLDKRR GRDPEMGGKP RRKNPQEGLY NELQKDKMAE  180
AYSEIGMKGE RRRGKGHDGL YQGLSTATKD TYDALHMQAL PPR                   223

SEQ ID NO: 598          moltype = DNA   length = 798
FEATURE                 Location/Qualifiers
misc_feature            1..798
                        note = CD8/CD28/4-1BB/CD3z sequence
source                  1..798
                        mol_type = other DNA
                        organism = synthetic construct
SEQUENCE: 598
acgacaaccc cggcccccag accaccaacg ccagccccca ccatcgccag ccaacccctg   60
tctctgagac cagaagcctg taggcctgcc gccggtggag ctgtgcacac aagaggactg  120
gatttcgcct gtgatatcta catttgggcc ccgctcgcag gcacatgtgg agtgctcctc  180
ctctccctgg tgattaccct gtactgcaga agcaagcggt ctcggctcct gcattctgat  240
tacatgaaca tgacccccaag aagaccaggc cccaccagga acattacca gccctacgct  300
ccgccacgcg acttcgctgc ctaccggtcc aaaaggggcc gcaaaaaact cctttacatt  360
tttaagcagc cttttatgag gccagtacag acgactcaag aggaagacgg gtgctcatgc  420
cgctttcctg aggaggagga aggagggtgc gaactgcgcg ttaagttctc ccgatcagcc  480
gacgccctg cttacaagca gggccagaac caactgtaca acgagctgaa tctcggtaga  540
cgggaagagt acgacgtgtt ggacaaacgg agaggccgcg acccagaaat gggcggcaag  600
cctcgcagga aaaccccca ggagggactg tacaatgagt tgcagaaaga taagatggca  660
gaagcttata gcgagatcgg aatgaagggg gaaaggagac gagggaaagg acacgacggc  720
ctttatcagg gcctgtccac agcaacaaaa gatacgtatg acgccctcca tatgcaggca  780
cttccaccac ggtgataa                                                798

SEQ ID NO: 599          moltype = AA   length = 264
FEATURE                 Location/Qualifiers
REGION                  1..264
                        note = CD8/CD28/4-1BB/CD3z sequence
source                  1..264
                        mol_type = protein
                        organism = synthetic construct
SEQUENCE: 599
TTTPAPRPPT PAPTIASQPL SLRPEACRPA AGGAVHTRGL DFACDIYIWA PLAGTCGVLL   60
LSLVITLYCR SKRSRLLHSD YMNMTPRRPG PTRKHYQPYA PPRDFAAYRS KRGRKKLLYI  120
FKQPFMRPVQ TTQEEDGCSC RFPEEEEGGC ELRVKFSRSA DAPAYKQGQN QLYNELNLGR  180
REEYDVLDKR RGRDPEMGGK PRRKNPQEGL YNELQKDKMA EAYSEIGMKG ERRRGKGHDG  240
LYQGLSTATK DTYDALHMQA LPPR                                        264

SEQ ID NO: 600          moltype = DNA   length = 1482
FEATURE                 Location/Qualifiers
misc_feature            1..1482
                        note = CAR-T C3 4-1BB/CD3z sequence
```

-continued

```
source                  1..1482
                        mol_type = other DNA
                        organism = synthetic construct
SEQUENCE: 600
atggccctgc ccgtgaccgc tttgctgctc ccctggcgc tgctgctgca cgccgccagg    60
ccacaggttc agctggtgca gtctggagct gaggtgaaga agcctggggc ctcagtgaag   120
gtctcctgca aggcttctgg ttacacctttt accgactacg ccatgaactg ggtgcgacag   180
gcccctggac aagggcttga gtggatggga gtgatcagca ccttcagcgg taacacaaac   240
ttcaaccaga agttcaaggg cagagtcacc atgaccacag acacatccac gagcacagcc   300
tacatggagc tgaggagcct gagatctgac gacacggccg tgtattactg tgcgagaagc   360
gactactacg cccatacttt cgactactgg ggccagggca ccaccctgac cgtgtccagc   420
ggcggtggcg gatccggcgg tggcggatcc ggcggtggcg gatccgatat tgtgatgacc   480
cagactccac tctctctgtc cgtcacccct ggacagccgc cctccatctc ctgcaggtct   540
agtcagacca ttgtccatag taatggaaac acctatttgg agtggtacct gcagaagcca   600
ggccagtctc cacagctcct gatctataag gtttccaacc ggttctctgg agtgccagat   660
aggttcagtg gcagcgggtc agggacagat ttcacactga aaatcagccg ggtggaggct   720
gaggatgttg ggttttatta ctgcttccaa ggtagccacg tgcctttcac cttcggcgga   780
gggaccaagg tggagatcaa acgaactacg acaacccgcc cccccagacc accaacgcca   840
gcccccacca tcgccagcca acccctgtct ctgagaccag aagcctgtag gcctgccgcc   900
ggtgagctg tgcacacaag aggactggat tcgcctgtg atatctacat ttgggccccg    960
ctcgcaggca catgtggagt gctcctcctc tccctggtga ttaccctgta ctgcaaaagg  1020
ggccgcaaaa aactccttta cattttaag cagccttttg tgaggcccagt acagacgact  1080
caagaggaag acgggtgctc atgccgcttt cctgaggagg aggaaggagg tgcgaactg  1140
cgcgttaagt tctcccgatc agccgacgcg cctgcttaca gcagggccag aaccaactg  1200
tacaacgagc tgaatctcgg tagacgggaa gagtacgacg tgttgacaa acggagaggc  1260
cgcgacccag aaatgggcgg caagcctcgc aggaaaaacc cccaggaggg actgtacaat  1320
gagttgcaga agataagat ggcagaagct tatagcgaga tcggaatgaa gggggaaggc   1380
agacgaggga aggacacga cggcctttat cagggcctgt ccacagcaac aaaagatacg  1440
tatgacgccc tccatatgca ggcacttcca ccacggtgat aa                    1482

SEQ ID NO: 601         moltype = AA   length = 471
FEATURE                Location/Qualifiers
REGION                 1..471
                       note = CAR-T C3 4-1BB/CD3z sequence
source                 1..471
                       mol_type = protein
                       organism = synthetic construct
SEQUENCE: 601
QVQLVQSGAE VKKPGASVKV SCKASGYTFT DYAMNWVRQA PGQGLEWMGV ISTFSGNTNF    60
NQKFKGRVTM TTDTSTSTAY MELRSLRSDD TAVYYCARSD YYGPYFDYWG QGTTLTVSSG   120
GGGSGGGGSG GGGSDIVMTQ TPLSLSVTPG QPASISCRSS QTIVHSNGNT YLEWYLQKPG   180
QSPQLLIYKV SNRFSGVPDR FSGSGSGTDF TLKISRVEAE DVGVYYCFQG SHVPFTFGGG   240
TKVEIKRTTT TPAPRPPTPA PTIASQPLSL RPEACRPAAG GAVHTRGLDF ACDIYIWAPL   300
AGTCGVLLLS LVITLYCKRG RKKLLYIFKQ PFMRPVQTTQ EEDGCSCRFP EEEEGGCELR   360
VKFSRSADAP AYKQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP R            471

SEQ ID NO: 602         moltype = DNA   length = 567
FEATURE                Location/Qualifiers
misc_feature           1..567
                       note = C3 CAR gBLOCK 1 sequence
source                 1..567
                       mol_type = other DNA
                       organism = synthetic construct
SEQUENCE: 602
atccacgctg ttttgacctc catagaagat tctagagcta gctgtagagc ttggtaccga    60
gggccaccat ggccctgccc gtgaccgctt tgctgctccc cctggcgctg ctgctgcacg   120
ccgccaggcc acaggttcag ctggtgcagt ctggagctga ggtgaagaag cctgggcct   180
cagtgaaggt ctcctgcaag gcttctggtt acaccttttc cgactacgcc atgaactggg   240
tgcgacaggc ccctggacaa gggcttgagt ggatgggagt gatcagcacc ttcagcggta   300
acacaaactt caaccagaag ttcaagggca gagtcaccat gaccacagac acatccacga   360
gcacagccta catggagctg aggagcctga gatctgacga cacggccgtg tattactgtg   420
cgagaagcga ctactacggc ccatacttcg actactgggg ccagggcacc accctgaccg   480
tgtccagcgg cggtggcgga tccggcggtg gcggatccgg cggtggcgga tccgatattg   540
tgatgaccca gactccactc tctctgt                                       567

SEQ ID NO: 603         moltype = DNA   length = 509
FEATURE                Location/Qualifiers
misc_feature           1..509
                       note = C3 CAR gBLOCK 2 sequence
source                 1..509
                       mol_type = other DNA
                       organism = synthetic construct
SEQUENCE: 603
tattgtgatg acccagactc cactctctct gtccgtcacc cctggacagc cggcctccat    60
ctcctgcagg tctagtcaga ccattgtcca tagtaatgga acacctatt tggagtggta   120
cctgcagaag ccaggccagt ctccacagct cctgatctat aaggtttcca accggttctc   180
tggagtgcca gataggttca gtggcagcgg gtcagggaca gatttcacac tgaaaatcag   240
ccgggtggag gctgaggatg ttgggtttta ttactgcttc caaggtagcc acgtgccttt   300
```

```
caccttcggc ggagggacca aggtggagat caaacgaact acgacaaccc cggcccccag    360
accaccaacg ccagccccca ccatcgccag ccaaccectg tctctgagac cagaagcctg    420
taggcctgcc gccggtggag ctgtgcacac aagaggactg gatttcgcct gtgatatcta    480
catttgggcc ccgctcgcag gcacatgtg                                      509

SEQ ID NO: 604         moltype = DNA   length = 455
FEATURE                Location/Qualifiers
misc_feature           1..455
                       note = E6 scFV gBLOCK 1 sequence
source                 1..455
                       mol_type = other DNA
                       organism = synthetic construct
SEQUENCE: 604
tgctctgggt tccaggttcc actggtgacg cggcccagcc ggccgaggtg cagctggtgg     60
agtctggggg aggcctggtc aagcctgggg gtccctgag actctcctgt gcagcctctg    120
gattcacctt cagtaggtat ggcatgagct gggtccgcca ggctcaggg aagaggctgg    180
agtgggtctc aaccattagt ggcggaggca cctacatata ctacccagac tcagtgaagg    240
gccgattcac catctccaga gacaacgcca agaacaccct gtatctgcaa atgaacagcc    300
tgagagccga ggacacggct gtgtattact gtaccagaga taactatggc cgcaactatg    360
attatggcat ggattattgg ggccaggga ccctggtgac cgtgagcagc ggcggtggcg    420
gatccggcgg tggcggatcc ggcggtggcg gatcc                               455

SEQ ID NO: 605         moltype = DNA   length = 432
FEATURE                Location/Qualifiers
misc_feature           1..432
                       note = E6 scFV gBLOCK 2 sequence
source                 1..432
                       mol_type = other DNA
                       organism = synthetic construct
SEQUENCE: 605
ggcggtggcg gatccggcgg tggcggatcc ggcggtggcg gatccgaaat tgtgttgaca     60
cagtctccag ccaccctgtc tttgtctcca ggggaaagag ccaccctcac ctgcagcgcc    120
accagcagtg ttagctacat ccactggtac aacagagagc ctggccagag ccccaggctc    180
ctcatctata gcacctccaa cctggccagc ggcatccag ccaggttcag tggcagtggg    240
tctgggagcg actacactct caccatcagc agcctagagc ctgaagattt tgcagtttat    300
tactgtcagc agcgtagcag ctcccctttc acctttggca gcggcaccaa agtggaaatt    360
aaaaccggtc atcatcacca tcaccactga taagtttaaa cccgctgatc agcctcgact    420
gtgccttcta gt                                                        432

SEQ ID NO: 606         moltype = DNA   length = 1359
FEATURE                Location/Qualifiers
misc_feature           1..1359
                       note = CAR-T C2 CD3z sequence
source                 1..1359
                       mol_type = other DNA
                       organism = synthetic construct
SEQUENCE: 606
atggccttgc cagtgacggc cctgctgctg ccattggctc ttctgttgca cgctgccagc     60
cctgaagtgc agctcgtaga gagtggcggg ggactggtga agcccggtgg aagcctcaga    120
ctcagttgcg ccgcctcagg tttcactttt tcaggttacg ccatgtcctg ggtaagacag    180
gcaccgggga aaggactcga gtgggtgtct actatcgagt caggaggcac ttatatatat    240
tatcctgact ctgtaaaagg ccgatttacg atttctcgcg acaatgcaaa gaactccctc    300
tacctccaaa tgaacagtct tagggcagaa gacactgctg tatactattg tgcacgcctc    360
ggcggcgaca actactacga gtactttgac gtgtgggga agggactac cgtgacagtt    420
tcaagcggag gaggtggctc aggtggaggc gggtcagggg ggggaggaag tgatattggt    480
ctcacacaat cccccagcctc cctggctgtg tctcccggcc aacgcgctac aattacatgt    540
cgggcctcca aaagcgtgag caccagcggc tacagctaca tgcactggta tcaacagaaa    600
ccaggacaac cccccaaact gttgatttat ctcgcttcaa acttggagtc cggcgtgcct    660
gcgcgcttt caggagtgg gagcggcaca gatttttacgc tgactatcaa ccccgtagaa    720
gcaaacgata cagcgaatta ttattgtcaa cattccccggg aactcccctt tacgttcggc    780
gggggcacaa aggtcgaaat taagagaacc acgacaaccc cggcccccag accaccaacg    840
ccagccccca ccatcgccag ccaaccctg tctctgagac cagaagcctg taggcctgcc    900
gccggtggag ctgtgcacac aagaggactg gatttcgcct gtgatatcta catttgggcc    960
ccgctcgcag gcacatgtgg agtgctcctc tctccctcg tgattaccct gtactgcgcc    1020
gttaagttct cccgatcagc cgacgcgcct gcttacaagc agggccagaa ccaactgtac    1080
aacgagctga atctcggtag acgggaagag tacgacgtgt tggacaaacg agaggccgc    1140
gacccagaaa tgggcggcaa gcctcgcagg aaaaaccccc aggagggact gtacaatgag    1200
ttgcagaaag ataagatggc agaagcttat agcgagatcg gaatgaaggg ggaaaggaga    1260
cgagggaaag gacacgacgg cctttatcag ggcctgtcca cagcaacaaa agatacgtat    1320
gacgccctcc atatgcaggc acttccacca cggtgataa                          1359

SEQ ID NO: 607         moltype = AA    length = 451
FEATURE                Location/Qualifiers
REGION                 1..451
                       note = CAR-T C2 CD3z sequence
source                 1..451
                       mol_type = protein
                       organism = synthetic construct
SEQUENCE: 607
```

```
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL   120
GGDNYYEYFD VWGKGTTVTV SSGGGGSGGG GSGGGGSDIV LTQSPASLAV SPGQRATITC   180
RASKSVSTSG YSYMHWYQQK PGQPPKLLIY LASNLESGVP ARFSGSGSGT DFTLTINPVE   240
ANDTANYYCQ HSRELPFTFG GGTKVEIKRT TTTPAPRPPT PAPTIASQPL SLRPEACRPA   300
AGGAVHTRGL DFACDIYIWA PLAGTCGVLL LSLVITLYCR VKFSRSADAP AYKQGQNQLY   360
NELNLGRREE YDVLDKRRGR DPEMGGKPRR KNPQEGLYNE LQKDKMAEAY SEIGMKGERR   420
RGKGHDGLYQ GLSTATKDTY DALHMQALPP R                                  451

SEQ ID NO: 608         moltype = DNA  length = 1482
FEATURE                Location/Qualifiers
misc_feature           1..1482
                       note = CAR-T C2 CD28/CD3z sequence
source                 1..1482
                       mol_type = other DNA
                       organism = synthetic construct
SEQUENCE: 608
atggccttgc cagtgacggc cctgctgctg ccattggctc ttctgttgca cgctgccagg    60
cctgaagtgc agctcgtaga gagtggcggg ggactggtga agcccggtgg aagcctcaga   120
ctcagttgcg ccgcctcagg tttcactttt tcaggttacg ccatgtcctg ggtaagacag   180
gcaccgggga aaggactcga gtgggtgtct actatcagct caggaggcac ttatatatat   240
tatcctgact ctgtaaaagg ccgatttacg atttctcgcg acaatgcaaa gaactcccta   300
tacctccaaa tgaacagtct tagggcagaa gacactgctg tatactattg tgcacgcctc   360
ggcggcgaca actactacga gtactttgac gtgtggggga aagggactac cgtgacagtt   420
tcaagcggag gaggtggctc aggtggaggc ggtcagggg ggaggaag tgatattgtg   480
ctcacacaat ccccagcctc cctggctgtg tctcccggcc aacgcgctac aattacatgt   540
cgggcctcca aaagcgtgag caccagcggc tacagctaca tgcactggta tcaacagaaa   600
ccaggacaaa cccccaaaact gttgatttat ctcgcttcaa acttggagtc cggcgtgcct   660
gcgcgctttt cagggagtgg gagcggcaca gattttacgc tgactatcaa ccccgtagaa   720
gcaaacgata cagcgaatta ttattgtcaa cattcccagc aactcccctt tacgttcggc   780
ggggggcacaa aggtcgaaat taagagaacc acgacaaccc cggccccaag accaccaacg   840
ccagccccca ccatcgccag caaccccctg tctctgagac agaagctg taggcctgcc   900
gccggtggag ctgtgcacac aagaggactg gatttcgcct gtgatatcta catttgggcc   960
ccgctcgcag gcacatgtgg agtgctcctc ctctcccctgg tgattaccct gtactgcagg  1020
agcaagcggt ctcggctcct gcattctgat tacatgaaca tgaccccaag aagaccaggc  1080
cccaccagga acattacca gccctacgct ccgccacgcg acttcgctgc ctaccggtcc  1140
cgcgttaagt tctcccgatc agccgacgcg cctgcttaca gcagggcca gaaccaactg  1200
tacaacgagc tgaatctcgg tagacgggaa gagtacgacg tgttggacaa acggagaggc  1260
cgcgacccag aaatggcgg caagcctcgc aggaaaaacc cccagagg actgtacaat  1320
gagttgcaga agataagat ggcagaagct tatagcgaga tcggaatgaa ggggaaagg  1380
agacgaggga aaggacacga cggcctttat cagggcctgt ccacagcaac aaaagatacg  1440
tatgacgccc tccatatgca ggcacttcca ccacggtgat aa                      1482

SEQ ID NO: 609         moltype = AA  length = 492
FEATURE                Location/Qualifiers
REGION                 1..492
                       note = CAR-T C2 CD28/CD3z sequence
source                 1..492
                       mol_type = protein
                       organism = synthetic construct
SEQUENCE: 609
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL   120
GGDNYYEYFD VWGKGTTVTV SSGGGGSGGG GSGGGGSDIV LTQSPASLAV SPGQRATITC   180
RASKSVSTSG YSYMHWYQQK PGQPPKLLIY LASNLESGVP ARFSGSGSGT DFTLTINPVE   240
ANDTANYYCQ HSRELPFTFG GGTKVEIKRT TTTPAPRPPT PAPTIASQPL SLRPEACRPA   300
AGGAVHTRGL DFACDIYIWA PLAGTCGVLL LSLVITLYCR SKRSRLLHSD YMNMTPRRPG   360
PTRKHYQPYA PPRDFAAYRS RVKFSRSADA PAYKQGQNQL YNELNLGRRE EYDVLDKRRG   420
RDPEMGGKPR RKNPQEGLYN ELQKDKMAEA YSEIGMKGER RRGKGHDGLY QGLSTATKDT   480
YDALHMQALP PR                                                       492

SEQ ID NO: 610         moltype = DNA  length = 1485
FEATURE                Location/Qualifiers
misc_feature           1..1485
                       note = CAR-T C2 4-1BB/CD3z sequence
source                 1..1485
                       mol_type = other DNA
                       organism = synthetic construct
SEQUENCE: 610
atggccttgc cagtgacggc cctgctgctg ccattggctc ttctgttgca cgctgccagg    60
cctgaagtgc agctcgtaga gagtggcggg ggactggtga agcccggtgg aagcctcaga   120
ctcagttgcg ccgcctcagg tttcactttt tcaggttacg ccatgtcctg ggtaagacag   180
gcaccgggga aaggactcga gtgggtgtct actatcagct caggaggcac ttatatatat   240
tatcctgact ctgtaaaagg ccgatttacg atttctcgcg acaatgcaaa gaactcccta   300
tacctccaaa tgaacagtct tagggcagaa gacactgctg tatactattg tgcacgcctc   360
ggcggcgaca actactacga gtactttgac gtgtggggga aagggactac cgtgacagtt   420
tcaagcggag gaggtggctc aggtggaggc ggtcagggg ggaggaag tgatattgtg   480
ctcacacaat ccccagcctc cctggctgtg tctcccggcc aacgcgctac aattacatgt   540
cgggcctcca aaagcgtgag caccagcggc tacagctaca tgcactggta tcaacagaaa   600
```

```
ccaggacaac ccccaaaact gttgatttat ctcgcttcaa acttggagtc cggcgtgcct    660
gcgcgctttt cagggagtgg gagcggcaca gattttacgc tgactatcaa ccccgtagaa    720
gcaaacgata cagcgaatta ttattgtcaa cattcccggg aactccccctt tacgttcggc   780
gggggcacaa aggtcgaaat taagagaacc acgacaaccc cggccccag accaccaacg    840
ccagccccca ccatcgccag ccaacccctg tctctgagac cagaagcctg taggcctgcc   900
gccggtggag ctgtgcacac aagaggactg gatttcgcct gtgatatcta catttgggcc   960
ccgctcgcag gcacatgtgg agtgctcctc ctctccctgg tgattaccct gtactgcaaa   1020
aggggccgca aaaaactcct ttacattttt aagcagcctt ttatgaggcc agtacagacg  1080
actcaagagg aagacgggtg ctcatgccgc tttcctgagg aggagaagg agggtgcgaa  1140
ctgcgcgtta agttctcccg atcagccgac gcgcctgctt acaagcaggg ccagaaccaa  1200
ctgtacaacg agctgaatct cggtagacga gaagagtacg acgtgttgga caaacggaga  1260
ggccgcgacc cagaaatggg cggcaagcct cgcaggaaaa accccagga gggactgtac  1320
aatgagttgc agaaagataa gatggcagaa gcttatagcg agatcggaat gaaggggaa  1380
aggagacgag ggaaaggaca cgacggcctg tatcaggcc tgtccacagc aacaaaagat  1440
acgtatgacg ccctccatat gcaggcactt ccaccacgg gataa                  1485

SEQ ID NO: 611           moltype = AA   length = 493
FEATURE                  Location/Qualifiers
REGION                   1..493
                         note = CAR-T C2 4-1BB/CD3z sequence
source                   1..493
                         mol_type = protein
                         organism = synthetic construct
SEQUENCE: 611
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL  120
GGDNYYEYFD VWGKGTTVTV SSGGGGSGGG GSGGGGSDIV LTQSPASLAV SPGQRATITC  180
RASKSVSTSG YSYMHWYQQK PGQPPKLLIY LASNLESGVP ARFSGSGSGT DFTLTINPVE  240
ANDTANYYCQ HSRELPFTFG GGTKVEIKRT TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 612           moltype = DNA   length = 1470
FEATURE                  Location/Qualifiers
misc_feature             1..1470
                         note = CAR-T C2 OX40/CD3z sequence
source                   1..1470
                         mol_type = other DNA
                         organism = synthetic construct
SEQUENCE: 612
atggccttgc cagtgacggc cctgctgctg ccattggctc ttctgttgca cgctgccagg    60
cctgaagtgc agctcgtaga gagtggcggg ggactggtga agcccggtgg aagcctcaga  120
ctcagttgcg ccgcctcagg tttcactttt caggttacg ccatgtcctg ggtaagacga  180
gcaccgggga aaggactcga gtgggtgtct actatcagct caggaggcac ttatatatat  240
tatcctgact ctgtaaaagg ccgatttacg atttctcgcg acaatgcaaa gaactccctc  300
tacctccaaa tgaacagtct tagggcagaa gacactgctg tatactattg tgcacgcctc  360
ggcggcgaca actactacga gtactttgac gtgtgggga aagggactac cgtgacagtt  420
tcaagcggag gaggtggctc aggtggaggc gggtcagggg gggaggaag tgatattgtg  480
ctcacacaat cccccagcctc cctggctgtg tctcccggcc aacgcgctac aattacatgc  540
cgggcctcca aaagcgtgag caccagcggc tacagctaca tgcactggta tcaacagaaa  600
ccaggacaac ccccaaaact gttgatttat ctcgcttcaa acttggagtc cggcgtgcct  660
gcgcgctttt cagggagtgg gagcggcaca gattttacgc tgactatcaa ccccgtagaa  720
gcaaacgata cagcgaatta ttattgtcaa cattcccggg aactccccctt tacgttcggc  780
gggggcacaa aggtcgaaat taagagaacc acgacaaccc cggccccag accaccaacg  840
ccagccccca ccatcgccag ccaacccctg tctctgagac cagaagcctg taggcctgcc  900
gccggtggag ctgtgcacac aagaggactg gatttcgcct gtgatatcta catttgggcc  960
ccgctcgcag gcacatgtgg agtgctcctc ctctccctgg tgattaccct gtactgccgg  1020
agggaccaga ggctgccccc cgatgcccac aagccccctg ggggaggcag tttccgggcc  1080
cccatccaag aggagcaggc cgacgcccac tccaccctgg ccaagatccg cgttaagttc  1140
tcccgatcag ccgacgcgcc tgcttacaag caggccaga accaactgta caacgagctg  1200
aatctcggta cgggaagga gtacgacgtg ttggacaaac ggagaggccg cgacccagaa  1260
atgggcggca agcctcgcag gaaaaacccc caggaggagc tgtacaatga gttgcagaaa  1320
gataagatgg cagaagctta tagcgagatc ggaatgaagg gggaaggag acgagggaaa  1380
ggacacgacg gcctttatca gggcctgtcc acagcaacaa aagatacgta tgacgccctc  1440
catatgcagg cacttccacc acggtgataa                                    1470

SEQ ID NO: 613           moltype = AA   length = 488
FEATURE                  Location/Qualifiers
REGION                   1..488
                         note = CAR-T C2 OX40/CD3z sequence
source                   1..488
                         mol_type = protein
                         organism = synthetic construct
SEQUENCE: 613
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL  120
GGDNYYEYFD VWGKGTTVTV SSGGGGSGGG GSGGGGSDIV LTQSPASLAV SPGQRATITC  180
```

```
RASKSVSTSG YSYMHWYQQK PGQPPKLLIY LASNLESGVP ARFSGSGSGT DFTLTINPVE   240
ANDTANYYCQ HSRELPFTFG GGTKVEIKRT TTTPAPRPPT PAPTIASQPL SLRPEACRPA   300
AGGAVHTRGL DFACDIYIWA PLAGTCGVLL LSLVITLYCR RDQRLPPDAH KPPGGGSFRT   360
PIQEEQADAH STLAKIRVKF SRSADAPAYK QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                           488

SEQ ID NO: 614          moltype = DNA   length = 1593
FEATURE                 Location/Qualifiers
misc_feature            1..1593
                        note = CAR-T C2 CD28/OX40/CD3z sequence
source                  1..1593
                        mol_type = other DNA
                        organism = synthetic construct
SEQUENCE: 614
atggccttgc cagtgacggc cctgctgctg ccattggctc ttctgttgca cgctgccagg    60
cctgaagtgc agctcgtaga gagtggcggg ggactggtga agcccggtgg aagcctcaga   120
ctcagttgcg ccgcctcagg tttcactttt tcaggttacg ccatgtcctg ggtaagacag   180
gcaccgggga aaggactcga gtgggtgtct actatcagct caggaggcac ttatatatat   240
tatcctgact ctgtaaaagg ccgatttacg atttctcgcg acaatgcaaa gaactccctc   300
tacctccaaa tgaacagtct tagggcagaa gacactgctg tatactattg tgcacgcctc   360
ggcggcgaca actactacga gtactttgac gtgtggggac aagggactac cgtgacagtt   420
tcaagcggag gaggtggctc aggtggaggc gggtcagggg ggggaggaag tgatattgtg   480
ctcacacaat cccagcctc cctgctgtgt ctcccggcc aacgcgctac aattacatgt   540
cgggcctcca aaagcgtgag caccagcggc tacagctaca tgcactggta tcaacagaaa   600
ccaggacaac cccccaaact gttgatttat tctcgcttca acttgagtc cggcgtgcct   660
gcgcgctttt cagggagtgg gagcggcaca gattttacgc tgactatcaa ccccgtagaa   720
gcaaacgata cagcgaatta ttattgtcaa cattcccggg aactccccttt acgttcggc   780
gggggcacaa aggtcgaaat taagagaacc acgacaaccc cggcccccag accaccaacg   840
ccagcccca ccatcgccag ccaaccctg tctctgagac cagaagcctg taggcctgcc   900
gccggtggag ctgtgcacac aagaggactg gatttcgcct gtgatatcta catttgggca   960
ccgctcgcag gcacatgtgg agtgctcctc ctctccctgg tgattaccct gtactgcaga  1020
agcaagcggt ctcggctcct gcattctgat tacatgaaca tgaccccaag aagaccaggc  1080
cccaccagga acattaccc aggcccacgc tccgccacgc acttcgctgc ctaccggtcc  1140
cggagggacc agaggctgcc ccccgatgcc acaagcccc ctgggggagg cagtttccgg  1200
acccccatcc aagaggagca ggccgacgcc cactccaccc tggccaagat ccgcgttaag  1260
ttctcccgat cagccgacgc gcctgcttac aagcagggcc agaaccaact gtacaacgag  1320
ctgaatctcg gtagacggga agagtacgac gtgttggaca acggagagg ccgcgaccca  1380
gaaatggggc gcaagcctcg caggaaaaac ccccaggagg gactgtacaa tgagttgcag  1440
aaagataaga tggcagaagc ttatagcgag atcggaatga aggggaaag gagacgaggg  1500
aaaggacacg acggccttta tcagggcctg tccacagcaa caaaagatac gtatgacgcc  1560
ctccatatgc aggcacttcc accacggtga taa                              1593

SEQ ID NO: 615          moltype = AA   length = 529
FEATURE                 Location/Qualifiers
REGION                  1..529
                        note = CAR-T C2 CD28/OX40/CD3z sequence
source                  1..529
                        mol_type = protein
                        organism = synthetic construct
SEQUENCE: 615
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL   120
GGDNYYEYFD VWGKGTTVTV SSGGGGSGGG GSGGGGSDIV LTQSPASLAV SPGQRATITC   180
RASKSVSTSG YSYMHWYQQK PGQPPKLLIY LASNLESGVP ARFSGSGSGT DFTLTINPVE   240
ANDTANYYCQ HSRELPFTFG GGTKVEIKRT TTTPAPRPPT PAPTIASQPL SLRPEACRPA   300
AGGAVHTRGL DFACDIYIWA PLAGTCGVLL LSLVITLYCR SKRSRLLHSD YMNMTPRRPG   360
PTRKHYQPYA PPRDFAAYRS RRDQRLPPDA HKPPGGGSFR TPIQEEQADA HSTLAKIRVK   420
FSRSADAPAY KQGQNQLYNE LNLGRREEYD VLDKRRGRDP EMGGKPRRKN PQEGLYNELQ   480
KDKMAEAYSE IGMKGERRRG KGHDGLYQGL STATKDTYDA LHMQALPPR              529

SEQ ID NO: 616          moltype = DNA   length = 1452
FEATURE                 Location/Qualifiers
misc_feature            1..1452
                        note = CAR-T E6 OX40/CD3z sequence
source                  1..1452
                        mol_type = other DNA
                        organism = synthetic construct
SEQUENCE: 616
atggccctgc ccgtgaccgc tttgctgctc cccctggcgc tgctgctgca cgccgccagg    60
ccagaggtcc agctggttga gagtggcggt gggctggtta agcctggcgg ctccctgcgg   120
ctgagctgcg ccgcgagtgg atttactttc agccgatatg gatgagttg ggtgcggcaa   180
gctcccggga gaggctgga atgggtctca acaatctccg gggggggcac ttacatctat   240
tacccgact cagtcaaggg agatttacc atttcacgag acaacgctaa gaatccctg   300
tatttgcaga tgaattctct gagagcagag gacacagctg tttactattg tacccgcgac   360
aactatggca gaactacga ctacgtatg gactattggg gacaagggac attggttaca   420
gtgagcagtg gcgcgggggg cagcggagga ggaggcagcg gtgggggggg cagcgagata   480
gtgctcacgc agtcacccgc gactctcagt ctctcacctg ggaacgagc taccctgacg   540
tgctctgcta cctcctcagt gtcatatatt cactggtatc agcaacggcc cggcagtcc   600
```

```
cctagattgc tcatttatag tacctctaat ctggcctcag gtatccctgc acgattttct    660
ggatctggtt caggttctga ttacaccctc actatctcta gcctggagcc tgaagacttt    720
gccgtttatt actgccagca gaggtctagc tccccattca cctttgggag tgggaccaag    780
gttgaaatta aaacgacaac cccggccccc agaccaccaa cgccagcccc caccatcgcc    840
agccaacccc tgtctctgag accagaagcc cgtaggcctg ccgccggtgg agctgtgcac    900
acaagaggac tggatttcgc ctgtgatatc tacatttggg ccccgctcgc aggcacatgt    960
ggagtgctcc tcctctccct ggtgattacc ctgtactgcc ggagggacca gaggctgccc   1020
cccgatgccc acaagccccc tgggggaggc agtttccgga ccccatcca agaggagcag    1080
gccgacgccc actccaccct ggccaagatc cgcgttaagt tctcccgatc agccgacgga   1140
cctgcttaca gcagggccca gaaccaactg tacaacgagc tgaatctcgg tagacgggga   1200
gagtacgacg tgttggacaa acggagaggc cgcgacccag aaatgggcgg caagcctcgc   1260
aggaaaaacc cccaggaggg actgtacaat gagttgcaga agataagat ggcagaagct    1320
tatagcgaga tcggaatgaa gggggaaagg agacgaggga aggacacga cggcctttat    1380
cagggcctgt ccacagcaac aaaagatacg tatgacgccc tccatatgca ggcacttcca   1440
ccacggtgat aa                                                       1452

SEQ ID NO: 617        moltype = AA  length = 482
FEATURE               Location/Qualifiers
REGION                1..482
                      note = CAR-T E6 OX40/CD3z sequence
source                1..482
                      mol_type = protein
                      organism = synthetic construct
SEQUENCE: 617
MALPVTALLL PLALLLHAAR PEVQLVESGG GLVKPGGSLR LSCAASGFTF SRYGMSWVRQ     60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKTTTPAP RPPTPAPTIA SQPLSLRPEA CRPAAGGAVH   300
TRGLDFACDI YIWAPLAGTC GVLLLSLVIT LYCRRDQRLP PDAHKPPGGG SFRTPIQEEQ   360
ADAHSTLAKI RVKFSRSADA PAYKQGQNQL YNELNLGRRE EYDVLDKRRG RDPEMGGKPR   420
RKNPQEGLYN ELQKDKMAEA YSEIGMKGER RRGKGHDGLY QGLSTATKDT YDALHMQALP   480
PR                                                                 482

SEQ ID NO: 618        moltype = DNA  length = 1575
FEATURE               Location/Qualifiers
misc_feature          1..1575
                      note = CAR-T E6 CD28/OX40/CD3z sequence
source                1..1575
                      mol_type = other DNA
                      organism = synthetic construct
SEQUENCE: 618
atggccctgc ccgtgaccgc tttgctgctc cccctggcgc tgctgctgca cgccgccagg     60
ccagaggtcc agctggttga gagtggcggt gggctggtta agcctggcgg ctccctgcgg   120
ctgagctgcg ccgcgagtgg atttactttc agccgatatg gatgagttg ggtgcggcaa    180
gctcccggga agaggctgga atgggtctca acaatctccg gggggggcac ttacatctat   240
tacccgact cagtcaaggg gagatttacc atttcacgag acaacgctaa gaatacccta    300
tatttgcaga tgaattctct gagagcagag gacacagctg tttactattg tacccgcgac   360
aactatggca ggaactacga ctacggtatg gactattggg gacaagggac attggttaca   420
gtgagcagtg gcggcggggg cagcggagga ggaggcagcg gtgggggggg cagcgagata   480
gtgctcacgc agtcacccgc gactctcagt ctctcacctg ggaacgatcc taccctgacg   540
tgctctgcta cctcctcagt gtcatatatt cactggtatc agcaacggcc cgggcagtcc   600
cctagattgc tcatttatag tacctctaat ctggcctcag gtatccctgc acgattttct    660
ggatctggtt caggttctga ttacaccctc actatctcta gcctggagcc tgaagacttt   720
gccgtttatt actgccagca gaggtctagc tccccattca cctttgggag tgggaccaag   780
gttgaaatta aaacgacaac cccggccccc agaccaccaa cgccagcccc caccatcgcc   840
agccaacccc tgtctctgag accagaagcc tgtaggcctg ccgccggtgg agctgtgcac   900
acaagaggac tggatttcgc ctgtgatatc tacatttggg ccccgctcgc aggcacatgt   960
ggagtgctcc tcctctccct ggtgattacc ctgtactgca gaagcaagcg gtctcggctg  1020
ctgcattctg attacatgaa catgaccccc agaagacccg gcccaccagg gaaacattac  1080
cagccctacg ctccgccacg cgacttcgct gcctaccgt cccggaggga ccagaggctg   1140
ccccccgatg cccacaagcc cctgggggga ggcagtttcc ggaccccat caagaggag    1200
caggccgacg cccactccac cctggccaag atccgcgtta agttctcccg atcagccgac  1260
gcgcctgctt acaagcaggg ccagaaccaa ctgtacaacg agctgaatct cggtagacgg  1320
gaagagtacg acgtgttgga caaacggaga ggccgcgacc cagaaatggg cggcaagcct  1380
cgcaggaaaa accccagga gggactgtac aatgagttgc agaaagataa gatggcagaa   1440
gcttatagcg agatcggaat gaaggggga aggagacgag ggaaaggaca cgacggcctt   1500
tatcagggcc tgtccacagc aacaaaagat acgtatgacg ccctccatat gcaggcactt  1560
ccaccacggt gataa                                                  1575

SEQ ID NO: 619        moltype = AA  length = 523
FEATURE               Location/Qualifiers
REGION                1..523
                      note = CAR-T E6 CD28/OX40/CD3z sequence
source                1..523
                      mol_type = protein
                      organism = synthetic construct
SEQUENCE: 619
MALPVTALLL PLALLLHAAR PEVQLVESGG GLVKPGGSLR LSCAASGFTF SRYGMSWVRQ     60
```

```
APGKRLEWVS TISGGGTYIY YPDSVKGRFT ISRDNAKNTL YLQMNSLRAE DTAVYYCTRD    120
NYGRNYDYGM DYWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF    240
AVYYCQQRSS SPFTFGSGTK VEIKTTTPAP RPPTPAPTIA SQPLSLRPEA CRPAAGGAVH    300
TRGLDFACDI YIWAPLAGTC GVLLLSLVIT LYCRSKRSRL LHSDYMNMTP RRPGPTRKHY    360
QPYAPPRDFA AYRSRRDQRL PPDAHKPPGG GSFRTPIQEE QADAHSTLAK IRVKFSRSAD    420
APAYKQGQNQ LYNELNLGRR EEYDVLDKRR GRDPEMGGKP RRKNPQEGLY NELQKDKMAE    480
AYSEIGMKGE RRRGKGHDGL YQGLSTATKD TYDALHMQAL PPR                     523

SEQ ID NO: 620          moltype = AA  length = 43
FEATURE                 Location/Qualifiers
REGION                  1..43
                        note = MUC1 FRAGMENT
source                  1..43
                        mol_type = protein
                        organism = synthetic construct
SEQUENCE: 620
SNIKFRPGSV VVQLTLAFRE GTINVHDVET QFNQYKTEAA SRY                      43

SEQ ID NO: 621          moltype = AA  length = 35
FEATURE                 Location/Qualifiers
REGION                  1..35
                        note = MUC1 FRAGMENT
source                  1..35
                        mol_type = protein
                        organism = synthetic construct
SEQUENCE: 621
SVVVQLTLAF REGTINVHDV ETQFNQYKTE AASRY                               35

SEQ ID NO: 622          moltype = AA  length = 24
FEATURE                 Location/Qualifiers
REGION                  1..24
                        note = Cytoplasmic MUC1 truncated segment
source                  1..24
                        mol_type = protein
                        organism = synthetic construct
SEQUENCE: 622
VQLTLAFREG TINVHDVETQ FNQY                                           24

SEQ ID NO: 623          moltype = AA  length = 24
FEATURE                 Location/Qualifiers
REGION                  1..24
                        note = Cytoplasmic MUC1 truncated segment
source                  1..24
                        mol_type = protein
                        organism = synthetic construct
SEQUENCE: 623
SNIKFRPGSV VVQLTLAFRE GTIN                                           24

SEQ ID NO: 624          moltype = DNA  length = 28
FEATURE                 Location/Qualifiers
misc_feature            1..28
                        note = Primer
source                  1..28
                        mol_type = other DNA
                        organism = synthetic construct
SEQUENCE: 624
attctaagct tgggccacca tggaactg                                       28

SEQ ID NO: 625          moltype = DNA  length = 41
FEATURE                 Location/Qualifiers
misc_feature            1..41
                        note = Primer
source                  1..41
                        mol_type = other DNA
                        organism = synthetic construct
SEQUENCE: 625
tctagagttt aaacttacta tttacccgga gacagggaga g                        41

SEQ ID NO: 626          moltype = DNA  length = 41
FEATURE                 Location/Qualifiers
misc_feature            1..41
                        note = Primer
source                  1..41
                        mol_type = other DNA
                        organism = synthetic construct
SEQUENCE: 626
agtatggccc agccggccga ggtgcagctg gtggagtctg g                        41
```

```
SEQ ID NO: 627           moltype = DNA   length = 26
FEATURE                  Location/Qualifiers
misc_feature             1..26
                         note = Primer
source                   1..26
                         mol_type = other DNA
                         organism = synthetic construct
SEQUENCE: 627
tagaaggcac agtcgaggct gatcag                                          26

SEQ ID NO: 628           moltype = DNA   length = 27
FEATURE                  Location/Qualifiers
misc_feature             1..27
                         note = Primer
source                   1..27
                         mol_type = other DNA
                         organism = synthetic construct
SEQUENCE: 628
attctaagct tgggccacca tggaagc                                         27

SEQ ID NO: 629           moltype = DNA   length = 40
FEATURE                  Location/Qualifiers
misc_feature             1..40
                         note = Primer
source                   1..40
                         mol_type = other DNA
                         organism = synthetic construct
SEQUENCE: 629
tctagagttt aaacttacta acactctccc ctgttgaagc                           40

SEQ ID NO: 630           moltype = DNA   length = 43
FEATURE                  Location/Qualifiers
misc_feature             1..43
                         note = Primer
source                   1..43
                         mol_type = other DNA
                         organism = synthetic construct
SEQUENCE: 630
agtatggccc agccggccga aattgtgttg acacagtctc cag                       43

SEQ ID NO: 631           moltype = DNA   length = 26
FEATURE                  Location/Qualifiers
misc_feature             1..26
                         note = Primer
source                   1..26
                         mol_type = other DNA
                         organism = synthetic construct
SEQUENCE: 631
tagaaggcac agtcgaggct gatcag                                          26

SEQ ID NO: 632           moltype = DNA   length = 33
FEATURE                  Location/Qualifiers
misc_feature             1..33
                         note = Primer
source                   1..33
                         mol_type = other DNA
                         organism = synthetic construct
SEQUENCE: 632
actgtcatat ggaggtgcag ctggtggagt ctg                                  33

SEQ ID NO: 633           moltype = DNA   length = 37
FEATURE                  Location/Qualifiers
misc_feature             1..37
                         note = Primer
source                   1..37
                         mol_type = other DNA
                         organism = synthetic construct
SEQUENCE: 633
actgtctcga gtttaatttc cactttggtg ccgctgc                              37

SEQ ID NO: 634           moltype = DNA   length = 33
FEATURE                  Location/Qualifiers
misc_feature             1..33
                         note = Primer
source                   1..33
                         mol_type = other DNA
                         organism = synthetic construct
SEQUENCE: 634
actgtcatat ggaggtgcag ctggtggagt ctg                                  33
```

```
SEQ ID NO: 635          moltype = DNA  length = 37
FEATURE                 Location/Qualifiers
misc_feature            1..37
                        note = Primer
source                  1..37
                        mol_type = other DNA
                        organism = synthetic construct
SEQUENCE: 635
actgtaccgg ttttaatttc cactttggtg ccgctgc                                   37

SEQ ID NO: 636          moltype = DNA  length = 29
FEATURE                 Location/Qualifiers
misc_feature            1..29
                        note = Primer
source                  1..29
                        mol_type = other DNA
                        organism = synthetic construct
SEQUENCE: 636
cttcttcctc aggagcaagc tcaccgtgg                                            29

SEQ ID NO: 637          moltype = DNA  length = 18
FEATURE                 Location/Qualifiers
misc_feature            1..18
                        note = Primer
source                  1..18
                        mol_type = other DNA
                        organism = synthetic construct
SEQUENCE: 637
gagccgtcgg agtccagc                                                        18

SEQ ID NO: 638          moltype = DNA  length = 18
FEATURE                 Location/Qualifiers
misc_feature            1..18
                        note = Primer
source                  1..18
                        mol_type = other DNA
                        organism = synthetic construct
SEQUENCE: 638
gcacctgaac tcctgggg                                                        18

SEQ ID NO: 639          moltype = DNA  length = 22
FEATURE                 Location/Qualifiers
misc_feature            1..22
                        note = Primer
source                  1..22
                        mol_type = other DNA
                        organism = synthetic construct
SEQUENCE: 639
tttaatttcc actttggtgc cg                                                   22

SEQ ID NO: 640          moltype = DNA  length = 32
FEATURE                 Location/Qualifiers
misc_feature            1..32
                        note = Primer
source                  1..32
                        mol_type = other DNA
                        organism = synthetic construct
SEQUENCE: 640
cgcggctagc ttaagcttgg taccgagggc ca                                        32

SEQ ID NO: 641          moltype = DNA  length = 36
FEATURE                 Location/Qualifiers
misc_feature            1..36
                        note = Primer
source                  1..36
                        mol_type = other DNA
                        organism = synthetic construct
SEQUENCE: 641
cgcggcggcc gcctgatcag cgggtttaaa cttatc                                    36

SEQ ID NO: 642          moltype = AA  length = 35
FEATURE                 Location/Qualifiers
REGION                  1..35
                        note = PSMGFR N-10
source                  1..35
                        mol_type = protein
                        organism = synthetic construct
SEQUENCE: 642
```

```
QFNQYKTEAA SRYNLTISDV SVSDVPFPFS AQSGA                                       35

SEQ ID NO: 643        moltype = AA  length = 35
FEATURE               Location/Qualifiers
REGION                1..35
                      note = PSMGFR C-10
source                1..35
                      mol_type = protein
                      organism = synthetic construct
SEQUENCE: 643
GTINVHDVET QFNQYKTEAA SRYNLTISDV SVSDV                                       35
```